(12) United States Patent
Rodgers et al.

(10) Patent No.: US 10,398,699 B2
(45) Date of Patent: *Sep. 3, 2019

(54) HETEROARYL SUBSTITUTED PYRROLO[2,3-B]PYRIDINES AND PYRROLO[2,3-B]PYRIMIDINES AS JANUS KINASE INHIBITORS

(71) Applicants: Incyte Corporation, Wilmington, DE (US); Incyte Holdings Corporation, Wilmington, DE (US)

(72) Inventors: James D. Rodgers, Jupiter, FL (US); Stacey Shepard, Wilmington, DE (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/960,069

(22) Filed: Apr. 23, 2018

(65) Prior Publication Data

US 2018/0338978 A1 Nov. 29, 2018

Related U.S. Application Data

(60) Continuation of application No. 15/356,957, filed on Nov. 21, 2016, now Pat. No. 9,974,790, which is a continuation of application No. 15/233,652, filed on Aug. 10, 2016, now Pat. No. 9,814,722, which is a continuation of application No. 15/173,057, filed on Jun. 3, 2016, now Pat. No. 9,662,335, which is a continuation of application No. 14/711,576, filed on May 13, 2015, now abandoned, which is a continuation of application No. 14/274,948, filed on May 12, 2014, now Pat. No. 9,079,912, which is a continuation of application No. 14/020,505, filed on Sep. 6, 2013, now Pat. No. 9,206,187, which is a division of application No. 13/076,220, filed on Mar. 30, 2011, now Pat. No. 8,530,485, which is a continuation of application No. 12/549,170, filed on Aug. 27, 2009, now Pat. No. 8,541,425, which is a continuation of application No. 11/637,545, filed on Dec. 12, 2006, now Pat. No. 7,598,257.

(60) Provisional application No. 60/859,404, filed on Nov. 16, 2006, provisional application No. 60/856,872, filed on Nov. 3, 2006, provisional application No. 60/850,625, filed on Oct. 10, 2006, provisional application No. 60/810,231, filed on Jun. 2, 2006, provisional application No. 60/749,905, filed on Dec. 13, 2005.

(51) Int. Cl.
| | | |
|---|---|---|
| A61K 31/519 | (2006.01) |
| A61P 35/04 | (2006.01) |
| C07D 487/04 | (2006.01) |
| C07D 471/04 | (2006.01) |
| A61K 45/06 | (2006.01) |
| C07D 417/04 | (2006.01) |
| C07B 59/00 | (2006.01) |
| A61K 9/00 | (2006.01) |
| A61K 9/20 | (2006.01) |
| A61K 31/573 | (2006.01) |

(52) U.S. Cl.
CPC .......... *A61K 31/519* (2013.01); *A61K 9/0014* (2013.01); *A61K 9/0053* (2013.01); *A61K 9/20* (2013.01); *A61K 31/573* (2013.01); *A61K 45/06* (2013.01); *A61P 35/04* (2018.01); *C07B 59/002* (2013.01); *C07D 417/04* (2013.01); *C07D 471/04* (2013.01); *C07D 487/04* (2013.01); *C07B 2200/05* (2013.01)

(58) Field of Classification Search
CPC ............................ C07D 487/04; A61K 31/519
USPC ....................................... 544/280; 514/265.1
See application file for complete search history.

(56) References Cited

U.S. PATENT DOCUMENTS

| | | |
|---|---|---|
| 2,985,589 A | 5/1961 | Broughton et al. |
| 3,832,460 A | 8/1974 | Kosti |
| 4,140,755 A | 2/1979 | Sheth |
| 4,402,832 A | 9/1983 | Gerhold |
| 4,498,991 A | 2/1985 | Oroskar |
| 4,512,984 A | 4/1985 | Seufert et al. |
| 4,548,990 A | 10/1985 | Mueller et al. |
| 4,814,477 A | 3/1989 | Wijnberg et al. |
| 5,378,700 A | 1/1995 | Sakuma et al. |
| 5,472,949 A | 12/1995 | Arasaki |
| 5,510,101 A | 4/1996 | Stroppolo |
| 5,521,184 A | 5/1996 | Zimmermann |
| 5,630,943 A | 5/1997 | Grill |
| 5,795,909 A | 8/1998 | Shashoua et al. |
| 5,856,326 A | 1/1999 | Anthony |
| 5,919,779 A | 7/1999 | Proudfoot et al. |
| 6,025,366 A | 2/2000 | Walsh et al. |
| 6,060,038 A | 5/2000 | Burns |
| 6,075,056 A | 6/2000 | Quigley, Jr. et al. |
| 6,136,198 A | 10/2000 | Adam et al. |
| 6,217,895 B1 | 4/2001 | Guo et al. |
| 6,335,342 B1 | 1/2002 | Longo et al. |
| 6,375,839 B1 | 4/2002 | Adam et al. |
| 6,413,419 B1 | 7/2002 | Adam et al. |
| 6,486,322 B1 | 11/2002 | Longo et al. |

(Continued)

FOREIGN PATENT DOCUMENTS

| | | |
|---|---|---|
| CN | 102026999 | 4/2011 |
| CN | 102985417 | 3/2013 |

(Continued)

OTHER PUBLICATIONS

26th Annual JPMorgan Healthcare Conference presentation dated Jan. 8, 2008, 28 pages.

(Continued)

*Primary Examiner* — Susanna Moore
(74) *Attorney, Agent, or Firm* — Fish & Richardson P.C.

(57) ABSTRACT

The present invention provides heteroaryl substituted pyrrolo[2,3-b]pyridines and heteroaryl substituted pyrrolo[2,3-b]pyrimidines that modulate the activity of Janus kinases and are useful in the treatment of diseases related to activity of Janus kinases including, for example, immune-related diseases, skin disorders, myeloid proliferative disorders, cancer, and other diseases.

7 Claims, No Drawings

(56) References Cited

U.S. PATENT DOCUMENTS

| | | |
|---|---|---|
| 6,518,265 B1 | 2/2003 | Kato et al. |
| 6,548,078 B2 | 4/2003 | Guo |
| 6,569,443 B1 | 5/2003 | Dawson |
| 6,579,882 B2 | 6/2003 | Stewart et al. |
| 6,624,138 B1 | 9/2003 | Sung et al. |
| 6,635,762 B1 | 10/2003 | Blumenkopf et al. |
| 6,712,973 B2 | 3/2004 | Adam et al. |
| 6,713,089 B1 | 3/2004 | Bertelsen et al. |
| 6,852,727 B2 | 2/2005 | Goulet et al. |
| 6,953,776 B2 | 10/2005 | Di Napoli |
| 7,005,436 B2 | 2/2006 | Lloyd et al. |
| 7,167,750 B2 | 1/2007 | Knudson et al. |
| 7,265,108 B2 | 9/2007 | Ozaki |
| 7,335,667 B2 | 2/2008 | Rodgers et al. |
| 7,358,255 B2 | 4/2008 | Nakamura |
| 7,517,870 B2 | 4/2009 | Auricchio |
| 7,598,257 B2 | 10/2009 | Rodgers et al. |
| 7,683,171 B2 | 3/2010 | Pitts et al. |
| 7,745,437 B2 | 6/2010 | Ren et al. |
| 7,750,007 B2 | 7/2010 | Bearss et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,440,679 B2 | 5/2013 | McAllister |
| 8,445,488 B2 | 5/2013 | Rodger et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,637,529 B2 | 1/2014 | Woller |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 8,987,442 B2 | 3/2015 | Tung et al. |
| 8,987,443 B2 | 3/2015 | Liu |
| 8,993,582 B2 | 3/2015 | Zhou et al. |
| 9,000,161 B2 | 4/2015 | Zhou et al. |
| 9,023,840 B2 | 5/2015 | Yao et al. |
| 9,034,884 B2 | 5/2015 | Rodgers et al. |
| 9,079,912 B2 | 7/2015 | Rodgers et al. |
| 9,090,611 B2 | 7/2015 | Rodgers et al. |
| 9,181,271 B2 | 11/2015 | Li et al. |
| 9,206,187 B2 | 12/2015 | Rodgers et al. |
| 9,216,984 B2 | 12/2015 | Li |
| 9,221,845 B2 | 12/2015 | Cao |
| 9,290,506 B2 | 3/2016 | Zhou et al. |
| 9,334,274 B2 | 5/2016 | Rodgers |
| 9,359,358 B2 | 6/2016 | Rodgers |
| 9,376,439 B2 | 6/2016 | Rodgers |
| 9,487,521 B2 | 11/2016 | Zhou et al. |
| 9,498,467 B2 | 11/2016 | Leopold et al. |
| 9,464,088 B2 | 12/2016 | Huang |
| 9,611,269 B2 | 4/2017 | Yao et al. |
| 9,623,029 B2 | 4/2017 | Li et al. |
| 9,655,854 B2 | 5/2017 | Yeleswaram |
| 9,974,790 B2 | 5/2018 | Rodgers et al. |
| 9,999,619 B2 | 6/2018 | Huang et al. |
| 2002/0111353 A1 | 8/2002 | Ledeboer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0099204 A1 | 5/2004 | Nestor |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling |
| 2005/0153989 A1 | 7/2005 | Grotzfeld et al. |
| 2006/0004010 A1 | 1/2006 | Habashita et al. |
| 2006/0020011 A1 | 1/2006 | Wu et al. |
| 2006/0079511 A1 | 4/2006 | Liu et al. |
| 2006/0106020 A1 | 5/2006 | Rodgers et al. |
| 2006/0106027 A1 | 5/2006 | Furet et al. |
| 2006/0128803 A1 | 6/2006 | Klimko |
| 2006/0135537 A1 | 6/2006 | Knegtel et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Wang et al. |
| 2007/0225286 A1 | 9/2007 | Ren et al. |
| 2007/0259904 A1 | 11/2007 | Noronha |
| 2008/0021026 A1 | 1/2008 | Borchardt et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088445 A1 | 4/2009 | Ledeboer et al. |
| 2009/0131403 A1 | 5/2009 | Kusuda |
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 | 5/2010 | Friedman et al. |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0224190 A1 | 9/2011 | Huang et al. |
| 2011/0288107 A1 | 11/2011 | Parikh et al. |
| 2012/0014989 A1 | 1/2012 | Rodgers |

(56) References Cited

U.S. PATENT DOCUMENTS

| | | |
|---|---|---|
| 2012/0077798 A1 | 3/2012 | Rodgers et al. |
| 2012/0149681 A1 | 6/2012 | Rodgers |
| 2012/0149682 A1 | 6/2012 | Rodgers et al. |
| 2012/0214825 A1 | 8/2012 | Vannucchi et al. |
| 2012/0225057 A1 | 9/2012 | Flynn |
| 2012/0252779 A1 | 10/2012 | Ramsden |
| 2012/0301464 A1 | 11/2012 | Friedman et al. |
| 2012/0329782 A1 | 12/2012 | Arvanitis et al. |
| 2013/0018034 A1 | 1/2013 | Yao et al. |
| 2013/0040973 A1 | 2/2013 | Vannucchi et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0274257 A1 | 10/2013 | Arvanitis et al. |
| 2013/0296299 A1 | 11/2013 | Rodgers et al. |
| 2014/0004516 A1 | 1/2014 | Sattler et al. |
| 2014/0005166 A1 | 1/2014 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li et al. |
| 2014/0094477 A1 | 4/2014 | Rodgers et al. |
| 2014/0121198 A1 | 5/2014 | Li et al. |
| 2014/0135350 A1 | 5/2014 | Ni et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |
| 2014/0303196 A1 | 10/2014 | Rodgers et al. |
| 2014/0343030 A1 | 11/2014 | Li et al. |
| 2014/0378400 A1 | 12/2014 | Rodgers et al. |
| 2015/0065447 A1 | 3/2015 | Sandor |
| 2015/0065484 A1 | 3/2015 | Yeleswaram et al. |
| 2015/0087632 A1 | 3/2015 | Rodgers et al. |
| 2015/0087662 A1 | 3/2015 | Li et al. |
| 2015/0152117 A1 | 6/2015 | Gibbons |
| 2015/0164900 A1 | 6/2015 | Rodgers et al. |
| 2015/0183805 A1 | 7/2015 | Liu et al. |
| 2015/0225411 A1 | 8/2015 | Yao et al. |
| 2015/0225412 A1 | 8/2015 | Brameld |
| 2015/0238492 A1 | 8/2015 | Rodgers et al. |
| 2015/0246046 A1 | 9/2015 | Vaddi |
| 2015/0250790 A1 | 9/2015 | Parikh et al. |
| 2015/0315185 A1 | 11/2015 | Rodgers et al. |
| 2015/0342952 A1 | 12/2015 | Leopold |
| 2015/0344497 A1 | 12/2015 | Zhou et al. |
| 2016/0000795 A1 | 1/2016 | Scherle |
| 2016/0015695 A1 | 1/2016 | Li et al. |
| 2016/0024109 A1 | 1/2016 | Li |
| 2016/0067253 A1 | 3/2016 | Li et al. |
| 2016/0272648 A1 | 9/2016 | Rodgers et al. |
| 2016/0346286 A1 | 12/2016 | Rodgers et al. |
| 2016/0347734 A1 | 12/2016 | Liu et al. |
| 2017/0015674 A1 | 1/2017 | Zhou et al. |
| 2017/0071947 A1 | 3/2017 | Rodgers et al. |
| 2017/0087158 A1 | 3/2017 | Friedman et al. |
| 2017/0246157 A1 | 8/2017 | Huang et al. |
| 2017/0253598 A1 | 9/2017 | Yao et al. |
| 2017/0319487 A1 | 11/2017 | Yeleswaram et al. |
| 2018/0353499 A1 | 12/2018 | Huang et al. |

FOREIGN PATENT DOCUMENTS

| | | |
|---|---|---|
| DE | 30 36 390 | 5/1982 |
| EA | 201590272 | 5/2015 |
| EP | 0223420 | 5/1987 |
| EP | 0587473 | 3/1994 |
| EP | 0727217 | 8/1996 |
| EP | 0795556 | 9/1997 |
| EP | 1104764 | 6/2001 |
| JP | 07-010876 | 1/1995 |
| JP | 2003-155285 | 5/2003 |
| JP | 2006-502183 | 1/2006 |
| JP | 2006-518341 | 8/2006 |
| JP | 2008-508241 | 3/2008 |
| JP | 2008-545660 | 12/2008 |
| JP | 2009-504619 | 2/2009 |
| JP | 2010-529209 | 8/2010 |
| WO | WO 96/030343 | 10/1996 |
| WO | WO 97/002262 | 1/1997 |
| WO | WO 97/002266 | 1/1997 |
| WO | WO 97/036587 | 10/1997 |
| WO | WO 97/038664 | 10/1997 |
| WO | WO 97/045412 | 12/1997 |
| WO | WO 98/044797 | 10/1998 |
| WO | WO 98/051391 | 11/1998 |
| WO | WO 99/000654 | 1/1999 |
| WO | WO 99/062908 | 12/1999 |
| WO | WO 99/065908 | 12/1999 |
| WO | WO 99/065909 | 12/1999 |
| WO | WO 00/009495 | 2/2000 |
| WO | WO 00/051614 | 9/2000 |
| WO | WO 00/053595 | 9/2000 |
| WO | WO 00/063168 | 10/2000 |
| WO | WO 01/014402 | 3/2001 |
| WO | WO 01/027104 | 4/2001 |
| WO | WO 01/042246 | 6/2001 |
| WO | WO 01/064655 | 9/2001 |
| WO | WO 01/081345 | 11/2001 |
| WO | WO 2001/081346 | 11/2001 |
| WO | WO 01/098344 | 12/2001 |
| WO | WO 02/000196 | 1/2002 |
| WO | WO 02/000661 | 1/2002 |
| WO | WO 02/016370 | 2/2002 |
| WO | WO 02/046184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 2003/000688 | 1/2003 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/092595 | 11/2003 |
| WO | WO 03/099771 | 12/2003 |
| WO | WO 03/099796 | 12/2003 |
| WO | WO 04/003026 | 1/2004 |
| WO | WO 04/005281 | 1/2004 |
| WO | WO 04/005282 | 1/2004 |
| WO | WO 04/026406 | 4/2004 |
| WO | WO 04/041814 | 5/2004 |
| WO | WO 04/046120 | 6/2004 |
| WO | WO 04/047843 | 6/2004 |
| WO | WO 04/056786 | 7/2004 |
| WO | WO 04/072063 | 8/2004 |
| WO | WO 04/080980 | 9/2004 |
| WO | WO 04/092154 | 10/2004 |
| WO | WO 04/099204 | 11/2004 |
| WO | WO 04/099205 | 11/2004 |
| WO | WO 05/005988 | 1/2005 |
| WO | WO 05/013986 | 2/2005 |
| WO | WO 05/020921 | 3/2005 |
| WO | WO 05/026129 | 3/2005 |
| WO | WO 05/028444 | 3/2005 |
| WO | WO 05/049033 | 6/2005 |
| WO | WO 05/051393 | 6/2005 |
| WO | WO 05/060972 | 7/2005 |
| WO | WO 05/061463 | 7/2005 |
| WO | WO 05/062795 | 7/2005 |
| WO | WO 05/089502 | 9/2005 |
| WO | WO 05/095400 | 10/2005 |
| WO | WO 05/105146 | 11/2005 |
| WO | WO 05/105814 | 11/2005 |
| WO | WO 05/105988 | 11/2005 |

(56) References Cited

FOREIGN PATENT DOCUMENTS

| | | |
|---|---|---|
| WO | WO 05/110410 | 11/2005 |
| WO | WO 05/117909 | 12/2005 |
| WO | WO 05/121130 | 12/2005 |
| WO | WO 05/123719 | 12/2005 |
| WO | WO 06/004984 | 1/2006 |
| WO | WO 06/013114 | 2/2006 |
| WO | WO 06/022459 | 3/2006 |
| WO | WO 06/039718 | 4/2006 |
| WO | WO 06/046023 | 5/2006 |
| WO | WO 06/046024 | 5/2006 |
| WO | WO 06/052913 | 5/2006 |
| WO | WO 06/056399 | 6/2006 |
| WO | WO 06/067445 | 6/2006 |
| WO | WO 06/069080 | 6/2006 |
| WO | WO 06/077499 | 7/2006 |
| WO | WO 06/096270 | 9/2006 |
| WO | WO 06/101783 | 9/2006 |
| WO | WO 06/108103 | 10/2006 |
| WO | WO 06/122806 | 11/2006 |
| WO | WO 06/127587 | 11/2006 |
| WO | WO 06/129199 | 12/2006 |
| WO | WO 06/136823 | 12/2006 |
| WO | WO 07/002433 | 1/2007 |
| WO | WO 07/025090 | 3/2007 |
| WO | WO 07/041130 | 4/2007 |
| WO | WO 07/043677 | 4/2007 |
| WO | WO 07/044894 | 4/2007 |
| WO | WO 2007/044050 | 4/2007 |
| WO | WO 07/049041 | 5/2007 |
| WO | WO 07/062459 | 6/2007 |
| WO | WO 07/070514 | 6/2007 |
| WO | WO 07/076423 | 7/2007 |
| WO | WO 07/077949 | 7/2007 |
| WO | WO 07/080766 | 7/2007 |
| WO | WO 07/084557 | 7/2007 |
| WO | WO 07/090141 | 8/2007 |
| WO | WO 07/090748 | 8/2007 |
| WO | WO 07/116313 | 10/2007 |
| WO | WO 07/117494 | 10/2007 |
| WO | WO 07/129195 | 11/2007 |
| WO | WO 07/135461 | 11/2007 |
| WO | WO 07/140222 | 12/2007 |
| WO | WO 08/013925 | 1/2008 |
| WO | WO 08/028937 | 3/2008 |
| WO | WO 08/035376 | 3/2008 |
| WO | WO 08/043031 | 4/2008 |
| WO | WO 08/058126 | 5/2008 |
| WO | WO 08/064157 | 5/2008 |
| WO | WO 08/067119 | 6/2008 |
| WO | WO 08/077712 | 7/2008 |
| WO | WO 08/079291 | 7/2008 |
| WO | WO 08/079292 | 7/2008 |
| WO | WO 08/082198 | 7/2008 |
| WO | WO 08/082839 | 7/2008 |
| WO | WO 08/082840 | 7/2008 |
| WO | WO 08/106692 | 9/2008 |
| WO | WO 08/124323 | 10/2008 |
| WO | WO 08/139161 | 11/2008 |
| WO | WO 08/145681 | 12/2008 |
| WO | WO 08/145688 | 12/2008 |
| WO | WO 08/157207 | 12/2008 |
| WO | WO 08/157208 | 12/2008 |
| WO | WO 09/007839 | 1/2009 |
| WO | WO 09/016460 | 2/2009 |
| WO | WO 09/049028 | 4/2009 |
| WO | WO 09/064486 | 5/2009 |
| WO | WO 09/064835 | 5/2009 |
| WO | WO 09/071577 | 6/2009 |
| WO | WO 09/100130 | 8/2009 |
| WO | WO 09/109576 | 9/2009 |
| WO | WO 09/114512 | 9/2009 |
| WO | WO 09/115572 | 9/2009 |
| WO | WO 09/155156 | 12/2009 |
| WO | WO 09/158687 | 12/2009 |
| WO | WO 10/000978 | 1/2010 |
| WO | WO 10/001169 | 1/2010 |
| WO | WO 10/020905 | 2/2010 |
| WO | WO 10/022076 | 2/2010 |
| WO | WO 10/022081 | 2/2010 |
| WO | WO 10/026121 | 3/2010 |
| WO | WO 10/026122 | 3/2010 |
| WO | WO 10/026124 | 3/2010 |
| WO | WO 10/039939 | 4/2010 |
| WO | WO 10/081692 | 7/2010 |
| WO | WO 10/083283 | 7/2010 |
| WO | WO 10/135621 | 11/2010 |
| WO | WO 10/135650 | 11/2010 |
| WO | WO 11/003418 | 1/2011 |
| WO | WO 11/025685 | 3/2011 |
| WO | WO 11/028685 | 3/2011 |
| WO | WO 11/029802 | 3/2011 |
| WO | WO 11/031554 | 3/2011 |
| WO | WO 11/035900 | 3/2011 |
| WO | WO 11/044481 | 4/2011 |
| WO | WO 11/057784 | 5/2011 |
| WO | WO 11/069141 | 6/2011 |
| WO | WO 2011/066369 | 6/2011 |
| WO | WO 11/112662 | 9/2011 |
| WO | WO 11/130146 | 10/2011 |
| WO | WO 11/144338 | 11/2011 |
| WO | WO 11/146808 | 11/2011 |
| WO | WO 12/003457 | 1/2012 |
| WO | WO 2012/045010 | 4/2012 |
| WO | WO 12/068440 | 5/2012 |
| WO | WO 12/068450 | 5/2012 |
| WO | WO 2012/071612 | 6/2012 |
| WO | WO 12/177606 | 12/2012 |
| WO | WO 13/007765 | 1/2013 |
| WO | WO 13/007768 | 1/2013 |
| WO | WO 13/023119 | 2/2013 |
| WO | WO 13/026025 | 2/2013 |
| WO | WO 13/036611 | 3/2013 |
| WO | WO 13/173720 | 11/2013 |
| WO | WO 2014/016396 | 1/2014 |
| WO | WO 14/071031 | 5/2014 |
| WO | WO 14/138168 | 9/2014 |
| WO | WO 2014/186706 | 11/2014 |
| WO | WO 2015/184087 | 4/2018 |

OTHER PUBLICATIONS

Abe et al., "Effective Methods for Introducing Some Aryl and Heteroaryl Substituent onto 1-Azaazulene Nuclei", Heterocycles, 2005, 66: 229-240.

Abelson et al., "Alternate reference values for tear film break-up time in normal and dry eye populations, Lacrimal Gland, Tear Film, and Dry Eye Syndromes 3 Part B", Adv Exp Med Biol, 2002, 506: 1121-1125.

Abelson et al., "Dry eye syndrome: diagnosis, clinical trials, and pharmaceutical treatment—'improving clinical trials'. Lacrimal Gland, Tear Film, and Dry Eye Syndromes 3 Part B", Adv Exp Med Biol, 2002, 506: 1079-86.

Ahmed et al., "Treatment of Pemphigus Vulgaris with Rituximab and Intravenous Immune Globulin," *The New England Journal of Medicine*, 2006, 1772-1779.

Aho et al., Expression of human pim family genes is selectively up-regulated by cytokines promoting T helper type 1, but not T helper type 2, cell differentiation, Immunology, 2005, 116: 82-88.

Albach et al., "Diagnosis of keratoconjunctivitis sicca in rheumatoid arthritis. The value of various tests", Ophthalmologe, Apr. 1994; 91(2):229-34—in German (with English abstract/summary contained therein).

Anderson et al., "Biochemical characterization of GSK1070916, a potent and selective inhibitor of Aurora B and Aurora C kinases with an extremely long residence time", Biochem. J., 2009, 420(2):259-265.

Anonymous, "Ruxolitinib for Patients with Low or Intermediate-1 Risk Myelodysplastic Syndrome (MDS)," ClinicalTrials.gov archive, Aug. 2013, XP002739581, Retrieved from the Internet: URL: clinicaltrials.gov/archive/NCT01895842/2013_08_19 [retrieved on Apr. 30, 2015], 5 pages.

(56) References Cited

OTHER PUBLICATIONS

Arber et al., "The 2016 revision to the World Health Organization classification of myeloid neoplasms and acute leukemia," Blood, May 2016, 2391-2405.
Bachmann et al., "The serine/threonine kinase Pim-1," The International Journal of Biochemistry and Cell Biology, 2005, 37: 726-730.
Bain et al., "Chronic neutrophilic leukaemia," in: Swerdlow, et al., eds. WHO Classification of Tumors of Haematopoietic and Lymphoid Tissues (ed 4th). Lyon: IARC Press, 2008: 38-39.
Banker et al., "Modern Pharmaceuticals" Third Edition, 1996, 596.
Barabino et al., "Tear film and ocular surface tests in animal models of dry eye; uses and limitations," Experimental Eye Research, 2004, 79: 613-621.
Barr et al., "Corneal scarring in the Collaborative Longitudinal Evaluation of Keratoconus (CLEK) Study: baseline prevalence and repeatability of detection", Cornea, 1999, 18(1):34-46.
Baudouin et al., "Flow cytometry in impression cytology specimens. A new method for evaluation of conjunctival Inflammation," Invest Ophthalmol Vis Sci, 1997, 38: 1458-1464.
Baxter et al., "Acquired mutation of the tyrosine kinase JAK2 in human myeloproliferative disorders," Lancet., 2005, 365:1054-1061.
Baxter et al., "Reductive Aminations of Carbonyl Compounds with Borohydride and Borane Reducing Agents," Organic Reactions, 2002, 1-57.
Baytel et al., "The human Pim-2 proto-oncogene and its testicular expression," Biochimica et Biophysica Acta, 1998, 1442: 274-285.
Beck et al., "Brief Report: Alleviation of Systemic Manifestations of Castleman's Disease by Monoclonal Anti-Interleukin-6 Antibody," N. Engl. J. Med., 1994, 330(9):602-605.
Begley et al., "Use of the dry eye questionnaire to measure symptoms of ocular irritation in patients with aqueous tear deficient dry eye", Cornea, 2002, 21: 664-70.
Bell and Zalay, "Synthesis of Substituted 3-Amino [6, 5-b] triazinoindoles." Journal of Heterocyclic Chemistry, Oct. 1975, 12(5):1001-1004.
Bennett et al., "Proposals for the classification of the myelodysplastic syndromes," British Journal of Haematology, 1982, 51: 189-199.
Berge et al., "Pharmaceutical salts", J. Pharma. Science, 1977, 66(1): 1-19.
Beyer, "Uber die Synthese von 2-Methylmercapto-1,3,4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).
Bhattacharya et al., "Polymorphism in Pharmaceutical Solids," Second Edition, 2009, 192:327-345.
Bhovi et al., "1 -Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, Jul.-Sep. 2004, 14: 15-18.
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blom, "Two-Pump at-Column-Dilution Configuration for Preparative Liquid Chromatography—Mass Spectrometry," J. Comb. Chem., 2002, 4: 295-301.
Blume-Jensen et al, "Oncogenic kinase signaling", Nature, 2001, 411(6835):355-365.
Bock et al. "Managing drug resistance in cancer: lessons from HIV therapy." Nature, Jul. 2012, 12: 494-501.
Bolen, "Nonreceptor tyrosine protein kinases", Oncogene, 1993, 8(8):2025-31.
Bollrath et al., "gp130-Mediated Stat Activation in Enterocytes Regulates Cell Survival and Cell-Cycle Progression during Colitis-Associated Tumorigenesis," Cancer Cell, 2009, 15:91-102.
Bondoux et al., "Palladium-catalyzed C—C coupling: efficient preparation of new 5-thio-B-D-xylopymnosides as oral venous antithrombotic drugs," Tetrahedron Letters, 2009, 50(27): 3872-3876.
Bone et al., "Combined Use of the Jak3 Inhibitor CP-690, 550 with Mycophenolate Mofetil to Prevent Kidney Allograft Rejection in Nonhuman Primates", Transplantation, Dec. 2005, 80(12): 1756-64.
Bosworth, "JAK1/JAK2 Inhibitor Ruxolitinib Is a Rising Start," Clinical Oncology, Apr. 2011, 06:04, 3 pages.
Boudny et al., "JAK/STAT signaling pathways and cancer," Neoplasm, 2002, 49:349-355.
Bourcier et al., "Expression of CD40 and CD40 ligand in the human conjunctival epithelium", Invest Ophthalmol Vis Sci, 2000, 41:120-126.
Bowman et al. "STATs in oncogenesis", Oncogene, 2000, 19:2474-2488.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders", Exp Eye Res, 1998, 67:687-697.
Brignole et al., "Flow cytometric analysis of inflammatory markers in conjunctival epithelial cells of patients with dry eyes," Invest Ophthalmol Vis Sci, 2000, 41:1356-1363.
Brignole et al., "Flow cytometric analysis of inflammatory markers in KCS: 6-month treatment with topical cyclosporin A," Invest Ophthalmol Vis Sci, 2001, 42:90-95.
Brignole et al., "Flow cytometry in conjunctival impression cytology: a new tool for exploring ocular surface pathologies," Exp Eye Res, 2004, 78:473-481.
Bromberg et al., "Inflammation and Cancer: IL-6 and STAT3 Complete the Link," Cancer Cell, 2009, 15:79-80.
Bron et al., "Grading of corneal and conjunctival staining in the context of other dry eye tests", Cornea, 2003, 22(7):640-50.
Bron et al., "Methodologies to Diagnose and Monitor Dry Eye Disease: Report of the Diagnostic Methodology Subcommittee of the International Dry Eye Workshop (2007)", The Ocular Surface, Apr. 2007, 5(2): 108-152.
Brunning et al., "Myelodysplastic syndromes/neoplasms, overview," WHO Classification of Tumours of Haematopoietic and Lymphoid Tissues, 4th edition, 2008, 88-103.
Brunton et al., "Chemotherapy of Neoplastic Diseases," Goodman & Gillman's: The Pharmacological Basis of Therapeutics, 11th edition, 2008, 853-908.
Burger et al., "Gp130 and ras mediated signaling in human plasma cell line IN/a-6: a cytokine-regulated tumor model for plasmacytoma", Hematol J., 2001, 2:42-53.
Burger et al., "Janus kinase inhibitor INCB20 has antiproliferative and apoptotic effects on human myeloma cells in vitro and in vivo", Mol. Cancer Ther., Jan. 2009, 8(1): 26-35.
Campas-Moya, "Ruxolitinib. Tyrosine-protein kinase JAK1/2 inhibitor, treatment of myelofibrosis, treatment of myeloproliferative neoplasms, treatment of psoriasis", Drugs of the Future, Jun. 2010, 35(6):457-465.
Candotti et al., "Molecular aspects of primary immuno-deficiencies: lessons from cytokine and other signaling pathways.", J Clin Invest, May 2002, 109(10): 1261-9.
Candotti et al., "Structural and functional basis for JAK3-deficient severe combined immunodeficiency.", Blood, 1997, 90(10): 3996-4003.
Carey and Sundberg, Advanced Organic Chemistry, Part B: Reactions and Synthesis, 4th ed., Kluwer Academic/Plenum Publishers:New York, 2001, 111-119.
Carey and Sundberg, Advanced Organic Chemistry, Part B: Reactions and Synthesis, Oxidations, 4th ed., Kluwer Academic/Plenum Publishers:New York, 2001, 747-757.
Cazzola et al., American Society of Hematology (ASH Education Book), 2011(1), 2011, 264-272.
Cermak et al, "Is complete androgen insensitivity syndrome associated with alterations in the meibomian gland and ocular surface," Cornea, 2003, 22:516-521.

(56) References Cited

OTHER PUBLICATIONS

Cetkovic-Cvrlje et al., "Targeting JAK3 with JANEX-1 for prevention of autoimmune type 1 diabetes in NOD mice.", Clin Immunol, 2003, 106(3): 213-25.
Chalandon, "Targeting mutated protein tyrosine kinases and their signaling pathways in hematologic malignancies," Haematologica, 2005, 90(7):949-68.
Changelian et al., "Prevention of Organ Allograft Rejection by a Specific Janus Kinase 3 Inhibitor", Science, 2003, 302: 875-878.
Chari et al., "Complete Remission Achieved with Single Agent CNTO 328, an Anti-IL-6 Monoclonal Antibody, in Relapsed and Refractory Myeloma," Clinical Lymphoma, Myeloma & Leukemia, 2013, 13(3):333-337.
Chauhan et al, "Autoimmunity in Dry Eye due to resistance of Th17 to Treg Suppression", J. Immunology, 2009, 182(3):1247-52.
Chauhan et al., "A concise review on sustained drug delivery system and its opportunities," International Journal on Pharmtech Research, Mar. 2012, 2: 227-238.
Chemical encyclopedia publication "Soviet Encyclopedia," Moscow, 1988, 1:242-243.
Chen et al., "Blockade of interleukin-6 signaling augments regulatory T-cell reconstitution and attenuates the severity of graft-versus-host disease," Blood, Jul. 2009, 114(4): 891-900.
Chen et al., "Stat3 Activation in Human Endometrial and Cervical Cancer", British Journal of Cancer, 2007, 96: 591-599.
Chen et al., "Induction of myelodysplasia by myeloid-derived suppressor cells," J Clin Invest, Nov. 2013, 123(11): 4595-611.
Cheson et al., "Report of an international working group to standardize response criteria for myelodysplastic syndromes," Blood, Dec. 2000, 96(12): 3671-4.
Chew et al., "An instrument for quantifying meibomian lipid on the lid margin: the Meibometer", Curr Eye Res, 1993, 12:247-254.
Chew et al., "The casual level of meibomianpids lipids in humans", Current Eye Research, 1993, 12:255-259.
Cho et al, "Review of the tear break-up time and a closer look at the tear break-up time of Hong Kong Chinese", Optom Vis Sci, 1993, 70(1):30-8.
Choi Ha-Soon et al., "Design and synthesis of 7H-pyrrolo[2,3-d]pyrimidines as focal adhesion kinase inhibitors. Part 1", Bioorg. & Med. Chem. Lett., 2006, 16(8):2173-2176.
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12)3143-3150.
Chu-Moyer et al., "Preparation of the Four Regioisomeric 2-(Methylthio)oxazolopyridines: Useful Synthons for Elaboration to 2-(Amino substituted)oxazolopyridines", J. Org. Chem., 1995, 60(17):5721-5725.
Cilloni et al., "Emerging drugs for chronic myeloid leukemia", Expert Opinion on Emerging Drugs, Jun. 2010, 15(2): 175-184.
Claessens et al., "In vitro proliferation and differentitation of erythyroid progenitors from patients with myelodysplastic syndromes: evidence for Fas-dependent apoptosis," Blood, Mar. 2002, 1594-1601.
Claridge et al., "Discovery of a novel and potent series of thieno[3,2-b]pyridine-based inhibitors of c-Met and VEGFR2 tyrosine kinases," Bioorganic & Medicinal Chemistry Letters, 2008, 2793-2798.
Clark et al., "Discovery and Development of Janus Kinase (JAK) inhibitors for Inflammatory Diseases," J Med Chem, 2014, A-P.
Clinical Trial NCT01787487 ('487 Trial), dated Feb. 7, 2013, 6 pages.
ClinicalTrials.gov, <http:clinicaltrials.gov/ct2/show/NCT00227591>, downloaded Dec. 6, 2016.
Conklyn et al., "The JAK3 inhibitor CP-0690550 selectively reduces NK and CD8+ cell numbers in cynomolgus monkey blood following chronic oral dosing," Journal of Leukocyte Biology, Dec. 2004, 76: 1248-1255.
Cottet and Schlosser, "Three Chloro(trifluoromethyl)pyridines as Model Substrates for Regioexhaustive Functionalization," Eur J Org Chem, 2004, 18:3793-3798.
Craig et al. "Tear lipid layer structure and stability following expression of the meibomian glands.", Ophthalmic Physiol Opt, 1995, 15(6):569-74.
Daniels et al., "Imatinib mesylate inhibits the profibrogenic activity of TGF-? and prevents bleomycinmediated lung fibrosis," J. Clin. Invest., Nov. 2004, 114(9):1308-1316.
Danjo et al., "Observation of precorneal tear film in patients with Sjogren's syndrome", Acta Ophthalmol Scand, 1995, 73:501-505.
De Paiva et al, "IL-17 disrupts corneal barrier following desiccating stress," Mucosal Immunol., 2009, 2(3):243-53.
De Vos et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 2000, 109(4): 823-8.
Deng Jun et al, "Rh-catalyzed asymmetric hydrogenation of gamma-phthalimido-substituted esters: an efficient enantioselective synthesis of beta-aryl-gamma-amino acids", Org. Lett., 2007, 9(23):4825-4827.
Deuse et al., "Novel Immunosuppression: R348, a JAK3- and Syk-Inhibitor Attenuates Acute Cardiac Allograft Rejection," Transplantation, 2008, 85(6): 885-892.
Divkovic et al., "Hapten-protein binding: from theory to practical application in the in vitro prediction of skin sensitization," Contact Dermatitis, 2005, 189-200.
Doane, "An instrument for in vivo tear film interferometry", Optom Vis Sci, 1989, 66: 383-8.
Doleschall et al., "Thermal and Acid Catalysed Degradations of 3-alkylthio-6,7-dihydro[1.2.4]triazino[1,6-c]quinazolin-5-ium-1-olates," Tetrahedron, 1974, 30:3997-4012.
Dorwald, "Side Reactions in Organic Synthesis: A Guide to Successful Synthesis Design," Wiley-VCH, 2005, Chapter 1, 32 pages.
Dudley et al. "A VEGF/JAK2/STATS axis may partially mediate endothelial cell tolerance to hypoxia", Biochem. J., 2005, 390(Pt 2):427-36.
Eghtedar et al., "Phase 2 study of the JAK kinase inhibitor ruxolitinib in patients with refractory leukemias, including postmyeloproliferative neoplasm acute myeloid leukemia," Blood, May 2012, 119(20): 4614-4618.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl et al., "Therapeutic applications of viscous and injectable poly(ortho esters)," Adv. Drug. Deliv. Rev., 2001, 53:45-73.
Eliason et al., "Staining of the conjunctiva and conjunctival tear film," Br J Ophthalmol, 1990, 75:519-22.
Elliott et al., "WHO-defined chronic neutrophilic leukemia: a long-term analysis of 12 cases and a critical review of the literature," Leukemia, 2005, 19:313-317.
Expert Scientific Group on Phase One Clinical Trials Final Report, Nov. 30, 2006, pp. C1, C35-C38.
Farrell et al., "A classification for dry eyes following comparison of tear thinning time with Schirmer tear test," Acta Ophthalmol (Copenh), 1992, 70(3):357-60.
Farrell et al., "A clinical procedure to predict the value of temporary occlusion therapy in keratoconjunctivitis sicca," Ophthal Physiol Opt, 2003, 23:1-8.
Farris, "Tear osmolarity—a new gold standard?" Adv Exp Med Biol, 1994, 350:495-503.
Fayad et al., "Interleukin-6 and interleukin-10 levels in chronic lymphocytic leukemia: correlation with phenotypic characteristics and outcome," Blood, Jan. 2001, 97(1): 256-263.
Fenaux et al., "A randomized phase 3 study of lenalidomide versus placebo in RBC transfusion-dependent patients with Low-/Intermediate-1-risk myelodysplastic syndromes with del5q," Blood, Oct. 2011, 118(14): 3765-76.
Fenaux et al., "Efficacy of azacitidine compared with that of conventional care regimens in the treatment of higher-risk myelodysplastic syndromes: a randomised, open-label, phase III study," Lancet Oncol, Mar. 2009, 10: 223-32.

(56) References Cited

OTHER PUBLICATIONS

Fiskus et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
Fleischman et al., "The CSF3R T6181 mutation causes a lethal neutrophilic neoplasia in mice that is responsive to therapeutic JAK inhibition," Blood, Nov. 2013, 122: 3628-3632.
Flex et al., "Somatically acquired JAK1 mutations in adult acute lymphoblastic leukemia", J. Exp Med., 2008, 205:751-8.
Fonseca et al., "Interleukin-6 as a key player in systemic inflammation and joint destruction", Autoimmunity Reviews, 2009, 8:538-42.
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Foucar, "Myelodysplastic/Myeloproliferative Neoplasms," Am J Olin Pathol, 2009, 132:281-289.
Fridman et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman et al., "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman et al., "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009 (1 page).
Fridman et al., "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, BOSTON, MA. Nov. 10, 2007. Abstract 1771, poster 285 (1 page).
Fridman et al., "Preclinical evaluation of local JAK1 and JAK2 inhibition in cutaneous inflammation", Journal of Investigative Dermatology, Sep. 2011, 131(9): 1838-1844.
Froberg et al., "Demonstration of clonality in neutrophils using FISH in a case of chronic neutrophilic leukemia," Leukemia, 1998, 12:623-626.
Fujihara et al., "Evaluation of human conjunctival epithelium by a combination of brush cytology and flow cytometry: an approach to the quantitative technique", Diagn Cytopathol, 1997, 17:456-60.
Fujii et al., "Aberrant expression of serine/threonine kinase Pim-3 in hepatocellular carcinoma development and its role in the proliferation of human hepatoma cell lines" International Journal of Cancer, 2005, 114: 209-218.
Fukagawa et al., "Histological evaluation of brush cytology of rabbit conjunctiva", Nippon Ganka Gakkai Zasshi, 1993, 97:1173-8 (contains English abstract within the article).
Gaertner, "Cyclization of 1-Alkylamino-3-halo-2-alkanols to 1-Alkyl-3-azetidinols," J. Org. Chem., 1967, 32: 2972-76.
Gaestel et al., "Targeting innate immunity protein kinase signalling in inflammation," Nat Rev Drug Discov., Jun. 2009, 8(6):480-99.
Ghelardi et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother., 2004, 48:3396-3401.
Gilchrist et al., "5H-2-Pyrindines from 2-Bromocyclopentene-l-calboxaldehyde," Tetrahedron, Jan. 1, 1995, 9119-9126.
Glasson et al., "Differences in clinical parameters and tear film of tolerant and intolerant contact lens wearers," Invest Ophthalmol Vis Sci, 2003, 44:5116-5124.
Glattfeld, "Improvements in the Preparation of DL-Threonic and DL-Erythronic Acids", J. Am. Chem. Soc., 1940, 62:974-977.
Gobbels et al., "Tear secretion in dry eyes as assessed by objective fluorophotometry.," Ger J Ophthalmol, 1992, 1:350-353.
Golding et al., "X-ray and scanning electron microscopic analysis of the structural composition of tear ferns", Cornea, Jan. 1994, 13(1):58-66.
Gomtsyan et al, "Design, synthesis, and structure-activity relationship of 6-alkynylpyrimidines as potent adenosine kinase inhibitors," J. Med. Chem., 2002, 45(17):3639-3648.
Goodman et al., "IL-6 Signaling in Psoriasis Prevents Immune Suppression by Regulatory T Cells," J. Immunol., Sep. 2009, 183: 3170-3176.
Gooseman et al., "The intramolecular b-fluorine . . . ammonium interaction in 4- and 8-membered rings", Chem. Commun, 2006, 30:3190-3192.
Gorre et al., "Clinical Resistance to STI-571 Cancer Therapy Caused by BCR-ABL Gene Mutation or Amplification." Science, 2001, 293:876-880.
Gotlieb, Alice, Presentation at the 2008 American Academy of Dermatology, 66th Annual Meeting, San Antonio, TX. Feb. 1, 2008, symposium-303 (12 pp.).
Goto et al., "Color mapping of tear lipid layer thickness distribution from the image analysis in DR-1 tear lipid layer interference images," ARVO abstract, 2004, 2 pages.
Goto et al., "Computer-synthesis of an interference color chart of human tear lipid layer by a colorimetric approach," Invest Ophthalmol Vis Sci, 2003, 44:4693-7.
Goto et al., "Differentiation of lipid tear deficiency dry eye by kinetic analysis of tear interference images,",Arch Ophthalmol, 2003, 121:173-80.
Goto et al., "Evaluation of the tear film stability after laser in situ keratomileusis using the tear film stability analysis system," Am J Ophthalmol, Jan. 2004, 137(1):116-20.
Goto et al., "Kinetic analysis of tear interference images in aqueous tear deficiency dry eye before and after punctal occlusion," Invest Ophthalmol Vis Sci, 2003, 44:1897-905.
Goto et al., "Tear Film Stability Analysis System: Introducing a new application for videokeratography", Cornea, Nov. 2004, 23(8):S65-S70.
Gottlieb, "Psoriasis: Emerging Therapeutic Strategies," Nat Rev Drug Disc., Jan. 2005, 4:19-34.
Grabbe et al., "Immunoregulatory mechanisms involved in elicitation of allergic—contact hypersensitivity," Immunol Today, Jan. 1998, 19(1):37-44 (only 1 page provide and marked "best available copy").
Greenberg, "The Role of Hemopoietic Growth Factors in the Treatment of Myelodysplastic Syndromes," International Journal of Pediatric Hematology/Oncology, 1997, 4(3): 231-238.
Greenberg, "The myelodysplastic syndromes" in Hoffman, et al, eds. Hematology: Basic Principles and Practice (3rd ed.), Churchill Livingston; 2000:1106-1129.
Greene et al., Greene's Protective Groups in Organic Synthesis, 2007, 4th Edition, 54-55.
Gregory et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Grossman et al., "Interleukin 6 is expressed in high levels in psoriatic skin and stimulates proliferation of cultured human keratinocytes," Proc. Natl. Acad., Sci. USA, Aug. 1989, 86: 6367-6371.
Guillon, "Tear film photography and contact lens wear", J Br Contact Lens Assoc, 1982;5:84-7.

(56) References Cited

OTHER PUBLICATIONS

Gura, "Systems for Identifying New Drugs Are Often Faulty," Science, Nov. 1997, 278(5340): 1041-1042.
Gurram et al., "C-C Cross-Coupling Reactions of )6-Alkyl-2-Haloinosine Derivatives and a One-Pot Cross-Coupling/)6-Deprotection Procedure," Chem Asian J., Aug. 2012, 7(8): 1853-1861.
Guschin et al, "A major role for the protein tyrosine kinase JAK1 in the JAK/STAT signal transduction pathway in response to interleukin-6", Embo J 14:1421-1429 (1995).
Hamze' et al., "Synthesis of Various 3-Substituted 1,2,4-Oxadiazole-Containing Chiral β3- and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Harris et al., "Alkyl 4-Chlorobenzoyloxycarbamates as Highly Effective Nitrogen Source Reagents for the Base-Free, Intermolecular Aminohydroxylation Reaction," J. Org. Chem., 2011, 76:358-372.
Harris et al., "World Health Organization classification of neoplastic diseases of the hematopoietic and lymphoid tissues: report of the Clinical Advisory Committee meeting-Airlie House, Virginia, Nov. 1997," J Clin Oncol, 1999, 17:3835-3849.
Heine et al., "The JAK-inhibitor ruxolitinib impairs dendritic cell function in vitro and in vivo," Blood, 2013, 122(7): 1192-1202.
Helal et al., "Stereoselective Synthesis of cis-1,3-Disubstituted Cyclobutyl Kinase Inhibitors," Organic Letters, (2004), 6(11), pp. 1853-1856.
Hernandez et al., "Clinical, hematological and cytogenetic characteristics of atypical chronic myeloid leukemia," Ann. Oncol., Apr. 2000, 11(4): 441-444.
Hickenbottom "Reactions of organic compounds," State Scientific-Technical Publishing Association, Chemical Literature Section, Moscow, 1939, pp. 360-362.
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong et al., "Total Synthesis of Onnamide A", J. Am. Chem. Soc., 113:9693-94 (1991).
Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
Hyung-Bae et al., "CP-690550, a Janus Kinase Inhibitor, Suppresses CD4+ T-Cell-Mediated Acute Graft-Versus-Host Disease by Inhibiting the Interferon-Y Pathway," *Transplantation*, 2010, 90(8):825-835.
Iranpoor, "A Rapid and Facile Conversion of Primary Amides and Aldoximes to Nitriles and Ketoximes to Amides with Triphenylphosphine and N-Chlorosuccinimide," G Syn., 2002, Commun 32:2535-41.
Ishizaki et al., "Pharmacological Properties of Y-27632, a Specific Inhibitor of Rho-Associated Kinases", Molecular Pharmacology, 2000, 57, 976-983.
Itagaki et al, "Expedient Synthesis of Potent Cannabinoid Receptor Agonist (-)-CP55,940", Organic Letters, 2005, 7(19): 4181-4183.
Jädersten et al., "Long-term outcome of treatment of anemia in MDS with erythropoietin and G-CSF," Blood, Aug. 2005, 106(3): 803-11.
James et al., "A unique clonal JAK2 mutation leading to constitutive signalling causes polycythaemia vera", Nature, 434 (7037):1144-8 (2005).
Janes et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Jee et al., "Overview: animal models of osteopenia and osteoporosis", J Musculoskel. Neuron, Interact., 2001, 1(3):193-207.

Jester et al., "In vivo biomicroscopy and photography of meibomian glands in a rabbit model of meibomian gland dysfunction", Invest Ophthalmol Vis Sci, 1982, 22:660-7.
Johnson et al., "The effect of instilled fluorescein solution volume on the values and repeatability of TBUT measurements", Cornea, 2005, 24:811-7.
Kaddis et al., "Second-Line Treatment for Pancreatic Cancer," Journal of the Pancreas, Jul. 2014, XP055147286, Retrieved from the Internet: URL: http://www.serena.unina.it/index.php/jop/article/viewFile/2691/2737 [retrieved on Oct. 17, 2014].
Kaercher, "Ocular symptoms and signs in patients with ectodermal dysplasia syddromes", Graefe's Arch Clin Exp Ophthalmol, 2004, 495-500.
Kamb, "What's wrong with our cancer models?," Nature Reviews, Feb. 2005, 161-165.
Kantarjian et al., "Decitabine improves patient outcomes in myelodysplastic syndromes: results of phase III randomized study," Cancer, Apr. 2006, 106(8): 1794-803.
Kaushansky, "Lineage-Specific Hematopoietic Growth Factors," NEJM, 2006, 354:2034-45.
Kawamura et al., "Molecular cloning of L-JAK, a Janus family protein-tyrosine kinase expressed in natural killer cells and activated leukocytes," Proc Natl Acad Sci USA, 1994, 91(14): 6374-8.
Kharas et al., "ABL Oncogenes and Phosphoinositide 3-Kinase: Mechanism of Activation and Downstream Effectors," Cancer Res., Mar. 2005, 65(6):2047-2053.
Killedar et al., "Early pathogenic events associated with Sjogren's syndrome (SjS)-like disease of the NOD mouse using microarray analysis," Lab Invest, Dec. 2006, 86(12): 1243-1260.
Kim et al., "Zinc-Modified Cyanoborohydride as a Selective Reducing Agent," J. Org. Chem., 1985, 50: 1927-1932.
King-Smith et al., "Three interferometric methods for measuring the thickness of layers of the tear film," Optom Vis Sci, 1999, 76:19-32.
Kiss, "Recent developments on JAK2 inhibitors: A patent review", Expert Opinion on Therapeutic Patents, Apr. 2010, 20(4):471-495.
Kojima et al., "A new noninvasive tear stability analysis system for the assessment of dry eyes", Invest Ophthalmol Vis Sci, 2004, 45(5):1369-74.
Kola, "Can the pharmaceutical industry reduce attrition rates?" Nature Reviews Drug Discovery, 2004, 3:711-715.
Komuro et al., "Assessment of meibomian gland function by a newly developed laser meibometer", Adv Exp Med Biol, 2002, 506:517-520.
Kontzias et al., "Jakinibs. A new class of kinase inhibitors in cancer and autoimmune disease," Curr. Opin. Pharm., 2012, 12: 464-470.
Korb et al., "Increase in tear film lipid layer thickness following treatment of meibomian gland dysfunction", Adv Exp Med Biol, 1994, 350:293-8.
Korb et al., "The effect of two novel lubricant eye drops on tear film lipid layer thickness in subjects with dry eye symptoms", Optom Vis Sci, 2005, 82: 594-601.
Korolev et al., "Pd-EDTA as an efficient catalyst for Suzuki-Miyaura reactions in water", Tet. Lett., 2005, 46: 5751-5754.
Kortylewski et al., "Regulation of the IL-23 and IL-12 balance by Stat3 signaling in the tumor microenvironment", Cancer Cell, 2009, 15:114-123.
Kruh et al., "The complete coding sequence of arg defines the Abelson subfamily of cytoplasmic tyrosine kinases ", Proc. Natl. Acad. Sci., Aug. 1990, 87:5802-5806.
Kubinyi, "QSAR: Hansch Analysis and Related Approaches," Methods and Principles in Medicinal Chemistry, Manhold, R. ed. Weinheim, NY, 1993, 42 pages.
Kudelacz et al. "The JAK-3 inhibitor CP-690550 is a potent anti-inflammatory agent in a murine model of pulmonary eosinophilia", European Journal of Pharmacology, 2008, 582: 154-161.
Kumar, "Kinase drug discovery approaches in chronic myeloproliferative disorders", Oncogene, Jun. 2009, 28(24): 2305-23.
Kuo et al., "Pd-EDTA as an efficient catalyst for Suzuki-Miyaura reactions in water", Chem Commun, 2007, 301-3.
Kuppens et al., "Basal tear turnover and topical timolol in glaucoma patients and healthy controls by Fluorophotometry", Invest Ophthalmol Vis Sci, 1992, 33:3442-3448.

(56) References Cited

OTHER PUBLICATIONS

Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Kuster, "Kinase Inhibitors," Methods and Protocols, 2012, 46 pages.
Lai et al., "Mechanistic Study on the Inactivation of General Acyl-CoA Dehydrogenase by a Metabolite of Hypoglycin A," J. Am. Chem. Soc., 1991, 113: 7388-7397.
Lam et al, "Tear Cytokine Profiles in Dysfunctional Tear Syndrome", Am J Ophthalmol., 2009, 147(2):198-205.
Larock, "Comprehensive Organic Transformations", Wiley-VCH, 2nd Ed. (1999) pp. 1949-1950, 1958-1959, 1976, and 1983-1985.
Larson, "Myelodysplasia: when to treat and how," Best Pract Res Clin Haematol, 2006, 19(2): 293-300.
Lasho et al., "Chronic neutrophilic leukemia with concurrent CSF3R and SETBP1 mutations: single colony clonality studies, in vitro sensitivity to JAK inhibitors and lack of treatment response to ruxolitnib," Leukemia, 2014, 3 pages.
Chan, "Skin inflammatory disorders," In in Vivo Models of Inflammation, 2006, 85-120.
Leaf, "Why are we losing the war on cancer (and how to win it)," Clifton, Health Administrator vol. XVII, 2005, 1:172-183.
Lemp "Report of National Eye Institute/Industry Workshop on clinical trials in dry eyes," CLAO J, 1995, 21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Levine et al., "Activating mutation in the tyrosine kinase JAK2 in polycythemia vera, essential thrombocythemia, and myeloid metaplasia with myelofibrosis", Cancer Cell, 2005, 7:387-397.
Levitzki, "Tyrosine kinases as targets for cancer therapy", Eur. J. Cancer, 2002, 38(suppl. 5):S11-S18.
Levy et al. "INCB018424 A Selective Janus Kinase 1/2 Inhibitor" Presentation at the 50th American Society of Hematology Annual Meeting (ASH), Dec. 8, 2008, 27 pages.
Li et al., "Pim-3, a proto-oncogene with serine/threonine kinase activity, is aberrantly expressed in human pancreatic cancer and phosphorylates Bad-mediated apoptosis in human pancreatic cell lines," Cancer Research, 2006, 66(13): 6741-7.
Li et al., "The synthesis and the antitumor activity of 5,7-disubstituted pyrazolo [1,5-a] pyrimidines," Chinese J Med Chem., Feb. 28, 2007, 17(1):18-22.
Liesveld and Lichtman, Chapter 88. "Myelodysplastic Syndromes (Clonal Cytopenias and Oligoblastic Myelogenous Leukemia)", in Prchal et al, eds. Williams Hematology. 8th ed., New York: McGraw-Hill; 2010.
Lima and Barreiro, "Bioisosterism: a useful strategy for molecular modification and drug design," Curr Med Chem., 2005, 12(1):23-49.
Lin et al., "Enantioselective synthesis of Janus kinase inhibitor INCB018424 via an organocatalytic aza-Michael reaction," Organic Letters, 2009, 11(9): 1999-2002.
Lin, "Constitutive Activation of JAK3/STAT3 in Colon Carcinoma Tumors and Cell Lines," Am J Pathol., 2005, 167(4):969-80.
Ling et al., "Knockdown of STAT3 Expression by RNA Interference Inhibits the Induction of Breast Tumors in Immunocompetent Mice," Cancer Res, Apr. 2005 65:2532.
List et al., "Efficacy of lenalidomide in myelodysplastic syndromes," N Engl J Med, Feb. 2005, 352(6): 549-57.
Liu et al., "Combined Inhibition of Janus Kinase 1/2 for the Treatment of JAK2V617F-Driven Neoplasms: Selective Effects on Mutant Cells and Improvements in Measures of Disease Severity," Clin Cancer Res, 2009, 15(22):6891-6900.
Lübbert et al., "Cytogenic responses in high-risk myelodysplastic syndrome following low-dose treatment with the DNA methylation inhibitor 5-aza-2'-deoxycytidine," Br J Haematol, Aug. 2001, 114(2): 349-57.
Lübbert et al., "Low-dose decitabine versus best supportive care in elderly patients with intermediate- or high-risk myelodysplastic syndrome (MDS) ineligible for intensive chemotherapy: final results of the randomized phase III study of the European Organisation for Research and Treatment of Cancer Leukemia Group and the German MDS Study Group," J Clin Oncol, May 2011, 29(15): 1987-96.
Lucet et al., "The structural basis of Janus kinas 2 inhibition by a potent and specific pan-Janus kinase inhibitor," Blood, 2006, 107(1):176-183.
Macchi et al., "Mutations of Jak-3 gene in patients with autosomal severe combined immune deficiency (SCID)", Nature, 1995, 377:65-8.
Madden et al., "Comparative study of two non-invasive tear film stability techniques," Curr Eye Res, 1994, 13(4):263-9.
Madhusudan et al., "Tyrosine kinase inhibitors in cancer therapy," Clin Biochem., 2004, 37(7):618-35.
Maffioli et al., "Mild and Reversible Dehydration of Primary Amides with PdC12 in Aqueous Acetonitrile", Organic Letters, 2005, 7(23): 5237-39.
Main et al, "High throughput synthesis of diverse 2,5-disubstituted indoles using titanium carbenoids bearing boronate functionality", Tetrahedron, 2007, 64(5):901-914.
Mainstone et al., "Tear meniscus measurement in the diagnosis of dry eye", Curr Eye Res, 1996, 15:653-661.
Mancini et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Mandal, "Cancer Classification," 2014. Available from: <http://www.news-medical.net/health/Cancer-Classification.aspx, 6 pages.
Manjula et al., "Rapid Method of Converting Primary Amides to Nitriles and Nitriles to Primary Amides by ZnC12 using Microwaves under Different Reaction Conditions", Syn. Commun, 2007, 37:1545-50.
Manning et al., "The Protein Kinase Complement of the Human Genome," Science, 2002, 298(5600):1912-16 and 1933-34.
Mao et al., "Advances in research of tyrosine kinases inhibitor of vascular endothelial growth factor receptor," Chinese J New Drugs, Dec. 31, 2008, 17(7):544-550.
March, Jerry, Advanced Organic Chemistry: Reactions, Mechanisms, and Structure, 3rd ed., John Wiley & Sons:New York, pp. 845-855 (1985).
Marelli et al., "Tumor targeting via integrin ligands," Frontiers in Oncology, 2013, 1-12.
Marquardt et al., "Modification of tear film break-up time test for increased reliability" in Holly ed. The Preocular Tear Film in Health, Disease and Contact Lens Wear. Lubbock, Texas: Dry Eye Institute, 1986:57-63.
Maruyama et al., "Effect of environmental conditions on tear dynamics in soft contact lens wearers," Invest Ophthalmol Vis Sci, 2004, 45(8):2563-8.
Mascarenhas et al., "Ruxolitinib: The First FDA Approvided Therapy for the Treatment of Myelofibrosis," Clinical Cancer Research, Jun. 2012, 18(11): 3008-3014.
Matano et al., "Deletion of the long arm of chormosome 20 in a patient with chronic neutrophilic leukemia: cytogenetic findings in chronic neutrophilic leukemia," Am. J. Hematol., Jan. 1997, 54(1): 72-5.
Mathers et al., "Assessment of the tear film with tandem scanning confocal microscopy", Cornea, 1997;16:162-8.
Mathers et al., "Tear film changes associated with normal aging", Cornea, 1996; 15:229-334.
Mathers et al., "Tear flow and evaporation in patients with and without dry eye", Ophthalmology, 1996, 103:664-669.

(56) References Cited

OTHER PUBLICATIONS

Mathers et al., "Video imaging of the meibomian gland", Arch Ophthalmol, 1994, 112:448-9.
Mathers, "Evaporation from the ocular surface", Exp Eye Res, 2004, 78:389-394.
Maxson et al., "Oncogenic CSF3R Mutations in Chronic Neutrophilic Leukemia and Atypical CML," N. Engl. J. Med., 2013, 368(19):1781-1790.
Mayo Clinic. Available at: < http://www.mayoclinic.com/health/pancreatic-cancer/DS00357 >. 2 pages, retrieved from the Internet Apr. 3, 2013.
Mayo Clinic. Available at: < http://www.mayoclinic.com/health/prostate-cancer-prevention/MC00027 >. 3 pages, retrieved from the Internet Apr. 3, 2013.
Mayo Clinic. Available at: <http://www.mayoclinic.com/health/crohns-disease/DS00104/dsection=treatments-and-drugs> 6 pages, retrieved from the Internet May 27, 2013.
Mayo Clinic. Available at: <http://www.mayoclinic.com/health/multiple-sclerosis/DS00188/dsection=treatments-and-drugs>. 3 pages, retrieved from the Internet May 27, 2013.
Mayo Clinic. Available at: <http://www.mayoclinic.com/health/myasthenia-gravis/DS00375> 2 pages, retrieved from the Internet May 27, 2013.
Mayo Clinic. Available at: <http://www.mayoclinic.com/health/rheumatoid-arthritis/DS00020/dsection=treatments-and-drugs> 3 pages, retrieved from the Internet Jun. 26, 2013.
Mayo Clinic. Available at: <http://www.mayoclinic.org/diseases-conditions/type-1-diabetes/basics/prevention> 2014, 19 pages.
McMillan, "The systemic inflammation-based Glasgow Prognostic Score: a decade of experience in patients with cancer," Cancer Treat Rev, Aug. 2013, 39(5): 534-40.
McNamara et al., "Fluorometry in contact lens research: The next step," Optom Vis Sci, 1998, 75:316-322.
MD Anderson Cancer Center. "Leukemia Prevention and Screening," 2014, 2 pages.
MD Anderson Cancer Center. "Myeloproliferative Disease Prevention and Screening," 2014, 2 pages.
Mengher et al., "Non-invasive tear film break-up time: sensitivity and specificity", Acta Ophthalmol (Copenh), 1986, 64(4):441-4.
Mesa et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa et al., "Emerging drugs for the therapy of primary and post essential thrombocythemia, post polycythemia vera myelofibrosis", Expert Opinion on Emerging Drugs England, 2009, 14(3): 471-479.
Mesa et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, Nov. 2011, 117(21): 4869-4877.
Meydan et al., "Inhibition of acute lymphoblastic leukaemia by a Jak-2 inhibitor", Nature, Feb. 1996, 379(6566):645-8.
Meyer et al., "Anti-inflammatory activity and neutrophil reductions mediated by the JAK1/JAK3 inhibitor, CP-690,550, in rat adjuvant-induced arthritis," Journal of Inflammation, 2010, 1-12.
Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).
Milici et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi et al., "Human Tyrosine Kinase 2 Deficiency Reveals Its Requisite Roles in Multiple Cytokine Signals Involved in Innate and Acquired Immunity", Immunity, 2006, 25:745-55.

Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol., Sep. 2010, 85(3):192-9 Epub Jun. 2, 2010.
Mishima et al., "Determination of tear volume and tear flow", Invest Ophthalmol, 1966, 5:264-276.
Mishima, "Some physiological aspects of the precorneal tear film", Arch Ophthalmol, 1965, 73:233-241.
Mitsunobu, "The Use of Diethyl Azodicarboxylate and Triphenylphosphine in Synthesis and Transformation of Natural Products." Synthesis, 1981, (1): 1-28.
Miyata et al., "Stereospecific nucleophilic addition reactions to olefins.", J. Org. Chem., 1991, 56:6556-6564.
Miyaura et al., "Palladium-Catalyzed Cross-Coupling Reactions of Organoboron Compounds," Chem. Rev., 1995, 95: 2457-2483.
Miyoshi et al., "Interleukin-8 concentrations in conjunctival epithelium brush cytology samples correlate with neutrophil, eosinophil infiltration, and corneal damage", Cornea, 2001, 20:743-7.
Molldrem et al., "Antithymocyte globulin for patients with myelodysplastic syndrome," Br J Haematol, Dec. 1997, 99(3): 699-705.
Moreland et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).
Moriarty et al., "The synthesis and SAR of 2-amino-pyrrolo[2,3-d]pyrimidines: A new class of Aurora-A kinase inhibitors", Bioorganic and Medicinal Chemistry Letters, 2006, 16(22), 5778-5783.
Mosby's Dictionary of Medicine, Nursing, & Health Professions, sicca complex, 2009, Elsevier, printed from http://www.credoreference.com/entry/ehsmosbymed/sicca_complex, 2 pages.
Mullighan et al, "JAK mutations in high-risk childhood acute lymphoblastic leukemia", Proc Natl Acad Sci USA, 2009, 106:9414-8.
Mundle et al., "Evidence for Involvement of Tumor Necrosis Factor-α in Apoptotic Death of Bone Marrow Cells in Myelodysplastic Syndromes," Am J Hematol, 1999, 60:36-47.
Naka, "The paradigm of IL-6: from basic science to medicine", Arthritis Res., 2002, 4 Suppl 3:S233-42.
Nakagawara, "Trk receptor tyrosine kinases. A bridge between cancer and neural development." Cancer Letters, 2001, 169:107-114.
Nally et al., "Ocular discomfort and tear film break-up time in dry eye patients: A correlation," Invest Ophthalmol Vis Sci, 2000, 41:4:1436 (Poster Presentation).
Naqvi et al., "A potential role of ruxolitinib in leukemia", Expert Opinion on Investigational Drugs, Aug. 2011, 20(8): 1159-1166.
National Cancer Institute, "FDA Approval for Ruxolitinib Phosphate", http://www.cancer.gov/cancertopics/druginfo/fda-ruxolitinibphosphate posted Nov. 18, 2011 (3 pages).
Naus et al., "6-(Het)aryl-7-Deazapurine Ribonucleosides as Novel Potent Cytostatic Agents", J. Med. Chem., 2010, 53(1):460-470.
Neidle Cancer Drug Design and Discovery, (Elsevier/Academic Press, 2008) 427-431.
Nelson et al., "Tear film osmolality determination: an evaluation of potential errors in measurement," Curr Eye Res, 1986, 5(9):677-81.
Neubauer et al., "Jak2 Deficiency Defines an Essential Developmental Checkpoint in Definitive Hematopoiesis", Cell, 1998, 93(3): 397-409.
Neuner et al., "Increased IL-6 Production by Monocytes and Keratinocytes in Patients with Psoriasis," J. Invest. Dermatol., 1991, 97: 27-33.
Nicholoff et al., "Recent Insights into the immunopathogenesis of psoriasis provide new therapeutic opportunities", J. Clin. Invest., 2004, 113: 1664-1675.
Nichols et al., "The lack of association between signs and symptoms in patients with dry eye disease", Cornea, 2004, 23(8):762-770.
Nichols et al., "The repeatability of clinical measurements of dry eye", Cornea, 2004, 23(3):272-85.
Nishimoto. et. al., "Improvement in Castleman's disease by humanized anti-interleukin-6 receptor antibody theraphy," Blood, 2000, 95(1):56-61.

(56) References Cited

OTHER PUBLICATIONS

Nishio et al., "Tyrosine kinase-dependent modulation by interferon-α of the ATP-sensitive K+ current in rabbit ventricular myocytes", FEBS Letters, 1999, 445: 87-91.
Nitta et al., "Peptide-Titanium Complex as Catalyst for Asymmetric Addition of Hydrogen Cyanide to Aldehyde", J. Am. Chem. Soc., 1992, 114: 7969-75.
Norman, "Selective JAK1 inhibitor and selective Tyk2 inhibitor patents," Expert Opinion, Informa Healthcare. 2012, available at: <http://informahealthcare.com/doi/pdfplus/10.1517/13543776.2012.723693>.
Norm, "Quantitative tear ferning. Clinical investigations", Acta Ophthalmol (Copenh), 1994, 72(3):369-72.
Oguz et al., "The height and radius of the tear meniscus and methods for examining these parameters", Cornea, 2000, 19:497-500.
Ortmann et al., "Janus kinases and signal transducers and activators of transcription: their roles in cytokine signaling, development and immunoregulation," Arthritis Res, 2000, 2(1): 16-32.
Ostojic et al., "Ruxolitinib: a new JAK1/2 inhibitor that offers promising options for treatment of myelofibrosis," Future Oncology, 2011, 7(9): 1035-1043.
Ostojic et al., "Ruxolitinib for the treatment of myelofibrosis," Drugs of Today, Nov. 2011, 47(11): 817-827.
Ousler et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer et al., "Multiple roles of ephrins in morphogenesis, neuronal networking, and brain function," Genes & Dev., 2003, 17:1429-1450.
Panteli et al., "Serum interleukin (IL)-1, IL-2, sIL-2Ra, IL-6 and thrombopoietin levels in patients with chronic myeloproliferative diseases," British Journal of Haematology, 2005, 130: 709-715.
Pardanani et al., "CSF3R T618I is a highly prevalent and specific mutation in chronic neutrophilic leukemia," Leukemia, 2013, 27: 1870-1873.
Pardanani, "JAK2 inhibitor therapy in myeloproliferative disorders: rationale, preclinical studies and ongoing clinical trials JAK2 inhibitor therapy in MPD," Leukemia, Jan. 2008, 22: 23-30.
Parganas et al., "Jak2 is Essential for Signaling through a Variety of Cytokine Receptors," Cell, 1998, 93(3): 385-95.
Park et al., "Homogeneous Proximity Tyrosine Kinase Assays: Scintillation Proximity Assay versus Homogeneous Time-Resolved Fluorescence", Analytical Biochemistry, 1999, 269: 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Patani et al., "Bioisosterism: A Rational Approach in Drug Design", Chem. Rev., 1996, 96: 3147-3176.
Patel et al., Am. J. PharmTech. Res., 2012 2(2).
Patrick, "An Introduction to medicinal chemistry" Oxford University Press Inc., New York, 1995 (31 pages) (cited in Opposition from India dated Nov. 12, 2012.
Pearce et al., "An improved fluorophotometric method for tear turnover assessment", Optom Vis Sci, 2001, 78(1):30-36.
Pearce et al., "Spatial location studies on the chemical composition of human tear ferns", Ophthalmic Physiol Opt, 2000, 20(4):306-13.
Pedranzini et al., "Pyridone 6, A Pan-Janus-Activated Kinase Inhibitor, Induces Growth Inhibition of Multiple Myeloma Cells," Cancer Res., 2006, 66(19):9714-9721.
Pensyl et al., "The repeatability of tear mucus ferning grading", Optom Vis Sci, 1998, 75(8):600-4.
Pernis et al., "JAK-STAT signaling in asthma." J Clin Invest, 2002, 109(10): 1279-83.
Peters et al., "Functional Significance of Tie2 Signaling in the Adult Vasculature", 2004, © The Endocrine Society (21 pages).

Pflugfelder et al., "Evaluation of subjective assessments and objective diagnostic tests for diagnosing tear-film disorders known to cause ocular irritation," Cornea, 1998, 17(1):38-56.
Pillonel "Evaluation of phenylaminopyrimidines as antifungal protein kinase inhibitors," Pest Jun. 2005, 61: 1069-1076.
Pirard et al., "Classification of Kinase Inhibitors Using BCUT Descriptors", J. Chem. Inf. Comput. Sci., 2000, 40: 1431-1440.
Pisella et al., "Conjunctival proinflammatory and proapoptotic effects of latanoprost, preserved timolol and unpreserved timolol: an ex vivo and in vitro study." Invest Ophthalmol Vis Sci, 2004, 45:1360-1368.
Pisella et al., "Flow cytometric analysis of conjunctival epithelium in ocular rosacea and keratoconjunctivitis sicca," Ophthalmology, 2000, 107:1841-1849.
Portnaya et. al., "Azomethine dyes. IV. Indoaniline dyes derived from heterocyclic N-substituted 1-hydroxy-2-naphthamide," Ts Vses Nauchn Issled Kinofotoinst, 1960, Issue 40, 106-8 (with English abstract 20 pages total).
Press Release dated Sep. 18, 2008: "Incyte's Topical JAK Inhibitor Demonstrates Positive Proof-of-Concept Results in Patients with Mild to Moderate Psoriasis" (4 pages).
Prezent et al., "Boron chelates as intermediates in the synthesis of new functionalized pyridines and pyrimidines from a, a-dioxoketene anlinals", Proceedings of the International Conference on the Chemistry of Boron, vol. 11 (2003) (abstract only—1 page).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Punwani, Naresh, et al. "Efficacy and safety of topical INCB018424, a selective Janus kinase 1 & 2 (JAK1&2) inhibitor in psoriasis." Journal of the American Academy of Dermatology. vol. 60. No. 3. 360 Park Avenue South, New York, NY 10010-1710 USA: Mosby-Elsevier, 2009.
Quesada et al, "One-pot conversion of activated alcohols into 1,1-dibromoalkenes and terminal alkynes using tandem oxidation processes with manganese dioxide", Tetrahedron, 2006, 62: 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Ravin, "Preformulation", Remington's Pharmaceutical Sciences, 17th ed., Mack Publishing Company, Easton, PA., 1985, Chapter 76, 1409-1423.
Raza et al., "Novel insights into the biology of myelodyplastic syndromes: excessive apoptosis and the role of cytokines," Int J Hematol, 1996, 63:265-278.
Raza et al., "The Myelodysplastic Syndromes in 1996: Complex Stem Cell Disorders Confounded by Dual Actions of Cytokines," Leuk Res, 1996, 20:881-890.
Raza et al., "Apoptosis in bone marrow biopsy samples involving stromal and hematopoietic cells in 50 patients with myelodysplastic syndromes," Blood, Jul. 1995, 86(1): 268-76.
Raza et al., "Phase 2 Study of lenalidomide in transfusion-dependent, low-risk, and intermediate-1 risk myelodysplastic syndromes with karyotypes other than deletion 5q," Blood, Jan. 2008, 111(1): 86-93.
Ren et al., "Compounds and Compositions as Protein Kinase Inhibitors," U.S. Appl. No. 60/578,491, filed Jun. 10, 2004 (56 pages).
Reuters, "Jakafi (ruxolitinib) improved advanced pancreas cancer outcomes in mid-stage trial," Internet Citation, Aug. 21, 2013, pp. 1-2, XP002717211, Retrieved from Internet: URL: http://www.curetoday.com/index.cfm/fuseaction/news.showNewsArticle/id/13/news_id/3785 [retrieved on Nov. 29, 2013].
Riese et al., "Inhibition of JAK kinases in patients with rheumatoid arthritis: scientific rationale and clinical outcomes," Best Practice & Research Clinical Rheumatology, 2010, 513-526.

(56) References Cited

OTHER PUBLICATIONS

Roberts et al., "Trends in the Risks and Benefits to Patients With Cancer Participating in Phase 1 Clinical Trials," JAMA, 2004, 292(17):2130-2140.
Robin et al., "In vivo transillumination biomicroscopy and photography of meibomian gland dysfunction," Ophthalmology, 1985, 92:1423-6.
Rodig et al., "Disruption of the Jak1 gene demonstrates obligatory and nonredundant roles of the Jaks in cytokine-induced biologic responses." Cell, 1998, 93(3): 373-83.
Rolando et al., "Tear mucus crystallization in children with cystic fibrosis", Ophthalmologica, 1988, 197(4):202-6.
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbock (Texas, USA), Dry Eye Institute, 1986, 203-210.
Rolando et al., "The effect of hyperosmolarity on tear mucus ferning", Fortschr Ophthalmol, 1986, 83:644-646.
Rolando et al., "The Ocular Surface and Tear Film and Their Dysfunction in Dry Eye Disease," Survey of Ophthalmology, Mar. 2001, 45(Supplement 2): S203-S210.
Rolando, "Tear mucus ferning test in normal and keratoconjunctivitis sicca eyes," Chibret Int J Ophthalmol, 1984, 2(4):32-41.
Rollison et al., "Epidemiology of myelodysplastic syndromes and chronic myeloproliferative disorders in the United States, 2001-2004, using data from the NAACCR and SEER programs," Blood, Jul. 2008, 112(1): 45-52.
Roudebush et al., "Pharmacologic manipulation of a four day marine delayed type hyper sensitivity model", Agents Actions, 1993, 38(1-2):116-21.
Rousvoal et al. "Janus kinase 3 inhibition with CP-690,550 prevents allograft vasculopathy", Transpl Int., 2006, 19(12):1014-21.
Saemann et al., "Suppression of early T-cell-receptor-triggered cellular activation by the Janus kinase 3 inhibitor MHI-P-154," Transplantation, 2003, 75(11): 1864-1872.
Saemann et al., "Prevention of CD40-triggered dendritic cell maturation and induction of T-cell hyporeactivity by targeting of Janus kinase 3," Am J Transplant, 2003, 3(11): 1341-9.
Saettone and Salminen, "Ocular inserts for topical delivery", Advanced Drug Delivery Reviews, 1995, 16:95-106.
Saettone et al., "Ocular inserts for topical delivery," Advanced Drug Delivery Reviews, 1995, 16: 95-106.
Samanta et al., "Janus kinase 2: a critical target in chronic myelogenous leukemia," Cancer Res., Jul. 2006, 66(13):6468-72.
Santini et al., "Hepcidin Levels and Their Determinants in Different Types of Myelodysplastic Syndromes," PLoS One, 2011, 6(8): e23109, pp. 1-8.
Namour et al., "Once-daily High Dose Regimens of GLPG0634 in Healthy Volunteers are Safe and Provide Continuous Inhibition of JAK1 but not JAK2," ACR/ARHP Annual Meeting 12, Nov. 9-14, 2012, Abstract No. 1331.
Sawada et al, "Increased Lipophilicity and Subsequent Cell Partitioning Decrease Passive Transcellular Diffusion of Novel, Highly Lipophilic Antioxidants", The Journal of Pharmacology and Experimental Therapeutics, 1999, 288(3):1317-1326, p. 1321, compound 26.
Schiffer, "Clinical issues in the management of patients with myelodysplasia," Hematology Am Soc Hematol Educ Program, 2006, 205-10.
Schiffer, "Myelodysplasia: the good, the fair and the ugly," Best Pract Res Clin Haematol, Mar. 2007, 20(1): 49-55.
Schindler et al., "Hormones and Signaling: Cytokines and STAT Signaling," Adv Pharmacol., 2000, 47:113-74.
Schmidt et al., "Rituximab in autoimmune bullous diseases: mixed responses and adverse effects," British Journal of Dermatology, 2007, 352-356.
Schrader et al., "Animal Models of Dry Eye," Developmental Ophthalmology, 2008, 41: 298-312.
Scott et al., "Jaks, STATs, Cytokines, and Sepsis." Clin Diagn Lab Immunol, 2002, 9(6): 1153-9.
Scott et al., (British Journal of Haematology), 148(6): 944-947, Mar. 2010.
Seefeld et al, "Discovery of 5-pyrrolopyridinyl-2-thiophenecarboxamides as potent AKT kinase," Bioorganic & Medicinal Chemistry Letters, 2009, 19(8):2244-2248.
Seela et al., "Synthesis of Pyrrolo[2,3-d]pyrimidine 2', 3'-Dideoxyribenucleosides Related to 2',3'—Dideoxyadenosine and 2',3'-Dideoxgtuanosine and Inhibitory Activity of 5'-Triphosphates on HIV-1 Reverse Transcriptase", Helvetica Chimica Acta, 1991, 74(3), 554-64.
Seki, "STAT3 and MAPK in human lung cancer tissues and suppression of oncogenic growth by JAB and dominant negative STAT3", Int J Oncol., 2004, 24(4):931-4.
Seto et al., "Enhanced Th2 cell-mediated allergic inflammation in Tyk2-deficient mice." J Immunol, 2003, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, Aug. 2002, 2:117-125.
Shi et al., "The pharmacokinetics, pharmacodynamics, and safety of orally dosed INCB018424 phosphate in healthy volunteers", Journal of Clinical Pharmacology, Dec. 2011, 51(12): 1644-1654.
Shimazaki et al., "Meibomian gland dysfunction in patients with Sjogren syndrome", Ophthalmology, 1998, 105(8):1485-8.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Sloand et al., "Factors affecting response and survival in patients with myelodysplasia treated with immunosuppressive therapy," J Clin Oncol, May 2008, 26(15): 2505-11.
Smith et al, "Basic pathogenic mechanisms operating in experimental model acute anterior uveitis," Immunology and Cell Biology, 1998, 76: 497-512.
Smolen et al, "Effect of interleukin-6 receptor inhibition with tocilizumab in patients with rheumatoid arthritis (OPTION study): a double-blind, placebo-controlled, randomized trial", Lancet, 2008, 371:987.
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., "Activity of therapeutic JAK 1/2 blockade in graft-versus-host disease," *Blood*, 2014, 123(24): 3832-3842.
Sriram et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodegeneration", J. Biol. Chem., 2004, 279(19):19936-47.
Staerk et. al., "JAK1 and Tyk2 activation by the homologous polycythemia vera JAK2 V617F mutation: cross-talk with IGF1 receptor", J Biol Chem., 2005, 280:41893-41899.
Steensma et al., "The JAK2 V617F activating tyrosine kinase mutation is an infrequent event in both "atypical" myeloproliferative disorders and mylodysplastic syndromes", Blood, Aug. 2005, 106(4): 1207-9.
Stirewalt et al., "Predictors of relapse and overall survival in Philadelphia chromosome-positive acute lymphoblastic leukemia after transplantation", Biol Blood Marrow Transplant., Mar. 2003, 9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).

(56) References Cited

OTHER PUBLICATIONS

STN Search, Oct. 20, 2009 (601 pages).
STN Search, Sep. 20, 2009 (864 pages).
Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Sullivan et al., "4th International Conference on the Lacrimal Gland, Tear Film & Ocular Surface and Dry Eye Syndromes, Nov. 20, 2004" (2 pages).
Symington et al., "The relationship of serum IL-6 levels to acute graft-versus-host disease and hepatorenal disease after human bone marrow transplantation," Transplantation, 1992, 54(3): 457-462 (Abstract only).
Takahashi et al., "Solvent-Free Reaction Using Phosphonium Salts: Chlorination of Hydroxyheteroaromatics and dehydration of Primary Amides", Heterocycles, 2006, 68: 1973-1979.
Takano et al., "Inflammatory cells in brush cytology samples correlate with the severity of corneal lesions in atopic keratoconjunctivitis", Br J Ophthalmol, 2004, 88:1504-5.
Takemoto et al., "Proliferation of adult T cell leukemia/lymphoma cells is associated with the constitutive activation of JAK/STAT proteins." Proc Natl Acad Sci USA, 1997, 94(25): 13897-902.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Tan et al, "Racemization processes at a quaternary carbon center in the context of the asymmetric Michael reaction", Tetrahedron Lett., 2001, 42(30):5021-5023.
Tang et al., "Knowledge-based design of 7-azaindoles as selective B-Raf inhibitors", Bioorganic & Medicinal Chemistry Letters, 2008, 18(16):4610-4614.
Tasian et al., "Understanding the biology of CRLF2-overexpressing acute lymphoblastic leukemia", Critical Reviews in Oncogenesis, 2011, 16(1): 13-24.
Tefferi et al. "The Clinical Phenotype of Myelofibrosis Encompasses a Chronic Inflammatory State that is Favorably Altered by INCB018424, a Selective Inhibitor of JAK1/2" Poster #2804 at the American Society of Hematology Annual Meeting (ASH), Dec. 7, 2008, (18 pages).
Tefferi et al., "Serious adverse events during ruxolitinib treatment discontinuation in patients with myelofibrosis", Mayo Clinic Proceedings, Dec. 2011, 86(12): 1188-1191.
Tefferi, "Primary myelofibrosis: 2012 update on diagnosis, risk stratification, and management," American Journal of Hematology, Dec. 2011, 86(12): 1017-1026.
Textbook of Clinical Trials 264 (D. Machin et al., eds., 2nd ed., 2006).
Thompson et al., "Photochemical Preparation of a Pyridone Containing Tetracycle: A Jak Protein.Kinase Inhibitor", Bioorganic & Medicinal Chemistry Letters, 2002, 12: 1219-1223.
Tiffany et al., Meniscectomy using the Tearscope-plus (ARVO abstract). Invest Ophthalmol Vis Sci, 2001,42: s37 (1 page).
Tiffany, "Refractive index of meibomian and other lipids", Curr Eye Res, 1986, 5:887-9.
Ting et al., "The Synthesis of substituted bipiperidine amide compounds as CCR3 antagonists", Bioorg. Med. Chem. Lett., 2005, 15(5): 1375-1378.
Toyonaga, "Blockade of constitutively activated Janus kinase/signal transducer and activator of transcription-3 pathway inhibits growth of human pancreatic cancer", Cancer Lett., 2003, 201(1):107-16.
Trikha et al., "Targeted anti-interleukin-6 monoclonal antibody therapy for cancer: a review of the rationale and clinical evidence," Clinical Cancer Research, 2003, 9: 4653-4665.
Tsubota et al., "Brush cytology for the evaluation of dry-eye", Nippon Ganka Gakkai Zasshi, 1990, 94:224-30 (English Abstract).
Tsubota et al., "Conjunctival brush cytology", Acta Cytol, 1990, 34(2):233-5.
Tsubota et al., "Detection by brush cytology of mast cells and eosinophils in allergic and vernal conjunctivitis," Cornea, 1991, 10(6):525-31.
Ueda et al., "1,2-Benzisoxazol-3-yl Diphenyl Phosphate: A New, Reactive Activating Agent for the Synthesis of Amides, Esters, and Peptides via Condensation", J. Org. Chem., 1985, 50:760-763.
Vaillant et al., "Turbidity of pulpy fruit juice: A key factor for predicting cross-flow microfiltration performance," J Membrane Sci., 2008, 325:404-412.
Van Best et al., "Measurement of basal tear turnover using a standardized protocol", Graefe's Arch Clin Exp Ophthalmol, 1995, 233:1-7.
Van Bijsterveld, "Diagnostic tests in the sicca syndrome", Arch Ophthalmol, 1969, 82:10-14.
Van Rhee et al., "Anti-Interleukin-6 Monoclonal man's Disease," J. Clin. Oncol., 2010, 28(23):3701-3708.
Vanhoutte, "Selective JAK1 Inhibition in the Treatment of Rheumatoid Arthritis: Proof of Concept with GLPG0634," Arthritis Rheum, 2012, 64.10: S1051-1.
Vannucchi et al., "Inhibitors of PI3K/Akt and/or mTOR Inhibit the Growth of Cells of Myeloproliferative Neoplasms and Synergize with JAK2 Inhibitor and Interferon", Blood, 2011, 118(21): 1638-1639, XP008150742ASH Annual Meeting Abstract 3835 American Society of Hematology.
Vannucchi et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, 2009, 114(22), 2 pages.
Vannucchi et al., "The mTOR Inhibitor, RAD001, Inhibits the Growth of Cells From Patients with Myeloproliferative Neoplasms", Blood: ASH Annual Meeting Abstracts, $51^{st}$ Annual Meeting of the American Society of Hematology, 2009, 114(22), 2 pages.
Vardiman et al., "Atypical chronic myeloid leukaemia, BCR-ABL1 negative," in: Swerdlow, et al., WHO Classification of Tumors of Haematopoietic and Lymphoid Tissues (ed 4th). Lyon: IARC Press; 2008:80-81.
Vardiman et al., "The 2008 revision of the World Health Organization (WHO) Classification of myeloid neoplasms and acute leukemia: rationale and important changes," Blood, 2009, 114:937-951.
Vardiman et al., "The World Health Organization (WHO) classification of the myeloid neoplasms," Blood, 2002, 100:2292-2302.
Vasilevsky et al., "Ethyl Vinyl Ether—an Agent for Protection of the Pyrazole NH-Fragment. A Convenient Method for the Preparation of N-Unsubstituted 6Alkynylpyrazoles", Heterocycles, 2003, 60(4):879-886.
Venugopal et al., "Special clinical concerns/problems in the management of MDS and secondary acute myeloid leukemias," Cancer Treat Res, 2001, 108: 257-65.
Verma et al., "Jak family of kinases in cancer", Cancer and Metastasis Reviews, 2003, 22(4): 423-434, DOI: 10.1023/A:1023805715476.
Verstovsek, "Therapeutic Potential of JAK2 Inhibitors", Hematology Am Soc Hematol Educ Program, 2009:636-42.
Verstovsek, et al., Blood (ASH Annual Meeting Abstracts) 2007 110: Abstract 558.
Verstovsek, et al., Blood (ASH Annual Meeting Abstracts) 2009 114: Abstract 311.
Verstovsek, et al., Blood (ASH Annual Meeting Abstracts) 2010 116: Abstract 313.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).

(56) References Cited

OTHER PUBLICATIONS

Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, Srdan et al., "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424," 50th ASH Annual Meeting and Exposition, Abstract No. 2802 (2008).
Vitali et al. "The European Community Study Group on diagnostic criteria for Sjogren's syndrome. Sensitivity and specificity of tests for ocular and oral involvement in Sjogren's syndrome," Ann Rheum Dis, 1994, 53(10): 637-47.
Wagh et al., "Polymers used in ocular dosage form and drug delivery systems", Asian J. Pharm., Jan. 2008, 12-17.
Wang and Deisboeck, "Mathematical modeling in cancer drug discovery," Drug Discovery Today, 2014, 145-150.
WebMD. "Diabetes Health Center." Available at: <http://diabetes.webmd.com/guide/diabetestreatment_care >. 3 pages, retrieved from the Internet May 28, 2013.
Webster's New World Medical Dictionary, Sjogren's syndrome, 2003, Wiley Publishing, printed fro http://www.credoreference.com/entry/webstermed/sjogren_s_syndrome, 2 pages.
Weiss et al., "Evaluation of a Series of Naphthamides as Potent, Orally Active Vascular Endothelial Growth Factor Receptor-2 Tyrosine Kinase Inhibitors", J. Med Chem., 2008, 51:1668-1680.
Welch et al., "An approach to a more standardized method of evaluating tear film break-up time", Invest Ophthalmol Vis Sci, 2003, 2485/B324 (abstract only—2 pages).
White et al., "Human basic tear fluid osmolality. I. Importance of sample collection strategy", Acta Ophthalmol (Copenh), Aug. 1993, 71(4):524-9.
Wilks, "The JAK kinases. Not just another kinase drug discovery target," Seminars in Cell & Developmental Biology, 2008, 319-328.
Williams and Ibrahim, "Carbodiimide Chemistry: Recent Advances", Chem. Rev., 1981, 81:589-636.
Williams et al., "Dissecting Specificity in the Janus Kinases: The Structures of JAK-Specific Inhibitors Complexed to the JAK1 and JAK2 Protein Tyrosine Kinase Domains," Journal of Molecular Biology, 2009, 219-232.
Williams, et al. "Initial Efficacy of INCB018424, a selective Janus Kinasel& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Winfield, Pharmaceutical Practice, Ophthalmic Products-pH adjustment, Churchill Livingstone, 2004, 264-271.
Wolf et al., "Burger's Medicinal Chemistry and Drug Discovery", 5th Ed. Part I, 1995, 975-977.
Wu et al., One-Pot Two-Step Microwave-Assisted Reaction in Construction 4,5-Disubstituted Pyrazolopyrimidines Organic Letters, 2003, 5(20): 3587-3590.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Yamamura et al., "Circulating interleukin-6 levels are elevated in adult T-cell leukaemia/lymphoma patients and correlate with adverse clinical features and survival," Br. J. Haematol., 1998, 100: 129-134.
Yamaoka et al., "Janus kinase (JAK) inhibitors in rheumatoid arthritis", Current Rheumatology Reviews, Nov. 2011, 7(4): 306-312.
Yang et al., "Constitutive NF-КB activation confers interleukin 6 (IL6) independence and resistance to dexamethasone and Janus kinase inhibitor INCB018424 in murine plasmacytoma cells", Journal of Biological Chemistry, Aug. 2011, 286(32):27988-27997.
Yao et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 2008, 58(11):3485-3497.
Yao, et al., "Glucocorticoid Excess in Mice Results in Early Activation of Osteoclastogenesis and Adipogenesis and Prolonged Suppression of Osteogenesis", Arthritis and Rheumatism, 2008, 58(6), 1674-1686.
Yokoi et al., "A newly developed video-meibography system featuring a newly designed probe", Jpn J Ophthalmol, 2007, 51: 53-6.
Yokoi et al., "Assessment of meibomian gland function in dry eye using meibometry", Arch Ophthalmol, 1999, 117:723-9.
Yokoi et al., "Correlation of tear lipid layer interference patterns with the diagnosis and severity of dry eye", Am J Ophthalmol, 1996, 122:818-24.
Yokoi et al., "Non-invasive methods of assessing the tear film", Exp Eye Res, 2004, 78:399-407.
Younes et al., "Phase I Study of a Novel Oral Janus Kinase 2 Inhibitor, SB1518, in Patients With Relapsed Lymphoma: Evidence of Clinical and Biologic Activity in Multiple Lymphoma Subtypes," J. Clin. Oncol., 2012, 30(33):4161-4167.
Yu et al., "Role of Janus Kinase/Signal Transducers and Activators of Transcription in the Pathogenesis of Pancreatitis and Pancreatic Cancer," Gut and Liver, Oct. 2012, 6(4): 417-422.
Yu et al., "Constitutive activation of the Janus kinase-STAT pathway in T lymphoma overexpressing the Lck protein tyrosine kinase," J Immunol., 1997, 159(11):5206-10.
Zaidi et al., "Dermatology in Clinical Practice," Springer, 2010, 157 pages.
Zheng et al., "Discovery of INCB108201PF-4178903, a potent, selective, and orally bioavailable dual CCR2 and CCR5 antagonist", Bioorganic & Medicinal Chemistry Letters, 2011, 21: 1442-45.
Zoppellaro et al., "A Multifunctional High-Spin Biradical Pyrazolylbipyridine-bisnitronylnitroxide", Org. Lett., 2004, 6(26):4929-4932.
Zou et al., "Signaling Pathways Activated by Oncogenic Forms of Abl Tyrosine Kinase." Journal of Biological Chemistry, 1999, 274(26):18141-18144.
Australian Office Action in Australian Application No. 2016204689, dated Mar. 22, 2017, 4 pages.
Abstract of Chilean patent application No. 3496-06 published in Official Gazette of the Republic of Chile (Jun. 1, 2007) and publication (2 pages).
Chinese Notice of Reexamination in Chinese Application No. 201080033675.6, dated May 10, 2016, 18 pages (English Translation).
Chinese Office Action in Chinese Application No. 201480024761.9, dated Oct. 8, 2016, 21 pages (English Translation).
Columbian Office Action in Columbian Application No. 12-213.010, dated Jun. 17, 2014, 20 pages.
European Communication in European Application No. 06839328.5, dated Jan. 22, 2009, 5 pages.
Costa Rican Office Action in Costa Rican Application No. 10065, dated Jul. 16, 2013, 8 pages.
Eurasian Office Action in Eurasian Application No. 201291310, dated Mar. 9, 2017, 4 pages (English Tmnslation).
Eurasian Search Report in Eurasian Application No. 201200132, dated Sep. 1, 2016, 6 pages (English Translation).
European Search Report in European Application No. 16197502.4, dated Mar. 20, 2017, 15 pages.
International Preliminary Report on Patentability (with Written Opinion) in International Application No. PCT/US2006/047369, dated Jun. 18, 2008, 10 pages.
International Preliminary Report on Patentability (with Written Opinion) in International Application No. PCT/US2010/047252, dated Mar. 6, 2012, 7 pages.
International Preliminary Report on Patentability (with Written Opinion) dated Nov. 22, 2011 for International Appln. No. PCT/US2010/035728, 8 pages.
International Preliminary Report on Patentability (with Written Opinion) dated Nov. 22, 2011 for International Appln. No. PCT/US2010/035783, 5 pages.

(56) References Cited

OTHER PUBLICATIONS

International Preliminary Report on Patentability for International Appln. No. PCT/US2008/066662 dated Dec. 17, 2009, 7 pages.
International Preliminary Report on Patentability for PCT/US2008/66658 dated Dec. 17, 2009, 7 pages.
International Preliminary Report on Patentability for PCT/US2009/036635 dated Sep. 14, 2010, 6 pages.
International Preliminary Report on Patentability for PCT/US2009/059203 dated Apr. 5, 2011, 6 pages.
International Preliminary Report on Patentability for PCT/US2010/021003 dated Jul. 19, 2011, 11 pages.
International Preliminary Report on Patentability for PCT/US2010/052011 dated Apr. 11, 2012, 4 pages.
International Preliminary Report on Patentability for PCT/US2011/025433 dated Aug. 21, 2012, 7 pages.
International Preliminary Report on Patentability for PCT/US2011/027665 dated Sep. 11, 2012, 7 pages.
International Preliminary Report on Patentability for PCT/US2011/037291 dated Nov. 27, 2012, 7 pages.
International Preliminary Report on Patentability for PCT/US2011/061351 dated May 30, 2013, 7 pages.
International Preliminary Report on Patentability for PCT/US2011/061374 dated May 30, 2013, 5 pages.
International Preliminary Report on Patentability for PCT/US2012/043099 dated Dec. 23, 2013, 6 pages.
International Preliminary Report on Patentability for PCT/US2012/050210 dated Feb. 11, 2014, 8 pages.
International Preliminary Report on Patentability for PCT/US2012/051439 dated Feb. 27, 2014, 7 pages.
International Preliminary Report on Patentability for PCT/US2012/053921 dated Mar. 20, 2014, 8 pages.
International Preliminary Report on Patentability for PCT/US2013/041601, dated Nov. 18, 2014, 7 pages.
International Preliminary Report on Patentability in International Application No. PCT/US2014/049940, dated Feb. 18, 2016, 9 pages.
International Preliminary Report on Patentability in International Application No. PCT/US2014/051678, dated Mar. 3, 2016, 15 pages.
International Preliminary Report on Patentability in International Application No. PCT/US2015/028224, dated Nov. 10, 2016, 7 pages.
International Search Report and the Written Opinion, PCT/US2012/051439, dated Nov. 30, 2012, 15 pages.
International Search Report and the Written Opinion, PCT/US2012/053921, dated Nov. 7, 2012, 19 pages.
International Search Report and Written Opinion dated Feb. 9, 2010 for International Appln. No. PCT/US2009/059203, 10 pages.
International Search Report and Written Opinion for International Appln. No. PCT/US2005/046207 dated May 15, 2007, 6 pages.
International Search Report and Written Opinion for International Appln. No. PCT/US2008/066662 dated Dec. 23, 2008, 11 pages.
International Search Report and Written Opinion for International Appln. No. PCT/US2009/036635 dated Jun. 3, 2009, 14 pages.
International Search Report and Written Opinion for PCT/US2006/047369, 16 pages (dated Apr. 24, 2007).
International Search Report and Written Opinion for PCT/US2008/083319, 29 pages dated Mar. 13, 2009.
International Search Report and Written Opinion for PCT/US2011/025433, 12 pages (dated Jul. 20, 2011).
International Search Report and Written Opinion for PCT/US2011/027665 dated Jun. 27, 2011, 14 pages.
International Search Report and Written Opinion for PCT/US2011/037291, 11 pages (dated Apr. 19, 2012).
International Search Report and Written Opinion for PCT/US2011/061351 dated Feb. 17, 2012, 12 pages.
International Search Report and Written Opinion for PCT/US2011/061374 dated Mar. 27, 2012, 10 pages.
International Search Report and Written Opinion for PCT/US2012/025581, 16 pages (dated Apr. 26, 2012).
International Search Report and Written Opinion for PCT/US2012/043099, 11 pages (dated Sep. 13, 2012).
International Search Report and Written Opinion for PCT/US2012/050252 dated Jan. 2, 2013, 17 pages.
International Search Report and Written Opinion in International Application No. PCT/US2013/067794, dated Dec. 17, 2013, 14 pages.
International Search Report and Written Opinion in International Application No. PCT/US2014/020554, dated Jul. 16, 2014, 17 pages.
International Search Report and Written Opinion in International Application No. PCT/US2014/049940, dated Nov. 4, 2014, 13 pages.
International Search Report and Written Opinion in International Application No. PCT/US2014/051678, dated Feb. 11, 2015, 22 pages.
International Search Report and Written Opinion in International Application No. PCT/US2015/017963, dated Jun. 5, 2015, 13 pages.
International Search Report and Written Opinion in International Application No. PCT/US2015/028224, dated Jul. 15, 2015, 9 pages.
International Search Report and Written Opinion in International Application No. PCT/US2015/033254, dated Oct. 7, 2015, 12 pages.
International Search Report for PCT/US2008/66658 dated Dec. 23, 2008, 4 pages.
International Search Report for PCT/US2010/021003 dated Aug. 16, 2010, 8 pages.
International Search Report for PCT/US2010/035728 dated Jul. 8, 2010, 3 pages.
International Search Report for PCT/US2010/035783 dated Aug. 23, 2010, 4 pages.
International Search Report for PCT/US2010/047252 dated Nov. 17, 2010, 4 pages.
International Search Report for PCT/US2010/052011 dated Nov. 30, 2010, 3 pages.
International Search Report in International Application No. PCT/US2013/041601, dated Sep. 3, 2013, 3 pages.
Japanese Office Action in Japanese Application No. 2013-540049, dated Aug. 11, 2015, 3 pages (English Tmnslation).
Japanese Office Action in Japanese Application No. 2015-042933, dated Feb. 2, 2016, 6 pages (English Tmnslation).
Japanese Office Action in Japanese Application No. 2015-219637, dated Oct. 4, 2016, 6 pages.
Japanese Office Action in Japanese Application No. 2015-241393, dated Sep. 27, 2016, 4 pages (English Translation).
Japanese Office Action in Japanese Application No. 2017-000685, dated Jan. 31, 2017, 7 pages (with English translation).
Korean Office Action in Korean Application No. 10-2012-7033308, dated Mar. 21, 2017, 6 pages (English Translation Only).
Letter translation of Office Action, Chilean Application No. 3496-2006 as received from the foreign associate (Jul. 5, 2010) (4 pages).
Malaysian Examination Report in Malaysian Application No. PI2013002970, dated May 31, 2016, 4 pages.
Notice of Allowance and Fee(s) Due dated Sep. 21, 2007 in connection with U.S. Appl. No. 11/313,394, 6 pages.
Notice of Hearing and Preliminary Report for EP Patent 1966202, dated Mar. 18, 2013 (7 pages).
Office Action (Non-final) dated Aug. 22, 2007 in connection with U.S. Appl. No. 11/115,702, 9 pages.
Office Action (Non-final) dated Dec. 3, 2007 in connection with U.S. Appl. No. 11/524,641, 13 pages.
Office Action (Non-final) dated Feb. 25, 2009 for U.S. Appl. No. 12/137,892, 13 pages.
Office Action (Final) dated Feb. 7, 2008 for U.S. Appl. No. 11/115,702, 5 pages.
Office Action (Final) dated Jan. 29, 2014 in U.S. Appl. No. 13/043,986, 10 pages.
Office Action (Final) dated Nov. 30, 2009 for U.S. Appl. No. 12/137,892 (9 pgs.).
Office Action (Non-final) dated Apr. 20, 2007 in connection with U.S. Appl. No. 11/313,394, 16 pages.

(56) References Cited

OTHER PUBLICATIONS

Office Action in U.S. Appl. No. 14/186,338, dated May 5, 2014, 18 pages.
Office Action received for European Application No. 06 839 328.9 (Jan. 22, 2009), 5 pages.
Office Action received for Japanese Application No. 2008-545733 dated Oct. 11, 2011 (5 pages).
Office Action received for New Zealand Application No. 569015 dated Feb. 24, 2010, 2 pages.
Office Action received for Singapore Application No. 2008-04386-1 (Aug. 24, 2010).
Office Action received for Vietnamese Patent Application No. 1-2011-03188 dated Mar. 8, 2012 as translated by foreign associate (10 pages).
Office Action, Canadian Patent Office, Application No. 2,632,466, dated May 8, 2012, 3 pages.
Office Action, China, Patent Application No. 201080033308.6 dated Aug. 2, 2013, 10 pages.
Office Action, Eurasian Patent Office, prepared Feb. 5, 2010.
Office Action, European Patent Office, Application No. 06 839 328.9 dated Oct. 21, 2010.
Office Action, European Patent Office, dated Nov. 6, 2009 Application 06839328.9.
Office Action, Mexico, Patent Appl. No. MX/a/2008/007635 as received from foreign associate dated Jun. 15, 2010, 1 page.
Office Action, Mexico, Patent Appl. No. MX/a/2008/007635 as received from foreign associate dated Nov. 13, 2009, 4 pages.
Office Action/Examination Report received for Pakistan Application No. 211/2009 dated Jan. 18, 2010, 1 page.
Opposition for EP Patent 1966202, filed on Jun. 21, 2012, 30 pages.
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate dated Jun. 13, 2012, 6 pages.
Opposition, Costa Rica, translation from Foreign Associate dated Nov. 20, 2013, 9 pages.
Opposition, Ecuador Patent Office, dated Nov. 18, 2008, 6 pages (English Translation).
Phillipines Examination Report in Phillipines Application No. 1-2013-501001, dated Mar. 23, 2017, 3 pages.
Response and Amendment dated Aug. 25, 2009 to non-final Office Action for U.S. Appl. No. 12/137,892, 34 pages.
Response and Amendment in Reply to Action of Apr. 20, 2007 filed Jul. 17, 2007 for U.S. Appl. No. 11/313,394, 39 pages.
Response to Action of Aug. 22, 2007 dated Nov. 19, 2007, U.S. Appl. No. 11/115,702, 7 pages.
Response to Restriction Requirement dated May 29, 2007, U.S. Appl. No. 11/115,702, 8 pages.
Restriction Requirement dated Mar. 6, 2007 in connection with U.S. Appl. No. 11/115,702, 8 pages.
Search Report in TW Application No. 100117866, dated Dec. 2014, 1 page.
State Intellectual Property Office, PR China, Office Action, dated Sep. 3, 2010 Pat. Appl. No. 200680052750.7 (8 pages).
Japanese Office Action in Japanese Application No. 2016-143513, dated May 23, 2017, 3 pages (English Summary).
European Office Action in European Application No. 15195698.4, dated Mar. 15, 2017, 4 pages.
Japanese Office Action in Japanese Application No. 2015-561582, dated Feb. 13, 2018, 9 pages (English Translation).
European Communication pursuant to Article 94(3) EPC in European Application No. 14753182.6, dated Nov. 6, 2017, 10 pages.
Chinese Office Action in Chinese Application No. 201480052299.3, dated Jan. 25, 2018, 13 pages.
Taiwanese Office Action in Taiwanese Application No. 103126987, dated Dec. 28, 2017, 9 pages (English Translation).
Costa Rican Office Action in Costa Rican Application No. 2013-506, dated May 21, 2018, 15 pages (English Tmnslation).
Phillipine Office Action in Phillipine Application No. 1-2015-502575, dated Jun. 27, 2018, 3 pages.
Prchal et al, "Williams Hematology," New York: McGraw-Hill, 2010, 8th ed., Front Matter, 7 pages.
Edward B. Roche, "Bioreversible Carriers in Drug Design," American Pharmaceutical Association and Pergamon Press, 1987, Front Matter, 4 pages.
"FDA prescribing information for Jakafi (Ruxolitinib dosage form)", (Nov. 1, 2011) Retrieved from the Internet: URL: http://www.accessdata.fda.gov/drugsatfda_docs/labels/2011/202192lb1.pdf [retrieved on Sep. 25, 2013] 22 pages.
Australian Office Action in Australian Application No. 2013344780, dated May 5, 2017, 5 pages.
Canadian Examination Report in Canadian Application No. 2,799,928, dated Nov. 26, 2018, 3 pages.
Cervantes et al., "Three-year efficacy, safety, and survival findings from COMFORT-II, a phase 3 study comparing ruxolitinib with best available therapy for mylefibrosis," Blood, Dec. 12, 2013, 122(25):4047-4053.
Chinese Office Action in Chinese Application No. 201380070296.8, dated Feb. 16, 2017, 19 pages.
Clevelandclinic.org, "Lupus," Feb. 2001, [retrieved on Dec. 15, 2018] retrieved from URL <https://my.clevelandclinic.org/health/diseases/4875-lupus>, 7 pages.
ClinicalTrials.gov, "Topical Ruxolitinib for the Treatment of Vitiligo," Retrieved on Dec. 19, 2018, retrieved from URL <clinicaltrials.gov/ct2/show/NCT02809976>, 6 pages.
ClinicalTrials.gov, "A Study to Evaluate the Safety and Efficacy of INCB018424 Phosphate Cream Applied Topically to Adults With Atopic Dermatitis," Retrieved on Dec. 19, 2018, retrieved from URL <https://clinicaltrials.gov/ct2/show/NCT03011892>, 7 pages.
Columbian Office Action in Columbian Application No. 15-114.028, dated Apr. 18, 2017, 7 pages.
Columbian Office Action in Columbian Application No. 15-114.028, dated Sep. 20, 2017, 8 pages.
Communication dated Jan. 22, 2009 for European Appln. No. 06839328.9 (5 pgs.).
Deisseroth et al., "U.S. Food and Drug Administration Approval: Ruxolitinib for the Treatment of Patients with Intermediate and High-Risk Myelofibrosis," Clin. Cancer Res., Jun. 2012, 18(12):3212-3217.
Ecuador Examination Report in Ecuador Application No. SP-08-8540, dated Jun. 13, 30 pages, (2017).
Eurasian Office Action in Eurasian Application No. 201590930, dated Apr. 5, 2016, 6 pages (English Translation).
European Communication in European Application No. 13798840.8, dated May 11, 2018, 5 pages.
European Communication pursuant to Article 94(3) EPC in European Application No. 14753182.6, dated Sep. 10, 2018, 7 pages.
European Extended Search Report in European Application No. 18191992.9, dated Jan. 18, 2019, 10 pages.
Furqan et al., "Dysregulation of JAK-STAT pathway in hematological malignancies and JAK inhibitors for clinical application," Biomarker Research 2013, 1(1):1-10.
Gadamasetti et al., "Process Chemistry in the Pharmaceutical Industry," Challenges in an Ever Changing Climate, 2008, vol. 2, pp. 49-63.
Harper Collins Publishers, Collins English Dictionary, "in vitro" and "in vivo", p. 852, 2007.
Harrison et al., "JAK Inhibition with Ruxolitinib versus Best Available Therapy for Myelofibrosis,"The New England Journal of Medicine, Mar. 2012, 366(9): 787-798.
Hengge et al., "Adverse Effects of Topical Glucocorticosteroids," J Am Acad Dermatol., Jan. 2006, 54(1):1-15.
Indian Office Action in Indian Application No. 2177/DELNP/2014, dated May 8, 2018, 4 pages.
International Preliminary Report on Patentability for PCT/US2013/070012, dated May 19, 2015, 8 pages.
International Search Report and Written Opinion in International Application No. PCT/US2013/070012, dated Jan. 23, 2014, 12 pages.
Jakavi, Highlights of Prescribing Information, Incyte Corporation, 2011, revised Mar. 2016, 11 pages.

(56) References Cited

OTHER PUBLICATIONS

No Author, Jakavi, Novatis, 2015, 19 pages.
Japanese Office Action in Japanese Application No. 2015-542764, dated Jul. 25, 2017, 5 Pages.
Japanese Office Action in Japanese Application No. 2017-246-134, dated Oct. 16, 2018, 12 pages.
Kantarjian et al., "Ruxolitinib for Myelofibrosis—An Update of Its Clinical Effects," Clinical Lymphoma, Myeloma & Leukemia, Dec. 2013, 638-645.
Kim et al., Abstract #1956, "A Phase 2, Randomized, Dose-Ranging, Vehicle-and Active-Controlled Study to Evaluate the Safety and Efficacy of Ruxolitinib Cream in Adult Patients with Atopic Dermatitis," Presentation, Presented at the 27th European Academy of Dermatology and Venereology Congress, Sep. 12-16, 2018, Paris, France, 11 pages.
Kim et al., "Clinical significances of preoperative serum interleukin-6 and C-reactive protein level in operable gastric cancer," BMC Cancer, May 20, 2009, 9(155):1-9.
Korean Office Action in Korean Application No. 10-2018-7025131, dated Oct. 31, 2018, 7 pages (English Translation Only).
Levy, et al., INCB18424 Discussion presentation at the American Society of Hematology, 49th Annual Meeting and Exposition, Atlanta, GA. Abstract #558, Dec. 10, 2007 (25 pages).
Malhotra, "Janus Activated Kinase Inhibition in Myelofibrosis," Indian Journal of Cancer, Sep. 2012, 49(3):260-265.
MayoClinic.org, "Heart Transplant," 2018, [retrieved Dec. 8, 2018] retrieved from URL <https://www.mayoclinic.org/tests-procedures/heart-transplant/about/pac-20384750>, 18 pages.
National Cancer Institute, "Cancer Types by Site," Mar. 14, 2011, [retrieved from Dec. 15, 2018] retrieved from URL <https://web.archive.org/web/20110314030905/https://training.seer.cancer.gov/disease/categories/site.html>, 3 pages.
National Institutes of Health, "Study of Ruxolitinib Sustained release formulations in Myelofibrosis Patients," Sep. 25, 2013, Retrieved from the Internet: URL:http://clinicaltrials.gov/ct2/show/results/NCT01340651 [retrieved on Jan. 2, 2014], 4 pages.
Nokhodchi et al., "The role of oral controlled release matrix tablets in drug delivery systems," BioImpacts, 2012, 2(4): 175-187.
Office Action Received for New Zealand Application No. 748000, dated Dec. 24, 2018, 2 pages.
Office Action, Intellectual Property Office of Singapore, Application No. 2012043428, dated Sep. 26, 2014 (25 pages).
Opposition (Actavis), European Patent Office, EP Patent No. EP2173752, dated Jan. 20, 2015, 20 pages.
Opposition (Generics), European Patent Office, EP2173752, dated Jan. 20, 2015, 18 pages.
Osteoporosis.aaos.org[online], "Osteoporosis," Feb. 2001, [retrieved on Dec. 15, 2018] retrieved from URL <https://orthoinfo.aaos.org/en/diseases-conditions/osteoporosis/>, 7 pages.
Press Release dated Sep. 13, 2018: "Incyte Announces Positive Data from Phase 2b Trial of Ruxolitinib Cream in Patients with Atopic Dermatitis" (2 pages).
Product Monograph, "Jakavi," Prepared Jun. 15, 2012, Last revised, Sep. 28, 2018, 51 pages.
Research Gate, "What is the difference between Ex vivo and in vitro?", Dec. 18, 2014, available at http://www.researchgate.net/post/What_is_the_difference_between_Ex_vivo_and_in_vitro, 6 pages.
Rowe et al., "Handbook of Pharmaceutical Excipients," Pharmaceutical Excipients, 2009, 6:697-699.
Shi et al., "The effect of CYP3A4 inhibition or induction on the pharmacokinetics and pharmacodynamics of orally administered ruxolitinib (INCB018424 Phosphate) in Healthy Volunteers," J. Clin. Pharmacol. Jun. 2012;52(6):809-818.
Srdan et al., "Safety and Efficacy of INCB018424, a JAK1 and JAK2 Inhibitor, in Myelfibrosis," The New England Journal of Medicine, Sep. 16, 2010, 363:1117-1127.
Stahl et al., "Topical Administration," Handbook of Pharmaceutical Salts, 22(43):110, (2002).
Submission in Opposition Proceedings in European Application No. 08770794.9, Actavis Group PTC ehf, dated Mar. 19, 2014, 7 pages.
Submission in Opposition Proceedings in European Application No. 08770794.9, Incyte Corporation, dated Jun. 5, 2015, 14 pages.
Summons to Attend Oral Proceedings in European Application No. 08770794.9, dated Jan. 29, 2016, 18 pages.
Summons to Attend Oral Proceedings in European Application No. 08770794.9, dated Nov. 30, 2015, 18 pages.
Swerdlow, et al., WHO Classification of Tumours of Haematopoietic and Lymphoid Tissues. 4th Edition. Lyon France: IARC Press; 2008:88-103.
Taiwan Search Report in Taiwanese Application No. 102141524, dated Apr. 27, 2017, 12 pages.
Thailand Office Action in Thailand Application No. 1501002638, dated Jul. 17, 2017 2 pages (English Translation).
U.S. National Institute of Health, "Single-Agent Glasdegib in Patients With Myelofibrosis Previously Treated With Ruxolitinib," dated Aug. 25, 2014, available at www.clinicaltrials.gov, 4 pages.
U.S. National Institute of Health, "Phase I/II Study of Nilotinib/Ruxolitnb Therapy for TK1 Resistant Ph-Leukemia," dated Jul. 28, 2013, available at www.clinicaltrials.gov, 5 pages.
U.S. National Institute of Health, "Phase III Study Investigating the Efficacy and Safety of Ruxolitnib in Early Myelofibrosis Patients With High Molecular Risk Mutations," dated Oct. 27, 2015, available at www.clinicaltrials.gov, 4 pages.
U.S. National Institute of Health, "Ruxolitinib and Pomalidomide Combination Therapy in Patients With Primary and Secondary MF (POMINC)," dated Jul. 16, 2012, available at www.clinicaltrials.gov, 4 pages.
U.S. National Institute of Health, "A Clinical Study of Ruxolitinib in Patients With Primary Myelofibrosis (PM), Post-polycythemia Vera (PV) Myelofibrosis, or Post-essential Thrombocythemia (ET) Myelofibrosis," dated Mar. 12, 2014, available at www.clinicaltrials.gov, 4 pages.
U.S. National Institute of Health, "A Dose Ranging Study of the Effect of INCB018424 Phosphate Cream When Applied to Patients With Plaque Psoriasis," dated Oct. 21, 2008, available at www.clinicaltrials.gov, 3 pages.
U.S. National Institute of Health, "A Phase Ib/II Dose-finding Study to Assess the Safety and Efficacy of LDE225 + INC424 in Patients With MF," dated Feb. 6, 2013, available at www.clinicaltrials.gov, 5 pages.
U.S. National Institute of Health, "A Phase II Study of Oral JAK1/JAK2 Inhibitor INC424 in Adult Patients With Relapsed/Refractory Classical Hodgkin's Lymphoma (HIJAK)," dated Jun. 11, 2013, available at www.clinicaltrials.gov, 4 pages.
U.S. National Institute of Health, "A Phase II Study of Re-treatment of Myelofibrosis Patients With Ruxolitinib/Jakavi After Treatment Interruption Due to Loss of Response and/or Adverse Event (Re Treatment Trial)," dated Mar. 6, 2014, available at www.clinicaltrials.gov, 3 pages.
U.S. National Institute of Health, "A Pilot Study of Ruxolitinib in Secondary Hemophagocytic Syndrome," dated Jan. 22, 2015, available at www.clinicaltrials.gov, 3 pages.
U.S. National Institute of Health, "A Sequential Two-Stage Dose Escalation Study to Evaluate the Safety and Efficacy of Ruxolitinib," dated Jan. 24, 2013, available at www.clinicaltrials.gov, 5 pages.
U.S. National Institute of Health, "A Study Exploring the Safety, Tolerability and Efficacy of a 4 Week Course of INCB018424 in Subjects With Active Rheumatoid Arthritis," dated Oct. 24, 2007, available at www.clinicaltrials.gov, 4 pages.
U.S. National Institute of Health, "A Study of INCB018424 Phosphate Cream When Applied to Patients With Plaque Psoriasis," dated Jan. 8, 2009, available at www.clinicaltrials.gov, 3 pages.
U.S. National Institute of Health, "A Study of LY2784544 in Participants With Myeloproliferative Neoplasms," dated May 1, 2012, available at www.clinicaltrials.gov, 3 pages.
U.S. National Institute of Health, "A Study of Ruxolitinib in Pancreatic Cancer Patients," dated Apr. 17, 2014, available at www.clinicaltrials.gov, 3 pages.
U.S. National Institute of Health, "A Study of Ruxolitnib in Combination With Capecitabine in Subjects With Advanced or Metastatic HER2-negative Breast Cancer," dated Apr. 18, 2014, available at www.clinicaltrials.gov, 3 pages.

(56) References Cited

OTHER PUBLICATIONS

U.S. National Institute of Health, "A Study to Determine the Effect and Safety of an Oral Janus Kinase 2 (JAK2)-Inhibitor (Ruxolitinib; INBC018424) in Patients With Multiple Myeloma," dated Mar. 12, 2008, available at www.clinicaltrials.gov, 3 pages.
U.S. National Institute of Health, "A Study to Evaluate Efficacy and Safety of Vismodegib (Erivedge) in Combination With Ruxolitinib for the Treatment of Intermediate- or High-Risk Myelofibrosis (MF)," dated Oct. 29, 2015, available at www.clinicaltrials.gov, 3 pages.
U.S. National Institute of Health, "A Study With INCB018424 Phosphate Cream Applied Topically to Subjects With Alopecia Areata (AA)," dated Sep. 16, 2015, available at www.clinicaltrials.gov, 3 pages.
U.S. National Institute of Health, "Adding Ruxolitinib to a Combination of Dasatinib Plus Dexamethasone in Remission Induction Therapy in Newly Diagnosed Philadelphia Chromosome-Positive Acute Lymphoblastic Leukemia Patients Aged 40 Years or Older," dated Jul. 8, 2015, available at www.clinicaltrials.gov, 4 pages.
U.S. National Institute of Health, "Administration of Jakafi (Ruxolitnib) for Symptom Control of Patients With Chronic Lymphocytic Leukemia (CLL): Phase II," dated May 2, 2014, available at www.clinicaltrials.gov, 4 pages.
U.S. National Institute of Health, "Alternative Dosing Strategy of Ruxolitinib in Patients With Myelofibrosis," dated Sep. 23, 2011, available at www.clinicaltrials.gov, 6 pages.
U.S. National Institute of Health, "An Open-Label Study of Ruxolitinib Given With Chemotherapy in Patients With Advanced Solid Tumors," dated Mar. 28, 2013, available at www.clinicaltrials.gov, 3 pages.
U.S. National Institute of Health, "Asian Phase II Study of INC424 in Patients With Primary Myelofibrosis (MF), Post-PV MF or Post-ET MF," dated Jul. 11, 2011, available at www.clinicaltrials.gov, 4 pages.
U.S. National Institute of Health, "CINC424A2X01B Rollover Protocol," dated Mar. 6, 2015, available at www.clinicaltrials.gov, 4 pages.
U.S. National Institute of Health, "Controlled MyeloFibrosis Study with Oral JAK Inhibitor Treatment: The COMFORT-I Trial," dated Aug. 4, 2009, available at www.clinicaltrials.gov, 5 pages.
U.S. National Institute of Health, "Controlled Myelofibrosis Study With Oral Janus-associated Kinase (JAK) Inhibitor Treatment-II: The COMFORT-II Trial," dated Jul. 6, 2009, available at.www.clinicaltrials.gov, 4 pages.
U.S. National Institute of Health, "Dose Escalation Study to Determine the Maxiumum Tolerated Dose of the Combination of Ruxolitinib and Bortezomib in Patients with Relapsed or Refractory Lymphoma," dated Nov. 20, 2015, available at www.clinicaltrials.gov, 4 pages.
U.S. National Institute of Health, "Efficacy and Safety of Simtuzumab in Adults With Primary, Post Polycythemia Vera or Post Essential Thrombocythemia Myelofibrosis," dated Jun. 6, 2011, available at www.clinicaltrials.gov, 4 pages.
U.S. National Institute of Health, "Efficacy of Momelotinib Versus Best Available Therapy in Anemic or Thrombocytopenic Subjects With Primary Myelofibrosis (MF), Post-polycythemia Vera MF, or Post-essential Thrombocythemia MF (Simplify 2)," dated Mar. 28, 2014, available at www.clinicaltrials.gov, 4 pages.
U.S. National Institute of Health, "Evaluating the Safety and Tolerability of Ruxolitinib in Antiretroviral-Treated HIV-Infected Adults," dated Jun. 16, 2015, availabe at www.clinicaltrials.gov, 6 pages.
U.S. National Institute of Health, "Evaluation of RUX and AZA Combination as a Therapy for Patients With Myelofibrosis and Myelodysplastic Syndrome/ Myeloproliferative Neoplasm," dated Feb. 6, 2013, available at www.clinicaltrials.gov, 5 pages.
U.S. National Institute of Health, "Expanded Treatment Protocol (ETP) of Ruxolitinib in Patients With Polycythemia Vera Who Are Hydroxyurea Resistant or Intolerant and for Whom no Treatment Alternatives Are Available," dated Nov. 5, 2014, availabe at www.clinicaltrials.gov, 3 pages.

U.S. National Institute of Health, "Exploratory Phase II Study of INC424 Patients With Primary Myelofibrosis (PMF) or Post Polycythaemia Myelofibrosis (PPV MF) or Post Essential Thrombocythaemia Myelofibrosis (PET-MF) (MACS2030)," dated Mar. 16, 2012, available at www.clinicaltrials.gov, 4 pages.
U.S. National Institute of Health, "Genomics-Based Target Therapy for Children With Relapsed or Refractory Malignancy," dated Nov. 29, 2015, available at www.clinicaltrials.gov, 3 pages.
U.S. National Institute of Health, "High Throughput Drug Sensitivity Assay and Genomics—Guided Treatment of Patients With Relapsed or Refractory Acute Leukemia," dated Aug. 25, 2015, available at www.clinicaltrials.gov, 4 pages.
U.S. National Institute of Health, "INC424 for Patients With Myelofibrosis, Post Polycythemia Myelofibrosis or Post-essential Thrombocythemia Myelofibrosis (JUMP)," dated Dec. 13, 2011, available at www.clinicaltrials.gov, 3 pages.
U.S. National Institute of Health, "INCB018424 in Patients With Advanced Hematologic Malignancies," dated May 5, 2008, available at www.clinicaltrials.org, 4 pages.
U.S. National Institute of Health, "INCB18424 in Treating Young Patients With Relapsed or Refractory Solid Tumor, Leukemia, or Myeloproliferative Disease," dated Jul. 15, 2010, available at www.clinicaltrials.gov, 5 pages.
U.S. National Institute of Health, "JAK2 Inhibitors RUXOLITINIB in Patients With Myelofibrosis," dated Dec. 21, 2012, available at www.clinicaltrials.gov, 4 pages.
U.S. National Institute of Health, "JAK-inhibition in Recurrent Classical Hodgkin Lymphoma (JeRiCHO)," dated Jun. 12, 2014, available at www.clinicaltrials.gov, 3 pages.
U.S. National Institute of Health, "Momelotinib Versus Ruxolitinib in Subjects With Myelofibrosis (Simplify 1)," dated Oct. 22, 2013, available at www.clinicaltrials.gov, 4 pages.
U.S. National Institute of Health, "N-of-1 Trial: Actionable Target Identification in Metastatic Cancer for Palliative Systemic Therapy (MetAction)," dated Apr. 13, 2014, available at www.clinicaltrials.gov, 4 pages.
U.S. National Institute of Health, "Open Label Ruxolitinib (INCB018424) in Patients With Myelofibrosis and Post Polycythemia Vera/Essential Thombrocythemia Myelofibrosis," dated Jul. 30, 2007, available at www.clinicaltrials.gov, 4 pages.
U.S. National Institute of Health, "Open Label, Safety and Efficacy Study of Topical Investigational Drug to Treat Patients With Psoriasis," dated Jan. 21, 2008, available at www.clinicaltrials.gov, 3 pages.
U.S. National Institute of Health, "Oral Pacritinib Versus Best Available Therapy to Treat Myelofibrosis With Thrombocytopenia (PAC326)," dated Feb. 3, 2014, available at www.clinicaltrials.gov, 3 pages.
U.S. National Institute of Health, "Panobinostat and Ruxolitinib in MyElofibrosis (PRIME Trial) (PRIME)," dated Sep. 14, 2012, available at www.clinicaltrials.gov, 4 pages.
U.S. National Institute of Health, "Panobinostat and Ruxolitinib in Primary Myelofibrosis, Post-polycythemia Vera-myelofibrosis or Post-essential Thrombocythemia-myelofibrosis," dated Jun. 27, 2011, available at www.clinicaltrials.gov, 4 pages.
U.S. National Institute of Health, "Pharmacodynamic Effects and Predictive Biomarkers With Ruxolitinib in Operable Head and Neck Cancer," dated Oct. 14, 2015, available at www.clinicaltrials.gov, 4 pages.
U.S. National Institute of Health, "Phase I Study of the Combination of Afatinib and Ruxolitinib in Patients With Treatment-refractory Non-Small Cell Lung Cancer (NSCLC)," dated Apr. 23, 2014, available at www.clinicaltrials.gov, 3 pages.
U.S. National Institute of Health, "Phase I/II Study of Ruxolitinib for Acute Leukemia," dated Nov. 30, 2010, available at www.clinicaltrials.gov, 3 pages.
U.S. National Institute of Health, "Phase II, Open Label, Single Arm Study of SAR302503 in Myelofibrosis Patients Previously Treated With Ruxolitinib (JAKARTA2)," dated Jan. 27, 2012, available at www.clinicaltrials.gov, 4 pages.

(56) References Cited

OTHER PUBLICATIONS

U.S. National Institute of Health, "Pilot Study of Ruxolitinib in Relapsed or Refractory Hodgkin Lymphoma and Primary Mediastinal Large B-cell Lymphoma (JAK2)," dated Oct. 9, 2013, available at www.clinicaltrials.gov, 4 pages.
U.S. National Institute of Health, "Pilot Study to Evaluate of Ruxolitinib in Alopecia Areata," dated Sep. 23, 2013, available at www.clinicaltrials.gov, 4 pages.
U.S. National Institute of Health, "Randomized Switch Study From Hydroxyurea to Ruxolitinib for Relief of Polycythemia Vera Symptoms: The Relief Study," dated Jun. 29, 2012, available at www.clinicaltrials.gov, 3 pages.
U.S. National Institute of Health, "Ruxolitinib (INCB018424) in Subjects With Primary Myelofibrosis, Post Essential Thrombocythemia-myelofibrosis and Post Polycythemia Vera-myelofibrosis," dated May 4, 2011, available at www.clinicaltrials.gov, 3 pages.
U.S. National Institute of Health, "Ruxolitinib and Lenalidomide for Patients With Myelofibrosis," dated Jun. 14, 2011, available at www.clinicaltrials.gov, 4 pages.
U.S. National Institute of Health, "Ruxolitinib Efficacy and Safety in Patients With HU Resistant or Intolerant Polycythemia Vera vs Best Available Therapy. (Response 2)," dated Jan. 14, 2014, available at www.clinicaltrials.gov, 4 pages.
U.S. National Institute of Health, "Ruxolitinib for Adult T-Cell Leukemia," dated Oct. 20, 2012, available at www.clinicaltrials.gov, 4 pages.
U.S. National Institute of Health, "Ruxolitinib for Chronic Myeloid Leukemia (CML) With Minimal Residual Disease (MRD)," Dec. 14, 2012, available at www.clinicaltrials.gov, 4 pages.
U.S. National Institute of Health, "Ruxolitinib for Chuvash Polycythemia," dated Nov. 7, 2012, available at www.clinicaltrials.gov, 2 pages.
U.S. National Institute of Health, "Ruxolitinib for Patients With Low or Intermediate-1 Risk Myelodysplastic Syndrome (MDS)," dated Jul. 5, 2013, available at www.clinicaltrials.gov, 3 pages.
U.S. National Institute of Health, "Ruxolitinib for Pracinostat Combination Therapy for Patients With Myelofibrosis (MF)," dated Oct. 14, 2014, available at www.clinicaltrials.gov, 4 pages.
U.S. National Institute of Health, "Ruxolitinib in Combination With Autotransplant," dated May 28, 2015, available at www.clinicaltrials.gov, 4 pages.
U.S. National Institute of Health, "Ruxolitinib in Combination With Nilotinib in Chronic Myeloid Leukemia (CML) Patients," dated Oct. 3, 2012, available at www.clinicaltrials.gov, 4 pages.
U.S. National Institute of Health, "Ruxolitinib in Combination With Pemetrexed/Cisplatin in Non Small Cell Lung Cancer," dated Apr. 17, 2014, available at www.clinicaltrials.gov, 4 pages.
U.S. National Institute of Health, "Ruxolitinib in Combination With Trastuzumab in Metastatic HER2 Positive Breast Cancer," dated Feb. 18, 2014, available at www.clinicaltrials.gov, 5 pages.
U.S. National Institute of Health, "Ruxolitinib in Estrogen Receptor Positive Breast Cancer," dated May 7, 2012, available at www.clinicaltrials.gov, 3 pages.
U.S. National Institute of Health, "Ruxolitinib in GvHD (RIG)," dated Mar. 10, 2015, available at www.clinicaltrials.gov, 4 pages.
U.S. National Institute of Health, "Ruxolitinib in Patients With Breast Cancer," dated Mar. 20, 2012, available at www.clinicaltrials.gov, 3 pages.
U.S. National Institute of Health, "Ruxolitinib in the Treatment of Chronic Lymphocytic Leukemia," dated Dec. 3, 2013, available at www.clinicaltrials.gov, 4 pages.
U.S. National Institute of Health, "Ruxolitinib or Dasatinib With Chemotherapy in Patients With Philadelphia Chromosome (Ph)-Like Acute Lymphoblastic Leukemia (ALL)," dated Apr. 15, 2015, available at www.clinicaltrials.gov, 8 pages.
U.S. National Institute of Health, "Ruxolitinib Phosphate (Oral JAK Inhibitor INCB18424) in Treating Patients With Relapsed or Refractory Diffuse Large B-Cell or Peripheral T-Cell Non-Hodgkin Lymphoma," dated Sep. 5, 2011, available at www.clinicaltrials.gov, 4 pages.

U.S. National Institute of Health, "Ruxolitinib Phosphate and Danazol in Treating Anemia in Patients With Myelofibrosis," dated Nov. 19, 2012, available at www.clinicaltrials.gov, 5 pages.
U.S. National Institute of Health, "Ruxolitinib Phosphate in Treating Patients With Chronic Neutrophilic Leukemia or Atypical Chronic Myeloid Leukemia," dated Mar. 18, 2014, available at www.clinicaltrials.gov, 5 pages.
U.S. National Institute of Health, "Ruxolitinib Phosphate, Tacrolimus and Sirolimus in Preventing Acute Graft-versus-Host Disease During Reduced Intensity Donor Hematopoietic Cell Transplant in Patients With Myelofibrosis," dated Aug. 18, 2015, available at www.clinicaltrials.gov, 6 pages.
U.S. National Institute of Health, "Ruxolitinib Prior to Transplant in Patients With Myelofibrosis," dated Feb. 8, 2013, available at www.clinicaltrials.gov, 6 pages.
U.S. National Institute of Health, "Ruxolitinib W/ Preop Chemo for Triple Negative Inflammatory Brca," dated Jan. 11, 2014, available at www.clinicaltrials.gov, 4 pages.
U.S. National Institute of Health, "Safety and Tolerability of Combined Treatment With Nilotinib and Ruxolitinib in Civil and Ph+ ALL Patients (CoRNea)," dated Sep. 17, 2014, available at www.clinicaltrials.gov, 4 pages.
U.S. National Institute of Health, "Safety, Tolerability, and Pharmacokinetics of Idelalisib in Adults Receiving Ruxolitinib as Therapy for Primary, Post-Polycythemia Vera, or Post-Essential Thrombocythemia Myelofibrosis With Progressive or Relapsed Disease," dated May 1, 2015, available at www.clinicaltrials.gov, 4 pages.
U.S. National Institute of Health, "Study of Combination Ruxolitinib and Decitabine Treatment for Accelerated Phase MPN or Post-MPN AML," dated Feb. 27, 2014, available at www.clinicaltrials.gov, 4 pages.
U.S. National Institute of Health, "Study of Efficacy and Safety of INC424 in Regularly Transfused Patients With Thalassemia," dated Jan. 28, 2014, available at www.clinicaltrials.gov, 3 pages.
U.S. National Institute of Health, "Study of Ruxolitinib (INCB018424) Administered Orally to Patients With Androgen Independent Metastatic Prostate Cancer," dated Mar. 12, 2008, available at www.clinicaltrials.gov, 4 pages.
U.S. National Institute of Health, "Study of Ruxolitinib (INCB018424) Sustained Release Formulation in Myelofibrosis Patients," dated Apr. 21, 2011, available at www.clinicaltrials.gov, 4 pages.
U.S. National Institute of Health, "Study of Ruxolitinib in Colorectal Cancer Patients," dated Apr. 17, 2014, available at www.clinicaltrials.gov, 4 pages.
U.S. National Institute of Health, "Study of Ruxolitinib in Pancreatic Cancer Patients (Janus 1)," dated Apr. 16, 2014, available at www.clinicaltrials.gov, 3 pages.
U.S. National Institute of Health, "Study of Ruxolitinib in Pancreatic Cancer Patients (RECAP)," dated Aug. 22, 2011, available at www.clinicaltrials.gov, 3 pages.
U.S. National Institute of Health, "Study of Ruxolitinib in the Treatment of Cachexia in Patients With Tumor-Associated Chronic Wasting Diseases," dated Feb. 21, 2014, available at www.clinicaltrials.gov, 4 pages.
U.S. National Institute of Health, "Study of Ruxolitinib Plus Decitabine in Patients With Acute Myeloid Leukemia (AML)," dated Sep. 26, 2014, available at www.clinicaltrials.gov, 4 pages.
U.S. National Institute of Health, "Study of the JAK Inhibitor Ruxolitinib Administered Orally to Patients With Primary Myelofibrosis (PMF), Post-Polycythemia Vera-Myelofibrosis (PPV-MF) or Post-Essential Thrombocythemia-Myelofibrosis (PET-MF)," dated Mar. 14, 2011, available at www.clinicaltrials.gov, 4 pages.
U.S. National Institute of Health, "Study of the Safety of PIM447 in Combination With Ruxolitinib (INC424) and LEE011 in Patients With Myelofibrosis," dated Feb. 6, 2015, available at www.clinicaltrials.gov, 5 pages.
U.S. National Institute of Health, "Study to Determine the Safety and Efficacy of Ruxolitinib (INCB018424) in Patients With Polycythemia Vera or Essential Thrombocythemia," dated Jul. 29, 2008, available at www.clinicaltrials.gov, 5 pages.
U.S. National Institute of Health, "TGR-1202 + Ruxolitinib PMF PPV-MF PET-MF MDS/MPN Polycythemia Vera Resistant to Hydroxyurea," dated Jul. 1, 2015, availabe at www.clinicaltrials.gov, 4 pages.

(56) References Cited

OTHER PUBLICATIONS

U.S. National Institute of Health, "The Role of JAK2 in Alveolar Macrophages (AM's) in Chronic Beryllium Disease (CBD)," dated Oct. 29, 2015, available at www.clinicaltrials.gov, 4 pages.

U.S. National Institute of Health, "The Ruxo-BEAT Trial in Patients With High-risk Polycythemia Vera or High-risk Essential Thrombocythemia (Ruxo-BEAT)," dated Oct. 1, 2015, available at www.clinicaltrials.gov, 5 pages.

U.S. National Institute of Health, "Trial of Ruxolitinib and Erlotinib in Patients With EGFR-mutant Lung Adenocarcinoma With Acquired Resistance to Erlotinib," dated Jun. 2, 2014, available at www.clinicaltrials.gov, 4 pages.

U.S. National Institute of Health, "Open Label Ruxolitinib (INCB018424) in Patients with Myelofibrosis and Post Polycythemia Vera/Essential Thrombocythemia Myelofibrosis," Dec. 19, 2014, available at www.clinicaltrials.gov, 4 pages.

U.S. National Institute of Health, "Study of Ruxolitinib," Dec. 3, 2008, available at www.clinicaltrials.gov, 11 pages.

U.S. National Institute of Helath, "Study of Efficacy and Safety in Polycythemia Vera Subjects Who Are Resistant to or Intolerant of Hydroxyurea: JAK Inhibitor INC424 (INCB018424) Tablets Versus Best Available Care: (The Response Trial)," dated Nov. 17, 2010, available at www.clinicaltrials.gov, 4 pages.

Ukraine Office Action in Ukraine Application No. a 2015 05798, dated Nov. 20, 2017, 9 pages (English Translation).

Verstovsek et al., "Efficacy, safety and survival with ruxolitinib in patients with mylefibrosis:resuts of a median 2-year follow-up of COMFORT-I," Haematologica, 2013, 98(12):1865-1871.

Xiaoyang et al., "Knockdown of STAT3 Expression by RNA Interference Inhibits the Induction of Breast Tumors in Immunocompetent Mice", Cancer Res Apr. 1, 2005 65; 2532.

Ye et al., "The synthesis and the antitumor activity of 5,7-disubstituted pyrazolo [1,5-a] pyrimidines," Chinese J Med Chem., Feb. 28, 2007, 17(1):18-22.

Yongjun et al., "Advances in research of tyrosine kinases inhibitor of vascular endothelial growth factor receptor," Chinese J New Drugs, Dec. 31, 2008, 17(7):544-550.

Wuts and Greene, Protective Groups in Organic Synthesis, 4th ed., John Wiley & Sons: New Jersey, 2007, 27 pages (Front Matter Only).

Higuchi et al., "Pro-drugs as Novel Delivery Systems," vol. 14 of the A.C.S. Symposium Series, 1975, 6 pages (Front Matter Only).

Coligan, J.E. et al, "Current Protocols in Immunology," vol. 3., Wiley Press, 1992, 21 pages (Unit Abstracts Only).

Winyard, P.G. and Willoughby, D.A., "Inflammation Protocols," Humana Press, Methods in Molecular Biology:, 2003, vol. 225, 359 pages.

HETEROARYL SUBSTITUTED PYRROLO[2,3-B]PYRIDINES AND PYRROLO[2,3-B]PYRIMIDINES AS JANUS KINASE INHIBITORS

CROSS REFERENCE TO RELATED APPLICATIONS

This application is a continuation of U.S. Ser. No. 15/356,957, filed Nov. 21, 2016, which is a continuation of U.S. Ser. No. 15/233,652, filed Aug. 10, 2016, now U.S. Pat. No. 9,814,722, which is a continuation of U.S. Ser. No. 15/173,057, filed Jun. 3, 2016, now U.S. Pat. No. 9,662,335, which is a continuation of U.S. Ser. No. 14/711,576, filed May 13, 2015, which is a continuation of U.S. Ser. No. 14/274,948, filed May 12, 2014, now U.S. Pat. No. 9,079,912, which is a continuation of U.S. Ser. No. 14/020,505, filed Sep. 6, 2013, now U.S. Pat. No. 9,206,187, which is a divisional of U.S. Ser. No. 13/076,220, filed Mar. 30, 2011, now U.S. Pat. No. 8,530,485, which is a continuation of U.S. Ser. No. 12/549,170, filed Aug. 27, 2009, now U.S. Pat. No. 8,541,425, which is a continuation of U.S. Ser. No. 11/637,545, filed Dec. 12, 2006, now U.S. Pat. No. 7,598,257, which claims the benefit of U.S. Ser. Nos. 60/749,905, filed Dec. 13, 2005; 60/810,231, filed Jun. 2, 2006; 60/850,625, filed Oct. 10, 2006; 60/856,872, filed Nov. 3, 2006; and 60/859,404, filed Nov. 16, 2006, the disclosures of each of which are incorporated herein by reference in their entireties.

FIELD OF THE INVENTION

The present invention provides heteroaryl substituted pyrrolo[2,3-b]pyridines and heteroaryl substituted pyrrolo[2,3-b]pyrimidines that modulate the activity of Janus kinases and are useful in the treatment of diseases related to activity of Janus kinases including, for example, immune-related diseases, skin disorders, myeloid proliferative disorders, cancer, and other diseases.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P et al, Nature 2001, 411(6835):355-365). Thus far, oncogenic protein kinases represent one of the largest and most attractive groups of protein targets for cancer intervention and drug development.

Protein kinases can be categorized as receptor type and non-receptor type. Receptor tyrosine kinases (RTKs) have an extracellular portion, a transmembrane domain, and an intracellular portion, while non-receptor tyrosine kinases are entirely intracellular. RTK mediated signal transduction is typically initiated by extracellular interaction with a specific growth factor (ligand), typically followed by receptor dimerization, stimulation of the intrinsic protein tyrosine kinase activity, and receptor transphosphorylation Binding sites are thereby created for intracellular signal transduction molecules and lead to the formation of complexes with a spectrum of cytoplasmic signaling molecules that facilitate the appropriate cellular response such as cell division, differentiation, metabolic effects, and changes in the extracellular microenvironment At present, at least nineteen (19) distinct RTK subfamilies have been identified. One RTK subfamily, designated the HER subfamily, includes EGFR, HER2, HER3 and HER4, and bind such ligands as epithelial growth factor (EGF), TGF-α, amphiregulin, HB-EGF, betacellulin and heregulin. A second family of RTKs, designated the insulin subfamily, includes the INS-R, the IGF-1R and the IR-R. A third family, the "PDGF" subfamily, includes the PDGF alpha and beta receptors, CSFIR, c-kit and FLK-II. Another subfamily of RTKs, referred to as the FLK subfamily, encompasses the Kinase insert Domain-Receptor fetal liver kinase-1 (KDR/FLK-1), the fetal liver kinase 4 (FLK-4) and the fms-like tyrosine kinase 1 (flt-1). Two other subfamilies of RTKs have been designated as the FGF receptor family (FGFR1, FGFR2, FGFR3 and FGFR4) and the Met subfamily (c-Met, Ron and Sea). For a detailed discussion of protein kinases, see for example, Blume-Jensen, P. et al., Nature. 2001, 411(6835):355-365, and Manning, G. et al., Science. 2002, 298(5600):1912-1934.

The non-receptor type of tyrosine kinases is also composed of numerous subfamilies, including Src, Btk, Abl, Fak, and Jak. Each of these subfamilies can be further subdivided into multiple members that have been frequently linked to oncogenesis. The Src family, for example, is the largest and includes Src, Fyn, Lck and Fgr among others. For a detailed discussion of these kinases, see Bolen J B. Nonreceptor tyrosine protein kinases. Oncogene. 1993, 8(8):2025-31.

A significant number of tyrosine kinases (both receptor and nonreceptor) are associated with cancer (see Madhusudan S, Ganesan T S. Tyrosine kinase inhibitors in cancer therapy. Clin Biochem. 2004, 37(7):618-35.). Clinical studies suggest that overexpression or dysregulation of tyrosine kinases may also be of prognostic value. For example, members of the HER family of RTKs have been associated with poor prognosis in breast, colorectal, head and neck and lung cancer. Mutation of c-Kit tyrosine kinase is associated with decreased survival in gastrointestinal stromal tumors. In acute myelogenous leukemia, Flt-3 mutation predicts shorter disease free survival. VEGFR expression, which is important for tumor angiogenesis, is associated with a lower survival rate in lung cancer. Tie-1 kinase expression inversely correlates with survival in gastric cancer. BCR-Abl expression is an important predictor of response in chronic myelogenous leukemia and Src tyrosine kinase is an indicator of poor prognosis in all stages of colorectal cancer.

The immune system responds to injury and threats from pathogens. Cytokines are low-molecular weight polypeptides or glycoproteins that stimulate biological responses in virtually all cell types. For example, cytokines regulate many of the pathways involved in the host inflammatory response to sepsis. Cytokines influence cell differentiation, proliferation and activation, and they can modulate both proinflammatory and anti-inflammatory responses to allow the host to react appropriately to pathogens.

Binding of a cytokine to its cell surface receptor initiates intracellular signaling cascades that transduce the extracellular signal to the nucleus, ultimately leading to changes in gene expression. The pathway involving the Janus kinase family of protein tyrosine kinases (JAKs) and Signal Transducers and Activators of Transcription (STATs) is engaged in the signaling of a wide range of cytokines. Generally, cytokine receptors do not have intrinsic tyrosine kinase activity, and thus require receptor-associated kinases to propagate a phosphorylation cascade. JAKs fulfill this function. Cytokines bind to their receptors, causing receptor dimerization, and this enables JAKs to phosphorylate each other as well as specific tyrosine motifs within the cytokine receptors. STATs that recognize these phosphotyrosine motifs are recruited to the receptor, and are then themselves activated by a JAK-dependent tyrosine phosphorylation event. Upon activation, STATs dissociate from the receptors, dimerize, and translocate to the nucleus to bind to specific DNA sites and alter transcription (Scott, M. J., C. J. Godshall, et al. (2002). "Jaks, STATs, Cytokines, and Sepsis." *Clin Diagn Lab Immunol* 9(6): 1153-9).

The JAK family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, Godshall et al. 2002, supra).

While JAK1, JAK2 and TYK2 are ubiquitously expressed, JAK3 is reported to be preferentially expressed in natural killer (NK) cells and not resting T cells, suggesting a role in lymphoid activation (Kawamura, M., D. W. McVicar, et al. (1994). "Molecular cloning of L-JAK, a Janus family protein-tyrosine kinase expressed in natural killer cells and activated leukocytes." *Proc Natl Acad Sci USA* 91(14): 6374-8).

Not only do the cytokine-stimulated immune and inflammatory responses contribute to normal host defense, they also play roles in the pathogenesis of diseases: pathologies such as severe combined immunodeficiency (SCID) arise from hypoactivity and suppression of the immune system, and a hyperactive or inappropriate immune/inflammatory response contributes to the pathology of autoimmune diseases such as rheumatoid and psoriatic arthritis, asthma and systemic lupus erythematosus, inflammatory bowel disease, multiple sclerosis, type I diabetes mellitus, myasthenia gravis, thyroiditis, immunoglobulin nephropathies, myocarditis as well as illnesses such as scleroderma and osteoarthritis (Ortmann, R. A., T. Cheng, et al. (2000). "Janus kinases and signal transducers and activators of transcription: their roles in cytokine signaling, development and immunoregulation." *Arthritis Res* 2(1): 16-32). Furthermore, syndromes with a mixed presentation of autoimmune and immunodeficiency disease are quite common (Candotti, F., L. Notarangelo, et al. (2002). "Molecular aspects of primary immunodeficiencies: lessons from cytokine and other signaling pathways." *J Clin Invest* 109(10): 1261-9). Thus, therapeutic agents are typically aimed at augmentation or suppression of the immune and inflammatory pathways, accordingly.

Deficiencies in expression of JAK family members are associated with disease states. Jak1–/– mice are runted at birth, fail to nurse, and die perinatally (Rodig, S. J., M. A. Meraz, et al. (1998). "Disruption of the Jak1 gene demonstrates obligatory and nonredundant roles of the Jaks in cytokine-induced biologic responses." *Cell* 93(3): 373-83). Jak2–/– mouse embryos are anemic and die around day 12.5 postcoitum due to the absence of definitive erythropoiesis. JAK2-deficient fibroblasts do not respond to IFN gamma, although responses to IFNalpha/beta and IL-6 are unaffected. JAK2 functions in signal transduction of a specific group of cytokine receptors required in definitive erythropoiesis (Neubauer, H., A. Cumano, et al. (1998). *Cell* 93(3): 397-409; Parganas, E., D. Wang, et al. (1998). *Cell* 93(3): 385-95.). JAK3 appears to play a role in normal development and function of B and T lymphocytes. Mutations of JAK3 are reported to be responsible for autosomal recessive severe combined immunodeficiency (SCID) in humans (Candotti, F., S. A. Oakes, et al. (1997). "Structural and functional basis for JAK3-deficient severe combined immunodeficiency." *Blood* 90(10): 3996-4003).

The JAK/STAT pathway, and in particular all four members of the JAK family, are believed to play a role in the pathogenesis of the asthmatic response, chronic obstructive pulmonary disease, bronchitis, and other related inflammatory diseases of the lower respiratory tract. For instance, the inappropriate immune responses that characterize asthma are orchestrated by a subset of CD4+ T helper cells termed T helper 2 (Th2) cells. Signaling through the cytokine receptor IL-4 stimulates JAK1 and JAK3 to activate STAT6, and signaling through IL-12 stimulates activation of JAK2 and TYK2, and subsequent phosphorylation of STAT4. STAT4 and STAT6 control multiple aspects of CD4+ T helper cell differentiation (Pernis, A. B. and P. B. Rothman (2002). "JAK-STAT signaling in asthma." *J Clin Invest* 109(10): 1279-83). Furthermore, TYK2-deficient mice were found to have enhanced Th2 cell-mediated allergic airway inflammation (Seto, Y., H. Nakajima, et al. (2003). "Enhanced Th2 cell-mediated allergic inflammation in Tyk2-deficient mice." *J Immunol* 170(2): 1077-83). Moreover, multiple cytokines that signal through JAK kinases have been linked to inflammatory diseases or conditions of the upper respiratory tract such as those affecting the nose and sinuses (e.g. rhinitis, sinusitis) whether classically allergic reactions or not.

The JAK/STAT pathway has also been implicated to play a role in inflammatory diseases/conditions of the eye including, but not limited to, iritis, uveitis, scleritis, conjunctivitis, as well as chronic allergic responses. Therefore, inhibition of JAK kinases may have a beneficial role in the therapeutic treatment of these diseases.

The JAK/STAT pathway, and in particular, JAK3, also plays a role in cancers of the immune system. In adult T cell leukemia/lymphoma (ATLL), human CD4+ T cells acquire a transformed phenotype, an event that correlates with acquisition of constitutive phosphorylation of JAKs and STATs. Furthermore, an association between JAK3 and STAT-1, STAT-3, and STAT-5 activation and cell-cycle progression was demonstrated by both propidium iodide staining and bromodeoxyuridine incorporation in cells of four ATLL patients tested. These results imply that JAK/STAT activation is associated with replication of leukemic cells and that therapeutic approaches aimed at JAK/STAT inhibition may be considered to halt neoplastic growth (Takemoto, S., J. C. Mulloy, et al. (1997). "Proliferation of adult T cell leukemia/lymphoma cells is associated with the constitutive activation of JAK/STAT proteins." *Proc Natl Acad Sci USA* 94(25): 13897-902).

Blocking signal transduction at the level of the JAK kinases holds promise for developing treatments for human cancers. Cytokines of the interleukin 6 (IL-6) family, which activate the signal transducer gp130, are major survival and growth factors for human multiple myeloma (MM) cells. The signal transduction of gp130 is believed to involve JAK1, JAK2 and Tyk2 and the downstream effectors STAT3 and the mitogen-activated protein kinase (MAPK) pathways. In IL-6-dependent MM cell lines treated with the JAK2 inhibitor tyrphostin AG490, JAK2 kinase activity and ERK2 and STAT3 phosphorylation were inhibited. Furthermore, cell proliferation was suppressed and apoptosis was induced (De Vos, J., M. Jourdan, et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells." *Br J Haematol* 109(4): 823-8). However, in some cases, AG490 can induce dormancy of tumor cells and actually then protect them from death.

Activation of JAK/STAT in cancers may occur by multiple mechanisms including cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Importantly, activation of STAT signaling, as well as other pathways downstream of JAKs (e.g. Akt), has been correlated with poor prognosis in many cancer types (Bowman, T., et al. *Oncogene* 19:2474-2488, 2000). Moreover, elevated levels of circulating cytokines that signal through JAK/STAT may adversely impact patient health as they are thought to play a causal role in cachexia and/or chronic fatigue. As such, JAK inhibition may be therapeutic for the treatment of cancer patients for reasons that extend beyond potential anti-tumor activity. The cachexia indication may gain further mechanistic support with realization that the satiety factor leptin signals through JAKs.

Pharmacological targeting of Janus kinase 3 (JAK3) has been employed successfully to control allograft rejection and graft versus host disease (GVHD). In addition to its involvement in signaling of cytokine receptors, JAK3 is also engaged in the CD40 signaling pathway of peripheral blood monocytes. During CD40-induced maturation of myeloid dendritic cells (DCs), JAK3 activity is induced, and increases in costimulatory molecule expression, IL-12 production, and potent allogeneic stimulatory capacity are observed. A rationally designed JAK3 inhibitor WHI-P-154 prevented these effects arresting the DCs at an immature level, suggesting that immunosuppressive therapies targeting the tyrosine kinase JAK3 may also affect the function of myeloid cells (Saemann, M. D., C. Diakos, et al. (2003). "Prevention of CD40-triggered dendritic cell maturation and induction of T-cell hyporeactivity by targeting of Janus kinase 3." *Am J Transplant* 3(11): 1341-9). In the mouse model system, JAK3 was also shown to be an important molecular target for treatment of autoimmune insulin-dependent (type 1) diabetes mellitus. The rationally designed JAK3 inhibitor JANEX-1 exhibited potent immunomodulatory activity and delayed the onset of diabetes in the NOD mouse model of autoimmune type 1 diabetes (Cetkovic-Cvrlje, M., A. L. Dragt, et al. (2003). "Targeting JAK3 with JANEX-1 for prevention of autoimmune type 1 diabetes in NOD mice." *Clin Immunol* 106(3): 213-25).

It has been suggested that inhibition of JAK2 tyrosine kinase can be beneficial for patients with myeloproliferative disorder. (Levin, et al., *Cancer Cell*, vol. 7, 2005: 387-397) Myeloproliferative disorder (MPD) includes polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES) and systemic mast cell disease (SMCD). Although the myeloproliferative disorder (such as PV, ET and MMM) are thought to be caused by acquired somatic mutation in hematopoietic progenitors, the genetic basis for these diseases has not been known. However, it has been reported that hematopoietic cells from a majority of patients with PV and a significant number of patients with ET and MMM possess a recurrent somatic activating mutation in the JAK2 tyrosine kinase. It has also been reported that inhibition of the JAK2V617F kinase with a small molecule inhibitor leads to inhibition of proliferation of hematopoietic cells, suggesting that the JAK2 tyrosine kinase is a potential target for pharmacologic inhibition in patients with PV, ET and MMM.

Inhibition of the JAK kinases is also envisioned to have therapeutic benefits in patients suffering from skin immune disorders such as psoriasis, and skin sensitization. In psoriasis vulgaris, the most common form of psoriasis, it has been generally accepted that activated T lymphocytes are important for the maintenance of the disease and its associated psoriatic plaques (Gottlieb, A. B., et al, *Nat Rev Drug Disc.,* 4:19-34). Psoriatic plaques contain a significant immune infiltrate, including leukocytes and monocytes, as well as multiple epidermal layers with increased keratinocyte proliferation. While the initial activation of immune cells in psoriasis occurs by an ill defined mechanism, the maintenance is believed to be dependent on a number of inflammatory cytokines, in addition to various chemokines and growth factors (JCI, 113:1664-1675). Many of these, including interleukins −2, −4, −6, −7, −12, −15, −18, and −23 as well as GM-CSF and IFNg, signal through the Janus (JAK) kinases (*Adv Pharmacol.* 2000;47:113-74). As such, blocking signal transduction at the level of JAK kinases may result in therapeutic benefits in patients suffering from psoriasis or other immune disorders of the skin.

It has been known that certain therapeutics can cause immune reactions such as skin rash or diarrhea in some patients. For instance, administration of some of the new targeted anti-cancer agents such as Iressa, Erbitux, and Tarceva has induced acneiform rash with some patients. Another example is that some therapeutics used topically induce skin irritation, skin rash, contact dermatitis or allergic contact sensitization. For some patients, these immune reactions may be bothersome, but for others, the immune reactions such as rash or diarrhea may result in inability to continue the treatment. Although the driving force behind these immune reactions has not been elucidated completely at the present time, these immune reactions are likely linked to immune infiltrate.

Inhibitors of Janus kinases or related kinases are widely sought and several publications report effective classes of compounds. For example, certain inhibitors are reported in WO 99/65909, US 2004/0198737; WO 2004/099204; WO 2004/099205; and WO 01/42246. Heteroaryl substituted pyrroles and other compounds are reported in WO 2004/72063 and WO 99/62908.

Thus, new or improved agents which inhibit kinases such as Janus kinases are continually needed that act as immunosuppressive agents for organ transplants, as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease), diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics, to name a few. The compounds, compositions and methods described herein are directed toward these needs and other ends.

SUMMARY OF THE INVENTION

The present invention provides compounds of Formula I:

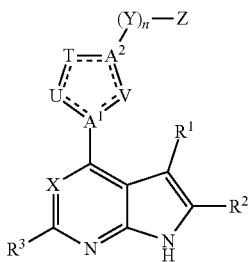

or pharmaceutically acceptable salt forms or prodrugs thereof, wherein constituent members are defined herein.

The present invention further provides compositions comprising a compound of Formula I, or pharmaceutically acceptable salt thereof, and a pharmaceutically acceptable carrier.

The present invention further provides methods of modulating an activity of JAK comprising contacting JAK with a compound of Formula I, or pharmaceutically acceptable salt thereof.

The present invention further provides methods of treating a disease in a patient, wherein the disease is associated with JAK activity, comprising administering to the patient a therapeutically effective amount of a compound of Formula I, or pharmaceutically acceptable salt thereof.

DETAILED DESCRIPTION

The present invention provides, inter alfa, compounds that modulate the activity of one or more JAKs and are useful, for example, in the treatment of diseases associated with JAK expression or activity. The compounds of the invention have Formula I:

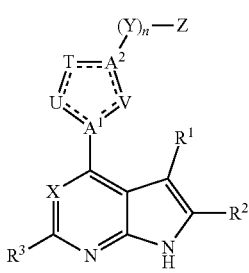

including pharmaceutically acceptable salt forms or prodrugs thereof, wherein:

$A^1$ and $A^2$ are independently selected from C and N;

T, U, and V are independently selected from O, S, N, $CR^5$, and $NR^6$;

wherein the 5-membered ring formed by $A^1$, $A^2$, U, T, and V is aromatic;

X is N or $CR^4$;

Y is $C_{1-8}$ alkylene, $C_{2-8}$ alkenylene, $C_{2-8}$ alkynylene, $(CR^{11}R^{12})_p$—$(C_{3-10}$ cycloalkylene$)$-$(CR^{11}R^{12})_q$, $(CR^{11}R^{12})_p$-(arylene)-$(CR^{11}R^{12})_q$, $(CR^{11}R^{12})_p$—$(C_{1-10}$ heterocycloalkylene$)$-$(CR^{11}R^{12})_q$, $(CR^{11}R^{12})_p$-(heteroarylene)-$(CR^{11}R^{12})_q$, $(CR^{11}R^{12})_pO(CR^{11}R^{12})_q$, $(CR^{11}R^{12})_pS(CR^{11}R^{12})_q$, $(CR^{11}R^{12})_pC(O)(CR^{11}R^{12})_q$, $(CR^{11}R^{12})_pC(O)NR^c(CR^{11}R^{12})_q$, $(CR^{11}R^{12})_pC(O)O(CR^{11}R^{12})_q$, $(CR^{11}R^{12})_pOC(O)(CR^{11}R^{12})_q$, $(CR^{11}R^{12})_pOC(O)NR^c(CR^{11}R^{12})_q$, $(CR^{11}R^{12})_pNR^c(CR^{11}R^{12})_q$, $(CR^{11}R^{12})_pNR^cC(O)NR^d(CR^{11}R^{12})_q$, $(CR^{11}R^{12})_pS(O)(CR^{11}R^{12})_q$, $(CR^{11}R^{12})_pS(O)NR^c(CR^{11}R^{12})_q$, $(CR^{11}R^{12})_pS(O)_2(CR^{11}R^{12})_q$, or $(CR^{11}R^{12})_pS(O)_2NR^c(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from -$D^1$-$D^2$-$D^3$-$D^4$;

Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, =C—$R^i$, =N—$R^i$, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$))R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$))R^b$, and $S(O)_2NR^cR^d$;

wherein when Z is H, n is 1;

or the —$(Y)_n$—Z moiety is taken together with i) $A^2$ to which the moiety is attached, ii) $R^5$ or $R^6$ of either T or V, and iii) the C or N atom to which the $R^5$ or $R^6$ of either T or V is attached to form a 4- to 20-membered aryl, cycloalkyl, heteroaryl, or heterocycloalkyl ring fused to the 5-membered ring formed by $A^1$, $A^2$, U, T, and V, wherein said 4- to 20-membered aryl, cycloalkyl, heteroaryl, or heterocycloalkyl ring is optionally substituted by 1, 2, 3, 4, or 5 substituents independently selected from —$(W)_m$-Q;

W is $C_{1-8}$ alkylenyl, $C_{2-8}$ alkenylenyl, $C_{2-8}$ alkynylenyl, O, S, C(O), $C(O)NR^{c'}$, C(O)O, OC(O), $OC(O)NR^{c'}$, $NR^{c'}$, $NR^{c'}C(O)NR^{d'}$, S(O), $S(O)NR^{c'}$, $S(O)_2$, or $S(O)_2NR^{c'}$;

Q is H, halo, CN, $NO_2$, $C_{1-8}$ alkyl, $C_{2-8}$ alkenyl, $C_{2-8}$ alkynyl, $C_{1-8}$ haloalkyl, halosulfanyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3 or 4 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^2$, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{b'}$, $NR^{c'}C(O)NR^{c'}R^{d'}$, $NR^{c'}C(O)OR^{a'}$, $S(O)R^{b'}$, $S(O)NR^{c'}R^{d'}$, $S(O)_2R^{b'}$, $NR^{c'}S(O)_2R^{b'}$, and $S(O)_2NR^{c'}R^{d'}$;

$Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{b''}$, NR$^{c''}$C(O)OR$^{a''}$, NR$^{c''}$S(O)R$^{b''}$, NR$^{c''}$S(O)$_2$R$^{b''}$, S(O)R$^{b''}$, S(O)NR$^{c''}$R$^{d''}$, S(O)$_2$R$^{b''}$, and S(O)$_2$NR$^{c''}$R$^{d''}$;

R$^1$, R$^2$, R$^3$, and R$^4$ are independently selected from H, halo, C$_{1-4}$ alkyl, C$_{2-4}$ alkenyl, C$_{2-4}$ alkynyl, C$_{1-4}$ haloalkyl, halosulfanyl, aryl, cycloalkyl, heteroaryl, heterocycloalkyl, CN, NO$_2$, OR$^7$, SR$^7$, C(O)R$^8$, C(O)NR$^9$R$^{10}$, C(O)OR$^7$OC(O)R$^8$, OC(O)NR$^9$R$^{10}$, NR$^9$R$^{10}$, NR$^9$C(O)R$^8$, NR$^9$C(O)OR$^7$, S(O)R$^8$, S(O)NR$^9$R$^{10}$, S(O)$_2$R$^8$, NR$^9$S(O)$_2$R$^8$, and S(O)$_2$NR$^9$R$^{10}$;

R$^5$ is H, halo, C$_{1-4}$ alkyl, C$_{2-4}$ alkenyl, C$_{2-4}$ alkynyl, C$_{1-4}$ haloalkyl, halosulfanyl, CN, NO$_2$, OR$^7$, SR$^7$, C(O)R$^8$, C(O)NR$^9$R$^{10}$, C(O)OR$^7$, OC(O)R$^8$, OC(O)NR$^9$R$^{10}$, NR$^9$R$^{10}$, NR$^9$C(O)R$^8$, NR$^9$C(O)OR$^7$, S(O)R$^8$, S(O)NR$^9$R$^{10}$, S(O)$_2$R$^8$, NR$^9$S(O)$_2$R$^8$, or S(O)$_2$NR$^9$R$^{10}$;

R$^6$ is H, C$_{1-4}$ alkyl, C$_{2-4}$ alkenyl, C$_{2-4}$ alkynyl, C$_{1-4}$ haloalkyl, OR$^7$, C(O)R$^8$, C(O)NR$^9$R$^{10}$, C(O)OR$^7$, S(O)R$^8$, S(O)NR$^9$R$^{10}$, S(O)$_2$R$^8$, or S(O)$_2$NR$^9$R$^{10}$;

R$^7$ is H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl;

R$^8$ is H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl;

R$^9$ and R$^{10}$ are independently selected from H, C$_{1-10}$ alkyl, C$_{1-6}$ haloalkyl, C$_{2-6}$ alkenyl, C$_{2-6}$ alkynyl, C$_{1-6}$ alkylcarbonyl, arylcarbonyl, C$_{1-6}$alkylsulfonyl, arylsulfonyl, aryl, heteroaryl, cycloalkyl, heterocycloalkyl, arylalkyl, heteroarylalkyl, cycloalkylalkyl and heterocycloalkylalkyl;

or R$^9$ and R$^{10}$ together with the N atom to which they are attached form a 4-, 5-, 6- or 7-membered heterocycloalkyl group;

R$^{11}$ and R$^{12}$ are independently selected from H and -E$^1$-E$^2$-E$^3$-E$^4$;

D$^1$ and E$^1$ are independently absent or independently selected from C$_{1-6}$ alkylene, C$_{2-6}$ alkenylene, C$_{2-6}$ alkynylene, arylene, cycloalkylene, heteroarylene, and heterocycloalkylene, wherein each of the C$_{1-6}$ alkylene, C$_{2-6}$ alkenylene, C$_{2-6}$ alkynylene, arylene, cycloalkylene, heteroarylene, and heterocycloalkylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

D$^2$ and E$^2$ are independently absent or independently selected from C$_{1-6}$ alkylene, C$_{2-6}$ alkenylene, C$_{2-6}$ alkynylene, (C$_{1-6}$ alkylene)$_r$-O—(C$_{1-6}$ alkylene)$_s$, (C$_{1-6}$ alkylene)$_r$-S—(C$_{1-6}$ alkylene)$_s$, (C$_{1-6}$ alkylene)$_r$-NR$^e$—(C$_{1-6}$ alkylene)$_s$, (C$_{1-6}$ alkylene)$_r$-CO—(C$_{1-6}$ alkylene)$_{s1}$, (C$_{1-6}$ alkylene)$_r$-COO—(C$_{1-6}$ alkylene)$_s$, (C$_{1-6}$ alkylene)$_r$-CONR$^e$—(C$_{1-6}$ alkylene)$_s$, (C$_{1-6}$ alkylene)$_r$-SO—(C$_{1-6}$ alkylene)$_s$, (C$_{1-6}$ alkylene)$_r$-SO$_2$—(C$_{1-6}$ alkylene)$_s$, (C$_{1-6}$ alkylene)$_r$-SONR$^e$—(C$_{1-6}$ alkylene)$_s$, and (C$_{1-6}$ alkylene)$_r$—NR$^e$CONR$^f$—(C$_{1-6}$ alkylene)$_s$, wherein each of the C$_{1-6}$ alkylene, C$_{2-6}$ alkenylene, and C$_{2-6}$ alkynylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

D$^3$ and E$^3$ are independently absent or independently selected from C$_{1-6}$ alkylene, C$_{2-6}$ alkenylene, C$_{2-6}$ alkynylene, arylene, cycloalkylene, heteroarylene, and heterocycloalkylene, wherein each of the C$_{1-6}$ alkylene, C$_{2-6}$ alkenylene, C$_{2-6}$ alkynylene, arylene, cycloalkylene, heteroarylene, and heterocycloalkylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

D$^4$ and E$^4$ are independently selected from H, halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl)R$^b$, and S(O)$_2$NR$^c$R$^d$, wherein said C$_{1-8}$ alkyl, C$_{2-8}$ alkenyl, or C$_{2-8}$ alkynyl, is optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl))R$^b$, and S(O)$_2$NR$^c$R$^d$;

R$^a$ is H, Cy$^1$, —(C$_{1-6}$ alkyl)-Cy$^1$, C$_{1-6}$ alkyl, C$_{1-6}$ haloalkyl, C$_{2-6}$ alkenyl, C$_{2-6}$ alkynyl, wherein said C$_{1-6}$ alkyl, C$_{1-6}$ haloalkyl, C$_{2-6}$ alkenyl, or C$_{2-6}$ alkynyl is optionally substituted with 1, 2, or 3 substituents independently selected from OH, CN, amino, halo, C$_{1-6}$ alkyl, C$_{1-6}$ haloalkyl, halosulfanyl, aryl, arylalkyl, heteroaryl, heteroarylalkyl, cycloalkyl and heterocycloalkyl;

R$^b$ is H, Cy$^1$, —(C$_{1-6}$ alkyl)-Cy$^1$, C$_{1-6}$ alkyl, C$_{1-6}$ haloalkyl, C$_{2-6}$ alkenyl, C$_{2-6}$ alkynyl, wherein said C$_{1-6}$ alkyl, C$_{1-6}$ haloalkyl, C$_{2-6}$ alkenyl, or C$_{2-6}$ alkynyl is optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^{a'}$ and R$^{a''}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, halosulfanyl, aryl, arylalkyl, heteroaryl, heteroarylalkyl, cycloalkyl and heterocycloalkyl;

R$^{b'}$ and R$^{b''}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^c$ and R$^d$ are independently selected from H, Cy$^1$, —(C$_{1-6}$ alkyl)-Cy$^1$, C$_{1-10}$ alkyl, C$_{1-6}$ haloalkyl, C$_{2-6}$ alkenyl, C$_{2-6}$ alkynyl, wherein said C$_{1-10}$ alkyl, C$_{1-6}$ haloalkyl, C$_{2-6}$ alkenyl, or C$_{2-6}$ alkynyl, is optionally substituted with 1, 2, or 3 substituents independently selected from Cy$^1$, —(C$_{1-6}$ alkyl)-Cy$^1$, OH, CN, amino, halo, C$_{1-6}$ alkyl, C$_{1-6}$ haloalkyl, C$_{1-6}$ haloalkyl, and halosulfanyl;

or R$^c$ and R$^d$ together with the N atom to which they are attached form a 4-, 5-, 6- or 7-membered heterocycloalkyl group optionally substituted with 1, 2, or 3 substituents independently selected from $Cy^1$, —($C_{1-6}$ alkyl)-$Cy^1$, OH, CN, amino, halo, $C_{1-6}$ alkyl, $C_{1-6}$ haloalkyl, $C_{1-6}$ haloalkyl, and halosulfanyl;

$R^{c'}$ and $R^{d'}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^{c''}$ and $R^{d''}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, halosulfanyl, $C_{1-6}$ haloalkyl, aryl, arylalkyl, heteroaryl, heteroarylalkyl, cycloalkyl and heterocycloalkyl;

or $R^{c''}$ and $R^{d''}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl; $R^i$ is H, CN, $NO_2$, or $C_{1-6}$ alkyl;

$R^e$ and $R^f$ are independently selected from H and $C_{1-6}$ alkyl;

$R^i$ is H, CN, or $NO_2$;
m is 0 or 1;
n is 0 or 1;
p is 0, 1, 2, 3, 4, 5, or 6;
q is 0, 1, 2, 3, 4, 5 or 6;
r is 0 or 1; and
s is 0 or 1.

In some embodiments, when X is N, n is 1, and the moiety formed by $A^1$, $A^2$, U, T, V, and —$(Y)_n$—Z has the formula:

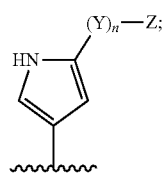

then Y is other than $(CR^{11}R^{12})_pC(O)NR^c(CR^{11}R^{12})_q$.

In some embodiments, when X is N, the 5-membered ring formed by $A^1$, $A^2$, U, T, and V is other than pyrrolyl.

In some embodiments, when X is CH, n is 1, and the moiety formed by $A^1$, $A^2$, U, T, V, and —$(Y)_n$—Z has the formula:

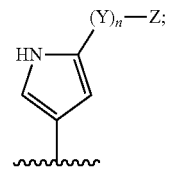

then —$(Y)_n$—Z is other than COOH.

In some embodiments, when X is CH or C-halo, $R^1$, $R^2$, and $R^3$ are each H, n is 1, and the moiety formed by $A^1$, $A^2$, U, T, V, and —$(Y)_n$—Z has the formula:

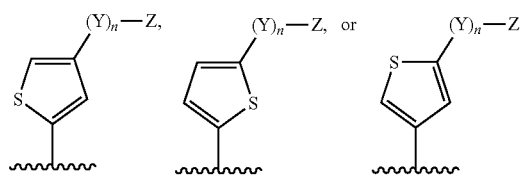

then Y is other than $(CR^{11}R^{12})_pC(O)NR^c(CR^{11}R^{12})_q$ or $(CR^{11}R^{12})_pC(O)(CR^{11}R^{12})_q$.

In some embodiments, when X is CH or C-halo, $R^1$, $R^2$, and $R^3$ are each H, n is 0, and the moiety formed by $A^1$, $A^2$, U, T, V, and —$(Y)_n$—Z has the formula:

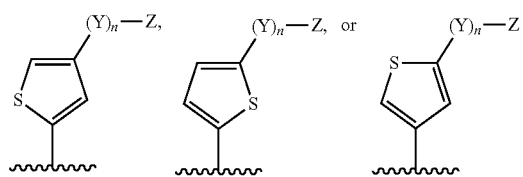

then Z is other than CN, halo, or $C_{1-4}$ alkyl.

In some embodiments, when X is CH or C-halo, $R^1$, $R^2$, and $R^3$ are each H, n is 1, and the moiety formed by $A^1$, $A^2$, U, T, V, and —$(Y)_n$—Z has the formula:

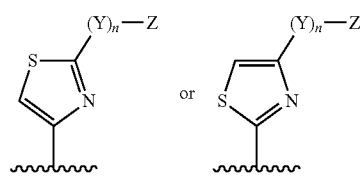

then Y is other than $(CR^{11}R^{12})_pC(O)NR^c(CR^{11}R^{12})_q$ or $(CR^{11}R^{12})_pC(O)(CR^{11}R^{12})_q$.

In some embodiments, when X is CH or C-halo, $R^1$, $R^2$, and $R^3$ are each H, n is 1, and the moiety formed by $A^1$, $A^2$, U, T, V, and —$(Y)_n$—Z has the formula:

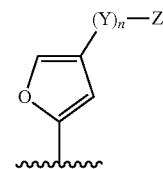

then Y is other than $(CR^{11}R^{12})_pNR^c(CR^{11}R^{12})_q$.

In some embodiments, when X is CH or C-halo and $R^1$, $R^2$, and $R^3$ are each H, then the moiety formed by $A^1$, $A^2$, U, T, V, and $-(Y)_n-Z$ has a formula other than:

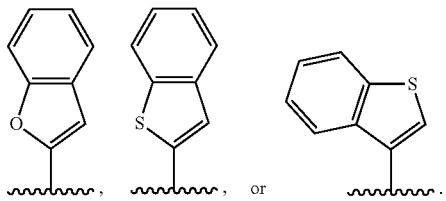

In some embodiments:

Z is H, halo, CN, $NO_2$, $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$;

Q is H, halo, CN, $NO_2$, $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3 or 4 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^2$, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{b'}$, $NR^{c'}C(O)NR^{c'}R^{d'}$, $NR^{c'}C(O)OR^{a'}$, $S(O)R^{b'}$, $S(O)NR^{c'}R^{d'}$, $S(O)_2R^{b'}$, $NR^{c'}S(O)_2R^{b'}$, and $S(O)_2NR^{c'}R^{d'}$;

$Cy^1$ and $Cy^2$ are independently selected from aryl, heteroaryl, cycloalkyl, and heterocyclo-alkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{b''}$, $NR^{c''}C(O)OR^{a''}$, $NR^{c''}S(O)R^{b''}$, $NR^{c''}S(O)_2R^{b''}$, $S(O)R^{b''}$, $S(O)NR^{c''}R^{d''}$, $S(O)_2R^{c''}$, and $S(O)_2NR^{c''}R^{d''}$;

$R^1$, $R^2$, $R^3$, and $R^4$ are independently selected from H, halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^7$, $SR^7$, $C(O)R^8$, $C(O)NR^9R^{10}$, $C(O)OR^7OC(O)R^8$, $OC(O)NR^9R^{10}$, $NR^9R^{10}$, $NR^9C(O)R^8$, $NR^cC(O)OR^7$, $S(O)R^8$, $S(O)NR^9R^{10}$, $S(O)_2R^8$, $NR^9S(O)_2R^8$, and $S(O)_2NR^9R^{10}$;

$R^5$ is H, halo, $C_{1-4}$ alkyl, $C_{2-4}$ alkenyl, $C_{2-4}$ alkynyl, $C_{1-4}$ haloalkyl, CN, $NO_2$, $OR^7$, $SR^7$, $C(O)R^8$, $C(O)NR^9R^{10}$, $C(O)OR^7$, $OC(O)R^8$, $OC(O)NR^9R^{10}$, $NR^9R^{10}$, $NR^9C(O)R^8$, $NR^9C(O)OR^7$, $S(O)R^8$, $S(O)NR^9R^{10}$, $S(O)_2R^8$, $NR^9S(O)_2R^8$, or $S(O)_2NR^9R^{10}$;

$R^6$ is H, $C_{1-4}$ alkyl, $C_{2-4}$ alkenyl, $C_{2-4}$ alkynyl, $C_{1-4}$ haloalkyl, $OR^7$, $C(O)R^8$, $C(O)NR^9R^{10}$, $C(O)OR^7$, $S(O)R^8$, $S(O)NR^9R^{10}$, $S(O)_2R^8$, or $S(O)_2NR^9R^{10}$;

$R^7$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^8$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^9$ and $R^{10}$ are independently selected from H, $C_{1-10}$ alkyl, $C_{1-6}$ haloalkyl, $C_{2-6}$ alkenyl, $C_{2-6}$ alkynyl, $C_{1-6}$ alkylcarbonyl, arylcarbonyl, $C_{1-6}$ alkylsulfonyl, arylsulfonyl, aryl, heteroaryl, cycloalkyl, heterocycloalkyl, arylalkyl, heteroarylalkyl, cycloalkylalkyl and heterocycloalkylalkyl;

or $R^9$ and $R^{10}$ together with the N atom to which they are attached form a 4-, 5-, 6- or 7-membered heterocycloalkyl group;

$R^{11}$ and $R^{12}$ are independently selected from H, halo, OH, CN, $C_{1-4}$ alkyl, $C_{1-4}$ haloalkyl, $C_{2-4}$ alkenyl, $C_{2-4}$ alkynyl, $C_{1-4}$ hydroxyalkyl, $C_{1-4}$ cyanoalkyl, aryl, heteroaryl, cycloalkyl, and heterocycloalkyl;

$R^a$, $R^{a'}$, and $R^{a''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cyclo-alkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, aryl, arylalkyl, heteroaryl, heteroarylalkyl, cycloalkyl and heterocycloalkyl;

$R^b$, $R^{b'}$ and $R^{b''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cyclo-alkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, hetero-aryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^{c'}$ and $R^{d'}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, hetero-aryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^{c''}$ and $R^{d''}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, hetero-aryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl; and or $R^{c''}$ and $R^{d''}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl aryl, arylalkyl, heteroaryl, heteroarylalkyl, cycloalkyl and heterocycloalkyl.

In some embodiments, X is N.
In some embodiments, X is $CR^4$.
In some embodiments, $A^1$ is C.
In some embodiments, $A^1$ is N.
In some embodiments, $A^2$ is C.
In some embodiments, $A^2$ is N.
In some embodiments, at least one of $A^1$, $A^2$, U, T, and V is N.

In some embodiments, the 5-membered ring formed by $A^1$, $A^2$, U, T, and V is pyrrolyl, pyrazolyl, imidazolyl, oxazolyl, thiazolyl, or oxadiazolyl.

In some embodiments, the 5-membered ring formed by $A^1$, $A^2$, U, T, and V is selected from:

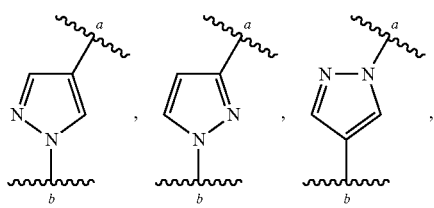

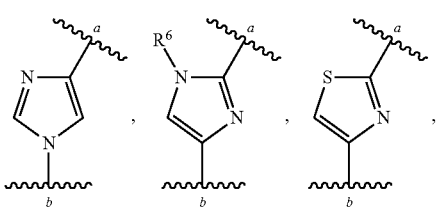

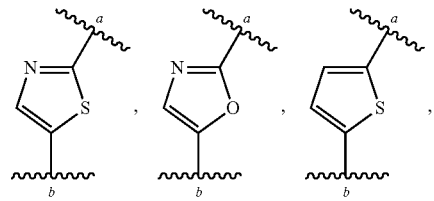

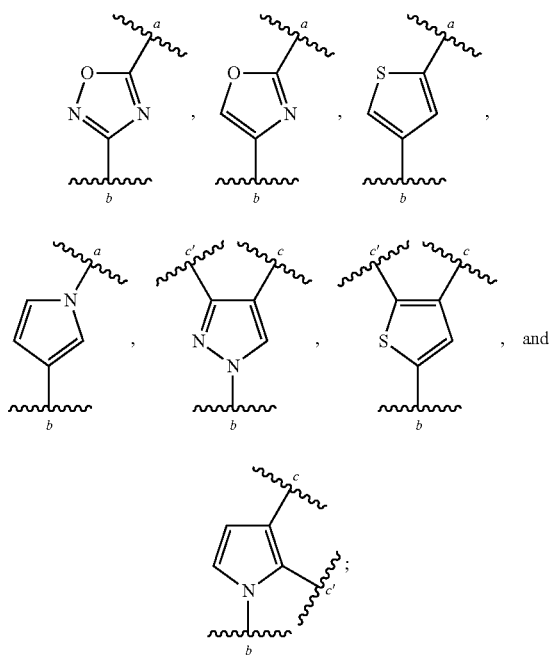

wherein:
a designates the site of attachment of moiety $-(Y)_n-Z$;
b designates the site of attachment to the core moiety:

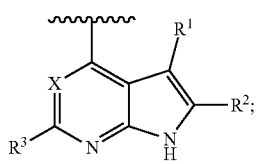

and c and c' designate the two sites of attachment of the fused 4- to 20-membered aryl, cycloalkyl, heteroaryl, or heterocycloalkyl ring.

In some embodiments, the 5-membered ring formed by $A^1$, $A^2$, U, T, and V is selected from:

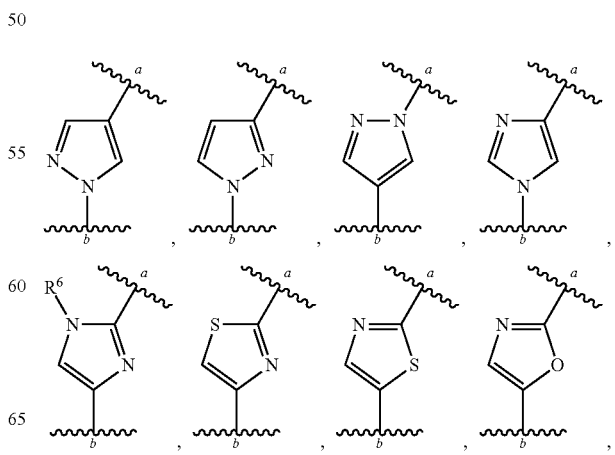

-continued

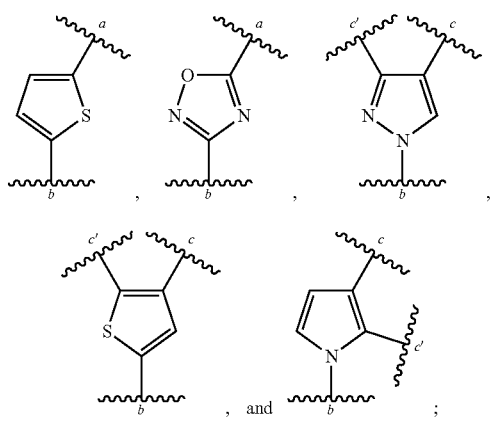

wherein:
a designates the site of attachment of moiety —(Y)$_n$—Z;
b designates the site of attachment to the core moiety:

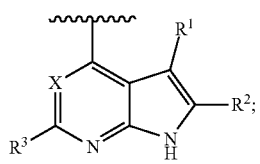

and
c and c' designate the two sites of attachment of the fused 4- to 20-membered aryl, cycloalkyl, heteroaryl, or heterocycloalkyl ring.

In some embodiments, the 5-membered ring formed by A$^1$, A$^2$, U, T, and V is selected from:

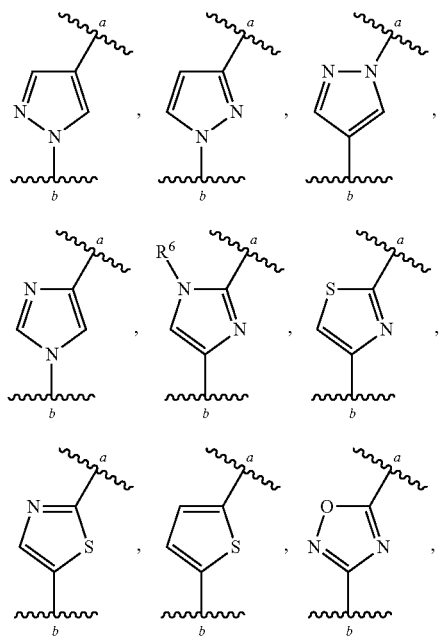

-continued

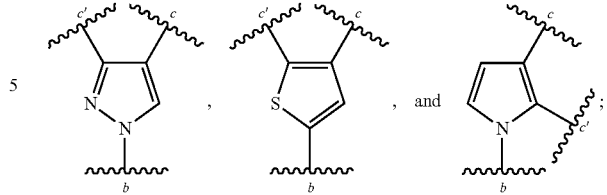

wherein:
a designates the site of attachment of moiety —(Y)$_n$—Z;
b designates the site of attachment to the core moiety:

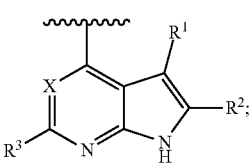

and
c and c' designate the two sites of attachment of the fused 4- to 20-membered aryl, cycloalkyl, heteroaryl, or heterocycloalkyl ring.

In some embodiments, the 5-membered ring formed by A$^1$, A$^2$, U, T, and V is selected from:

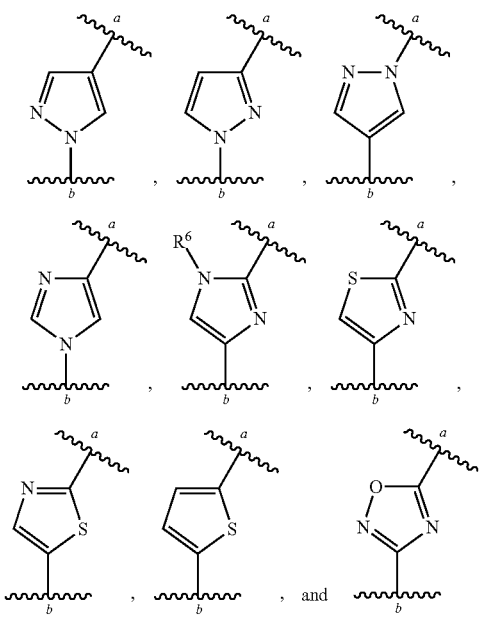

wherein:
a designates the site of attachment of moiety —(Y)$_n$—Z;
b designates the site of attachment to the core moiety:

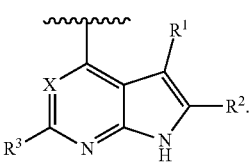

In some embodiments, the 5-membered ring formed by A$^1$, A$^2$, U, T, and V is selected from:

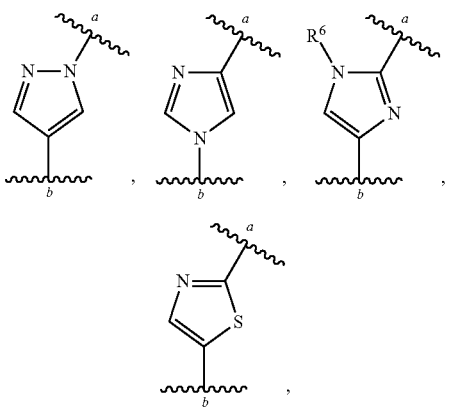

wherein:
  a designates the site of attachment of moiety —(Y)$_n$—Z;
  b designates the site of attachment to the core moiety:

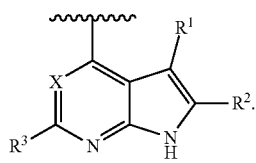

In some embodiments, the 5-membered ring formed by A$^1$, A$^2$, U, T, and V is selected from:

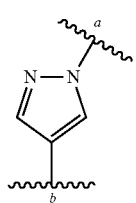 [SMILES: *c1cnn(*)c1]

wherein:
  a designates the site of attachment of moiety —(Y)$_n$—Z;
  b designates the site of attachment to the core moiety:

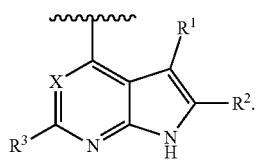

In some embodiments, n is 0.
In some embodiments, n is 1.
In some embodiments, n is 1 and Y is C$_{1-8}$ alkylene, C$_{2-8}$ alkenylene, (CR$^{11}$R$^{12}$)$_p$C(O)(CR$^{11}$R$^{12}$)$_q$, (CR$^{11}$R$^{12}$)$_p$C(O)NR$^c$(CR$^{11}$R$^{12}$)$_q$, (CR$^{11}$R$^{12}$)$_p$C(O)O(CR$^{11}$R$^{12}$)$_q$, (CR$^{11}$R$^{12}$)$_p$OC(O)(CR$^{11}$R$^{12}$)$_q$, wherein said C$_{1-8}$ alkylene or C$_{2-8}$ alkenylene, is optionally substituted with 1, 2, or 3 halo, OH, CN, amino, C$_{1-4}$ alkylamino, or C$_{2-8}$ dialkylamino.
In some embodiments, n is 1 and Y is C$_{1-8}$ alkylene, (CR$^{11}$R$^{12}$)$_p$C(O)(CR$^{11}$R$^{12}$)$_q$, (CR$^{11}$R$^{12}$)$_p$C(O)NR$^c$(CR$^{11}$R$^{12}$)$_q$, (CR$^{11}$R$^{12}$)$_p$C(O)O(CR$^{11}$R$^{12}$)$_q$, wherein said C$_{1-8}$ alkylene is optionally substituted with 1, 2, or 3 halo, OH, CN, amino, C$_{1-4}$ alkylamino, or C$_{2-8}$ dialkylamino
In some embodiments, n is 1 and Y is C$_{1-8}$ alkylene optionally substituted with 1, 2, or 3 halo, OH, CN, amino, C$_{1-4}$ alkylamino, or C$_{2-8}$ dialkylamino.
In some embodiments, n is 1 and Y is ethylene optionally substituted with 1, 2, or 3 halo, OH, CN, amino, C$_{1-4}$ alkylamino, or C$_{2-8}$ dialkylamino.
In some embodiments, n is 1 and Y is (CR$^{11}$R$^{12}$)$_p$C(O)(CR$^{11}$R$^{12}$)$_q$(CR$^{11}$R$^{12}$)$_p$C(O)NR$^c$—(CR$^{11}$R$^{12}$)$_q$, or CR$^{11}$R$^{12}$)$_p$C(O)O(CR$^{11}$R$^{12}$)$^q$.
In some embodiments, Y is C$_{1-8}$ alkylene, C$_{2-8}$ alkenylene, C$_{2-8}$ alkynylene, (CR$^{11}$R$^{12}$)$_p$—(C$_{3-10}$ cycloalkylene)-(CR$^{11}$R$^{12}$)$_q$, (CR$^{11}$R$^{12}$)$_p$-(arylene)-(CR$^{11}$R$^{12}$)$_q$, (CR$^{11}$R$^{12}$)$_p$—(C$_{1-10}$ heterocycloalkylene)-(CR$^{11}$R$^{12}$)$_q$, (CR$^{11}$R$^{12}$)$_p$-(heteroarylene)-(CR$^{11}$R$^{12}$)$_q$, (CR$^{11}$R$^{12}$)$_p$O(CR$^{11}$R$^{12}$)$_q$, or (CR$^{11}$R$^{12}$)$_p$S(CR$^{11}$R$^{12}$)$_q$, wherein said C$_{1-8}$ alkylene, C$_{2-8}$ alkenylene, C$_{2-8}$ alkynylene, cycloalkylene, arylene, heterocycloalkylene, or heteroarylene, is optionally substituted with 1, 2, or 3 substituents independently selected from -D$^1$-D$^2$-D$^3$-D$^4$.
In some embodiments, Y is C$_{1-8}$ alkylene, C$_{2-8}$ alkenylene, C$_{2-8}$ alkynylene, (CR$^{11}$R$^{12}$)$_p$—(C$_{3-10}$ cycloalkylene)-(CR$^{11}$R$^{12}$)$_q$, (CR$^{11}$R$^{12}$)$_p$-(arylene)-(CR$^{11}$R$^{12}$)$_q$, (CR$^{11}$R$^{12}$)$_p$—(C$_{1-10}$ heterocycloalkylene)-(CR$^{11}$R$^{12}$)$_q$, (CR$^{11}$R$^{12}$)$_p$-(heteroarylene)-(CR$^{11}$R$^{12}$)$_q$, (CR$^{11}$R$^{12}$)$_p$O(CR$^{11}$R$^{12}$)$_q$, or (CR$^{11}$R$^{12}$)$_p$S(CR$^{11}$R$^{12}$)$_q$, wherein said C$_{1-8}$ alkylene, C$_{2-8}$ alkenylene, C$_{2-8}$ alkynylene, cycloalkylene, arylene, heterocycloalkylene, or heteroarylene, is optionally substituted with 1, 2, or 3 substituents independently selected from D$^4$.
In some embodiments, Y is C$_{1-8}$ alkylene, C$_{2-8}$ alkenylene, C$_{2-8}$ alkynylene, or (CR$^{11}$R$^{12}$)$_p$—(C$_{3-10}$ cycloalkylene)-(CR$^{11}$R$^{12}$)$_q$, wherein said C$_{1-8}$ alkylene, C$_{2-8}$ alkenylene, C$_{2-8}$ alkynylene, or cycloalkylene, is optionally substituted with 1, 2, or 3 substituents independently selected from -D$^1$-D$^2$-D$^3$-D$^4$.
In some embodiments, Y is C$_{1-8}$ alkylene, C$_{2-8}$ alkenylene, C$_{2-8}$ alkynylene, or (CR$^{11}$R$^{12}$)$_p$—(C$_{3-10}$ cycloalkylene)-(CR$^{11}$R$^{12}$)$_q$, wherein said C$_{1-8}$ alkylene, C$_{2-8}$ alkenylene, C$_{2-8}$ alkynylene, or cycloalkylene, is optionally substituted with 1, 2, or 3 substituents independently selected from D$^4$.
In some embodiments, Y is C$_{1-8}$ alkylene, C$_{2-8}$ alkenylene, or C$_{2-8}$ alkynylene, each optionally substituted with 1, 2, or 3 substituents independently selected from -D$^1$-D$^2$-D$^3$-D$^4$.
In some embodiments, Y is C$_{1-8}$ alkylene optionally substituted with 1, 2, or 3 substituents independently selected from -D$^1$-D$^2$-D$^3$-D$^4$.
In some embodiments, Y is C$_{1-8}$ alkylene optionally substituted with 1, 2, or 3 substituents independently selected from D$^4$.
In some embodiments, Y is C$_{1-8}$ alkylene, C$_{2-8}$ alkenylene, C$_{2-8}$ alkynylene, (CR$^{11}$R$^{12}$)$_p$O—(CR$^{11}$R$^{12}$)$_q$, (CR$^{11}$R$^{12}$)$_p$S(CR$^{11}$R$^{12}$)$_q$, (CR$^{11}$R$^{12}$)$_p$C(O)(CR$^{11}$R$^{12}$)$_q$, (CR$^{11}$R$^{12}$)$_p$C(O)NR$^c$(CR$^{11}$R$^{12}$)$_q$, (CR$^{11}$R$^{12}$)$_p$C(O)O(CR$^{11}$R$^{12}$)$_q$, (CR$^{11}$R$^{12}$)$_p$OC(O)(CR$^{11}$R$^{12}$)$_q$, (CR$^{11}$R$^{12}$)$_p$OC(O)NR$^c$(CR$^{11}$R$^{12}$)$_q$, (CR$^{11}$R$^{12}$)$_p$NR$^c$(CR$^{11}$R$^{12}$)$_q$, (CR$^{11}$R$^{12}$)$_p$NR$^c$C(O)NR$^d$(CR$^{11}$R$^{12}$)$_q$, (CR$^{11}$R$^{12}$)$_p$S(O)(CR$^{11}$R$^{12}$)$_q$, (CR$^{11}$R$^{12}$)$_p$S(O)NR$^c$(CR$^{11}$R$^{12}$)$_q$, (CR$^{11}$R$^{12}$)$_p$S(O)$_2$(CR$^{11}$R$^{12}$)$_q$, or (CR$^{11}$R$^{12}$)$_p$S(O)$_2$NR$^c$(CR$^{11}$R$^{12}$)$_q$, wherein said C$_{1-8}$ alkylene, C$_{2-8}$ alkenylene, C$_{2-8}$ alkynylene is optionally substituted with 1, 2, or 3 substituents independently selected from halo, OH, CN, amino, C$_{1-4}$ alkylamino, and C$_{2-8}$ dialkylamino.

In some embodiments, Y is $C_{1-8}$ alkylene, $C_{2-8}$ alkenylene, $C_{2-8}$ alkynylene, $(CR^{11}R^{12})_p$—$(C_{3-10}$ cycloalkylene$)$-$(CR^{11}R^{12})_q$, $(CR^{11}R^{12})_p$-(arylene)-$(CR^{11}R^{12})_q$, $(CR^{11}R^{12})_p$-$(C_{1-10}$ heterocycloalkylene$)$-$(CR^{11}R^{12})_q$, $(CR^{11}R^{12})_p$-(heteroarylene)-$(CR^{11}R^{12})_q$, $(CR^{11}R^{12})_p O$ $(CR^{11}R^{12})_q$, $(CR^{11}R^{12})_p S(CR^{11}R^{12})_q$, $(CR^{11}R^{12})_p C(O)$ $(CR^{11}R^{12})_q$, $(CR^{11}R^{12})_p C(O)NR^c(CR^{11}R^{12})_q$, $(CR^{11}R^{12})_p C(O)O(CR^{11}R^{12})_q$, $(CR^{11}R^{12})_p OC(O)(CR^{11}R^{12})_q$, $(CR^{11}R^{12})_p OC(O)NR^c(CR^{11}R^{12})_q$, $(CR^{11}R^{12})_p NR^c(CR^{11}R^{12})_q$, $(CR^{11}R^{12})_p NR^c C(O)NR^d(CR^{11}R^{12})_q$, $(CR^{11}R^{12})_p S(O)$ $(CR^{11}R^{12})_q$, $(CR^{11}R^{12})_p S(O)NR^c(CR^{11}R^{12})_q$, $(CR^{11}R^{12})_p S(O)_2(CR^{11}R^{12})_q$, or $(CR^{11}R^{12})_p S(O)_2 NR^c(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from halo, OH, CN, amino, $C_{1-4}$ alkylamino, and $C_{2-8}$ dialkylamino.

In some embodiments, p is 0.

In some embodiments, p is 1.

In some embodiments, p is 2.

In some embodiments, q is 0.

In some embodiments, q is 1.

In some embodiments, q is 2.

In some embodiments, one of p and q is 0 and the other of p and q is 1, 2, or 3.

In some embodiments, Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$)R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$))R^b$, and $S(O)_2NR^cR^d$.

In some embodiments, Z is aryl, cycloalkyl, heteroaryl, or heterocycloalkyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, CN, $NO_2$, $OR^a$, $SR^a$, $C(O)R^b$, $C(O)NR^cR^d$, $C(O)OR^a$, $OC(O)R^b$, $OC(O)N^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is aryl, cycloalkyl, heteroaryl, or heterocycloalkyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is aryl or heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is aryl or heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is phenyl or 5- or 6-membered heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is phenyl or 5- or 6-membered heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is phenyl optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxy-alkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is phenyl optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is cycloalkyl or heterocycloalkyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is cycloalkyl or heterocycloalkyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is cyclopropyl, cyclobutyl, cyclopentyl, cyclohexyl, or cycloheptyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is $C_{1-8}$ alkyl, $C_{2-8}$ alkenyl, or $C_{2-8}$ alkynyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is $C_{1-8}$ alkyl, $C_{2-8}$ alkenyl, or $C_{2-8}$ alkynyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_1$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is aryl, cycloalkyl, heteroaryl, or heterocycloalkyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is aryl, cycloalkyl, heteroaryl, or heterocycloalkyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is aryl or heteroaryl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is aryl or heteroaryl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is phenyl or 5- or 6-membered heteroaryl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is phenyl or 5- or 6-membered heteroaryl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is phenyl optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is phenyl optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is cycloalkyl or heterocycloalkyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is cycloalkyl or heterocycloalkyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is $C_{1-8}$ alkyl, $C_{2-8}$ alkenyl, or $C_{2-8}$ alkynyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is $C_{1-8}$ alkyl, $C_{2-8}$ alkenyl, or $C_{2-8}$ alkynyl, each optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, Z is $C_{1-8}$ alkyl, $C_{2-8}$ alkenyl, $C_{2-8}$ alkynyl, aryl, cycloalkyl, heteroaryl, or heterocycloalkyl, each optionally substituted with 1, 2, 3, 4, 5, or 6 substituents independently selected from halo, $C_{1-4}$ alkyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $C(O)NR^cR^d$, $C(O)OR^a$, $NR^cR^d$, $NR^cC(O)R^b$, and $S(O)_2R^b$.

In some embodiments, Z is $C_{1-8}$ alkyl, $C_{2-8}$ alkenyl, $C_{2-8}$ alkynyl, aryl, cycloalkyl, heteroaryl, or heterocycloalkyl, each optionally substituted with 1, 2, 3, 4, 5, or 6 substituents independently selected from halo, $C_{1-4}$ alkyl, $C_{1-4}$ haloalkyl, $C_{1-4}$ hydroxyalkyl, $C_{1-4}$ cyanoalkyl, $Cy^1$, CN, $NO_2$, $OR^a$, $C(O)NR^cR^d$, $C(O)OR^a$, $NR^cR^d$, $NR^cC(O)R^b$, and $S(O)_2R^b$.

In some embodiments, Z is $C_{1-8}$ alkyl, $C_{2-8}$ alkenyl, $C_{2-8}$ alkynyl, aryl, cycloalkyl, heteroaryl, or heterocycloalkyl, each optionally substituted with 1, 2, or 3 substituents independently selected from halo, $C_{1-4}$ alkyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $C(O)NR^cR^d$, $C(O)OR^a$, $NR^cR^d$, $NR^cC(O)R^b$, and $S(O)_2R^b$.

In some embodiments, Z is $C_{1-8}$ alkyl, $C_{2-8}$ alkenyl, $C_{2-8}$ alkynyl, aryl, cycloalkyl, heteroaryl, or heterocycloalkyl, each optionally substituted with 1, 2, or 3 substituents independently selected from halo, $C_{1-4}$ alkyl, $C_{1-4}$ haloalkyl, $C_{1-4}$ hydroxyalkyl, $C_{1-4}$ cyanoalkyl, $Cy^1$, CN, $NO_2$, $OR^a$, $C(O)NR^cR^d$, $C(O)OR^a$, $NR^cR^d$, $NR^cC(O)R^b$, and $S(O)_2R^b$.

In some embodiments, Z is substituted with at least one substituent comprising at least one CN group.

In some embodiments, Z is $C_{1-8}$ alkyl, $C_{2-8}$ alkenyl, $C_{2-8}$ alkynyl, aryl, cycloalkyl, heteroaryl, or heterocycloalkyl, each substituted with at least one CN or $C_{1-4}$ cyanoalkyl and optionally substituted with 1, 2, 3, 4, or 5 further substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2 R^b$, $NR^cS(O)_2R^b$, and $S(O)_2NR^cR^d$.

In some embodiments, Z is $C_{1-8}$ alkyl, $C_{2-8}$ alkenyl, $C_{2-8}$ alkynyl, aryl, cycloalkyl, heteroaryl, or heterocycloalkyl, each substituted with at least one CN or $C_{1-4}$ cyanoalkyl and optionally substituted with 1, 2, 3, 4, or 5 further substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, wherein the $—(Y)_n—Z$ moiety is taken together with i) $A^2$ to which said moiety is attached, ii) $R^5$ or $R^6$ of either T or V, and iii) the C or N atom to which said $R^5$ or $R^6$ of either T or V is attached to form a 4- to 20-membered aryl, cycloalkyl, heteroaryl, or heterocycloalkyl ring fused to the 5-membered ring formed by $A^1$, $A^2$, U, T, and V, wherein said 4- to 20-membered aryl, cycloalkyl, heteroaryl, or heterocycloalkyl ring is optionally substituted by 1, 2, 3, 4, or 5 substituents independently selected from $—(W)_m-Q$.

In some embodiments, wherein the $—(Y)_n—Z$ moiety is taken together with i) $A^2$ to which said moiety is attached, ii) $R^5$ or $R^6$ of either T or V, and iii) the C or N atom to which said $R^5$ or $R^6$ of either T or V is attached to form a 4- to 8-membered aryl, cycloalkyl, heteroaryl, or heterocycloalkyl ring fused to the 5-membered ring formed by $A^1$, $A^2$, U, T, and V, wherein said 4- to 8-membered aryl, cycloalkyl, heteroaryl, or heterocycloalkyl ring is optionally substituted by 1, 2, 3, 4, or 5 substituents independently selected from $—(W)_m-Q$.

In some embodiments, the $—(Y)_n—Z$ moiety is taken together with i) $A^2$ to which said moiety is attached, ii) $R^5$ or $R^6$ of either T or V, and iii) the C or N atom to which said $R^5$ or $R^6$ of either T or V is attached to form a 6-membered aryl, cycloalkyl, heteroaryl, or heterocycloalkyl ring fused to the 5-membered ring formed by $A^1$, $A^2$, U, T, and V, wherein said 6-membered aryl, cycloalkyl, heteroaryl, or heterocycloalkyl ring is optionally substituted by 1, 2, or 3 substituents independently selected from halo, CN, $NO_2$, $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted by 1, 2 or 3 CN.

In some embodiments, $Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{b''}$, $NR^{c''}C(O)OR^{a''}$, $S(O)R^{b''}$, $S(O)NR^{c''}R^{d''}$, $S(O)_2R^{b''}$, and $S(O)_2NR^{c''}R^{d''}$.

In some embodiments, $Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$ $OC(O)NR^{c''}R^{d''}$, $NR^{c''}R^{d''}$, $NR^{c''}C(O)R^{b''}$, $NR^{c''}(O)OR^{a''}$, $S(O)R^{b''}$, $S(O)NR^{c''}R^{d''}$, $S(O)_2R^{b''}$, and $S(O)_2NR^{c''}R^{d''}$.

In some embodiments, $Cy^1$ and $Cy^2$ are independently selected from cycloalkyl and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{b''}$, $NR^{c''}C(O)OR^{a''}$, $S(O)R^{b''}$, $S(O)NR^{c''}R^{d''}$, $S(O)_2R^{b''}$, and $S(O)_2NR^{c''}R^{d''}$.

In some embodiments, $Cy^1$ and $Cy^2$ are independently selected from cycloalkyl optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{b''}$, $NR^cR^{d''}C(O)OR^{a''}$, $S(O)R^{b''}$, $S(O)NR^{c''}R^{d''}$, $S(O)_2R^{b''}$, and $S(O)_2NR^{c''}R^{d''}$.

In some embodiments, $R^1$, $R^2$, $R^3$, and $R^4$ are independently selected from H, halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^7$, $SR^7$, $C(O)R^8$, $C(O)NR^9R^{10}$, $C(O)OR^7OC(O)R^8$, $OC(O)NR^9R^{10}$, $NR^9R^{10}$, $NR^9C(O)R^8$, $NR^9C(O)OR^7$, $S(O)R^8$, $S(O)NR^9R^{10}$, $S(O)_2R^8$, $NR^9S(O)_2R^8$, and $S(O)_2NR^9R^{10}$.

In some embodiments, $R^1$, $R^2$, $R^3$, and $R^4$ are independently selected from H, halo, and $C_{1-4}$ alkyl.

In some embodiments, $R^1$, $R^2$, $R^3$, and $R^4$ are each H.

In some embodiments, $R^1$ is H, halo, or $C_{1-4}$ alkyl.

In some embodiments, $R^5$ is H, halo, $C_{1-4}$ alkyl, $C_{2-4}$ alkenyl, $C_{2-4}$ alkynyl, $C_{1-4}$ haloalkyl, CN, $NO_2$, $OR^7$, $SR^7$, $C(O)R^8$, $C(O)NR^9R^{10}$, $C(O)OR^7$, $OC(O)R^8$, $OC(O)NR^9R^{10}$, $NR^9R^{10}$, $NR^9C(O)R^8$, $NR^9C(O)OR^7$, $S(O)R^8$, $S(O)NR^9R^{10}$, $S(O)_2R^8$, $NR^9S(O)_2R^8$, or $S(O)_2NR^9R^{10}$.

In some embodiments, $R^5$ is H, halo, $C_{1-4}$ alkyl, $C_{1-4}$ haloalkyl, halosulfanyl, CN, or $NR^9R^{10}$.

In some embodiments, $R^5$ is H, halo, $C_{1-4}$ alkyl, $C_{1-4}$ haloalkyl, CN, or $NR^9R^{10}$.

In some embodiments, $R^5$ is H.

In some embodiments, $R^6$ is H or $C_{1-4}$ alkyl.

In some embodiments, $R^6$ is H.

In some embodiments, $R^{11}$ and $R^{12}$ are independently selected from H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$))R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)$ NR$^c$R$^d$, NR$^c$C(=NR$^i$)NR$^c$NR$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl))R$^b$, and S(O)$_2$NR$^c$R$^d$.

In some embodiments, R$^{11}$ and R$^{12}$ are independently selected from H, halo, OH, CN, C$_{1-4}$ alkyl, C$_{1-4}$ haloalkyl, halosulfanyl, SCN, C$_{2-4}$ alkenyl, C$_{2-4}$ alkynyl, C$_{1-4}$ hydroxyalkyl, C$_{1-4}$ cyanoalkyl, aryl, heteroaryl, cycloalkyl, and heterocycloalkyl.

In some embodiments, R$^{11}$ and R$^{12}$ are independently selected from H, halo, OH, CN, C$_{1-4}$ alkyl, C$_{1-4}$ haloalkyl, C$_{2-4}$ alkenyl, C$_{2-4}$ alkynyl, C$_{1-4}$ hydroxyalkyl, C$_{1-4}$ cyanoalkyl, aryl, heteroaryl, cycloalkyl, and heterocycloalkyl.

In some embodiments, the compound has Formula Ia or Ib:

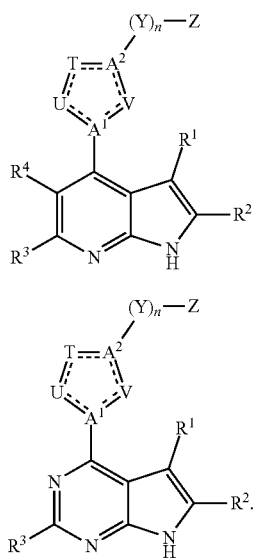

In some embodiments, the compound has Formula II:

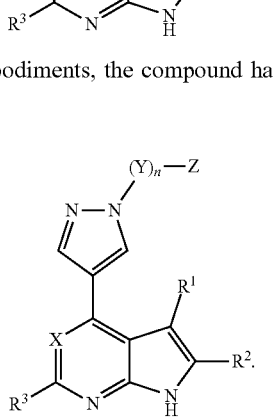

In some embodiments, the compound has Formula IIIa or IIIb:

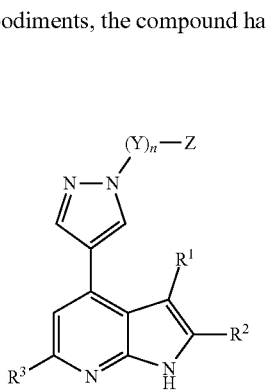

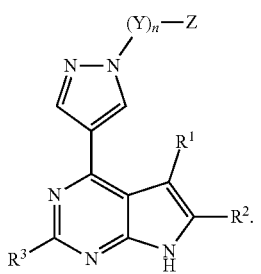

In some embodiments, the compound has Formula IV:

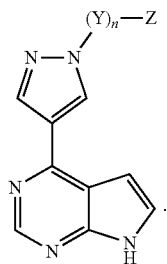

In some embodiments, the compound has Formula Va:

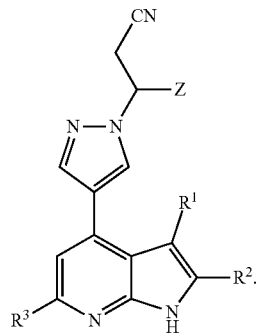

In some embodiments, the compound has Formula Vb:

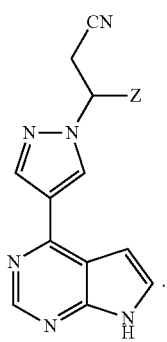

In some embodiments, the compound has Formula VIa:

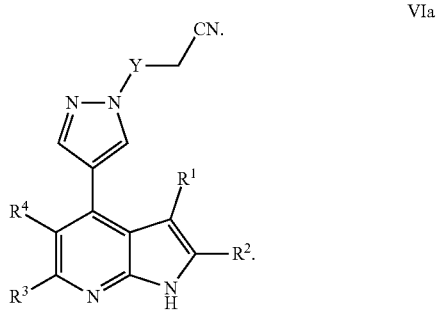

VIa

In some embodiments, the compound has Formula VIb:

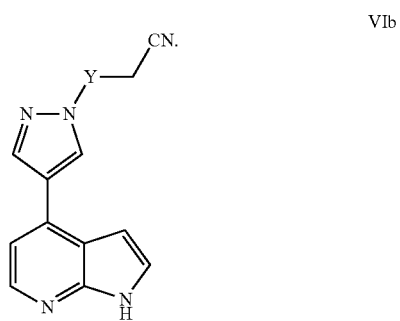

VIb

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, linking substituents are described. It is specifically intended that each linking substituent include both the forward and backward forms of the linking substituent. For example, —NR(CR'R")$_n$— includes both NR(CR'R")$_n$ and —(CR'R")$_n$NR—. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. A linking alkyl group is referred to herein as "alkylene."

As used herein, "alkenyl" refers to an alkyl group having one or more double carbon-carbon bonds. Example alkenyl groups include ethenyl, propenyl, cyclohexenyl, and the like. A linking alkenyl group is referred to herein as "alkenylene."

As used herein, "alkynyl" refers to an alkyl group having one or more triple carbon-carbon bonds. Example alkynyl groups include ethynyl, propynyl, and the like. A linking alkynyl group is referred to herein as "alkynylene."

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "halosulfanyl" refers to a sulfur group having one or more halogen substituents. Example halosulfanyl groups include pentahalosulfanyl groups such as $SF_5$.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms. A linking aryl group is referred to herein as "arylene."

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like. A cycloalkyl group containing a fused aromatic ring can be attached through any ring-forming atom including a ring-forming atom of the fused aromatic ring. A linking cycloalkyl group is referred to herein as "cycloalkylene."

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms. A linking heteroaryl group is referred to herein as "heteroarylene."

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Heterocycloalkyl groups include monocyclic and polycyclic (e.g., having 2, 3 or 4 fused rings) systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. The heterocycloalkyl group can be attached through a ring-forming carbon atom or a ring-forming heteroatom. The heterocycloalkyl group containing a fused aromatic ring can be attached through any ring-forming atom including a ring-forming atom of the fused aromatic ring. In some embodiments, the heterocycloalkyl group has from 1 to about 20 carbon atoms, and in further embodiments from about 3 to about 20 carbon atoms. In some embodiments, the heterocycloalkyl group contains 3 to about 14, 4 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double or triple bonds. In some embodiments, the heterocycloalkyl group contains 0 to 2 double or triple bonds. A linking heterocycloalkyl group is referred to herein as "heterocycloalkylene."

As used herein, "halo" or "halogen" includes fluoro, chloro, bromo, and iodo.

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocycloalkylalkyl" refers to alkyl substituted by heterocycloalkyl.

As used herein, "amino" refers to $NH_2$.

As used herein, "alkylamino" refers to an amino group substituted by an alkyl group.

As used herein, "dialkylamino" refers to an amino group substituted by two alkyl groups.

As used herein, "hydroxylalkyl" refers to an alkyl group substituted by hydroxyl.

As used herein, "cyanoalkyl" refers to an alkyl group substituted by cyano. The carbon of the cyano group is typically not counted if a carbon count precedes the term. For example, cyanomethyl is considered herein to be a $C_1$ cyanoalkyl group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention further include hydrates and solvates, as well as anhydrous and non-solvated forms.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, and salts thereof, are substantially isolated. By "substantially isolated" is meant that the compound is at least partially or substantially separated from the environment in which is was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The expressions, "ambient temperature" and "room temperature," as used herein, are understood in the art, and refer generally to a temperature, e.g a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, both of which are hereby incorporated by reference in their entirety.

Synthesis

Compounds of the invention, including salts thereof, can be prepared using known organic synthesis techniques and can be synthesized according to any of numerous possible synthetic routes. The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Green and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Compounds of the invention can be prepared according to numerous preparatory routes known in the literature. Example synthetic methods for preparing compounds of the invention are provided in the Schemes below.

As shown in Scheme 1, pyrazole-containing cores 1-9 and 1-6 can be synthesized starting with pyrrolo[2,3-b]pyridine or pyrrolo[2,3-b]pyrimidine 1-1. The compound 1-1 can be converted to an active species such as an N-oxide analog (1-2) by using an oxidant such as m-CPBA. The N-oxide 1-2 can be halogenated with a halogenating agent such as a combination of tetramethylammonium bromide and methanesulfonic anhydride to form a 4-halo compound 1-3 such as a 4-bromo compound while the N-oxide is reduced at the same time. The amine group of the compound 1-3 can be protected by a suitable amine protecting group to afford the protected compound 1-7, which subsequently undergoes a Suzuki coupling with a boric acid 1-8 to afford the pyrazole-containing cores 1-9a which can be further reacted with reagent L-(Y)n-Z (where L is a leaving group) to give compounds of the invention 1-9b. Alternatively, the N-oxide 1-2 can be halogenated with a halogenating agent such as MeSO$_2$Cl to form a 4-halo compound 1-4 such as a 4-chloro compound while the N-oxide is reduced at the same time. The 4-halo compound 1-4 can be coupled to a bromo-substituted pyrazole compound 1-5 under suitable conditions such as heating to afford the pyrazole-containing core 1-6, which may contain some functional groups such as bromo or cyano suitable for further chemical modification.

Similarly, an imidazole core 1-11 can be synthesized by coupling of the 4-halo compound 1-4 to an imidazole derivative 1-10 under suitable conditions such as heating to afford the imidazole-containing core 1-11, which may contain some functional groups such as bromo or cyano suitable for further chemical modification.

Scheme 1
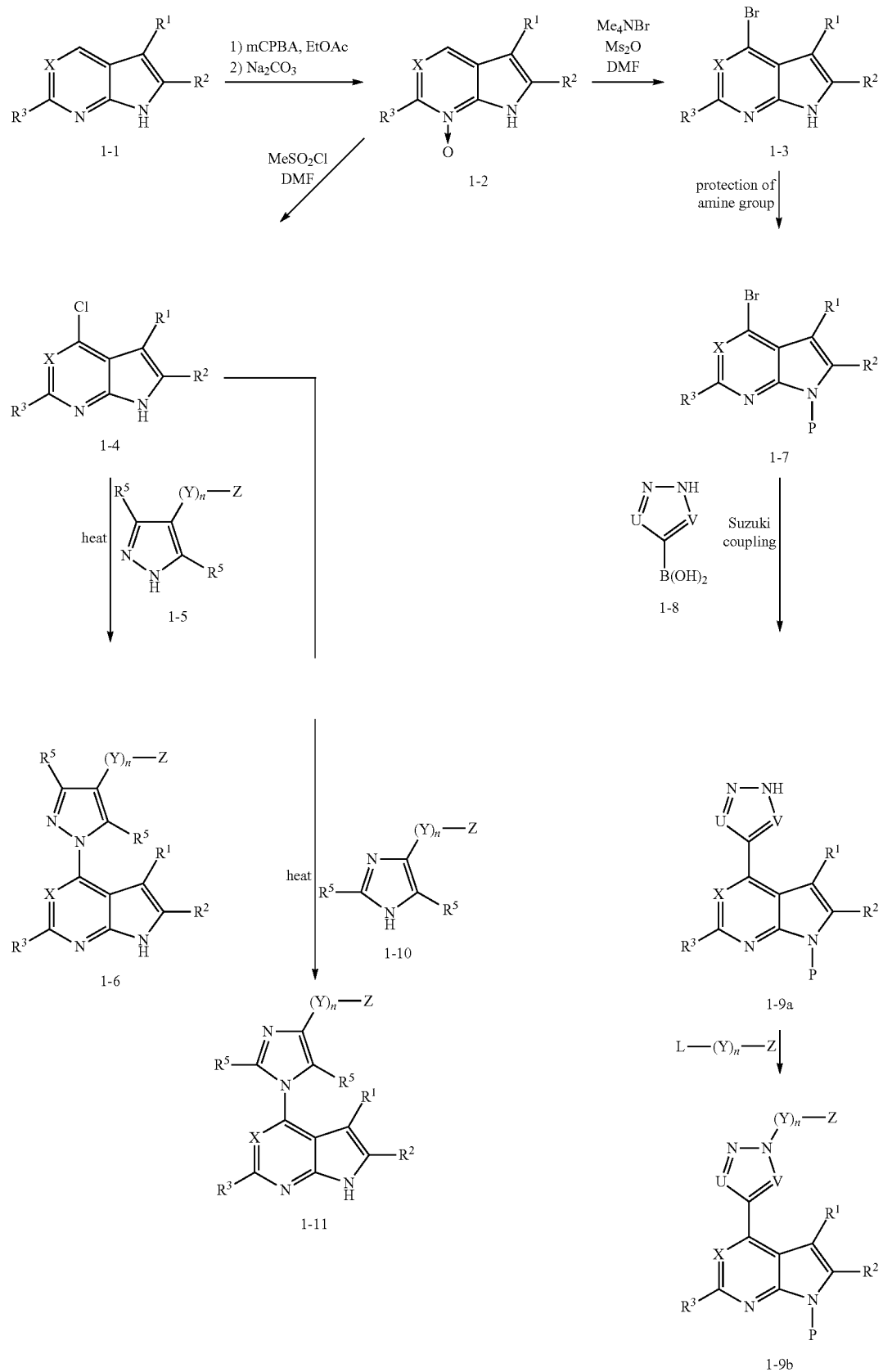

As shown in Scheme 2, pyrazole-containing cores 2-3, 2-5 and 2-6 can be synthesized starting with a bromo-substituted pyrazole derivative 2-1 (a compound 1-6 in Scheme 1 wherein one of $R^5$ is Br). The bromo-substituted pyrazole derivative 2-1 can be coupled to boron-containing aromatic species such as an aromatic boric acid 2-2 using Suzuki coupling wherein Ar is aryl or heteroaryl, each of which can be optionally substituted by one or more substituents such as alky, aryl, CN, nitro, alkoxy, etc. Alternatively, an alkene- or alkyne-containing compound such as an alkene-containing 2-5 can be obtained by coupling the bromo-substituted pyrazole derivative 2-1 to an unsaturated compound such as an alkene 2-4 in the presence of a metal catalyst such as bis(triphenylphos-phine)palladium (II) chloride wherein t can be 0, 1, 2, and the like; and R can be a substituent such as alkyl, aryl, CN, nitro, alkoxy, etc. The alkene group of compound 2-5 can be reduced by hydrogenation to afford the corresponding compound 2-6.

as a cesium salt $R^5CO_2Cs$ to afford a compound 3-4. In the presence of a suitable ammonia source such as ammonium acetate, the compound 3-4 can react with ammonia under suitable conditions such as at a high temperature to form the imidazole ring of the compound 3-5. The free amine nitrogen of the imidazole derivative 3-5 can undergo further modification such as reacting with a compound X—$(Y)_n$—Z where X is a leaving group such as chloro, bromo or iodo so as to afford compound 3-6. The protecting group of compound 3-6 can be removed by an appropriate method according to the nature of the protecting group to yield compound 3-7. It should be noted that if there are functional groups present within the R, $R^5$, and —$(Y)_n$—Z group, further modification can be made. For example, a CN group can be hydrolyzed to afford an amide group; a carboxylic acid can be converted to a ester, which in turn can be further reduced to an alcohol, which in turn can be further modified. One skilled in the art will recognize appropriate further modifications.

Scheme 2

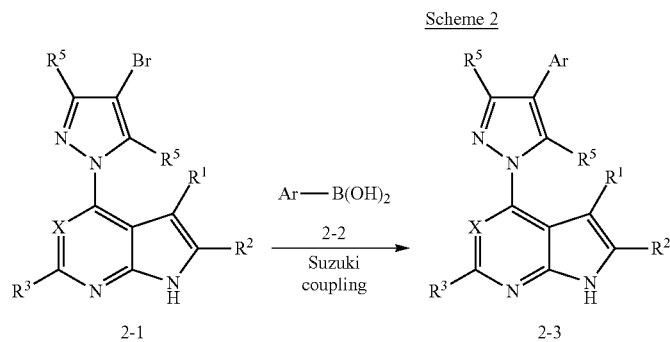

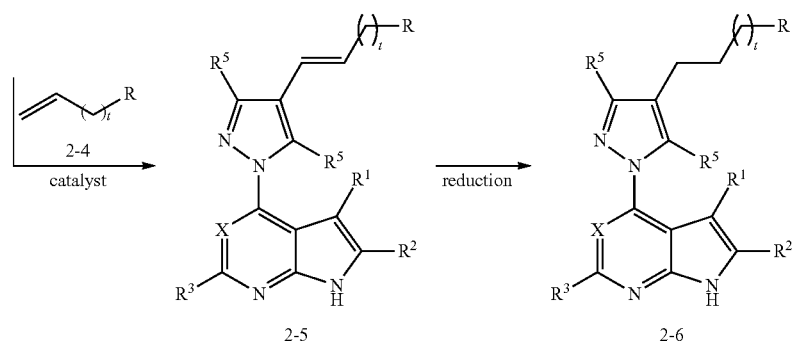

As shown in Scheme 3, imidazole-containing cores 3-7 can be synthesized starting with an N-protected 4-bromo-pyrrolo[2,3-b]pyridine or an N-protected 4-bromo-pyrrolo[2,3-b]pyrimidine 3-1 wherein P is a suitable amine protecting group such as {[2-(trimethylsilyl)ethoxy]methyl} (SEM). Compound 3-1 can be reacted with a Grignard reagent such as isopropyl magnesium chloride to generate an aromatic anion through ion exchange. The subsequent addition of a chloroacetyl-containing compound such as 2-chloro-N-methoxy-N-methylacetamide 3-2 to the anion will typically afford the chloroacetyl derivative 3-3. The derivative 3-3 can be reacted with an organic acid salt such Scheme 3

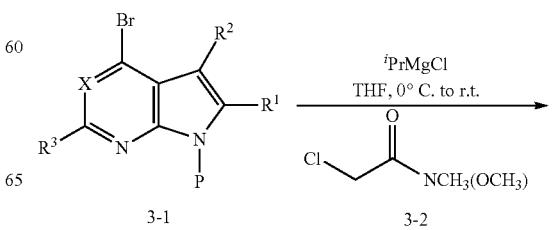

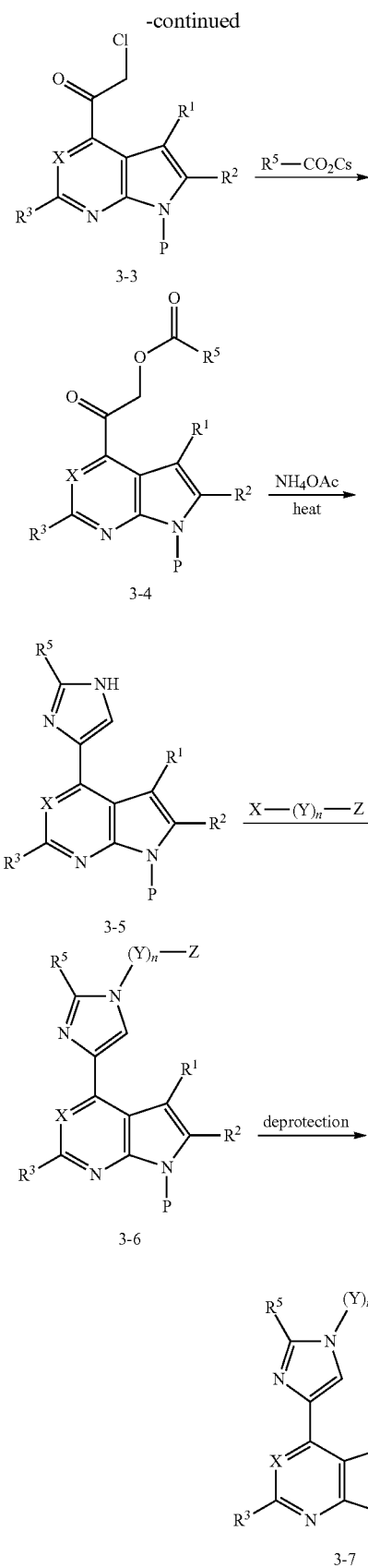

3-3

3-4

3-5

3-6

3-7

As shown in Scheme 4, thiazole-containing cores 4-3 can be synthesized starting with an N-protected chloroacetyl derivative 4-1 wherein P is a suitable amine protecting group such as SEM. Compound 4-1 can be reacted with a thioamide 4-2 to form the thiazole ring, followed by deprotection of the amine nitrogen of the pyrrole ring by removal of the P group to afford the compound 4-3. Various thioureas 4-5 (equivalent to compound 4-2 wherein —(Y)$_n$—Z is NR'R"; and R' and R" are H, alkyl, aryl or the like; or R' and R" together with the N atom to which they are attached form a heterocycloalkyl) useful in preparing the thiazole compounds 4-3 can be made from secondary amines 4-4. A secondary amine 4-4 can be reacted with 1,1'-thiocarbonyl-diimidazole; and the resulting intermediate can further be reacted with ammonia to afford a thiourea 4-5.

Scheme 4

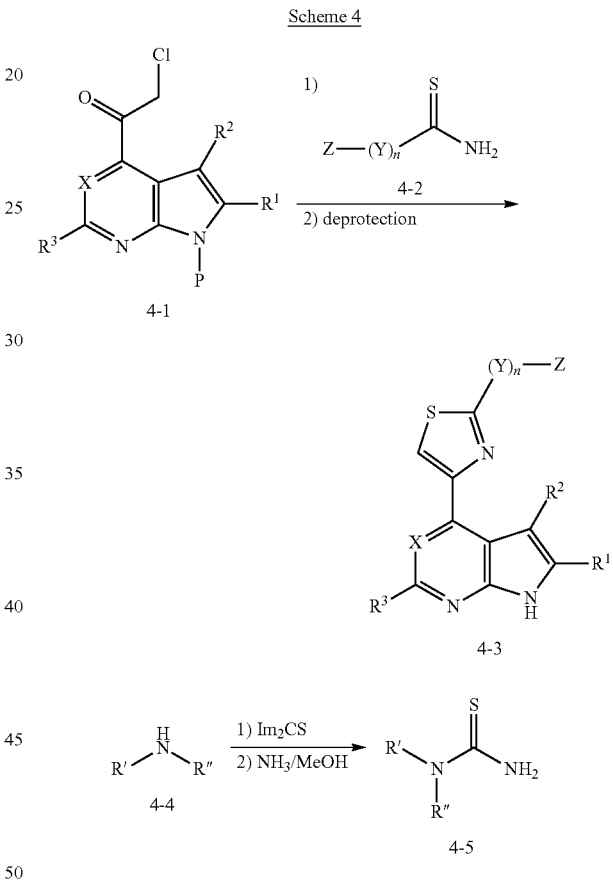

As shown in Scheme 5, thiazole-containing cores 5-5 can be synthesized starting with a thiazole compound 5-1. The compound 5-1 can be reacted with a metal alkyl such as n-butyl lithium via ion exchange to generate an aromatic anion in situ. The subsequent addition of boric acid trimethyl ester followed by hydrolysis will typically afford the boric acid 5-2. The boric acid 5-2 can undergo Suzuki coupling with an N-protected 4-bromo-pyrrolo[2,3-b]pyridine or an N-protected 4-bromo-pyrrolo[2,3-b]pyrimidine 5-3 wherein P is a suitable amine protecting group such as SEM. The protecting group P of the coupling product 5-4 can be removed by an appropriate method according to the nature of the protecting group to yield the compound of the invention 5-5.

Scheme 5

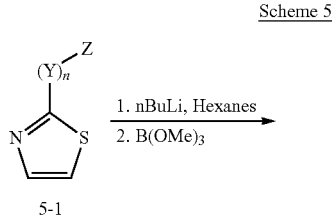

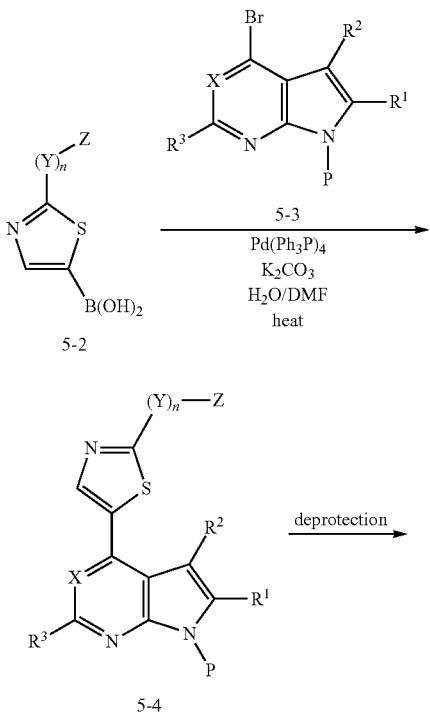

Additionally, compound 6-1 can be reacted with alkene 6-3 (wherein R' and R" can be H, alkyl, cycloalkyl and the like; and Z' can be an electron withdrawing group such as an ester or CN) to afford the compound 6-4. Further, substitution can be made on alkene 6-3 at the alpha position (alpha to Z') to generate a substituted derivatives of product, 6-4 (see, e.g., Example 68).

Compounds 6-2 and 6-4 can be deprotected by appropriate methods according to the nature of the protecting group used to afford their corresponding de-protected counterpart.

Scheme 6

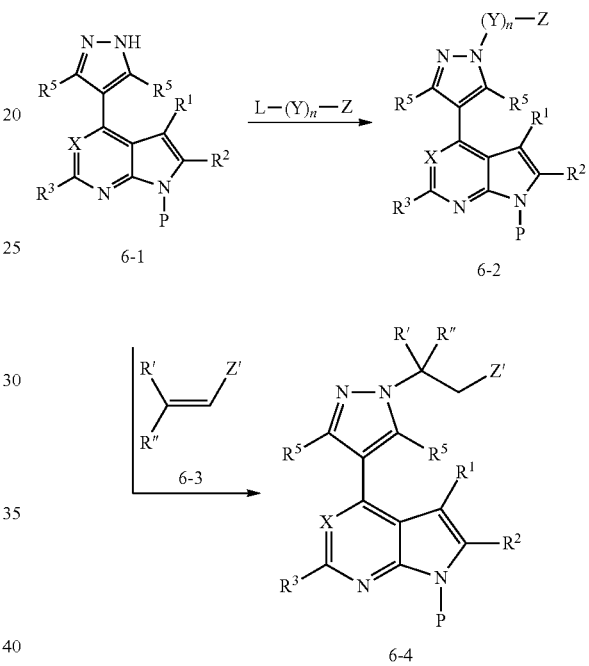

As shown in Scheme 6, pyrazole-containing compounds 6-1 can further be modified by substitution on the pyrazole NH group with appropriate reagents. For example, a compound 6-1 wherein P is a suitable amine protecting group such as SEM can be reacted with L-(Y)$_n$—Z where L represents a leaving group such as halo, triflate or the like to afford compound 6-2 under basic condition. If there are some functional groups present within the Y and/or Z group, further modification can be made. For example, a CN group can be hydrolyzed to afford an amide group; a carboxylic acid can be converted to a ester, which in turn can be further reduced to alcohol. One skilled in the art will recognize the further modifications if appropriate.

As shown in Scheme 7, bromo pyrazole containing compounds 7-1 can be further modified by metallation with reagents like butyl lithium and reaction with electrophiles like aldehydes to give the alcohol containing compounds 7-2 which can be deprotected to yield compounds of the invention having formula 7-3. One skilled in the art will recognize the further modifications where appropriate.

Scheme 7

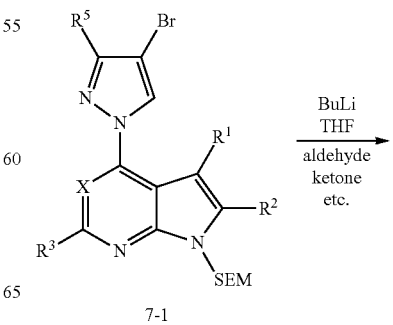

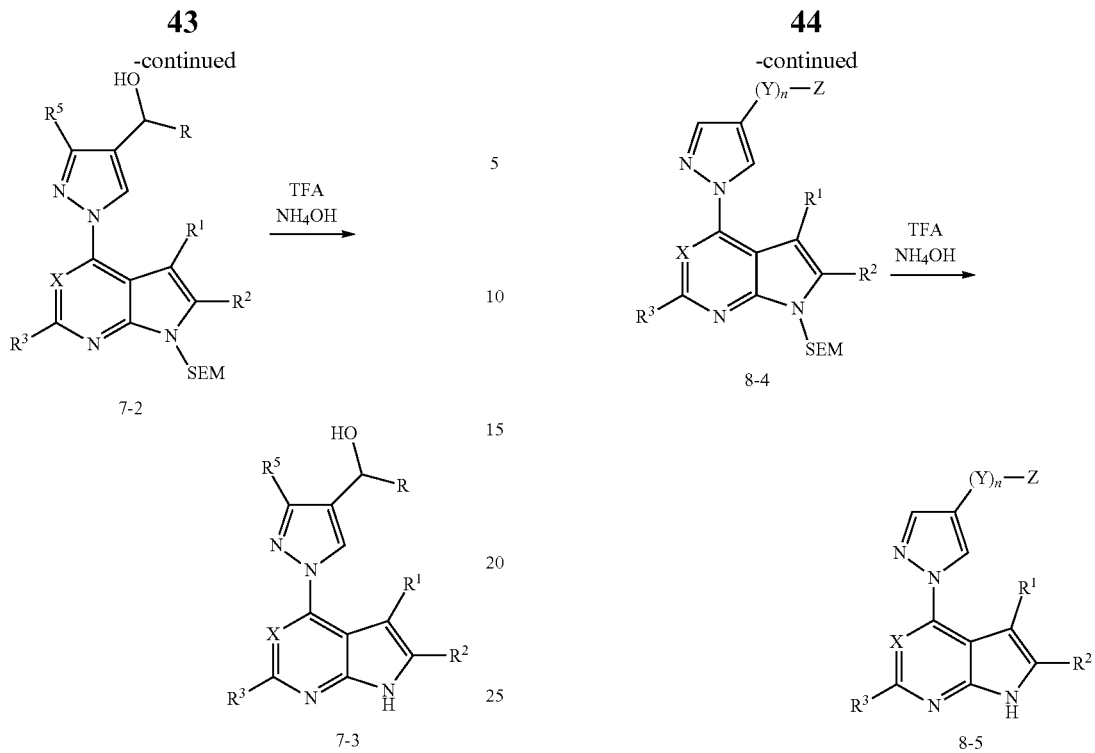

As shown in Scheme 8, pyrazole-containing compounds 8-4 and 8-5 can be prepared by reaction of the N-protected bromo compound 8-1 with hydrazine in an appropriate solvent such as N,N-dimethylformamide (DMF) to give the hydrazine intermediate 8-2. The hydrazino intermediate 8-2 is reacted with an appropriately substituted 1,3 bis-aldehyde like 8-3 to give the pyrazole containing compound 8-4. If there are some functional groups present within the Y and/or Z group, further modification can be made. For example, a CN group can be hydrolyzed to afford an amide group; a carboxylic acid can be converted to a ester, which in turn can be further reduced to alcohol. One skilled in the art will recognize further potential modifications.

As shown in Scheme 9, the 1,2,4-oxadiazole compound 9-6 can prepared from the N-protected bromo compound 9-1 by treatment with zinc cyanide in DMF in the presence of a catalyst like bis(tributyl) palladium to give the N-protected cyano compound 9-2. The N-hydroxy carbox-imidamide compound 9-3 can be prepared by heating the N-protected cyano compound 9-2 with hydroxylamine hydrochloride in an appropriate solvent like ethanol and a base like potassium carbonate at a temperature below the boiling point of the solvent. The N-protected 1,2,4-oxadiazole compound can be prepared by treating the N-hydroxy carboximidamide compound 9-3 with an appropriately substituted acid chloride compound 9-4 in a solvent like pyridine at a sufficient temperature to complete the ring closure. If there are some functional groups present within the Y and/or Z group, further modification can be made. For example, a CN group can be hydrolyzed to afford an amide group; a carboxylic acid can be converted to an ester, which in turn can be further reduced to alcohol. One skilled in the art will recognize further modifications where appropriate.

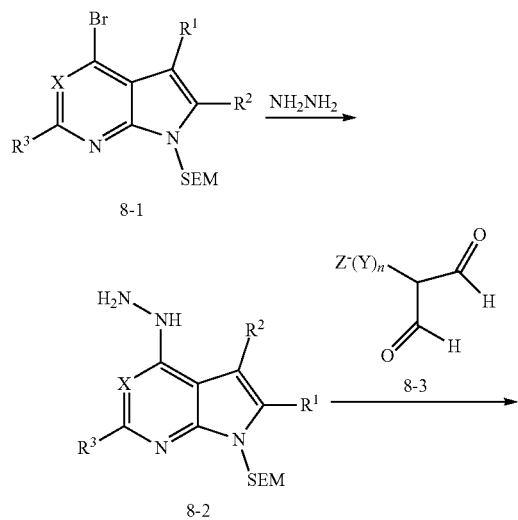

Scheme 8

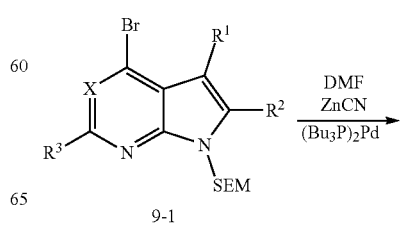

Scheme 9

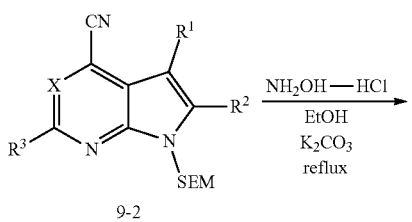

9-2

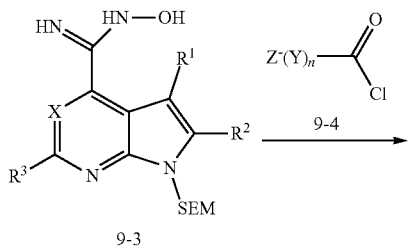

9-3

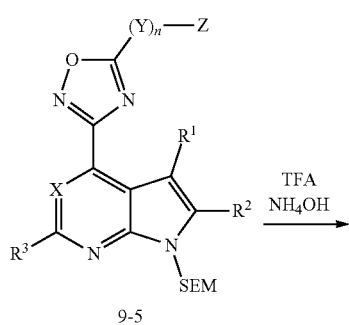

9-5

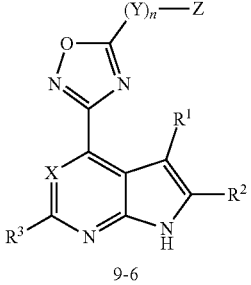

9-6

As shown in Scheme 10, the 3- and 4-arylpyrazolo compounds 10-9 can be prepared by reaction of the respective 3-arylpyrazolo compound 10-4 or 4-aryl pyrazolo compound 10-7 with an appropriately substituted bromo compound 10-8 as previously described. The 3-aryl pyrazolo compound 10-4 can be prepared by reacting an appropriately substituted aryl group containing a halogen like bromo or a triflate with the N-protected boronic acid or boronic acid ester pyrazole compound 10-2 under Suzuki-like conditions known in the literature. The N-protecting group of 10-3 can be removed by conditions previously described and known in the literature for removing groups like SEM.

The 4-arylpyrazolo compounds 10-7 can be prepared by reacting the appropriately substituted acetophenone compound 10-5 with DMF acetal in DMF at elevated temperatures to give the dimethylamino compound 10-6. The 4-arylpyrazolo compounds 10-7 can be prepared by treating the dimethylamino compound 10-6 with hydrazine in a solvent such as ethanol.

Scheme 10

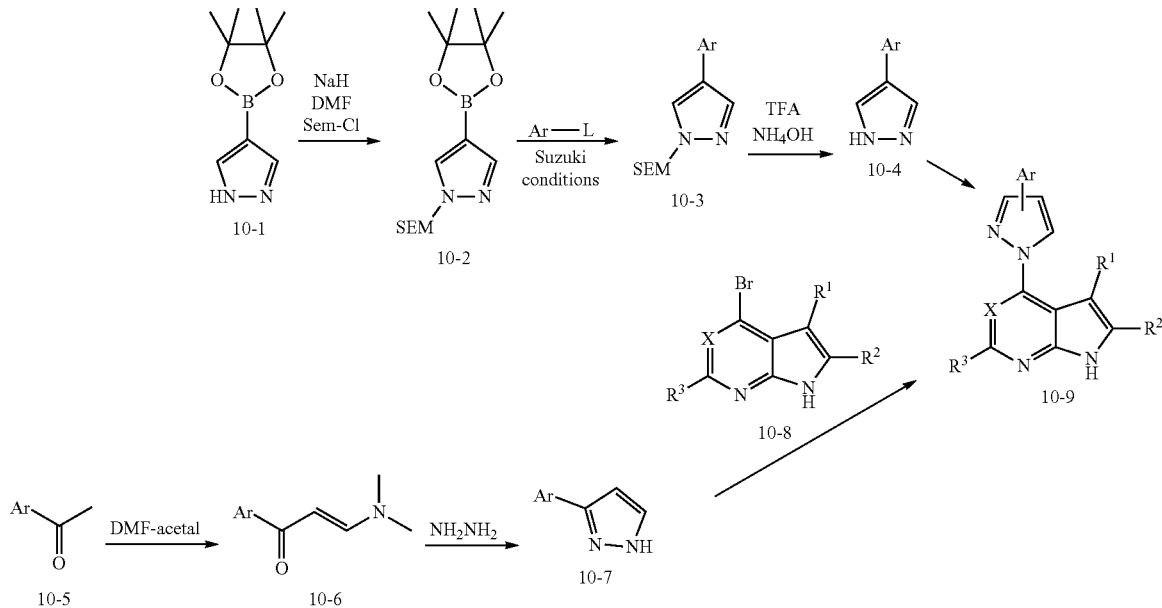

As shown in Scheme 11 the substituted pyrazole compound 11-5 can be prepared by a variety of methods, such as by removing the protecting group e.g., SEM from compound 11-4 under conditions previously described. For example the substituted pyrazole N-protected compound 11-4 can be prepared by reaction of the intermediate pyrazole N-protected compound 11-3 with an appropriately substituted alkyl halide, benzyl halide, alkyl sulfonates, e.g., mesylate or tosylate, or other suitable leaving group L, in an appropriate solvent such as MeCN, DMF or tetrahydrofuran (THF), in the presence of a base such a sodium hydride or cesium carbonate. The N-aryl pyrazole 11-4 (wherein Y is aromatic) may be prepared by reacting the intermediate pyrazole 11-3 with an appropriately substituted aryl boronic acid in a solvent such as dichloromethane (DCM) with copper acetate and pyridine. Alternatively the N-aryl pyrazole 11-4 (wherein Y is aromatic) can be prepared by reacting the intermediate pyrazole 11-3 with an appropriately substituted aryl-fluoride in a solvent such as DMF at elevated temperature. Or, the substituted pyrazole compounds 11-4 (wherein Z is a group such as nitrile or ester and Y is at least two carbons) can be prepared by the reaction of intermediate pyrazole 11-3 with an appropriately substituted acrylate, acrylonitrile or other Michael-like acceptors in a solvent such as DMF in the presence of a base such as 1,8-diazabicyclo[5.4.0]undec-7-ene (DBU) or triethylamine (TEA) and at a temperature below the boiling point of the solvent. If there are some functional groups present within the Y and/or Z group, further modification can be made. For example, a CN group can be hydrolyzed to afford an amide group; a carboxylic acid can be converted to a ester, which in turn can be further reduced to alcohol. One skilled in the art will recognize the further modifications if appropriate.

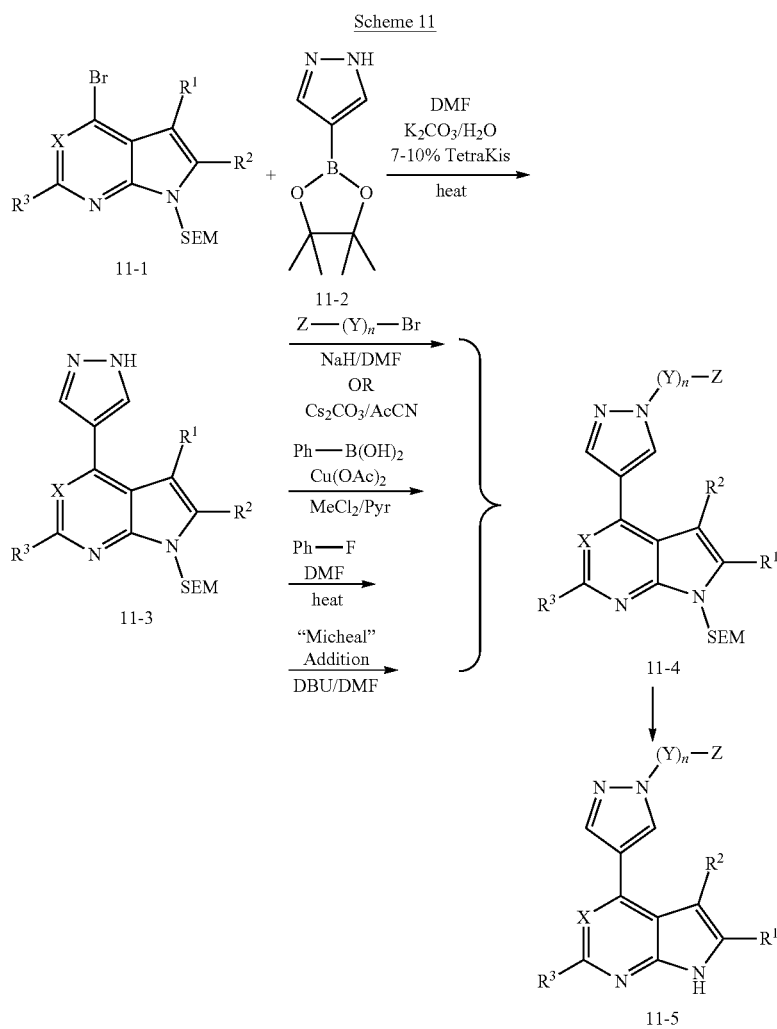

Scheme 11

As shown in Scheme 12, pyrazole 12-1 wherein P is a suitable amine protecting group such as SEM can be reacted with an alkyne-containing conjugate acceptor such as 12-2, wherein Z is an electron-withdrawing group (for example, —CN) optionally in the presence of a base (DBU or $K_2CO_3$ and the like) in a solvent such as DMF or MeCN for variable lengths of time to provide olefin-containing adducts 12-3. Compounds represented by the formula 12-3 can be deprotected by appropriate methods according to the nature of the protecting group used to afford compounds of the invention 12-4.

Scheme 12

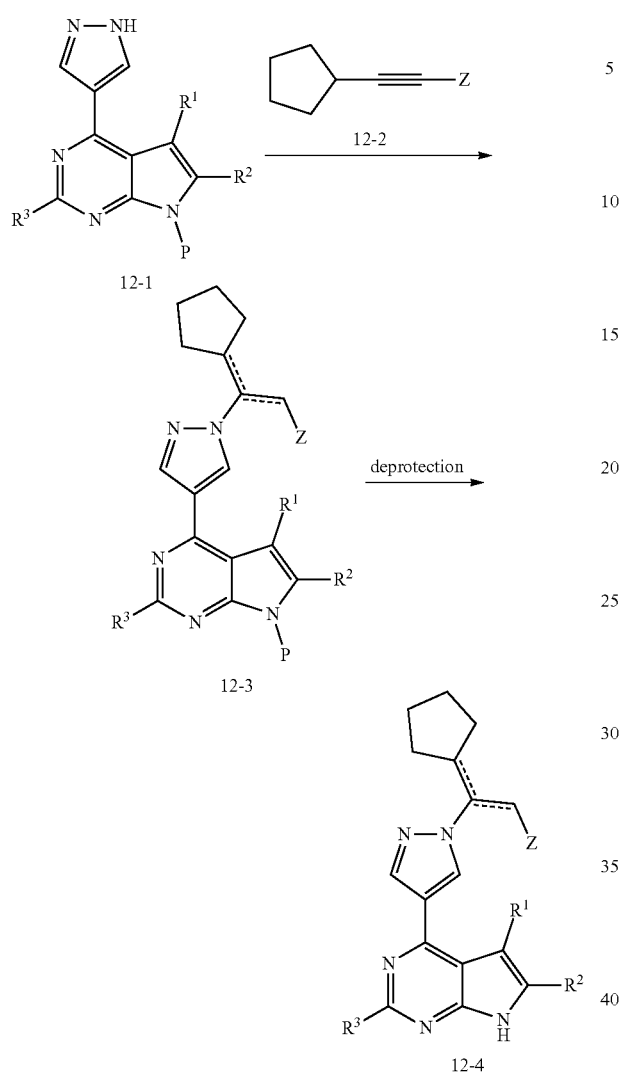

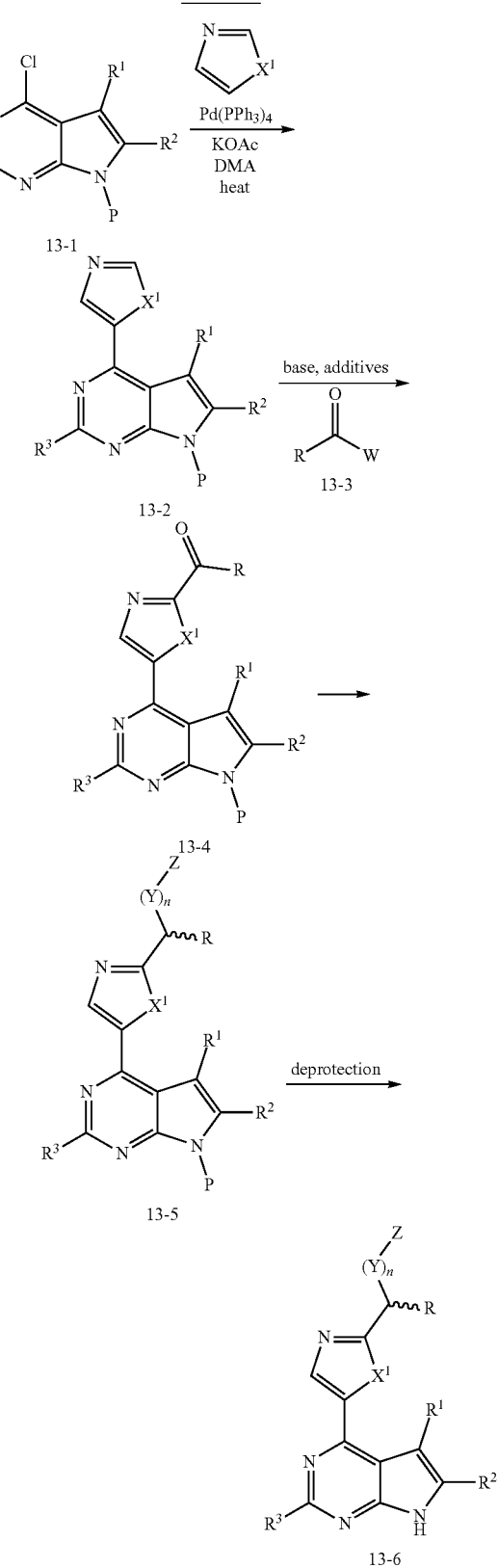

As shown in Scheme 13, oxazole- or thiazole-containing compounds 13-6 can be prepared starting with N-protected 4-chloro-pyrrolo[2,3-b]pyrimidine 13-1 wherein P is a suitable amine protecting group such as SEM. Oxazole- or thiazole-containing products of formula 13-2 can be prepared by palladium-catalyzed coupling of 13-1 with oxazole or thiazole. The compound 13-2 can be reacted with a metal alkyl such as n-butyllithium to generate the aromatic anion in situ to which can be added at low temperatures (preferably between −78° C. and 0° C.) derivatives of carboxylic acids 13-3 (wherein W=N(Me)(OMe) when $X^1$=S; and W=Cl when $X^1$=O), in the presence of other additives such as zinc chloride and copper(I) iodide when $X^1$=O, in a suitable solvent such as THF to generate a variety of ketones 13-4. Ketones 13-4 can be caused to react with a variety of reagents such as diethyl (cyanomethyl)phosphonate or triethylphosphonoacetate in the presence of a base like potassium tert-butoxide followed by reduction (including hydrogenation or a copper-hydride catalyzed conjugate reduction), or with reagents such as tosylmethyl isocyanide to provide products of formula 13-5 wherein Z is an electron-withdrawing group such as ester or —CN. If there are functional groups present within the R group or encompassed by the Z group, further modification can be made, and such appropriate further modifications will be recognized by one skilled in the art. Compounds 13-5 can be deprotected by appropriate methods according to the nature of the protecting group used to afford their corresponding deprotected counterparts 13-6.

As shown in Scheme 14, aminothiazole-containing cores 14-5 can be synthesized starting with thiazole-containing core 14-1 wherein P is a suitable amine protecting group such as SEM. The compound 14-1 can be treated with a metal alkyl such as n-butyllithium to generate the aromatic anion in situ to which can be added a suitable source of electrophilic halogen such as carbon tetrabromide to afford the halogenated derivative 14-2. The protecting group P of 14-2 can be removed by an appropriate method according to the nature of the protecting group to yield product 14-3. The compound 14-3 can be reacted with amines 14-4 at elevated temperatures in a suitable solvent such as DMF to afford the compound of the invention, 14-5.

pound 15-1 can be reacted with 1-(triisopropylsilyl)pyrrole-3-boronic acid under Suzuki coupling conditions to afford the simultaneously pyrrole-deprotected core 15-2. Pyrrole-containing compounds 15-2 can be reacted with alkenes 15-3 containing an electron-withdrawing group Z (such as —CN) in the presence of an appropriate base (such as DBU) at various temperatures (e.g., between room temperature and 40° C.) followed by an in situ or separate deprotection step that is suitable for the selected protecting group to afford compounds of the invention 15-4.

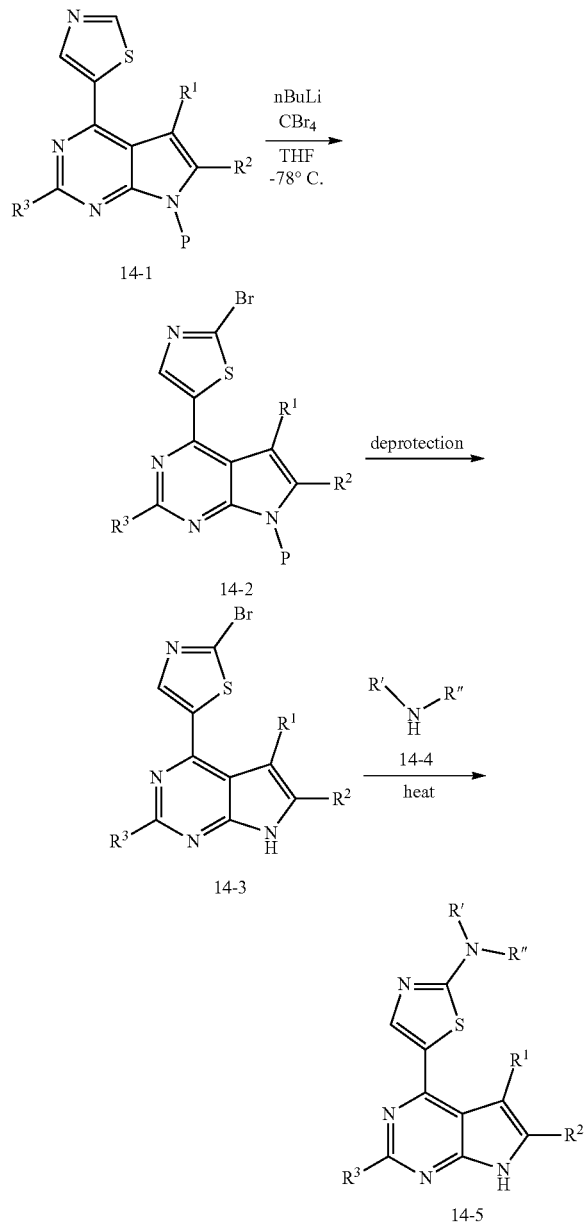

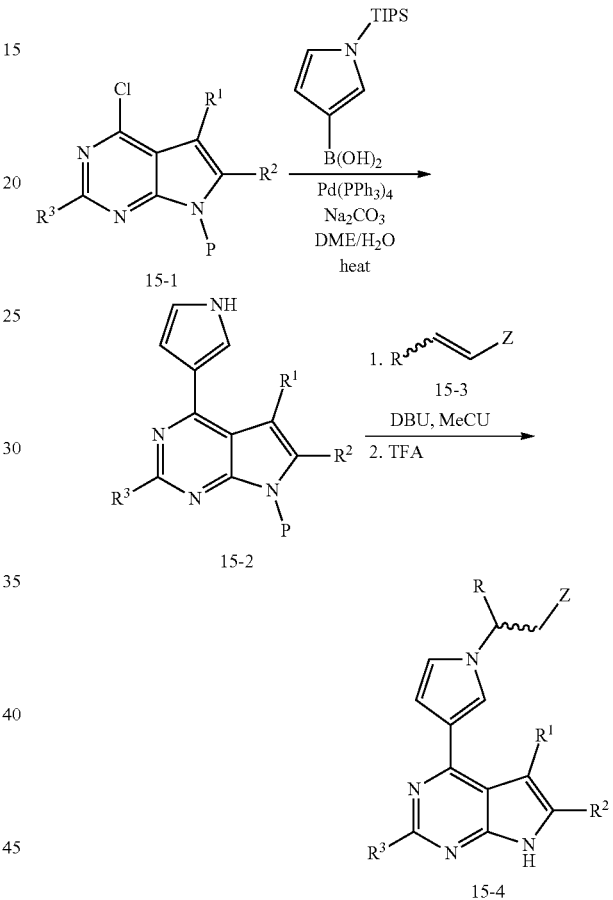

As shown in Scheme 15, pyrrole-containing cores 15-4 can be synthesized starting with N-protected 4-chloro-pyrrolo[2,3-b]pyrimidine 15-1 wherein P is a suitable amine protecting group such as DEM (diethoxymethyl). The com- As shown in Scheme 16, a substituted pyrazole compound containing a sulfone or sulfoxide functionality as in 16-6 can be prepared by a variety of methods, such as starting with an appropriately substituted bromo thiophenyl ether 16-2. Thioether 16-2 may be readily prepared by alkylation of the thiophenol 16-1 with an alkyl halide, mesylate or the like using a base like DBU, potassium carbonate or sodium hydride. The cinnamyl nitrile 16-3 may be prepared by Heck chemistry and the like, using palladium acetate and triphenylphosphine in DMF at an appropriate temperature with acrylonitrile. The SEM protected intermediate 16-4 may be prepared by methods previously described for performing the Michael like addition of the pyrazole core to an appropriately substituted α-β unsaturated nitrile like 16-3. The sulfoxide 16-5, where n=1, and sulfone 16-5, where n=2, may be prepared by methods well known in the literature for the oxidation of the thio ether 16-4 like m-chloroperbenzoic acid (MCPBA) in DCM. The final compounds 16-6, where n=0, 1 or 2, may be prepared by methods previously described for the removal of the SEM protecting group.

Alternatively, the sulfur oxidation may be performed on compounds 16-2 or 16-3 depending on the compatibility of the substitution in the synthetic scheme.

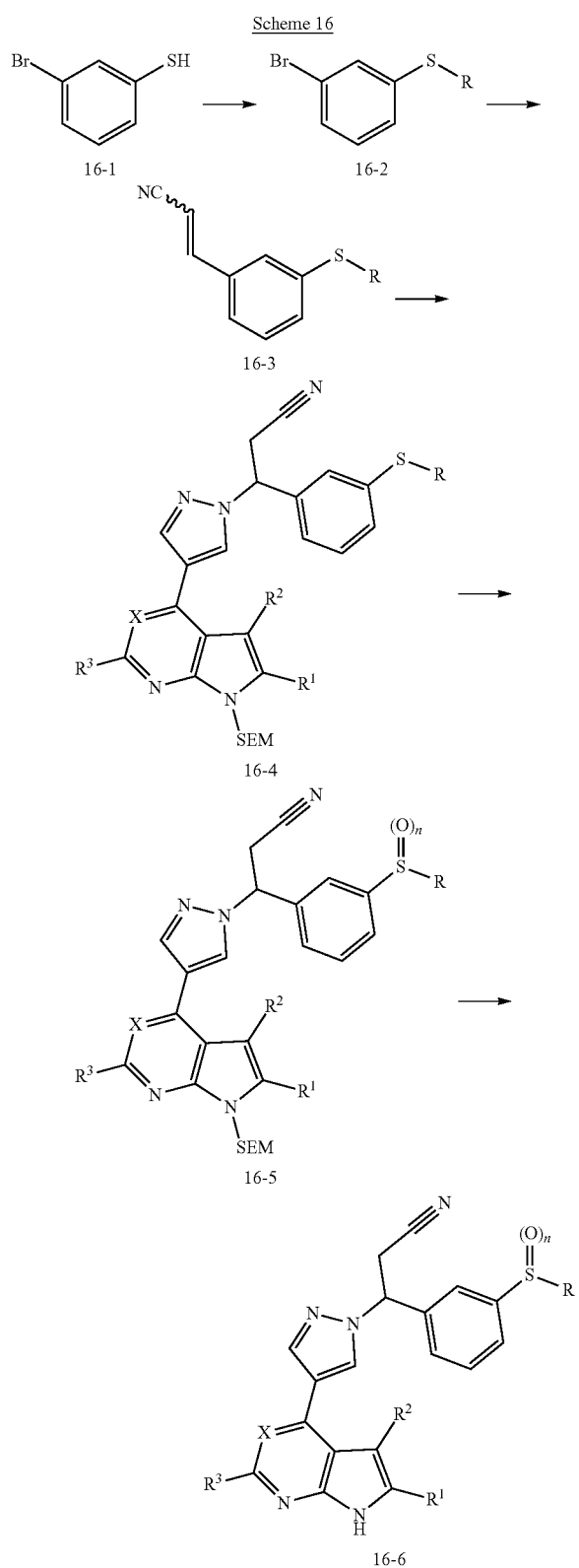

Also, as shown in Scheme 17, substituted pyrazole compounds containing a sulfonamide functionality, such as 17-6 can be prepared by a variety of methods. For example, one may start with an appropriately substituted bromo phenyl sulfonamide 17-2, where $R^c$ and $R^d$ are suitable substituents. A compound 17-2 may be readily prepared by reaction of the bromo phenyl sulfonyl chloride 17-1 and an appropriately substituted amine such as an aniline, or a primary or secondary amine in a suitable solvent such as DCM, THF or pyridine. The cinnamyl nitrile 17-3 may be prepared by Heck chemistry or the like, using palladium acetate and triphenylphosphine in DMF at an appropriate temperature with acrylonitrile. The final compounds 17-6 where $R^c$ and $R^d$ are part of the sulfonamide functional group may be prepared by methods analogous to those described in Scheme 16 starting with the cinnamyl nitrile 17-3.

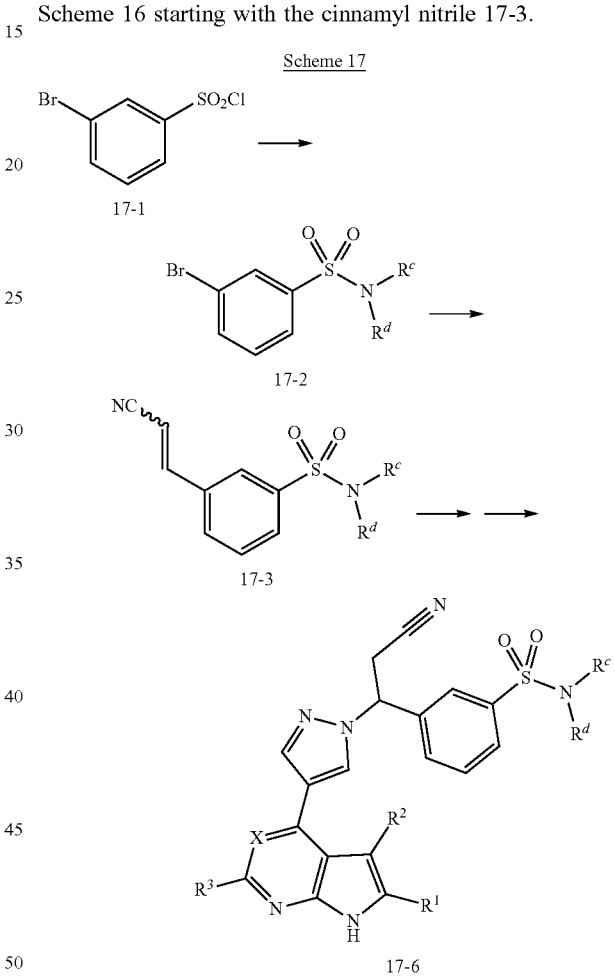

Also, as shown in Scheme 18, substituted pyrazole compounds containing an alpha-allyl cyclopentylmethylene functionality, such as 18-8, can be prepared by, for example, reacting a pyrazole 18-3, wherein P is a suitable amine protecting group such as SEM and X is N or C, with a cyclopentylacrylate ester 18-4 to form the ester 18-5. The ester 18-5 may then be reduced to the corresponding aldehyde, 18-6, for example, by the two-step procedure of reducing to the alcohol and selectively oxidizing the intermediate alcohol to the aldehyde, e.g., via a Swern oxidation. The aldehyde, 18-6, may then be converted to the corresponding olefin, 18-7, for example by reaction with a Wittig reagent. The olefin 18-7, may then be deprotected, as described earlier, to produce the formula 18-7 compound. The intermediate, 18-4, may be prepared, for example as shown in Scheme 18, stearting with cyclopentylaldehyde.

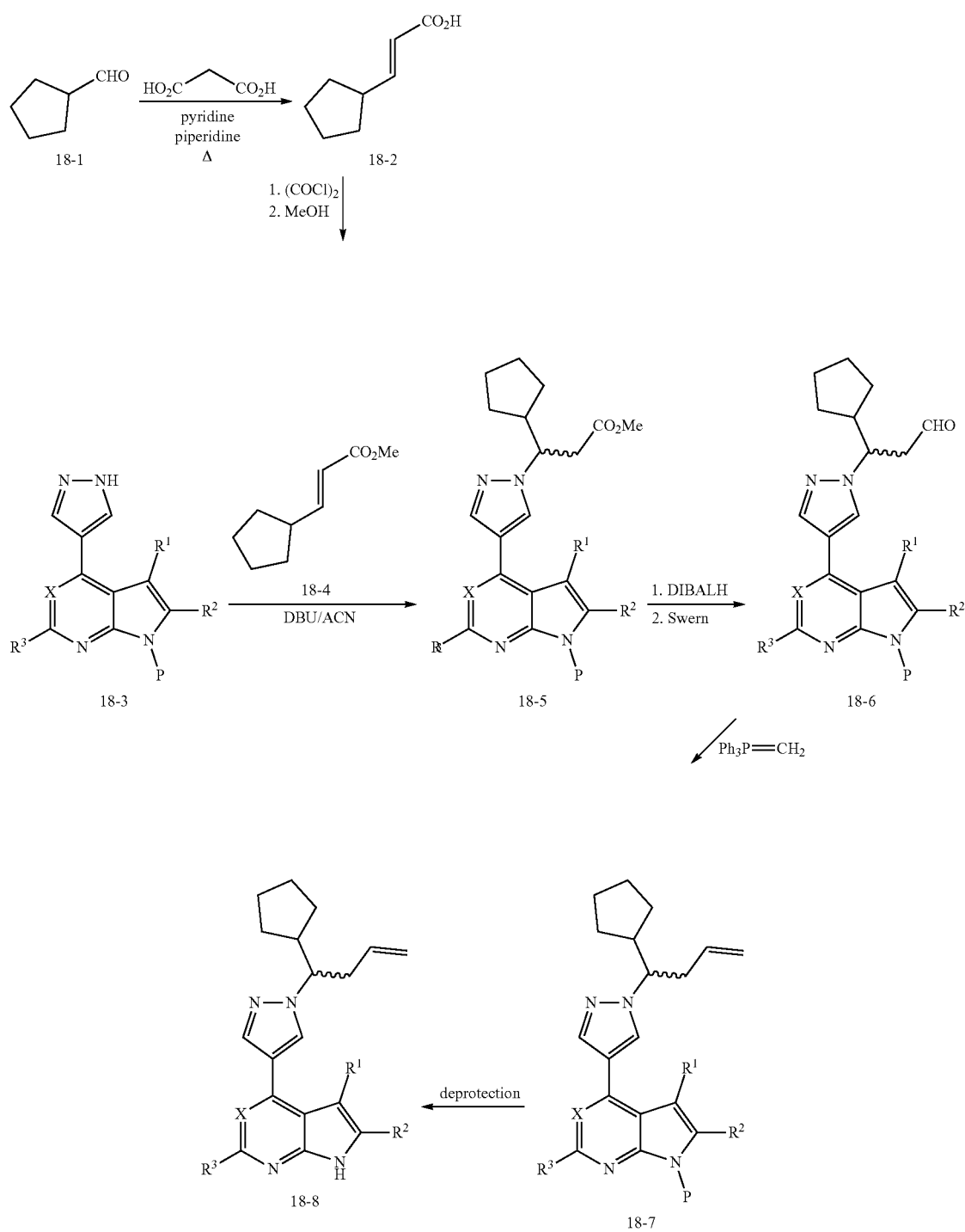

Also, as shown in Scheme 19, the cyanoguanidine derivative 19-6 can be prepared starting from substituted pyrazole compounds such as pyrazole 18-3, wherein P is a suitable protecting group such as SEM and X is N or C. A compound 18-3 may, for example, be reacted with olefin 19-1, prepared by Homer-Wadsworth Emmons reaction of the corresponding Boc-protected piperidone, in the presence of a suitable basic catalyst, in a suitable solvent, to form 19-2. The intermediate 19-2 is deprotected using a suitable deprotection reaction, to provide the amine compound 19-3, which then reacts selectively with a cyanoimidocarbonate reagent such as 19-4, in a polar solvent at a suitable temperature, for example, about 20° C. to give a cyanoimidocarbamate such as 19-5, which can then be reacted with any of a variety of amines at elevated temperature to give product 19-6.

Scheme 19

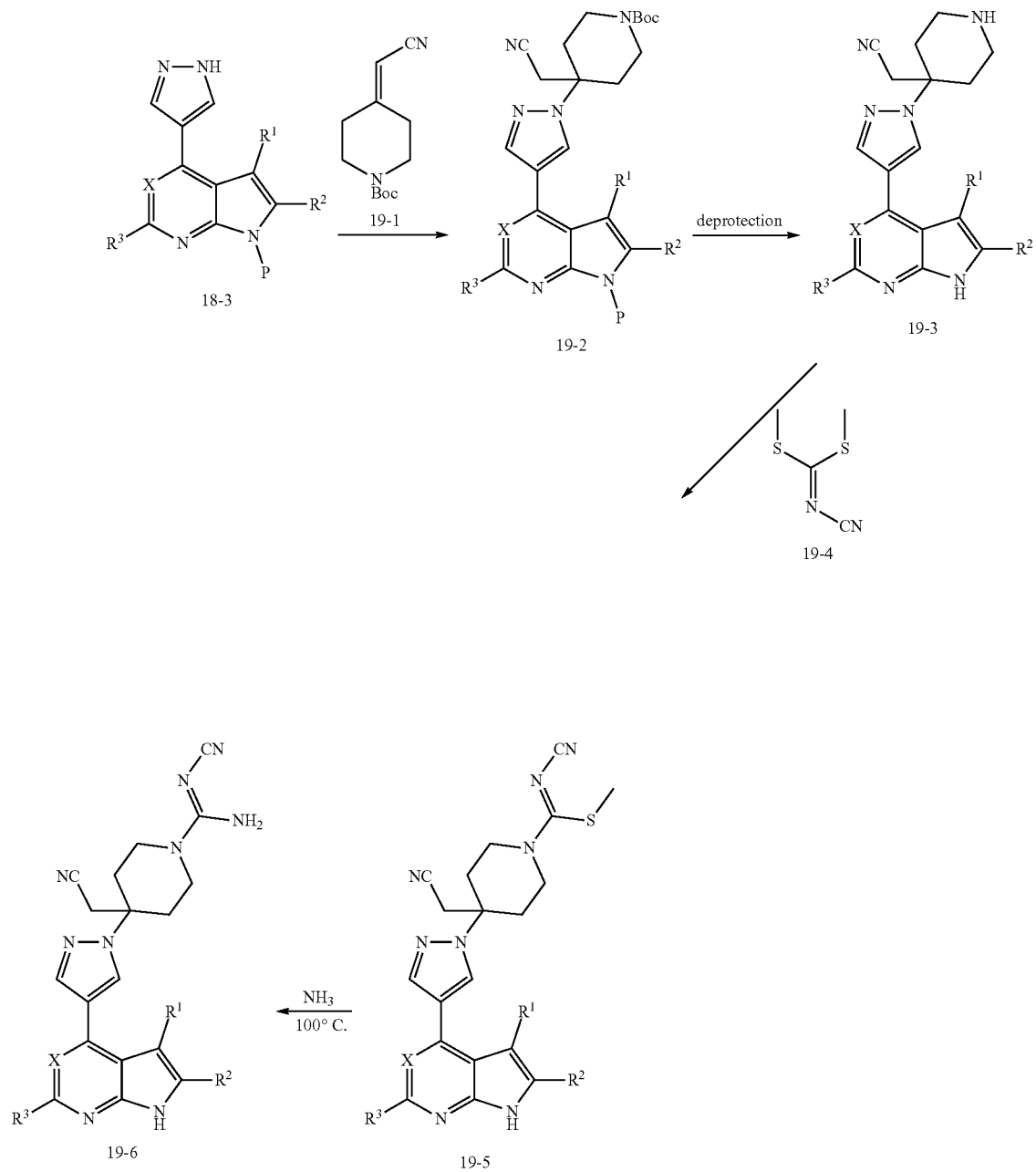

The intermediate compounds 20-5 and 20-6 may be prepared by a variety of methods in the literature, for example, methods such as are outlined in Scheme 20. The intermediate compound 20-3 may be prepared by reaction of the aldehyde compound 20-1 with an appropriately substituted Wittig reagent or Homer Emmons reagents to give the α-β unsubstituted ester 20-3. Alternatively, 20-3 may be prepared by a Heck-like reaction with an appropriately substituted aryl bromide 20-2 and an acrylic ester in the presence of a palladium reagent at elevated temperatures. The compound 20-4 may be prepared by methods previously described for the Michael-like addition of an appropriately substituted pyrrole 18-3 on the α-β unsaturated ester compound 20-3. The aldehyde compound 20-5 may be prepared by reduction of the ester compound 20-4 with reagents such as diisobutyl aluminium hydride at low temperatures such as about −78° C. in an appropriate solvent. The aldehyde compound 20-5 can be further reduced to the corresponding alcohol compound 20-6 with reagents such as sodium borohydride in methanol. Alternatively the alcohol compound 20-6 may be prepared directly by reduction of the ester 20-4 with reagents such as lithium aluminium hydride in appropriate solvent and at appropriate temperatures.

Scheme 20

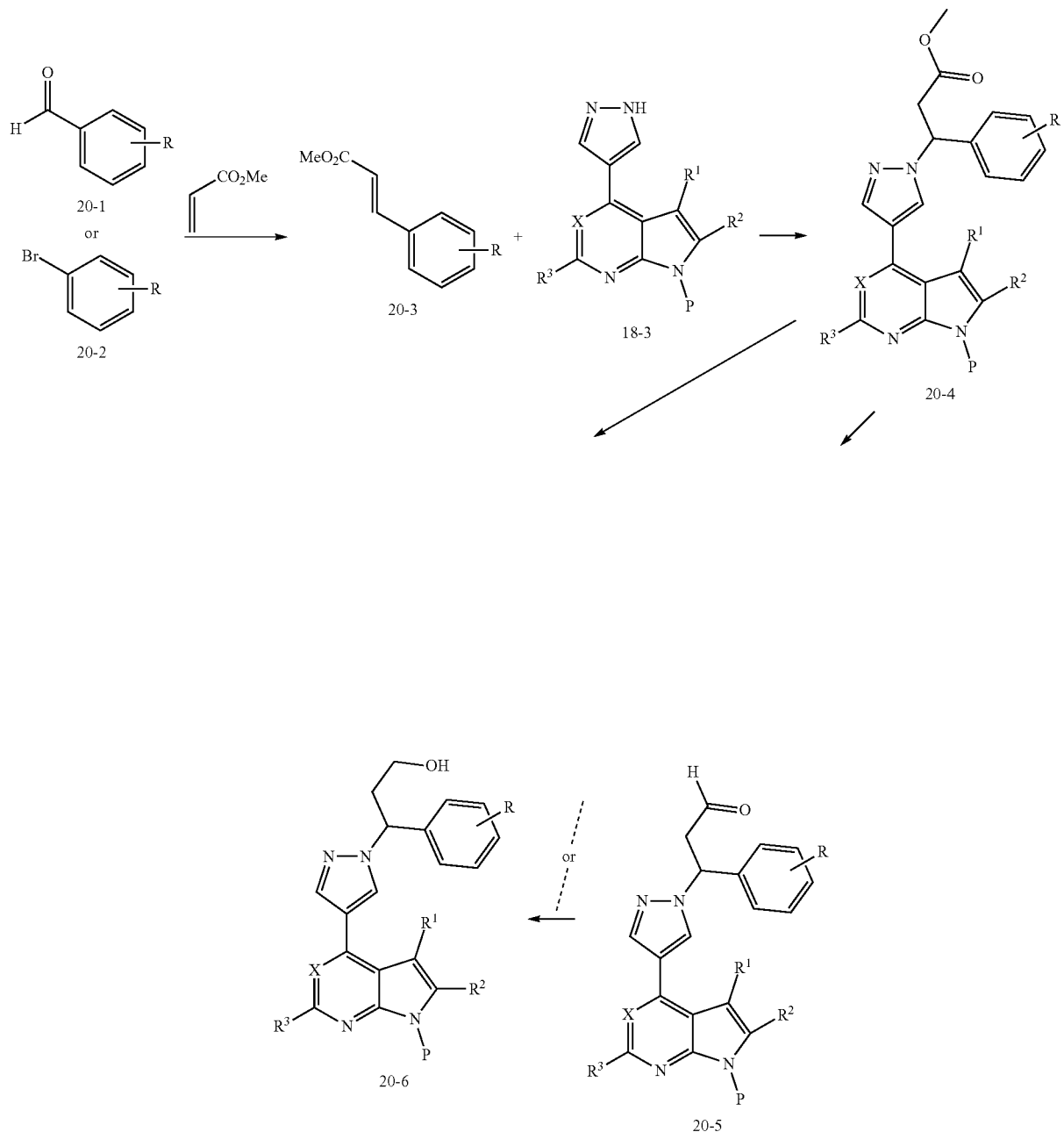

The compounds 21-2 and 21-3 may be prepared by using a variety of methods in the literature, such as, for example, methods outlined in Scheme 21. The olefin compound 21-1 may be prepared by the reaction of aldehyde compound 20-5 with an appropriately substituted Wittig reagent or Homer Emmons reagents using a base such as sodium hydride or potassium t-butoxide in an appropriate solvent and conducted at temperature. The olefin compound compound 21-1 may be reduced to the saturated compound 21-2, for example, using hydrogenation conditions well known in the literature, e.g., hydrogen in the presence of palladium on carbon in a solvent such as methanol. The acetylenic compound 21-3 may be prepared by methods previously described, or by reaction of the aldehyde 20-5 with Bestmann-Ohira reagent (E. Quesada et al, *Tetrahedron*, 62 (2006) 6673-6680) as described in the literature. Alternatively the alcohol compound 20-6 in Scheme 20 may be oxidized to the aldehyde 20-5 with methods well known in the literature, e.g., Swern oxidation conditions, followed by reaction with the Bestmann-Ohira reagent, wherein this reaction sequence may be carried out either as a one pot two-step reaction sequence, or in two separate reaction steps.

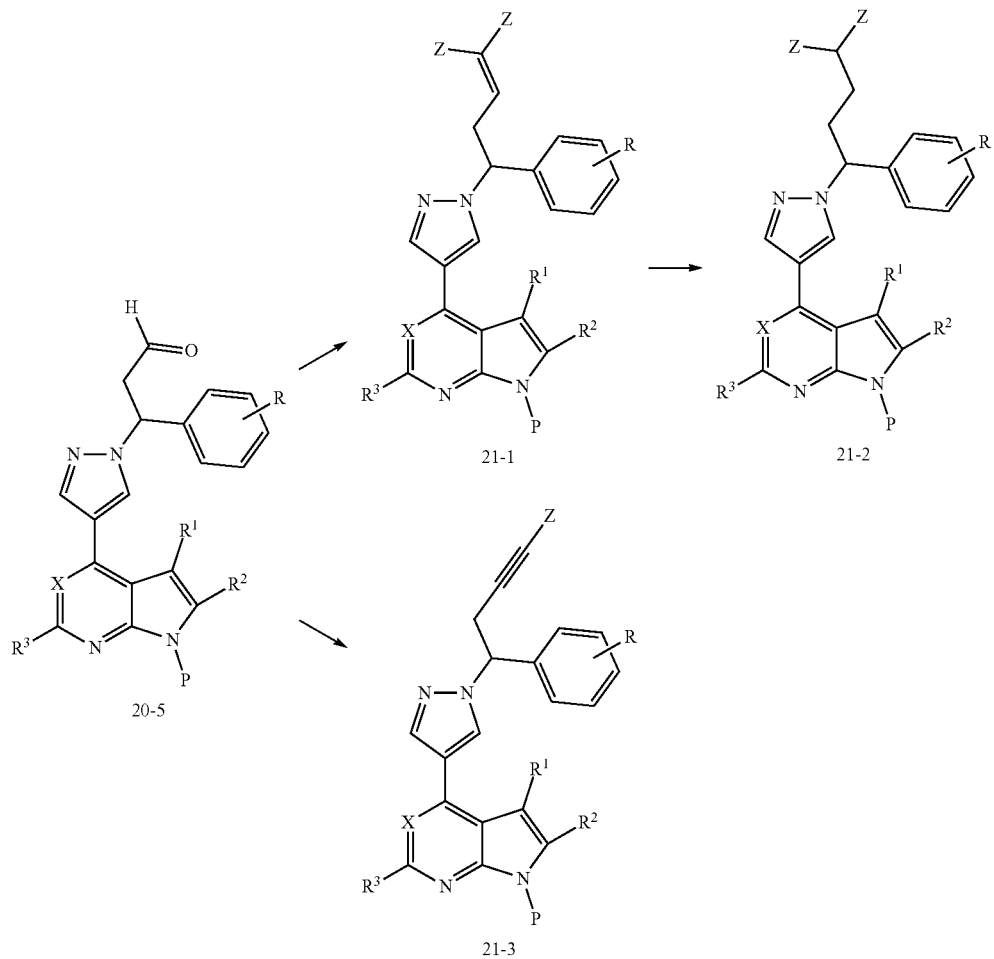

Scheme 21

The compounds 22-1 and 22-3 may be prepared by using a variety of methods in the literature, for example, via methods outlined in Scheme 22. The oxygen-substituted compound 22-1 may be prepared, for example, by reaction of an appropriately substituted alcohol 20-6 (in Scheme 20), wherein X is N or C, and P is a protecting group, with a base such as sodium hydride and an appropriate agent such as an alkyl iodide, carbonate, or isocyanate, carried out in a suitable solvent and at a suitable temperature. Alternatively, the alcohol group on the compound 20-6 may be converted to a leaving group LG, as in compound 22-2, where the leaving group can be, for example, bromide or mesylate. The compound 22-2 serves as a substrate for subsequent reaction with a nucleophile, such as, for example, sodium ethoxide (Nuc=ethoxy).

Scheme 22

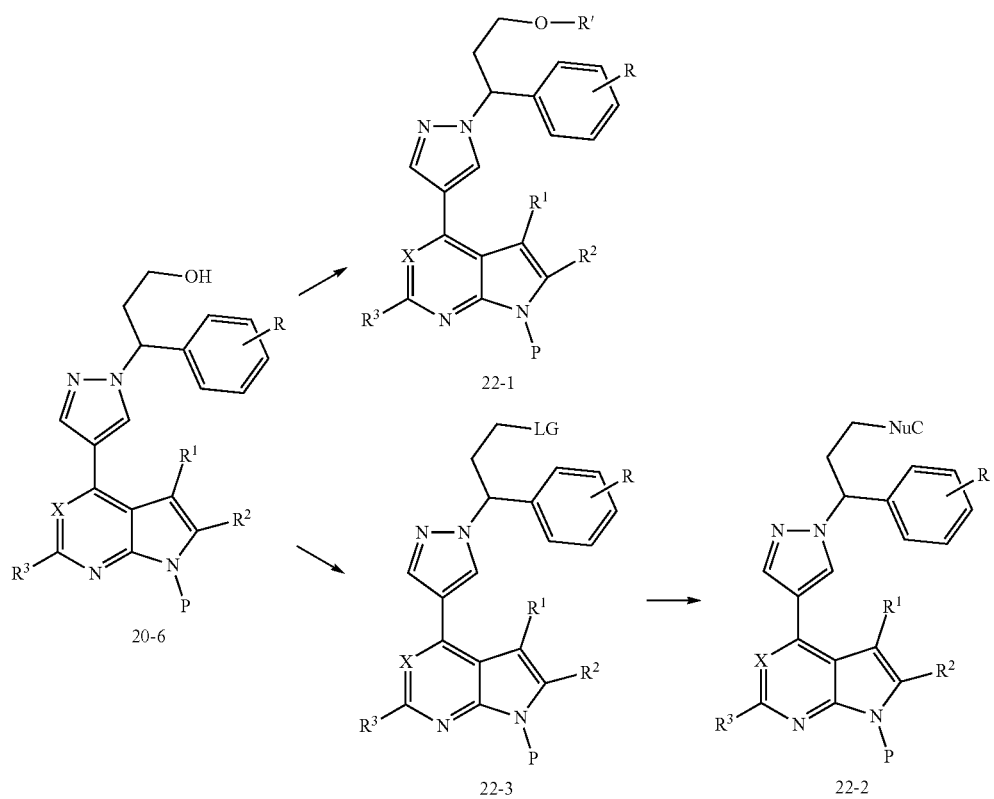

It should noted that in all of the Schemes described herein, if there are functional groups present on a substituent group such as Y, Z, R, $R^1$, $R^2$, $R^5$, etc., further modification can be made if appropriate and desired. For example, a CN group can be hydrolyzed to afford an amide group; a carboxylic acid can be converted to a ester, which in turn can be reduced to an alcohol, which in turn can be further modified. In another example, an OH group can be converted into a better leaving group such as mesylate, which in turn is suitable for nucleophilic substitution, such as by CN. One skilled in the art will recognize such further modifications.

Methods

Compounds of the invention can modulate activity of one or more Janus kinas es (JAKs). The term "modulate" is meant to refer to an ability to increase or decrease the activity of one or more members of the JAK family of kinases. Accordingly, compounds of the invention can be used in methods of modulating a JAK by contacting the JAK with any one or more of the compounds or compositions described herein. In some embodiments, compounds of the present invention can act as inhibitors of one or more JAKs. In some embodiments, compounds of the present invention can act to stimulate the activity of one or more JAKs. In further embodiments, the compounds of the invention can be used to modulate activity of a JAK in an individual in need of modulation of the receptor by administering a modulating amount of a compound of Formula la, Ib, or Ic.

JAKs to which the present compounds bind and/or modulate include any member of the JAK family. In some embodiments, the JAK is JAK1, JAK2, JAK3 or TYK2. In some embodiments, the JAK is JAK1 or JAK2. In some embodiments, the JAK is JAK2. In some embodiments, the JAK is JAK3.

The compounds of the invention can be selective. By "selective" is meant that the compound binds to or inhibits a JAK with greater affinity or potency, respectively, compared to at least one other JAK. In some embodiments, the compounds of the invention are selective inhibitors of JAK1 or JAK2 over JAK3 and/or TYK2. In some embodiments, the compounds of the invention are selective inhibitors of JAK2 (e.g., over JAK1, JAK3 and TYK2). Without wishing to be bound by theory, because inhibitors of JAK3 can lead to immunosuppressive effects, a compound which is selective for JAK2 over JAK3 and which is useful in the treatment of cancer (such as multiple myeloma, for example) can offer the additional advantage of having fewer immunosuppressive side effects. Selectivity can be at least about 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the Km of each enzyme. In some embodiments, selectivity of compounds of the invention for JAK2 over JAK3 can be determined by the cellular ATP concentration.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including over-expression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, or multiple myeloma), and skin cancer such as cutaneous T-cell lymphoma (CTCL) and cutaneous B-cell lymphoma. Example cutaneous T-cell lymphomas include Sezary syndrome and mycosis fungoides.

JAK-associated diseases can further include those characterized by expression of a mutant JAK2 such as those having at least one mutation in the pseudo-kinase domain (e.g., JAK2V617F).

JAK-associated diseases can further include myeloproliferative disorders (MPDs) such as polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), systemic mast cell disease (SMCD), and the like.

Further JAK-associated diseases include inflammation and inflammatory diseases. Example inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The JAK inhibitors described herein can further be used to treat ischemia reperfusion injuries or a disease or condition related to an inflammatory ischemic event such as stroke or cardiac arrest. The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder (i.e., arresting further development of the pathology and/or symptomatology), and (3) ameliorating the disease; for example, ameliorating a disease, condition or disorder in an individual who is experiencing or displaying the pathology or symptomatology of the disease, condition or disorder (i.e., reversing the pathology and/or symptomatology).

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, or other agents can be used in combination with the compounds of the present invention for treatment of JAK-associated diseases, disorders or conditions. The one or more additional pharmaceutical agents can be administered to a patient simultaneously or sequentially.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, EP2005/009967, EP2005/010408, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionucleotide that is incorporated in the instant radio-labeled compounds will depend on the specific application of that radio-labeled compound. For example, for in vitro metalloprotease labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner Those of skill in the art will readily recognize a variety of noncritical parameters which can be changed or modified to yield essentially the same results. The compounds of the Examples have been found to be JAK inhibitors according to at least one assay described herein.

EXAMPLES

Example 1

3-[3-Methyl-1-(1H-pyrrolo[2,3-b]pyridin-4-yl)-1H-pyrazol-4-yl]benzonitrile

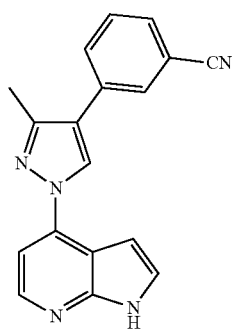 [SMILES: Cc1nn(-c2ccnc3[nH]ccc23)cc1-c1cccc(C#N)c1]

Step 1. 1H-Pyrrolo[2,3-b]pyridine 7-oxide

To a solution of 1H-pyrrolo[2,3-b]pyridine (4.90 g, 0.0415 mol) in ethyl acetate (41 mL, 0.42 mol) was added a solution of meta-chloroperbenzoic acid (MCPBA; 9.3 g, 0.054 mol) in ethyl acetate (27 mL, 0.28 mol) at 0° C. The reaction mixture was solidified when ~20 mL solution of MCPBA was added. An additional ~10 mL of ethyl acetate was added so that a solution resulted. The reaction mixture was allowed to warm to room temperature (rt) and stirred overnight, then was cooled at 0° C., filtered and washed with ethyl acetate three times to give 10.94 g wet solid. The wet solid (8.45 g) was then suspended in water (35 mL), and to the suspension was added 13 mL of sat. $Na_2CO_3$ dropwise, and the resulting mixture was stirred at room temperature overnight. The mixture was then cooled at 0° C., filtered and washed with water (×4) to give 3.55 g of pale purple solid which was dried at 40° C. overnight to give the desired product (2.47 g, 44.4% yield).

$^1$H NMR (400 MHz, $CD_3OD$): δ 8.2 (1H, d); 7.95 (1H, d); 7.5 (1H, d); 7.2 (1H, m); 6.65 (1H, d). MS $(M+H)^+$: 136.

Step 2. 4-Chloro-1H-pyrrolo[2,3-b]pyridine

To a pink solution of 1H-pyrrolo[2,3-b]pyridine 7-oxide (2.47 g, 0.0184 mol) in dimethylformamide (DMF) (13.3 mL, 0.172 mol) was added methanesulfonyl chloride (4.0 mL, 0.052 mol) at 50° C., and the pink color changed to orange. The reaction mixture was heated at 73° C. for 2 h, then cooled to 40° C. Water (35 mL) was added, and the resulting suspension was cooled at 0° C. NaOH was added to adjust the pH of the mixture to about 7. The mixture was filtered and washed with water (×3) to give 3.8 g of a wet pale orange solid that was dried at 40° C. overnight to give the product (2.35 g, 82.2% yield).

$^1$H NMR (400 MHz, $CDCl_3$): δ 10.8 (1H, br); 8.21 (1H, d); 7.41(1H, d); 7.18 (1H, d); 6.61 (1H, d). MS $(M+H)^+$: 153.

Step 3. 4-(4-Bromo-3-methyl-1H-pyrazol-1-yl)-1H-pyrrolo[2,3-b]pyridine

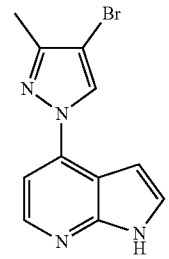 [SMILES: Cc1nn(-c2ccnc3[nH]ccc23)cc1Br]

A mixture of 4-chloro-1H-pyrrolo[2,3-b]pyridine (0.050 g, 0.00033 mol) and 4-bromo-3-methyl-1H-pyrazole (0.10 g, 0.00066 mol) was heated at 130° C. overnight. The reaction mixture then was subjected to column chromatography (eluting with 5% MeOH/DCM, 0.5% $NH_4OH$, on silica gel) to give 80 mg pale yellow solid which was triturated with MeOH (1.5 mL) to yield the product as a pale yellow solid (44 mg, 44% yield).

$^1$H NMR (400 MHz, $CD_3OD$): δ 8.32 (1H, s); 8.25 (1H, d); 7.6 (1H, s); 7.45 (1H, d); 7.37 (1H, d); 6.96 (1H, d); 2.4 (3H, s). MS $(M+H)^+$: 276.

Step 4. 3-[3-Methyl-1-(1H-pyrrolo[2,3-b]pyridin-4-yl)-1H-pyrazol-4-yl]benzonitrile A mixture of 4-(4-bromo-3-methyl-1H-pyrazol-1-yl)-1H-pyrrolo[2,3-b]pyridine (0.032 g, 0.00012 mol), (3-cyanophenyl)boronic acid (0.027 g, 0.00018 mol), sodium carbonate (0.032 g, 0.00030 mol) and tetrakis (triphenylphosphine)palladium(0) (7.0 mg, 0.0000060 mol) in 1,2-dimethoxyethane (0.3 mL, 0.003 mol) and water (0.3 mL, 0.02 mol) was heated at 130° C. (a liquid resulted, but with two layers) for 4 h. The reaction mixture then was cooled to room temperature (rt), filtered and was washed with water (×2) and dimethyl ether (DME) (×2) to give the product as a pale orange solid (15 mg, 44% yield).

$^1$H NMR (400 MHz, CD$_3$OD): δ 8.57 (1H, s); 8.31 (1H, d); 7.8 (2H, m); 7.75 (2H, m); 7.55 (1H, s); 7.45 (2H, m); 7.01 (1H, d); 2.6 (3H, s). MS (M+H)$^+$: 299.

Example 2

(2E)-3-[3-Methyl-1-(1H-pyrrolo[2,3-b]pyridin-4-yl)-1H-pyrazol-4-yl]acrylonitrile trifluoroacetate salt

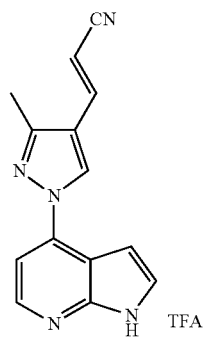 [SMILES: Cc1nn(-c2ccnc3[nH]ccc23)cc1/C=C/C#N]

Step 1. 4-Bromo-1H-pyrrolo[2,3-b]pyridine

To a solution of 1H-pyrrolo[2,3-b]pyridine 7-oxide (8.0 g, 0.060 mol), prepared by the procedure outlined in Example 1, Step 1 in DMF (100 mL, 1 mol) was added methanesulphonic anhydride (20.8 g, 0.119 mol, in four portions) at 0° C. The mixture was stirred at 0° C. for an additional 20 min followed by an addition of tetramethylammonium bromide (23.0 g, 0.149 mol). The resulting mixture was stirred overnight. Water (0.1 L) was added, and a slight exotherm was observed. A solution of sodium hydroxide in water (12.5 M, 12 mL) was added to adjust the pH of the mixture to about 8, followed by an addition of ~0.25 L of water. The resulting mixture was stirred for additional 2 h then filtered. The solid obtained was washed with water ×3 to give 6.72 g of a reddish solid which was dried at 50° C. over a weekend to give the product (5.75 g, 49% yield).

$^1$H NMR (400 MHz, CDCl$_3$): δ 10.8 (1H, br); 8.2 (1H, d); 7.41(1H, d); 7.19 (1H, d); 6.61 (1H, d). MS (M+H)$^+$: 196.

Step 2. 4-Bromo-1-[2-(trimethylsily)ethoxy]methyl-1H-pyrrolo[2,3-b]pyridine

To a solution of 4-bromo-1H-pyrrolo[2,3-b]pyridine (6.2 g, 0.031 mol) and [β-(trimethylsilyl)ethoxy]methyl chloride (6.7 mL, 0.038 mol) in DMF (62 mL, 0.80 mol) was added sodium hydride (1.5 g, 0.038 mol) at 0° C., and the resulting solution turned opaque. The mixture was stirred for additional 4 h, then diluted with methyl tert-butyl ether (MTBE). The organic layer was separated and washed with water (×2) and brine aqueous solution successively. The organic phase was dried and concentrated in vacuo to give 14.1 g of a product as a pale orange oil. The oil was purified by column chromatography eluting with 5-20% ethyl acetate/hexanes to give the purified product as a colorless oil (9.66 g, 94% yield).

$^1$H NMR (400 MHz, CDCl$_3$): δ 8.2 (1H, d); 7.49 (1H, d); 7.19 (1H, d); 6.62 (1H, d); 5.78 (2H, s); 3.6 (2H, t); 0.98 (2H, t); 0.0 (9H, s). MS (M+H)$^+$: 326.

Step 3. (2E)-3-[3-Methyl-1-(1H-pyrrolo[2,3-b]pyridin-4-yl)-1H-pyrazol-4-yl]acrylonitrile A solution of 2-propenenitrile (0.043 mL, 0.00065 mol), bis(triphenylphosphine)palladium(II) chloride (0.0091 g, 0.000013 mol), 4-(4-bromo-3-methyl-1H-pyrazol-1-yl)-1H-pyrrolo[2,3-b]pyridine (0.036 g, 0.00013 mol), and tetraethylamine (TEA) (0.15 mL, 0.0011 mol) in DMF (0.15 mL, 0.0019 mol) was microwaved at 120° C. for 2 h. The solution was then diluted with ethyl acetate and washed with water (×2) and brine successively. The organic phase was dried and concentrated in vacuo to give 62 mg of the product as an orange solid. The orange solid was purified by prep-LCMS to give 12 mg of an off-white solid as a trifluoroacetic acid (TFA) salt which was triturated with MTBE (1 mL) to provide the purified product as a pale green solid. (dried at 60° C. for 4 h, 9 mg, 28% yield).

$^1$H NMR (400 MHz, CD$_3$OD): 2:1 of trans:cis isomers. For trans: δ 8.95 (NH, 1H, s); 7.75 (olefin, 1H, d); 6.1 (olefin, 1H, d); 2.45 (Me, 3H, s). MS (M+H)$^+$: 249.

Example 3

3-[3-Methyl-1-(1H-pyrrolo[2,3-b]pyridin-4-yl)-1H-pyrazol-4-yl]propanenitrile, trifluoroacetate salt

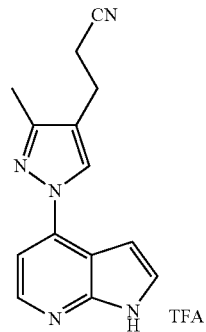 [SMILES: Cc1nn(-c2ccnc3[nH]ccc23)cc1CCC#N]

A mixture of (2E)-3-[3-methyl-1-(1H-pyrrolo[2,3-b]pyridin-4-yl)-1H-pyrazol-4-yl) acrylo-nitrile, TFA salt, (0.0050 g, 0.000020 mol, prepared according to Example 2) and palladium (5.8 mg, 0.0000054 mol) in methanol (1 mL, 0.02 mol) and 1,2-dichloroethane (1 mL, 0.01 mol) was degassed and then was stirred under an atmosphere of hydrogen for 3 h. The reaction mixture then was filtered and the filtrate was concentrated in vacuo to give 8 mg of the product as an off-white solid. The crude material was purified by prep-LCMS to give 5.1 mg of a white solid as a TFA salt which was triturated with MTB (1 mL) to give the product as a white solid (1.7 mg, 34% yield).

$^1$H NMR (400 MHz, CD$_3$OD): δ 8.52 (1H, s); 8.35 (1H, d); 7.72(1H, d); 7.6 (1H, s); 7.38 (1H, d); 6.96 (1H, d); 2.7-2.9 (4H, m); 2.4 (3H, s). MS (M+H)$^+$: 251.

Example 13

4-(4-Phenyl-1H-imidazol-1-yl)-1H-pyrrolo[2,3-b]pyridine

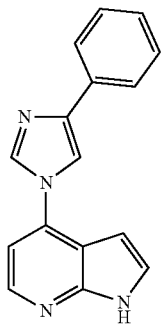 [SMILES: c1ccc(-c2cn(-c3ccnc4[nH]ccc34)cn2)cc1]

A melt of 4-chloro-1H-pyrrolo[2,3-b]pyridine (0.050 g, 0.00033 mol) in 4-phenyl-1H-imidazole (0.24 g, 0.0016 mol) was heated at 200° C. overnight. The reaction was partitioned between ethyl acetate and saturated NaHCO$_3$, separated and the organic phase was washed with brine. The organic layer was then dried and evaporated to give 250 mg of an orange oil. The oil was chromatographed with 7% MeOH/DCM, 0.7% NH$_4$OH, sample in solvent system. Collected 74 mg of the product as an orange glass. The glass was triturated with hot DCE (1.5 mL) to give 51 mg of a brown solid which was dried at 60° C. for 4 h to afford the desired product (50 mg, 59 yield).

$^1$H NMR (400 MHz, dimethylsulxoxide (DMSO)): δ 12.5 (1H, s); 8.5 (1H, s); 8.4 (1H, s); 8.38 (1H, d); 7.8 (2H, m); 7.62 (1H, d); 7.4 (3H, m); 7.3 (1H, m); 6.81 (1H, d). MS (M+H)$^+$: 260

Example 14

[3-Methyl-1-(1H-pyrrolo[2,3-b]pyridin-4-yl)-1H-pyrazol-4-yl)-piperidin-1-yl-methanone

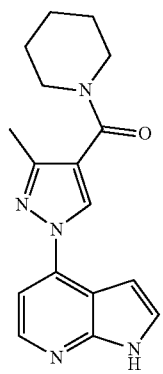 [SMILES: Cc1nn(-c2ccnc3[nH]ccc23)cc1C(=O)N1CCCCC1]

Step 1. 3-Methyl-1-(1-12-(trimethylsilyl)ethoxy]methyl-1H-pyrrolo[2,3-b]pyridin-4-yl)-1H-pyrazole-4-carboxylic acid To a −70° C. solution of 4-(4-bromo-3-methyl-1H-pyrazol-1-yl)-1-[2-(trimethylsilyl)ethoxy]-methyl-1H-pyrrolo[2,3-b]pyridine (0.107 g, 0.000263 mol) in THF (1 mL, 0.01 mol), and n-butyllithium in hexane (0.23 mL of 1.6M), 0.5g of CO$_2$ solid was added. After 15 min, the reaction was quenched with NH$_4$Cl. Ethyl acetate and water were added. The organic phase was washed with brine, and was evaporated to give 84 mg of an off-white glass/solid. The solid was chromatographed with 50% ethyl acetate/hexanes, 0.5% AcOH, sample on silica gel to give 40 mg of a purified product as a white solid (37% yield).

$^1$H NMR (400 MHz, CDCl$_3$): δ 8.5 (1H, d); 7.45 (1H, d); 7.25 (1H, d); 7.02 (1H, s); 6.6 (1H, d); 5.75 (2H, s); 3.6 (2H, t); 2.48 (3H, s); 0.98 (3H, t); 0.0 (9H, s). MS (M+H)$^+$: 372.

Step 2. 4-[3-Methyl-4-(piperidin-1-ylcarbonyl)-1H-pyrazol-1-yl]-1-[2-(trimethylsilyl)ethoxy]methyl-1H-pyrrolo[2,3-b]pyridine A solution of 3-methyl-1-(1-[2-(trimethylsilyl)ethoxy]methyl-1H-pyrrolo[2,3-b]pyridin-4-yl)-1H-pyrazole-4-carboxylic acid (0.040 g, 0.00011 mol) (1:1 of AcOH) and N,N-carbonyldiimidazole (0.035 g, 0.00021 mol) in THF (1 mL, 0.01 mol) was stirred for 1.2 h, after which time piperidine (32 μL, 0.00032 mol) was added. After another 2 h, another portion of piperidine (15 μL) was added and the resulting mixture was stirred overnight. The reaction mixture was then partitioned between ethyl acetate and water, and washed sequentially with sat. NaHCO$_3$ and brine. The organic phase was dried and evaporated to give 49 mg of the crude product as an orange oil/glass. The crude product was chromatographed with 75-100% ethyl acetate/hexanes, sample in DCM. Collected 25 mg of the purified product as a colorless glass/oil (50% yield).

$^1$H NMR (400 MHz, CDCl$_3$): δ 8.45 (1H, d); 8.23 (1H, s); 7.5 (1H, d); 7.4 (1H, d); 7.05 (1H, d); 5.8 (2H, s); 3.7 (4H, br); 3.6 (2H, t); 2.55 (3H, s); 1.7 (6H, br); 1.0 (3H, t); 0.0 (9H, s). MS (M+H)$^+$: 439.

Step 3. 3-Methyl-1-(1H-pyrrolo[2,3-b]pyridin-4-yl)-1H-pyrazol-4-yl]-piperidin-1-yl-methanone A solution of 4-[3-methyl-4-(piperidin-1-ylcarbonyl)-1H-pyrazol-1-yl]-1-[2-(trimethylsilyl)-ethoxy]methyl-1H-pyrrolo[2,3-b]pyridine (0.025 g, 0.000057 mol) in TFA (1 mL, 0.01 mol) was stirred for 1.5 h. The reaction mixture was then concentrated and partitioned between DCM and sat. NaHCO$_3$ ×2, and brine. The organic layer was then dried and concentrated to give 28 mg of the product as a white foam. The foam was dissolved in methanol (1 mL, 0.02 mol) and treated with ammonium hydroxide in water (8.0M, 1 mL) for 1.5 h. The reaction was concentrated using a rotary evaporator to give 24 mg of a pale yellow glass. The glass was triturated with methyl t-butyl ether (MTBE) to give 13 mg of a white solid which was dried at rt over a weekend. A total of 8 mg of the product was obtained after drying (45% yield).

$^1$H NMR (400 MHz, CDCl$_3$): δ 9.7 (1H, s); 8.4 (1H, d); 8.2 (1H, s); 7.42 (1H, d); 7.4 (1H, d); 6.99 (1H, d); 3.4-3.8 (4H, br); 2.47 (3H, s); 1.5-1.8 (6H, br). MS (M+H)$^+$: 309.

Example 15

[3-Methyl-1-(1H-pyrrolo[2,3-b]pyridin-4-yl)-1H-pyrazol-4-ylmethyl]-phenyl- amine

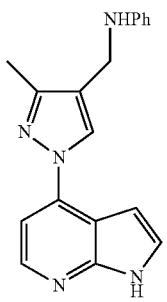

Step 1. 3-Methyl-1-(1-[2-(trimethylsilyl)ethoxy]methyl-1H-pyrrolo[2,3-b]pyridin-4-yl)-1H-pyrazole-4-carbaldehyde To a −70° C. solution of 4-(4-bromo-3-methyl-1H-pyrazol-1-yl)-1-[2-(trimethylsilyl)ethoxy]-methyl-1H-pyrrolo[2,3-b]pyridine (0.25 g, 0.00061 mol) in THF (2 mL, 0.03 mol), 1.6 M n-butyllithium in hexane (0.54 mL). After 10 min, DMF (120 µL, 0.0015 mol) was added. The reaction was allowed to warm to rt and stirred overnight. The reaction was then quenched with NH$_4$Cl. Ethyl acetate/water was added. The organic phase was separated and washed with brine, then dried and concentrated to give 180 mg of an orange oil. The crude product was chromatographed with 25% ethyl acetate/hexanes, sample in DCM. Collected 40 mg of a pale yellow oil (18% yield). $^1$H NMR (400 MHz, CDCl$_3$): δ 10.15 (1H, s); 8.7 (1H, s); 8.47 (1H, d); 7.58 (1H, d); 7.5 (1H, d); 7.05 (1H, d); 5.8 (2H, s); 3.63 (2H, t); 2.7 (3H, s); 0.98 (3H, t); 0.0 (9H, s). MS (M+H)$^+$: 356.

Step 2. N-[3-Methyl-1-(1-[2-(trimethylsilyl)ethoxy]methyl-1H-pyrrolo[2,3-b]pyridin-4-yl)-1H-pyrazol-4-yl]methylaniline A solution of 3 -methyl-1-(1-[2 -(trimethylsilyl)ethoxy]methyl-1H-pyrrolo [2,3 -b]pyridin-4-yl)-1H-pyrazole-4-carbaldehyde (0.025 g, 0.000070 mol) and aniline (1M in DCM, 0.070 mL), in DCM (1 mL, 0.02 mol) was stirred for 1 min. Acetic acid (20 µL, 0.0004 mol), aniline (1M in DCM, 140 µL) and sodium triacetoxyborohydride (0.022 g, 0.00010 mol) were added. The reaction was stirred overnight and partitioned between DCM and sat. NaHCO$_3$, washed with brine. The organic phase was dried and evaporated to give 21 mg of a product as a pale orange glass (70% yield).

$^1$H NMR (400 MHz, CDCl$_3$): δ 8.4 (1H, d); 8.15 (1H, s); 7.65 (1H, d); 7.35 (3H, m); 7.09 (1H, d); 6.82 (1H, m); 6.89 (2H, m); 5.8 (2H, s); 4.35 (2H, s); 3.6 (2H, t); 2.5 (3H, s); 0.99 (3H, t); 0.0 (9H, s). MS (M+H)$^+$: 433.

Step 3. [3-Methyl-1-(1H-pyrrolo[2,3-b]pyridin-4-yl)-1H-pyrazol-4-ylmethyl]-phenyl-amine Deprotection of N-[3-methyl-1-(1-[2-(trimethylsilyl)ethoxy]methyl-1H-pyrrolo [2,3-b]pyridin-4-yl)-1H-pyrazol-4-yl]methylaniline was carried out according to the procedures of Example 14, Step 3 to give the desired product (58% yield).

$^1$H NMR (400 MHz, CDCl$_3$): δ 9.9 (1H, s); 8.38 (1H, d); 8.1 (1H, s); 7.4 (1H, d); 7.35 (1H, d); 7.3 (2H, m); 7.0 (1H, d); 6.79 (1H, m); 6.77 (2H, m); 4.25 (2H, s); 3.81 (1H, s); 2.41 (3H, s). MS (M+H)$^+$: 303.

Example 25

3-[3-Methyl-1-(1H-pyrrolo[2,3-b]pyridin-4-yl)-1H-pyrazol-4-yl]-cyclohexanol

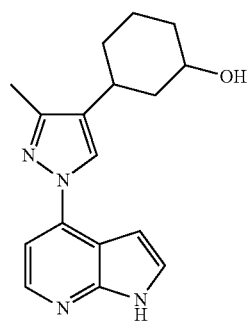 [SMILES: Cc1nn(-c2ccnc3[nH]ccc23)cc1C1CCCC(O)C1]

Step 1. 3-Ethoxy-1-[3-methyl-1-(1-1-[2-(trimethylsilyl)ethoxy]methyl-1H-pyrrolo[2,3-b]pyridin-4-yl)-1H-pyrazol-4-yl]cyclohex-2-en-1-ol

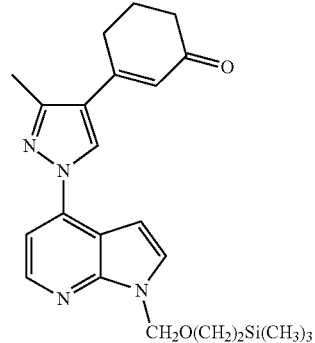

To a −75° C. solution of 4-(4-bromo-3-methyl-1H-pyrazol-1-yl)-1-[2-(trimethylsilyl)ethoxy]-methyl-1H-pyrrolo[2,3-b]pyridine (0.11 g, 0.00027 mol) in THF (1.5 mL, 0.018 mol) was added 1.6 M n-butyllithium in hexane (0.22 mL). The reaction mixture turned dark orange. After ~10 min, 1.0 M magnesium dibromide in ether (0.35 mL) was added. After another 50 min, a solution of 3-ethoxy-2-cyclohexen-1-one (41.5 µL, 0.000308 mol) in THF (~0.3 mL) was added. The resulting mixture was warmed to −40° C. over ~1 h and quenched with NH$_4$Cl. Then ethyl acetate/water was added. The organic phase was washed with brine, and concentrated to give 145 mg of an orange oil. The crude product was chromatographed with 0-50% ethyl acetate/hexane gradient, sample in DCM. Collected 35 mg of the produce as an oil (30% yield).

$^1$H NMR (400 MHz, CDCl$_3$): δ 8.49 (1H, d); 8.38 (1H, s); 7.55 (1H, d); 7.4 (1H, d); 7.1 (1H, d); 6.0 (2H, s); 3.6 (2H, t); 2.81 (2H, m); 2.62 (3H, s); 2.58 (2H, m); 2.27 (2H, m); 1.0 (3H, t); 0.0 (9H, s). MS (M+H)+: 422.

Step 2. 3-[3-Methyl-1-(1-[2-(trimethylsilyl)ethoxy]methyl-1H-pyrrolo[2,3-]pyridin-4-yl)-1H-pyrazol-4-yl]cyclohexanol A mixture of 3-[3-methyl-1-(1-[2-(trimethylsilyl)ethoxy]methyl-1H-pyrrolo[2,3-b]pyridin-4-yl)-1H-pyrazol-4-yl]cyclohex-2-en-1-one (0.019 g, 0.000045 mol) and palladium on carbon (Pd/C) (0.018 g, 0.000017 mol) in methanol (2 mL, 0.05 mol) was degassed and was stirred under a hydrogen atmosphere overnight. An additional 48 mg of 10% Pd/C was added and stirred under a hydrogen atmosphere for 8 h. The palladium was filtered and the filtrate was stirred with sodium tetrahydroborate (0.032 g, 0.00084 mol) for 5 h. The reaction was purified by prep-HPLC to give 5 mg of the desired product. MS (M+H)+: 426.

Step 3. 3-[3-Methyl-1-(1H-pyrrolo[2,3-]pyridin-4-yl)-1H-pyrazol-4-yl]-cyclohexanol Deprotection of 3-[3-methyl-1-(1-[2-(trimethylsilyl)ethoxy]methyl-1H-pyrrolo[2,3-b]pyridin-4-yl)-1H-pyrazol-4-yl]cyclohexanol was carried out according to the procedures of Example 14, Step 3 to give the desired product (40% yield).
$^1$H NMR (400 MHz, CDCl$_3$): δ 9.72 (1H, s); 8.35 (1H, d); 7.95 (1H, s); 7.41 (1H, d); 7.35 (1H, d); 7.02 (1H, d); 3.78 (1H, m); 2.6 (1H, m); 2.4 (3H, s); 1.2-2.4 (8H, m). MS (M+H)+: 296.

Example 40

4-[1-(3-Methoxy-1-methyl-propyl)-1H-pyrazol-4-yl]-1H-pyrrolo[2,3-b]pyridine

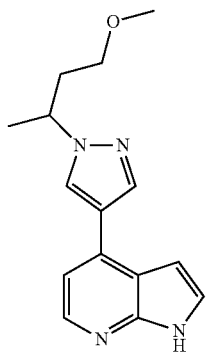 [SMILES: COCCC(C)n1cc(-c2ccnc3[nH]ccc23)cn1]

Step 1. 4-[1-(3-Methoxy-1-methylpropyl)-1H-pyrazol-4-yl]-1-[2-(trimethylsilyl)ethoxy]-methyl-1H-pyrrolo[2,3-b]pyridine To a 0° C. solution of 3-[4-(1-[2-(trimethylsilyl)ethoxy]methyl-1H-pyrrolo[2,3-b]pyridin-4-yl)-1H-pyrazol-1-yl]butan-1-ol (the alcohol was made by DIBAL reduction of the ester in Example 58) (0.056 g, 0.00014 mol)) in DMF (1 mL, 0.01 mol), was added sodium hydride (0.0107 g, 0.000268 mol). After 5 min, methyl iodide (18 µL, 0.00029 mol) was added and the resulting mixture was stirred over a weekend. The mixture was then partitioned between ethyl acetate and water, separated and the organic phase was washed with brine. The organic phase was concentrated to give a pale orange oil.
$^1$ H NMR (400 MHz, CDCl$_3$): δ 8.4 (1H, d); 8.3 (1H, s); 8.0 (1H, s); 7.65 (1H, d); 7.27 (1H, d); 6.8 (1H, d); 5.8 (2H, s); 4.7 (1H, m); 3.63 (2H, t); 3.2-3.4 (2H, m); 3.38 (3H, s); 2.1-2.3 (2H, m); 1.7 (3H, d); 1.0 (2H, t); 0.0 (9H, s). MS (M+H)+: 400.

Step 2. 4-[1-(3-Methoxy-1-methyl-propyl)-1H-pyrazol-4-yl]-1H-pyrrolo[2,3-b]pyridine Deprotection of 4-[1-(3-methoxy-1-methylpropyl)-1H-pyrazol-4-yl]-1-[2-(trimethylsilyl)-ethoxy]-methyl-1H-pyrrolo[2,3-b]pyridine was carried out according to the procedures of Example 14, Step 3 to give the desired product (25% yield).
$^1$H NMR (400 MHz, CDCl$_3$): δ 10.0 (1H, s); 8.35 (1H, d); 8.18 (1H, s); 7.95 (1H, s); 7.41 (1H, d); 7.21 (1H, d); 6.75 (1H, d); 4.63 (1H, m); 3.15-3.4 (2H, m); 3.35 (3H, s); 2.21-2.05 (2H, m); 1.6 (3H, d). MS (M+H)+: 270.

Example 42

4-[1-(1-Methyl-3-pyrazol-1-yl-propyl)-1H-pyrazol-4-yl]-1H-pyrrolo[2,3-b]pyridine

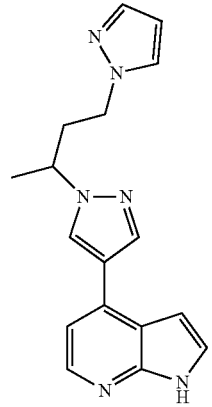 [SMILES: CC(CCn1cccn1)n1cc(-c2ccnc3[nH]ccc23)cn1]

Step 1. 4-1-[1-Methyl-3-(1H-pyrazol-1-yl)propyl]-1H-pyrazol-4-yl-1-[2-(trimethylsilyl)ethoxy]methyl-1H-pyrrolo[2,3-b]pyridine To a 0° C. solution of 3-[4-(1-[2-(trimethylsilyl)ethoxy]methyl-1H-pyrrolo[2,3-b]pyridin-4-yl)-1H-pyrazol-1-yl]butyl methanesulfonate (prepared by mesylation of the alcohol as in Example 59, Step 1) (0.055 g, 0.00012 mol) and 1H-pyrazole (0.025 g, 0.00036 mol) in DMF (1 mL, 0.01 mol) was added sodium hydride (0.014 g, 0.00036 mol). The resulting solution was stirred overnight and then partitioned between ethyl acetate and 0.1 N HCl, water. the organic phase was separated and washed with brine. The organic layer was then concentrated to give 49 mg of a pale orange glass (87% yield).
$^1$H NMR (400 MHz, CDCl$_3$): δ 8.4 (1H, d); 8.18 (1H, s); 7.99 (1H, s); 7.6 (1H, t); 7.5 (1H, d); 7.4 (1H, t); 7.27 (1H, d); 6.8 (1H, d); 6.3 (1H, m); 5.8 (2H, s); 4.2 (1H, m); 4.0-4.2 (2H, m); 3.61 (2H, t); 2.58 (2H, m); 1.65 (3H, d); 1.0 (2H, t); 0.0 (9H, s). MS (M+H)+: 436.

Step 2. 4-[1-(1-Methyl-3-pyrazol-1-yl-propyl)-1H-pyrazol-4-yl]-1H-pyrrolo[2,3-b]pyridine Deprotection of 4-1-[1-methyl-3-(1H-pyrazol-1-yl)propyl]-1H-pyrazol-4-yl-1-[2-(trimethyl-silyl)ethoxy]methyl-1H-pyrrolo[2,3-b]pyridine was carried out according to the procedures of Example 14, Step 3 to give the desired product (38% yield).

$^1$H NMR (400 MHz, CDCl$_3$): δ 9.7 (1H, s); 8.38 (1H, d); 8.1 (1H, s); 7.7(1H, s); 7.59 (1H, t); 7.4 (1H, d); 7.35 (1H, t); 7.21 (1H, d); 6.75 (1H, d); 6.25 (1H, m); 4.4 (1H, m); 3.9-4.15 (2H, m); 2.55 (2H, m); 1.63 (3H, d). MS (M+H)$^+$: 306.

The following compounds in Table 1 were made by methods analogous to the procedures above as indicated. "Purification A" indicates that the product following deprotection was purified by preparative-HPLC under the following conditions: C18 eluting with a gradient of MeCN/H$_2$O containing 0.15% NH$_4$OH.

TABLE 1

| Ex. No. | Structure | Name | MS (M + H) | Prep. Ex. No. |
|---|---|---|---|---|
| 4 | 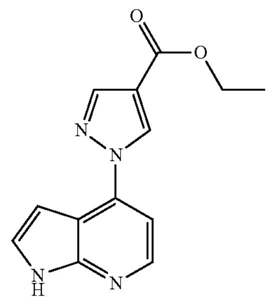 [SMILES: CCOC(=O)c1cnn(-c2ccnc3[nH]ccc23)c1] | 1-(1H-Pyrrolo[2,3-b]pyridin-4-yl)-1H-pyrazole-4-carboxylic acid ethyl ester | 256 | 1 |
| 5 | 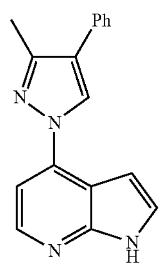 [SMILES: Cc1nn(-c2ccnc3[nH]ccc23)cc1-c1ccccc1] | 4-(3-Methyl-4-phenyl-pyrazol-1-yl)-1H-pyrrolo[2,3-b]pyridine | 274 | 1 |
| 6 | 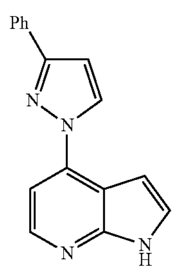 [SMILES: c1ccc(-c2ccn(-c3ccnc4[nH]ccc34)n2)cc1] | 4-(3-Phenyl-pyrazol-1-yl)-1H-pyrrolo[2,3-b]pyridine | 260 | 1 |
| 7 | 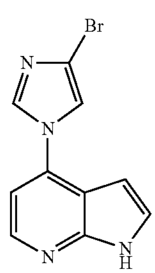 [SMILES: Brc1cn(-c2ccnc3[nH]ccc23)cn1] | 4-(4-Bromo-imidazol-1-yl)-1H-pyrrolo[2,3-b]pyridine | 262 | 13 |

TABLE 1-continued

| Ex. No. | Structure | Name | MS (M + H) | Prep. Ex. No. |
|---|---|---|---|---|
| 8 | 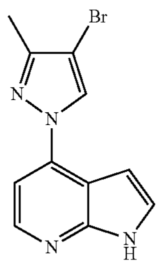 [SMILES: Cc1nn(-c2ccnc3[nH]ccc23)cc1Br] | 4-(4-Bromo-3-methyl-pyrazol-1-yl)-1H-pyrrolo[2,3-b]pyridine | 262 | 1 |
| 9 | 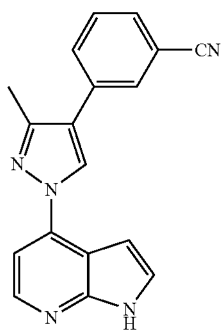 [SMILES: Cc1nn(-c2ccnc3[nH]ccc23)cc1-c1cccc(C#N)c1] | 3-[3-Methyl-1-(1H-pyrrolo[2,3-b]pyridin-4-yl)-1H-pyrazol-4-yl]-benzonitrile | 299 | 1 |
| 10 | 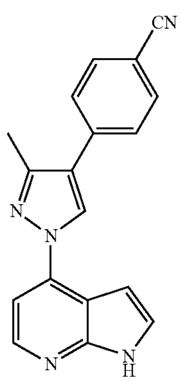 [SMILES: Cc1nn(-c2ccnc3[nH]ccc23)cc1-c1ccc(C#N)cc1] | 4-[3-Methyl-1-(1H-pyrrolo[2,3-b]pyridin-4-yl)-1H-pyrazol-4-yl]-benzonitrile | 299 | 1 |
| 16 | 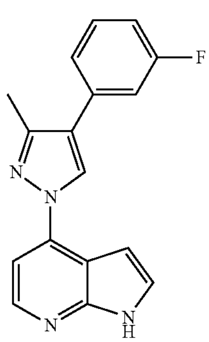 [SMILES: Cc1nn(-c2ccnc3[nH]ccc23)cc1-c1cccc(F)c1] | 4-[4-(3-Fluoro-phenyl)-3-methyl-pyrazol-1-yl]-1H-pyrrolo[2,3-b]pyridine | 292 | 1 |

TABLE 1-continued

| Ex. No. | Structure | Name | MS (M + H) | Prep. Ex. No. |
| --- | --- | --- | --- | --- |
| 17 | 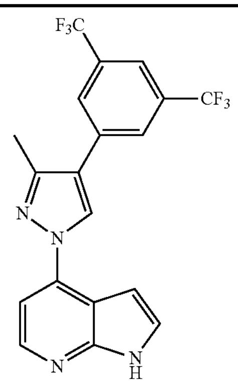 | 4-[4-(3,5-Bis-trifluoromethyl-phenyl)-3-methyl-pyrazol-1-yl]-1H-pyrrolo[2,3-b]pyridine | 410 | 1 |
| 18 | 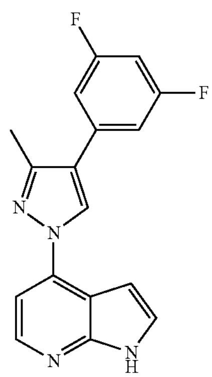 [SMILES: Cc1nn(-c2ccnc3[nH]ccc23)cc1-c1cc(F)cc(F)c1] | 4-[4-(3,5-Difluoro-phenyl)-3-methyl-pyrazol-1-yl]-1H-pyrrolo[2,3-b]pyridine | 310 | 1 |
| 19 | 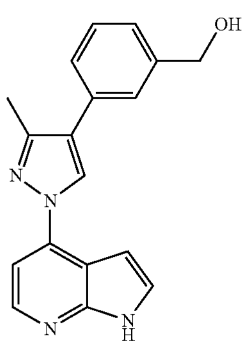 [SMILES: Cc1nn(-c2ccnc3[nH]ccc23)cc1-c1cccc(CO)c1] | {3-[3-Methyl-1-(1H-pyrrolo[2,3-b]pyridin-4-yl)-1H-pyrazol-4-yl]-phenyl}-methanol | 304 | 1 |
| 20 | 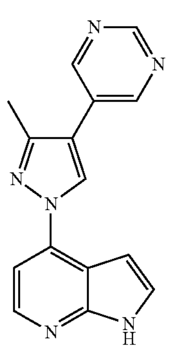 [SMILES: Cc1nn(-c2ccnc3[nH]ccc23)cc1-c1cncnc1] | 4-(3-Methyl-4-pyrimidin-5-yl-pyrazol-1-yl)-1H-pyrrolo[2,3-b]-pyridine | 276 | 1 |

TABLE 1-continued

| Ex. No. | Structure | Name | MS (M + H) | Prep. Ex. No. |
|---|---|---|---|---|
| 21 | 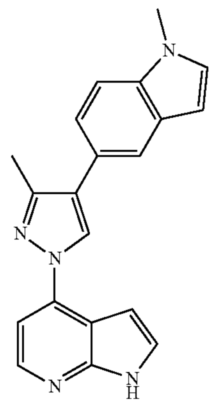 [SMILES: Cc1nn(-c2ccnc3[nH]ccc23)cc1-c1ccc2c(ccn2C)c1] | 4-[3-Methyl-4-(1-methyl-1H-indol-5-yl)-pyrazol-1-yl]-1H-pyrrolo[2,3-b]pyridine | 327 | 1 |
| 22 | 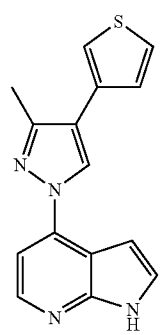 [SMILES: Cc1nn(-c2ccnc3[nH]ccc23)cc1-c1ccsc1] | 4-(3-Methyl-4-thiophen-3-yl-pyrazol-1-yl)-1H-pyrrolo[2,3-b]-pyridine | 280 | 1 |
| 23 | 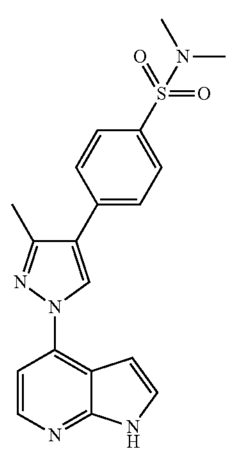 | N,N-Dimethyl-4-[3-methyl-1-(1H-pyrrolo[2,3-b]pyridin-4-yl)-1H-pyrazol-4-yl]-benzenesulfonamide | 381 | 1 |

TABLE 1-continued

| Ex. No. | Structure | Name | MS (M + H) | Prep. Ex. No. |
|---|---|---|---|---|
| 24 | 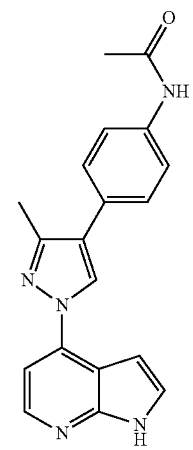 [SMILES: CC(=O)Nc1ccc(-c2cn(-c3ccnc4[nH]ccc34)nc2C)cc1] | N-{4-[3-Methyl-1-(1H-pyrrolo[2,3-b]pyridin-4-yl)-1H-pyrazol-4-yl]-phenyl}-acetamide | 331 | 1 |
| 26 | 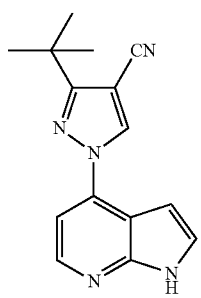 [SMILES: CC(C)(C)c1nn(-c2ccnc3[nH]ccc23)cc1C#N] | 3-tert-Butyl-1-(1H-pyrrolo[2,3-b]pyridin-4-yl)-1H-pyrazole-4-carbonitrile | 265 | 1 |
| 27 | 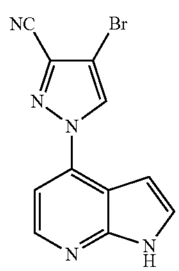 [SMILES: N#Cc1nn(-c2ccnc3[nH]ccc23)cc1Br] | 4-Bromo-1-(1H-pyrrolo[2,3-b]-pyridin-4-yl)-1H-pyrazole-3-carbonitrile | 287 | 1 |
| 28 | 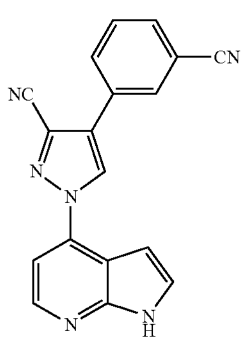 [SMILES: N#Cc1cccc(-c2cn(-c3ccnc4[nH]ccc34)nc2C#N)c1] | 4-(3-Cyano-phenyl)-1-(1H-pyrrolo[2,3-b]pyridin-4-yl)-1H-pyrazole-3-carbonitrile | 310 | 1 |

TABLE 1-continued

| Ex. No. | Structure | Name | MS (M + H) | Prep. Ex. No. |
|---|---|---|---|---|
| 29 | 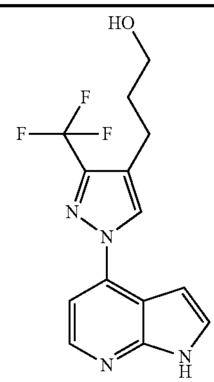 | 3-[1-(1H-Pyrrolo[2,3-b]pyridin-4-yl)-3-trifluoromethyl-1H-pyrazol-4-yl]-propan-1-ol | 254 | 1 |
| 30 | 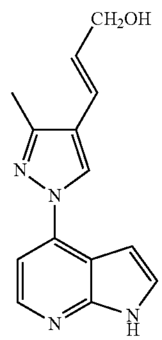 [SMILES: Cc1nn(-c2ccnc3[nH]ccc23)cc1/C=C/CO] | 3-[3-Methyl-1-(1H-pyrrolo[2,3-b]pyridin-4-yl)-1H-pyrazol-4-yl]-prop-2-en-1-ol | 310 | 1 |
| 31 | 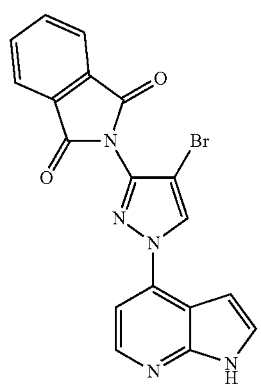 [SMILES: O=C1c2ccccc2C(=O)N1c1nn(-c2ccnc3[nH]ccc23)cc1Br] | 2-[4-Bromo-1-(1H-pyrrolo[2,3-b]pyridin-4-yl)-1H-pyrazol-3-yl]-isoindole-1,3-dione | 408 | 1 |
| 32 | 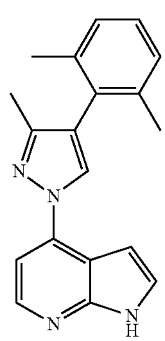 | 4-[4-(2,6-Dimethyl-phenyl)-3-methyl-pyrazol-1-yl]-1H-pyrrolo[2,3-b]pyridine | 302 | 1 |

TABLE 1-continued

| Ex. No. | Structure | Name | MS (M + H) | Prep. Ex. No. |
|---|---|---|---|---|
| 33 | 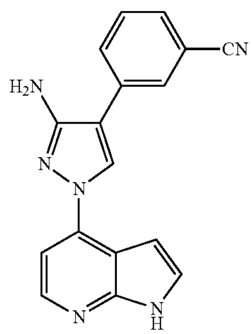 [SMILES: N#Cc1cccc(-c2cn(-c3ccnc4[nH]ccc34)nc2N)c1] | 3-[3-Amino-1-(1H-pyrrolo[2,3-b]pyridin-4-yl)-1H-pyrazol-4-yl]-benzonitrile | 300 | 1 |
| 34 | 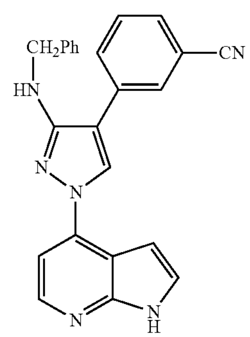 | 3-[3-Benzylamino-1-(1H-pyrrolo[2,3-b]pyridin-4-yl)-1H-pyrazol-4-yl]-benzonitrile | 390 | 1, 15 |
| 35 | 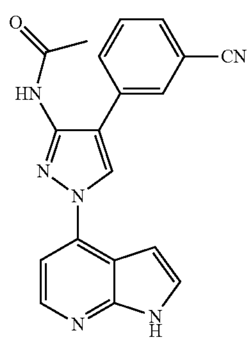 [SMILES: CC(=O)Nc1nn(-c2ccnc3[nH]ccc23)cc1-c1cccc(C#N)c1] | N-[4-(3-Cyano-phenyl)-1-(1H-pyrrolo[2,3-b]pyridin-4-yl)-1H-pyrazol-3-yl]-acetamide | 342 | 1, 14 |
| 36 | 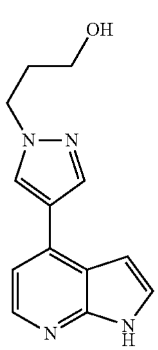 [SMILES: OCCCn1cc(-c2ccnc3[nH]ccc23)cn1] | 3-[4-(1H-Pyrrolo[2,3-b]pyridin-4-yl)-pyrazol-1-yl]-propan-1-ol | 242 | 58 Purification A |

TABLE 1-continued

| Ex. No. | Structure | Name | MS (M + H) | Prep. Ex. No. |
|---|---|---|---|---|
| 37 | 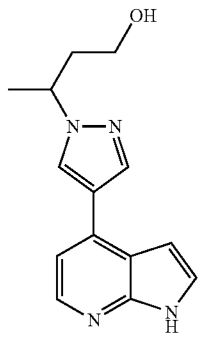 [SMILES: CC(CCO)n1cc(-c2ccnc3[nH]ccc23)cn1] | 3-[4-(1H-Pyrrolo[2,3-b]pyridin-4-yl)-pyrazol-1-yl]-butan-1-ol | 256 | 58 Purification A |
| 38 | 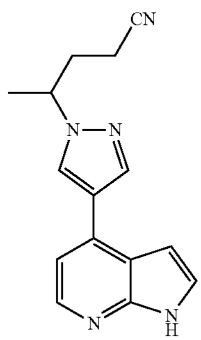 [SMILES: CC(CCC#N)n1cc(-c2ccnc3[nH]ccc23)cn1] | 4-[4-(1H-Pyrrolo[2,3-b]pyridin-4-yl)-pyrazol-1-yl]-pentanenitrile | 265 | 59 Purification A |
| 39 | 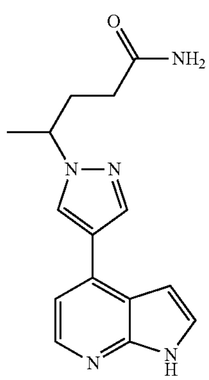 [SMILES: CC(CCC(N)=O)n1cc(-c2ccnc3[nH]ccc23)cn1] | 4-[4-(1H-Pyrrolo[2,3-b]pyridin-4-yl)-pyrazol-1-yl]-pentanoic acid amide | 283 | 60 Purification A |
| 41 | 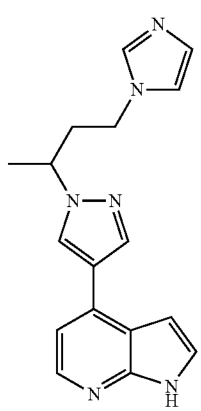 [SMILES: CC(CCn1ccnc1)n1cc(-c2ccnc3[nH]ccc23)cn1] | 4-[1-(3-Imidazol-1-yl-1-methyl-propyl)-1H-pyrazol-4-yl]-1H-pyrrolo[2,3-b]pyridine | 306 | 42 |

TABLE 1-continued

| Ex. No. | Structure | Name | MS (M + H) | Prep. Ex. No. |
|---|---|---|---|---|
| 43 | 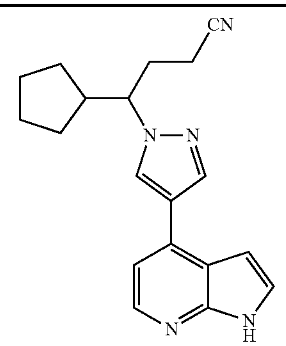 | 4-Cyclopentyl-4-[4-(1H-pyrrolo[2,3-b]pyridin-4-yl)-pyrazol-1-yl]-butyronitrile | 319 | 59 Purification A |
| 44 | 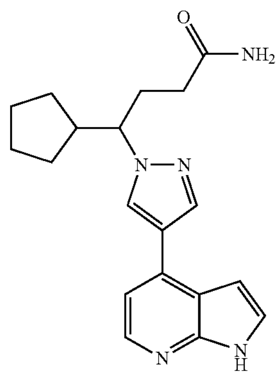 [SMILES: NC(=O)CCC(C1CCCC1)n1cc(-c2ccnc3[nH]ccc23)cn1] | 4-Cyclopentyl-4-[4-(1H-pyrrolo[2,3-b]pyridin-4-yl)-pyrazol-1-yl]-butyramide | 337 | 60 Purification A |
| 45 | 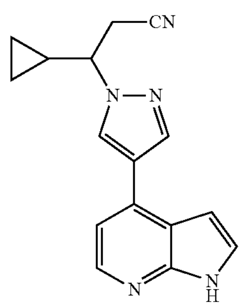 [SMILES: N#CCC(C1CC1)n1cc(-c2ccnc3[nH]ccc23)cn1] | 3-Cyclopropyl-3-[4-(7H-pyrrolo[2,3-d]pyrimidin-4-yl)-pyrazol-1-yl]-propionitrile | 278 | 61 Purification A |

Example 46

4-(2-tert-Butyl-1-methyl-1H-imidazol-4-yl)-1H-pyrrolo[2,3-b]pyridine trifluoro-acetate salt

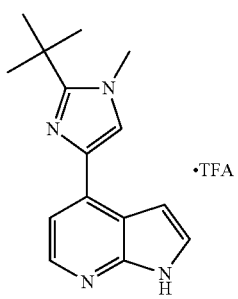 [SMILES: Cn1cc(-c2ccnc3[nH]ccc23)nc1C(C)(C)C]

Step 1. 4-(2-tert-butyl-1H-imidazol-5-yl)-1-1-[2-(trimethylsilyl)ethoxy]methyl-1H-pyrrolo[2,3-b]pyridine To a solution of trimethylacetic acid (0.169 mL, 0.00147 mol) in ethanol (6 mL, 0.1 mol) was added cesium carbonate (0.24 g, 0.00073 mol), and the resulting mixture was stirred for 2 hours. The solvent was removed in vacuo to afford cesium pivalate.

To a solution of 2-chloro-1-(1-[2-(trimethylsilyl)ethoxy]methyl-1H-pyrrolo[2,3-b]pyridin-4-yl)ethanone (prepared, e.g., as in Ex. 50, Step 1) (0.054 g, 0.00017 mol) in DMF (1.8 mL, 0.023 mol) was added cesium pivalate (0.0389 g, 0.000166 mol) and the reaction was stirred at room temperature for 16 hours. Ammonium acetate (0.45 g, 0.0058 mol) was added, and the reaction was heated in the microwave to 170° C. for 5 minutes. Water was added and the product was extracted with MTBE. The combined organic extracts were dried over sodium sulfate, then filtered and concentrated. The crude residue was purified by flash column chromatography (2.5% MeOH/DCM) to yield 4-(2-tert-butyl-1H-imidazol-5-yl)-1-[2-(trimethylsilyl)ethoxy]methyl-1H-pyrrolo[2,3-b]pyridine (32 mg, 52%). $^1$H NMR (400 MHz, CDCl$_3$): δ □8.31 (d, 1H), 7.50 (s, 1H), 7.40 (d, 1H), 7.37 (d, 1H), 6.94 (d, 1H), 5.69 (s, 2H), 3.52 (dd, 2H), 1.46 (s, 9H), 0.90 (dd, 2H), −0.08 (s, 9H); MS(ES):371(M+1).

Step 2. 4-(2-tert-butyl-1-methyl-1H-imidazol-4-yl)-1-[2-(trimethylsilyl)ethoxy]methyl-1H-pyrrolo-[2,3-b]pyridine To a mixture of 4-(2-tert-butyl-1H-imidazol-5-yl)-1-[2-(trimethylsilyl)ethoxy]methyl-1H-pyrrolo[2,3-b]pyridine (0.019 g, 0.000051 mol) and potassium carbonate (0.15 g, 0.0011 mol) in DMF (3 mL, 0.04 mol) was added methyl iodide (0.01 mL, 0.00015 mol) in two portions over 48 hours. Water was then added and the product was extracted with MTBE. The combined extracts were dried with sodium sulfate, filtered, and concentrated in vacuo, then purified by silica gel chromatography (20% ethyl acetate/hexanes) to afford 4-(2-tert-butyl-1-methyl-1H-imidazol-4-yl)-1-[2-(trimethylsilyl)ethoxy]methyl-1H-pyrrolo[2,3-b]pyridine (10 mg, 51%).

$^1$H NMR (400 MHz, CDCl$_3$): δ □8.37 (d, 1H), 7.54 (d, 1H), 7.44-7.22 (m, 2H), 7.19 (d, 1H), 5.78 (s, 2H), 3.93 (s, 3H), 3.60 (dd, 2H), 1.61 (s, 9H), 0.98 (dd, 2H), 0.00 (s, 9H); MS(ES):385(M+1).

Step 3

A solution of 4-(2-tert-butyl-1-methyl-1H-imidazol-4-yl)-1-[2-(trimethylsilyl)-ethoxy]-methyl-1H-pyrrolo[2,3-b]pyridine (0.010 g, 0.000026 mol) in TFA (3 mL, 0.04 mol) was stirred for 2 hours. Then the excess TFA was evaporated and the residue was stirred in methanol (3 mL, 0.07 mol) and NH$_4$OH (1 mL) for 16 hours. The solvents were removed and the product was purified by preparative-HPLC (C18 eluting with a gradient of ACN/H$_2$O containing 0.1% TFA) to afford 4-(2-tert-butyl-1-methyl-1H-imidazol-4-yl)-1H-pyrrolo [2,3-b]pyridine, trifluoroacetate salt (9 mg, 90%).

$^1$H NMR (400 MHz, d$_6$-DMSO): δ □12.24 (s, 1H), 8.38 (br s, 1H), 8.24 (s, 1H), 7.70-7.63 (m, 2H), 7.08 (br s, 1H), 2.55 (s, 3H), 1.51 (s, 9H); MS(ES):255(M+1).

Additional analogs were prepared as shown in Table 2 using analogous procedures to those described in Example 46 with different starting materials such as alternative carboxylic acids in Step 1. When the analogs were obtained as the free base, the product was obtained by preparative-HPLC (C18 eluting with a gradient of ACN/H$_2$O containing 0.15% NH$_4$OH). The results are summarized in Table 2 according to the following structure:

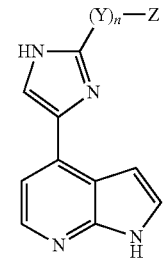

TABLE 2

| Ex. No. | Name | —(Y)$_n$—Z | MS (ES) (M + 1) |
|---|---|---|---|
| 47 | 4-(2-phenyl-1H-imidazol-5-yl)-1H-pyrrolo[2,3-b]pyridine | | 261 |
| 48 | 4-(2-benzyl-1H-imidazol-5-yl)-1H-pyrrolo[2,3-b]pyridine trifluoroacetate salt | | 275 |
| 49 | 4-[2-(1-phenylethyl)-1H-imidazol-5-yl]-1H-pyrrolo[2,3-b]pyridine trifluoroacetate salt | (racemic) | 289 |

Example 50

4-(2-Phenyl-1,3-thiazol-4-yl)-1H-pyrrolo[2,3-b]pyridine trifluoroacetate salt

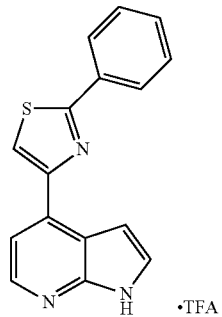 [SMILES: c1ccc(-c2nc(-c3ccnc4[nH]ccc34)cs2)cc1]

Step 1. 2-Chloro-1-(1-[2-(trimethylsilyl)ethoxy]methyl-1H-pyrrolo[2,3-b]pyridin-4-yl)ethanone To a solution of 4-bromo-1-[2-(trimethylsilyl)ethoxy]methyl-1H-pyrrolo[2,3-b]pyridine (2.05 g, 0.00626 mol) in THF (10 mL, 0.123 mol) at 0° C. was added dropwise a solution of isopropylmagnesium chloride in ether (2.0 M, 9.4 mL). The mixture was allowed to warm to room temperature and stirred for 4 hours. This mixture was then transferred via cannula to a solution of 2-chloro-N-methoxy-N-methylacetamide (2.84 g, 0.0207 mol) in THF (10 ml). After 30 minutes reaction time, the solution was quenched by the addition of saturated ammonium chloride aqueous solution. The product was extracted with ethyl acetate, the combined organic extracts were washed with brine, dried over $Na_2SO_4$, filtered and concentrated. The crude residue was purified by flash column chromatography (0-20% ethyl acetate/hexanes) to afford 2-chloro-1-(1-[2-(trimethylsilyl)-ethoxy]methyl-1H-pyrrolo[2,3-b]pyridin-4-yl)ethanone (711 mg, 35%). NMR (400 MHz, $CDCl_3$): δ □8.56 (d, 1H), 7.66 (d, 1H), 7.60 (d, 1H), 7.23 (d, 1H), 5.80 (s, 2H), 4.91 (s, 2H), 3.60 (dd, 2H), 0.98 (dd, 2H), 0.01 (s, 9H); MS(ES): 325(M+1).

Step 2. 4-(2-Phenyl-1,3-thiazol-4-yl)-1H-pyrrolo[2,3-b]pyridine trifluoroacetate salt A solution of 2-chloro-1-(1-[2-(trimethylsilyl)ethoxy]methyl-1H-pyrrolo[2,3-b]pyridin-4-yl)-ethanone (0.050 g, 0.00015 mol) and benzenecarbothioamide (0.031 g, 0.00022 mol) in ethanol (2 mL, 0.03 mol) was heated to reflux for 1 hour. The solvent was removed in vacuo. Ethyl acetate was added, and the resulting solid was isolated by filtration. The crude solid was stirred with TFA for 1 hour, then excess TFA was removed in vacuo. The crude residue was then stirred with aq. $NH_4OH$ and MeOH for 16 hours. The solvent was removed and the product was purified by preparative-HPLC (C18 eluting with a gradient of $ACN/H_2O$ containing 0.1% TFA) to afford 4-(2-phenyl-1,3-thiazol-4-yl)-1H-pyrrolo[2,3-b]pyridine as the trifluoroacetate salt (11 mg, 18%). $^1$H NMR (400 MHz, $d_6$-DMSO): δ □12.01 (s, 1H), 8.58 (s, 1H), 8.39 (br s, 1H), 8.13-8.07 (m, 2H), 7.81 (d, 1H), 7.67-7.64 (m, 1H), 7.62-7.52 (m, 3H), 7.22 (d, 1H); MS(ES):278(M+1).

Example 51

N-Methyl-N-propyl-4-(1H-pyrrolo[2,3-b]pyridin-4-yl)-1,3-thiazol-2-amine, trifluoroacetate salt

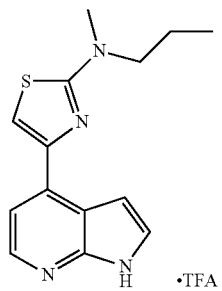 [SMILES: CCCN(C)c1nc(-c2ccnc3[nH]ccc23)cs1]

Step 1. N-Methyl-N-propylthiourea

N-Methyl-N-propylamine (0.501 mL, 0.00488 mol) was added to a solution of 1,1'-thiocarbonyldiimidazole (0.957 g, 0.00537 mol) in THF (9 mL, 0.1 mol), and the resulting solution was stirred for 16 hours. The intermediate from the reaction mixture was isolated by silica gel chromatography (5% MeOH in DCM) and this intermediate was stirred with ammonia (7M solution in MeOH) (6 mL) for 48 hours. The solvent was removed in vacuo. N-methyl-N-propylthiourea was obtained after flash column chromatography (4% MeOH in DCM).

Step 2

A solution of 2-chloro-1-(1-[2-(trimethylsilyl)ethoxy]methyl-1H-pyrrolo[2,3-b]pyridin-4-yl)-ethanone (0.050 g, 0.00015 mol) and N-methyl-N-propylthiourea (0.030 g, 0.00022 mol) in ethanol (2 mL, 0.03 mol) was heated to reflux for 2 hours. Then, the ethanol was removed in vacuo and the residue was dissolved in 2 mL TFA and stirred for 40 minutes. The excess TFA was removed in vacuo and the residue was dissolved in 3 mL of MeOH. To this was added 0.5 mL of $NH_4OH$ and 100 μL of ethylenediamine, and the resulting solution was stirred for 16 hours. Solvent was removed, then water was added to give a white precipitate which was purified by preparative-HPLC (C18 eluting with a gradient of $ACN/H_2O$ containing 0.1% TFA) to afford N-methyl-N-propyl-4-(1H-pyrrolo[2,3b]pyridin-4-yl)-1,3-thiazol-2-amine as the trifluoroacetate salt (39 mg, 67%). $^1$H NMR (300 MHz, $CD_3OD$): δ □8.46-8.12 (br s, 1H), 7.92 (br s, 1H), 7.72 (s, 1H), 7.63 (d, 1H), 7.45 (br s, 1H), 3.56 (t, 2H), 3.20 (s, 3H), 1.78 (dq, 2H), 1.00 (t, 3H); MS(ES):273 (M+1).

Additional aminothiazole analogs were prepared by procedures analogous to those described in Example 51, using different starting materials such as alternative thioureas in Step 2. In Examples 52 and 53, the white precipitate obtained by the procedure of Example 51 was isolated by filtration, washed with water and dried under high vacuum to afford the analogs as the free amine The results are summarized in Table 3 according to the following structure:

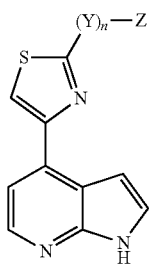

TABLE 3

| Ex. No. | Name | R | MS (ES) (M + 1) |
|---|---|---|---|
| 52 | N-phenyl-4-(1H-pyrrolo[2,3-b]pyridin-4-yl)-1,3-thiazol-2-amine | | 293 |
| 53 | N-methyl-N-phenyl-4-(1H-pyrrolo[2,3-b]pyridin-4-yl)-1,3-thiazol-2-amine | | 307 |

Example 54

4-(2-Phenyl-1,3-thiazol-5-yl)-1H-pyrrolo[2,3-b]pyridine trifluoroacetate salt

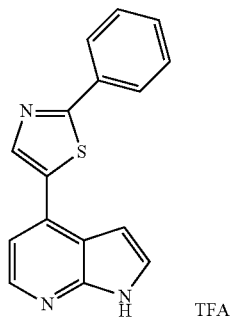 [SMILES: c1ccc(-c2ncc(-c3ccnc4[nH]ccc34)s2)cc1]

Step 1. (2-Phenyl-1,3-thiazol-5-yl)boronic acid

To a solution of n-butyllithium in hexane (1.6 M, 2.1 mL) in ether (20 mL) at −78° C., a solution of 2-phenyl-1,3-thiazole (449 mg, 0.00278 mol) in ether (5 mL) was added dropwise. The mixture was stirred for one hour at −78° C. followed by the addition of boric acid trimethyl ester (0.949 mL, 0.00835 mol). The mixture was stirred at −78° C. for 15 minutes, then was allowed to warm to room temperature and stirred for an additional 40 minutes. Saturated NH$_4$Cl aqueous solution was added, followed by 1.0 N aqueous HCl. The acidified mixture was stirred for 15 minutes, and the desired product was extracted with four portions of DCM containing 15% isopropanol. The combined organic extracts were dried over sodium sulfate and concentrated to give 566 mg of a white solid containing the desired (2-phenyl-1,3-thiazol-5-yl)boronic acid as a mixture with 2-phenyl-1,3-thiazole. This mixture was used in Step 2 without further purification. MS(ES):206(M+1).

Step 2

To a mixture of (2-phenyl-1,3-thiazol-5-yl)boronic acid (75.0 mg, 0.000366 mol) and 4-bromo-1-[2-(trimethylsilyl)ethoxy]methyl-1H-pyrrolo[2,3-b]pyridine (80 mg, 0.000244 mol) in DMF (4 mL, 0.0516 mol) was added a solution of potassium carbonate (101 mg, 0.000732 mol) in water (1 mL, 0.0555 mol). The mixture was purged with a steady stream of nitrogen for 15 minutes.

Tetrakis(triphenylphosphine)palladium(0) (20 mg, 0.000018 mol) was added and the resulting mixture was heated to 125° C. for 30 minutes. The product was purified by preparative-HPLC (C18 eluting with a gradient of ACN/H$_2$O containing 0.1% TFA) to afford 12 mg of a yellow solid containing the desired product as the major component. The mixture was stirred in TFA (1 mL) for 1 hour. Then excess TFA was removed in vacuo and the resulting residue was stirred with 2 mL MeOH, 0.5 mL NH$_4$OH and 100 µL ethylenediamine for 16 hours. The product was isolated by preparative-HPLC (C18 eluting with a gradient of ACN/H$_2$O containing 0.1% TFA) to afford 4-(2-phenyl-1,3-thiazol-5-yl)-1H-pyrrolo[2,3-b]pyridine trifluoroacetate salt (5 mg, 5%). $^1$H NMR (400 MHz, CD$_3$OD): δ □8.64 (s, 1H), 8.34 (d, 1H), 8.10-8.04 (m, 2H), 7.73 (d, 1H), 7.71 (d, 1H), 7.56-7.51 (m, 3H), 7.14 (d, 1H); MS(ES):278(M+1).

Example 55

Ethyl 2-methyl-2-[4-(1H-pyrrolo[2,3-b]pyridin-4-yl)-1H-pyrazol-1-yl]propanoate trifluoroacetate salt (55a) AND 2-Methyl-2-[4-(1H-pyrrolo[2,3-b]pyridin-4-yl)-1H-pyrazol-1-yl]propanoic acid (55b)

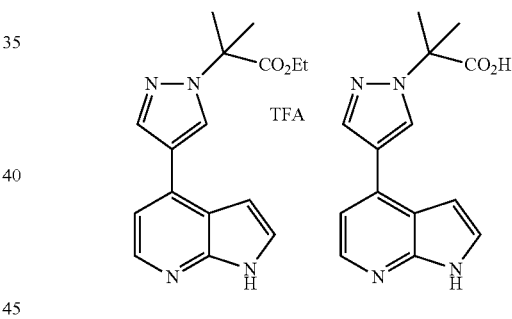

4-(1H-Pyrazol-4-yl)-1-[2-(trimethylsilyl)ethoxy]methyl-1H-pyrrolo[2,3-b]pyridine (60 mg, 0.00019 mol) was dissolved in DMF (1.5 mL), and the solution was cooled to 0° C. with a cold bath. Sodium hydride (15 mg, 0.00038 mol) was added. After stirring for 10 min, 2-bromo-2-methyl-propanoic acid ethyl ester (42 µL, 0.00028 mol) was added. The cold bath was then removed and the reaction mixture was allowed to warm to room temperature over 1 hour. The reaction mixture was quenched with saturated ammonium chloride solution. More water was added, and the product was extracted with MTBE. The combined extracts were dried over sodium sulfate, filtered and concentrated. The residue was dissolved in 2 mL TFA and stirred for 1 h. Then excess TFA was removed in vacuo and the resulting residue was stirred in 2 mL EtOH containing 0.6 mL NH$_4$OH solution for 16 hours. Volatiles were removed, and purification of the mixture was carried out via preparative-HPLC (C18 eluting with a gradient of ACN/H$_2$O containing 0.1% TFA) afforded ethyl 2-methyl-2-[4-(1H-pyrrolo[2,3-b]pyridin-4-yl)-1H-pyrazol-1-yl]propanoate trifluoroacetate salt (13 mg, 17%): $^1$H NMR (300 MHz, d$_6$-DMSO): δ □12.03 (s, 1H), 8.67 (s, 1H), 8.31-8.19 (m, 2H), 7.59 (t, 1H), 7.48 (d, 1H), 6.98 (br s, 1H), 4.10 (q, 2H), 1.84 (s, 6H), 1.12 (t, 3H); MS(ES):299(M+1) and 2-methyl-2-[4-(1H-pyrrolo[2,3-b]pyridin-4-yl)-1H-pyrazol-1-yl]propanoic acid (27 mg, 53%): $^1$H NMR (300 MHz, d$_6$-DMSO): δ 12.04 (s, 1H), 8.64 (s, 1H), 8.26 (s, 2H), 7.59 (br s, 1H), 7.48 (d, 1H), 6.99 (br s, 1H), 1.83 (s, 6H); MS(ES):271(M+H).

Example 56

2-Methyl-2-[4-(1H-pyrrolo[2,3-b]pyridin-4-yl)-1H-pyrazol-1-yl]propanamide

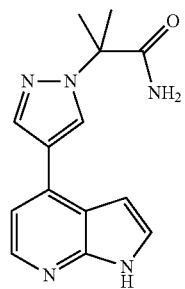 [SMILES: CC(C)(C(N)=O)n1cc(-c2ccnc3[nH]ccc23)cn1]

A mixture of 2-methyl-2-[4-(1H-pyrrolo[2,3-b]pyridin-4-yl)-1H-pyrazol-1-yl]propanoic acid (23 mg, 0.000085 mol) and N,N-carbonyldiimidazole (CDI) (21 mg, 0.00013 mol) in 2 mL of DMF was stirred for 3 hours. An excess of solid NH$_4$Cl and TEA was added to the mixture and this was stirred for 3 hours. The majority of solvent was removed in vacuo, and the crude residue was purified by preparative-HPLC (C18 eluting with a gradient of ACN/H$_2$O containing 0.1% TFA) followed by re-purification via preparative-HPLC (C18 eluting with a gradient of ACN/H$_2$O containing 0.15% NH$_4$OH) to afford 2-methyl-2-[4-(1H-pyrrolo[2,3-b]pyridin-4-yl)-1H-pyrazol-1-yl]propanamide (6 mg, 26%). $^1$H NMR (400 MHz, d$_6$-DMSO): δ 11.63 (s, 1H), 8.44 (s, 1H), 8.16 (s, 1H), 8.14 (s, 1H), 7.47 (t, 1H), 7.29 (d, 1H), 7.21 (s, 1H), 6.93 (s, 1H), 6.80 (dd, 1H), 1.77 (s, 6H); MS(ES):270(M+1).

Example 57

Ethyl 3-methyl-3-[4-(1H-pyrrolo[2,3-b]pyridin-4-yl)-1H-pyrazol-1-yl]butanoate trifluoroacetate salt

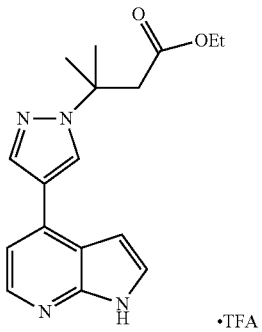 [SMILES: CCOC(=O)CC(C)(C)n1cc(-c2ccnc3[nH]ccc23)cn1]

Step 1. Ethyl 3-methyl-3-[4-(1-[2-(trimethylsilyl)ethoxy]methyl-1H-pyrrolo[2,3-b]pyridin-4-yl)-1H-pyrazol-1-yl]butanoate 4-(1H-Pyrazol-4-yl)-1-[2-(trimethylsilyl)ethoxy]methyl-1H-pyrrolo[2,3-b]pyridine (220 mg, 0.0006996 mol) and 3-methyl-2-butenoic acid ethyl ester (292 μL, 0.00210 mol) were dissolved in DMF (10 mL). Cesium carbonate (912 mg, 0.00280 mol) was added and the resulting mixture was stirred at room temperature for 3 hours. The reaction mixture was diluted with water, and the product was extracted with MTBE several times. The combined extracts were dried over sodium sulfate and concentrated. The crude residue was purified by flash column chromatography (0-60% EtOAc/Hexanes) to afford ethyl 3-methyl-3-[4-(1-[2-(trimethylsilyl)ethoxy]methyl-1H-pyrrolo[2,3-b]pyridin-4-yl)-1H-pyrazol-1-yl]butanoate (244 mg, 79%). $^1$H NMR (300 MHz, CDCl$_3$): δ 8.37 (d, 1H), 8.11 (s, 1H), 8.09 (s, 1H), 7.45 (d, 1H), 7.24 (d, 1H), 6.79 (d, 1H), 5.77 (s, 2H), 4.10 (q, 2H), 3.62 (dd, 2H), 3.04 (s, 2H), 1.88 (s, 6H), 1.20 (t, 3H), 0.98 (dd, 2H), 0.00 (s, 9H); MS(ES):443(M+1).

Step 2

Ethyl 3-methyl-3-[4-(1-[2-(trimethylsilyl)ethoxy]methyl-1H-pyrrolo[2,3-b]pyridin-4-yl)-1H-pyrazol-1-yl]butanoate (20 mg, 0.0000452 mol) was stirred in 1 mL TFA for 1 hour. Then excess TFA was removed in vacuo. The residue was stirred for 16 hours in 2 mL MeOH containing 0.5 mL NH$_4$OH. Evaporation of the volatiles was followed by purification by preparative-HPLC (C18 eluting with a gradient of ACN/H$_2$O containing 0.1% TFA) to afford ethyl 3-methyl-3-[4-(1H-pyrrolo[2,3-b]-pyridin-4-yl)-1H-pyrazol-1-yl]butanoate, trifluoroacetate salt (5 mg, 26%). $^1$H NMR (400 MHz, d$_6$-DMSO): δ 12.19 (s, 1H), 8.61 (br s, 1H), 8.34-8.22 (br m, 2H), 7.62 (br s, 1H), 7.51 (br d, 1H), 7.02 (br s, 1H), 3.91 (q, 2H), 2.96 (s, 2H), 1.70 (s, 6H), 1.02 (t, 3H); MS(ES):313(M+1).

Example 58

3-Methyl-3-[4-(1H-pyrrolo[2,3-b]pyridin-4-yl)-1H-pyrazol-1-yl]butan-1-ol trifluoroacetate salt

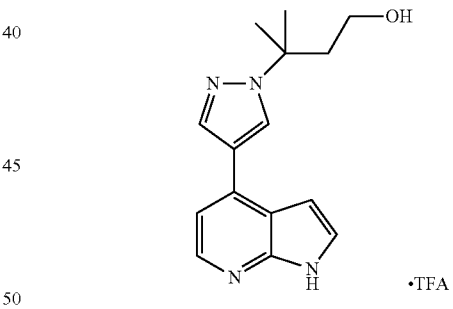

To a solution of ethyl 3-methyl-3-[4-(1-[2-(trimethylsilyl)ethoxy]methyl-1H-pyrrolo[2,3-b]-pyridin-4-yl)-1H-pyrazol-1-yl]butanoate (213 mg, 0.000481 mol) in THF (5 mL, 0.0616 mol) at −78° C. was added diisobutylaluminum hydride in DCM (1.00 M, 1.1 mL) dropwise. The reaction mixture was stirred for 3 hours during which time the reaction slowly warmed to −10° C. To the mixture at −10° C. was carefully added K/Na tartrate tetrahydrate in water. The mixture was stirred for 2 hours, then was extracted with three portions of ethyl acetate. The combined organic extracts were washed with two portions of water and one portion of brine, then dried over sodium sulfate, filtered and concentrated to afford 3-methyl-3-[4-(1-[2-(trimethylsilyl)ethoxy]methyl-1H-pyrrolo[2,3-b]-pyridin-4-yl)-1H-pyrazol-1-yl]butan-1-ol (185 mg, 96%), which was used without further purification. A portion of the alcohol so obtained (15 mg, 0.000037 mol) was stirred in TFA (1 mL) for 2 hours.

The TFA was removed in vacuo and the residue was stirred with 2 mL MeOH containing 0.5 mL NH₄OH for 16 hours. Volatiles were removed and the product was purified by preparative-HPLC (C18 eluting with a gradient of ACN/H₂O containing 0.1% TFA) to afford 3-methyl-3-[4-(1H-pyrrolo[2,3-b]pyridin-4-yl)-1H-pyrazol-1-yl]butan-1-ol as the trifluoroacetate salt (8.0 mg, 57%). ¹H NMR (300 MHz, d₆-DMSO): δ □12.17 (s, 1H), 8.58 (br s, 1H), 8.32-8.22 (br m, 2H), 7.62 (br s, 1H), 7.53 (br d, 1H), 7.03 (br s, 1H), 3.25 (t, 2H), 2.07 (t, 2H), 1.62 (s, 6H); MS(ES):271(M+1).

Example 59

4-Methyl-4-[4-(1H-pyrrolo[2,3-b]pyridin-4-yl)-1H-pyrazol-1-yl]pentanenitrile trifluoroacetate salt

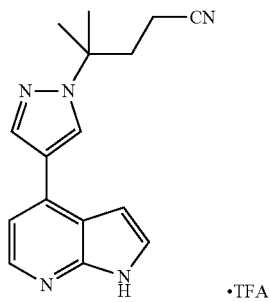 [SMILES: CC(C)(CCC#N)n1cc(-c2ccnc3[nH]ccc23)cn1]

Step 1. 4-Methyl-4-[4-(1-[2-(trimethylsilyl)ethoxy]methyl-1H-pyrrolo[2,3-b]pyridin-4-yl)-1H-pyrazol-1-yl]pentanenitrile TEA (38.0 µL, 0.000273 mol) and methanesulfonyl chloride (21.1 µL, 0.000273 mol) were added sequentially to a solution of 3-methyl-3-[4-(1-[2-(trimethylsilyl)ethoxy]methyl-1H-pyrrolo[2,3-b]pyridin-4-yl)-1H-pyrazol-1-yl]butan-1-ol (prepared as in Example 58) (81 mg, 0.00020 mol) in DCM (4 mL, 0.05 mol) at 0° C. The reaction mixture was held at this temperature for 1.5 hours, then was quenched by the addition of water. The reaction mixture was extracted with DCM four times. The combined extracts were dried over sodium sulfate, filtered and concentrated to afford crude 3-methyl-3-[4-(1-[2-(trimethylsilyl)ethoxy]methyl-1H-pyrrolo[2,3-b]pyridin-4-yl)-1H-pyrazol-1-yl]butyl methanesulfonate (87 mg). MS(ES):479(M+1).

A mixture of 3-methyl-3-[4-(1-[2-(trimethylsilyl)ethoxy]methyl-1H-pyrrolo[2,3-b]pyridin-4-yl)-1H-pyrazol-1-yl]butyl methanesulfonate (42 mg, 0.000088 mol) and potassium cyanide (46 mg, 0.000702 mol) in DMF (1 mL) was heated in the microwave reactor for 30 min at 125° C. followed by additional 30 min at 135° C. The mixture was then diluted with water, and the product was extracted with three portions of MTBE. The combined extracts were dried over sodium sulfate, filtered and concentrated to give 61 mg of crude 4-methyl-4-[4-(1-[2-(trimethylsilyl)ethoxy]methyl-1H-pyrrolo-[2,3-b]pyridin-4-yl)-1H-pyrazol-1-yl]pentanenitrile, which was used without further purification. MS(ES):410(M+1).

Step 2

4-Methyl-4-[4-(1-[2-(trimethylsilyl)ethoxy]methyl-1H-pyrrolo[2,3-b]pyridin-4-yl)-1H-pyrazol-1-yl]pentanenitrile (57 mg, 0.00014 mol) was stirred in DCM (4 ml) and TFA (1 mL) for 2 hours. The solvents were removed in vacuo and the residue was stirred in 2 mL MeOH containing 0.2 mL ethylenediamine for 16 hours. The volatiles were evaporated and the product was isolated from the reaction mixture by preparative-HPLC (C18 eluting with a gradient of ACN/H₂O containing 0.1% TFA) affording 4-methyl-4-[4-(1H-pyrrolo[2,3-b]pyridin-4-yl)-1H-pyrazol-1-yl]pentanenitrile as the trifluoroacetate salt (10 mg, 18%). ¹H NMR (400 MHz, d₆-DMSO): δ □12.09 (s, 1H), 8.58 (s, 1H), 8.29 (s, 1H), 8.25 (d, 1H), 7.60 (t, 1H), 7.48 (d, 1H), 7.00 (br s, 1H), 2.33-2.21 (m, 4H), 1.61 (s, 6H); MS(ES):280(M+1).

Example 60

4-Methyl-4-[4-(1H-pyrrolo[2,3-b]pyridin-4-yl)-1H-pyrazol-1-yl]pentanamide trifluoroacetate salt

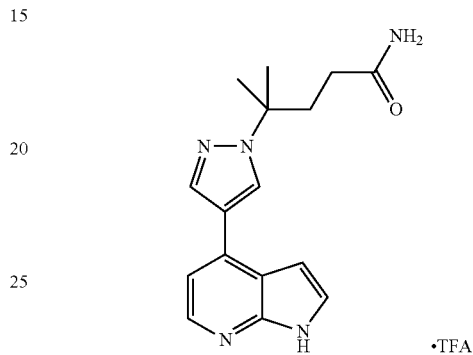

The crude 4-methyl-4-[4-(1-[2-(trimethylsilyl)ethoxy]methyl-1H-pyrrolo[2,3-b]pyridin-4-yl)-1H-pyrazol-1-yl]pentanenitrile (36 mg, 0.000088 mol, see preparation in Example 59), was stirred in TFA (2 mL) for 1 hour. The mixture was concentrated to remove excess TFA, and the resulting residue was stirred in 2 mL methanol containing 0.5 mL NH₄OH for 16 hours. The product was purified by preparative-HPLC (C18 eluting with a gradient of ACN/H₂O containing 0.1% TFA) to afford 4-methyl-4-[4-(1H-pyrrolo[2,3-b]pyridin-4-yl)-1H-pyrazol-1-yl]pentanamide as the trifluoro-acetate salt (21 mg, 58%). ¹H NMR (400 MHz, d₆-DMSO): δ □12.18 (s, 1H), 8.60 (s, 1H), 8.33-8.21 (m, 2H), 7.62 (br s, 1H), 7.53 (d, 1H), 7.22 (br s, 1H), 7.04 (br s, 1H), 6.71 (br s, 1H), 2.14-2.07 (m, 2H), 1.86-1.79 (m, 2H), 1.58 (s, 6H); MS(ES):298(M+1).

Example 61

(3S)-3-[4-(1H-Pyrrolo[2,3-b]pyridin-4-yl)-1H-pyrazol-1-yl]butanenitrile trifluoro-acetate salt, AND
(3R)-3-[4-(1H-Pyrrolo[2,3-b]pyridin-4-yl)-1H-pyrazol-1-yl]butanenitrile trifluoroacetate salt

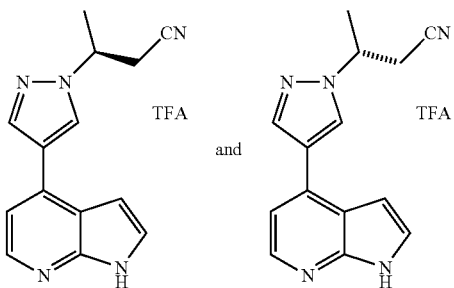 [SMILES: C[C@@H](CC#N)n1cc(-c2ccnc3[nH]ccc23)cn1 ; C[C@H](CC#N)n1cc(-c2ccnc3[nH]ccc23)cn1]

To a solution of 4-(1H-pyrazol-4-yl)-1-[2-(trimethylsilyl)ethoxy]methyl-1H-pyrrolo[2,3-b]pyridine (0.050 g, 0.00016 mol) in ACN were added 2-butenenitrile (0.014 mL, 0.00017 mol) and DBU (0.029 mL, 0.00020 mol). The resulting mixture was stirred for 16 hours. Then the volatiles were evaporated and the residue was dissolved in ethyl acetate. The resulting solution was washed successively with 1.0 N HCl, water, and brine, then was dried over sodium sulfate, filtered and concentrated. To obtain the enantiomers in substantially pure form, Method A (vide infra) was used.

The crude residue was dissolved in TFA (7 mL, 0.09 mol) and the solution was stirred for 1 hour. Then excess TFA was evaporated and the residue was then stirred with ethylenediamine (0.1 mL, 0.001 mol) in methanol (4 mL, 0.09 mol) for 16 hours. The mixture was concentrated, and the product was purified by preparative-HPLC (C18 eluting with a gradient of ACN/H$_2$O containing 0.1% TFA) to afford 3-[4-(1H-pyrrolo[2,3-b]pyridin-4-yl)-1H-pyrazol-1-yl]butanenitrile trifluoroacetate salt (35 mg, 61%). $^1$H NMR (300 MHz, d$_6$-DMSO): δ □12.16 (s, 1H), 8.73 (s, 1H), 8.32 (s, 1H), 8.28 (d, 1H), 7.65-7.61 (m, 1H), 7.48 (d, 1H), 6.99 (d, 1H), 4.86 (q, 1H), 3.17 (d, 2H), 1.57 (d, 3H); MS(ES):252 (M+1).

Additional analogs were prepared by procedures analogous to those described in Example 61 using different starting materials for alkylation of the pyrazole ring. For example, the (1,13-unsaturated nitriles were prepared by procedures analogous to the following, illustrated for (2E)- and (2Z)-hexenenitrile: To a solution of 1.00 M potassium tert-butoxide in THF at 0° C. (24.2 mL) was added a solution of diethyl cyanomethylphosphonate (4.10 mL, 0.025 mol) in THF (30 mL) dropwise. The bath was removed and the solution was allowed to warm to room temperature. After reaching room temperature, the solution was re-cooled to 0° C. and a solution of butanal (2.00 mL, 0.023 mol) in THF (7 mL) was added dropwise. The reaction mixture was allowed to warm to room temperature and stir overnight. The mixture was diluted with ethyl acetate and water. The layers were separated and the aqueous layer was extracted with three portions of ethyl acetate. The combined organic extracts were washed with brine, dried over sodium sulfate, filtered and concentrated. This afforded 1.6 g of a crude mixture containing both (2E)- and (2Z)-hexenenitrile, which was used without further purification in the subsequent alkylation step. $^1$H NMR (400 MHz, CDCl$_3$): δ □6.72 (dt, 1H trans olefin), 6.48 (dt, 1H cis olefin), 5.34 (dt, 1H trans olefin), 5.31-5.30 (m, 1H cis olefin).

Where it was desirable to obtain the enantiomers in substantially pure form, chiral separation was performed by one of the following methods:

A) The separation was performed on the SEM-protected intermediate after silica gel chromatography (ethyl acetate/hexanes) by preparative chiral HPLC (OD-H column, eluting with 15% ethanol in hexanes);

B) The separation was performed on the deprotected free base by preparative chiral HPLC (OD-H column, eluting with 15% ethanol in hexanes);

C) The separation was performed on the SEM-protected intermediate after silica gel chromatography (ethyl acetate/hexanes) by preparative chiral HPLC (AD-H column, eluting with 10% ethanol in hexanes);

D) The separation was performed on the SEM-protected intermediate after silica gel chromatography (ethyl acetate/hexanes) by preparative chiral HPLC (AD-H column, eluting with 15% ethanol in hexanes);

E) The separation was performed on the SEM-protected intermediate after silica gel chromatography (ethyl acetate/hexanes) by preparative chiral HPLC (OD-H column, eluting with 20% ethanol in hexanes; or F) The separation was performed on the SEM-protected intermediate after silica gel chromatography (ethyl acetate/hexanes) by preparative chiral HPLC (OD-H column, eluting with 30% ethanol in hexanes. An OD-H column refers to Chiralcel OD-H from Chiral Technologies, Inc 3×25 cm, 5 μm. An AD-H column refers to ChiralPak AD-H from Chiral Technologies, Inc. 2×25 cm, 5 μm. The results are summarized for compounds in Table 4 below.

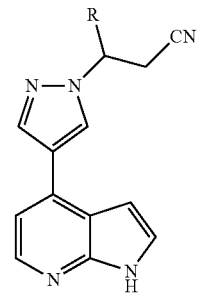

TABLE 4

| Ex. No. | Name | R | MS (ES) (M + 1) | Method of preparation and chiral separation |
|---|---|---|---|---|
| 62 | 3-[4-(1H-pyrrolo[2,3-b]pyridin-4-yl)-1H-pyrazol-1-yl]propanenitrile trifluoroacetate salt | H | 238 | Ex. 61 |
| 63 | (3S)-3-[4-(1H-pyrrolo[2,3-b]pyridin-4-yl)-1H-pyrazol-1-yl]hexanenitrile trifluroracetate salt and (3R)-3-[4-(1H-pyrrolo[2,3-b]pyridin-4-yl)-1H-pyrazol-1-yl]hexanenitrile trifluroracetate salt | Pr | 280 | Ex. 61 Method B |
| 64 | (3S)-3-cyclopentyl-3-[4-(1H-pyrrolo[2,3-b]pyridin-4-yl)-1H-pyrazol-1-yl]-propanenitrile trifluoroacetate salt and (3R)-3-cyclopentyl-3-[4-(1H-pyrrolo[2,3-b]pyridin-4-yl)-1H-pyrazol-1-yl]-propanenitrile trifluoroacetate salt | cyclopentyl | 306 | Ex. 61 Method C |

TABLE 4-continued

| Ex. No. | Name | R | MS (ES) (M + 1) | Method of preparation and chiral separation |
|---|---|---|---|---|
| 64a | (3S)-3-cyclohexyl-3-[4-(1H-pyrrolo[2,3-b]pyridin-4-yl)-1H-pyrazol-1-yl]-propanenitrile and (3R)-3-cyclohexyl-3-[4-(1H-pyrrolo[2,3-b]pyridin-4-yl)-1H-pyrazol-1-yl]-propanenitrile | | 320 | Ex. 61 Method D |

Example 65

(3R)-3-[4-(7H-Pyrrolo[2,3-d]pyrimidin-4-yl)-1H-pyrazol-1-yl]hexanenitrile trifluoroacetate salt and (3S)-3-[4-(7H-Pyrrolo[2,3-d]pyrimidin-4-yl)-1H-pyrazol-1-yl]hexanenitrile trifluoroacetate salt

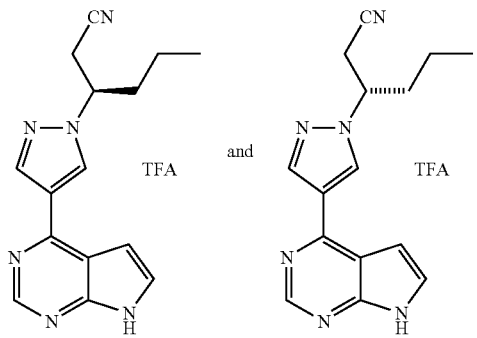 [SMILES: CCC[C@H](CC#N)n1cc(-c2ncnc3[nH]ccc23)cn1 ; CCC[C@@H](CC#N)n1cc(-c2ncnc3[nH]ccc23)cn1]

Step 1. 4-Chloro-7-[2-(trimethylsilyl)ethoxy]methyl-7H-pyrrolo[2,3-d]pyrimidine To a solution of 4-chloropyrrolo[2,3-d]pyrimidine (0.86 g, 0.0056 mol) in DMF (20 mL, 0.2 mol) at 0° C. was added sodium hydride (0.27 g, 0.0067 mol) in several portions. The reaction mixture was stirred for an additional 45 minutes followed by a dropwise addition of β-(trimethylsilyl)ethoxy]-methyl chloride (1.2 mL, 0.0067 mol). The resulting reaction mixture was stirred at 0° C. for 45 min, then was quenched with water and extracted with ethyl acetate. The organic extract was washed with water, brine, dried over sodium sulfate, filtered and concentrated to give an oil. The crude residue was purified by flash column chromatography (0-15% ethyl acetate/hexanes) to yield 4-chloro-7-[2-(trimethylsilyl)ethoxy]methyl-7H-pyrrolo[2,3-d]pyrimidine (1.40 g, 88%).

$^1$H NMR (400 MHz, CDCl$_3$): δ ☐8.71 (s, 1H), 7.46 (d, 1H), 6.72 (d, 1H), 5.71 (s, 2H), 3.59 (dd, 2H), 0.97 (dd, 2H), 0.00 (s, 9H); MS(ES):284(M+1).

Step 2. 4-(1H-Pyrazol-4-yl)-7-[2-(trimethylsilyl)ethoxy]methyl-7H-pyrrolo[2,3-d]pyrimidine To a mixture of 4-chloro-7-[2-(trimethylsilyl)ethoxy]methyl-7H-pyrrolo[2,3-d]pyrimidine (1.4 g, 0.0049 mol) and 4-(4,4,5,5-tetramethyl-1,3,2-dioxaborolan-2-yl)-1H-pyrazole (1.4 g, 0.0074 mol) in DMF (40 mL, 0.5 mol) was added potassium carbonate (2.0 g, 0.015 mol) in 15 mL of water. The mixture was purged with a steady stream of nitrogen for 15 minutes. Tetrakis(triphenyl-phosphine)palladium(0) (0.41 g, 0.00036 mol) was added and the reaction was heated to 125° C. for 30 min. The mixture was allowed to cool then diluted with ethyl acetate. The diluted reaction mixture was washed with water, brine, dried over Na$_2$SO$_4$ and concentrated to give a solution in a small volume of DMF (about 2-3 mL). Water was added, causing the material to form a gum on the walls of the flask. Then water was decanted, and the solids were dissolved in ethyl acetate. The solution was dried over Na$_2$SO$_4$, and concentrated in vacuo to afford a yellow solid. The product was triturated with ethyl ether to yield 4-(1H-pyrazol-4-yl)-7-[2-(trimethylsilyl)ethoxy]methyl-7H-pyrrolo[2,3-d]pyrimidine as a white powder which was dried under vacuum (1 g, 60%). $^1$H NMR (300 MHz, CDCl$_3$): δ ☐10.80 (br s, 1H), 8.93 (s, 1H), 8.46 (s, 2H), 7.46 (d, 1H), 6.88 (d, 1H), 5.73 (s, 2H), 3.61 (dd, 2H), 0.98 (dd, 2H), 0.00 (s, 9H); MS(ES):316(M+1).

Step 3

To a solution of 4-(1H-pyrazol-4-yl)-7-[2-(trimethylsilyl)ethoxy]methyl-7H-pyrrolo[2,3-d]pyrimidine (0.050 g, 0.00016 mol) in ACN (1 mL, 0.02 mol) was added hex-2-enenitrile (0.100 g, 0.00105 mol) (as a mixture of cis and trans isomers), followed by DBU (60 µL, 0.0004 mol). The resulting mixture was stirred at room temperature for 16 hours. The ACN was removed in vacuo. The crude residue was dissolved in ethyl acetate, and was washed with 1.0 N HCl, brine, dried over Na$_2$SO$_4$ and concentrated. The crude residue was purified by flash column chromatography (0-70% EtOAc/Hexane) to afford 56 mg of product, which was stirred with 1:1 TFA/DCM for 1 hour and the solvents were evaporated. The resulting product was stirred with methanol (4 mL, 0.1 mol) containing ethylenediamine (0.1 mL, 0.001 mol) overnight. The solvent was evaporated and the product was purified by preparative-HPLC (C18 eluting with a gradient of ACN/H$_2$O containing 0.1% TFA) to afford 3-[4-(7H-pyrrolo[2,3-d]pyrimidin-4-yl)-1H-pyrazol-1-yl]hexanenitrile as the trifluoroacetate salt. Where desired, the enantiomers were isolated in substantially pure form by Method A described above for Example 61. $^1$H NMR (300 MHz, CD$_3$OD): δ ☐☐8.93 (s, 1H), 8.88 (s, 1H), 8.52 (s, 1H), 7.85 (d, 1H), 7.28 (d, 1H), 4.87-4.77 (m, 1H), 3.26-3.05 (m, 2H), 2.20-2.05 (m, 1H), 2.00-1.86 (m, 1H), 1.40-1.10 (m, 2H), 0.95 (t, 3H); MS(ES):281(M+1).

Example 67

(3R)- and (3S)-3-Cyclopentyl-3-[4-(7H-pyrrolo[2,3-d]pyrimidin-4-yl)-1H-pyrazol-1-yl]propanenitrile

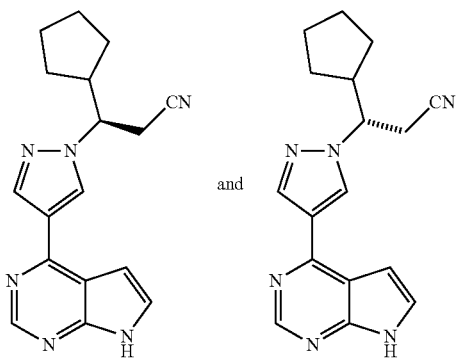 [SMILES: N#CC[C@H](C1CCCC1)n1cc(-c2ncnc3[nH]ccc23)cn1 ; N#CC[C@@H](C1CCCC1)n1cc(-c2ncnc3[nH]ccc23)cn1]

Step 1. (2E)- and (2Z)-3-Cyclopentylacrylonitrile

To a solution of 1.0 M potassium tert-butoxide in THF (235 mL) at 0° C. was added dropwise a solution of diethyl cyanomethylphosphonate (39.9 mL, 0.246 mol) in THF (300 mL). The cold bath was removed and the reaction was warmed to room temperature followed by recooling to 0° C., at which time a solution of cyclopentanecarbaldehyde (22.0 g, 0.224 mol) in THF (60 mL) was added dropwise. The bath was removed and the reaction warmed to ambient temperature and stirred for 64 hours. The mixture was partitioned between diethyl ether and water, the aqueous was extracted with three portions of ether, followed by two portions of ethyl acetate. The combined extracts were washed with brine, then dried over sodium sulfate, filtered and concentrated in vacuo to afford a mixture containing 24.4 g of olefin isomers which was used without further purification (89%).

$^1$H NMR (400 MHz, CDCl$_3$): δ 6.69 (dd, 1H, trans olefin), 6.37 (t, 1H, cis olefin), 5.29 (dd, 1H, trans olefin), 5.20 (d, 1H, cis olefin), 3.07-2.95 (m, 1H, cis product), 2.64-2.52 (m, 1H, trans product), 1.98-1.26 (m, 16H).

Step 2. (3R)- and (3S)-3-Cyclopentyl-3-[4-(7-[2-(trimethylsilyl)ethoxy]methyl-7H-pyrrolo[2,3-d]-pyrimidin-4-yl)-1H-pyrazol-1-yl]propanenitrile To a solution of 4-(1H-pyrazol-4-yl)-7-[2-(trimethylsilyl)ethoxy]methyl-7H-pyrrolo[2,3-d]-pyrimidine (15.0 g, 0.0476 mol) in ACN (300 mL) was added 3-cyclopentylacrylonitrile (15 g, 0.12 mol) (as a mixture of cis and trans isomers), followed by DBU (15 mL, 0.10 mol). The resulting mixture was stirred at room temperature overnight. The ACN was evaporated. The mixture was diluted with ethyl acetate, and the solution was washed with 1.0 N HCl. The organic layer was back-extracted with three portions of ethyl acetate. The combined organic extracts were washed with brine, dried over sodium sulfate, filtered and concentrated. The crude product was purified by silica gel chromatography (gradient of ethyl acetate/hexanes) to yield a viscous clear syrup, which was dissolved in ethanol and evaporated several times to remove ethyl acetate, to afford 19.4 g of racemic adduct (93%). The enantiomers were separated by preparative-HPLC, (OD-H, 15% ethanol/hexanes) and used separately in the next step to generate their corresponding final product. The final products (see Step 3) stemming from each of the separated enantiomers were found to be active JAK inhibitors; however, the final product stemming from the second peak to elute from the preparative-HPLC was more active than its enantiomer.

$^1$H NMR (300 MHz, CDCl$_3$): δ 8.85 (s, 1H), 8.32 (s, 2H), 7.39 (d, 1H), 6.80 (d, 1H), 5.68 (s, 2H), 4.26 (dt, 1H), 3.54 (t, 2H), 3.14 (dd, 1H), 2.95 (dd, 1H), 2.67-2.50 (m, 1H), 2.03-1.88 (m, 1H), 1.80-1.15 (m, 7H), 0.92 (t, 2H), -0.06 (s, 9H); MS(ES):437 (M+1).

Step 3

To a solution of 3-cyclopentyl-3-[4-(7-[2-(trimethylsilyl)ethoxy]methyl-7H-pyrrolo[2,3-d]-pyrimidin-4-yl)-1H-pyrazol-1-yl]propanenitrile (6.5 g, 0.015 mol, R or S enantiomer as isolated above) in DCM (40 mL) was added TFA (16 mL) and this was stirred for 6 hours. The solvent and TFA were removed in vacuo. The residue was dissolved in DCM and concentrated using a rotary evaporator two further times to remove as much as possible of the TFA. Following this, the residue was stirred with ethylenediamine (4 mL, 0.06 mol) in methanol (30 mL) overnight. The solvent was removed in vacuo, water was added and the product was extracted into three portions of ethyl acetate. The combined extracts were washed with brine, dried over sodium sulfate, decanted and concentrated to afford the crude product which was purified by flash column chromatography (eluting with a gradient of methanol/DCM). The resulting mixture was further purified by preparative-HPLC/MS (C18 eluting with a gradient of ACN/H$_2$O containing 0.15% NH$_4$OH) to afford product (2.68 g, 58%).

$^1$H NMR (400 MHz, D$_6$-dmso) δ 12.11 (br s, 1H), 8.80 (s, 1H), 8.67 (s, 1H), 8.37 (s, 1H), 7.60 (d, 1H), 6.98 (d, 1H), 4.53 (dt, 1H), 3.27 (dd, 1H), 3.19 (dd, 1H), 2.48-2.36 (m, 1H), 1.86-1.76 (m, 1H), 1.68-1.13 (m, 7H); MS(ES):307 (M+1).

Additional analogs provided in the following Tables were prepared by procedures analogous to those described in, for example, Examples 61 and 65, using different starting materials such as different α,β-unsaturated nitriles in Step 3. Isolation of the enantiomers in substantially pure form was achieved by the indicated chiral separation method described above (A-F) preceding Table 4. Where the product was isolated as the free amine, the product following deprotection was purified by preparative-HPLC (C18 eluting with a gradient of ACN/H$_2$O containing 0.15% NH$_4$OH) instead of preparative-HPLC (C18 eluting with a gradient of ACN/H$_2$O containing 0.1% TFA). This is referred to as "modification G". The results are summarized in Table 5 according to the following structure:

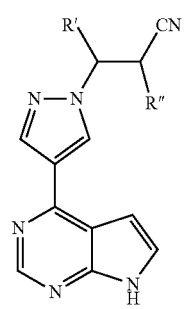

TABLE 5

| Ex. No. | Name | R', R" | MS (ES) (M + 1) | Method of preparation and chiral separation |
|---|---|---|---|---|
| 66 | (3R)-3-[4-(7H-pyrrolo[2,3-d]pyrimidin-4-yl)-1H-pyrazol-1-yl]butanenitrile trifluoroacetate salt and (3S)-3-[4-(7H-pyrrolo[2,3-d]pyrimidin-4-yl)-1H-pyrazol-1-yl]butanenitrile trifluoroacetate salt | Me, H | 253 | Example 65, Method A |
| 67 | (3R)-3-cyclopentyl-3-[4-(7H-pyrrolo[2,3-d]pyrimidin-4-yl)-1H-pyrazol-1-yl]propanenitrile trifluoroacetate salt and (3S)-3-cyclopentyl-3-[4-(7H-pyrrolo[2,3-d]pyrimidin-4-yl)-1H-pyrazol-1-yl]propanenitrile trifluoroacetate salt | cyclopentyl, H | 307 | Example 67 |
| 68 | 2-methyl-3-[4-(7H-pyrrolo[2,3-d]pyrimidin-4-yl)-1H-pyrazol-1-yl]propanenitrile trifluoroacetate salt | H, Me | 253 | Example 65, Not separated |
| 68a | (3R)-3-[4-(7H-pyrrolo[2,3-d]pyrimidin-4-yl)-1H-pyrazol-1-yl]pentanenitrile and (3S)-3-[4-(7H-pyrrolo[2,3-d]pyrimidin-4-yl)-1H-pyrazol-1-yl]pentanenitrile | Et, H | 267 | Example 65, modification G, Method E |
| 68b | (3R)-5-methyl-3-[4-(7H-pyrrolo[2,3-d]pyrimidin-4-yl)-1H-pyrazol-1-yl]hexanenitrile and (3S)-5-methyl-3-[4-(7H-pyrrolo[2,3-d]pyrimidin-4-yl)-1H-pyrazol-1-yl]hexanenitrile | isobutyl, H | 295 | Example 65, modification G, Method A |
| 68c | (3R)-3-cyclohexyl-3-[4-(7H-pyrrolo[2,3-d]pyrimidin-4-yl)-1H-pyrazol-1-yl]propanenitrile and (3S)-3-cyclohexyl-3-[4-(7H-pyrrolo[2,3-d]pyrimidin-4-yl)-1H-pyrazol-1-yl]propanenitrile | cyclohexyl, H | 321 | Example 65, modification G, Method A |
| 68d | (3R)-4-cyclopropyl-3-[4-(7H-pyrrolo[2,3-d]pyrimidin-4-yl)-1H-pyrazol-1-yl]butanenitrile and (3S)-4-cyclopropyl-3-[4-(7H-pyrrolo[2,3-d]pyrimidin-4-yl)-1H-pyrazol-1-yl]butanenitrile | cyclopropylmethyl, H | 279 | Example 65, modification G, Method F |

Example 69

4-{1-[(1S)-1-Methylbutyl]-1H-pyrazol-4-yl}-7H-pyrrolo[2,3-d]pyrimidine trifluoroacetate salt and 4-{1-[(1R)-1-Methylbutyl]-1H-pyrazol-4-yl}-7H-pyrrolo[2,3-d]pyrimidine trifluoroacetate salt

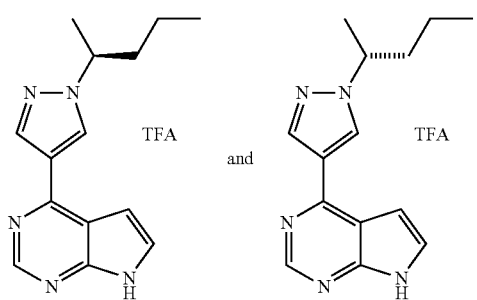 [SMILES: CCC[C@H](C)n1cc(-c2ncnc3[nH]ccc23)cn1 ; CCC[C@@H](C)n1cc(-c2ncnc3[nH]ccc23)cn1]

A solution of 4-(1H-pyrazol-4-yl)-7-[2-(trimethylsilyl)ethoxy]methyl-7H-pyrrolo[2,3-d]-pyrimidine (0.050 g, 0.00016 mol) in DMF (2 mL, 0.02 mol) was cooled in an ice bath and to this was added sodium hydride (0.013 g, 0.00032 mol). The resulting mixture was stirred for 10 minutes, followed by an addition of 2-bromopentane (0.030 mL, 0.00024 mol). The cooling bath was then removed and the reaction was stirred at room temperature for 3 hours, at which time a further portion of 2-bromopentane (0.015 mL, 0.00012 mol) was added. After 45 minutes, water was added and the reaction mixture was extracted with three portions of ethyl acetate. The combined extracts were washed with brine, dried over sodium sulfate, filtered, and concentrated. The residue was stirred with TFA (3 mL, 0.04 mol) and DCM (3 mL, 0.05 mol) for 3.5 hours, then the solvent was removed in vacuo. The residue was then stirred with NH$_4$OH (1.5 mL) in MeOH (4 mL) for 16 hours. The solvent was evaporated and the product was purified by preparative-HPLC (C18 eluting with a gradient of ACN/H$_2$O containing 0.1% TFA) to afford 4-[1-(1-methylbutyl)-1H-pyrazol-4-yl]-7H-pyrrolo[2,3-d]pyrimidine as the trifluoroacetate salt (25 mg, 44%). ¹H NMR (300 MHz, CD₃OD): δ 8.83 (s, 1H), 8.75 (s, 1H), 8.43 (s, 1H), 7.77 (d, 1H), 7.24 (d, 1H), 4.63-4.50 (m, 1H), 2.07-1.91 (m, 1H), 1.88-1.74 (m, 1H), 1.58 (d, 3H), 1.38-1.09 (m, 2H), 0.93 (t, 3H); MS(ES):256 (M+1).

Isolation of the enantiomers in substantially pure form was achieved by separation of the racemic free base (isolated by flash column chromatography after deprotection, eluting with a MeOH/DCM gradient) using HPLC (OD-H, eluting with 5% isopropanol/hexanes).

Example 69a

4-Methyl-4-[4-(7H-pyrrolo[2,3-d]pyrimidin-4-yl)-1H-pyrazol-1-yl]pentanenitrile

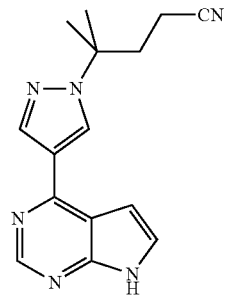 [SMILES: CC(C)(CCC#N)n1cc(-c2ncnc3[nH]ccc23)cn1]

Step 1. Ethyl 3-methyl-3-[4-(7-[2-(trimethylsilyl)ethoxy]methyl-7H-pyrrolo[2,3-d]pyrimidin-4-yl)-1H-pyrazol-1-yl]butanoate A solution of 4-(1H-pyrazol-4-yl)-7-[2-(trimethylsilyl)ethoxy]methyl-7H-pyrrolo[2,3-d]-pyrimidine (12.1 g, 0.0384 mol), 2-butenoic acid, 3-methyl-, ethyl ester (16.0 mL, 0.115 mol) and DBU (14.3 mL, 0.0959 mol) in ACN (100 mL) was heated at reflux for 3.5 hours. The solvent was removed in vacuo. The residue was diluted with water, extracted with ethyl acetate, and the combined organic extracts were washed with saturated ammonium chloride, dried over sodium sulfate, and concentrated. The crude residue was purified by flash column chromatography (ethyl acetate/hexanes) to yield the desired product (15.5 g, 91%).

¹H NMR (400 MHz, CDCl₃): δ □8.83 (s, 1H), 8.36 (s, 1H), 8.27 (s, 1H), 7.37 (d, 1H), 6.80 (d, 1H), 5.66 (s, 2H), 4.03 (q, 2H), 3.54 (dd, 2H), 2.98 (s, 2H), 1.80 (s, 6H), 1.13 (t, 3H), 0.91 (dd, 2H), −0.07 (s, 9H); MS(ES):444(M+1).

Step 2. 3-Methyl-3-[4-(7-[2-(trimethylsilyl)ethoxy]methyl-7H-pyrrolo[2,3-d]pyrimidin-4-yl)-1H-pyrazol-1-yl]butan-1-ol To a solution of ethyl 3-methyl-3-[4-(7-[2-(trimethylsilyl)ethoxy]methyl-7H-pyrrolo[2,3-d]-pyrimidin-4-yl)-1H-pyrazol-1-ylibutanoate (15.4 g, 0.0347 mol) in THF (151 mL) at −78° C. was added 1.00 M diisobutylaluminum hydride in DCM (84.5 mL) dropwise. The reaction was stirred for 2 hours with slow warming to −10° C. The mixture was quenched with water, then was treated with potassium sodium tartrate tetrahydrate and water. The mixture was stirred for 1 hour, then was extracted with ethyl acetate. The extracts were washed with water and brine, then dried with sodium sulfate, filtered, and concentrated in vacuo. The crude residue was purified by flash column chromatography to yield the desired product (13.8 g, 99%).

¹H NMR (300 MHz, CDCl₃): δ 8.83 (s, 1H), 8.38 (s, 1H), 8.26 (s, 1H), 7.38 (d, 1H), 6.80 (d, 1H), 5.67 (s, 2H), 3.65 (dd, 2H), 3.54 (dd, 2H), 2.21 (t, 2H), 1.72 (s, 6H), 0.91 (dd, 2H), -0.07 (s, 9H); MS(ES):402(M+1).

Step 3. 3-Methyl-3-[4-(7H-pyrrolo[2,3-d]pyrimidin-4-yl)-1H-pyrazol-1-yl]butan-1-ol A solution of 3-methyl-3-[4-(7-[2-(trimethylsilyl)ethoxy]methyl-7H-pyrrolo[2,3-d]pyrimidin-4-yl)-1H-pyrazol-1-yl]butan-1-ol (13.8 g, 0.0344 mol) in TFA (20 mL) was stirred for 1 hour. The mixture was then concentrated in vacuo and the residue was stirred for 2 hours in a mixture of methanol (30 mL), ammonium hydroxide (30 mL), and ethylenediamine (8 mL). The mixture was then concentrated, and the residue was diluted with water and extracted with several portions of 15% IPA/CH₂Cl₂. The combined extracts were dried over sodium sulfate and concentrated in vacuo to give 20 g of white solid. The solid was triturated with ether and the product was isolated by filtration to give the product as a white solid (7.75 g, 83%).

¹H NMR (400 MHz, CDCl₃): δ □9.99 (s, 1H), 8.83 (s, 1H), 8.39 (s, 1H), 8.28 (s, 1H), 7.38 (dd, 1H), 6.80 (dd, 1H), 3.66 (t, 2H), 2.72 (br s, 1H), 2.22 (t, 2H), 1.74 (s, 6H); MS(ES):272(M+1).

Step 4. 3-Methyl-3-[4-(7H-pyrrolo[2,3-d]pyrimidin-4-yl)-1H-pyrazol-1-yl]butyl methanesulfonate A solution of 3-methyl-3-[4-(7H-pyrrolo[2,3-d]pyrimidin-4-yl)-1H-pyrazol-1-yl]butan-1-ol (6.61 g, 0.0244 mol) in DCM (300 mL) at 0° C. was treated with TEA (3.74 mL, 0.0268 mol), followed by methanesulfonyl chloride (2.07 mL, 0.0268 mol). The reaction was stirred for 1 hour, and was then concentrated in vacuo. The crude residue was purified by flash column chromatography to afford the desired product (4.9 g, 57%).

¹H NMR (400 MHz, d₆-dmso) δ □12.45 (s, 1H), 9.50 (s, 1H), 9.35 (s, 1H), 8.83 (s, 1H), 7.79 (dd, 1H), 7.11 (dd, 1H), 4.75 (t, 1H), 3.30 (s, 3H), 2.85 (t, 1H), 1.75 (s, 6H); MS(ES):254(M−CH₃SO₃H+1).

Step 5. 4-Methyl-4-[4-(7H-pyrrolo[2,3-d]pyrimidin-4-yl)-1H-pyrazol-1-yl]pentanenitrile 3-methyl-3-[4-(7H-pyrrolo[2,3-d]pyrimidin-4-yl)-1H-pyrazol-1-yl]butyl methanesulfonate (2.97 g, 8.50 mmol), DMF (120 mL) and sodium cyanide (6.21 g, 0.127 mol) were distributed evenly into six 20 mL microwavable vessels, each of which was heated in the microwave reactor for 4000 seconds at 125° C. The contents of the vials were combined and were diluted with 400 mL water and extracted with five 150 mL portions of ethyl acetate. The combined extracts were dried over sodium sulfate, and the solvent was removed in vacuo. The crude residue was purified by flash column chromatography to yield the desired product (1.40 g, 59%).

¹H NMR (400 MHz, CDCl₃): δ □9.52 (br s, 1H), 8.83 (s, 1H), 8.34 (s, 1H), 8.29 (s, 1H), 7.39 (dd, 1H), 6.81 (dd, 1H), 2.38 (dd, 2H), 2.16 (dd, 2H), 1.73 (s, 6H); MS(ES):281(M+1).

The analogs in Table 5a were prepared according to the above method described for Example 69a. For Example 69b, a conjugate acceptor was used and prepared as described in

*Perkin Trans.* 1, 2000, (17), 2968-2976, and Steps 4 & 5 were performed before Step 3.

TABLE 5a

| Ex. No. | Structure | Name | MS (ES) (M + 1) |
|---|---|---|---|
| 69b | 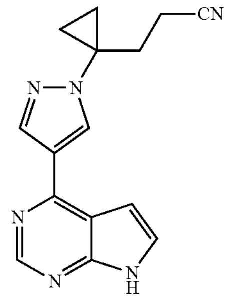 [SMILES: N#CCCC1(n2cc(-c3ncnc4[nH]ccc34)cn2)CC1] | 3-1-[4-(7H-pyrrolo[2,3-d]-pyrimidin-4-yl)-1H-pyrazol-1-yl]cyclopropylpropanenitrile | 279 |
| 69c | 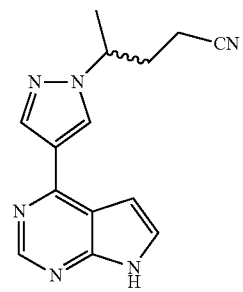 [SMILES: CC(CCC#N)n1cc(-c2ncnc3[nH]ccc23)cn1] | (4S)- and (4R)-4-[4(7H-pyrrolo[2,3-d]pyrimidin-4-yl)-1H-pyrazol-1-yl]pentanenitrile | 267 |

Example 69d

3-Methyl-3-[4-(7H-pyrrolo[2,3-d]pyrimidin-4-yl)-1H-pyrazol-1-yl]butanenitrile

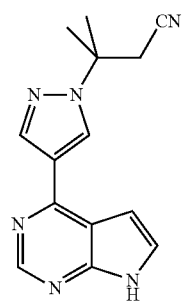 [SMILES: CC(C)(CC#N)n1cc(-c2ncnc3[nH]ccc23)cn1]

Step 1. Senecionitrile

To a solution of 1.0 M potassium tert-butoxide in THF (2.0 mL) at 0° C. was added a solution of diethyl cyanomethylphosphonate (0.33 mL, 2.06 mmol) in THF (4 mL) dropwise. The cold bath was removed and the reaction was warmed to room temperature. The reaction was then re-cooled to 0° C. and acetone (0.20 mL, 2.81 mmol) was added dropwise. The cooling bath was then removed and the reaction was allowed to warm to room temperature and stir overnight. The reaction was diluted with water, the layers separated, and the aqueous extracted with ethyl acetate. The extracts were washed with brine, dried over sodium sulfate, filtered and concentrated. The product was used without further purification (339 mg, 67%).

$^1$H NMR (300 MHz, CDCl$_3$): δ □5.10 (br s, 1H), 2.05 (s, 3H), 1.92 (s, 3H).

Step 2. 3-Methyl-3-[4-(7H-pyrrolo[2,3-d]pyrimidin-4-yl)-1H-pyrazol-1-yl]butanenitrile To a solution of 4-(1H-pyrazol-4-yl)-7-[2-(trimethylsilyl)ethoxy]methyl-7H-pyrrolo[2,3-d]-pyrimidine (0.216 g, 0.684 mmol) in ACN (4 mL, 0.08 mol) was added crude senecionitrile (0.111 g, 1.37 mmol), followed by DBU (200 μL, 0.002 mol) and the resulting mixture was heated to 60° C. for 23 hours. The mixture was cooled to room temperature and the ACN was evaporated. The mixture was diluted with ethyl acetate and washed with dilute HCl and brine. The organic solution was dried over sodium sulfate, filtered and concentrated. Purification by silica gel chromatography (ethyl acetate/hexanes) afforded the desired product.

$^1$H NMR (300 MHz, d$_6$-dmso) δ □8.83 (s, 1H), 8.38 (s, 1H), 8.28 (s, 1H), 7.39 (d, 1H), 6.80 (d, 1H), 5.66 (s, 2H), 3.54 (dd, 2H), 3.08 (s, 2H), 1.84 (s, 6H), 0.91 (dd, 2H), −0.07 (s, 9H); MS(ES):397(M+1).

To a solution of this product in DCM at 0° C. was added TFA sufficient to comprise 20% of the total volume. The solution was stirred at this temperature for 30 min, then at ambient temperature for 2 hours and 15 minutes. The solvents were removed in vacuo and the residue was stirred with methanol (10 mL) and ethylenediamine (0.4 mL, 0.006 mol) overnight. The solvent was evaporated and the product was purified by preparative-HPLC/MS (C18 column eluting with a gradient of ACN/H$_2$O containing 0.15% NH$_4$OH) to afford the product (25 mg, 14%).

$^1$H NMR (300 MHz, d$_6$-dmso) δ □12.08 (s, 1H), 8.68 (s, 2H), 8.39 (s, 1H), 7.59 (d, 1H), 7.05 (d, 1H), 3.32 (s, 2H), 1.73 (s, 6H); MS(ES):267(M+1).

Examples 69e and 69f in Table 5b were prepared by a method analogous to that described above for Example 69d, with unsaturated nitriles prepared either according to published literature procedures, or by the method in Step 1.

TABLE 5b

| Ex. No. | Structure | Name | MS (ES) (M + 1) |
|---|---|---|---|
| 69e | 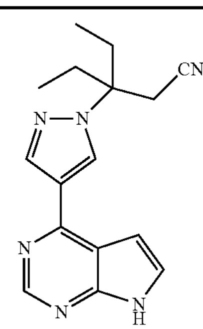 | 3-ethyl-3-[4-(7H-pyrrolo[2,3-d]pyrimidin-4-yl)-1H-pyrazol-1-yl]pentanenitrile | 295 |

TABLE 5b-continued

| Ex. No. | Structure | Name | MS (ES) (M + 1) |
|---|---|---|---|
| 69f | 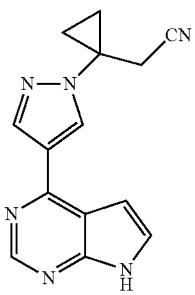 [SMILES: N#CCC1(n2cc(-c3ncnc4[nH]ccc34)cn2)CC1] | 1-[4-(7H-pyrrolo[2,3-d]-pyrimidin-4-yl)-1H-pyrazol-1-yl]cyclopropylacetonitrile | 265 |

Additional analogs were prepared by procedures analogous to those described in Example 69, using different starting materials such as alternative bromide or mesylate compounds for the nucleophilic substitution step. Where the free amine was obtained as the product, the product was purified after deprotection either by silica gel chromatography (eluting with 5% methanol in DCM) or by preparative-HPLC (C18 eluting with a gradient of ACN/H₂O containing 0.15% NH₄OH). The results are summarized for compounds listed in Table 6.

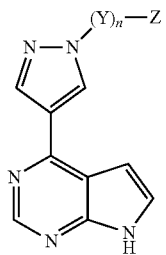

TABLE 6

| Ex. No. | Name | —(Y)ₙ—Z | MS (ES) (M + 1) |
|---|---|---|---|
| 70 | 4-1-[(2R)-pyrrolidin-2-ylmethyl]-1H-pyrazol-4-yl-7H-pyrrolo[2,3-d]-pyrimidine | | 269 |
| 71 | 4-(1-[(2R)-1-(methylsulfonyl)pyrrolidin-2-yl]methyl-1H-pyrazol-4-72yl)-7H-pyrrolo[2,3-d]pyrimidine | | 347 |
| 73 | ethyl 2-methyl-2-[4-(7H-pyrrolo[2,3-d]-pyrimidin-4-yl)-1H-pyrazol-1-yl]-propanoate trifluoroacetate salt | | 300 |

Example 74

(2Z)-3-Cyclopentyl-3-[4-(7H-pyrrolo[2,3-d]pyrimidin-4-yl)-1H-pyrazol-1-yl]-acrylonitrile

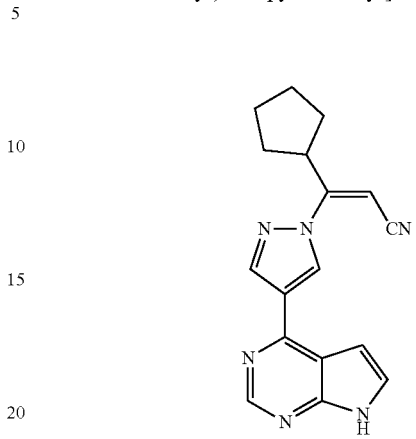

Step 1. 3-Cyclopentylprop-2-ynenitrile

To a solution of cyclopentylacetylene (0.50 g, 5.3 mmol) in THF (5 mL) at −78° C. was added 2.5 M n-butyllithium in hexane (2.23 mL). The mixture was stirred for 15 min followed by the dropwise addition of phenyl cyanate (0.70 g, 5.8 mmol) in THF (3 mL). The reaction was warmed to room temperature. Into the reaction mixture was poured 6 N NaOH, and the mixture was stirred for 5 minutes. The product was extracted with diethyl ether. The extracts were washed with 6 N NaOH and with brine, then dried over sodium sulfate, decanted and the solvent was removed in vacuo to afford product (600 mg, 95%). ¹H NMR (300 MHz, CDCl₃): δ □2.81-2.68 (m, 1H), 2.07-1.54 (m, 8H).

Step 2. (2Z)-3-Cyclopentyl-3-[4-(7-[2-(trimethylsilyl)ethoxy]methyl-7H-pyrrolo[2,3-d]pyrimidin-4-yl)-1H-pyrazol-1-yl]acrylonitrile To a mixture of 4-(1H-pyrazol-4-yl)-7-[2-(trimethylsilyl)ethoxy]methyl-7H-pyrrolo[2,3-d]-pyrimidine (0.40 g, 1.2 mmol) and 3-cyclopentylprop-2-ynenitrile (0.30 g, 2.5 mmol) in DMF (8 mL) was added potassium carbonate (0.09 g, 0.6 mmol). The mixture was stirred for 35 min. The reaction was diluted with ethyl acetate and brine, and the aqueous portion extracted with three volumes of ethyl acetate. The combined organic extracts were washed with brine again, then were dried over sodium sulfate, decanted and concentrated in vacuo. The crude residue was purified by flash column chromatography (ethyl acetate/hexanes) to yield the desired product (290 mg, 53%).

¹H NMR (400 MHz, CDCl₃): δ □8.98 (s, 1H), 8.87 (s, 1H), 8.46 (s, 1H), 7.42 (d, 1H), 6.84 (d, 1H), 5.67 (s, 2H), 5.21 (s, 1H), 3.64-3.55 (m, 1H), 3.53 (t, 2H), 2.13-2.01 (m, 2H), 1.83-1.66 (m, 4H), 1.57-1.46 (m, 2H), 0.91 (t, 2H), −0.07 (s, 9H); MS(ES):435(M+1).

Step 3. (2Z)-3-Cyclopentyl-3-[4-(7H-pyrrolo[2,3-d]pyrimidin-4-yl)-1H-pyrazol-1-yl]acrylonitrile A solution of (2Z)-3-cyclopentyl-3-[4-(7-[2-(trimethylsilyl)ethoxy]methyl-7H-pyrrolo[2,3-d]-pyrimidin-4-yl)-1H-pyrazol-1-yl]acrylonitrile (0.030 g, 0.069 mol) in DCM (3 mL) and TFA (2 mL) was stirred for 1 hour. The solvents were removed in vacuo and the product was stirred with THF (1.5 mL), sodium hydroxide, 50% aqueous solution (0.75 mL) and water (0.75 mL) for 2 hours. The reaction mixture was neutralized by the dropwise addition of conc. HCl. The product was extracted with ethyl acetate. The combined organics were dried over sodium sulfate, filtered and concentrated in vacuo. The crude residue was purified by preparative-HPLC/MS (C18 column eluting with a gradient of ACN/H$_2$O containing 0.15% NH$_4$OH) to afford the desired product (16 mg, 76%).

$^1$H NMR (400 MHz, d$_6$-dmso) δ □9.08 (s, 1H), 8.74 (s, 1H), 8.63 (s, 1H), 7.66 (d, 1H), 7.05 (d, 1H), 5.82 (d, 1H), 3.62-3.54 (m, 1H), 2.00-1.90 (m, 2H), 1.76-1.48 (m, 6H); MS(ES):305(M+1).

Example 75

3-Cyclopentylidene-3-[4-(7H-pyrrolo[2,3-d]pyrimidin-4-yl)-1H-pyrazol-1-yl]-propanenitrile

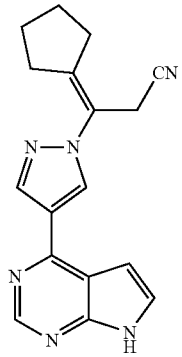 [SMILES: N#CCC(=C1CCCC1)n1cc(-c2ncnc3[nH]ccc23)cn1]

Step 1. 3-Cyclopentylidene-3-[4-(7-[2-(trimethylsilyl)ethoxy]methyl-7H-pyrrolo[2,3-d]pyrimidin-4-yl)-1H-pyrazol-1-yl]propanenitrile To a suspension of 3-cyclopentylprop-2-ynenitrile (0.4 g, 0.003 mol) in ACN (10 mL) was added 4-(1H-pyrazol-4-yl)-7-[2-(trimethylsilyl)ethoxy]methyl-7H-pyrrolo[2,3-d]pyrimidine (0.53 g, 1.7 mmol) and DBU (0.33 mL, 2.2 mmol). This mixture was stirred at room temperature for 50 minutes. The reaction mixture was partitioned between ethyl acetate and dilute HCl. The aqueous portion was separated and extracted with ethyl acetate. The combined organic extracts were washed with dilute HCl and brine, were dried over sodium sulfate, filtered and concentrated in vacuo. The crude residue was purified by flash column chromatography (ethyl acetate/hexanes) to yield the desired product (540 mg, 74%).

$^1$H NMR (300 MHz, CDCl$_3$): δ □8.85 (s, 1H), 8.36 (s, 1H), 8.35 (s, 1H), 7.40 (d, 1H), 6.78 (d, 1H), 5.67 (s, 2H), 3.70 (s, 2H), 3.54 (dd, 2H), 2.55 (t, 2H), 2.45 (t, 2h), 1.85 (dddd, 2H), 1.73 (dddd, 2H), 0.91 (dd, 2H), −0.06 (s, 9H); MS(ES):435(M+1).

Step 2. 3-Cyclopentylidene-3-[4-(7H-pyrrolo[2,3-d]pyrimidin-4-yl)-1H-pyrazol-1-yl]propanenitrile A solution of 3-cyclopentylidene-3-[4-(7-[2-(trimethylsilyl)ethoxy]methyl-7H-pyrrolo[2,3-d]-pyrimidin-4-yl)-1H-pyrazol-1-yl]propanenitrile (0.030 g, 0.069 mmol) in DCM (3 mL) and TFA (2 mL) was stirred for 1 hour. The solvents were evaporated in vacuo and the product was stirred with sodium hydroxide, 50% aqueous solution (0.75 mL) and water (0.75 mL) and THF (1.5 mL) for 2 hours. The reaction mixture was neutralized by dropwise addition of concentrated HCl. The product was extracted with ethyl acetate. The combined organic extracts were dried over sodium sulfate, filtered and concentrated in vacuo. The crude residue was purified by preparative-HPLC/MS (C18 column eluting with a gradient of ACN/H$_2$O containing 0.15% NH$_4$OH) to afford the desired product (7 mg, 33%).

$^1$H NMR (400 MHz, d$_6$-dmso): δ □12.23-12.01 (br s, 1H), 8.78 (s, 1H), 8.69 (s, 1H), 8.46 (s, 1H), 7.60 (d, 1H), 7.04 (d, 1H), 3.95 (s, 2H), 2.53 (t, 2H), 2.42 (t, 2H), 1.76 (dddd, 2H), 1.65 (dddd, 2H); MS(ES):305(M+1).

Example 76

3-Methyl[5-(7H-pyrrolo[2,3-d]pyrimidin-4-yl)-1,3-thiazol-2-yl]aminopropane-nitrile trifluoroacetate salt

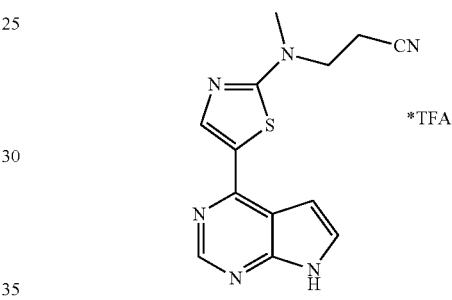

Step 1. 4-(1,3-Thiazol-5-yl)-7-[2-(trimethylsilyl)ethoxy]methyl-7H-pyrrolo[2,3-d]pyrimidine 4-Chloro-7-[2-(trimethylsilyl)ethoxy]methyl-7H-pyrrolo[2,3-d]pyrimidine (3.00 g, 0.0106 mol), and 1,3-thiazole (7.50 mL, 0.106 mol) were dissolved in N,N-dimethylacetamide (40.0 mL). The solution was distributed in equal portions into four 20 mL microwavable vessels. Into each reaction vessel was then added potassium acetate (0.777 g, 7.93 mmol) followed by tetrakis(triphenyl-phosphine)palladium(0) (0.60 g, 2.1 mmol). Each reaction vessel was heated at 200° C. in the microwave reactor for 30 minutes. The reactions were combined and most of the solvent was removed in vacuo. The residue was diluted with DCM, filtered and concentrated. Purification by flash column chromatography (ethyl acetate/hexanes) afforded the desired product (2.25 g, 64%).

$^1$H NMR (300 MHz, CDCl$_3$): δ 8.99 (s, 1H), 8.90 (s, 1H), 8.72 (s, 1H), 7.49 (d, 1H), 6.91 (d, 1H), 5.70 (s, 2H), 3.56 (dd, 2H), 0.93 (dd, 2H), −0.05 (s, 9H); MS(ES):333(M+1).

Step 2. 4-(2-Bromo-1,3-thiazol-5-yl)-7-[2-(trimethylsilyl)ethoxy]methyl-7H-pyrrolo[2,3-d]pyrimidine 2.5 M n-Butyllithium in hexane (0.860 mL) was added dropwise to a −78° C. solution of 4-(1,3-thiazol-5-yl)-7-[2-(trimethylsilyl)ethoxy]methyl-7H-pyrrolo[2,3-d]pyrimidine (550 mg, 0.0016 mol) in THF (20 mL). The mixture was stirred for 30 minutes at −78° C., followed by the slow addition of carbon tetrabromide (658 mg, 0.00198 mol) as a solution in THF (10 mL). After 30 minutes, the mixture was quenched with a small amount of saturated ammonium chloride, diluted with ether, and dried over sodium sulfate. The residue obtained after filtration and concentration was purified by flash column chromatography (ethyl acetate/hexanes) to afford the desired product (387 mg, 57%).

$^1$H NMR (300 MHz, CDCl$_3$): δ 8.85 (s, 1H), 8.33 (s, 1H), 7.49 (d, 1H), 6.83 (d, 1H), 5.69 (s, 2H), 3.55 (dd, 2H), 0.92 (dd, 2H), −0.05 (s, 9H); MS(ES):411, 413(M+1).

Step 3. 4-(2-Bromo-1,3-thiazol-5-yl)-7H-pyrrolo[2,3-d]pyrimidine

A solution of 4-(2-bromo-1,3-thiazol-5-yl)-7-[2-(trimethylsilyl)ethoxy]methyl-7H-pyrrolo-[2,3-d]pyrimidine (370 mg, 0.90 mmol) in DCM (5.0 mL) and TFA (1.0 mL) was stirred at room temperature for 7 hours. The mixture was then concentrated, re-dissolved in methanol (2 mL), and ethylenediamine (0.5 mL) was added. The mixture was stirred for 6 hours at room temperature. The mixture was diluted with DCM (10 mL), and the precipitate was isolated by filtration and washed with a small amount of DCM to afford desired product (182 mg, 72%).

$^1$H NMR (300 MHz, d$_6$-dmso) δ □8.74 (s, 1H), 8.70 (s, 1H), 7.76 (d, 1H), 7.15 (d, 1H); MS(ES):281,283(M+1).

Step 4. 3-Methyl[5-(7H-pyrrolo[2,3-d]pyrimidin-4-yl)-1,3-thiazol-2-yl]aminopropanenitrile A solution of 4-(2-bromo-1,3-thiazol-5-yl)-7H-pyrrolo[2,3-d]pyrimidine (31 mg, 0.11 mmol) and 3-(methylamino)propionitrile (103 μL, 0.00110 mol) in DMF (1.0 mL, 0.013 mol) was stirred at 90° C. for 2 hours. The crude reaction mixture was purified by preparative-HPLC/MS (C18 column eluting with a gradient of ACN/H$_2$O containing 0.15% NH$_4$OH) and again by preparative-HPLC/MS (C18 column eluting with a gradient of ACN/H$_2$O containing 0.1% TFA) to yield the desired product as the trifluoroacetate salt (30 mg, 68%).

$^1$H NMR (300 MHz, d$_6$-DMSO): δ □12.25 (s, 1H), 8.60 (s, 1H), 8.31 (s, 1H), 7.60 (dd, 1H), 7.00 (dd, 1H), 3.89 (t, 2H), 3.20 (s, 3H), 2.94 (t, 2H); MS(ES):285(M+1).

Example 77

(3S)- and (3R)-3-[5-(7H-Pyrrolo[2,3-d]pyrimidin-4-yl)-1,3-thiazol-2-yl]hexane-nitrile

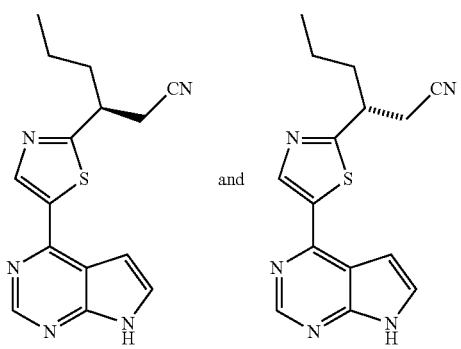 [SMILES: CCC[C@@H](CC#N)c1ncc(-c2ncnc3[nH]ccc23)s1 ; CCC[C@H](CC#N)c1ncc(-c2ncnc3[nH]ccc23)s1]

Step 1. N-Methoxy-N-methylbutanamide

To a mixture of butanoic acid (1.01 g, 0.0115 mol) and N,O-dimethylhydroxylamine hydro-chloride (1.12 g, 0.0115 mol) in DCM (50 mL) was added benzotriazol-1-yloxytris(dimethylamino)-phosphonium hexafluorophosphate (5.6 g, 0.013 mol) and TEA (3.2 mL, 0.023 mol). The mixture was stirred overnight at room temperature. The solution was then washed with water and brine, dried over sodium sulfate, and concentrated in vacuo. The crude product was purified by flash column chromatography (ether/hexanes). The solvent was removed (235 mbar/40° C.) to afford the product (1.33g, 88%). $^1$H NMR (300 MHz, CDCl$_3$): δ □3.68 (s, 3H), 3.18 (s, 3H), 2.40 (t, 2H), 1.74-1.59 (m, 2H), 0.96 (t, 3H).

Step 2. 1-[5-(7-[2-(Trimethylsilyl)ethoxy]methyl-7H-pyrrolo[2,3-d]pyrimidin-4-yl)-1,3-thiazol-2-yl]-butan-1-one 2.5 M n-Butyllithium in hexane (878 μL) was added slowly dropwise to a −78° C. solution of 4-(1,3-thiazol-5-yl)-7-[2-(trimethylsilyl)ethoxy]methyl-7H-pyrrolo[2,3-d]pyrimidine (501 mg, 1.37 mmol) in THF (20 mL). After 45 minutes, N-methoxy-N-methylbutanamide (0.360 g, 2.74 mmol) was added. The reaction was continued at −78° C. for 30 min, and was then allowed to reach room temperature. The reaction was quenched with saturated ammonium chloride, and was extracted with ethyl acetate. The extracts were washed with water and brine, dried over sodium sulfate and concentrated in vacuo. Flash column chromatography (ethyl acetate/hexanes) afforded the product (235 mg, 42%).

$^1$H NMR (300 MHz, CDCl$_3$): δ □8.93 (s, 1H), 8.76 (s, 1H), 7.52 (d, 1H), 6.92 (d, 1H), 5.71 (s, 2H), 3.56 (dd, 2H), 3.19 (t, 2H), 1.92-1.77 (m, 2H), 1.05 (t, 3H), 0.93 (dd, 2H), −0.05 (s, 9H); MS(ES):403(M+1).

Step 3. (2E)- and (2Z)-3-[5-(7-[2-(Trimethylsilyl)ethoxy]methyl-7H-pyrrolo[2,3-d]pyrimidin-4-yl)-1,3-thiazol-2-yl]hex-2-enenitrile To a solution of 1.0 M potassium tert-butoxide in THF (0.605 mL) in THF (4.0 mL) at 0° C. was added diethyl cyanomethylphosphonate (0.102 mL, 0.634 mmol) dropwise. The cooling bath was removed and the reaction was warmed to room temperature. After 30 minutes, a solution of 1-[5-(7-[2-(trimethylsilyl)ethoxy]methyl-7H-pyrrolo[2,3-d]pyrimidin-4-yl)-1,3-thiazol-2-yl]butan-1-one (232 mg, 0.576 mmol) in THF (3.0 mL) was added dropwise. The reaction was stirred for 2 hours, and the crude mixture was then adsorbed onto silica gel and purified by flash column chromatography (ethyl acetate/hexanes) to afford the product as a mixture of olefin isomers (225 mg, 92%).

$^1$H NMR (300 MHz, CDCl$_3$), major isomer: δ □8.89 (s, 1H), 8.65 (s, 1H), 7.52 (d, 1H), 6.89 (d, 1H), 6.35 (s, 1H), 5.70 (s, 2H), 3.56 (dd, 2H), 2.96 (t, 2H), 1.88-1.72 (m, 2H), 1.08 (t, 3H), 0.93 (dd, 2H), −0.07 (s, 9H); MS(ES):426(M+1).

Step 4. (3S)- and (3R)-3-[5-(7-[2-(Trimethylsilyl)ethoxy]methyl-7H-pyrrolo[2,3-d]pyrimidin-4-yl)-1,3-thiazol-2-yl]hexanenitrile Cupric acetate, monohydrate (0.7 mg, 0.004 mmol) and (oxydi-2,1-phenylene)bis(diphenyl-phosphine) (2 mg, 0.004 mol) was mixed in toluene (0.24 mL). PMHS (30 μL) was added. The mixture was stirred for 25 minutes at room temperature followed by the addition of (2E)-3-[5-(7-[2-(trimethylsilyl)ethoxy]methyl-7H-pyrrolo[2,3-d]pyrimidin-4-yl)-1,3-thiazol-2-yl]hex-2-enenitrile (51 mg, 0.12 mol) in toluene (0.24 mL) and finally, tert-butyl alcohol (0.043 mL). The resulting mixture was stirred overnight. The crude mixture was purified directly by flash column chromatography (ethyl acetate/hexanes) to afford the desired product (39 mg, 76%).

$^1$H NMR (300 MHz, CDCl$_3$): δ □8.87 (s, 1H), 8.52 (s, 1H), 7.48 (d, 1H), 6.87 (d, 1H), 5.69 (s, 2H), 3.60-3.46 (m, 3H), 2.99-2.82 (m, 2H), 2.05-1.89 (m, 2H), 1.50-1.34 (m, 2H), 0.97 (t, 3H), 0.92 (t, 2H), −0.06 (s, 9H); MS(ES):428 (M+1).

Step 5. (3S)- and (3R)-3-[5-(7H-Pyrrolo[2,3-d]pyrimidin-4-yl)-1,3-thiazol-2-yl]hexanenitrile TFA (1.0 mL) was added to a solution of 3-[5-(7-[2-(trimethylsilyl)ethoxy]methyl-7H-pyrrolo[2,3-d]pyrimidin-4-yl)-1,3-thiazol-2-yl]hexanenitrile (36 mg, 0.084 mmol) in DCM (4.0 mL) and the mixture was stirred at room temperature for 3 hours. The mixture was concentrated, and re-dissolved in methanol (3 mL), to which ethylenediamine (0.1 mL) was added. After 2 hours reaction time, the mixture was concentrated and directly purified by preparative-HPLC/MS (C18 column eluting with a gradient of ACN/H$_2$O containing 0.15% NH$_4$OH) to afford the desired product (10 mg, 40%). $^1$H NMR (300 MHz, CDCl$_3$): δ □9.96 (br s, 1H), 8.87 (s, 1H), 8.54 (s, 1H), 7.51-7.45 (m, 1H), 6.90-6.86 (m, 1H), 3.59-3.44 (m, 1H), 3.01-2.82 (m, 2H), 2.06-1.87 (m, 2H), 1.51-1.34 (m, 2H), 0.98 (t, 3H); MS(ES): 298(M+1).

Example 78

(3R)- and (3S)-3-Cyclopentyl-3-[5-(7H-pyrrolo[2,3-d]pyrimidin-4-yl)-1,3-thiazol-2-yl]propanenitrile

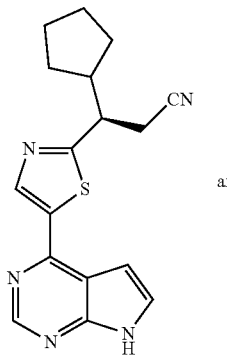 and 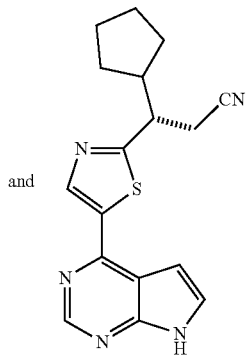

To a solution of (2E)- and (2Z)-3-cyclopentyl-3-[5-(7-[2-(trimethylsilyl)ethoxy]methyl-7H-pyrrolo[2,3-d]pyrimidin-4-yl)-1,3-thiazol-2-yl]acrylonitrile (199 mg, 0.440 mmol) (prepared, for example, as in Example 77, steps 1 through 3) in a mixture of ethanol (10 mL) and ethyl acetate (10 mL) was added a catalytic amount of 10% palladium on carbon. The mixture was stirred at room temperature under one atmosphere of hydrogen overnight. It was then subjected to 50 PSI H$_2$ until the reaction was complete. Filtration and removal of solvent afforded an oil which was dissolved in DCM (4 mL) and TFA (1 mL). The solution was stirred until starting material was consumed and the mixture was then concentrated and re-dissolved in methanol (3 mL), to which ethylenediamine (0.4 mL) was added. The solution was stirred at room temperature for one hour, and was concentrated in vacuo. The crude mixture was purified by preparative-HPLC/MS (C18 column eluting with a gradient of ACN/H$_2$O containing 0.15% NH$_4$OH) to afford the desired product (36 mg, 25%).

$^1$H NMR (400 MHz, CDCl$_3$): δ □10.44 (br s, 1H), 8.89 (s, 1H), 8.56 (s, 1H), 7.50 (dd, 1H), 6.89 (dd, 1H), 3.34 (dt, 1H), 2.98 (dd, 1H), 2.89 (dd, 1H), 2.44-2.31 (m, 1H), 2.07-1.96 (m, 1H), 1.80-1.52 (m, 5H), 1.40-1.24 (m, 2H); MS(ES):324(M+1).

The following compounds of Table 5c were prepared (as racemic mixtures) as described by Example 77, 78 or 86, as indicated in the following table, by using different Weinreb amides (as prepared in Example 77, Step 1):

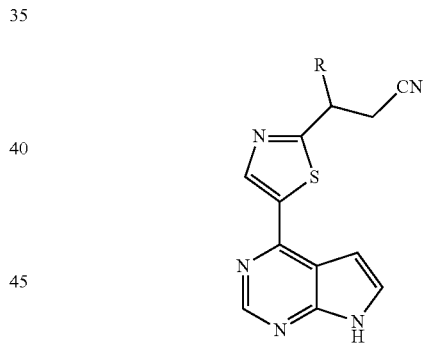

TABLE 5c

| Ex. No. | Name | R | MS (ES) (M + 1) | Method of preparation |
|---|---|---|---|---|
| 79 | 5-methyl-3-[5-(7H-pyrrolo[2,3-d]-pyrimidin-4-yl)-1,3-thiazol-2-yl]-hexanenitrile | | 312 | Ex. 77 |
| 80 | 3-pyridin-3-yl-3-[5-(7H-pyrrolo[2,3-d]-pyrimidin-4-yl)-1,3-thiazol-2-yl]-propanenitrile | | 333 | Ex. 78 |

TABLE 5c-continued

| Ex. No. | Name | R | MS (ES) (M + 1) | Method of preparation |
|---|---|---|---|---|
| 81 | 3-(5-bromopyridin-3-yl)-3-[5-(7H-pyrrolo[2,3-d]pyrimidin-4-yl)-1,3-thiazol-2-yl]propanenitrile | Br-pyridinyl | 411, 413 | Ex. 77 |
| 82 | 5-2-cyano-1-[5-(7H-pyrrolo[2,3-d]-pyrimidin-4-yl)-1,3-thiazol-2-yl]-ethylnicotinonitrile | CN-pyridinyl | 358 | Ex. 77 through Step 4, then Ex. 431 excluding purification, then Ex. 77, Step 5 |
| 83 | 3-[5-(7H-pyrrolo[2,3-d]pyrimidin-4-yl)-1,3-thiazol-2-yl]butanenitrile | Me | 270 | Ex. 86, Step 3 subjected to conditions of Ex. 77, Steps 4&5 |
| 83A | 3-pyridin-4-yl-3-[5-(7H-pyrrolo[2,3-d]pyrimidin-4-yl)-1,3-thiazol-2-yl]propanenitrile | pyridin-4-yl | 333 | Ex. 78 |
| 83B | 4-2-cyano-1-[5-(7H-pyrrolo[2,3-d]-pyrimidin-4-yl)-1,3-thiazol-2-yl]-ethylpyridine-2-carbonitrile trifluoroacetate salt | 2-CN-pyridin-4-yl | 358 | Ex. 77 through Step 3, then Ex. 431 excluding purification, then Ex. 78, purified by prep-HPLC/MS using H₂O/ACN containing 0.1% TFA |
| 83C | 3-pyridin-2-yl-3-[5-(7H-pyrrolo[2,3-d]-pyrimidin-4-yl)-1,3-thiazol-2-yl]-propanenitrile | pyridin-2-yl | 333 | Ex. 78 |

Example 84

(2S)- and (2R)-2-[5-(7H-Pyrrolo[2,3-d]pyrimidin-4-yl)-1,3-thiazol-2-yl]pentane-nitrile

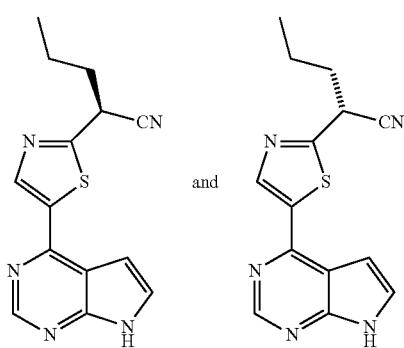 [SMILES: CCC[C@@H](C#N)c1ncc(-c2ncnc3[nH]ccc23)s1 ; CCC[C@H](C#N)c1ncc(-c2ncnc3[nH]ccc23)s1]

Step 1. (2S)- and (2R)-2-[5-(7-[2-(Trimethylsilyl)ethoxy]methyl-7H-pyrrolo[2,3-d]pyrimidin-4-yl)-1,3-thiazol-2-yl]pentanenitrile To a mixture of 1-[5-(7-[2-(trimethylsilyl)ethoxy]methyl-7H-pyrrolo[2,3-d]pyrimidin-4-yl)-1,3-thiazol-2-yl]butan-1-one (prepared as in Example 77) (101 mg, 0.251 mmol) and p-tolylsulfonyl-methyl isocyanide (147 mg, 0.753 mmol) in a mixture of DMSO (5.0 mL) and ethanol (61 µL) was added 1.0 M potassium tert-butoxide in THF (753 µL). The mixture was then heated to 45° C. for 2 hours. Upon cooling to room temperature, the mixture was quenched by the addition of saturated ammonium chloride, followed by water. The product was extracted with ether, and the extracts were washed with water and brine, dried over sodium sulfate, filtered and concentrated in vacuo. Flash column chromatography (ethyl acetate/hexanes) afforded the product (39 mg, 25%).

$^1$H NMR (400 MHz, CDCl$_3$): δ 8.88 (s, 1H), 8.52 (s, 1H), 7.50 (d, 1H), 6.87 (d, 1H), 5.70 (s, 2H), 4.32 (dd, 1H), 3.55

(dd, 2H), 2.20-2.11 (m, 2H), 1.71-1.57 (m, 2H), 1.03 (t, 3H), 0.93 (dd, 2H); MS(ES):414(M+1).

Step 2. (2S)- and (2R)-2-[5-(7H-Pyrrolo[2,3-d]pyrimidin-4-yl)-1,3-thiazol-2-yl]pentanenitrile A solution of 2-[5-(7-[2-(trimethylsilyl)ethoxy]methyl-7H-pyrrolo[2,3-d]pyrimidin-4-yl)-1,3-thiazol-2-yl]pentanenitrile (59 mg, 0.093 mmol) in DCM (3 mL) and TFA (0.5 mL) was stirred at room temperature for 4 hours. The mixture was then concentrated, and the residue was then dissolved in methanol (3 mL) to which ethylenediamine (0.3 mL) was then added. The solution was stirred at room temperature for 40 minutes. The solvent was removed in vacuo, and the crude mixture was purified by preparative-HPLC/MS (C18 column eluting with a gradient of ACN/$H_2O$ containing 0.15% $NH_4OH$) to afford the desired product (20 mg, 76%).

$^1$H NMR (400 MHz, $CDCl_3$): δ ⎯9.66 (br s, 1H), 8.88 (s, 1H), 8.54 (s, 1H), 7.49 (dd, 1H), 6.88 (dd, 1H), 4.33 (dd, 1H), 2.23-2.12 (m, 2H), 1.75-1.60 (m, 2H), 1.04 (t, 3H); MS(ES):284(M+1).

Example 85

(4S)- and (4R)-4-[5-(7H-Pyrrolo[2,3-d]pyrimidin-4-yl)-1,3-thiazol-2-yl]heptane-nitrile

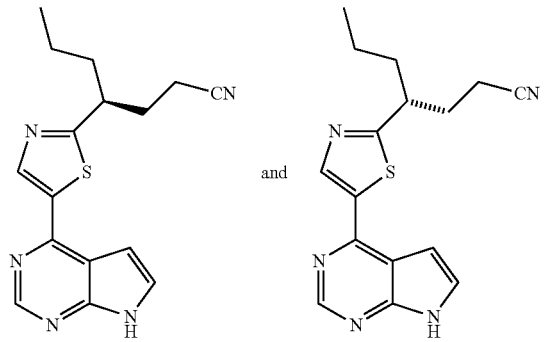 [SMILES: CCC[C@@H](CCC#N)c1ncc(-c2ncnc3[nH]ccc23)s1 ; CCC[C@H](CCC#N)c1ncc(-c2ncnc3[nH]ccc23)s1]

To a solution of triethyl phosphonoacetate (188 mg, 0.838 mmol) in THF (6.0 mL) at 0° C. was added 1.0 M potassium tert-butoxide in THF (840 μL). The mixture was then allowed to warm to room temperature followed by re-cooling to 0° C., at which time 1-[5-(7-[2-(trimethylsilyl) ethoxy]-methyl-7H-pyrrolo[2,3-d]pyrimidin-4-yl)-1,3-thiazol-2-yl]butan-1-one (prepared as in Example 77) (225 mg, 0.559 mmol) in THF (4.0 mL) was added. The mixture was stirred at room temperature for 1.5 hours, at which time it was quenched with water and extracted with ethyl acetate. The combined extracts were washed with water and brine, dried over sodium sulfate and concentrated in vacuo. Flash column chromatography afforded the product as a mixture of olefin isomers (222 mg, 84%). MS(ES):473(M+1).

Ethyl 3-[5-(7-[2-(trimethylsilyl)ethoxy]methyl-7H-pyrrolo[2,3-d]pyrimidin-4-yl)-1,3-thiazol-2-yl]hex-2-enoate as a mixture of (2E)- and (2Z)- isomers (222 mg, 0.470 mmol) was dissolved in ethanol (10 mL), and a catalytic amount of 10% Pd-C was added. The mixture was stirred under an atmosphere of hydrogen, provided by a balloon, for 16 hours. Filtration and concentration in vacuo afforded the desired product (201 mg, 90%). MS(ES):475(M+1).

To a solution of ethyl 3-[5-(7-[2-(trimethylsilyl)ethoxy] methyl-7H-pyrrolo[2,3-d]pyrimidin-4-yl)-1,3-thiazol-2-yl] hexanoate (201 mg, 0.423 mmol) in THF (5.0 mL) at −78° C. was added 1.00 M diisobutylaluminum hydride in DCM (1.06 mL). The mixture was allowed to warm to −10° C. slowly over 1.5 hours, followed by the addition of potassium sodium tartrate tetrahydrate, water, and ether. The mixture was stirred for 1 hour, then layers were separated, and the aqueous layer was extracted further with ethyl acetate. The organic extracts were washed with water and brine, dried over sodium sulfate and concentrated in vacuo to afford desired product (176 mg, 96%). MS(ES):433(M+1).

A solution of 3-[5-(7-[2-(trimethylsilyl)ethoxy]methyl-7H-pyrrolo[2,3-d]pyrimidin-4-yl)-1,3-thiazol-2-yl]hexan-1-ol (88 mg, 0.20 mmol) in TFA (2 mL) was stirred for 30 minutes. The TFA was then evaporated and the residue was stirred in methanol (2 mL) containing ethylenediamine (0.2 mL) and a drop of water for 30 minutes. Purification via preparative-HPLC/MS (C18 eluting with a gradient of ACN/$H_2O$ containing 0.15% $NH_4OH$) afforded the desired product (36 mg, 58%). MS(ES):303(M+1).

To a mixture of 3-[5-(7H-pyrrolo[2,3-d]pyrimidin-4-yl)-1,3-thiazol-2-yl) hexan-1-ol (36 mg, 0.12 mmol) and TEA (19.9 μL, 0.143 mmol) in DCM (5 mL) at 0° C. was added methanesulfonyl chloride (11.0 μL, 0.143 mmol). After stirring for 10 minutes, the solution was concentrated and dissolved in DMSO (1.6 mL) and sodium cyanide (23 mg, 0.48 mmol) was added. The mixture was then heated at 125° C. in the microwave for 30 minutes. The mixture was then purified directly using preparative-HPLC/MS (C18 eluting with a gradient of ACN/$H_2O$ containing 0.15% $NH_4OH$) to afford the desired product (10 mg, 27%).

$^1$H NMR (400 MHz, $CDCl_3$): δ ☐9.37 (br s, 1H), 8.86 (s, 1H), 8.52 (s, 1H), 7.46 (dd, 1H), 6.88 (dd, 1H), 3.34-3.25 (m, 1H), 2.47-2.30 (m, 2H), 2.22-2.12 (m, 2H), 1.95-1.71 (m, 2H), 1.44-1.31 (m, 2H), 0.94 (t, 3H); MS(ES):312(M+1).

Example 86

3-[5-(7H-Pyrrolo[2,3-d]pyrimidin-4-yl)-1,3-thiazol-2-yl]pentanedinitrile

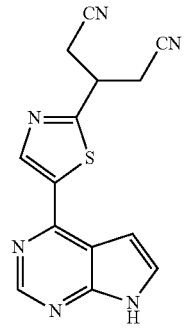 [SMILES: N#CCC(CC#N)c1ncc(-c2ncnc3[nH]ccc23)s1]

Step 1. N-Methoxy-2-[(4-methoxybenzyl)oxy]-N-methylacetamide

To a mixture of [(4-methoxybenzypoxy]acetic acid (*Bio-organic and Medicinal Chemistry Letters*, 2001, pp. 2837-2841) (6.86 g, 0.0350 mol) and N,O-dimethylhydroxylamine hydrochloride (3.41 g, 0.0350 mol) in DCM (100 mL) was added benzotriazol-1-yloxytris(dimethylamino)-phosphonium hexafluorophosphate (17 g, 0.038 mol) followed by TEA (9.7 mL, 0.070 mol). The resulting mixture was stirred overnight at room temperature. The solution was then washed with water, 0.5 M HCl, saturated NaHCO₃, and brine, then was dried over sodium sulfate, filtered and concentrated in vacuo. Flash column chromatography (ether/hexanes) afforded the desired product (5.75 g, 69%).

Step 2. 2-[(4-Methoxybenzyl)oxy]-1-[5-(7-[2-(trimethylsilyl)ethoxy]methyl-7H-pyrrolo[2,3-d]-pyrimidin-4-yl)-1,3-thiazol-2-yl]ethanone To a solution of 4-(1,3-thiazol-5-yl)-7-[2-(trimethylsilyl)ethoxy]methyl-7H-pyrrolo[2,3-d]-pyrimidine (2.12 g, 6.38 mmol) in THF (70 mL) at −78° C. was added 2.5 M n-butyllithium in hexane (3.06 mL) slowly dropwise. After stirring for 30 minutes, N-methoxy-2-[(4-methoxybenzypoxy]-N-methylacetamide (2.29 g, 9.56 mmol) was added. The reaction was continued for 30 minutes following the addition, at −78° C., then the cooling bath was removed and the reaction was quenched with saturated ammonium chloride and extracted with ether. The extracts were dried with sodium sulfate and concentrated in vacuo. The crude mixture was purified by flash column chromatography (ethyl acetate/hexanes) to afford desired product (2.16 g, 66%).
$^1$H NMR (300 MHz, CDCl₃): δ □8.93 (s, 1H), 8.72 (s, 1H), 7.53 (d, 1H), 7.37 (d, 2H), 6.91 (d, 2H), 6.89 (d, 1H), 5.70 (s, 2H), 5.00 (s, 2H), 4.70 (s, 2H), 3.81 (s, 3H), 3.56 (dd, 2h), 0.93 (dd, 2H), −0.05 (s, 9H); MS(ES):511(M+1).

Step 3. (2E)- and (2Z)-4-[(4-Methoxybenzyl)oxy]-3-[5-(7-[2-(trimethylsilyl)ethoxy]methyl-7H-pyrrolo[2,3-d]pyrimidin-4-yl)-1,3-thiazol-2-yl]but-2-enenitrile To a solution of 1 M potassium tert-butoxide in THF (4.44 mL) in THF (30 mL) at 0° C. was added diethyl cyanomethylphosphonate (820 mg, 0.0046 mol) dropwise. The bath was removed and the reaction was warmed to room temperature. After 30 minutes, a solution of 2-[(4-methoxybenzyl)-oxy]-1-[5-(7-[2-(trimethylsilyl)ethoxy]methyl-7H-pyrrolo[2,3-d]pyrimidin-4-yl)-1,3-thiazol-2-yl]-ethanone (2.16 g, 0.00423 mol) in THF (20 mL) was added dropwise. The reaction was stirred for 1 hour, and was then quenched with a small amount of saturated ammonium chloride, diluted with ether, dried over sodium sulfate and concentrated in vacuo. Purification by flash column chromatography, eluting with a gradient of 0-35% ethyl acetate/hexanes afforded the desired product as a mixture of olefin isomers in nearly equal amounts (1.76 g, 78%).
$^1$H NMR (400 MHz, CDCl₃): δ 8.90 (s, 1H), 8.88 (s, 1H), 8.71 (s, 1H), 8.67 (s, 1H), 7.50 (d, 2H), 7.35 (dd, 2H), 7.31 (dd, 2H), 6.92 (dd, 2H), 6.90 (dd, 2H), 6.86 (d, 2H), 6.62 (s, 1H), 6.10 (t, 1H), 5.70 (s, 4H), 4.75 (s, 2H), 4.72 (d, 2H), 4.64 (s, 4H), 3.82 (s, 3H), 3.81 (s, 3H), 3.56 (dd, 2H), 3.55 (dd, 2H), 0.96-0.90 (m, 4H), −0.05 (s, 9H), −0.054 (s, 9H); MS(ES):534(M+1).

Step 4. 4-[(4-Methoxybenzyl)oxy]-3-[5-(7-[2-(trimethylsilyl)ethoxy]methyl-7H-pyrrolo[2,3-d]-pyrimidin-4-yl)-1,3-thiazol-2-yl]butanenitrile (2E)- and (2Z)-4-[(4-Methoxybenzyl)oxy]-3-[5-(7-[2-(trimethylsilyl)ethoxy]methyl-7H-pyrrolo[2,3-d]pyrimidin-4-yl)-1,3-thiazol-2-yl]but-2-enenitrile (880 mg, 1.6 mmol) was dissolved in a mixture of ethanol (20 mL) and ethyl acetate (20 mL). A catalytic amount of 10% Pd—C was added. The mixture was shaken under 50 PSI of hydrogen. The mixture was filtered and concentrated in vacuo to afford the desired product (0.85 g, 99%). MS(ES):536(M+1).

Step 5. 3-[5-(7H-Pyrrolo[2,3-d]pyrimidin-4-yl)-1,3-thiazol-2-yl]pentanedinitrile 4-[(4-Methoxybenzyl)oxy]-3-[5-(7-[2-(trimethylsilyl)ethoxy]methyl-7H-pyrrolo[2,3-d]-pyrimidin-4-yl)-1,3-thiazol-2-yl]butanenitrile (251 mg, 0.468 mmol) in DCM (10 mL) was treated with dichlorodicyanoquinone (DDQ) (434 mg, 1.87 mmol), followed by water (376 µL). After 1.5 hours, saturated sodium bicarbonate and water were added, and the reaction was extracted with ethyl acetate three times. The extracts were washed with water, brine, dried over sodium sulfate, filtered and concentrated in vacuo to afford the crude product which was used without further purification.

A solution of the above prepared 4-hydroxy-3-[5-(7-[2-(trimethylsilyl)ethoxy]methyl-7H-pyrrolo[2,3-d]pyrimidin-4-yl)-1,3-thiazol-2-ylibutanenitrile in DCM (12 mL) at 0° C. was treated sequentially with TEA (130 µL, 0.94 mmol) and methanesulfonyl chloride (73 µL, 0.94 mmol). After 1 hour reaction time, the mixture was diluted with water and extracted with ethyl acetate three times. The extracts were washed with water and brine, dried over sodium sulfate, filtered and concentrated in vacuo. The residue was then dissolved in DMSO (5 mL) and sodium cyanide (110 mg, 2.3 mmol) was added. After 30 minutes, the mixture was diluted with water, extracted with ether, washed with water, brine and dried over sodium sulfate. Concentration and purification by flash column chromatography (ethyl acetate/hexanes) afforded the desired product (14 mg, 7%). MS(ES): 425(M+1).

A solution of 3-[5-(7-[2-(trimethylsilyl)ethoxy]methyl-7H-pyrrolo[2,3-d]pyrimidin-4-yl)-1,3-thiazol-2-ylipentanedinitrile (14 mg, 0.033 mmol) in DCM (3 mL) containing TFA (0.6 mL) was stirred for 4 hours. The mixture was then concentrated and the residue was redissolved in methanol (2 mL) to which ethylenediamine (0.4 mL) was then added. After 1 hour reaction time, the product was purified by preparative-HPLC/MS (C18 eluting with a gradient of ACN/H₂O containing 0.15% NH₄OH) to afford the desired product (6 mg, 62%).
$^1$H NMR (400 MHz, d₆-dmso): δ □12.27 (br s, 1H), 8.84 (s, 1H), 8.76 (s, 1H), 7.75 (d, 1H), 7.14 (d, 1H), 4.14 (m, 1H), 3.17 (d, 4H); MS(ES):295(M+1).

Example 87

(3R)-3-Cyclopentyl-3-[5-(7H-pyrrolo[2,3-d]pyrimidin-4-yl)-1,3-oxazol-2-yl]-propanenitrile, and (3S)-3-Cyclopentyl-3-[5-(7H-pyrrolo[2,3-d]pyrimidin-4-yl)-1,3-oxazol-2-yl]propanenitrile

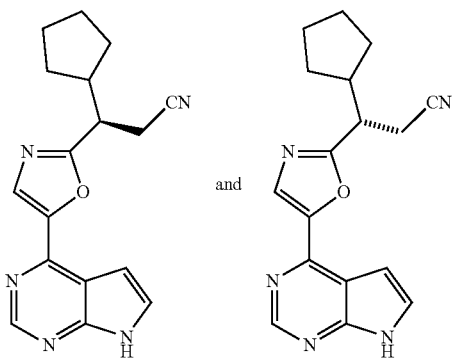 [SMILES: N#CC[C@@H](c1ncc(-c2ncnc3[nH]ccc23)o1)C1CCCC1 ; N#CC[C@H](c1ncc(-c2ncnc3[nH]ccc23)o1)C1CCCC1]

Step 1. 4-(1,3-Oxazol-5-yl)-7-[2-(trimethylsilyl)ethoxy]methyl-7H-pyrrolo[2,3-d]pyrimidine A mixture of 4-chloro-7-[2-(trimethylsilyl)ethoxy]methyl-7H-pyrrolo[2,3-d]pyrimidine (0.440 g, 1.55 mmol), 1,3-oxazole (0.306 mL, 4.65 mmol), potassium acetate (0.456 g, 4.65 mmol) and tetrakis(triphenylphosphine)palladium(0) (0.179 g, 0.155 mmol) in N,N-dimethylacetamide (8.0 mL) was heated to 200° C. in the microwave reactor for 30 minutes. Most of the solvent was removed in vacuo. The resulting residue was diluted with DCM, and was filtered and concentrated. Flash column chromatography (ethyl acetate/hexanes) afforded the product (330 mg, 67%).

$^1$H NMR (400 MHz, CDCl$_3$): δ 8.96 (s, 1H), 8.21 (s, 1H), 8.08 (s, 1H), 7.54 (d, 1H), 7.08 (d, 1H), 5.76 (s, 2H), 3.60 (t, 2H), 0.98 (t, 2H), 0.00 (s, 9H); MS(ES):317(M+1).

Step 2. Cyclopentyl[5-(7-[2-(trimethylsilyl)ethoxy]methyl-7H-pyrrolo[2,3-d]pyrimidin-4-yl)-1,3-oxazol-2-yl]methanone n-Butyllithium in hexane (1.6 M, 0.30 mL) was added slowly dropwise to a −78° C. solution of 4-(1,3-oxazol-5-yl)-7-[2-(trimethylsilyl)ethoxy]methyl-7H-pyrrolo[2,3-d]pyrimidine (140.0 mg, 0.44 mmol) in THF (10.0 mL). After 20 minutes, 1.0 M zinc dichloride in ether (0.53 mL) was added. The reaction mixture was then stirred for 60 min at 0° C. Following this, copper(I) iodide (84 mg, 0.44 mmol) was added, and this mixture was allowed to stir for 10 minutes. Cyclopentanecarbonyl chloride (108 μL, 0.885 mmol) was then added. The reaction was stirred at 0° C. for a further 1 hour, at which time it was allowed to warm to room temperature. The reaction was quenched by the addition of saturated NH$_4$Cl solution, and was extracted with ethyl acetate. The extracts were washed with water and brine, dried over sodium sulfate, filtered and concentrated in vacuo. Flash column chromatography (ethyl acetate/hexanes) afforded the product (97 mg, 53%).

$^1$H NMR (400 MHz, CDCl$_3$): δ 8.96 (s, 1H), 8.21 (s, 1H), 7.56 (d, 1H), 7.22 (d, 1H), 5.76 (s, 2H), 3.60 (t, 2H), 3.56 (t, 1H), 2.23-1.56 (m, 8H), 0.98 (t, 2H), 0.00 (s, 9H); MS(ES): 413(M+1).

Step 3. (3R)- and (3S)-3-Cyclopentyl-3-[5-(7-[2-(trimethylsilyl)ethoxy]methyl-7H-pyrrolo[2,3-d]pyrimidin-4-yl)-1,3-oxazol-2-yl]propanenitrile To a solution of 1.0 M potassium tert-butoxide in THF (0.355 mL) and THF (3 mL) at 0° C. was added diethyl cyanomethylphosphonate (66 mg, 0.37 mmol) dropwise. The cold bath was removed and the reaction was warmed to room temperature. After 30 minutes, a solution of cyclopentyl[5-(7-[2-(trimethylsilyl)ethoxy]methyl-7H-pyrrolo[2,3-d]pyrimidin-4-yl)-1,3-oxazol-2-yl]methanone (1.40E2 mg, 0.338 mmol) in THF (2.0 mL) was added dropwise. After 3 hours reaction time, the mixture was adsorbed onto silica gel, and flash column chromatography (ethyl acetate/hexanes) afforded the desired product as a mixture of olefin isomers (89 mg, 60%). MS(ES):436(M+1).

To a mixture of cupric acetate, monohydrate (4.0 mg, 0.020 mmol) and (oxydi-2,1-phenylene)bis(diphenylphosphine) (11 mg, 0.020 mmol) in toluene (0.40 mL, 0.0038 mol) was added PMHS (50 μL). The resulting mixture was stirred for 25 minutes at room temperature, followed by the addition of (2E)- and (2Z)-3-cyclopentyl-3-[5-(7-[2-(trimethylsilyl)ethoxy]methyl-7H-pyrrolo-[2,3-d]pyrimidin-4-yl)-1,3-oxazol-2-yl]acrylonitrile (88 mg, 0.20 mmol) in toluene (0.40 mL), and then tert-butyl alcohol (0.072 mL). After failure to react at room temperature over 16 hours, additional cupric acetate, monohydrate and (oxydi-2,1-phenylene)bis(diphenylphosphine) (0.10 mol equivalent each) were added and the reaction mixture was heated at 60° C. for 16 hours. The crude mixture was subjected to flash column chromatography (ethyl acetate/hexanes) to afford the desired product (21 mg, 23%).

$^1$H NMR (400 MHz, CDCl$_3$): δ 8.96 (s, 1H), 8.02 (s, 1H), 7.56 (d, 1H), 7.10 (d, 1H), 5.76 (s, 2H), 3.60 (t, 2H), 3.38-3.30 (m, 1H), 3.03 (dd, 1H), 2.95 (dd, 1H), 2.60-2.40 (m, 1H), 2.10-2.00 (m, 1H), 1.85-1.15 (m, 7H), 0.98 (t, 2H), 0.00 (s, 9H); MS(ES):438(M+1).

Step 4. (3R)- and (3S)-3-Cyclopentyl-3-[5-(7H-pyrrolo[2,3-d]pyrimidin-4-yl)-1,3-oxazol-2-yl]-propanentrile A solution of 3-cyclopentyl-3-[5-(7-[2-(trimethylsilyl)ethox]methyl-7H-pyrrolo[2,3-d]-pyrimidin-4-yl)-1,3-oxazol-2-yl]propanenitrile (20.0 mg, 0.0457 mmol) was stirred with TFA (0.1 mL) in DCM (0.2 mL) for 6 hours. The solvent was removed, and the resulting residue was stirred overnight with ethylenediamine (0.1 mL) in methanol (0.2 mL). The solvent was removed in vacuo. The desired product was obtained via preparative-HPLC/MS (C18 column eluting with a gradient of ACN/H$_2$O containing 0.15% NH$_4$OH) (5.3 mg, 38%).

$^1$H NMR (400 MHz, CDCl$_3$): δ 10.25 (br s, 1H), 8.90 (s, 1H), 8.00 (s, 1H), 7.50 (d, 1H), 7.06 (d, 1H), 3.36-3.28 (m, 1H), 2.98 (dd, 1H), 2.90 (dd, 1H), 2.51-2.38 (m, 1H), 2.08-1.96 (m, 1H), 1.80-1.51 (m, 5H), 1.44-1.30 (m, 2H); MS(ES):308(M+1).

The following compound of Table 5d was also prepared as a racemic mixture, according to the procedure of the above Example 87.

TABLE 5d

| Ex. No. | Structure | Name | R | MS (ES) (M + 1) |
|---|---|---|---|---|
| 88 | 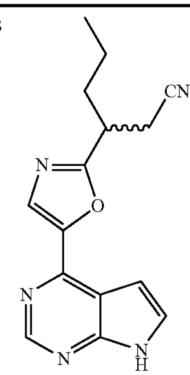 | 3-[5-(7H-pyrrolo[2,3-d]-pyrimidin-4-yl)-1,3-oxazol-2-yl]-hexanenitrile | Pr | 282 |

Example 90

5-(Methylthio)-3-[4-(7H-pyrrolo[2,3-d]pyrimidin-4-yl)-1H-pyrazol-1-yl]pentane-nitrile

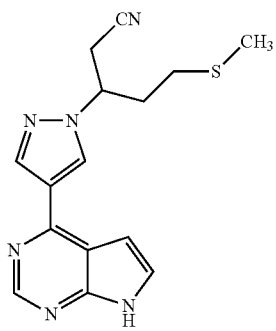 [SMILES: CSCCC(CC#N)n1cc(-c2ncnc3[nH]ccc23)cn1]

Step 1. (2E)-5-(Methylthio)pent-2-enenitrile

To a 0° C. mixture of [chloro(triphenyl)phosphoranyl] ACN (2.5 g, 0.0073 mol) in THF (10 mL, 0.1 mol) was added TEA (2.0 mL, 0.014 mol), and the resulting mixture was stirred for 30 min. The ice bath was removed for 30 min, then the mixture was re-cooled back to 0° C., A solution of 3-(methylthio)-propanol (0.68 mL, 0.0072 mol) in THF (1 mL, 0.02 mol) was added and the mixture was stirred overnight. Water was added and the mixture was filtered. The filtrate was washed with water ×3 and brine. The organic phase was dried and the solvent was removed by rotary evaporation to give 2.1 g of an off-white solid. The solid was triturated with MTBE and was filtered. The filtrate was washed with 1N HCl, water, sat. NaHCO$_3$ and brine. The organic phase was dried and was concentrated using a rotary evaporator to give 0.62 g orange oil (44% yield, trans:cis ~2:1).

$^1$H NMR for trans (400 MHz, CDCl$_3$): δ 6.68 (1H, m); 5.14 (1H, d); 2.6 (2H, m); 2.55 (2H, t); 2.1 (3H, s).

Step 2. 5-(Methylthio)-3-[4-(7-[2-(trimethylsilyl)ethoxy]methyl-7H-pyrrolo[2,3-d]pyrimidin-4-yl)-1H-pyrazol-1-yl]pentanenitrile A mixture of 4-(1H-pyrazol-4-yl)-7-[2-(trimethylsilyl)ethoxy]methyl-7H-pyrrolo[2,3-d]-pyrimidine (0.30 g, 0.00095 mol), (2E)-5-(methylthio)pent-2-enenitrile (0.28 g, 0.0016 mol) and DBU (45 µL, 0.00030 mol) in ACN (3 mL, 0.06 mol) was stirred at rt for 5 days. The solvent was removed by rotary evaporation to give an orange oil. The crude oil was chromatographed with 30-70 ethyl acetate/hex, to give 0.35 g of a colorless oil (83% yield).

$^1$H NMR (400 MHz, CDCl$_3$): δ 8.95 (1H, s); 8.41 (1H, s); 8.4 (1H, s); 7.48 (1H, d); 6.84 (1H, d); 5.75 (2H, s); 4.95 (1H, br); 3.6 (2H, t); 3.1 (2H, m); 2.58 (2H, m); 2.28 (2H, m); 2.1 (3H, s); 1.99 (2H, t); 0.0 (9H, s). MS (M+H): 443.

Step 3. 5-(Methylthio)-3-[4-(7H-pyrrolo[2,3-d]pyrimidin-4-yl)-1H-pyrazol-1-yl]pentanenitrile A solution of 5-(methylthio)-3-[4-(7-[2-(trimethylsilyl)ethoxy]methyl-7H-pyrrolo[2,3-d]-pyrimidin-4-yl)-1H-pyrazol-1-yl]pentanenitrile (0.35 g, 0.00079 mol) in THF (4 mL, 0.05 mol) and 3.0 M HCl (HCl) in water (4 mL) was heated to reflux overnight. The solvent was removed by rotary evaporation to give a pale orange oil. The oil was stirred in ethanol (3 mL, 0.05 mol) and 8.0 M ammonium hydroxide in water (1 mL) overnight. The reaction was concentrated and purified by prep LCMS (C18 column eluting with a gradient of ACN/H$_2$O containing 0.15% NH$_4$OH) to give 125 mg of a white foam. The white foam was triturated with MTBE (~1.5 mL). The resulting solid was filtered, washed and dried to give 80 mg of the product (32% yield).

$^1$H NMR (400 MHz, CDCl$_3$): δ 10.38 (1H, s); 8.88 (1H, s); 8.39 (1H, s); 8.38 (1H, s); 7.44 (1H, d); 6.8 (1H, d); 5.75 (2H, s); 4.9 (1H, br); 3.05 (2H, m); 2.5 (2H, m); 2.23 (2H, d); 2.1 (3H, s). MS (M+H): 313.

Example 91

5-(Methylsulfinyl)-3-[4-(7H-pyrrolo[2,3-d]pyrimidin-4-yl)-1H-pyrazol-1-yl]-pentanenitrile

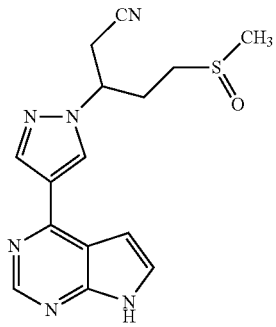 [SMILES: CS(=O)CCC(CC#N)n1cc(-c2ncnc3[nH]ccc23)cn1]

A solution of 5-(methylthio)-3-[4-(7H-pyrrolo[2,3-d]pyrimidin-4-yl)-1H-pyrazol-1-yl]-pentanenitrile (0.065 g, 0.00021 mol) and hydrogen peroxide (0.022 mL, 0.00023 mol) in ACN (1 mL, 0.02 mol) was stirred overnight. The reaction was concentrated and purified by HPLC to give 21 mg of a solid. The solid was triturated with MTBE (1 mL)/DCM (10 drops). The solid was filtered and washed to give 13 mg of a white solid (20% yield) which was dried rt to 50° C. for 2 h.

$^1$H NMR (400 MHz, CDCl$_3$): δ 9.95 (1H, s); 8.85 (1H, s); 8.4 (2H, m); 7.4 (1H, d); 6.8 (1H, s); 4.9 (1H, br); 3.15 (2H, m); 3.0 (2H, m); 2.8-2.5 (2H, m); 2.6 (3H, s). MS (M+H): 329.

Example 92

5-(Methylsulfonyl)-3-[4-(7H-pyrrolo[2,3-d]pyrimidin-4-yl)-1H-pyrazol-1-yl]-pentanenitrile

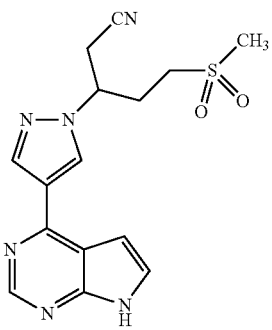 [SMILES: CS(=O)(=O)CCC(CC#N)n1cc(-c2ncnc3[nH]ccc23)cn1]

A solution of 5-(methylthio)-3-[4-(7H-pyrrolo[2,3-d]pyrimidin-4-yl)-1H-pyrazol-1-yl]-pentanenitrile (0.040 g, 0.00013 mol) and hydrogen peroxide (0.5 mL, 0.005 mol) in ACN (1 mL, 0.02 mol) was refluxed overnight. The reaction was purified by HPLC to give 16 mg of a white glass/solid which was triturated with EtOH (~0.8 mL) to give 13 mg of a white solid (30% yield).

$^1$H NMR (400 MHz, CDCl$_3$): δ 8.75 (1H, s); 8.48 (1H, d); 8.4 (1H, d); 7.43 (1H, d); 6.8 (1H, s); 5.0 (1H, br); 3.4 (2H, m); 3.2-3.0 (2H, m); 2.8-2.5 (2H, m); 2.95 (3H, s). MS (M+H): 345.

Example 93

4,4,4-Trifluoro-3-[4-(7H-pyrrolo[2,3-d]pyrimidin-4-yl)-pyrazol-1-yl]-butyronitrile

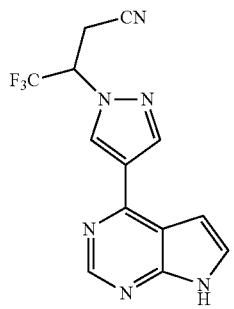 [SMILES: N#CCC(n1cc(-c2ncnc3[nH]ccc23)cn1)C(F)(F)F]

Step 1. 4,4,4-Trifluoro-3-[4-(7-[2-(trimethylsilyl)ethoxy]methyl-7H-pyrrolo[2,3-d]pyrimidin-4-yl)-1H-pyrazol-1-yl]butanenitrile A mixture of 4-(1H-pyrazol-4-yl)-7-[2-(trimethylsilyl)ethoxy]methyl-7H-pyrrolo[2,3-d]-pyrimidine (6.9 g, 0.022 mol), (2E)-4,4,4-trifluorobut-2-enenitrile (2.8 g, 0.023 mol) and DBU (0.18 mL, 0.0012 mol) in ACN (70 mL, 1 mol) was stirred for 20 min. The reaction was filtered and filtrate was removed by rotary evaporation to give an orange oil. The crude oil was chromatographed with 20-50% ethyl acetate/hex to give to give 9.1 g of a solid/oil (96% yield). A single enantiomer (peak 2) was separated by chiral column chromatography (OD-H column, 30% EtOH/hex) as a greenish solid/glass (3.3 g, 32% yield).

$^1$H NMR (400 MHz, CDCl$_3$): δ 8.93 (1H, s); 8.46 (1H, s); 8.45 (1H, s); 7.5 (1H, d); 6.85 (1H, d); 5.75 (2H, s); 5.2 (1H, m); 3.6 (2H, t); 3.7-3.3 (2H, m); 1.99 (2H, t); 0.0 (9H, s). MS (M+H): 438.

Step 2. 4,4,4-Trifluoro-3-[4-(7H-pyrrolo[2,3-d]pyrimidin-4-yl)-pyrazol-1-yl]-butyronitrile A solution of 4,4,4-trifluoro-3-[4-(7-[2-(trimethylsilyl)ethoxy]methyl-7H-pyrrolo[2,3-d]-pyrimidin-4-yl)-1H-pyrazol-1-yl]butanenitrile (3.1 g, 0.0071 mol) from Step 1 in THF (35 mL, 0.43 mol) and 3.0 M HCl in water (35 mL) was heated to reflux overnight. The solvent was removed by rotary evaporation to give a greenish orange oil/glass. The oil was stirred with ethyl acetate and sat. NaHCO$_3$ (50 mL). The aqueous phase was extracted with ethyl acetate. The organic layers were washed with brine and reduced by rotary evaporation to give an oil/glass residue. The residue was stirred in ethanol (20 mL, 0.3 mol) and 8.0 M ammonium hydroxide in water (10 mL) over a weekend. The solvent was removed by rotary evaporation to give a pale orange foam/solid. The crude was chromatographed with 0-7% MeOH/DCM, 0-0.7% NH$_4$OH to give 3 g of a pale orange paste/solid. The solid was recrystallized from EtOH to give 1.6 g of an off-white crystals (74% yield).

$^1$H NMR (400 MHz, DMSO): δ 12.2 (1H, s); 8.95 (1H, s); 8.7 (1H, s); 8.5 (1H, s); 7.63 (1H, d); 6.96 (1H, d); 6.01 (1H, m); 3.7 (2H, m). MS (M+H): 306.

The following compounds of Table 5e were prepared as indicated in the column labeled "Prep. Ex. No."

TABLE 5e

| Ex. No. | Structure | Name | MS (M + H) | Prep. Ex. No. |
|---|---|---|---|---|
| 94 | 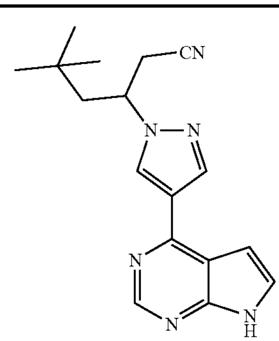 | 5,5-Dimethyl-3-[4-(7H-pyrrolo[2,3-d]pyrimidin-4-yl)-pyrazol-1-yl]-hexanenitrile | 308 | 61 modification G |

TABLE 5e-continued

| Ex. No. | Structure | Name | MS (M + H) | Prep. Ex. No. |
|---|---|---|---|---|
| 95 | 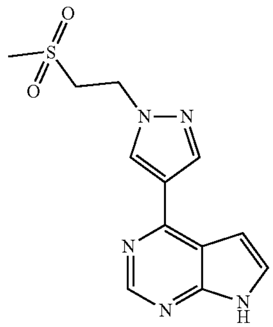 [SMILES: CS(=O)(=O)CCn1cc(-c2ncnc3[nH]ccc23)cn1] | 4-[1-(2-Methanesulfonyl-ethyl)-1H-pyrazol-4-yl]-7H-pyrrolo[2,3-d]pyrimidine | 291 | 61 modification G |
| 96 | 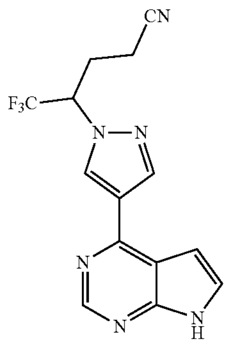 [SMILES: N#CCCC(n1cc(-c2ncnc3[nH]ccc23)cn1)C(F)(F)F] | 5,5,5-Trifluoro-4-[4-(7H-pyrrolo[2,3-d]pyrimidin-4-yl)-pyrazol-1-yl]-pentanenitrile | 320 | 59 modification G |

Example 97

3-(2-Cyano-1-[4-(7H-pyrrolo[2,3-d]pyrimidin-4-yl)-1H-pyrazol-1-yl]ethyl)-cyclo-pentane-carbonitrile trifluoroacetate

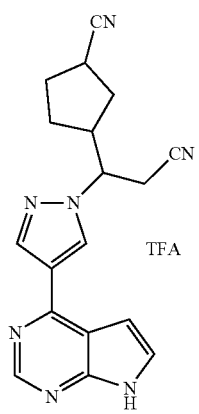 [SMILES: N#CCC(C1CCC(C#N)C1)n1cc(-c2ncnc3[nH]ccc23)cn1]

Step 1:
3-(Dimethoxymethyl)cyclopentanecarbaldehyde

Into a 3-neck round bottom flask 2-norbornene (5.500 g, 0.05841 mol) was dissolved in DCM (198.0 mL,) and methanol (38.5 mL) and was cooled at −78° C. Ozone was passed through the reaction until it turned blue and was stirred at −78° C. for 30 minutes. Then nitrogen was passed through for 20 minutes and p-toluenesulfonic acid (0.95 g, 0.0055 mol) was added The reaction was allowed to warm at 20° C. and was stirred for 90 minutes. Into the reaction was added sodium bicarbonate (1.67 g, 0.0199 mol) and the resulting mixture was stirred at 20° C. for 30 minutes and dimethyl sulfide (9.4 mL, 0.13 mol) was added. The reaction was stirred for 16 hours and was reduced by rotary evaporation to ~50 mL. The reaction was extracted with DCM and the organic extracts were washed with water and brine, dried (MgSO$_4$), and stripped in vacuo. The reaction was distilled at 135° C. (bath temperature) at high pump vacuum to give the product (7.5 g) as a ~2:1 mixture of diastereomers. $^1$H NMR (300 MHz, CDCl$_3$): 9.64 & 9.62 (d, 1H), 4.15 & 4.12 (s, 1H), 3.35 & 3.34 (s, 6H), 2.77 m, 1H), 2.34 (m, 1H), 1.35-2.00 (m, 6H).

Step 2. (2E,Z)-3-[3-(Dimethoxymethyl)cyclopentyl]acrylonitrile

Into a flask containing a 0° C. solution of t-BuOK in THF (1.0 M, 6.10 mL) was added a solution of diethyl cyanomethylphosphonate (1.1 g, 6.4 mmol) in THF (8 mL). The cooling bath was removed and the reaction was warmed to ambient temperature, then a solution of 3-(dimethoxymethyl)cyclopentanecarbaldehyde (1.00 g, 5.81 mmol) in THF (2 mL) was added dropwise. Shortly after completion of the addition orange gel-like particulates began to form, after approximately 1 hour the reaction was gelatinous. The reaction was held with stirring at ambient temperature for 16 hours at which time tlc indicated complete reaction. The reaction was partitioned between water and EtOAc and the aqueous phase was washed with additional EtOAc. The combined organic phase was washed with water, then sat'd NaCl, and then was dried over MgSO$_4$ and reduced in vacuo, and the resulting residue was purified by column chromatography with 6:1 hexanes:EtOAc+1% TEA to obtain the product as a 1:1 mixture of E/Z isomers (760 mg, 61%). $^1$H NMR (400 MHz, CDCl$_3$): δ vinylic protons at 6.69 (m, 0.5H), 6.37 (m, 0.5H), 5.32 (m, 0.5H), 5.23 (m, 0.5H), acetal methine proton at 4.14 (m, 1H), methyl protons at 3.34 (s, 6H).

Step 3. 3-[3-(Dimethoxymethyl)cyclopentyl]-3-[4-(7-[2-(trimethylsilyl)ethoxy]methyl-7H-pyrrolo[2,3-d]pyrimidin-4-yl)-1H-pyrazol-1-yl]propanenitrile To a solution of 4-(1H-pyrazol-4-yl)-7-[2-(trimethylsilyl)ethoxy]methyl-7H-pyrrolo[2,3-d]pyrimidine (230 mg, 0.74 mmol) in ACN (5 mL) was added (2E,Z)-3-[3-(dimethoxymethyl)cyclo-pentyl]acrylonitrile (289 mg, 1.48 mmol), followed by DBU (300 µL, 2.0 mmol). The mixture was stirred at ambient temperature for 16 hours, at which point LCMS and TLC indicated complete reaction. The reaction was reduced to dryness in vacuo, and the residue was purified by column chromatography to obtain the product as a mixture of diastereomers (293 mg, 77%). $^1$H NMR (400 MHz, CDCl$_3$): δ 8.85 (s, 1H), 8.31 (s, 2H), 7.40 (d, 1H), 6.80 (d, 1H), 5.68 (s, 2H), 4.28 (m, 1H), 4.11 (m, 1H), 3.54 (t, 2H), 3.36 (s, 1.5H), 3.34 (s, 1.5H), 3.30 (s, 1.5H), 3.26 (s, 1.5H), 3.12 (m, 1H), 2.94 (m, 1H), 2.65 (m, 1H), 2.34 (m, 1H), 2.0-1.0 (m, 6H), 0.92 (t, 2H), -0.56 (s, 9H). MS (EI) m/z=511.3 (M+H).

Step 4. 3-(3-Formylcyclopentyl)-3-[4-(7-[2-(trimethylsilyl)ethoxy]methyl-7H-pyrrolo[2,3-d]-pyrimidin-4-yl)-1H-pyrazol-1-yl]propanenitrile To a solution of 3-[3-(dimethoxymethyl)cyclopentyl]-3-[4-(7-[2-(trimethylsilyl)ethoxy]-methyl-7H-pyrrolo[2,3-d]pyrimidin-4-yl)-1H-pyrazol-1-yl]propanenitrile (293 mg, 0.574 mmol) in THF (4.5 mL) was added aqueous HCl (1.0 M, 1.5 mL). The reaction was held at ambient temperature for 2.5 hours at which point TLC and LCMS indicated complete deprotection to the corresponding aldehyde. The reaction was partitioned between water and EtOAc and the aqueous phase was extracted with additional EtOAc. The combined organic phase was washed with water, then sat'd NaHCO$_3$, then sat'd NaCl, and then was dried over MgSO$_4$ and filtered and stripped to dryness to leave the crude product as a mixture of diastereomers. $^1$H NMR (400 MHz, CDCl$_3$): δ 9.69 (d, 0.5H), 9.64 (d, 0.5H), 8.85 (s, 0.5H), 8.84 (s, 0.5H), 8.35 (s, 0.5H), 8.34 (s, 0.5H), 8.32 (s, 0.5H), 8.30 (s, 0.5H), 7.41 (d, 0.5H), 7.40 (d, 0.5H), 6.80 (d, 0.5H), 6.79 (d, 0.5H), 5.68 (s, 1H), 5.67 (s, 1H), 4.32 (m, 1H), 3.54 (m, 2H), 3.14 (m, 1H), 2.96 (m, 2H), 2.76 (m, 1H), 2.1-1.1 (m, 6H), 0.92 (m, 2H), -0.058 (s, 9H). MS (EI) m/z=465.1 (M+H).

Step 5. 3-3-[(E,Z)-(Hydroxyimino)methyl]cyclopentyl-3-[4-(7-[2-(trimethylsilyl)ethoxy]methyl-7H-pyrrolo[2,3-d]pyrimidin-4-yl)-1H-pyrazol-1-yl]propanenitrile To a solution of 3-(3-formylcyclopentyl)-3-[4-(7-[2-(trimethylsilyl)ethoxy]methyl-7H-pyrrolo[2,3-d]pyrimidin-4-yl)-1H-pyrazol-1-yl]propanenitrile (336 mg, 0.000723 mol) in CH$_3$OH (5.0 mL, 0.12 mol) was added hydroxylamine hydrochloride (60 mg, 0.00087 mol) and KHCO$_3$ (110 mg, 0.0011 mol) and the reaction was held at ambient temperature for 16 hours, at which point LCMS indicated complete reaction. The reaction was reduced to dryness in vacuo and the residue was partitioned between water and EtOAc, and the aqueous phase was extracted with additional EtOAc. The combined organic phase was washed with water, then sat'd NaCl, then was dried over MgSO$_4$ and concentrated to leave the crude product, which was carried forward to the subsequent reaction without purification. NMR indicated disappearance of aldehydic protons. MS (EI) m/z=480.2 (M+H).

Step 6. 3-(2-Cyano-1-[4-(7-[2-(trimethylsilyl)ethoxy]methyl-7H-pyrrolo[2,3-d]pyrimidin-4-yl)-1H-pyrazol-1-yl]ethyl)cyclopentanecarbonitrile To a solution of 3-3-[(E,Z)-(hydroxyimino)methyl]cyclopentyl-3-[4-(7-[2-(trimethylsilyl)-ethoxy]-methyl-7H-pyrrolo[2,3-d]pyrimidin-4-yl)-1H-pyrazol-1-yl]propanenitrile (324 mg, 0.67 mmol) in pyridine (1.2 mL), was added methanesulfonyl chloride (210 µL, 2.7 mmol) dropwise. The reaction was heated to 60° C. for 2.5 hours, at which point LCMS indicated complete reaction. The reaction was partitioned between water and EtOAc, and the aqueous phase was extracted with additional EtOAc. The combined organic phase was washed with water, then 0.1N HCl, then sat'd NaCl, and then was dried over MgSO$_4$. The crude product was purified by column chromatography to obtain the product as a mixture of diastereomers (164 mg, 52%). The diastereomers were then separated by chiral HPLC to provide four distinct diastereomers, which were taken directly on to the deprotection step. MS (EI) m/z=462.1 (M+H).

Step 7. 3-(2-Cyano-1-[4-(7H-pyrrolo[2,3-d]pyrimidin-4-yl)-1H-pyrazol-1-yl]ethyl)-cyclopentane-carbonitrile trifluoroacetate The four diastereomers were then separately deprotected in this representative manner To 3-2-cyano-1-[4-(7-[2-(trimethylsilyl)ethoxy]methyl-7H-pyrrolo[2,3-d]pyrimidin-4-yl)-1H-pyrazol-1-yl]ethylcyclopentanecarbonitrile (35 mg, 0.076 mmol) dissolved in CH$_2$Cl$_2$ (2.0 mL) was added TFA (1.0 mL) and the reaction was stirred for 2 hours at ambient temperature at which point LCMS indicated complete cleavage to the N-hydroxymethyl intermediate. The solvent was removed and to the residue was added methanol (1.0 mL) followed by ethylenediamine (40 µL, 0.61 mmol), the reaction was stirred for 16 hours at which point LCMS indicated complete reaction. The solvent was removed and the residue was purified by preparative LCMS to provide the product as a TFA salt. NOE experiments confirm that all isomers have cis geometry on cyclopentyl ring. Isomers 1 and 2:

$^1$H NMR (400 MHz, CD$_3$OD): δ 8.95 (s, 1H), 8.89 (s, 1H), 8.54 (s, 1H), 7.86 (d, 1H), 7.29 (d, 1H), 4.72 (m, 1H), 3.27 (m, 1H), 3.19 (m, 1H), 2.95 (m, 1H), 2.72 (m, 1H), 2.2-1.9 (m, 4H), 1.67 (m, 2H). Isomers 3 and 4: $^1$H NMR (400 MHz, CD$_3$OD): δ 8.95 (s, 1H), 8.88 (s, 1H), 8.52 (s, 1H), 7.85 (d, 1H), 7.28 (d, 1H), 4.72 (m, 1H), 3.27 (m, 1H), 3.19 (m, 1H), 3.05 (m, 1H), 2.71 (m, 1H), 2.44 (m, 1H), 2.05 (m, 1H), 1.92 (m, 1H), 1.72 (m, 1H), 1.58 (m, 2H).MS (EI) m/z=332.2 (M+H).

Example 98

3-[3-(Hydroxymethyl)cyclopentyl]-3-[4-(7H-pyrrolo[2,3-d]pyrimidin-4-yl)-1H-pyrazol-1-yl]propanenitrile

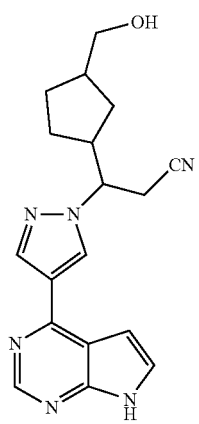 [SMILES: N#CCC(C1CCC(CO)C1)n1cc(-c2ncnc3[nH]ccc23)cn1]

Step 1: 3-[3-(Hydroxymethyl)cyclopentyl]-3-[4-(7-[2-(trimethylsily)ethoxy]methyl-7H-pyrrolo[2,3-d]pyrimidin-4-yl)-1H-pyrazol-1-yl]propanenitrile A solution of 3-(3-formylcyclopentyl)-3-[4-(7-[2-(trimethylsilyl)ethoxy]methyl-7H-pyrrolo-[2,3-d]pyrimidin-4-yl)-1H-pyrazol-1-yl]propanenitrile (50.0 mg, 0.108 mmol) in methanol (280 μL) was cooled to 0° C., then sodium tetrahydroborate (14 mg, 0.37 mmol) was added. The reaction was held at 0° C. for 10 minutes, at which point LCMS and TLC indicated complete reaction. The reaction was quenched by cautious addition of 1N HCl (3 drops) and methanol (1 mL), followed by addition of aqueous NaHCO$_3$ and CHCl$_3$. The phases were separated and the aqueous phase was washed with additional CHCl$_3$. The combined organic phase was washed with sat'd NaCl, dried over MgSO$_4$ and reduced to dryness. The residue was purified by column chromatography to obtain the product as a mixture of diastereomers (37.4 mg, 74%). $^1$H NMR (400 MHz, CDCl$_3$): δ □8.84 (s, 1H), 8.31 (s, 2H), 7.40 (d, 1H), 6.80 (d, 1H), 5.67 (s, 2H), 4.29 (m, 1H), 3.53 (m, 1H), 3.53 (t, 2H), 3.14 (m, 1H), 2.95 (m, 1H), 2.68 (m, 1H), 2.2-1.0 (m, 9H), 0.92 (t, 2H), −0.059 (s, 9H). MS (EI) m/z=467.2 (M+H).

Step 2. 3-[3-(Hydroxymethyl)cyclopentyl]-3-[4-(7H-pyrrolo[2,3-d]pyrimidin-4-yl)-1H-pyrazol-1-yl]propanenitrile To 3-[3-(hydroxymethyl)cyclopentyl]-3-[4-(7-[2-(trimethylsilyl)ethoxy]methyl-7H-pyrrolo-[2,3-d]pyrimidin-4-yl)-1H-pyrazol-1-ylipropanenitrile (60.4 mg, 0.129 mmol) dissolved in CH$_2$Cl$_2$ (2.0 mL) was added TFA (1.0 mL) and the reaction was stirred for 1 hour at which point LCMS indicated complete cleavage to the N-hydroxymethyl intermediate (m/z=367). The trifluoroacetate ester of the hydroxymethyl of the cyclopentyl ring was also observed (m/z=463). The solvent was removed and to the residue was added methanol (1.0 mL) followed by ethylenediamine (80 μL, 1.19 mmol). The resulting mixture was stirred for 16 hours at which point LCMS indicated complete reaction to the desired product. The solvent was removed and the residue was purified by chiral HPLC to provide four distinct diastereomers (20.2 mg total of four isomers, 46%). NOE experiments suggest that all isomers have cis geometry on the cyclopentyl ring. Isomers 1 and 2: $^1$H NMR (400 MHz, CD$_3$OD): δ 8.65 (s, 1H), 8.62 (s, 1H), 8.38 (s, 1H), 7.50 (d, 1H), 6.95 (d, 1H), 4.51 (m, 1H), 3.40 (m, 2H), 3.22 (m, 1H), 3.11 (m, 1H), 2.61 (m, 1H), 2.10 (m, 1H), 1.94 (m, 1H), 1.82 (m, 1H), 1.6-1.4 (m, 3H), 1.03 (m, 1H). Isomers 3 and 4: $^1$H NMR (400 MHz, CD$_3$OD): δ 8.66 (s, 1H), 8.62 (s, 1H), 8.37 (s, 1H), 7.50 (d, 1H), 6.95 (d, 1H), 4.51 (m, 1H), 3.46 (m, 2H), 3.21 (m, 1H), 3.11 (m, 1H), 2.61 (m, 1H), 2.22 (m, 1H), 2.09 (m, 1H), 1.71 (m, 1H), 1.55-1.25 (m, 3H), 1.04 (m, 1H). MS (EI) m/z=337.1 (M+H).

Example 100

1-(1H-Pyrrolo[2,3-b]pyridin-4-yl)-1H-indazole (100a) and 2-(1H-pyrrolo[2,3-b]-pyridin-4-yl)-2H-indazole (100b)

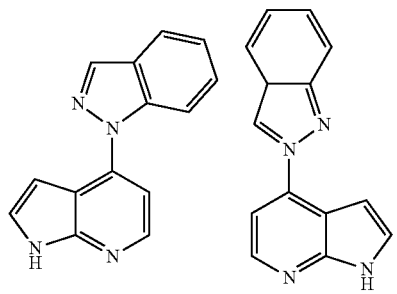

4-Bromo-1H-pyrrolo[2,3-b]pyridine (0.078 g, 0.00040 mol) and 1H-indazole (0.283 g, 0.00240 mol) was heated neat in a sealed tube at 200° C. (an oil bath) overnight with stirring. The reaction was allowed to cool to rt and the crude product was purified by prep LC-MS on a C-18 column eluting with a water/ACN gradient containing 0.2% TFA to give the title compound (0.015 gm, 15%), as an amorphous white solid, LC/MS (M+H)$^+$ 235, $^1$H NMR (DMSO-d$_6$) δ 12.01 (bs, 1H), 9.17(s, 1H), 8.31(s, 1H), 7.73(d, 1H, J=9.0), 7.67(m, 2H), 7.58(m, 1H), 7.28(m, 1H), 7.07(m, 2H).

Example 106

3-[3-(1H-Pyrrolo[2,3-b]pyridin-4-yl)-1,2,4-oxadiazol-5-yl]benzonitrile

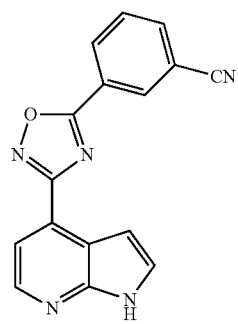 [SMILES: N#Cc1cccc(-c2nc(-c3ccnc4[nH]ccc34)no2)c1]

Step 1. 1-1-[2-Ttrimethylsilyl)ethoxy]methyl-1H-pyrrolo[2,3-b]pyridine-4-carbonitrile

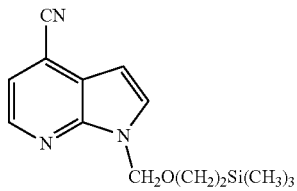

4-Bromo-1-(trimethylsilyl)ethoxy]methyl-1H-pyrrolo[2,3-b]pyridine (0.300 g, 0.000917 mol) was dissolved in DMF (6.5 mL, 0.084 mol) and then zinc cyanide (0.30 g, 0.0026 mol) was added. The solution was degassed with nitrogen and then bis(tri-t-butylphosphine)palladium (0.1 g, 0.0002 mol) was added. The reaction was sealed and heated in the microwave to 100° C. for 30 minutes. The reaction was allowed to cool to rt, taken up in ethyl acetate and washed with water saturated sodium carbonate, brine, dried over magnesium sulfate and concentrated to give an oil. The crude product was purified by flash column chromatography (FCC) on silica gel, eluting with a hexane: ethyl acetate gradient to give the product (0.25 gm) as a colorless oil. LC/M S (M+H)$^+$ 274, $^1$H NMR (CDCl$_3$) δ 8.22 (d, 1H), 7.53 (d, 1H), 7.40 (d, 1H), 6.73(d, 1H), 5.65(s, 2H), 3.50(m, 2H), 0.90(m, 2H), 0.0 (s, 9H).

Step 2. N-Hydroxy-1-[2-(trimethylsilyl)ethoxy]methyl-1H-pyrrolo[2,3-klpyridine-4-carboximidamide

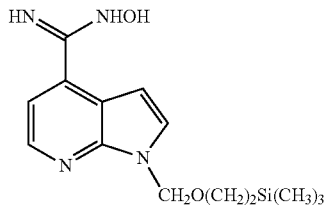

1-[2-(Trimethylsilyl)ethoxy]methyl-1H-pyrrolo[2,3-b]pyridine-4-carbonitrile (0.05 g, 0.0002 mol) was dissolved in ethanol (2.0 mL, 0.034 mol), and then hydroxylamine hydrochloride (0.023 g, 0.00033 mol) and potassium carbonate (0.10 g, 0.00073 mol) were added. The reaction was heated to reflux for 5 h, and the reaction was then allowed to cool to rt and filtered to remove the solids. The filtrate was concentrated to give the product 0.06 g as yellow oily residue, LC/MS (M+H)$^+$ 307.

Step 3. 3-[3-(1-[2-(Trimethylsilyl)ethoxy]methyl-1H-pyrrolo[2,3-b]pyridin-4-yl)-1,2,4-oxadiazol-5-yl]benzonitrile

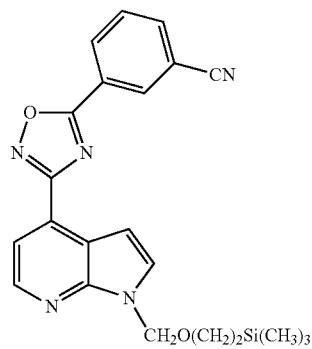

The crude product N-hydroxy-1-[2-(trimethylsilyl)ethoxy]methyl-1H-pyrrolo[2,3-b]pyridine-4-carboximidamide (0.06 gm, 0.0002 mol) was dissolved in pyridine (1.0 mL, 0.012 mol) and then 3-cyanobenzoyl chloride (0.040 g, 0.00024 mol) was added at rt. This mixture was stirred for 1 h and heated to 80° C. in an oil bath. After heating for 18 h the reaction was allowed to cool to rt and then diluted with ACN and concentrated in vacuo to give 3-[3-(1-[2-(trimethylsilyl)ethoxy]methyl-1H-pyrrolo[2,3-b]pyridin-4-yl)-1,2,4-oxadiazol-5-yl]benzonitrile 0.08 gm as an off white residue, LC/M S (M+H)$^+$ 418.

Step 4. 3-[3-(1H-Pyrrolo[2,3-b]pyridin-4-yl)-1,2,4-oxadiazol-5-yl]benzonitrile The crude 3-[3-(1-[2-(trimethylsilyl)ethoxy]methyl-1H-pyrrolo[2,3-b]pyridin-4-yl)-1,2,4-oxa-diazol-5-yl]benzonitrile (0.08 g, 0.0002 mol) was dissolved in TFA (3.0 mL, 0.039 mol) under nitrogen and then heated to 60° C. After heating for 2 h the reaction was allowed to cool to rt and concentrated in vacuo. The resulting residue was taken up in methanol and concentrated to remove as much of the TFA as possible. The residue was taken up in methanol (2.0 mL, 0.049 mol) and ammonium hydroxide (1 mL). This mixture was stirred at rt for 2 h and the reaction was then complete. The reaction was concentrated in vacuo to give the crude product which was purified by prep HPLC on a C-18 column eluting with a ACN:water gradient with 0.2% TFA to give the title compound (0.025 gm, 43%) (M+H)$^+$ 288. $^1$H NMR (DMSO-d$_6$) δ 12.1 (bs, 1H), 8.65(s, 1H), 8.48(d, 1H,J=6.4), 8.39(d, 1H, J=4.8), 8.16(d, 1H, J=6.4), 7.84(t, 1H, J=6.4), 7.75(d, 1H, J=4.8), 7.68(m, 1H), 6.99 (m, 1H).

Example 107

4-(1-Benzothien-2-yl)-1H-pyrrolo[2,3-b]pyridine

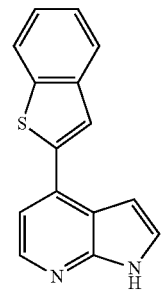 [SMILES: c1ccc2sc(-c3ccnc4[nH]ccc34)cc2c1]

Step 1. 4-(1-Benzothien-2-yl)-1-[2-(trimethylsilyl)ethoxy]methyl-1H-pyrrolo[2,3-b]pyridine

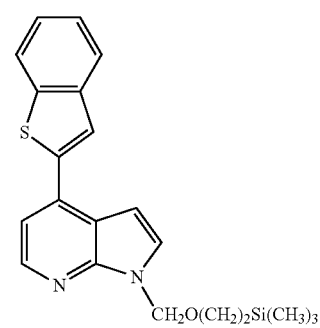

1-Benzothien-2-ylboronic acid (0.05 g, 0.0003 mol) and 4-bromo-1-[2-(trimethylsilyl)-ethoxy]methyl-1H-pyrrolo[2,3-b]pyridine (0.10 g, 0.00031 mol) were combined in toluene (3.0 mL, 0.028 mol) and ethanol (1.0 mL, 0.017 mol). Potassium carbonate (0.085 g, 0.00062 mol) dissolved in water (1.0 mL) then was added and the reaction was degassed with nitrogen. Then tetrakis(triphenylphosphine)palladium(0) (0.05 g, 0.00004 mol) was added and the reaction was heated to 120° C. in a sealed tube in the microwave for 60 minutes. This was allowed to cool to rt, taken up in ethyl acetate and washed with water 2×, brine, dried over magnesium sulfate and concentrated to give 4-(1-benzothien-2-yl)-1-[2-(trimethylsilyl)ethoxy]methyl-1H-pyrrolo[2,3-b]-pyridine (0.10 gm) as an oil, LC/MS (M+H)+ 381.

Step 2. 4-(1-Benzothien-2-yl)-1H-pyrrolo[2,3-b]pyridine

Using a procedure analogous to Example 106, Step 4, but using 4-(1-benzothien-2-yl)-1-[2-(trimethylsilyl)ethoxy]methyl-1H-pyrrolo[2,3-b]pyridine, the title compound was prepared as a yellow powder (0.015 g, 18%), LC/MS (M+H)+: 251, $^1$H NMR (DMSO-$d_6$) δ 11.95 (bs, 1H), 8.28(d, 1H, J=5.4), 8.15(s, 1H), 8.03(m, 1H), 7.96(m, 1H), 7.64(m, 1H), 7.42(m, 2H), 7.39(d, 1H, J=5.4), 6.95(m, 1H).

Example 120

4-Fluoro-2-[1-(1H-pyrrolo[2,3-b]pyridin-4-yl)-1H-pyrazol-3-yl]phenol

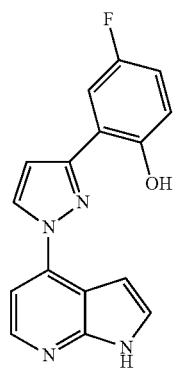 [SMILES: Oc1ccc(F)cc1-c1ccn(-c2ccnc3[nH]ccc23)n1]

4-Bromo-1H-pyrrolo[2,3-b]pyridine (0.050 g, 0.00025 mol) and 4-fluoro-2-(1H-pyrazol-3-yl)phenol (0.150 g, 0.000842 mol) were heated neat to 160° C. for 5 h. The reaction was allowed to cool to rt and the residue was purified by prep LC-MS on a C-18 column eluting with a water/ACN gradient containing 0.2% TFA to give the title compound, (0.052 g, 20%, as an amorphous white solid, LC/MS (M+H)+ 295, $^1$H NMR (DMSO-$d_6$) δ 12.01 (bs, 1H), 10.25(bs, 1H), 8.81(s,1H), 8.35(d, 1H, J=5.5), 7.77(d, 1H, J=9.5), 7.64(m, 1H), 7.59(d, 1H, J=5.5), 7.32(s, 1H), 7.09 (m, 1H), 7.05(m, 1H), 7.01(m, 1H).

Example 127

4-3-[3-(Trifluoromethyl)phenyl]-1H-pyrazol-1-yl-1H-pyrrolo[2,3-b]pyridine

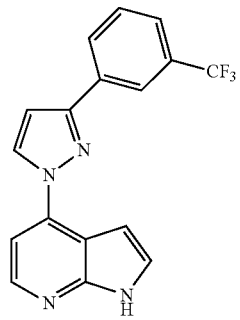 [SMILES: FC(F)(F)c1cccc(-c2ccn(-c3ccnc4[nH]ccc34)n2)c1]

Step 1. (2E)-3-(Dimethylamino)-1-[3-(trifluoromethyl)phenyl]prop-2-en-1-one

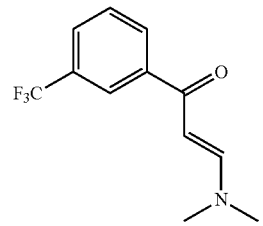 [SMILES: CN(C)/C=C/C(=O)c1cccc(C(F)(F)F)c1]

1-[5-(Trifluoromethyl)phenyl]ethanone (0.20 mL, 0.0013 mol) and 1,1-dimethoxy-N,N-dimethylmethanamine (0.17 mL, 0.0013 mol) were combined in a sealed tube and heated in a microwave to 120° C. for 15 minutes, the reaction was allowed to cool and was concentrated to remove the residual DMF acetal, to give (2E)-3-(dimethylamino)-1-[3-(trifluoromethyl)phenyl]prop-2-en-1-one, 0.32 gm, as a red oil, LC/MS (M+H)+: 244.

Step 2: 3-[3-(Trifluoromethyl)phenyl]-1H-pyrazole

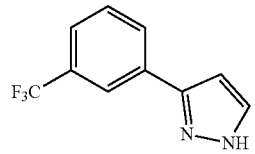

The (2E)-3-(dimethylamino)-1-[3-(trifluoromethyl)phenyl]prop-2-en-1-one (0.32 g, 0.0013 mol) was dissolved in ethanol (10.0 mL, 0.171 mol) and hydrazine (0.24 mL, 0.0078 mol) under nitrogen and heated to reflux. The reaction was monitored by HPLC and was complete almost immediately. The mixture was allowed to cool to rt and concentrated to give the crude product as an oil. The product was purified by FCC on silica gel eluting with a hexane:ethyl acetate gradient to give 3-[3-(trifluoromethyl)phenyl]-1H-pyrazole as an oil (0.25 g, 89%), LC/MS (M+H)+: 213, $^1$H NMR (CDCl$_3$) δ 8.06 (s, 1H), 7.99(d, 1H, J=7.5), 7.66(d, 1H, J=2.4), 7.57(m, 1H), 7.55(d, 1H, J=7.5), 6.69(d, 1H, J=2.4).

Step 3. 4-3-[3-(Trifluoromethyl)phenyl]-1H-pyrazol-1-yl-1H-pyrrolo[2,3-b]pyridine 4-Bromo-1H-pyrrolo[2,3-b]pyridine (0.028 g, 0.00014 mol) and 3-[3-(trifluoromethyl)-phenyl]-1H-pyrazole (0.03 g, 0.0001 mol) were combined neat. The reaction was heated in a sealed tube in an oil bath to 175° C. for 20 to produce a crude product that was a black viscous gum. The crude product was purified by HPLC on a C-18 column eluting with a water:ACN gradient with 0.2% TFA to give the title product (0.025 gm, 50%) as a white amorphous solid, LC/MS (M+H)$^+$: 329, $^1$H NMR (DMSO-d$_6$) δ 11.95 (bs, 1H), 8.83(d, 1H, J=2.7), 8.31(m, 3H), 7.75(m, 2H), 7.60(m, 2H), 7.35(d, 1H, J=2.7), 7.14(m, 1H).

Example 128

3-[1-(1H-Pyrrolo[2,3-b]pyridin-4-yl)-1H-pyrazol-3-yl]benzonitrile

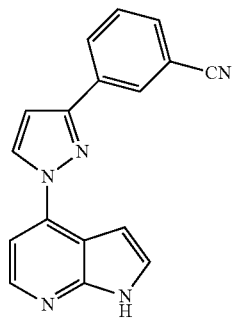 [SMILES: N#Cc1cccc(-c2ccn(-c3ccnc4[nH]ccc34)n2)c1]

Step 1. 3-[(2E)-3-(Dimethylamino)prop-2-enoyl]benzonitrile

3-Acetylbenzonitrile (0.435 g, 0.00300 mol) and 1,1-dimethoxy-N,N-dimethylmethanamine (0.400 mL, 0.00301 mol) were combined and heated in sealed tube to 120° C. in the microwave for 15 min. The reaction was then allowed to cool to rt giving the 3-[(2E)-3-(dimethylamino)prop-2-enoyl]-benzonitrile as a red-orange crystalline material, LC/MS (M+H)$^+$: 201.

Step 2. 3-(1H-Pyrazol-3-yl)benzonitrile

The 3-[(2E)-3-(dimethylamino)prop-2-enoyl]benzonitrile (0.600 g, 0.00300 mol) was dissolved in ethanol (20.0 mL, 0.342 mol) and hydrazine (0.56 mL, 0.018 mol) under an atmosphere of nitrogen was stirred at room temperature for 1.5 h. The reaction was concentrated in vacuo to give a dark product which was purified by FCC on silica gel, eluting with ethyl acetate-hexane 1:1 to give 3-(1H-pyrazol-3-yl)benzonitrile as an oil (0.430g, 84%), LC/MS (M+H)$^+$: 170.

Step 3. 3-[1-(1H-Pyrrolo[2,3-b]pyridin-4-yl)-1H-pyrazol-3-yl]benzonitrile

4-Bromo-1H-pyrrolo[2,3-b]pyridine (0.075 g, 0.00038 mol) and 3-(1H-pyrazol-3-yl)benzo-nitrile (0.161 g, 0.000952 mol) were heated in sealed tube to 160° C. for 18 h. The resulting product, dark viscous gum, was purified by HPLC on a C-18 column eluting with a water:ACN gradient with 0.2% TFA to give the title product (0.030 g, 27%) as a white amorphous solid, LC/MS (M+H)$^+$: 286, $^1$H NMR (DMSO-d$_6$) δ 11.95 (bs, 1H), 8.76(s, 1H), 8.36(s, 1H), 8.29(d, 1H, J=7.5), 8.25(d, 1H, J=5.0), 7.79(d, 1H, J=7.5), 7.62(t, 1H, J=7.5), 7.53(m, 2H), 7.25(s, 1H), 7.11(m, 1H).

Example 153

3-[1-(1H-Pyrrolo[2,3-b]pyridin-4-yl)-1H-pyrazol-4-yl]benzonitrile

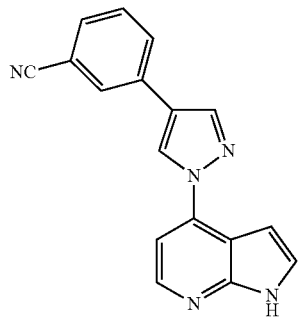 [SMILES: N#Cc1cccc(-c2cnn(-c3ccnc4[nH]ccc34)c2)c1]

Step 1. 4-(4,4,5,5-Tetramethyl-1,3,2-dioxaborolan-2-yl)-1-[2-(trimethylsilyl)ethoxy]methyl-1H-pyrazole A solution of 4-(4,4,5,5-tetramethyl-1,3,2-dioxaborolan-2-yl)-1H-pyrazole (2.0 g, 0.010 mol) and DMF (30.0 mL, 0.387 mol) was cooled to 0° C. Sodium hydride (320 mg, 0.013 mol) (60% in oil) was added and the mixture was stirred for 10 min. [β-(Trimethylsilyl)ethoxy]methyl chloride (2.4 mL, 0.013 mol) was added and the resulting mixture was stirred for 20 min at 0° C. and 2 h at room temperature. The reaction was partitioned between water and ethyl acetate. The organic layer was washed with brine, dried over MgSO$_4$ and concentrated to give 4-(4,4,5,5-tetramethyl-1,3,2-dioxaborolan-2-yl)-1-[2-(trimethylsilyl)ethoxy]methyl-1H-pyrazole as a crude material. LC/MS (M+H)$^+$: 325, $^1$H NMR (CDCl$_3$) δ 7.85 (s, 1H), 7.80(s, 1H), 5.45(s, 2H), 3.55(t, 2H), 1.35(s, 12H), 0.95(t, 2H), 0.0(s, 9H).

Step 2. 3-(1-[2-(Trimethylsilyl)ethoxy]methyl-1H-pyrazol-4-yl)benzonitrile

A mixture of 4-(4,4,5,5-tetramethyl-1,3,2-dioxab orolan-2-yl)-1-[2-(trimethylsilyl)ethoxy]-methyl-1H-pyrazole (150.0 mg, 0.0004625 mol) and 3-bromobenzonitrile (0.10 g, 0.00056 mol) in toluene (2.0 mL, 0.019 mol) and ethanol (0.3 mL, 0.005 mol) was treated with sodium carbonate (98 mg, 0.00092 mol) in water (0.5 mL, 0.03 mol). The mixture was degassed by bubbling nitrogen. Tetrakis(triphenylphosphine)palladium(0) (53 mg, 0.000046 mol) was added and nitrogen was bubbled for 3 min. The reaction was heated in a microwave at 80° C. for 30 min, then allowed to cool to rt and taken up in water and ethyl acetate. The organic layer was dried over MgSO$_4$, filtered and concentrated to give a crude product, which was purified by FCC on silica gel,

Step 3. 3-(1H-Pyrazol-4-yl)benzonitrile trifluoroacetate

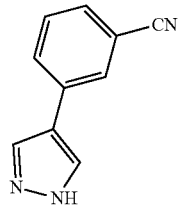 [SMILES: N#Cc1cccc(-c2cn[nH]c2)c1]

eluting with EtOAc/Hexanes (1:5) to give 3-(1-[2-(trimethylsilyl)ethoxy]methyl-1H-pyrazol-4-yl)benzonitrile, as an oil, LC/MS (M+H)+: 300.

A solution of 3-(1-[2-(trimethylsilyl)ethoxy]methyl-1H-pyrazol-4-yl)benzonitrile (110.0 mg, 0.0003673 mol) was taken up in TFA (3.0 mL, 0.039 mol) and the mixture was heated in microwave at 120° C. for 3 min. The reaction mixture was allowed to cool to rt, and then concentrated to give a crude residue. The product was purified by HPLC on a C-18 column eluting with a water/ACN gradient containing 0.2% TFA to give 3-(1H-pyrazol-4-yl)benzonitrile trifluoroacetate as an amorphous white solid, LC/MS (M+H)+: 170.

Step 4. 3-[1-(1H-Pyrrolo[2,3-b]pyridin-4-yl)-1H-pyrazol-4-yl]benzonitrile

A mixture of 4-bromo-1H-pyrrolo[2,3-b]pyridine (25.0 mg, 0.000127 mol) and 3-(1H-pyrazol-4-yl)benzonitrile trifluoroacetate (23.6 mg, 0.0000833 mol) was heated at 180° C., neat overnight. The crude residue was purified by HPLC on a C-18 column eluting with a water; ACN gradient containing 0.2% TFA to give the title compound as an amorphous white solid, LC/MS (M+H)+: 286, ¹H NMR (DMSO-d₆) δ 11.85 (bs, 1H), 9.18(s, 1H), 8.42(s, 1H), 8.28(s, 1H), 8.25(d, 1H, J=5.0), 8.07(d, 1H, J=7.0), 7.64(d, 1H, J=7.0), 7.56(t, 1H, J=7.0), 7.51(m, 1H), 7.47(d, 1H, J=5.0), 7.03(m,1H).

Example 170

2-[1-(1H-Pyrrolo[2,3-b]pyridin-4-yl)-1H-pyrazol-4-yl]-1,3-benzoxazole

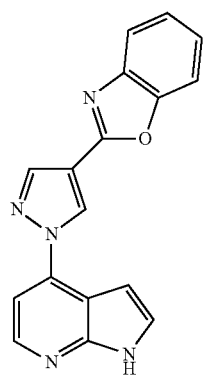 [SMILES: c1ccc2oc(-c3cnn(-c4ccnc5[nH]ccc45)c3)nc2c1]

Step 1. 4-Hydrazino-1-[2-(trimethylsilyl)ethoxy]methyl-1H-pyrrolo[2,3-b]pyridine

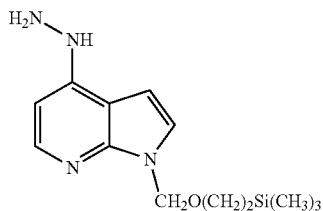

To 4-bromo-1-[2-(trimethylsilyl)ethoxy]methyl-1H-pyrrolo[2,3-b]pyridine (1.98 g, 0.00605 mol) was added hydrazine (11.0 mL, 0.350 mol) followed by addition of methanol (1.0 mL, 0.025 mol) (to improve solubility). The reaction mixture was heated in a sealed tube at 97° C. (an oil bath) for 18 h. The reaction mixture was cooled to rt and formed an off-white solid precipitate. The solid was filtered off and rinsed with cold water and dried to give 4-hydrazino-1-[2-(trimethylsilyl)ethoxy]-methyl-1H-pyrrolo[2,3-b]pyridine (1.55 gm) as a light yellow solid, LC/MS (M+H)+: 279, ¹H NMR (DMSO-d₆) δ 7.98(d, 1H), 7.91(s, 1H), 7.28(d, 1H), 6.69(s, 1H), 6.61(d, 1H), 5.58(s, 2H), 4.37(s, 2H), 3.56(t, 2H), 0.90(t, 2H), 0.0(s, 9H).

Step 2. 2-[1-(1-[2-(Trimethylsilyl)ethoxy]methyl-1H-pyrrolo[2,3-b]pyridin-4-yl)-1H-pyrazol-4-yl]-1,3-benzoxazole

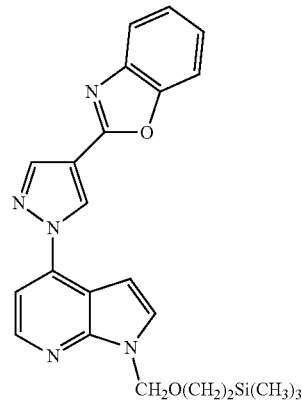

To 4-hydrazino-1-[2-(trimethylsilyl)ethoxy]methyl-1H-pyrrolo[2,3-b]pyridine (0.083 g, 0.00030 mol) 3782-117-1 and 1,3-benzoxazol-2-ylmalonaldehyde (0.056 g, 0.00030 mol) in toluene (1.5 mL, 0.014 mol) was added molecular sieves. The mixture was heated in a sealed tube at 70° C. (an oil bath) with stirring for 2 h. The solvent was removed in vacuo and the crude product was purified by FCC on silica using ethyl acetate:hexanes 3:7 to give 2-[1-(1-[2-(trimethylsilyl)ethoxy]-methyl-1H-pyrrolo[2,3-b]pyridin-4-yl)-1H-pyrazol-4-yl]-1,3-benzoxazole (0.090 gm) as an oil, LC/MS (M+H)+: 432.

Step 3

Using a procedure analogous to Example 106, Step 4, but using 2-[1-(1-[2-(trimethylsilyl)-ethoxy]methyl-1H-pyrrolo[2,3-b]pyridin-4-yl)-1H-pyrazol-4-yl]-1,3-benzoxazole, the title compound was prepared as a white amorphous powder (0.015 gm, 18%), LC/MS (M+H)+: 302, ¹H NMR (DMSO-d₆) δ 11.85 (bs, 1H), 9.45(s,1H), 8.53(s, 1H), 8.36(bs, 1H), 7.7-7.6(m, 2H), 7.65(d, 1H), 7.56(bs, 1H), 7.38-7.34(m, 2H),7.01(d,1H).

Example 172

Cyclohexyl[1-(1H-pyrrolo[2,3-b]pyridin-4-yl)-1H-pyrazol-4-yl]methanol

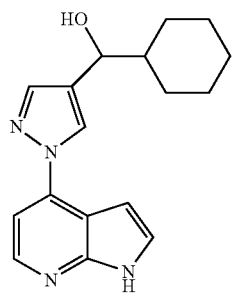 [SMILES: OC(c1cnn(-c2ccnc3[nH]ccc23)c1)C1CCCCC1]

Step 1. 4-(4-Bromo-1H-pyrazol-1-yl)-1H-pyrrolo[2,3-b]pyridine

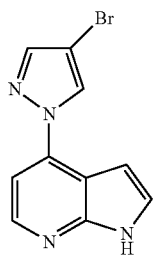 [SMILES: Brc1cnn(-c2ccnc3[nH]ccc23)c1]

A mixture of 4-bromo-1H-pyrrol o [2,3-b]pyridine (1.10 g, 0.00558 mol) and 4-bromo-1H-pyrazole (1.2 g, 0.0084 mol) was heated neat to 150° C. for 2 h. DMF was added to dissolve the crude residue. This residue was taken up in EtOAc and washed with 1N NaOH. The organic layer was washed with brine, dried over MgSO₄, filtered and concentrated to give a crude 4-(4-bromo-1H-pyrazol-1-yl)-1H-pyrrolo[2,3-b]pyridine residue, LC/MS (M+H)⁺: 263, 265.

Step 2. 4-(4-Bromo-1H-pyrazol-1-yl)-1-[2-(trimethylsilyl)ethoxy]methyl-1H-pyrrolo[2,3-b]pyridine

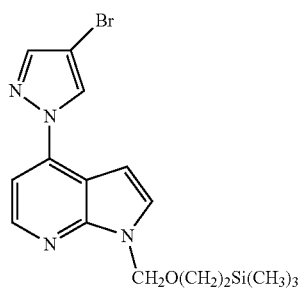

A solution of 4-(4-bromo-1H-pyrazol-1-yl]-1-[2-(trimethylsilyl)ethoxy]methyl chloride (1.4 mL, 0.0079 mol) was added and stirred for 20 min at 0° C. The reaction was partitioned between ethyl acetate and water. The organic layer was washed with brine, dried over MgSO₄ and concentrated to give the crude material. The product was purified by FCC on silica gel (EtOAc/Hexanes, 1/10) to give 4-(4-bromo-1H-pyrazol-1 -yl)-1- [2-(trimethylsilyl)ethoxy] methyl-1H-pyrrolo[2,3-b]pyridine as a solid product, LC/MS (M+H)⁺: 393, 394, ¹H NMR (CDCl₃) δ 8.47 (d, 1H, J=7.0), 8.27 (s, 1H), 7.88(s, 1H), 7.52(d, 1H, J=4.5), 7.39(d, 1H, J=7.0), 7.069(d, 1H, J=4.5), 5.80(s, 2H), 3.6(t, 2H), 1.95(t, 2H), 0.0(s, 9H).

Step 3. Cyclohexyl[1-(1-[2-(trimethylsilyl)ethoxy]methyl-1H-pyrrolo[2,3-Npyridin-4-yl)-1H-pyrazol-4-yl]methanol

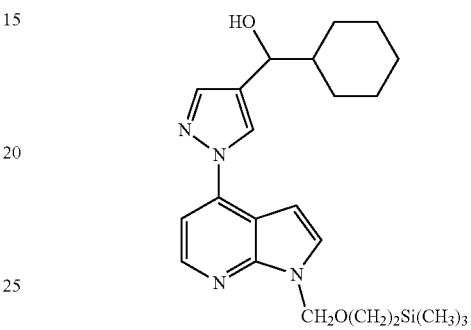

A mixture of 4-(4-bromo-1H-pyrazol-1-yl) -1-[2-(trimethylsilyl)ethoxy]methyl-1H-pyrrolo[2,3 -b]pyridine (50.0 mg, 0.000127 mol) in THF (2.0 mL, 0.025 mol) under a nitrogen atmosphere was cooled to −78° C. and 1.6 M n-butyllithium in water (1.00 mL, 0.0555 mol). The mixture was stirred for 3 min. The reaction was partitioned between water and EtOAc. The organic layer was dried over MgSO₄, filtered and concentrated to give the cyclohexyl[1-(1:5) to give 4-yl)-1H-pyrazol-4-yl]methanol as a crude residue, LC/MS (M+H)⁺: 417.

Step 4. Cyclohexyl[1-phenylvinyl)-1H-pyrazol-4-yl]methanol

Using a procedure analogous to Example 106, Step 4, but using cyclohexyl[1-(1-[2-(trimethylsilyl)ethoxy]methyl-1H-pyrrolo[2,3-b]pyridine, the title compound was prepared as a white amorphous powder (0.015 gm, 18%), LC/MS (M+H)⁺: 297. ¹H NMR (DMSO-d₆) δ 11.85 (bs, 1H), 8.44(s, 1H), 7.74(s, 1H), 7.50(m, 1H), 7.44(d, 1H, J=6.5.70(s, 1H), 5.37(s, 1H).

Example 173

4-[4-(1-Phenylvinyl)-1H-pyrazol-1-yl]-1H-pyrrolo[2,3-b]pyridine

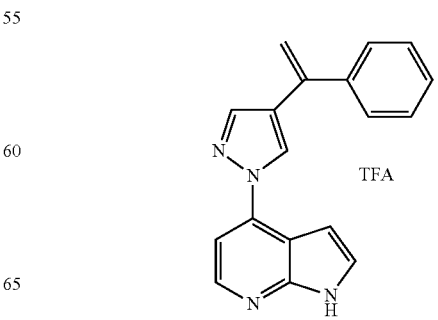

Step 1. 4-1-[4-(1-Phenylvinyl)-1H-pyrazol-1-yl]-1-[2-(trimethylsilyl)ethoxy]-methyl-1H-pyrrolo[2,3-b]pyridine

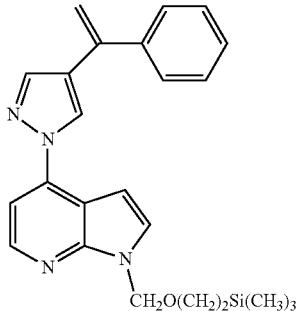

A mixture of (1-phenylvinyl)boronic acid (24.0 mg, 0.000162 mol) and 4-(4-bromo-1H-pyrazol-1-yl)-1-[2-(trimethylsilyl)ethoxy]methyl-1H-pyrrolo[2,3-b]pyridine (50.0 mg, 0.000127 mol) in toluene (2.00 mL, 0.0188 mol) and ethanol (0.50 mL, 0.0086 mol) was treated with potassium carbonate (35 mg, 0.00025 mol) in water (1.00 mL, 0.0555 mol). The mixture was degassed by bubbling nitrogen. Tetrakis(triphenylphosphine)palladium(0) (10 mg, 0.00001 mol) was added and nitrogen was bubbled for 3 min. The reaction was heated in a sealed tube in the microwave at 100° C. for 30 min. The reaction was allowed to cool to rt and partitioned between ethyl acetate and water. The combined organic layer was dried over MgSO$_4$, filtered and concentrated to give the crude material The crude product was purified by FCC on silica gel eluting with EtOAc/Hexanes (1:5) to give 4-[4-(1-phenylvinyl)-1H-pyrazol-1-yl]-1-[2-(trimethylsilyl)ethoxy]methyl-1H-pyrrolo[2,3-b]-pyridine as a solid residue, LC/MS (M+H)$^+$: 417.

Step 2

Using a procedure analogous to Example 106, Step 4, but using 4-[4-(1-phenylvinyl)-1H-pyrazol-1-yl]-1-[2-(trimethylsilyl)ethoxy]methyl-1H-pyrrolo[2,3-b]pyridine, the title compound was prepared as an white amorphous powder (0.015 gm, 31%), LC/MS (M+H)$^+$: 287, $^1$H NMR (DMSO-d$_6$) δ 11.85 (bs, 1H), 8.63(s, 1H), 7.99(s, 1H), 7.55(bs, 1H), 7.48(m, 2H), 7.43-7.37(m, 5H), 7.01(m,1H), 5.70(s, 1H), 5.37(s, 1H).

Example 200

4-(1-Benzyl-1H-pyrazol-4-yl)-1H-pyrrolo[2,3-b]pyridine

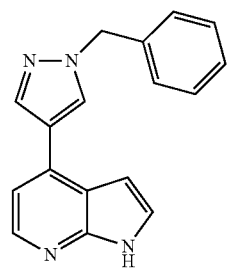 [SMILES: c1ccc(Cn2cc(-c3ccnc4[nH]ccc34)cn2)cc1]

Step 1. 4-(1-Benzyl-1H-pyrazol-4-yl)-1-[2-(trimethylsilyl)ethoxy]methyl-1H-pyrrolo[2,3-b]pyridine

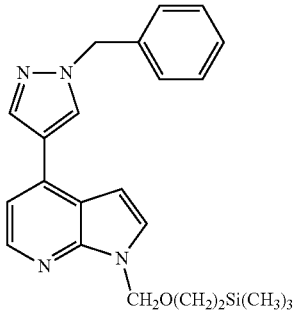

4-Bromo-1-[2-(trimethylsilyl)ethoxy]methyl-1H-pyrrolo[2,3-b]pyridine (0.100 g, 0.000306 mol) was combined with 1-benzyl-4-(4,4,5,5-tetramethyl-1,3,2-dioxaborolan-2-yl)-1H-pyrazole (0.113 g, 0.000398 mol) in toluene (3.0 mL, 0.028 mol) and ethanol (0.5 mL, 0.008 mol). Potassium carbonate (0.084 g, 0.00061 mol) dissolved in water (1.0 mL, 0.056 mol) was added and the reaction mixture was degassed with nitrogen. Tetrakis(triphenylphosphine)palladium(0) (0.080 g, 0.000069 mol) was added, and again the mixture was degassed with nitrogen for 5 min. The reaction was heated in sealed tube to 100° C. in a microwave for 30 minutes. The reaction was partitioned between ethyl acetate and water. The organic layer was washed with water, brine, dried over magnesium sulfate and concentrated to give a crude residue. The product was purified by FCC on silica gel using ethyl acetate:hexane 3:7, to give 4-(1-benzyl-1H-pyrazol-4-yl)-1-[2-(trimethylsilyl)ethoxy]methyl-1H-pyrrolo[2,3-b]pyridine 0.092 g as a semisolid residue, LC/MS (M+H)$^+$: 405.

Step 2. 4-(1-Benzyl-1H-pyrazol-4-yl)-1H-pyrrolo[2,3-b]pyridine

Using a procedure analogous to Example 106, Step 4, but using 4-(1-benzyl-1H-pyrazol-4-yl)-1-[2-(trimethylsilyl)ethoxy]methyl-1H-pyrrolo[2,3-b]pyridine, the title compound was prepared as a white amorphous powder (0.054 gm), LC/MS (M+H)$^+$: 275, $^1$H NMR (DMSO-d$_6$) δ 12.21 (bs, 1H), 8.80(s, 1H), 8.25(vbs, 1H), 8.23(s, 1H), 7.63(s, 1H), 7.49(bs, 1H), 7.4-7.2(m, 5H), 6.99(s, 1H), 5.42(s, 2H).

Example 201

4-[1-(2-Naphthylmethyl)-1H-pyrazol-4-yl]-1H-pyrrolo[2,3-b]pyridine

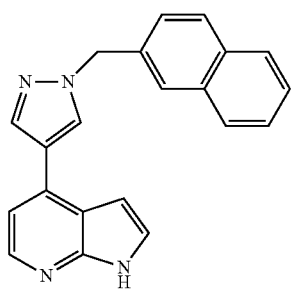 [SMILES: c1ccc2cc(Cn3cc(-c4ccnc5[nH]ccc45)cn3)ccc2c1]

Step 1. 1-(2-Naphthylmethyl)-4-(4,4,5,5-tetramethyl-1,3,2-dioxaborolan-2-yl)-1H-pyrazole The 4-(4,4,5,5-tetramethyl-1,3,2-dioxaborolan-2-yl)-1H-pyrazole (0.10 g, 0.00052 mol) was combined with naphthalene, 2-(bromomethyl)-(0.12 g, 0.00057 mol) in ACN (3.0 mL, 0.057 mol) under nitrogen at rt. Then cesium carbonate (0.50 g, 0.0015 mol) was added and the reaction was complete after stirring for 1 h. This was partitioned between ethyl acetate and brine. The organic layer was washed with brine, dried over magnesium sulfate and concentrated to give 1-(2-naphthylmethyl)-4-(4,4,5,5-tetramethyl-1,3,2-dioxaborolan-2-yl)-1H-pyrazole 0.17 gm, as an oil, LC/MS (M+H)$^+$: 335, $^1$H NMR (CDCl$_3$) δ 7.89 (s, 1H), 7.79-7.84(m, 3H), 7.69(bs, 2H), 7.49-7.4(m, 2H), 7.46-7.33 (m, 1H), 5.47(s, 2H), 1.31(s, 12H).

Step 2. 4-[1-(2-Naphthylmethyl)-1H-pyrazol-4-yl]-1-[2-(trimethylsilyl)ethoxy]methyl-1H-pyrrolo[2,3-b]pyridine

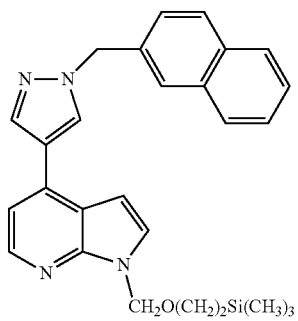

4-Bromo-1-[2-(trimethylsilyl)ethoxy]methyl-1H-pyrrolo[2,3-b]pyridine (0.06 g, 0.0002 mol) and 1-(2-naphthylmethyl)-4-(4,4,5,5-tetramethyl-1,3,2-dioxaborolan-2-yl)-1H-pyrazole (0.074 g, 0.00022 mol) were combined in toluene (2.0 mL, 0.019 mol) and ethanol (1.0 mL, 0.017 mol), and then potassium carbonate (0.063 g, 0.00046 mol, in 1 mL water) was added. The reaction mixture was degassed with nitrogen, then tetrakis(triphenylphosphine)palladium(0) (0.02 g, 0.00002 mol) was added, sealed in a tube and heated to 120° C. in a microwave for 30 minutes. This was allowed to cool and then partitioned between ethyl acetate and brine. The organic layer was dried over magnesium sulfate and concentrated to give 4-[1-(2-naphthylmethyl)-1H-pyrazol-4-yl]-1-[2-(trimethylsilyl)ethoxy]methyl-1H-pyrrolo[2,3-b]pyridine 0.08 g, as an oily residue, LC/MS (M+H)$^+$: 455.

Step 3

Using a procedure analogous to Example 106, Step 4, but using 4-[1-(2-naphthylmethyl)-1H-pyrazol-4-yl]-1-[2-(trimethylsilyl)ethoxy]methyl-1H-pyrrolo[2,3-b]pyridine, the title compound was prepared as a white amorphous powder (0.053 g, 88%), LC/MS (M+H)$^+$: 325, $^1$H NMR (DMSO-d$_6$) δ 12.0(bs, 1H), 8.79(s, 1H), 8.24(s, 1H), 8.19(d, 1H, J=5.7), 7.82(m, 4H), 7.56(m, 1H), 7.43(m, 4H), 6.92(m, 1H), 5.54(s, 2H).

Example 219

4-(1-Phenyl-1H-pyrazol-4-yl)-1H-pyrrolo[2,3-b]pyridine

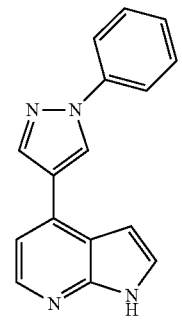 [SMILES: c1ccc(-n2cc(-c3ccnc4[nH]ccc34)cn2)cc1]

Step 1. 1-phenyl-4-(4,4,5,5-Tetramethyl-1,3,2-dioxaborolan-2-yl)-1H-pyrazole 4-(4,4,5,5-Tetramethyl-1,3,2-dioxaborolan-2-yl)-1H-pyrazole (0.07 g, 0.0003 mol) and phenylboronic acid (0.083 g, 0.00068 mol) were combined in DMF (1.50 mL, 0.0194 mol). Then copper(II) diacetate (0.010 g, 0.000055 mol) and pyridine (0.069 mL, 0.00085 mol) were added. The reaction was heated in an open tube to 80° C. for 40 minutes. The reaction was complete by HPLC, allowed to cool to rt, taken up in ethyl acetate, and washed with water saturated with sodium carbonate. The organic layer was washed with brine, dried over magnesium sulfate and concentrated to give 1-phenyl-4-(4,4,5,5-tetramethyl-1,3,2-dioxaborolan-2-yl)-1H-pyrazo, 0.09 gm as an oily residue, LC/MS (M+H)$^+$: 271.

Step 2. 4-(1-Phenyl-1H-pyrazol-4-yl)-1-[2-(trimethylsilyl)ethoxy]methyl-1H-pyrrolo[2,3-b]pyridine Using a procedure analogous to Example 201, Steps B and C, but using 1-phenyl-4-(4,4,5,5-tetramethyl-1,3,2-dioxaborolan-2-yl)-1H-pyrazo, the title compound was prepared as an white amorphous powder (0.015 gm, 18%), LC/MS (M+H)$^+$: 261, $^1$H NMR (DMSO-d$_6$) δ 12.05 (bs, 1H), 9.23(s, 1H), 8.53(s, 1H), 8.31(m, 1H), 8.01(m, 2H), 7.63(m, 1H), 7.57-7.52 (m, 3H), 7.36(m, 1H), 7.13(m, 1H).

Example 231

3-[4-(1H-Pyrrolo[2,3-b]pyridin-4-yl)-1H-pyrazol-1-yl]benzonitrile

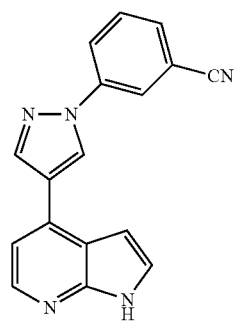 [SMILES: N#Cc1cccc(-n2cc(-c3ccnc4[nH]ccc34)cn2)c1]

Step 1. 4-(1H-Pyrazol-4-yl)-1-[2-(trimethylsilyl)ethoxy]methyl-1H-pyrrolo[2,3-b]pyridine

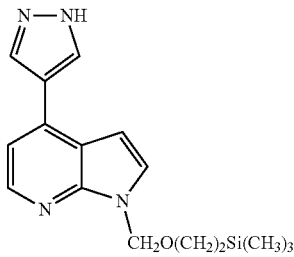

4-Bromo-1-[2-(trimethylsilyl)ethoxy]methyl-1H-pyrrolo[2,3-b]pyridine (0.20 g, 0.00061 mol) and 4-(4,4,5,5-tetramethyl-1,3,2-dioxaborolan-2-yl)-1H-pyrazole (0.15 g, 0.00079 mol) were combined in DMF (5.0 mL, 0.064 mol) and then potassium carbonate (0.25 g, 0.0018 mol) in 1 mL water was added. The reaction was degassed with nitrogen, then tetrakis(triphenylphosphine)-palladium(0) (0.08 g, 0.00007 mol) was added and in a sealed tube the reaction was heated to 120° C. oil bath. The reaction was heated for 30 minutes, allowed to cool and then taken up in ethyl acetate. The reaction mixture was washed with brine, dried over magnesium sulfate and concentrated to give an oil. The product was purified by FCC on silica gel eluting with a hexane:ethyl acetate gradient to give 4-(1H-pyrazol-4-yl)-1-(trimethylsilyl)ethoxy]methyl-1H-pyrrolo[2,3-b]pyridine (0.13 gm, 70%) as a crystalline white powder, LC/MS (M+H)$^+$: 315, $^1$H NMR (DMSO-d$_6$) δ 13.35 (bs, 1H), 8.59(bs, 1H), 8.32(d, 1H, J=8.5), 8.26(bs, 1H), 7.76(d, 1H, J=6.0), 7.45(d, 1H, J=8.5), 7.01(d, 1H, J=6.0), 5.73(s, 2H), 3.61(t, 2H), 0.92(t, 2H), 0.0(s, 9H).

Step 2. 3-[4-(1-[2-(Trimethylsilyl)ethoxy]methyl-1H-pyrrolo[2,3-b]pyridin-4-yl)-1H-pyrazol-1-yl]benzonitrile

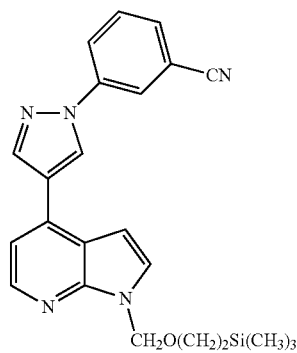

4-(1H-Pyrazol-4-yl)-1-[2-(trimethylsilyl)ethoxy]methyl-1H-pyrrolo[2,3-b]pyridine (0.025 g, 0.000080 mol) and (3-cyanophenyl)boronic acid (0.023 g, 0.00016 mol) were combined in DMF (1.50 mL, 0.0194 mol). Then copper(II) diacetate (0.002 g, 0.00001 mol) and pyridine (0.019 mL, 0.00024 mol) were added. The reaction was heated in an open tube to 125° C. for 40 minutes, allowed to cool to rt, taken up in ethyl acetate, and washed with water saturated with sodium carbonate. The organic layer was washed with brine, dried over magnesium sulfate and concentrated to give 3-[4-(1-[2-(trimethylsilyl)ethoxy]methyl-1H-pyrrolo[2,3-b]pyridin-4-yl)-1H-pyrazol-1-yl]-benzonitrile (0.025 gm, 92%) as an oily residue, LC/MS (M+H)$^+$: 316.

Step 3

Using a procedure analogous to Example 106, Step 4, but using 3-[4-(1-[2-(trimethylsilyl)-ethoxy]methyl-1H-pyrrolo[2,3-b]pyridin-4-yl)-1H-pyrazol-1-yl]benzonitrile, the title compound was prepared as an white crystalline powder (0.012 gm, 60%), LC/MS (M+H)$^+$: 286, $^1$H NMR (DMSO-d$_6$) δ 12.05 (bs, 1H), 9.32(s, 1H), 8.59(m, 1H), 8.55(m, 1H), 8.36(m, 1H), 8.30(d, 1H, J=5.2), 7.83(m, 1H), 7.75(m, 1H), 7.63(m, 1H), 7.51(d, 1H, J=5.2), 7.12(m, 1H).

Example 250

4-{1-[(1R)-1-Methylbutyl]-1H-pyrazol-4-yl}-1H-pyrrolo[2,3-b]pyridine (250a) and

4-{1-[(1S)-1-Methylbutyl]-1H-pyrazol-4-yl)-1H-pyrrolo[2,3-b]pyridine (250b)

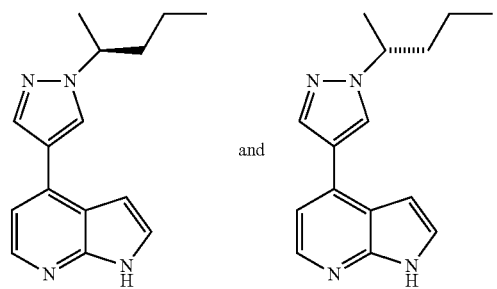 [SMILES: CCC[C@H](C)n1cc(-c2ccnc3[nH]ccc23)cn1 ; CCC[C@@H](C)n1cc(-c2ccnc3[nH]ccc23)cn1]

Step 1. 4-[1-(1-Methylbutyl)-1H-pyrazol-4-yl]-1-[2-(trimethylsilyl)ethoxy]-methyl-1H-pyrrolo[2,3-b]pyridine 4-(1H-Pyrazol-4-yl) -1-[2-(trimethylsilyl)ethoxy]methyl-1H-pyrrolo[2,3-b]pyridine (50 mg, 0.0002 mol) (see, Example 231, Step 1) was dissolved in DMF (2 mL, 0.02 mol) and cooled at 0° C. This solution was treated with sodium hydride (7.0 mg, 0.00029 mol) (60% in oil) and stirred for 15 min. The mixture was then treated with 2-bromopentane (40 mg, 0.0002 mol) and was stirred for 5 h. The reaction was partitioned between ethyl acetate and water. The organic layer was washed with brine, dried over MgSO$_4$, filtered and concentrated to give the crude product 4-[1-(1-methylbutyl)-1H-pyrazol-4-yl]-1-[2-(trimethylsilyl)ethoxy]methyl-1H-pyrrolo[2,3-b]pyridine as an oil, LC/MS (M+H)$^+$: 286.

Step 2. 4-[1-(1-Methylbutyl)-1H-pyrazol-4-yl]-1H-pyrrolo[2,3-b]pyridine

Using a procedure analogous to Example 106, Step 4, but using 4-[1-(1-methylbutyl)-1H-pyrazol-4-yl]-1-[2-(trimethylsilyl)ethoxy]methyl-1H-pyrrolo[2,3-b]pyridine, the title compound was prepared as an white amorphous powder (0.025 gm, 60%), LC/MS (M+H)$^+$: 255, $^1$H NMR (DMSO-d$_6$) δ 12.21 (bs, 1H), 8.66(s, 1H), 8.27(bs, 1H), 8.25(s, 1H), 7.62(m, 1H), 7.49(m, 1H), 7.02(m, 1H), 4.46(m, 1H), 1.9-1.8(m, 1H), 1.7-1.6(m, 1H), 1.47(d, 3H), 1.2-1.0(m, 2H), 0.83(t, 3H).

Step 3. Separation of Enantiomers

The separation of the enantiomers of 4-[1-(1-methylbutyl)-1H-pyrazol-4-yl]-1H-pyrrolo[2,3-b]pyridine from Step 2 was performed by chiral column preparative HPLC separation using an OD-H column eluting with an isopropanol:hexane gradient to give the title compounds as amorphous white residues, LC/MS (M+H)$^+$: 255, $^1$H NMR (DMSO-d$_6$) δ 12.21 (bs, 1H), 8.66(s, 1H), 8.27(bs, 1H), 8.25(s, 1H), 7.62(m, 1H), 7.49(m, 1H), 7.02(m, 1H), 4.46(m, 1H), 1.9-1.8(m, 1H), 1.7-1.6(m, 1H), 1.47(d, 3H), 1.2-1.0(m, 2H), 0.83(t, 3H).

Example 286

4-Methyl-3-[4-(1H-pyrrolo[2,3-b]pyridin-4-yl)-1H-pyrazol-1-yl]benzonitrile

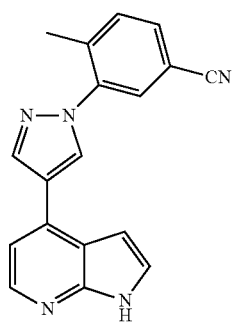 [SMILES: Cc1ccc(C#N)cc1-n1cc(-c2ccnc3[nH]ccc23)cn1]

Step 1. 4-Methyl-3-[4-(1-[2-(trimethylsilyl)ethoxy]methyl-1H-pyrrolo[2,3-b]pyridin-4-yl)-1H-pyrazol-1-yl]benzonitrile

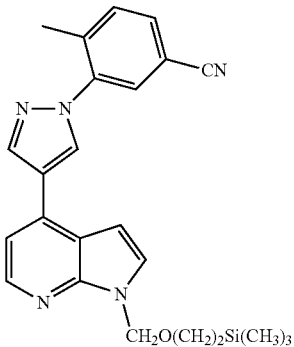

To a mixture of 4-(1H-pyrazol-4-yl)-1-[2-(trimethylsilyl)ethoxy]methyl-1H-pyrrolo[2,3-b]-pyridine (0.050 g, 0.00016 mol) (see, Example 231, Step 1) and cesium carbonate (0.10 g, 0.00032 mol) in dry DMF (1.0 mL, 0.013 mol) was added 3-fluoro-4-methylbenzonitrile (0.043 g, 0.00032 mol). The reaction mixture was heated in sealed tube to 120° C. for 5.5 hours. The reaction was allowed to cool and partitioned between ethyl acetate and water. The organic layer was washed with water, brine, dried over magnesium sulfate, filtered, and concentrated to give 4-methyl-3-[4-(1-[2-(trimethylsilyl)ethoxy]methyl-1H-pyrrolo[2,3-b]pyridin-4-yl)-1H-pyrazol-1-yl]benzonitrile as a crude product, LC/MS (M+H)$^+$: 430.

Step 2. 4-Methyl-3-[4-(1H-pyrrolo[2,3-b]pyridin-4-yl)-1H-pyrazol-1-yl]benzonitrile Using a procedure analogous to Example 106, Step 4, but using 4-methyl-3-[4-(1-[2-(trimethylsilyl)ethoxy]methyl-1H-pyrrolo[2,3-b]pyridin-4-yl)-1H-pyrazol-1-yl]benzonitrile, the title compound was prepared as a white amorphous powder (0.037 gm, 88%), LC/MS (M+H)$^+$: 300, $^1$H NMR (DMSO-d$_6$) δ 12.19 (bs, 1H), 8.98(s, 1H), 8.57(s, 1H), 8.31(d, 1H, J=7.0), 8.08(s, 1H), 7.89(d, 1H, J=10), 7.66(d, 1H, J=10), 7.63(m, 1H), 7.55(d, 1H), 7.07(m, 1H), 2.4(s, 3H).

Further example compounds of the invention are provided in Tables 7, 8, 9, 10, and 11 below. The compounds listed in Tables 7, 8, 9, 10 and 11 are racemic unless the enantiomers are indicated separately.

TABLE 7

| Ex. No. | R | MS (M + H)$^+$ | Name | Preparation |
|---|---|---|---|---|
| 101 |  | 239 | 2-(1H-pyrrolo[2,3-b]pyridin-4-yl)-4,5,6,7-tetrahydro-2H-indazole | Ex 100 |

TABLE 7-continued

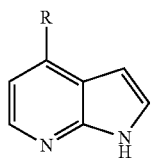

| Ex. No. | R | MS (M + H)+ | Name | Preparation |
|---|---|---|---|---|
| 102 | | 280 | 5-nitro-2-(1H-pyrrolo[2,3-b]-pyridin-4-yl)-2H-indazole | Ex 100 |
| 103 | | 280 | 6-nitro-2-(1H-pyrrolo[2,3-b]-pyridin-4-yl)-2H-indazole | Ex 100 |
| 104 | | 286 | 3-[1-(1H-pyrrolo[2,3-b]pyridin-4-yl)-1H-imidazol-4-yl]-benzonitrile | Ex 100 |
| 105 | | 291 | 4-[4-(3-methoxyphenyl)-1H-imidazol-1-yl]-1H-pyrrolo[2,3-b]pyridine | Ex 100 |
| 108 | | 277 | 4-(5-phenyl-2-thienyl)-1H-pyrrolo[2,3-b]pyridine | Ex 107 |

TABLE 8

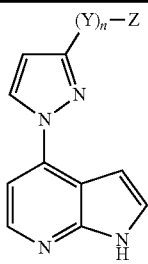

| Ex. No. | —(Y)n—Z | MS (M + H)+ | Name | Preparation |
|---|---|---|---|---|
| 121 | | 279 | 4-[3-(4-fluorophenyl)-1H-pyrazol-1-yl]-1H-pyrrolo[2,3-b]pyridine | Ex 120 |

TABLE 8-continued

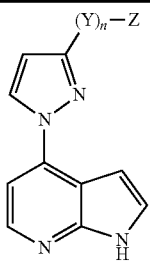

| Ex. No. | —(Y)ₙ—Z | MS (M + H)⁺ | Name | Preparation |
|---|---|---|---|---|
| 122 | 3-NO₂-phenyl | 306 | 4-[3-(3-nitrophenyl)-1H-pyrazol-1-yl]-1H-pyrrolo[2,3-b]pyridine | Ex 120 |
| 123 | 4-Cl-phenyl | 295 | 4-[3-(4-chlorophenyl)-1H-pyrazol-1-yl]-1H-pyrrolo[2,3-b]pyridine | Ex 120 |
| 124 | 4-OCH₃-phenyl | 291 | 4-[3-(4-methoxyphenyl)-1H-pyrazol-1-yl]-1H-pyrrolo[2,3-b]pyridine | Ex 120 |
| 125 | 4-CN-phenyl | 286 | 4-[1-(1H-pyrrolo[2,3-b]pyridin-4-yl)-1H-pyrazol-3-yl]benzonitrile | Ex 120 |
| 126 | 3-NH₂-phenyl | 276 | 3-[1-(1H-pyrrolo[2,3-b]pyridin-4-yl)-1H-pyrazol-3-yl]aniline | Ex 120 |
| 129 | 3-OCH₃-phenyl | 291 | 4-[3-(3-methoxyphenyl)-1H-pyrazol-1-yl]-1H-pyrrolo[2,3-b]pyridine | Ex 128 |
| 130 | 3-OCH₂CN-phenyl | 316 | {3-[1-(1H-pyrrolo[2,3-b]pyridin-4-yl)-1H-pyrazol-3-yl]-phenoxy}acetonitrile | Ex 128 |
| 131 | 3-NHCOCH₂CN-phenyl | 343 | 2-cyano-N-{3-[1-(1H-pyrrolo[2,3-b]pyridin-4-yl)-1H-pyrazol-3-yl]-phenyl}acetamide | Ex 128 |

TABLE 8-continued

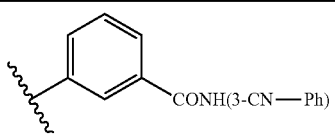

| Ex. No. | —(Y)ₙ—Z | MS (M + H)⁺ | Name | Preparation |
|---|---|---|---|---|
| 132 | CONH(3-CN—Ph) | 405 | 3-cyano-N-{3-[1-(1H-pyrrolo[2,3-b]-pyridin-4-yl)-1H-pyrazol-3-yl]-phenyl}benzamide | Ex 128 |

TABLE 9

| Ex. No. | —(Y)ₙ—Z | Mass Spec (M + H)⁺ | Name | Prep. |
|---|---|---|---|---|
| 150 | 4-NO₂-phenyl | 306 | 4-[4-(4-nitrophenyl)-1H-pyrazol-1-yl]-1H-pyrrolo[2,3-b]pyridine | Ex 153 |
| 151 | 4-NH₂-phenyl | 276 | 4-[1-(1H-pyrrolo[2,3-b]pyridin-4-yl)-1H-pyrazol-4-yl]aniline | Ex 153 |
| 152 | phenyl | 261 | 4-(4-phenyl-1H-pyrazol-1-yl)-1H-pyrrolo[2,3-b]pyridine | Ex 153 |
| 154 | pyridin-3-yl | 262 | 4-(4-pyridin-3-yl-1H-pyrazol-1-yl)-1H-pyrrolo[2,3-b]pyridine | Ex 153 |
| 155 | 2-CN-phenyl | 286 | 2-[1-(1H-pyrrolo[2,3-b]pyridin-4-yl)-1H-pyrazol-4-yl]benzonitrile | Ex 153 |

TABLE 9-continued

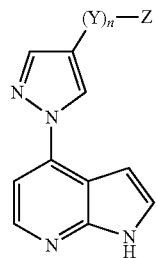

| Ex. No. | —(Y)$_n$—Z | Mass Spec (M + H)$^+$ | Name | Prep. |
|---|---|---|---|---|
| 156 | 2-CH₂CN phenyl | 300 | {2-[1-(1H-pyrrolo[2,3-b]pyridin-4-yl)-1H-pyrazol-4-yl]phenyl}acetonitrile | Ex 153 |
| 157 | 3-NO₂ phenyl | 306 | 4-[4-(3-nitrophenyl)-1H-pyrazol-1-yl]-1H-pyrrolo[2,3-b]pyridine | Ex 153 |
| 158 | 3-NH₂ phenyl | 276 | 3-[1-(1H-pyrrolo[2,3-b]pyridin-4-yl)-1H-pyrazol-4-yl]aniline | Ex 153 |
| 159 | 3-CH₂CN phenyl | 300 | {3-[1-(1H-pyrrolo[2,3-b]pyridin-4-yl)-1H-pyrazol-4-yl]phenyl}acetonitrile | Ex 153 |
| 160 | 4-CN phenyl | 286 | 4-[1-(1H-pyrrolo[2,3-b]pyridin-4-yl)-1H-pyrazol-4-yl]benzonitrile | Ex 153 |
| 161 | 3-OH phenyl | 277 | 3-[1-(1H-pyrrolo[2,3-b]pyridin-4-yl)-1H-pyrazol-4-yl]phenol | Ex 153 |
| 162 | 3-CO₂CH₃ phenyl | 319 | methyl 3-[1-(1H-pyrrolo[2,3-b]pyridin-4-yl)-1H-pyrazol-4-yl]benzoate | Ex 153 |
| 163 | 4-CH₂CN phenyl | 300 | {4-[1-(1H-pyrrolo[2,3-b]pyridin-4-yl)-1H-pyrazol-4-yl]phenyl}acetonitrile | Ex 153 |

TABLE 9-continued

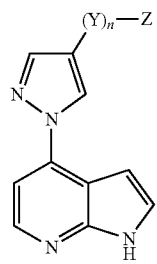

| Ex. No. | —(Y)$_n$—Z | Mass Spec (M + H)$^+$ | Name | Prep. |
|---|---|---|---|---|
| 164 | (3-NHCOCH$_2$CN phenyl) | 343 | 2-cyano-N-{3-[1-(1H-pyrrolo[2,3-b]-pyridin-4-yl)-1H-pyrazol-4-yl]-phenyl}acetamide | Ex 153 |
| 165 | (4-OH phenyl) | 277 | 4-[1-(1H-pyrrolo[2,3-b]pyridin-4-yl)-1H-pyrazol-4-yl]phenol | Ex 153 |
| 166 | (5-CN pyridin-3-yl) | 287 | 5-[1-(1H-pyrrolo[2,3-b]pyridin-4-yl)-1H-pyrazol-4-yl]nicotinonitrile | Ex 153 |
| 167 | (4-OCH$_2$CN phenyl) | 316 | {4-[1-(1H-pyrrolo[2,3-b]pyridin-4-yl)-1H-pyrazol-4-yl]phenoxy}acetonitrile | Ex 153 |
| 168 | cyclohex-1-en-1-yl | 265 | 4-(4-cyclohex-1-en-1-yl-1H-pyrazol-1-yl)-1H-pyrrolo[2,3-b]pyridine | Ex 172 |
| 169 | (4-OCH$_3$ phenyl) | 291 | 4-[4-(4-methoxyphenyl)-1H-pyrazol-1-yl]-1H-pyrrolo[2,3-b]pyridine | Ex 153 |
| 171 | pyrimidin-4-yl | 263 | 4-(4-pyrimidin-4-yl-1H-pyrazol-1-yl)-1H-pyrrolo[2,3-b]pyridine | Ex 171 |
| 174 | (3-CN, α-OH benzyl) | 316 | 3-{hydroxy[1-(1H-pyrrolo[2,3-b]-pyridin-4-yl)-1H-pyrazol-4-yl]-methyl}benzonitrile | Ex 172 |

TABLE 9-continued

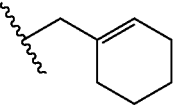 [SMILES: *CC1=CCCCC1]

| Ex. No. | —(Y)ₙ—Z | Mass Spec (M + H)⁺ | Name | Prep. |
|---|---|---|---|---|
| 175 | 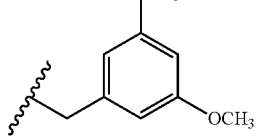 | 279 | 4-[4-(cyclohex-1-en-1-ylmethyl)-1H-pyrazol-1-yl]-1H-pyrrolo[2,3-b]pyridine | Ex 172 |

TABLE 10

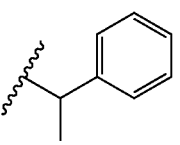 [SMILES: *C(C)c1ccccc1]

| Ex. No. | MS (M + H)⁺ | —(Y)ₙ—Z | Name | Prep. |
|---|---|---|---|---|
| 202 | 335 | 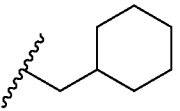 [SMILES: *CC1CCCCC1] | 4-[1-(3,5-dimethoxybenzyl)-1H-pyrazol-4-yl]-1H-pyrrolo[2,3-b]pyridine | Ex 201 |
| 203 | 289 | 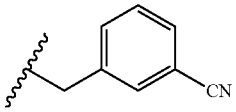 [SMILES: *Cc1cccc(C#N)c1] | 4-[1-(1-phenylethyl)-1H-pyrazol-4-yl]-1H-pyrrolo[2,3-b]pyridine | Ex 201 |
| 204 | 281 | 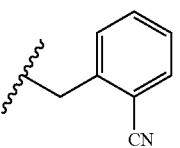 [SMILES: *Cc1ccccc1C#N] | 4-[1-(cyclohexylmethyl)-1H-pyrazol-4-yl]-1H-pyrrolo[2,3-b]pyridine | Ex 201 |
| 205 | 300 | | 3-{[4-(1H-pyrrolo[2,3-b]pyridin-4-yl)-1H-pyrazol-1-yl]methyl}benzonitrile | Ex 201 |
| 206 | 300 | | 2-{[4-(1H-pyrrolo[2,3-b]pyridin-4-yl)-1H-pyrazol-1-yl]methyl}benzonitrile | Ex 201 |

TABLE 10-continued

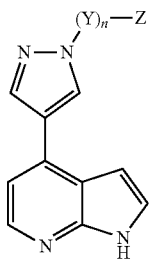

| Ex. No. | MS (M + H)+ | —(Y)n—Z | Name | Prep. |
|---|---|---|---|---|
| 207 | 300 | (4-cyanobenzyl) | 4-{[4-(1H-pyrrolo[2,3-b]pyridin-4-yl)-1H-pyrazol-1-yl]methyl}benzonitrile | Ex 201 |
| 208 | 303 | (2-oxo-2-phenylethyl) | 1-phenyl-2-[4-(1H-pyrrolo[2,3-b]pyridin-4-yl)-1H-pyrazol-1-yl]ethanone | Ex 201 |
| 209 | 283 | (3,3-dimethyl-2-oxobutyl) | 3,3-dimethyl-1-[4-(1H-pyrrolo[2,3-b]pyridin-4-yl)-1H-pyrazol-1-yl]butan-2-one | Ex 201 |
| 210 | 280 | [(5-methylisoxazol-3-yl)methyl] | 4-{1-[(5-methylisoxazol-3-yl)methyl]-1H-pyrazol-4-yl}-1H-pyrrolo[2,3-b]pyridine | Ex 201 |
| 211 | 283 | (tetrahydro-2H-pyran-2-ylmethyl) | 4-[1-(tetrahydro-2H-pyran-2-ylmethyl)-1H-pyrazol-4-yl]-1H-pyrrolo[2,3-b]pyridine | Ex 201 |
| 212 | 265 | (cyclohex-2-en-1-yl) | 4-(1-cyclohex-2-en-1-yl-1H-pyrazol-4-yl)-1H-pyrrolo[2,3-b]pyridine | Ex 201 |
| 213 | 255 | (1-ethylpropyl) | 4-[1-(1-ethylpropyl)-1H-pyrazol-4-yl]-1H-pyrrolo[2,3-b]pyridine | Ex 201 |
| 214 | 267 | cyclohexyl | 4-(1-cyclohexyl-1H-pyrazol-4-yl)-1H-pyrrolo[2,3-b]pyridine | Ex 201 |
| 215 | 242 | (carbamoylmethyl) | 2-[4-(1H-pyrrolo[2,3-b]pyridin-4-yl)-1H-pyrazol-1-yl]acetamide | Ex 201 |

TABLE 10-continued

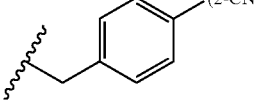

| Ex. No. | MS (M + H)+ | —(Y)n—Z | Name | Prep. |
|---|---|---|---|---|
| 216 | 376 | 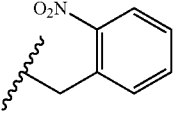 [SMILES: *Cc1ccccc1[N+](=O)[O-]] (2-CN—Ph) | 4'-{[4-(1H-pyrrolo[2,3-b]pyridin-4-yl)-1H-pyrazol-1-yl]methyl}biphenyl-2-carbonitrile | Ex 201 |
| 217 | 320 | 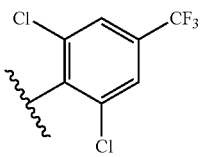 | 4-[1-(2-nitrobenzyl)-1H-pyrazol-4-yl]-1H-pyrrolo[2,3-b]pyridine | Ex 201 |
| 218 | 397, 399 | 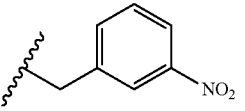 [SMILES: *Cc1cccc([N+](=O)[O-])c1] | 4-{1-[2,6-dichloro-4-(trifluoromethyl)phenyl]-1H-pyrazol-4-yl}-1H-pyrrolo[2,3-b]pyridine | Ex 201 |
| 220 | 320 | 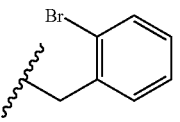 [SMILES: *Cc1ccccc1Br] | 4-[1-(3-nitrobenzyl)-1H-pyrazol-4-yl]-1H-pyrrolo[2,3-b]pyridine | Ex 201 |
| 221 | 353, 355 | 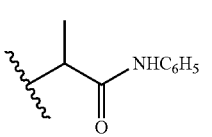 | 4-[1-(2-bromobenzyl)-1H-pyrazol-4-yl]-1H-pyrrolo[2,3-b]pyridine | Ex 201 |
| 222 | 332 | 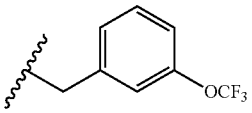 [SMILES: *Cc1cccc(OC(F)(F)F)c1] | N-phenyl-2-[4-(1H-pyrrolo[2,3-b]pyridin-4-yl)-1H-pyrazol-1-yl]propanamide | Ex 201 |
| 223 | 359 | 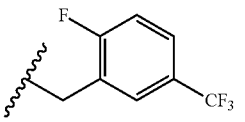 [SMILES: *Cc1cc(C(F)(F)F)ccc1F] | 4-{1-[3-(trifluoromethoxy)benzyl]-1H-pyrazol-4-yl}-1H-pyrrolo[2,3-b]pyridine | Ex 201 |
| 224 | 361 | 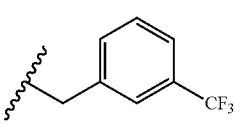 [SMILES: *Cc1cccc(C(F)(F)F)c1] | 4-{1-[2-fluoro-5-(trifluoromethyl)-benzyl]-1H-pyrazol-4-yl}-1H-pyrrolo[2,3-b]pyridine | Ex 201 |
| 225 | 343 | 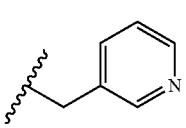 [SMILES: *Cc1cccnc1] | 4-{1-[3-(trifluoromethyl)benzyl]-1H-pyrazol-4-yl}-1H-pyrrolo[2,3-b]pyridine | Ex 201 |
| 226 | 276 | | 4-[1-(pyridin-3-ylmethyl)-1H-pyrazol-4-yl]-1H-pyrrolo[2,3-b]pyridine | Ex 201 |

TABLE 10-continued

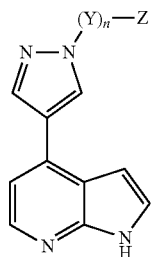

| Ex. No. | MS (M + H)+ | —(Y)n—Z | Name | Prep. |
|---|---|---|---|---|
| 227 | 317 | (1S)-1-phenylbutyl (C3H7, phenyl) | 4-{1-[(1S)-1-phenylbutyl]-1H-pyrazol-4-yl}-1H-pyrrolo[2,3-b]pyridine | Ex 201 |
| 228 | 317 | (1R)-1-phenylbutyl (C3H7, phenyl) | 4-{1-[(1R)-1-phenylbutyl]-1H-pyrazol-4-yl}-1H-pyrrolo[2,3-b]pyridine | Ex 201 |
| 229 | 317 | CH3, C(=O)phenyl | 1-phenyl-2-[4-(1H-pyrrolo[2,3-b]pyridin-4-yl)-1H-pyrazol-1-yl]propan-1-one | Ex 201 |
| 230 | 343, 345 | 2,6-dichlorobenzyl | 4-[1-(2,6-dichlorobenzyl)-1H-pyrazol-4-yl]-1H-pyrrolo[2,3-b]pyridine | Ex 201 |
| 232 | 289 | 2,6-dimethylphenyl | 4-[1-(2,6-dimethylphenyl)-1H-pyrazol-4-yl]-1H-pyrrolo[2,3-b]pyridine | Ex 231 |
| 233 | 354 | 2-CN-5-CF3-phenyl | 2-[4-(1H-pyrrolo[2,3-b]pyridin-4-yl)-1H-pyrazol-1-yl]-5-(trifluoromethyl)benzonitrile | Ex 286 |
| 234 | 393, 395 | 4-bromo-3,5,6-trifluoropyridin-2-yl | 4-[1-(4-bromo-3,5,6-trifluoropyridin-2-yl)-1H-pyrazol-4-yl]-1H-pyrrolo[2,3-b]pyridine | Ex 286 |
| 235 | 239 | cyclopropylmethyl | 4-[1-(cyclopropylmethyl)-1H-pyrazol-4-yl]-1H-pyrrolo[2,3-b]pyridine | Ex 201 |

TABLE 10-continued

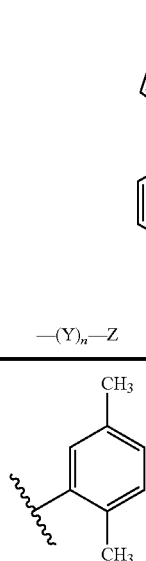

| Ex. No. | MS (M + H)+ | —(Y)ₙ—Z | Name | Prep. |
|---|---|---|---|---|
| 236 | 289 | 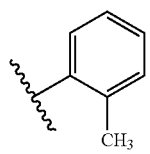 | 4-[1-(2,5-dimethylphenyl)-1H-pyrazol-4-yl]-1H-pyrrolo[2,3-b]pyridine | Ex 231 |
| 237 | 275 | 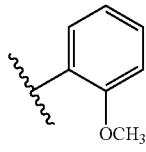 [SMILES: *c1ccccc1OC] | 4-[1-(2-methylphenyl)-1H-pyrazol-4-yl]-1H-pyrrolo[2,3-b]pyridine | Ex 231 |
| 238 | 291 | 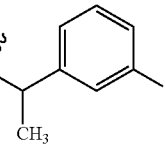 | 4-[1-(2-methoxyphenyl)-1H-pyrazol-4-yl]-1H-pyrrolo[2,3-b]pyridine | Ex 231 |
| 239 | 314 | 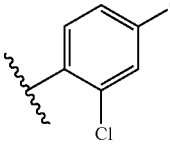 | 3-{1-[4-(1H-pyrrolo[2,3-b]pyridin-4-yl)-1H-pyrazol-1-yl]ethyl}benzonitrile | Ex 250 |
| 240 | 320 | 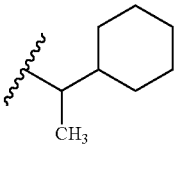 [SMILES: *C(C)C1CCCCC1] | 3-chloro-4-[4-(1H-pyrrolo[2,3-b]pyridin-4-yl)-1H-pyrazol-1-yl]benzonitrile | Ex 286 |
| 241 | 295 | 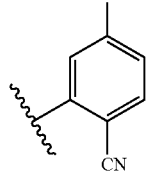 | 4-[1-(1-cyclohexylethyl)-1H-pyrazol-4-yl]-1H-pyrrolo[2,3-b]pyridine | Ex 250 |
| 242 | 304 |  | 4-fluoro-2-[4-(1H-pyrrolo[2,3-b]pyridin-4-yl)-1H-pyrazol-1-yl]benzonitrile | Ex 286 |

TABLE 10-continued

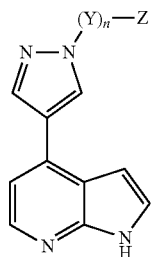

| Ex. No. | MS (M + H)+ | —(Y)n—Z | Name | Prep. |
|---|---|---|---|---|
| 243 | 304 | 2-fluoro-4-cyanophenyl | 2-fluoro-4-[4-(1H-pyrrolo[2,3-b]pyridin-4-yl)-1H-pyrazol-1-yl]benzonitrile | Ex 286 |
| 244 | 304 | 3-fluoro-4-cyanophenyl | 3-fluoro-4-[4-(1H-pyrrolo[2,3-b]pyridin-4-yl)-1H-pyrazol-1-yl]benzonitrile | Ex 286 |
| 245 | 357 | 1-[3-(trifluoromethyl)phenyl]ethyl | 4-(1-{1-[3-(trifluoromethyl)phenyl]ethyl}-1H-pyrazol-4-yl)-1H-pyrrolo[2,3-b]pyridine | Ex 250 |
| 246 | 289 | 3,5-dimethylphenyl | 4-[1-(3,5-dimethylphenyl)-1H-pyrazol-4-yl]-1H-pyrrolo[2,3-b]pyridine | Ex 231 |
| 247 | 286 | 4-cyanophenyl | 4-[4-(1H-pyrrolo[2,3-b]pyridin-4-yl)-1H-pyrazol-1-yl]benzonitrile | Ex 231 |
| 248 | 300 | 4-(cyanomethyl)phenyl | {4-[4-(1H-pyrrolo[2,3-b]pyridin-4-yl)-1H-pyrazol-1-yl]phenyl}acetonitrile | Ex 231 |
| 249 | 283 | 1-methylhexyl | 4-[1-(1-methylhexyl)-1H-pyrazol-4-yl]-1H-pyrrolo[2,3-b]pyridine | Ex 250 |
| 251 | 241 | sec-butyl | 4-(1-sec-butyl-1H-pyrazol-4-yl)-1H-pyrrolo[2,3-b]pyridine | Ex 250 |

TABLE 10-continued

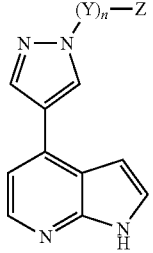

| Ex. No. | MS (M + H)+ | —(Y)n—Z | Name | Prep. |
|---|---|---|---|---|
| 252 | 303 | 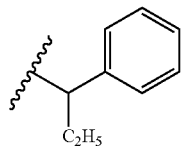 [SMILES: *C(CC)c1ccccc1] | 4-[1-(1-phenylpropyl)-1H-pyrazol-4-yl]-1H-pyrrolo[2,3-b]pyridine | Ex 250 |
| 253 | 367 | 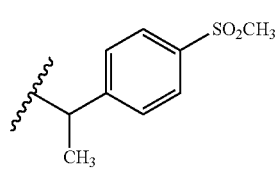 [SMILES: *C(C)c1ccc(S(C)(=O)=O)cc1] | 4-(1-{1-[4-(methylsulfonyl)-phenyl]ethyl}-1H-pyrazol-4-yl)-1H-pyrrolo[2,3-b]pyridine | Ex 250 |
| 254 | 337 | 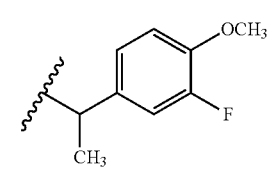 [SMILES: *C(C)c1ccc(OC)c(F)c1] | 4-{1-[1-(3-fluoro-4-methoxy-phenyl)ethyl]-1H-pyrazol-4-yl}-1H-pyrrolo[2,3-b]pyridine | Ex 250 |
| 255 | 357 | 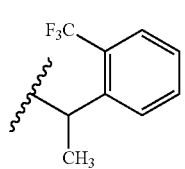 | 4-(1-{1-[2-(trifluoromethyl)-phenyl]ethyl}-1H-pyrazol-4-yl)-1H-pyrrolo[2,3-b]pyridine | Ex 250 |
| 256 | 425 | 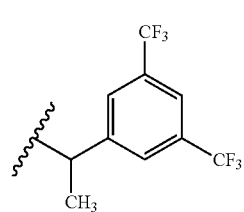 [SMILES: *C(C)c1cc(C(F)(F)F)cc(C(F)(F)F)c1] | 4-(1-{1-[3,5-bis(trifluoromethyl)-phenyl]ethyl}-1H-pyrazol-4-yl)-1H-pyrrolo[2,3-b]pyridine | Ex 250 |
| 257 | 314 | 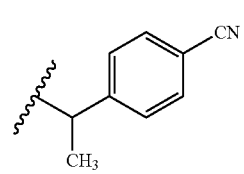 | 4-{1-[4-(1H-pyrrolo[2,3-b]pyridin-4-yl)-1H-pyrazol-1-yl]ethyl}benzonitrile | Ex 250 |
| 258 | 374 | 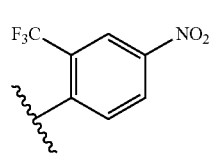 [SMILES: *c1ccc([N+](=O)[O-])cc1C(F)(F)F] | 4-{1-[4-nitro-2-(trifluoromethyl)phenyl]-1H-pyrazol-4-yl}-1H-pyrrolo[2,3-b]pyridine | Ex 286 |

TABLE 10-continued

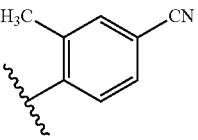

| Ex. No. | MS (M + H)+ | —(Y)n—Z | Name | Prep. |
|---|---|---|---|---|
| 259 | 300 | 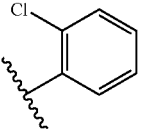 | 3-methyl-4-[4-(1H-pyrrolo[2,3-b]pyridin-4-yl)-1H-pyrazol-1-yl]benzonitrile | Ex 286 |
| 260 | 295, 297 | 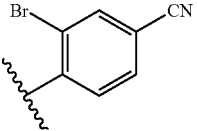 [SMILES: *c1ccc(C#N)cc1Br] | 4-[1-(2-chlorophenyl)-1H-pyrazol-4-yl]-1H-pyrrolo[2,3-b]pyridine | Ex 231 |
| 261 | 364, 366 | 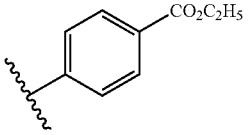 [SMILES: *c1ccc(C(=O)OCC)cc1] | 3-bromo-4-[4-(1H-pyrrolo[2,3-b]pyridin-4-yl)-1H-pyrazol-1-yl]benzonitrile | Ex 286 |
| 262 | 333 | 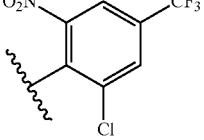 | ethyl 4-[4-(1H-pyrrolo[2,3-b]pyridin-4-yl)-1H-pyrazol-1-yl]benzoate | Ex 286 |
| 263 | 408, 410 | 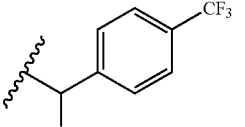 | 4-{1-[2-chloro-6-nitro-4-(trifluoromethyl)phenyl]-1H-pyrazol-4-yl}-1H-pyrrolo[2,3-b]pyridine | Ex 286 |
| 264 | 357 | 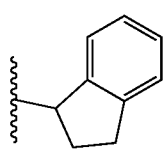 [SMILES: *C1CCc2ccccc21] | 4-(1-{1-[4-(trifluoromethyl)phenyl]ethyl}-1H-pyrazol-4-yl)-1H-pyrrolo[2,3-b]pyridine | Ex 250 |
| 265 | 301 | 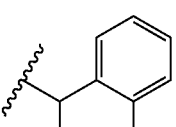 | 4-[1-(2,3-dihydro-1H-inden-1-yl)-1H-pyrazol-4-yl]-1H-pyrrolo[2,3-b]pyridine | Ex 250 |
| 266 | 315 | | 4-[1-(1,2,3,4-tetrahydronaphthalen-1-yl)-1H-pyrazol-4-yl]-1H-pyrrolo[2,3-b]pyridine | Ex 250 |

TABLE 10-continued

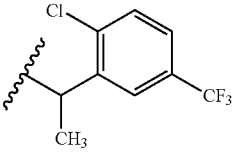 [SMILES: *C(C)c1cc(C(F)(F)F)ccc1Cl]

| Ex. No. | MS (M + H)+ | —(Y)n—Z | Name | Prep. |
|---|---|---|---|---|
| 267 | 391 | 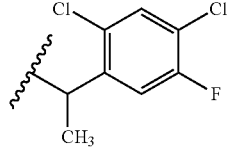 [SMILES: *C(C)c1cc(F)c(Cl)cc1Cl] | 4-(1-{1-[2-chloro-5-(trifluoromethyl)-phenyl]ethyl}-1H-pyrazol-4-yl)-1H-pyrrolo[2,3-b]pyridine | Ex 250 |
| 268 | 375 | 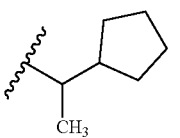 | 4-{1-[1-(2,4-dichloro-5-fluoro-phenyl)ethyl]-1H-pyrazol-4-yl}-1H-pyrrolo[2,3-b]pyridine | Ex 250 |
| 269 | 281 | 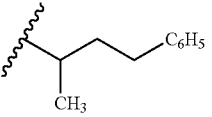 | 4-[1-(1-cyclopentylethyl)-1H-pyrazol-4-yl]-1H-pyrrolo[2,3-b]pyridine | Ex 250 |
| 270 | 317 | 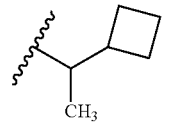 [SMILES: *C(C)C1CCC1] | 4-[1-(1-methyl-3-phenylpropyl)-1H-pyrazol-4-yl]-1H-pyrrolo[2,3-b]pyridine | Ex 250 |
| 271 | 267 | 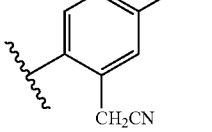 | 4-[1-(1-cyclobutylethyl)-1H-pyrazol-4-yl]-1H-pyrrolo[2,3-b]pyridine | Ex 250 |
| 272 | 368 | 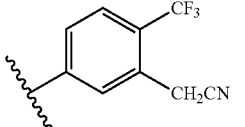 | [2-[4-(1H-pyrrolo[2,3-b]pyridin-4-yl)-1H-pyrazol-1-yl]-5-(trifluoromethyl)phenyl]acetonitrile | Ex 286 |
| 273 | 368 | 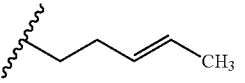 [SMILES: *CC/C=C/C] | [5-[4-(1H-pyrrolo[2,3-b]pyridin-4-yl)-1H-pyrazol-1-yl]-2-(trifluoromethyl)phenyl]acetonitrile | Ex 286 |
| 274 | 253 | 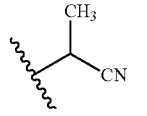 | 4-{1-[(3E)-pent-3-en-1-yl]-1H-pyrazol-4-yl}-1H-pyrrolo[2,3-b]pyridine | Ex 250 |
| 275 | 238 | | 2-[4-(1H-pyrrolo[2,3-b]pyridin-4-yl)-1H-pyrazol-1-yl]propanenitrile | Ex 250 |

TABLE 10-continued

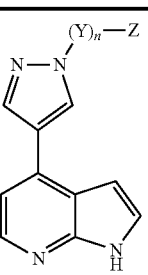

| Ex. No. | MS (M + H)+ | —(Y)n—Z | Name | Prep. |
|---|---|---|---|---|
| 276 | 315 | 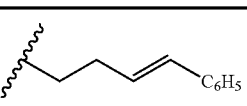 | 4-{1-[(3E)-4-phenylbut-3-en-1-yl]-1H-pyrazol-4-yl}-1H-pyrrolo[2,3-b]pyridine | Ex 250 |
| 277 | 280 |  | 6-[4-(1H-pyrrolo[2,3-b]pyridin-4-yl)-1H-pyrazol-1-yl]hexanenitrile | Ex 250 |
| 278 | 314 | 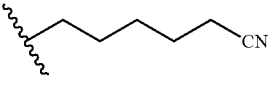 [SMILES: *CCCCCC#N] | ethyl 3-amino-2-{[4-(1H-pyrrolo[2,3-b]pyridin-4-yl)-1H-pyrazol-1-yl]-methyl}propanoate | Ex 250 |
| 279 | 285 |  | ethyl 2-[4-(1H-pyrrolo[2,3-b]pyridin-4-yl)-1H-pyrazol-1-yl]propanoate | Ex 250 |
| 280 | 283 | 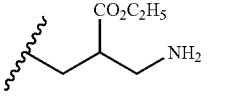 | 4-[1-(1-propylbutyl)-1H-pyrazol-4-yl]-1H-pyrrolo[2,3-b]pyridine | Ex 250 |
| 281 | 252 |  | 4-[4-(1H-pyrrolo[2,3-b]pyridin-4-yl)-1H-pyrazol-1-yl]butanenitrile | Ex 250 |
| 282 | 402, 404 | 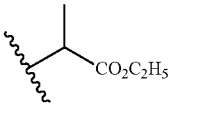 | [3-chloro-2-[4-(1H-pyrrolo[2,3-b]pyridin-4-yl)-1H-pyrazol-1-yl]-5-(trifluoromethyl)phenyl]acetonitrile | Ex 286 |
| 283 | 354 |  | 5-[4-(1H-pyrrolo[2,3-b]pyridin-4-yl)-1H-pyrazol-1-yl]-2-(trifluoromethyl)benzonitrile | Ex 286 |
| 284 | 363, 365 | 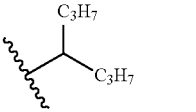 | 4-{1-[2-chloro-4-(trifluoromethyl)phenyl]-1H-pyrazol-4-yl}-1H-pyrrolo[2,3-b]pyridine | Ex 286 |
| 285 | 354 |  | 4-[4-(1H-pyrrolo[2,3-b]pyridin-4-yl)-1H-pyrazol-1-yl]-2-(trifluoromethyl)benzonitrile | Ex 286 |

TABLE 10-continued

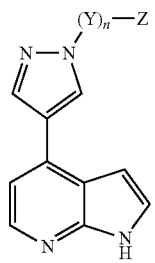

| Ex. No. | MS (M + H)+ | —(Y)ₙ—Z | Name | Prep. |
|---|---|---|---|---|
| 287 | 286 | 2-cyanophenyl | 2-[4-(1H-pyrrolo[2,3-b]pyridin-4-yl)-1H-pyrazol-1-yl]benzonitrile | Ex 286 |
| 288 | 320, 322 | 3-chloro-2-cyanophenyl | 3-chloro-2-[4-(1H-pyrrolo[2,3-b]pyridin-4-yl)-1H-pyrazol-1-yl]benzonitrile | Ex 286 |
| 289 | 362 | 3-amino-2,4-dicyano-5,6-difluorophenyl | 4-amino-5,6-difluoro-2-[4-(1H-pyrrolo[2,3-b]pyridin-4-yl)-1H-pyrazol-1-yl]isophthalonitrile | Ex 286 |
| 290 | 264 | (1-cyanocyclopropyl)methyl | 1-{[4-(1H-pyrrolo[2,3-b]pyridin-4-yl)-1H-pyrazol-1-yl]methyl}-cyclopropanecarbonitrile | Ex 250 |
| 291 | 280 | 5-cyano-2-methylpentyl | 5-[4-(1H-pyrrolo[2,3-b]pyridin-4-yl)-1H-pyrazol-1-yl]hexanenitrile | Ex 250 |
| 292 | 308 | 5-cyano-5,5-dimethylpentyl | 2,2-dimethyl-6-[4-(1H-pyrrolo[2,3-b]pyridin-4-yl)-1H-pyrazol-1-yl]-hexanenitrile | Ex 250 |
| 293 | 269 | 1-ethyl-2-methylpropyl | 4-[1-(1-ethyl-2-methylpropyl)-1H-pyrazol-4-yl]-1H-pyrrolo[2,3-b]pyridine | Ex 250 |
| 294 | 364, 366 | 4-bromo-2-cyanophenyl | 5-bromo-2-[4-(1H-pyrrolo[2,3-b]pyridin-4-yl)-1H-pyrazol-1-yl]benzonitrile | Ex 286 |

TABLE 10-continued

| Ex. No. | MS (M + H)+ | —(Y)n—Z | Name | Prep. |
|---|---|---|---|---|
| 295 | 354 | (F3C, CN phenyl) | 3-[4-(1H-pyrrolo[2,3-b]pyridin-4-yl)-1H-pyrazol-1-yl]-4-(trifluoromethyl)-benzonitrile | Ex 286 |
| 296 | 354 | (F3C, CN phenyl) | 2-[4-(1H-pyrrolo[2,3-b]pyridin-4-yl)-1H-pyrazol-1-yl]-3-(trifluoromethyl)-benzonitrile | Ex 286 |
| 297 | 372 | (F3C, CONH2 phenyl) | 3-[4-(1H-pyrrolo[2,3-b]pyridin-4-yl)-1H-pyrazol-1-yl]-4-(trifluoromethyl)-benzamide | Ex 286 |
| 298 | 281 | (cyclohexanone) | 3-[4-(1H-pyrrolo[2,3-b]pyridin-4-yl)-1H-pyrazol-1-yl]cyclohexanone | Ex 61 |
| 299 | 283 | (HO-cyclohexyl) | 2-[4-(1H-pyrrolo[2,3-b]pyridin-4-yl)-1H-pyrazol-1-yl]cyclohexanol | Ex 250 |
| 300 | 360 | (piperidine-SO2CH3) | 4-(1-{[1-(methylsulfonyl)piperidin-4-yl]methyl}-1H-pyrazol-4-yl)-1H-pyrrolo[2,3-b]pyridine | Ex 250 |
| 301 | 292 | (NC-cyclohexyl) | 2-[4-(1H-pyrrolo[2,3-b]pyridin-4-yl)-1H-pyrazol-1-yl]cyclohexanecarbonitrile | Ex 61 |
| 302 | 329 | (F3C-phenyl) | 4-{1-[2-(trifluoromethyl)phenyl]-1H-pyrazol-4-yl}-1H-pyrrolo[2,3-b]pyridine | Ex 286 |

TABLE 10-continued

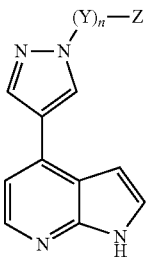

| Ex. No. | MS (M + H)+ | —(Y)n—Z | Name | Prep. |
|---|---|---|---|---|
| 303 | 329, 331 | 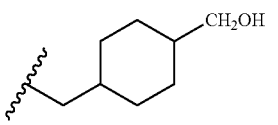 [SMILES: *CC1CCC(CO)CC1] | 4-[1-(2,6-dichlorophenyl)-1H-pyrazol-4-yl]-1H-pyrrolo[2,3-b]pyridine | Ex 286 |
| 304 | 311 | 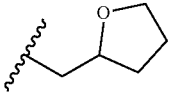 | (4-{[4-(1H-pyrrolo[2,3-b]pyridin-4-yl)-1H-pyrazol-1-yl]methyl}-cyclohexyl)methanol | Ex 250 |
| 305 | 269 | 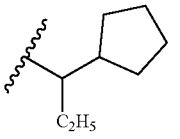 [SMILES: *C(CC)C1CCCC1] | 4-[1-(tetrahydrofuran-2-ylmethyl)-1H-pyrazol-4-yl]-1H-pyrrolo[2,3-b]pyridine | Ex 250 |
| 306 | 295 | 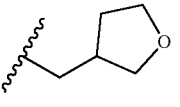 | 4-[1-(1-cyclopentylpropyl)-1H-pyrazol-4-yl]-1H-pyrrolo[2,3-b]pyridine | Ex 250 |
| 307 | 269 | 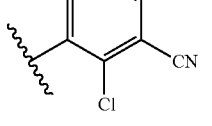 | 4-[1-(tetrahydrofuran-3-ylmethyl)-1H-pyrazol-4-yl]-1H-pyrrolo[2,3-b]pyridine | Ex 250 |
| 308 | 320 | 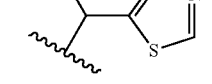 | 2-chloro-3-[4-(1H-pyrrolo[2,3-b]pyridin-4-yl)-1H-pyrazol-1-yl]benzonitrile | Ex 286 |
| 309 | 321 | 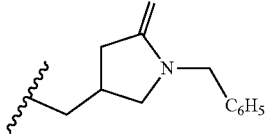 | 3-[4-(1H-pyrrolo[2,3-b]pyridin-4-yl)-1H-pyrazol-1-yl]-3-(1,3-thiazol-5-yl)-propanenitrile | Ex 61 |
| 310 | 372 | 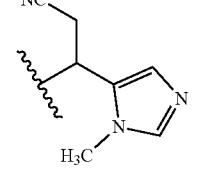 | 1-benzyl-4-{[4-(1H-pyrrolo[2,3-b]-pyridin-4-yl)-1H-pyrazol-1-yl]-methyl}pyrrolidin-2-one | Ex 250 |
| 311 | 318 | | 3-(1-methyl-1H-imidazol-5-yl)-3-[4-(1H-pyrrolo[2,3-b]pyridin-4-yl)-1H-pyrazol-1-yl]propanenitrile | Ex 61 |

TABLE 10-continued

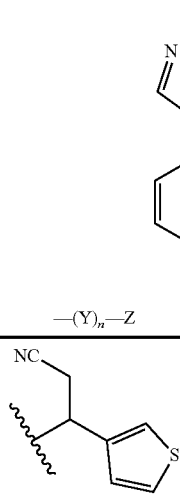

| Ex. No. | MS (M + H)+ | —(Y)ₙ—Z | Name | Prep. |
|---|---|---|---|---|
| 312 | 320 | 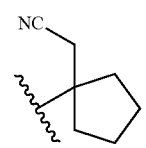 [SMILES: *C1(CC#N)CCCC1] | 3-[4-(1H-pyrrolo[2,3-b]pyridin-4-yl)-1H-pyrazol-1-yl]-3-(3-thienyl)propanenitrile | Ex 61 |
| 313 | 292 | 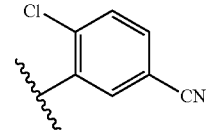 [SMILES: *c1cc(C#N)ccc1Cl] | {1-[4-(1H-pyrrolo[2,3-b]pyridin-4-yl)-1H-pyrazol-1-yl]cyclopentyl}acetonitrile | Ex 61 |
| 314 | 320, 322 | 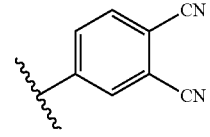 [SMILES: *c1ccc(C#N)c(C#N)c1] | 4-chloro-3-[4-(1H-pyrrolo[2,3-b]pyridin-4-yl)-1H-pyrazol-1-yl]benzonitrile | Ex 286 |
| 315 | 311 | 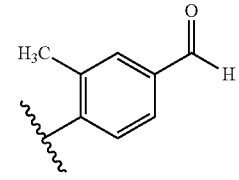 [SMILES: *c1ccc(C=O)cc1C] | 4-[4-(1H-pyrrolo[2,3-b]pyridin-4-yl)-1H-pyrazol-1-yl]phthalonitrile | Ex 286 |
| 316 | 303 | 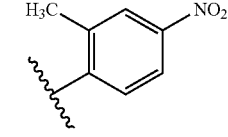 [SMILES: *c1ccc([N+](=O)[O-])cc1C] | 3-methyl-4-[4-(1H-pyrrolo[2,3-b]pyridin-4-yl)-1H-pyrazol-1-yl]benzaldehyde | Ex 286 |
| 317 | 320 | 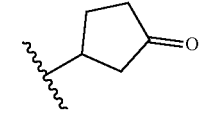 [SMILES: *C1CCC(=O)C1] | 4-[1-(2-methyl-4-nitrophenyl)-1H-pyrazol-4-yl]-1H-pyrrolo[2,3-b]pyridine | Ex 286 |
| 318 | 267 | 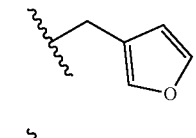 | 3-[4-(1H-pyrrolo[2,3-b]pyridin-4-yl)-1H-pyrazol-1-yl]cyclopentanone | Ex 201 |
| 319 | 265 | 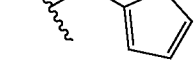 | 4-[1-(3-furylmethyl)-1H-pyrazol-4-yl]-1H-pyrrolo[2,3-b]pyridine | Ex 201 |
| 320 | 265 |  | 4-[1-(2-furylmethyl)-1H-pyrazol-4-yl]-1H-pyrrolo[2,3-b]pyridine | Ex 201 |

TABLE 10-continued

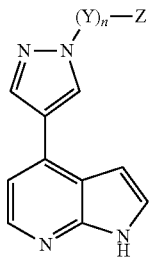

| Ex. No. | MS (M + H)+ | —(Y)n—Z | Name | Prep. |
|---|---|---|---|---|
| 321 | 339 | | 3-{2-cyano-1-[4-(1H-pyrrolo[2,3-b]-pyridin-4-yl)-1H-pyrazol-1-yl]ethyl}-benzonitrile | Ex 61 |
| 322 | 305 | | {3-methyl-4-[4-(1H-pyrrolo[2,3-b]-pyridin-4-yl)-1H-pyrazol-1-yl]-phenyl}methanol | Ex 286 |
| 323 | 283 | | 4-methyl-4-[4-(1H-pyrrolo[2,3-b]pyridin-4-yl)-1H-pyrazol-1-yl]pentan-2-one | Ex 61 |
| 324 | 354 | | 3-(1-benzofuran-2-yl)-3-[4-(1H-pyrrolo[2,3-b]pyridin-4-yl)-1H-pyrazol-1-yl]propanenitrile trifluoroacetate | Ex 61 |
| 325 | 304 | | 3-(3-furyl)-3-[4-(1H-pyrrolo[2,3-b]-pyridin-4-yl)-1H-pyrazol-1-yl]-propanenitrile | Ex 61 |
| 326 | 314 | | {3-methyl-4-[4-(1H-pyrrolo[2,3-b]-pyridin-4-yl)-1H-pyrazol-1-yl]-phenyl}acetonitrile | Ex 286 |

TABLE 11

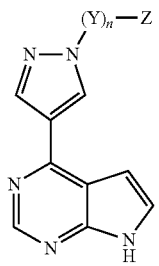

| Ex. No. | —(Y)ₙ—Z | MS (M + H)⁺ | Name | Prep. |
|---|---|---|---|---|
| 400 | (3-methyl-4-cyanophenyl group with H₃C and CN) | 301 | 4-methyl-3-[4-(7H-pyrrolo[2,3-d]-pyrimidin-4-yl)-1H-pyrazol-1-yl]-benzonitrile trifluoroacetate | Ex 286 |
| 401 | (1-cyclopentylpropyl group with C₂H₅) | 296 | 4-[1-(1-cyclopentylpropyl)-1H-pyrazol-4-yl]-7H-pyrrolo[2,3-d]-pyrimidine trifluoroacetate | Ex 201 |
| 402 | (cyclopentyl with CH₂CN) | 293 | {1-[4-(7H-pyrrolo[2,3-d]pyrimidin-4-yl)-1H-pyrazol-1-yl]cyclo-pentyl}acetonitrile trifluoroacetate | Ex 61 |
| 403R | (1R-configuration 3-cyanophenyl ethyl with CH₂CN) | 340 | 3-{(1R)-2-cyano-1-[4-(7H-pyrrolo[2,3-d]pyrimidin-4-yl)-1H-pyrazol-1-yl]ethyl}benzonitrile trifluoroacetate | Ex 61 |
| 403S | (1S-configuration 3-cyanophenyl ethyl with CH₂CN) | 340 | 3-{(1S)-2-cyano-1-[4-(7H-pyrrolo[2,3-d]pyrimidin-4-yl)-1H-pyrazol-1-yl]ethyl}benzonitrile trifluoroacetate | Ex 61 |
| 404 | (3-thienyl propanenitrile) | 321 | 3-[4-(7H-pyrrolo[2,3-d]pyrimidin-4-yl)-1H-pyrazol-1-yl]-3-(3-thienyl)propanenitrile trifluoroacetate | Ex 61 |
| 405 | (4-chloro-3-cyanophenyl group with Cl and CN) | 321, 323 | 4-chloro-3-[4-(7H-pyrrolo[2,3-d]-pyrimidin-4-yl)-1H-pyrazol-1-yl]-benzonitrile | Ex 286 |
| 406 | (3-furyl propanenitrile) | 305 | 3-(3-furyl)-3-[4-(7H-pyrrolo[2,3-d]-pyrimidin-4-yl)-1H-pyrazol-1-yl]-propanenitrile | Ex 61 |

TABLE 11-continued

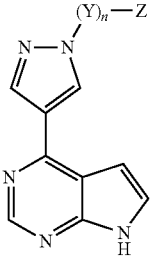

| Ex. No. | —(Y)ₙ—Z | MS (M + H)⁺ | Name | Prep. |
|---|---|---|---|---|
| 407 | 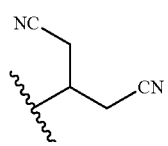 | 278 | 3-[4-(7H-pyrrolo[2,3-d]pyrimidin-4-yl)-1H-pyrazol-1-yl]-pentanedinitrile | Ex 407 |
| 408 | 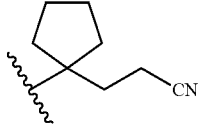 [SMILES: *C1(CCC#N)CCCC1] | 307 | 3-{1-[4-(7H-pyrrolo[2,3-d]-pyrimidin-4-yl)-1H-pyrazol-1-yl]-cyclopentyl}propanenitrile | Ex 61 |
| 409 | 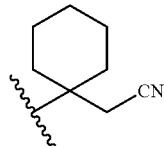 [SMILES: *C1(CC#N)CCCCC1] | 307 | {1-[4-(7H-pyrrolo[2,3-d]pyrimidin-4-yl)-1H-pyrazol-1-yl]cyclohexyl}-acetonitrile trifluoroacetate | Ex 61 |
| 410 | 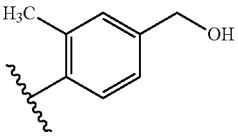 | 306 | {3-methyl-4-[4-(7H-pyrrolo[2,3-d]-pyrimidin-4-yl)-1H-pyrazol-1-yl]-phenyl}methanol trifluoroacetate | Ex 286 |
| 411 | 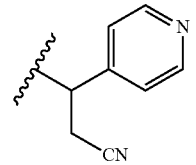 [SMILES: *C(CC#N)c1ccncc1] | 316 | 3-pyridin-4-yl-3-[4-(7H-pyrrolo-[2,3-d]pyrimidin-4-yl)-1H-pyrazol-1-yl]propanenitrile | Ex 61 |
| 412 | 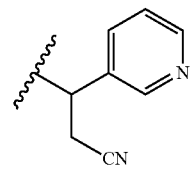 [SMILES: *C(CC#N)c1cccnc1] | 316 | 3-pyridin-3-yl-3-[4-(7H-pyrrolo-[2,3-d]pyrimidin-4-yl)-1H-pyrazol-1-yl]propanenitrile trifluoroacetate | Ex 61 |
| 413 | 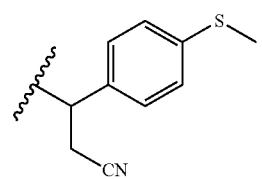 [SMILES: *C(CC#N)c1ccc(SC)cc1] | 360 | 3-[4-(methylthio)phenyl]-3-[4-(7H-pyrrolo[2,3-d]pyrimidin-4-yl)-1H-pyrazol-1-yl]propanenitrile trifluoroacetate | Ex 61 |

TABLE 11-continued

| Ex. No. | —(Y)ₙ—Z | MS (M + H)⁺ | Name | Prep. |
|---|---|---|---|---|
| 414 | | 345 | 3-(3-methoxyphenyl)-3-[4-(7H-pyrrolo[2,3-d]pyrimidin-4-yl)-1H-pyrazol-1-yl]propanenitrile trifluoroacetate | Ex 61 |
| 415 | | 345 | 3-(4-methoxyphenyl)-3-[4-(7H-pyrrolo[2,3-d]pyrimidin-4-yl)-1H-pyrazol-1-yl]propanenitrile | Ex 61 |
| 416 | | 314 | {3-methyl-4-[4-(7H-pyrrolo[2,3-d]pyrimidin-4-yl)-1H-pyrazol-1-yl]phenyl}acetonitrile trifluoroacetate | Ex 153 |
| 417 | | 376 | 3-[4-(methylsulfinyl)phenyl]-3-[4-(7H-pyrrolo[2,3-d]pyrimidin-4-yl)-1H-pyrazol-1-yl]propanenitrile | Ex 61 |
| 418 | | 392 | 3-[4-(methylsulfonyl)phenyl]-3-[4-(7H-pyrrolo[2,3-d]pyrimidin-4-yl)-1H-pyrazol-1-yl]propanenitrile | Ex 61 |
| 419 | | 369 | 3-[3-(cyanomethoxy)phenyl]-3-[4-(7H-pyrrolo[2,3-d]pyrimidin-4-yl)-1H-pyrazol-1-yl]propanenitrile | Ex 61 |
| 420 | | 349, 351 | 3-(6-chloropyridin-3-yl)-3-[4-(7H-pyrrolo[2,3-d]pyrimidin-4-yl)-1H-pyrazol-1-yl]propanenitrile | Ex 61 |

TABLE 11-continued

| Ex. No. | —(Y)ₙ—Z | MS (M + H)⁺ | Name | Prep. |
|---|---|---|---|---|
| 421 | (5-cyanopyridin-2-yl with CH₂CN) | 340 | 5-{2-cyano-1-[4-(7H-pyrrolo-[2,3-d]pyrimidin-4-yl)-1H-pyrazol-1-yl]ethyl}pyridine-2-carbonitrile trifluoroacetate | Ex 421 |
| 422 | (3,5-dimethylisoxazol-4-yl with CH₂CN) | 334 | 3-(3,5-dimethylisoxazol-4-yl)-3-[4-(7H-pyrrolo[2,3-d]pyrimidin-4-yl)-1H-pyrazol-1-yl]propanenitrile trifluoroacetate | Ex 61 |
| 423 | (6-trifluoromethylpyridin-3-yl with CH₂CN) | 384 | 3-[4-(7H-pyrrolo[2,3-d]pyrimidin-4-yl)-1H-pyrazol-1-yl]-3-[6-(trifluoromethyl)pyridin-3-yl]-propanenitrile trifluoroacetate | Ex 61 |
| 424 | (6-methoxypyridin-3-yl with CH₂CN) | 345 | 3-(6-methoxypyridin-3-yl)-3-[4-(7H-pyrrolo[2,3-d]pyrimidin-4-yl)-1H-pyrazol-1-yl]propanenitrile trifluoroacetate | Ex 61 |
| 425 | (pyridin-2-yl with CH₂CN) | 316 | 3-pyridin-2-yl-3-[4-(7H-pyrrolo-[2,3-d]pyrimidin-4-yl)-1H-pyrazol-1-yl]propanenitrile | Ex 61 |
| 426 | (6-bromopyridin-2-yl with CH₂CN) | 394 396 | 3-(6-bromopyridin-2-yl)-3-[4-(7H-pyrrolo[2,3-d]pyrimidin-4-yl)-1H-pyrazol-1-yl]propanenitrile trifluoroacetate | Ex 61 |
| 427 | (6-cyanopyridin-2-yl with CH₂CN) | 341 | 6-{2-cyano-1-[4-(7H-pyrrolo[2,3-d]pyrimidin-4-yl)-1H-pyrazol-1-yl]-ethyl}pyridine-2-carbonitrile trifluoroacetate | Ex 421 |

TABLE 11-continued

| Ex. No. | —(Y)ₙ—Z | MS (M + H)⁺ | Name | Prep. |
|---|---|---|---|---|
| 428 | (chain with two CN groups) | 306 | 4-[4-(7H-pyrrolo[2,3-d]pyrimidin-4-yl)-1H-pyrazol-1-yl]-heptanedinitrile | Ex 428 |
| 429 | (5-bromopyridin-3-yl with CH₂CN) | 393 395 | 3-(5-bromopyridin-3-yl)-3-[4-(7H-pyrrolo[2,3-d]pyrimidin-4-yl)-1H-pyrazol-1-yl]propanenitrile | Ex 429 |
| 430 | (chain with two OH groups) | 288 | 4-[4-(7H-pyrrolo[2,3-d]pyrimidin-4-yl)-1H-pyrazol-1-yl]-heptanedinitrile | Ex 430 |
| 431 | (5-cyanopyridin-3-yl with CH₂CN) | 340 | 5-{2-cyano-1-[4-(7H-pyrrolo-[2,3-d]pyrimidin-4-yl)-1H-pyrazol-1-yl]ethyl}nicotinonitrile trifluoroacetate | Ex 431 |
| 432 | (2-methoxypyridin-3-yl with CH₂CN) | 345 | 3-(2-methoxypyridin-3-yl)-3-[4-(7H-pyrrolo[2,3-d]pyrimidin-4-yl)-1H-pyrazol-1-yl]propanenitrile trifluoroacetate | Ex 61 |
| 433 | (4-(cyanomethoxy)phenyl with CH₂CN) | 369 | 3-[4-(cyanomethoxy)phenyl]-3-[4-(7H-pyrrolo[2,3-d]pyrimidin-4-yl)-1H-pyrazol-1-yl]propanenitrile trifluoroacetate | Ex 61 |

TABLE 11-continued

| Ex. No. | —(Y)ₙ—Z | MS (M + H)⁺ | Name | Prep. |
|---|---|---|---|---|
| 434 | (2-(cyanomethoxy)phenyl with CH-CH2-CN) | 369 | 3-[2-(cyanomethoxy)phenyl]-3-[4-(7H-pyrrolo[2,3-d]pyrimidin-4-yl)-1H-pyrazol-1-yl]propanenitrile trifluoroacetate | Ex 61 |
| 435 | (3,5-dibromophenyl with CH-CH2-CN) | 473 | 3-(3,5-dibromophenyl)-3-[4-(7H-pyrrolo[2,3-d]pyrimidin-4-yl)-1H-pyrazol-1-yl]propanenitrile | Ex 61 |
| 436 | (3,5-dicyanophenyl with CH-CH2-CN) | 365 | 5-{2-cyano-1-[4-(7H-pyrrolo-[2,3-d]pyrimidin-4-yl)-1H-pyrazol-1-yl]ethyl}isophthalonitrile trifluoroacetate | Ex 431 |
| 437 | (6-(dimethylamino)pyridin-2-yl with CH-CH2-CN) | 359 | 3-[6-(dimethylamino)pyridin-2-yl]-3-[4-(7H-pyrrolo[2,3-d]pyrimidin-4-yl)-1H-pyrazol-1-yl]propanenitrile trifluoroacetate | Ex 421 |
| 438 | (4-bromo-2-thienyl with CH-CH2-CN) | 401, 399 | 3-(4-bromo-2-thienyl)-3-[4-(7H-pyrrolo[2,3-d]pyrimidin-4-yl)-1H-pyrazol-1-yl]propanenitrile trifluoroacetate | Ex 61 |
| 439 | (4-cyano-2-thienyl with CH-CH2-CN) | 346 | 5-{2-cyano-1-[4-(7H-pyrrolo-[2,3-d]pyrimidin-4-yl)-1H-pyrazol-1-yl]ethyl}thiophene-3-carbonitrile trifluoroacetate | Ex 431 |
| 440 | (5-bromo-2-fluorophenyl with CH-CH2-CN) | 410, 412 | 3-(5-bromo-2-fluorophenyl)-3-[4-(7H-pyrrolo[2,3-d]pyrimidin-4-yl)-1H-pyrazol-1-yl]propanenitrile trifluoroacetate | Ex 61 |

TABLE 11-continued

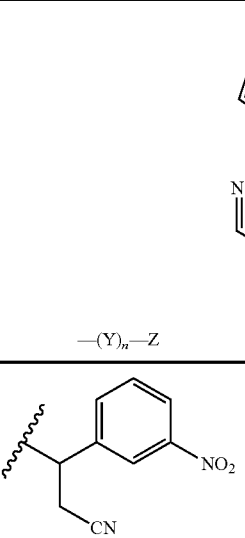

| Ex. No. | —(Y)$_n$—Z | MS (M + H)$^+$ | Name | Prep. |
|---|---|---|---|---|
| 441 | 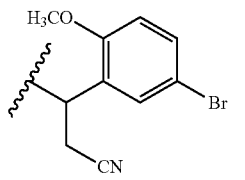 [SMILES: *C(CC#N)c1cc(Br)ccc1OC] | 359 | 3-(3-nitrophenyl)-3-[4-(7H-pyrrolo[2,3-d]pyrimidin-4-yl)-1H-pyrazol-1-yl]propanenitrile trifluoroacetate | Ex 61 |
| 442 | 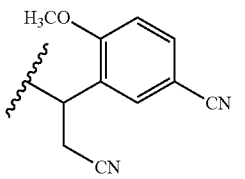 [SMILES: *C(CC#N)c1cc(C#N)ccc1OC] | 422 424 | 3-(5-bromo-2-methoxyphenyl)-3-[4-(7H-pyrrolo[2,3-d]pyrimidin-4-yl)-1H-pyrazol-1-yl]propanenitrile | Ex 61 |
| 443 | 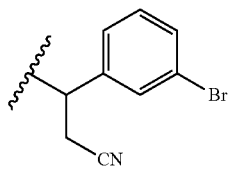 [SMILES: *C(CC#N)c1cccc(Br)c1] | 369 | 3-{2-cyano-1-[4-(7H-pyrrolo-[2,3-d]pyrimidin-4-yl)-1H-pyrazol-1-yl]ethyl}-4-methoxybenzonitrile trifluoroacetate | Ex 61 |
| 444 | 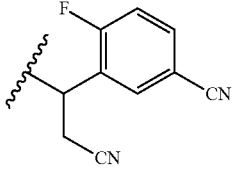 [SMILES: *C(CC#N)c1cc(C#N)ccc1F] | 392 394 | 3-(3-bromophenyl)-3-[4-(7H-pyrrolo[2,3-d]pyrimidin-4-yl)-1H-pyrazol-1-yl]propanenitrile trifluoroacetate | Ex 61 |
| 445 | 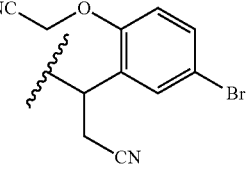 | 357 | 3-{2-cyano-1-[4-(7H-pyrrolo-[2,3-d]pyrimidin-4-yl)-1H-pyrazol-1-yl]ethyl}-4-fluorobenzonitrile trifluoroacetate | Ex 61 |
| 446 | 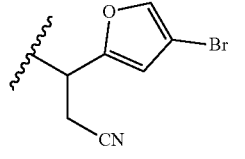 [SMILES: *C(CC#N)c1cc(Br)co1] | 447 449 | 3-[5-bromo-2-(cyanomethoxy)-phenyl]-3-[4-(7H-pyrrolo[2,3-d]-pyrimidin-4-yl)-1H-pyrazol-1-yl]-propanenitrile | Ex 61 |
| 447 |  | 385 383 | 3-(4-bromo-2-furyl)-3-[4-(7H-pyrrolo[2,3-d]pyrimidin-4-yl)-1H-pyrazol-1-yl]propanenitrile | Ex 61 |

TABLE 11-continued

| Ex. No. | —(Y)ₙ—Z | MS (M + H)⁺ | Name | Prep. |
|---|---|---|---|---|
| 448 | | 394 | 4-(cyanomethoxy)-3-{2-cyano-1-[4-(7H-pyrrolo[2,3-d]pyrimidin-4-yl)-1H-pyrazol-1-yl]ethyl}-benzonitrile trifluoroacetate | Ex 61 |
| 449 | | 396 394 | 3-(4-bromopyridin-2-yl)-3-[4-(7H-pyrrolo[2,3-d]pyrimidin-4-yl)-1H-pyrazol-1-yl]propanenitrile | Ex 61 |
| 450 | | 341 | 2-{2-cyano-1-[4-(7H-pyrrolo-[2,3-d]pyrimidin-4-yl)-1H-pyrazol-1-yl]ethyl}isonicotinonitrile trifluoroacetate | Ex 431 |
| 451 | | 330 | 5-{2-cyano-1-[4-(7H-pyrrolo[2,3-d]pyrimidin-4-yl)-1H-pyrazol-1-yl]-ethyl}-3-furonitrile trifluoroacetate | Ex 431 |
| 452 | | 447 449 | 3-[2-bromo-5-(cyanomethoxy)-phenyl]-3-[4-(7H-pyrrolo[2,3-d]-pyrimidin-4-yl)-1H-pyrazol-1-yl]-propanenitrile | Ex 61 |
| 453 | | 394 | 4-(cyanomethoxy)-2-{2-cyano-1-[4-(7H-pyrrolo[2,3-d]pyrimidin-4-yl)-1H-pyrazol-1-yl]ethyl}-benzonitrile trifluoroacetate | Ex 61 |
| 454 | | 317 | 3-pyrimidin-5-yl-3-[4-(7H-pyrrolo-[2,3-d]pyrimidin-4-yl)-1H-pyrazol-1-yl]propanenitrile trifluoroacetate | Ex 61 |

TABLE 11-continued

| Ex. No. | —(Y)ₙ—Z | MS (M + H)⁺ | Name | Prep. |
|---|---|---|---|---|
| 455 | (2-bromopyridin-4-yl with CH₂CN) | 396 394 | 3-(2-bromopyridin-4-yl)-3-[4-(7H-pyrrolo[2,3-d]pyrimidin-4-yl)-1H-pyrazol-1-yl]propanenitrile trifluoroacetate | Ex 61 |
| 456 | (4-pyridyl-2-CN with CH₂CN) | 341 | 4-{2-cyano-1-[4-(7H-pyrrolo-[2,3-d]pyrimidin-4-yl)-1H-pyrazol-1-yl]ethyl}pyridine-2-carbonitrile trifluoroacetate | Ex 421 |
| 457 | (5-methoxypyridin-3-yl with CH₂CN) | 346 | 3-(5-methoxypyridin-3-yl)-3-[4-(7H-pyrrolo[2,3-d]pyrimidin-4-yl)-1H-pyrazol-1-yl]propanenitrile trifluoroacetate | Ex 61 |
| 458 | (3-chlorophenyl with CH₂CN) | 348 | 3-(3-chlorophenyl)-3-[4-(7H-pyrrolo[2,3-d]pyrimidin-4-yl)-1H-pyrazol-1-yl]propanenitrile trifluoroacetate | Ex 61 |
| 459 | (3-CF₃-phenyl with CH₂CN) | 382 | 3-[4-(7H-pyrrolo[2,3-d]pyrimidin-4-yl)-1H-pyrazol-1-yl]-3-[3-(trifluoromethyl)phenyl]-propanenitrile trifluoroacetate | Ex 61 |
| 460 | (3-phenoxyphenyl with CH₂CN) | 406 | 3-(3-phenoxyphenyl)-3-[4-(7H-pyrrolo[2,3-d]pyrimidin-4-yl)-1H-pyrazol-1-yl]propanenitrile trifluoroacetate | Ex 61 |
| 461 | (3-OCF₃-phenyl with CH₂CN) | 398 | 3-[4-(7H-pyrrolo[2,3-d]pyrimidin-4-yl)-1H-pyrazol-1-yl]-3-[3-(trifluoromethoxy)phenyl]propane-nitrile trifluoroacetate | Ex 61 |

TABLE 11-continued

| Ex. No. | —(Y)ₙ—Z | MS (M + H)⁺ | Name | Prep. |
|---|---|---|---|---|
| 462 | | 373 | methyl 3-{2-cyano-1-[4-(7H-pyrrolo[2,3-d]pyrimidin-4-yl)-1H-pyrazol-1-yl]ethyl}benzoate | Ex 61 |
| 463 | | 359 | 3-{2-cyano-1-[4-(7H-pyrrolo-[2,3-d]pyrimidin-4-yl)-1H-pyrazol-1-yl]ethyl}benzoic acid | Ex 61 |
| 464 | | 380 | 3-[3-(1H-pyrazol-4-yl)phenyl]-3-[4-(7H-pyrrolo[2,3-d]pyrimidin-4-yl)-1H-pyrazol-1-yl]propanenitrile | Ex 482 |
| 467 | | 329 | 3-(3-aminophenyl)-3-[4-(7H-pyrrolo[2,3-d]pyrimidin-4-yl)-1H-pyrazol-1-yl]propanenitrile Bis trifluoroacetate | Ex 467 |
| 468 | | 371 | N-(3-{2-cyano-1-[4-(7H-pyrrolo[2,3-d]pyrimidin-4-yl)-1H-pyrazol-1-yl]ethyl}phenyl)-acetamide trifluoroacetate | Ex 468 |
| 469 | | 407 | N-(3-{2-cyano-1-[4-(7H-pyrrolo[2,3-d]pyrimidin-4-yl)-1H-pyrazol-1-yl]ethyl}phenyl)-methanesulfonamide | Ex 468 |
| 470 | | 346 | 4-{2-cyano-1-[4-(7H-pyrrolo-[2,3-d]pyrimidin-4-yl)-1H-pyrazol-1-yl]ethyl}thiophene-2-carbonitrile trifluoroacetate | Ex 470 |

TABLE 11-continued

| Ex. No. | —(Y)ₙ—Z | MS (M + H)⁺ | Name | Prep. |
|---|---|---|---|---|
| 471 | (5-cyanothiophen-2-yl with CH(CH₂CN)) | 346 | 5-{2-cyano-1-[4-(7H-pyrrolo-[2,3-d]pyrimidin-4-yl)-1H-pyrazol-1-yl]ethyl}thiophene-2-carbonitrile trifluoroacetate | Ex 471 |
| 472 | (3-(morpholin-4-ylcarbonyl)phenyl with CH(CH₂CN)) | 428 | 3-[3-(morpholin-4-ylcarbonyl)-phenyl]-3-[4-(7H-pyrrolo[2,3-d]-pyrimidin-4-yl)-1H-pyrazol-1-yl]-propanenitrile trifluoroacetate | Ex 472 |
| 475 | (3-(N-(2-aminoethyl)carbamoyl)phenyl with CH(CH₂CN)) | 401 | N-(2-aminoethyl)-3-{2-cyano-1-[4-(7H-pyrrolo[2,3-d]pyrimidin-4-yl)-1H-pyrazol-1-yl]ethyl}benzamide Bis trifluoroacetate | Ex 472 |
| 476 | (5-formyl-3-thienyl with CH(CH₂CN)) | 349 | 3-(5-formyl-3-thienyl)-3-[4-(7H-pyrrolo[2,3-d]pyrimidin-4-yl)-1H-pyrazol-1-yl]propanenitrile trifluoroacetate | Ex 61 |
| 477 | (3-(N-methylcarbamoyl)phenyl with CH(CH₂CN)) | 372 | 3-{2-cyano-1-[4-(7H-pyrrolo-[2,3-d]pyrimidin-4-yl)-1H-pyrazol-1-yl]ethyl}-N-methylbenzamide trifluoroacetate | Ex 472 |
| 478 | (3-(cyanoacetamido)phenyl with CH(CH₂CN)) | 396 | 2-cyano-N-(3-{2-cyano-1-[4-(7H-pyrrolo[2,3-d]pyrimidin-4-yl)-1H-pyrazol-1-yl]ethyl}phenyl)-acetamide trifluoroacetate | Ex 472 |
| 479 | (3-(nicotinamido)phenyl with CH(CH₂CN)) | 434 | N-(3-{2-cyano-1-[4-(7H-pyrrolo[2,3-d]pyrimidin-4-yl)-1H-pyrazol-1-yl]ethyl}phenyl)-nicotinamide Bis trifluoroacetate | Ex 478 |

TABLE 11-continued

| Ex. No. | —(Y)ₙ—Z | MS (M + H)⁺ | Name | Prep. |
| --- | --- | --- | --- | --- |
| 480 | | 414 | N-(3-{2-cyano-1-[4-(7H-pyrrolo[2,3-d]pyrimidin-4-yl)-1H-pyrazol-1-yl]ethyl}phenyl)-N'-isopropylurea trifluoroacetate | Ex 468 |
| 481 | | 415 | isopropyl (3-{2-cyano-1-[4-(7H-pyrrolo[2,3-d]pyrimidin-4-yl)-1H-pyrazol-1-yl]ethyl}phenyl)-carbamate trifluoroacetate | Ex 468 |
| 482 | | 392 | 3-(5-phenylpyridin-3-yl)-3-[4-(7H-pyrrolo[2,3-d]pyrimidin-4-yl)-1H-pyrazol-1-yl]propanenitrile-trifluoroacetate | Ex 482 |
| 483 | | 393 | 3-(3,3'-bipyridin-5-yl)-3-[4-(7H-pyrrolo[2,3-d]pyrimidin-4-yl)-1H-pyrazol-1-yl]propanenitrile-trifluoroacetate | Ex 482 |
| 484 | | 394 | 3-(5-pyrimidin-5-ylpyridin-3-yl)-3-[4-(7H-pyrrolo[2,3-d]pyrimidin-4-yl)-1H-pyrazol-1-yl]propanenitrile | Ex 482 |
| 485 | | 396 | 3-[5-(1-methyl-1H-pyrazol-4-yl)-pyridin-3-yl]-3-[4-(7H-pyrrolo[2,3-d]pyrimidin-4-yl)-1H-pyrazol-1-yl]-propanenitrile trifluoroacetate | Ex 482 |

TABLE 11-continued

| Ex. No. | —(Y)ₙ—Z | MS (M + H)⁺ | Name | Prep. |
|---|---|---|---|---|
| 486 | | 339 | 3-(5-ethynylpyridin-3-yl)-3-[4-(7H-pyrrolo[2,3-d]pyrimidin-4-yl)-1H-pyrazol-1-yl]propanenitrile trifluoroacetate | Ex 486 |
| 488 | | 424 | 3-[5-(phenylthio)pyridin-3-yl]-3-[4-(7H-pyrrolo[2,3-d]pyrimidin-4-yl)-1H-pyrazol-1-yl]propanenitrile trifluoroacetate | Ex 488 |
| 489 | | 402 400 | 3-(2-bromo-1,3-thiazol-5-yl)-3-[4-(7H-pyrrolo[2,3-d]pyrimidin-4-yl)-1H-pyrazol-1-yl]propanenitrile | Ex 61 |
| 490 | | 300 | ethyl 3-[4-(7H-pyrrolo[2,3-d]-pyrimidin-4-yl)-1H-pyrazol-1-yl]-butanoate | Ex 61 |
| 491 | | 401 | 3-(5-morpholin-4-ylpyridin-3-yl)-3-[4-(7H-pyrrolo[2,3-d]pyrimidin-4-yl)-1H-pyrazol-1-yl]propanenitrile | Ex 491 |
| 492 | | 319 | 3-(1-methyl-1H-pyrazol-4-yl)-3-[4-(7H-pyrrolo[2,3-d]pyrimidin-4-yl)-1H-pyrazol-1-yl]propanenitrile | Ex 61 |

TABLE 11-continued

| Ex. No. | —(Y)ₙ—Z | MS (M + H)⁺ | Name | Prep. |
|---|---|---|---|---|
| 493 | | 357 | 4-{1-[1-phenyl-2-(1H-1,2,4-triazol-1-yl)ethyl]-1H-pyrazol-4-yl}-7H-pyrrolo[2,3-d]pyrimidine | Ex 250 |
| 494 | | 357 | 4-{1-[1-phenyl-2-(4H-1,2,4-triazol-4-yl)ethyl]-1H-pyrazol-4-yl}-7H-pyrrolo[2,3-d]pyrimidine | Ex 250 |
| 495 | | 392 | 3-(3-pyridin-3-ylphenyl)-3-[4-(7H-pyrrolo[2,3-d]pyrimidin-4-yl)-1H-pyrazol-1-yl]propanenitrile | Ex 482 |
| 496 | | 440 | 3-[5-(phenylsulfinyl)pyridin-3-yl]-3-[4-(7H-pyrrolo[2,3-d]pyrimidin-4-yl)-1H-pyrazol-1-yl]propanenitrile trifluoroacetate | Ex 496 |
| 497 | | 456 | 3-[5-(phenylsulfonyl)pyridin-3-yl]-3-[4-(7H-pyrrolo[2,3-d]pyrimidin-4-yl)-1H-pyrazol-1-yl]propanenitrile trifluoroacetate | Ex 497 |
| 498 | | 272 | 3-[4-(7H-pyrrolo[2,3-d]pyrimidin-4-yl)-1H-pyrazol-1-yl]pentan-1-ol | Ex 498 |
| 499 | | 330 | methyl 3-[4-(7H-pyrrolo[2,3-d]pyrimidin-4-yl)-1H-pyrazol-1-yl]pentyl carbonate | Ex 499 |

TABLE 11-continued

| Ex. No. | —(Y)$_n$—Z | MS (M + H)$^+$ | Name | Prep. |
|---|---|---|---|---|
| 500(a) | (ethyl-CH-CH$_2$-CH=N-OH) | 285 | (1E)-3-[4-(7H-pyrrolo[2,3-d]pyrimidin-4-yl)-1H-pyrazol-1-yl]-pentanal oxime | Ex 500 |
| 501 | (ethyl-CH-CH$_2$-CH=N-OCH$_3$) | 299 | (1E)-3-[4-(7H-pyrrolo[2,3-d]pyrimidin-4-yl)-1H-pyrazol-1-yl]-pentanal O-methyloxime | Ex 501 |
| 502 | (ethyl-CH-CH$_2$-CH=N-OCH$_3$, Z isomer) | 299 | (1Z)-3-[4-(7H-pyrrolo[2,3-d]pyrimidin-4-yl)-1H-pyrazol-1-yl]-pentanal O-methyloxime | Ex 502 |
| 503 | (ethyl-CH-CH$_2$-CH=CBr$_2$) | 426 | 4-[1-(4,4-dibromo-1-ethylbut-3-en-1-yl)-1H-pyrazol-4-yl]-7H-pyrrolo[2,3-d]pyrimidine trifluoroacetate | Ex 503 |
| 504 | (CH(CH$_2$CN)-pyridin-3-yl-5-S-thiazol-2-yl) | 431 | 3-[4-(7H-pyrrolo[2,3-d]pyrimidin-4-yl)-1H-pyrazol-1-yl]-3-[5-(1,3-thiazol-2-ylthio)pyridin-3-yl]-propanenitrile bis(trifluoroacetate) | Ex 488 |
| 505 | (CH(CH$_2$CN)-pyridin-3-yl-5-S-ethyl) | 376 | 3-[5-(ethylthio)pyridin-3-yl]-3-[4-(7H-pyrrolo[2,3-d]pyrimidin-4-yl)-1H-pyrazol-1-yl]propanenitrile | Ex 488 |
| 506 | (ethyl-CH-CH$_2$-C≡CH) | 266 | 4-[1-(1-ethylbut-3-yn-1-yl)-1H-pyrazol-4-yl]-7H-pyrrolo[2,3-d]pyrimidine trifluoroacetate | Ex 506 |

TABLE 11-continued

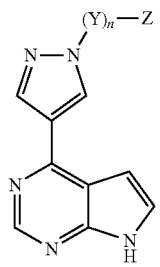

| Ex. No. | —(Y)ₙ—Z | MS (M + H)⁺ | Name | Prep. |
|---|---|---|---|---|
| 507 | | 295 | 4-{1-[1-methyl-2-(1H-1,2,4-triazol-1-yl)ethyl]-1H-pyrazol-4-yl}-7H-pyrrolo[2,3-d]pyrimidine | Ex 250 |
| 508 | | 270 | 4-[4-(7H-pyrrolo[2,3-d]pyrimidin-4-yl)-1H-pyrazol-1-yl]pentan-2-one trifluoroacetate | Ex 61 |
| 509 | | 318 | 1-phenyl-2-[4-(7H-pyrrolo-[2,3-d]pyrimidin-4-yl)-1H-pyrazol-1-yl]propan-1-one | Ex 250 |
| 510 | | 392 | 3-[5-(ethylsulfinyl)pyridin-3-yl]-3-[4-(7H-pyrrolo[2,3-d]pyrimidin-4-yl)-1H-pyrazol-1-yl]propanenitrile | Ex 496 |
| 511 | | 408 | 3-[5-(ethylsulfonyl)pyridin-3-yl]-3-[4-(7H-pyrrolo[2,3-d]pyrimidin-4-yl)-1H-pyrazol-1-yl]propanenitrile | Ex 497 |
| 512 | | 430 | 3-[5-(cyclohexylthio)pyridin-3-yl]-3-[4-(7H-pyrrolo[2,3-d]pyrimidin-4-yl)-1H-pyrazol-1-yl]-propanenitrile | Ex 488 |

TABLE 11-continued

| Ex. No. | —(Y)ₙ—Z | MS (M + H)⁺ | Name | Prep. |
|---|---|---|---|---|
| 513 de#1 | | 320 | 1-phenyl-2-[4-(7H-pyrrolo-[2,3-d]pyrimidin-4-yl)-1H-pyrazol-1-yl]propan-1-ol | Ex 509 |
| 513 de#2 | | 320 | 1-phenyl-2-[4-(7H-pyrrolo[2,3-d]-pyrimidin-4-yl)-1H-pyrazol-1-yl]-propan-1-ol | Ex 509 |
| 514 | | 375 | 3-[3-(ethylthio)phenyl]-3-[4-(7H-pyrrolo[2,3-d]pyrimidin-4-yl)-1H-pyrazol-1-yl]propanenitrile | Ex 516 |
| 515 | | 391 | 3-[3-(ethylsulfinyl)phenyl]-3-[4-(7H-pyrrolo[2,3-d]pyrimidin-4-yl)-1H-pyrazol-1-yl]propanenitrile | Ex 516 |
| 516 ee#1 | | 407 | 3-[3-(ethylsulfonyl)phenyl]-3-[4-(7H-pyrrolo[2,3-d]pyrimidin-4-yl)-1H-pyrazol-1-yl]propanenitrile | Ex 516 |
| 516 ee#2 | | 407 | 3-[3-(ethylsulfonyl)phenyl]-3-[4-(7H-pyrrolo[2,3-d]pyrimidin-4-yl)-1H-pyrazol-1-yl]propanenitrile | Ex 516 |
| 517 | | 462 | 3-[5-(cyclohexylsulfonyl)pyridin-3-yl]-3-[4-(7H-pyrrolo[2,3-d]-pyrimidin-4-yl)-1H-pyrazol-1-yl]-propanenitrile | Ex 497 |

TABLE 11-continued

| Ex. No. | —(Y)ₙ—Z | MS (M + H)⁺ | Name | Prep. |
|---|---|---|---|---|
| 518 | | 446 | 3-[5-(cyclohexylsulfinyl)pyridin-3-yl]-3-[4-(7H-pyrrolo[2,3-d]-pyrimidin-4-yl)-1H-pyrazol-1-yl]-propanenitrile | Ex 496 |
| 519 | | 304 | 4-[1-(1-methyl-2-phenylethyl)-1H-pyrazol-4-yl]-7H-pyrrolo[2,3-d]-pyrimidine | Ex 250 |
| 520 | | 310 | 4-{1-[1-methyl-2-(3-thienyl)ethyl]-1H-pyrazol-4-yl}-7H-pyrrolo-[2,3-d]pyrimidine | Ex 250 |
| 521 | | 315 | 3-{1-[4-(7H-pyrrolo[2,3-d]-pyrimidin-4-yl)-1H-pyrazol-1-yl]-ethyl}benzonitrile | Ex 250 |
| 522 | | 294 | 4-{1-[2-(1H-imidazol-1-yl)-1-methylethyl]-1H-pyrazol-4-yl}-7H-pyrrolo[2,3-d]pyrimidine | Ex 250 |
| 523 | | 310 | 4-{1-[1-methyl-2-(3-methyl-1,2,4-oxadiazol-5-yl)ethyl]-1H-pyrazol-4-yl}-7H-pyrrolo[2,3-d]pyrimidine | Ex 250 |
| 524 | | 393 | 3-[3-(methylsulfonyl)phenyl]-3-[4-(7H-pyrrolo[2,3-d]pyrimidin-4-yl)-1H-pyrazol-1-yl]propanenitrile | Ex 516 |
| 525 | | 392 | 3-(3-pyridin-4-ylphenyl)-3-[4-(7H-pyrrolo[2,3-d]pyrimidin-4-yl)-1H-pyrazol-1-yl]propanenitrile | Ex 482 |

TABLE 11-continued

| Ex. No. | —(Y)ₙ—Z | MS (M + H)⁺ | Name | Prep. |
|---|---|---|---|---|
| 526 | (2-ethyl-pent-4-enyl group) | 268 | 4-[1-(1-ethylbut-3-en-1-yl)-1H-pyrazol-4-yl]-7H-pyrrolo[2,3-d]-pyrimidine | Ex 526 |
| 527 | (1,3-dimethylbut-3-enyl group) | 268 | 4-[1-(1,3-dimethylbut-3-en-1-yl)-1H-pyrazol-4-yl]-7H-pyrrolo[2,3-d]pyrimidine | Ex 526 |
| 528 | (3-[5-(isopropylthio)pyridin-3-yl]propanenitrile group) | 390 | 3-[5-(isopropylthio)pyridin-3-yl]-3-[4-(7H-pyrrolo[2,3-d]pyrimidin-4-yl)-1H-pyrazol-1-yl]propanenitrile | Ex 488 |
| 529 | (3-[5-(isopropylsulfinyl)pyridin-3-yl]propanenitrile group) | 406 | 3-[5-(isopropylsulfinyl)pyridin-3-yl]-3-[4-(7H-pyrrolo[2,3-d]-pyrimidin-4-yl)-1H-pyrazol-1-yl]-propanenitrile | Ex 496 |
| 530 | (3-[5-(isopropylsulfonyl)pyridin-3-yl]propanenitrile group) | 422 | 3-[5-(isopropylsulfonyl)pyridin-3-yl]-3-[4-(7H-pyrrolo[2,3-d]-pyrimidin-4-yl)-1H-pyrazol-1-yl]-propanenitrile | Ex 497 |
| 531 ee#1 | (3-[5-(trifluoromethyl)pyridin-3-yl]propanenitrile group) | 384 | 3-[4-(7H-pyrrolo[2,3-d]pyrimidin-4-yl)-1H-pyrazol-1-yl]-3-[5-(trifluoromethyl)pyridin-3-yl]-propanenitrile | Ex 431 |
| 531 ee#2 | (3-[5-(trifluoromethyl)pyridin-3-yl]propanenitrile group) | 384 | 3-[4-(7H-pyrrolo[2,3-d]pyrimidin-4-yl)-1H-pyrazol-1-yl]-3-[5-(trifluoromethyl)pyridin-3-yl]-propanenitrile | Ex 431 |

TABLE 11-continued

| Ex. No. | —(Y)ₙ—Z | MS (M + H)⁺ | Name | Prep. |
|---|---|---|---|---|
| 532 | (isopropylamide with 3-CF₃-phenyl) | 401 | 2-[4-(7H-pyrrolo[2,3-d]pyrimidin-4-yl)-1H-pyrazol-1-yl]-N-[3-(trifluoromethyl)phenyl]-propanamide | Ex 250 |
| 533 | (isopropylamide with 2-naphthyl) | 383 | N-2-naphthyl-2-[4-(7H-pyrrolo-[2,3-d]pyrimidin-4-yl)-1H-pyrazol-1-yl]propanamide | Ex 250 |
| 534 | (isopropylamide with 1-naphthyl) | 383 | N-1-naphthyl-2-[4-(7H-pyrrolo-[2,3-d]pyrimidin-4-yl)-1H-pyrazol-1-yl]propanamide | Ex 250 |
| 535 | (isopropylamide with 3-CN-phenyl) | 358 | N-(3-cyanophenyl)-2-[4-(7H-pyrrolo[2,3-d]pyrimidin-4-yl)-1H-pyrazol-1-yl]propanamide | Ex 250 |
| 536 | (isopropylamide with benzyl) | 347 | N-benzyl-2-[4-(7H-pyrrolo-[2,3-d]pyrimidin-4-yl)-1H-pyrazol-1-yl]propanamide | Ex 250 |
| 537 | (sec-butylamide with phenyl) | 347 | N-phenyl-2-[4-(7H-pyrrolo[2,3-d]-pyrimidin-4-yl)-1H-pyrazol-1-yl]-butanamide | Ex 250 |
| 538 | (sec-butylamide with 4-OC₆H₅-phenyl) | 439 | N-(4-phenoxyphenyl)-2-[4-(7H-pyrrolo[2,3-d]pyrimidin-4-yl)-1H-pyrazol-1-yl]butanamide | Ex 250 |
| 539 | (sec-butylamide with 2-naphthyl) | 397 | N-2-naphthyl-2-[4-(7H-pyrrolo-[2,3-d]pyrimidin-4-yl)-1H-pyrazol-1-yl]butanamide | Ex 250 |

TABLE 11-continued

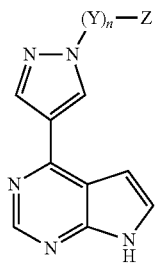

| Ex. No. | —(Y)ₙ—Z | MS (M + H)⁺ | Name | Prep. |
|---|---|---|---|---|
| 540 | | 372 | N-(3-cyanophenyl)-2-[4-(7H-pyrrolo[2,3-d]pyrimidin-4-yl)-1H-pyrazol-1-yl]butanamide | Ex 250 |
| 541 | | 423 | N-biphenyl-4-yl-2-[4-(7H-pyrrolo[2,3-d]pyrimidin-4-yl)-1H-pyrazol-1-yl]butanamide | Ex 250 |
| 542 | | 437 | N-(biphenyl-4-ylmethyl)-2-[4-(7H-pyrrolo[2,3-d]pyrimidin-4-yl)-1H-pyrazol-1-yl]butanamide | Ex 250 |
| 543 | | 437 | N-(biphenyl-3-ylmethyl)-2-[4-(7H-pyrrolo[2,3-d]pyrimidin-4-yl)-1H-pyrazol-1-yl]butanamide | Ex 250 |
| 544 | | 372 | N-(4-cyanophenyl)-2-[4-(7H-pyrrolo[2,3-d]pyrimidin-4-yl)-1H-pyrazol-1-yl]butanamide | Ex 250 |
| 545 | | 397 | N-1-naphthyl-2-[4-(7H-pyrrolo[2,3-d]pyrimidin-4-yl)-1H-pyrazol-1-yl]butanamide | Ex 250 |
| 546 | | 435 | 5-{2-cyano-1-[4-(7H-pyrrolo[2,3-d]pyrimidin-4-yl)-1H-pyrazol-1-yl]ethyl}-N-phenylnicotinamide trifluoroacetate | Ex 431 |

TABLE 11-continued

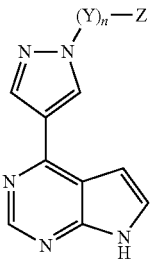

| Ex. No. | —(Y)ₙ—Z | MS (M + H)⁺ | Name | Prep. |
|---|---|---|---|---|
| 547 | 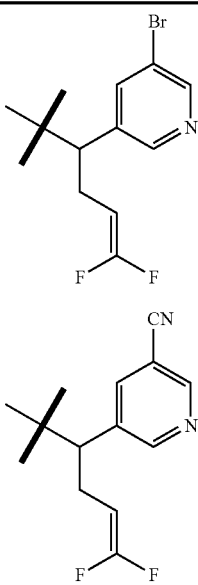 | 430, 432 | 4-{1-[1-(5-bromopyridin-3-yl)-4,4-difluorobut-3-en-1-yl]-1H-pyrazol-4-yl}-7H-pyrrolo[2,3-d]pyrimidine | Ex 717 |
| 548 | 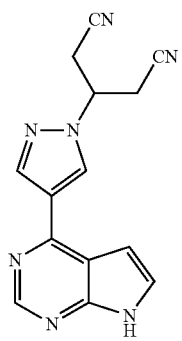 [SMILES: N#CCC(CC#N)n1cc(-c2ncnc3[nH]ccc23)cn1] | 378 | 5-{4,4-difluoro-1-[4-(7H-pyrrolo[2,3-d]pyrimidin-4-yl)-1H-pyrazol-1-yl]but-3-en-1-yl}nicotinonitrile | Ex 717 |

Example 407

3-[4-(7H-Pyrrolo[2,3-d]pyrimidin-4-yl)-1H-pyrazol-1-yl]pentanedinitrile

Step 1: Dimethyl 3-[4-(7-{[2-(trimethylsilyl)ethoxy]methyl}-7H-pyrrolo[2,3-d]pyrimidin-4-yl)-1H-pyrazol-1-yl]pentanedioate 4-(1H-Pyrazol-4-yl)-7-[2-(trimethylsilyl)ethoxy]methyl-7H-pyrrolo[2,3-d]pyrimidine (31.0 g, 0.0983 mol) was suspended in ACN (620 mL, 12 mol), and DBU (9.3 mL, 0.062 mol) was added under nitrogen. The reaction was heated to 65° C. and dimethyl (2E)-pent-2-enedioate (16 mL, 0.12 mol) was added in 5 mL portions over 2 h. After stirring overnight, the reaction was complete. The reaction was allowed to cool to room temperature and was concentrated in vacuo to give a dark oil. The oil was partitioned between ethyl acetate and water. The organic layer was washed with 1.0 N HCl, brine, dried over magnesium sulfate, and then concentrated to give a dark oil. The viscous oil was triturated with ethyl ether 3×500 mL to give a dark precipitate. The oil was taken up in ethyl acetate to form a solid. The solids were collected, washed with ethyl ether and dried to give dimethyl 3-[4-(7-{[2-(trimethylsilyl)ethoxy]methyl}-7H-pyrrolo[2,3-d]pyrimidin-4-yl)-1H-pyrazol-1-yl]pentanedioate as a white powder (29.5 gm, 64%), LC/MS (M+H)⁺: 474, ¹H NMR (DMSO-d6) δ 9.1 (s,1H), 9.02 (s,1H), 8.65 (s, 1H), 8.11 (d, 1H), 7.42(d, 1H), 5.78(s, 2H), 5.27(m, 1H), 3.65(m, 8H), 3.15(m, 4H), 0.95(t, 2H), 0.1(s, 9H).

Step 2: 3-[4-(7-[2-(Trimethylsilyl)ethoxy]methyl-7H-pyrrolo[2,3-d]pyrimidin-4-yl)-1H-pyrazol-1-yl]-pentanedioic acid Dimethyl 3-[4-(7-{[2-(trimethylsilyl)ethoxy]methyl}-7H-pyrrolo[2,3-d]pyrimidin-4-yl)-1H-pyrazol-1-yl]pentanedioate (43.0 g, 0.0908 mol) was dissolved in methanol (271.2 mL, 6.695 mol) and lithium hydroxide monohydrate (15 g, 0.36 mol) dissolved in water (125 mL) was added. The reaction was stirred at rt for 2 h. The methanol was removed in vacuo and a resulting aqueous layer was cooled in an ice bath. The solution was made acidic pH ~4 with 1N HCl to give a white precipitate. The solid precipitate was collected, washed with water, dried to give 3-[4-(7-[2-(trimethylsilyl) ethoxy]methyl-7H-pyrrolo[2,3-d]pyrimidin-4-yl)-1H-pyrazol-1pentanedioic acid as a white crystalline powder (31.8 gm, 80%), LC/MS (M+H)$^+$: 446, $^1$H NMR (DMSO-d$_6$) δ 8.85□s□□ 1H), 8.75 (s, 1H), 8.42(s, 1H), 7.85(d, 1H), 7.17(d, 1H), 5.71(s, 2H), 5.18(m,1H), 3.65(t, 2H), 3.05(m, 4H), 0.92(t, 2H), 0.1(s, 9H).

Step 3: 3-[4-(7-[2-(Trimethylsilyl)ethoxy]methyl-7H-pyrrolo[2,3-d]pyrimidin-4-yl)-1H-pyrazol-1-yl]-pentanediamide 3-[4-(7-[2-(Trimethylsilyl)ethoxy]methyl-7H-pyrrolo[2,3-d]pyrimidin-4-yl)-1H-pyrazol-1-yl]pentanedioic acid (31.80 g, 0.07137 mol) was dissolved in DMF (636 mL, 8.21 mol) under nitrogen cooled in an ice bath and CDI (34.7 g, 0.214 mol) was added. This mixture was allowed to stir for 30 minutes and then allowed to warm to rt. After stirring for 2 h ammonia (12.2 g, 0.714 mol) was bubbled through the solution for 30 minutes giving a cloudy suspension. The reaction mixture was concentrated to remove some of the DMF (~200 mL) and then water was added slowly to give a white precipitate. This mixture was cooled in an ice bath and the solid precipitate was collected, washed with water and dried in vacuo to give 3-[4-(7-[2-(trimethylsilyl)ethoxy] methyl-7H-pyrrolo[2,3-d]pyrimidin-4-yl)-1H-pyrazol-1-yl] pentanediamide as a white powder (29.0 gm, 91%), LC/MS (M+H)$^+$: 444, $^1$H NMR (DMSO-d$_6$) δ 8.85(s, 1H), 8.59(s, 1H), 8.40(s, 1H), 7.87(d,1H), 7.75(s, 2H), 7.15(d, 1H), 6.95(s, 2H), 5.73(s, 2H), 5.29(m, 1H), 3.63(t, 2H), 2.82(m, 2H), 2.73(m, 2H), 0.90(t, 2H), 0.1(s, 9H).

Step 4: 3-[4-(7-[2-(Trimethylsilyl)ethoxy]methyl-7H-pyrrolo[2,3-d]pyrimidin-4-yl)-1H-pyrazol-1-yl]-pentanedinitrile 3-[4-(7-[2-(Trimethylsilyl)ethoxy]methyl-7H-pyrrolo[2,3-d]pyrimidin-4-yl)-1H-pyrazol-1-yl]pentanediamide (29.0 g, 0.0654 mol) was partially dissolved in DMF (200 mL, 2 mol), DCM (200 mL, 3 mol) and TEA (36 mL, 0.26 mol) and cooled in an ice bath under nitrogen atmosphere. The trichloroacetyl chloride (15 mL, 0.14 mol) was added dropwise turning the reaction to a dark solution. This was stirred at 0° C. for ½ h. The reaction was then concentrated to remove the DCM and the resulting DMF solution was diluted with water to precipitate the product. The solid precipitate was collected and washed with water to give a dark solid. The solid was then dissolved in DCM and washed with brine, dried over magnesium sulfate and concentrated to give a very dark oily residue. The residue was taken up in DCM, and hexane was added until the solution became slightly cloudy. This was stirred at rt to precipitate 3-[4-(7-[2-(trimethylsilyl)ethoxy]methyl-7H-pyrrolo[2,3-d]-pyrimidin-4-yl)-1H-pyrazol-1-yl]pentanedinitrile as white needle-like crystals (22.7 gm, 85%), LC/MS (M+H)$^+$: 408, $^1$H NMR (DMSO-d$_6$) δ 9.07(s, 1H), 8.87(s, 1H), 8.59(s, 1H), 7.88(d, 1H), 7.19(d, 1H), 5.75(s, 2H), 5.30(m,1H), 3.62(t, 2H), 3.40(m, 4H), 0.91(t, 2H), 0.10(s, 9H).

Step 5: 3-[4-(7H-Pyrrolo[2,3-d]pyrimidin-4-yl)-1H-pyrazol-1-yl]pentanedinitrile

3-[4-(7-[2-(Trimethylsilyl)ethoxy]methyl-7H-pyrrolo[2,3-d]pyrimidin-4-yl)-1H-pyrazol-1-yl]pentanedinitrile (10.0 g, 0.0245 mol) was dissolved in ACN (200 mL, 3.83 mol) and water (20 g, 1.1 mol) at rt. To this lithium tetrafluoroborate (23.0 g, 0.245 mol) was added giving a cloudy solution. The reaction was heated to reflux and monitored by HPLC. After heating for 24 h the reaction was allowed to cool to rt and then cooled in an ice bath. To this, ammonium hydroxide (23 mL, 0.59 mol) was added slowly. The reaction was allowed to warm to rt. After stirring for 18 hs the reaction was diluted with water and concentrated in vacuo to remove the ACN, giving a precipitate.

The solids were collected, washed with water and dried to give the title compound as an off-white solid (6. 2 gm, 91%), LC/MS (M+H)$^+$: 278, $^1$H NMR (DMSO-d$_6$) δ 8.9(s, 1H), 8.72(s,1H), 8.43(s, 1H), 7.59(d, 1H), 6.92(d, 1H), 5.21(m, 1H), 3.25(m, 4H).

Example 421

5-{2-Cyano-1-[4-(7H-pyrrolo[2,3-d]pyrimidin-4-yl)-1H-pyrazol-1-yl]ethyl}-pyridine-2-carbonitrile trifluoroacetate

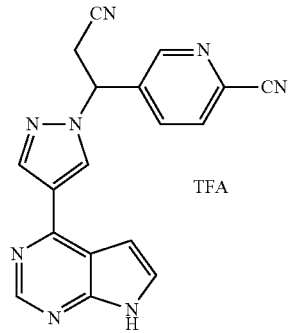 [SMILES: N#CCC(c1ccc(C#N)nc1)n1cc(-c2ncnc3[nH]ccc23)cn1]

Step 1: 3-(6-Chloropyridin-3-yl)-3-[4-(7H-pyrrolo [2,3-d]pyrimidin-4-yl)-1H-pyrazol-1-yl]propane-nitrile 3-(6-Chloropyridin-3-yl)-3-[4-(7-[2-(trimethylsilyl) ethoxy]methyl-7H-pyrrolo[2,3-d]-pyrimidin-4-yl)-1H-pyrazol-1-yl]propanenitrile (prepared by methods analogous to those described for Example 61) (0.070 g, 0.00014 mol) in TFA (3.0 mL, 0.039 mol) and DCM (3.0 mL, 0.047 mol) was stirred at room temperature for 1 hour. Solvent was removed in vacuo, and the residue was dissolved in methanol (4.0 mL, 0.099 mol) and ethylenediamine (0.07 mL, 0.001 mol). The reaction mixture was stirred at room temperature overnight. Solvent was removed in vacuo, the crude product was purified by preparative HPLC eluting with an ACN; water gradient buffered with ammonium hydroxide to pH=10, to give 3-(6-chloropyridin-3-yl)-3-[4-(7H-pyrrolo[2,3-d]pyrimidin-4-yl)-1H-pyrazol-1-yl]propanenitrile as a white powder (35 mg, 69%), LCMS (M+1)$^+$: 350, $^1$H NMR (DMSO-d$_6$)□ δ 12.21 (b, 1H), 9.00 (s, 1H), 8.78 (s, 1H), 8.62 (s, 1H), 8.58 (s, 1H), 8.00(m, 1H), 7.70(m, 2H), 7.00(s, 1H), 6.22(m, 1H), 3.90(m, 1H), 3.78(m, 1H)

Step 2: 5-2-Cyano-1-[4-(7H-pyrrolo[2,3-d]pyrimidin-4-yl)-1H-pyrazol-1-yl]ethylpyridine-2-carbonitrile trifluoroacetate A mixture of 3-(6-chloropyridin-3-yl)-3-[4-(7H-pyrrolo [2,3-d]pyrimidin-4-yl)-1H-pyrazol-1-yl]propanenitrile (0.025 g, 0.000071 mol) and zinc cyanide (0.08 g, 0.0007 mol) in DMF (1.0 mL, 0.013 mol) was degassed with nitrogen. To this mixture, tetrakis(triphenylphosphine)palladium(0) (0.04 g, 0.00004 mol) was added and the resulting mixture degassed again with dinitrogen. The reaction mixture was heated in a sealed tube at 170° C. for 15 minutes in a microwave (Personal Chemistry). After cooling to room temperature, the solids were filtered, rinsed with DMF and the combined solvent was concentrated in vacuo. The residue was triturated with hexanes (3×), and hexanes washes were discarded. The crude product was purified by preparative HPLC eluting with an ACN; water gradient containing 0.2% TFA to give the title compound as a white powder (16 mg, 49.27%), LCMS (M+1)+: 341, 1H NMR (DMSO-$d_6$) δ 12.50(b, 1H), 9.05(s, 1H), 8.89(s, 1H), 8.80(s, 1H), 8.58(s, 1H), 8.18(m, 2H), 7.78(s, 1H), 7.05(s, 1H), 6.20(m, 1H), 3.90(m, 1H), 3.77(m, 1H).

Example 428

4-[4-(7H-Pyrrolo[2,3-d]pyrimidin-4-yl)-1H-pyrazol-1-yl]heptanedinitrile

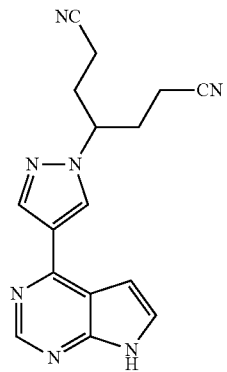 [SMILES: N#CCCC(CCC#N)n1cc(-c2ncnc3[nH]ccc23)cn1]

Step 1: 3-[4-(7-[2-(Trimethylsilyl)ethoxy]methyl-7H-pyrrolo[2,3-d]pyrimidin-4-yl)-1H-pyrazol-1-yl]pentane-1,5-diol Diethyl 3-[4-(7-[2-(trimethylsilyl)ethoxy]methyl-7H-pyrrolo[2,3 -d]pyrimidin-4-yl)-1H-pyrazol-1-yl]pentanedioate, prepared substantially as described in Example 407 (0.80 g, 0.0016 mol), was dissolved in THF (40 mL, 0.49 mol) and cooled in an ice bath under a nitrogen atmosphere. To this mixture, 1.0 M lithium tetrahydroaluminate in THF (3.2 mL) was added slowly. The reaction was stirred for 1 h, quenched with ice and partitioned between ethyl acetate and 1 N HCl. The organic layer was washed with brine, dried over magnesium sulfate and concentrated to give an amber oil. The product was purified by FCC on silica gel eluting with an ethyl acetate: methanol gradient to give 3-[4-(7-[2-(trimethylsilyl)ethoxy]methyl-7H-pyrrolo[2,3-d]pyrimidin-4-yl)-1H-pyrazol-1-yl]pentane-1,5-diol as a clear viscous oil (0.51 gm, 76%), LC/MS (M+H)+: 418, $^1$H NMR (DMSO-$d_6$) δ 8.85(s, 1H), 8.41(s, 1H), 8.37(s, 1H), 7.45(d, 1H), 6.83(d, 1H), 5.73(s, 2H), 4.91(m, 1H), 3.75(m, 2H), 3.59(m, 2H), 3.45(m, 2H), 2.18(m, 4H), 0.95(m, 2H), 0.1(s, 9H).

Step 2: 3-[4-(7-[2-(Trimethylsilyl)ethoxy]methyl-7H-pyrrolo[2,3-d]pyrimidin-4-yl)-1H-pyrazol-1-yl]pentane-1,5-diyl dimethanesulfonate A mixture of 3-[4-(7-[2-(trimethylsilyl)ethoxy]methyl-7H-pyrrolo[2,3-d]pyrimidin-4-yl)-1H-pyrazol-1-yl]pentane-1,5-diol (50 mg, 0.0001 mol) in DCM (2 mL, 0.03 mol) was cooled at 0° C. To this mixture, TEA (50 μL, 0.0004 mol) was added. The reaction was stirred for 15 minutes. Methanesulfonyl chloride (23 μL, 0.00030 mol) was added and the resulting mixture was stirred for 1 hour. Water was added and the product was extracted with ethyl acetate. The combined extracts were washed with saturated sodium chloride, dried over magnesium sulfate, filtered and concentrated to give 3-[4-(7-[2-(trimethylsilyl)ethoxy]methyl-7H-pyrrolo[2,3-d]pyrimidin-4-yl)-1H-pyrazol-1-yl]-pentane-1,5-diyl dimethanesulfonate (57 mg, 80%) as an oil. MS(ES): 574 (M+1).

Step 3: 4-[4-(7-[2-(Trimethylsilyl)ethoxy]methyl-7H-pyrrolo[2,3-d]pyrimidin-4-yl)-1H-pyrazol-1-yl]heptanedinitrile To a mixture of 3-[4-(7-[2-(trimethylsilyl)ethoxy]methyl-7H-pyrrolo[2,3-d]pyrimidin-4-yl)-1H-pyrazol-1-yl]pentane-1,5-diyl dimethanesulfonate (57 mg, 0.000099 mol) in DMSO (1 mL, 0.01 mol), sodium cyanide (10 mg, 0.0003 mol) was added and the mixture was stirred for 2 hours. The mixture was heated at 60° C. for 1 hour. Water was added and the product was extracted with ethyl acetate. The combined extracts were washed with saturated sodium chloride, dried over magnesium sulfate, filtered and concentrated to give 4-[4-(7-[2-(trimethylsilyl)ethoxy]methyl-7H-pyrrolo[2,3-d]pyrimidin-4-yl)-1H-pyrazol-1-yl]heptanedinitrile (40 mg, 90%) as an oil. MS(ES): 436 (M+1).

Step 4: 4-[4-(7H-Pyrrolo[2,3-d]pyrimidin-4-yl)-1H-pyrazol-1-yl]heptanedinitrile

Using a procedure analogous to Example 61 for the removal of the SEM protecting group, the title compound was prepared as a white amorphous solid, (17 mg, 60%) $^1$H NMR (400 MHz, DMSO): δ □8.75 (s, 1H), 8.65 (s, 1H), 8.4 (s, 1H), 7.6 (d, 1H), 7.0 (d, 1H), 4.5 (m, 1H), 2.35 (m, 4H), 2.2 (m, 4H). MS(ES): 306 (M+1).

Example 429

3-(5-Bromopyridin-3-yl)-3-[4-(7H-pyrrolo[2,3-d]pyrimidin-4-yl)-1H-pyrazol-1-yl]propanenitrile

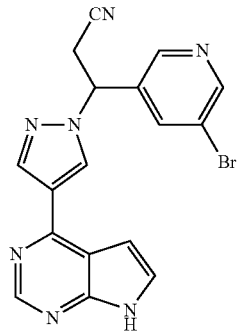 [SMILES: N#CCC(c1cncc(Br)c1)n1cc(-c2ncnc3[nH]ccc23)cn1]

Step 1: (2Z & E)-3-(5-Bromopyridin-3-yl]acrylonitrile

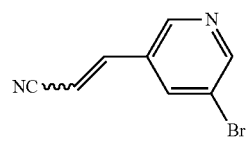 [SMILES: N#CC=Cc1cncc(Br)c1]

To a mixture of 1.0 M potassium tert-butoxide in THF (2.7 mL) at 0° C. (water-ice bath, under an atmosphere of nitrogen) was added diethyl cyanomethylphosphonate (0.48 mL, 0.0030 mol) in THF (4.0 mL, 0.049 mol), dropwise. The reaction mixture was warmed to room temperature, and then was cooled to 0° C., followed by dropwise addition of 5-bromonicotinaldehyde (0.5 g, 0.003 mol) in THF (1.0 mL, 0.012 mol). After stirring at room temperature for 20 hours, the reaction mixture was quenched with water and extracted with ethyl acetate. The organic layer was washed with brine, dried over anhydrous magnesium sulfate, filtered, and concentrated to give a crude product as a dark oil. The crude product was purified by flash chromatography on silica gel using ethyl acetate-hexanes 3:7 as eluent to give a mixture of cis and trans isomers (2)-3-(5-bromopyridin-3-yl)acrylonitrile as an off-white solid (268 mg, 47.69%). LCMS (M+1)+: 209, 211, 1H NMR (400 MHz, CDCl3): δ □8.75 (s,1H), 8.62(s,1H), 7.90(s,1H), 7.40(d, 1H), 6.00(d, 1H).

Step 2: 3-(5-Bromopyridin-3-yl)-3-[4-(7-[2-(trimethylsilyl)ethoxy]methyl-7H-pyrrolo[2,3-d]pyrimidin-4-yl)-1H-pyrazol-1-yl]propanenitrile To 4-(1H-pyrazol-4-yl)-7-[2 -(trimethylsilyl)ethoxy]methyl-7H-pyrrolo[2,3-d]pyrimidine (0.200 g, 0.000634 mol) in 1.0 mL of dry ACN was added DBU (0.10 mL, 0.00067 mol), followed by the addition of (2Z & E)-3-(5-bromopyridin-3-yl)acrylonitrile (0.234 g, 0.00112 mol) in 1.0 mL of ACN. The reaction mixture was stirred at 67° C. for 4 hours. Upon cooling, the mixture was partitioned between dilute hydrochloric acid and ethyl acetate. The organic layer was washed with saturated sodium chloride, dried over anhydrous sodium sulfate, and concentrated. The crude product was purified by flash chromatography on silica gel using ethyl acetate:hexanes (7:3) to give 3-[5-bromopyridin-3-yl)-3-[4-(7-[2-(trimethylsilyl)-ethoxy]-methyl-7H-pyrrolo[2,3 -d]pyrimidin-4-yl)-1H-pyrazol-1-yl] propanenitrile as an off-white solid (225 mg, 67.66%). LCMS (M+1)+: 524, 526: 1H NMR (400 MHz, CDCl3): δ□ 8.90(s, 1H), 8.80(s, 1H), 8.70(s, 1H), 8.42(s, 1H), 8.40(s, 1H), 8.00(s, 1H), 7.50(d, 1H), 6.82(d, 1H), 5.81(m, 1H), 5.75(s, 2H), 3.70(m,1H), 3.60(m, 2H), 3.42(m, 1H), 1.00(m, 2H), 0.08(s, 9H).

Step 3: 3-(5-Bromopyridin-3-yl)-3-[4-(7H-pyrrolo[2,3-d]pyrimidin-4-yl)-1H-pyrazol-1-yl]propanenitrile The 3-(5-bromopyridin-3-yl)-3-[4-(7-[2-(trimethylsilyl)ethoxy]methyl-7H-pyrrolo[2,3-d]-pyrimidin-4-yl)-1H-pyrazol-1-yl]propanenitrile (0.220 g, 0.000419 mol) in DCM (9.0 mL, 0.14 mol) and TFA (9.0 mL, 0.12 mol) was stirred at room temperature for 1 hour. The reaction was concentrated in to give a residue. This crude intermediate was dissolved in methanol (12 mL, 0.30 mol) and ethylenediamine (0.2 mL, 0.003 mol) and was stirred overnight at room temperature. The reaction was concentrated in vacuo to give the crude product which was purified by preparative HPLC eluting with a water:ACN gradient buffered with ammonium hydroxide (pH=10) to give 3-(5-bromopyridin-3-yl)-3-[4-(7H-pyrrolo[2,3-d]pyrimidin-4-yl)-1H-pyrazol-1-yl) propanenitrile as an amorphous white powder (118 mg, 71.36%). LCMS (M+1)+:394, 396, 1H NMR (400 MHz, DMSO-d6): δ □12.05(bs, 1H), 8.98(s, 1H), 7.0(s, 1H), 6.50(m, 2H), 8.50(s, 1H), 8.10(s, 1H), 7.80(s, 1H), 6.98(s, 1H), 6.21(m, 1H), 3.90(m, 1H), 3.70(m, 1H).

Example 430

3-[4-(7H-Pyrrolo[2,3-d]pyrimidin-4-yl)-1H-pyrazol-1-yl]pentane-1,5-diol

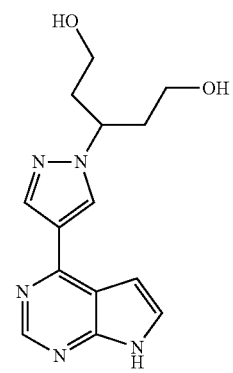 [SMILES: OCCC(CCO)n1cc(-c2ncnc3[nH]ccc23)cn1]

Using a procedure analogous to Example 61 for the removal of the SEM protecting group but using 3-[4-(7-[2-(trimethylsilyl)ethoxy]methyl-7H-pyrrolo[2,3-d]pyrimidin-4-yl)-1H-pyrazol-1-yl]-pentane-1,5-diol from Example 428, the title compound was prepared as a white amorphous solid, (25 mg, 70%) 1H NMR (400 MHz, DMSO): δ □8.65 (s, 1H), 8.6 (s, 1H), 8.25 (s, 1H), 7.6 (d, 1H), 6.0 (d, 1H), 4.6 (m, 1H), 3.3 (m, 2H), 3.2 (m, 2H), 2.1 (m, 2H), 1.9 (m, 2H). MS(ES): 288 (M+1).

Example 431

5-(2-Cyano-1-[4-(7H-pyrrolo[2,4-d]pyrimidin-4-yl)-1H-pyrazol-1-yl]ethyl)-nicotinonitrile bis(trifluoroacetate)

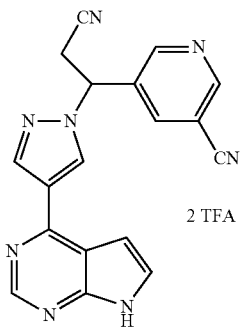 [SMILES: N#CCC(c1cncc(C#N)c1)n1cc(-c2ncnc3[nH]ccc23)cn1]

A slurry of 3-(5-bromopyridin-3-yl)-3-[4-(7H-pyrrolo[2, 3-d]pyrimi din-4-yl)-1H-pyrazol-1-yl]propanenitrile (0.050 g, 0.00013 mol) (from Example 429), DMF (2.0 mL, 0.026 mol) and zinc cyanide (0.1 g, 0.001 mol) was degassed by purging with nitrogen. Then tetrakis(triphenyl-phosphine) palladium(0) (0.07 g, 0.00006 mol) was added and the resulting slurry again was degassed with nitrogen. The reaction was sealed and heated at 170° C. for 15 minutes in a microwave (Personal Chemistry). The reaction was allowed to cool and the solids were filtered off. The combined DMF fractions were concentrated in vacuo. The residue was triturated with ethyl acetate-hexanes 2:8, then with ethyl ether to removed by-products. The crude product was purified by preparative HPLC eluting with a water: acetontrile gradient containing 0.2% TFA to give the racemic title compound (43 mg, 59.65%). LCMS (M+1)+: 341, ¹H NMR (400 MHz, DMSO-d₆): δ ☐12.60(bs, 1H), 9.10(s, 1H), 8.90(s, 1H), 8.80(s, 1H), 8.50(s, 1H), 8.42(s, 1H), 7.78(s, 1H), 7.10(s, 1H), 6.30(m, 1H), 3.90(m, 1H), 3.70(m, 1H).

Example 431R and Example 431S

The enantiomers R-5-(2-cyano-1-[4-(7H-pyrrolo[2,3-d]pyrimidin-4-yl)-1H-pyrazol-1-yl]-ethyl)nicotinonitrile and S-5-(2-cyano-1-[4-(7H-pyrrolo[2,3-d]pyrimidin-4-yl)-1H-pyrazol-1-yl]-ethyl)nicotinonitrile were separated by chiral column HPLC.

Example 467

3-(3-Aminophenyl)-3-[4-(7H-pyrrolo[2,3-d]pyrimidin-4-yl)-1H-pyrazol-1-yl]-propanenitrile bis(trifluoroacetate)

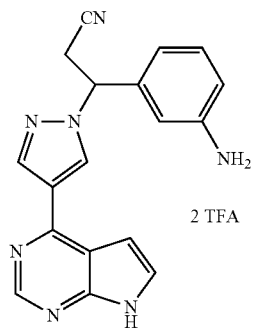 [SMILES: N#CCC(c1cccc(N)c1)n1cc(-c2ncnc3[nH]ccc23)cn1]

2 TFA

Step 1: 3-(3-Nitrophenyl)-3-[4-(7-[2-(trimethylsilyl)ethoxy]methyl-7H-pyrrolo[2,3-d]pyrimidin-4-yl)-1H-pyrazol-1-yl]propanenitrile To 4-(1H-pyrazol-4-yl)-7-[2-(trimethylsilyl)ethoxy]methyl-7H-pyrrolo [2,3-d]pyrimidine (0.500 g, 0.00158 mol) in 8.0 mL of dry ACN was added DBU (0.24 mL, 0.0016 mol) followed by addition of (2Z)-3-(3-nitrophenyl)acrylonitrile (0.36 g, 0.0021 mol) in 2.0 mL of ACN. The reaction mixture was heated at 67° C. for 18 hours. This was cooled to room temperature, and the mixture was partitioned between diluted hydrochloric acid and ethyl acetate. The organic layer was washed with saturated sodium chloride, dried over anhydrous magnesium sulfate, and concentrated. The crude product was purified by flash chromatography on silica gel using ethyl acetate-hexanes 6:4, to give 3-(3-nitrophenyl)-3-[4-(7-[2-(trimethylsilyl)ethoxy]methyl-7H-pyrrolo[2,3-d]pyrimidin-4-yl)-1H-pyrazol-1-yl]propanenitrile as a dark orange oil, (688 mg, 88.65%). LCMS (M+1)+: 490

Step 2. 3-(3-Aminophenyl)-3-(4-7-[2-(trimethylsilyl)ethoxy]-7H-pyrrolo[2,3-d]pyrimidin-4-yl-1H-pyrazol-1-yl)propanenitrile The 3-(3-nitrophenyl)-3-[4-(7-[2-(trimethylsilyl)ethoxy]methyl-7H-pyrrolo[2,3-d]pyrimidin-4-yl)-1H-pyrazol-1-yl]propanenitrile (0.630 g, 0.00129 mol) was dissolved in ethanol (65 mL, 1.1 mol), degassed with nitrogen, and then palladium (0.55 g, 0.0052 mol) (10% on carbon) was added. The reaction mixture was again purged with nitrogen, and it was then charged at 50 psi hydrogen in a Parr shaker for 60 minutes. The reaction mixture was filtered and concentrated to give 3-(3-amino-phenyl)-3-(4-7-[2-(trimethylsilyl)ethoxy]-7H-pyrrolo[2,3-d]pyrimidin-4-yl-1H-pyrazol-1-yl) propane-nitrile as a colorless oil (550 mg, 95.92%), LCMS (M+1)+=460, Step 3. 3-(3-Aminophenyl)-3-[4-(7H-pyrrolo[2,3-d]pyrimidin-4-yl)-1H-pyrazol-1-yl]propanenitrile bis(trifluoroacetate)

Using a procedure analogous to that of Example 61 for the removal of the SEM protecting group, the title compound was prepared as a white amorphous solid (18 mg, 38%), LCMS (M+1)+=329: ¹H NMR (DMSO-d₆) δ 12.61 (b, 1H), 9.00 (s, 1H), 8.80 (s, 1H), 8.50 (s, 1H),7.78 (m, 1H), 7.25(m, 1H), 7.18(m, 1H), 6.85(m, 2H), 6.02 (m, 1H), 3.78(m, 1H), 3.60 (m, 1H).

Example 468

N-(3-(2-Cyano-1-[4-(7H-pyrrolo[2,3-d]pyrimidin-4-yl)-1H-pyrazol-1-yl]ethyl)-phenyl)acetamide trifluoroacetate

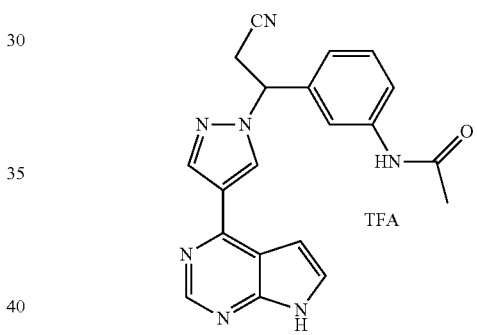

TFA

Step 1-(3-2-Cyano-1-[4-(7-[2-(trimethylsilyl)ethoxy]methyl-7H-pyrrolo[2,3-d]pyrimidin-4-yl)-1H-pyrazol-1-yl]ethylphenyl)acetamide To 3-(3-aminophenyl)-3-[4-(7-[2-(trimethylsilyl)ethoxy]methyl-7H-pyrrolo [2,3-d]pyrimidin-4-yl)-1H-pyrazol-1-yl]propanenitrile (0.070 g, 0.00015 mol) (from Example 467) in dry DCM (1.0 mL, 0.016 mol) was added TEA (0.042 mL, 0.00030 mol). The reaction was cooled in an ice bath and acetyl chloride (0.016 mL, 0.00023 mol) was added. The reaction mixture stirred for 30 minutes and was diluted with water and extracted with ethyl acetate (2×). The combined organic layers were washed with saturated sodium chloride, dried over anhydrous magnesium sulfate, filtered, and concentrated in vacuo to give N-(3-2-cyano-[4-(7-[2-(trimethylsilyl)ethoxy]methyl-7H-pyrrolo[2,3-d]pyrimidin-4-yl)-1H-pyrazol-1-yl]ethylphenyl)acetamide as a colorless oil, (65 mg, 85.08%), LCMS(M+1)+=502.

Step 2N-(3-2-Cyano-1-[4-(7H-pyrrolo[2,3-d]pyrimidin-4-yl)-1H-pyrazol-1-yl]ethylphenyl)acetamide trifluoroacetate Using a procedure analogous to that of Example 61 for the removal of the SEM protecting group, the title compound was prepared as a white amorphous solid (40 mg, 68.9%), LCMS(M+1)$^+$=372, $^1$H NMR (DMSO-d$_6$) δ 12.61 (b,1H), 9.05 (s,1H), 8.79 (s,1H), 8.44 (s,1H), 7.85 (s,1H), 7.55 (s,1H), 7.48 (d,1H), 7.24 (m,1H), 7.10 (m,2H)), 6.05 (m,1H), 3.70 (m,1H), 3.48 (m,1H), 1.98 (s,3H).

Example 470

4-(2-Cyano-1-[4-(7H-pyrrolo[2,3-d]pyrimidin-4-yl)-1H-pyrazol-1-yl]ethyl)-thiophene-2-carbonitrile trifluoroacetate

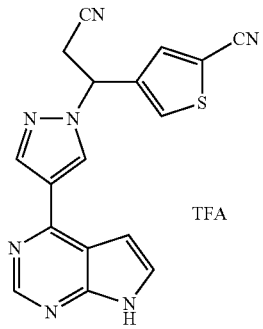 [SMILES: N#CCC(c1csc(C#N)c1)n1cc(-c2ncnc3[nH]ccc23)cn1]

Step 1 4-Bromo-2-(diethoxymethyl)thiophene

A mixture of 4-bromothiophene-2-carbaldehyde (1.2 g, 0.0063 mol) in ethanol (10 mL, 0.2 mol) was treated with ammonium chloride (0.42 g, 0.0078 mol) and ethyl orthoformate (1.2 g, 0.0078 mol). The mixture was stirred at 60° C. for 2 hours. The reaction was quenched with water and extracted with ethyl acetate. The combined organic layer was washed with saturated sodium chloride, dried over magnesium sulfate, filtered and concentrated to give 4-bromo-2-(diethoxymethyl)thiophene as an oil (1.3 g, 81%). $^1$H NMR (400 MHz, CDCl$_3$): δ 7.22 (s, 1H), 6.99 (s, 1H), 5.68 (s, 1H), 3.63 (q, 4H) 1.24 (t, 6H).

Step 2
5-(Diethoxymethyl)thiophene-3-carbaldehyde

A solution of 4-bromo-2-(diethoxymethyl)thiophene (500 mg, 0.002 mol) in ether (5 mL, 0.05 mol) was cooled at −78° C. To this solution, 2.5 M n-butyllithium in hexane (0.83 mL) was added dropwise. The reaction was stirred at −78° C. for 1 hour. To the reaction was added DMF (0.4 g, 0.006 mol) at −78° C. and the mixture was stirred for 30 minutes. The reaction was quenched with water and extracted with ethyl acetate. The combined organic layers were washed with saturated sodium chloride, dried over magnesium sulfate, filtered and concentrated. The crude residue was purified by flash column chromatography to yield the 5-(diethoxymethyl)thiophene-3-carbaldehyde as an oil (170 mg, 42.0%). By $^1$H NMR two different regioisomers of aldehydes were formed and were not separated; (note: NMR shifts are for the major isomer only) $^1$H NMR (400 MHz, CDCl$_3$): δ 9.85 (s, 1H), 8.05, 7.7 (s, 1H), 7.45, 7.15 (s, 1H), 5.7 (s, 1H), 3.65 (m, 2H), 1.25 (m, 2H).

Step 3 (2E)-3-[5-(Diethoxymethyl)-3-thienyl]acrylonitrile

To a solution of diethyl cyanomethylphosphonate (100 mg, 0.0008 mol) in THF (2 mL, 0.02 mol) cooled at 0° C. and 1.0 M potassium tert-butoxide in THF (0.8 mL) was added dropwise. The bath was removed and the reaction was warmed to room temperature for 30 minutes. The reaction was cooled to 0° C. and a solution of 5-(diethoxymethyl)thiophene-3-carbaldehyde (170 mg, 0.00079 mol) in THF (2 mL, 0.02 mol) was added drop wise. The reaction was stirred overnight at room temperature. The reaction was partitioned between water and ethyl acetate. The combined extracts were washed with saturated sodium chloride, dried over magnesium sulfate, filtered and concentrated. The crude residue was purified by flash column chromatography on silica gel eluting (ethyl acetate:hexane, 1:5) to give (2E)-3-[5-(diethoxymethyl)-3-thienyl]acrylonitrile as an oil (160 mg, 84.9%). $^1$H NMR (300 MHz, CDCl$_3$): δ 7.4-7.0 (m, 3H), 5.65 (m 1H), 4.2 (m, 1H), 3.65 (m, 4H), 1.25 (m, 6H).

Step 4 3-[5-(Diethoxymethyl)-3-thienyl]-3-[4-(7-[2-(trimethylsilyl)ethoxy]methyl-7H-pyrrolo[2,3-d]pyrimidin-4-yl)-1H-pyrazol-1-yl]propanenitrile To a solution of 4-(1H-pyrazol-4-yl)-7-[2-(trimethylsilyl)ethoxy]methyl-7H-pyrrolo[2,3-d]-pyrimidine (200 mg, 0.0007 mol) in ACN (2 mL, 0.04 mol) and (2E)-3-[5-(diethoxymethyl)-3-thienyl]acrylonitrile (160 mg, 0.00067 mol) (mixture of regioisomers) DBU (80 μL, 0.0005 mol) was added. The reaction was stirred overnight than water was added and the product was extracted with ethyl acetate. The combined extracts were washed with saturated sodium chloride, dried over magnesium sulfate, filtered and concentrated. The crude residue was purified by flash column chromatography on silica gel eluting (50% EtOAc/Hexane) to give 3-[5-(diethoxymethyl)-3-thienyl]-3-[4-(7-[2-(trimethylsilyl)ethoxy]methyl-7H-pyrrolo[2,3-d]pyrimidin-4-yl)-1H-pyrazol-1-yl]propane-nitrile (160 mg, 43%). $^1$H NMR (400 MHz, CDCl$_3$): δ 8.92 (s, 1H), 8.41 (s, 1H), 8.29 (b, 1H), 7.45(d, 1H), 7.41(d, 1H), 7.15 (s, 1H), 7.05 (d, 1H), 6.82 (m, 1H), 5.74 (d, 2H), 3.74 (m, 2H), 3.71 (m, 8H), 3.59 (m, 1H), 1.32 (m, 4H), 0.95 (m, 2H), −0.08 (s, 9H); MS(ES):553 (M+1).

Step 5 3-(5-Formyl-3-thienyl)-3-[4-(7-[2-(trimethylsilyl)ethoxy]methyl-7H-pyrrolo[2,3-d]pyrimidin-4-yl)-1H-pyrazol-1-yl]propanenitrile A solution of 3-[5-(diethoxymethyl)-3-thienyl]-3-[4-(7-[2-(trimethylsilyl)ethoxy]methyl-7H-pyrrolo[2,3-d]pyrimidin-4-yl)-1H-pyrazol-1-yl]propanenitrile (70 mg, 0.0001 mol) in THF (1 mL, 0.01 mol) was treated with 1 M HCl in water (400 μL). The reaction was stirred at room temperature. Water was added and the product was extracted with ethyl acetate. The combined extracts were washed with saturated sodium chloride, dried over magnesium sulfate, filtered and concentrated to give 3-(5-formyl-3-thienyl)-3-[4-(7-[2-(trimethylsilyl)ethoxy]methyl-7H-pyrrolo[2,3-d]pyrimidin-4-yl)-1H-pyrazol-1-yl]propanenitrile as a semi-solid residue (60 mg, 98%). $^1$H NMR (400 MHz, CDCl$_3$): δ 9.96 (s, 1H), 8.89 (s, 1H), 8.44 (m, 2H), 7.46 (1H), 5.73 (s, 2H), 4.15 (m, 1H), 3.73-3.43 (m, 3H), 1.35 (m, 1H), 1.01 (m, 2H), 0.03 (s, 9H); MS(ES): 479 (M+1).

Step 6: 5-[(E)-(Hydroxyimino)methyl]-3-thienyl-3-[4-(7-[2-(trimethylsilyl)ethoxy]methyl-7H-pyrrolo[2,3-d]pyrimidin-4 yl)-1H pyrazol-1yl]propanenitrile A solution of 3-(5-formyl-3-thienyl)-3-[4-(7-[2-(trimethylsilyl)ethoxy]methyl-7H-pyrrolo-[2,3-d]pyrimidin-4-yl)-1H-pyrazol-1-yl]propanenitrile (65 mg, 0.00014 mol) in methanol (2 mL, 0.05 mol) was treated with hydroxylamine hydrochloride (11 mg, 0.00016 mol) and potassium bicarbonate (23 mg, 0.00023 mol). The reaction was stirred at room temperature for 4 hours. Water was added and the product was extracted with ethyl acetate. The combined extracts were washed with saturated sodium chloride, dried over magnesium sulfate, filtered and concentrated to give 3-5-[(E)-(hydroxyimino)methyl]-3-thienyl-3-[4-(7-[2-(trimethylsilyl)ethoxy]methyl-7H-pyrrolo[2,3-d]-pyrimidin-4-yl)-1H-pyrazol-1-yl]propanenitrile as a semisolid oil (60 mg, 89.5%). (The crude product contained both isomers of oxime and also both regioisomers of thiophene). MS (ES): 494 (M+1).

Step 7: 4-(2-Cyano-1-[4-(7-[2-(trimethylsilyl)ethoxy]methyl-7H-pyrrolo[2,3-d]pyrimidin-4-yl)-1H-pyrazol-1-yl]ethyl)thiophene-2-carbonitrile To a mixture of 3-5-[(E)-(hydroxyimino)methyl]-3-thienyl-3-[4-(7-[2-(trimethylsilyl)ethoxy]-methyl-7H-pyrrolo[2,3-d]pyrimidin-4-yl)-1H-pyrazol-1-yl) propanenitril e (70 mg, 0.0001 mol) in pyridine (1 mL, 0.01 mol), methanesulfonyl chloride (100 µL, 0.001 mol) was added. The mixture was stirred at 60° C. for 2 hours. Water was added and the product was extracted with ethyl acetate. The combined extracts were washed with 0.1 N HCl, brine, dried over magnesium sulfate, filtered and concentrated to give 4-(2-cyano-1-[4-(7-[2-(trimethylsilyl)ethoxy]methyl-7H-pyrrolo[2,3-d]-pyrimidin-4-yl)-1H-pyrazol-1-yl]ethyl)thiophene-2-carbonitrile as a crude product (30 mg, 44%). MS (ES): 476 (M+1).

Step 8: 4-(2-Cyano-1-[4-(7H-pyrrolo[2,3-d]pyrimidin-4-yl)-1H-pyrazol-1-yl]ethyl)thiophene-2-carbonitrile trifluoroacetate A mixture of 4-(2-cyano-1-[4-(7-[2-(trimethylsilyl)ethoxy]methyl-7H-pyrrolo[2,3-d]-pyrimidin-4-yl)-1H-pyrazol-1-yl]ethyl)thiophene-2-carbonitrile (50 mg, 0.0001 mol) in DCM (2 mL, 0.03 mol) and TFA (1 mL, 0.01 mol) was stirred for 1 hour. The starting material was consumed and the desired methyl hydroxy compound was formed. The mixture was concentrated in vacuo to remove TFA. The crude intermediate was dissolved in methanol (3 mL, 0.07 mol) and was treated with ethylenediamine (1 mL, 0.01 mol). The mixture was stirred overnight and concentrated in vacuo. The products were purified by preparative HPLC eluting with ACN: water with 0.2% TFA to give two regioisomers, the title compound as an amorphous white solid (30 mg, 60%).

¹H NMR (500 MHz, DMSO): δ □8.95 (s, 1H), 8.76 (s, 1H), 8.48 (s, 1H), 8.06 (s, 1H), 8.04 (s, 1H), 7.70 (d, 1H), 7.05 (d, 1H), 6.25 (m, 1H), 3.80-3.60 (m, 2H); MS (ES): 346 (M+1).

Example 471

5-(2-Cyano-1-[4-(7H-pyrrolo[2,3-d]pyrimidin-4-yl)-1H-pyrazol-1-yl]ethyl)-thiophene-2-carbonitrile trifluoroacetate

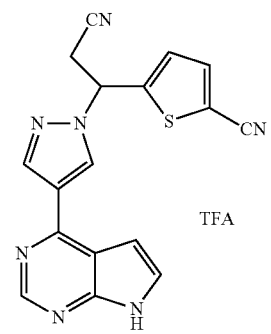 [SMILES: N#CCC(c1ccc(C#N)s1)n1cc(-c2ncnc3[nH]ccc23)cn1]

Isolated as the second regioisomer from Example 470, the title compound was isolated as an amorphous white solid (4 mg, 8%). ¹H NMR (500 MHz, DMSO): δ □9.0 (s, 1H0, 8.75 (s, 1H), 8.50 (s, 1H), 7.95 (s, 1H), 7.65 (s, 1H), 7.45 (s, 1H), 7.0 (d, 1H), 6.45 (m, 1H), 3.8 (dd, 2 H); MS (ES): 346 (M+1).

Example 472

3-[3-(Morpholin-4-yl]carbonyl)phenyl]-3-[4-(7H-pyrrolo[2,3-d]pyrimidin-4-yl)-1H-pyrazol-1-yl]propanenitrile trifluoroacetate

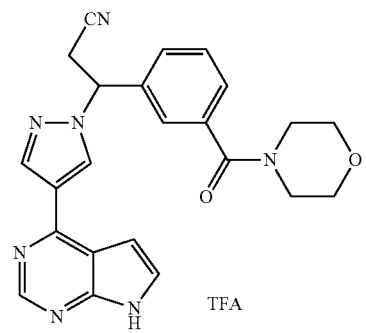 [SMILES: N#CCC(c1cccc(C(=O)N2CCOCC2)c1)n1cc(-c2ncnc3[nH]ccc23)cn1]

Step 1: 3-(2-cyano-1-[4-(7-[2-(trimethylsilyl)ethoxy]methyl-7H-pyrrolo[2,3-d]pyrimidin-4-yl)-1H-pyrazol-1-yl]ethyl)benzoic acid To a solution of methyl 3-2-cyano-1-[4-(7-[2-(trimethylsilyl)ethoxy]methyl-7H-pyrrolo[2,3-d]pyrimidin-4-yl)-1H-pyrazol-1-yl]ethylbenzoate (50 mg, 0.0001 mol) (prepared as in Example 61) in methanol (2 mL, 0.05 mol), lithium hydroxide (1 mg, 0.0001 mol) in water (1 mL, 0.06 mol) was added slowly. Water was added and also some 1N HCl was added until the solution was slightly acidic. The aqueous layer was extracted with ethyl acetate. The combined extracts were dried over magnesium sulfate, filtered and concentrated to give 3-(2-cyano-1-[4-(7-[2-(trimethylsilyl)ethoxy]-methyl-7H-pyrrolo[2,3-d]pyrimidin-4-yl)-1H-pyrazol-1-yl]ethyl)benzoic acid as a crude residue (35 mg, 72.0%). MS (ES): 489 (M+1).

Step 2: 3-[3-(Morpholine-1-ylcarbonyl)phenyl]-3-[4-(7-{[2-(trimethylsilyl)ethoxy]methyl}-7H-pyrrolo[2,3-d]pyrimidine-4-yl)-1H-pyrazole-1-yl]propanenitrile To a solution of 3-(2-cyano-1-[4-(7-[2-(trimethylsilyl)ethoxy]methyl-7H-pyrrolo[2,3-d]-pyrimidin-4-yl)-1H-pyrazol-1-yl]ethyl)benzoic acid (40 mg, 0.00008 mol) in DMF (1 mL, 0.01 mol), N,N,N',N'-tetramethyl-O-(7-azabenzotriazol-1-yl)uronium hexafluorophosphate (36 mg, 0.000095 mol) and DIPEA (30 µL, 0.0002 mol) were added. The reaction was stirred for 10 minutes and then morpholine (10 mg, 0.00012 mol) was added and the resulting mixture was stirred for 3 hours. Water was added and the product was extracted with ethyl acetate. The combined organic extracts were washed with 1N HCl, brine, dried over magnesium sulfate, filtered and concentrated to give 3-[3-(morpholine-1-ylcarbonyl)phenyl]-3-[4-(7-{[2-(trimethylsilyl)ethoxy]methyl}-7H-pyrrolo[2,3-d]pyrimidine-4-yl)-1H-pyrazole-1-yl]propanenitrile as a crude (40 mg, 88%) product. MS (ES): 558 (M+1).

Step 3: 3-[3-(Morpholin-4-ylcarbonyl)phenyl]-3-[4-(7H-pyrrolo[2,3-d]pyrimidin-4-yl)-1H-pyrazol-1-yl]propanenitrile trifluoroacetate Using a procedure analogous to that of Example 61 for the removal of the SEM protecting group, the title compound was isolated as an amorphous white solid (18 mg, 50%). ¹H NMR (400 MHz, DMSO): δ □9.05 (s, 1H), 8.75 (s, 1H), 8.44 (s, 1H), 7.85 (b, 1H), 7.665 (s, 1H), 7.55-7.35 (m, 3H), 7.15 (s, 1H), 6.15 (m, 1H), 3.85 (m, 1H), 3.65-3.4 (m, 6H), 3.25 (m, 2H), 3.05 (m, 1H); MS(ES): 428 (M+1).

Example 482

3-(5-Phenylpyridin-3-yl)-3-[4-(7H-pyrrolo[2,3-d]pyrimidin-4-yl)-1H-pyrazol-1-yl]propanenitrile trifluoroacetate

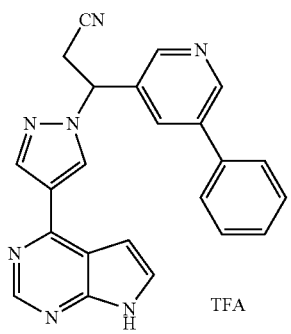 [SMILES: N#CCC(c1cncc(-c2ccccc2)c1)n1cc(-c2ncnc3[nH]ccc23)cn1]

Step 1: 3-(5-Phenylpyridin-3-yl)-3-[4-(7-[2-(trimethylsilyl)ethoxy]methyl-7H-pyrrolo[2,3-d]-pyrimidin-4-yl)-1H-pyrazol-1-yl]propanenitrile To a solution of 3-(5-bromopyridin-3-yl)-3-[4-(7-[2-(trimethylsilyl)ethoxy]methyl-7H-pyrrolo[2,3-d]pyrimidin-4-yl)-1H-pyrazol-1-yl]propanenitrile (from Example 429) (60 mg, 0.0001 mol) in 1,4-dioxane (2 mL, 0.02 mol), phenylboronic acid (15 mg, 0.00012 mol) and sodium bicarbonate (30 mg, 0.0003 mol) in water (0.5 mL, 0.03 mol) were added. The resulting mixture was degassed using nitrogen. Tetrakis(triphenylphosphine)palladium(0) (10 mg, 0.00001 mol) was added and nitrogen was bubbled through the reaction again. The reaction was heated at 80° C. in oil bath for 1 hour. Water was added and the product was extracted with ethyl acetate. The combined extracts were washed with saturated sodium chloride, dried over magnesium sulfate, filtered and concentrated to give 3-(5-phenylpyridin-3-yl)-3-[4-(7-[2-(trimethylsilyl)ethoxy]methyl-7H-pyrrolo[2,3-d]-pyrimidin-4-yl)-1H-pyrazol-1-yl]propanenitrile (50 mg, 80%) as a crude product. MS (ES): 522 (M+1).

Step 2: 3-(5-Phenylpyridin-3-yl)-3-[4-(7H-pyrrolo[2,3-d]pyrimidin-4-yl)-1H-pyrazol-1-yl]propanenitrile trifluoroacetate Using a procedure analogous to that of Example 61 for the removal of the SEM protecting group, the title compound was isolated as an amorphous white solid (20 mg, 40%). ¹H NMR (400 MHz, DMSO): δ □9.15 (s, 1H), 8.85 (s, 1H), 8.80 (s, 1H), 8.65 (s, 1H), 8.45 (s, 1H), 8.22 (s,1H), 7.85 (b, 1H), 7.67 (m, 2H), 7.45(m 2 H), 7.43 (m, 1H), 7.15 (s, 1H), 6.25 (m 1H), 3.95 (dd, 1H), 3.80 (dd, 1H), 3.0 (m, 1H); MS (ES): 392.1 (M+1)

Example 486

3-(5-Ethynylpyridin-3-yl)-3-[4-(7H-pyrrolo[2,3-d]pyrimidin-4-yl)-1H-pyrazol-1-yl]propanenitrile trifluoroacetate

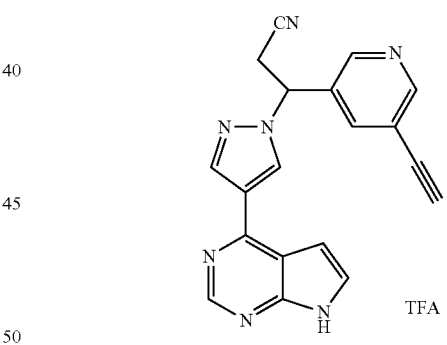

Step 1: 3-[4-(7-[2-(Trimethylsilyl)ethoxy]methyl-7H-pyrrolo[2,3-d]pyrimidin-4-yl)-1H-pyrazol-1-yl]-3-5-[(trimethylsilyl)ethynyl]pyridin-3-ylpropanenitrile To a solution of 3-(5-bromopyridin-3-yl)-3-[4-(7-[2-(trimethylsilyl)ethoxy]methyl-7H-pyrrolo[2,3-d]pyrimidin-4-yl)-1H-pyrazol-1-yl]propanenitrile (from Example 429) (0.080 g, 0.00015 mol) in TEA (0.300 mL, 0.00215 mol) was degassed with nitrogen, and then copper(I) iodide (0.005 g, 0.00003 mol), (trimethylsilyl)acetylene, and bis(triphenylphosphine)palladium(II)chloride were added. The reaction mixture was sealed in a tube and stirred at room temperature overnight. The resulting black solution was partitioned between water (10 mL) and ethyl ether. The organic layer was washed with saturated sodium chloride, dried over magnesium sulfate and concentrated in vacuo to give 3-[4-(7-[2-(trimethylsilyl)ethoxy]methyl-7H-pyrrolo [2,3-d]pyrimidin-4-yl)-1H-pyrazol-1-yl]-3-5-[(trimethylsilyl)ethynyl]pyridin-3-ylpropanenitrile as a yellow oil (60 mg,72.6), LCMS (M+1)+: 542).

Step 2: 3-(5-Ethynylpyridin-3-yl)-3-[4-(7H-pyrrolo [2,3-d]pyrimidin-4-yl)-1H-pyrazol-1-yl]propanenitrile trifluoroacetate 3-[4-(7-[2-(Trimethylsilyl)ethoxy]methyl-7H-pyrrolo[2, 3-d]pyrimidin-4-yl)-1H-pyrazol-1-yl]-3-5-[(trimethylsilyl) ethynyl]pyridin-3-ylpropanenitrile (0.050 g, 0.000092 mol) was dissolved in DCM (5.0 mL, 0.078 mol) and TFA (2.0 mL, 0.026 mol). The reaction mixture was stirred at room temperature, for 90 minutes and was concentrated in vacuo. The dry residue dissolved in methanol cooled in an ice bath and a solution of potassium hydroxide (0.482 g, 0.00859 mol) in methanol (10 mL, 0.2 mol) was added. The reaction solution was stirred for 30 min was concentrated and the crude product was purified by preparative HPLC eluting with a water: ACN gradient with 0.2% TFA, to give the title compound as a white amorphous solid (15 mg, 35.85%). LCMS (M+1)+: 340, $^1$H NMR (400 MHz, DMSO-$d_6$): δ ☐12.1(bs, 1H), 9.02(s, 1H), 8.80(s, 1H), 8.70(m, 2H), 8.48(s, 1H), 8.00(s, 1H), 7.80(d, 1H), 7.15(d, 1H), 6.20(m, 1H), 4.82(s, 1H), 3.90(m, 1H), 3.70(m, 1H).

Example 488

3-[5-(Phenylthio)pyridin-3-yl]-3-[4-(7H-pyrrolo[2,3-d]pyrimidin-4-yl)-1H-pyrazol-1-yl]propanenitrile trifluoroacetate

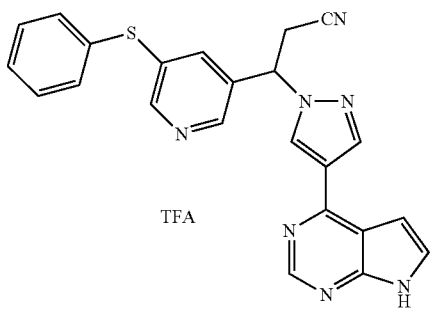 [SMILES: N#CCC(c1cncc(Sc2ccccc2)c1)n1cc(-c2ncnc3[nH]ccc23)cn1]

Step 1: 3-[5-(Phenylthio)pyridin-3-yl]-3-[4-(7-[2-(trimethylsilyl)ethoxy]methyl-7H-pyrrolo[2,3-d]-pyrimidin-4-yl)-1H-pyrazol-1-yl]propanenitrile To the 3-(5-bromopyridin-3-yl)-3-[4-(7-[2-(trimethylsilyl)ethoxy]methyl-7H-pyrrolo[2,3-d]-pyrimidin-4-yl)-1H-pyrazol-1-yl]propanenitrile (0.130 g, 0.000248 mol) from Example 429 Step 2, in dry 1,4-dioxane (1.60 mL, 0.0205 mol) was added DIPEA (0.085 mL, 0.00049 mol). The solution was degassed with nitrogen, followed by addition of (9,9-dimethyl-9H-xanthene-4,5-diyl)bis(diphenylphosphine) (0.007 g, 0.00001 mol), bis(dibenzylideneacetone) palladium(0) (0.0036 g, 0.0000062 mol), and benzenethiol (0.025 mL, 0.00025 mol). Again the solution was purged with nitrogen. The reaction mixture in a sealed tube was heated to reflux for 3 h. The reaction mixture was diluted with ethyl acetate, washed with water (2×), brine (1×), dried over magnesium sulfate, filtered, and the solvent was evaporated in vacuo. The crude product was triturated with hexane-ethyl acetate 9:1 to yield 3-[5-(phenylthio)pyridin-3-yl]-3-[4-(7-[2-(trimethylsilyl)ethoxy]methyl-7H-pyrrolo [2,3-d]pyrimidin-4-yl)-1H-pyrazol-1-yl]propanenitrile (110 mg, 80%). LC/MS (M+H)+: m/z=554.2.

Step 2: 3-[5-(Phenylthio)pyridin-3-yl]-3-[4-(7H-pyrrolo[2,3-d]pyrimidin-4-yl)-1H-pyrazol-1-yl]-propanenitrile trifluoroacetate The 3-[5-(phenylthio)pyridin-3-yl]-3-[4-(7-[2-(trimethylsilyl)ethoxy]methyl-7H -pyrrolo[2,3-d]pyrimidin-4-yl)-1H-pyrazol-1-yl]propanenitrile (0.110 g, 0.000199 mol) was dissolved in DCM (5.0 mL, 0.078 mol) and TFA (2.0 mL, 0.026 mol), and the mixture was stirred at room temperature for 1 hour. The solvent was removed in vacuo, and the resulting residue was dissolved in methanol (5.0 mL, 0.12 mol), and ethylenediamine (0.1 mL, 0.002 mol) was added. This reaction mixture was stirred at room temperature overnight. The mixture was concentrated in vacuo, and the crude product was purified by LCMS (pH=2) to yield the title compound as an amorphous solid (62 mg, 58.07%).

$^1$H NMR (400 MHz, DMSO): δ ☐12.80 (s), 9.10 (s) 8.87(d), 8.60 (s), 8.50 (s), 8.43 (s), 7.82 (s), 7.78 (m), 7.39 (m), 7.25 (m), 7.18 (d), 6.20 (m), 3.84 (m), 3.70 (m). LC/MS (M+H)+: m/z=424.15

Example 491

3-(5-Morpholin-4-ylpyridin-3-yl)-3-[4-(7H-pyrrolo [2,3-d]pyrimidin-4-yl)-1H-pyrazol-1-yl]propanenitrile

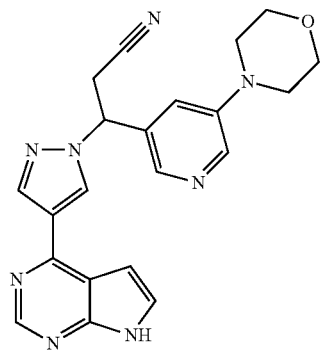 [SMILES: N#CCC(c1cncc(N2CCOCC2)c1)n1cc(-c2ncnc3[nH]ccc23)cn1]

Step 1: 4-(5-Bromopyridin-3-yl)morpholine

To a solution of [3,5-dibromopyridine (1000 mg, 0.004 mol) in 1,4-dioxane (8 mL, 0.1 mol), morpholine (400 mg, 0.004 mol) and sodium tert-butoxide (400 mg, 0.004 mol) were added. The reaction was bubbled with nitrogen. Tetrakis(triphenylphosphine)palladium(0) (200 mg, 0.0002 mol) was added and nitrogen was bubbled through for couple of minutes. The mixture was heated at 80° C. overnight. The reaction was allowed to cool to rt and was then partitioned between water and ethyl acetate. The organic layer was washed with saturated sodium chloride, dried over magnesium sulfate, filtered and concentrated to give a crude residue. The crude product was purified by FCC on silica gel eluting with 1:1, EtOAC:Hexane gave to give 4-(5-bromopyridin-3-yl)morpholine as a viscous oil (400 mg, 40%). $^1$H NMR (400 MHz, CDCl$_3$): δ 8.2 (s, 1H), 8.1 (s, 1H), 7.2 (s, 1H), 3.8 (m, 4H), 3.2 (m, 4H).

Step 2: 5-Morpholin-4-ylnicotinaldehyde

A solution of 4-(5-bromopyridin-3-yl)morpholine (100 mg, 0.0004 mol) in ether (2 mL, 0.02 mol) cooled at −78° C. was treated with 2.5 M n-butyllithium in hexane (0.2 mL) and was stirred for 1 h. To this mixture was added DMF (0.5 mL, 0.006 mol) dropwise. The reaction was quenched with water and extracted with ethyl acetate. The combined organic layers were washed with saturated sodium chloride, dried over magnesium sulfate, filtered and concentrated to give 5-morpholin-4-ylnicotinaldehyde (70 mg, 90%) as a crude product. $^1$H NMR (400 MHz, CDCl$_3$): δ 10.1 (s, 1H), 8.0 (s, 2H), 7.6 (s, 1H), 3.8 (m, 4H), 3.2 (m, 4H).

Step 3: (2E)-3-(5-Morpholin-4-ylpyridin-3-yl)acrylonitrile

To a solution of diethyl cyanomethylphosphonate (70 mg, 0.0004 mol) in THF (2 mL, 0.02 mol) cooled at 0° C. was added 1.0 M potassium tert-butoxide in THF (0.50 mL) dropwise. The cold bath was removed and the reaction was warmed to room temperature over 30 minutes. The reaction was cooled to 0° C. and a solution of 5-morpholin-4-ylnicotinaldehyde (70 mg, 0.0004 mol) in THF (2 mL, 0.02 mol) was added dropwise. The reaction was stirred at room temperature for 4 h, quenched with water and extracted with ethyl acetate. The combined organic layers were washed with saturated sodium chloride, dried over magnesium sulfate, filtered and concentrated to give (2E)-3-(5-morpholin-4-ylpyridin-3-yl)acrylonitrile (75 mg, 100%) as a mixture of isomers; LC/MS: 216 (M+1).

Step 4: 3-(5-Morpholin-4-ylpyridin-3-yl)-3-[4-(7-[2-(trimethylsilyl)ethoxy]methyl-7H-pyrrolo[2,3-d]-pyrimidin-4-yl)-1H-pyrazol-1-yl]propanenitrile To a solution of 4-(1H-pyrazol-4-yl)-7-[2-(trimethylsilyl)ethoxy]methyl-7H-pyrrolo[2,3-d]-pyrimidine (120 mg, 0.00038 mol) in ACN (10 mL, 0.2 mol) and (2E)-3-(5-morpholin-4-ylpyridin-3-yl)acrylonitrile (70 mg, 0.0003 mol) (mixture of isomers), DBU (50 µL, 0.0003 mol) was added and the resulting mixture was stirred overnight. The mixture was partitioned between water and ethyl acetate. The combined organic layers were washed with saturated sodium chloride, dried over magnesium sulfate, filtered and concentrated to give 3-(5-morpholin-4-ylpyridin-3-yl)-3-[4-(7-[2-(trimethylsilyl)ethoxy]methyl-7H-pyrrolo[2,3-d]pyrimidin-4-yl)-1H-pyrazol-1-y]propanenitrile (200 mg, 100%) as a crude product; L/MS=531 (M+1).

Step 5: 3-(5-Morpholin-4-ylpyridin-3-yl)-3-[4-(7H-pyrrolo[2,3-d]pyrimidin-4-yl)-1H-pyrazol-1-yl)-propanenitrile Using a procedure analogous to Example 61 for the removal of the SEM protecting the title compound was isolated as an amorphous white solid (18 mg, 50%). $^1$H NMR (400 MHz, DMSO): δ 8.8 (s, 1H), 8.6 (s, 1H), 8.4 (s, 1H), 8.2 (s, 1H), 8.0 (s, 1H), 7.6 (d, 1H), 7.4 (m, 1H), 6.9 (d, 1H), 6 (m, 1H), 3.8 (dd, 1H), 3.7(m, 4H), 3.6 (dd, 1H), 3.1 (m, 4 H); LC/MS: 401 (M+1).

Example 496

3-[5-(Phenylsulfinyl)pyridin-3-yl]-3-[4-(7H-pyrrolo [2,3-d]pyrimidin-4-yl)-1H-pyrazol-1-yl]propanenitrile, and Example 497

3-[5-(Phenylsulfonyl)pyridin-3-yl]-3-[4-(7H-pyrrolo [2,3-d]pyrimidin-4-yl)-1H-pyrazol-1-yl]propanenitrile

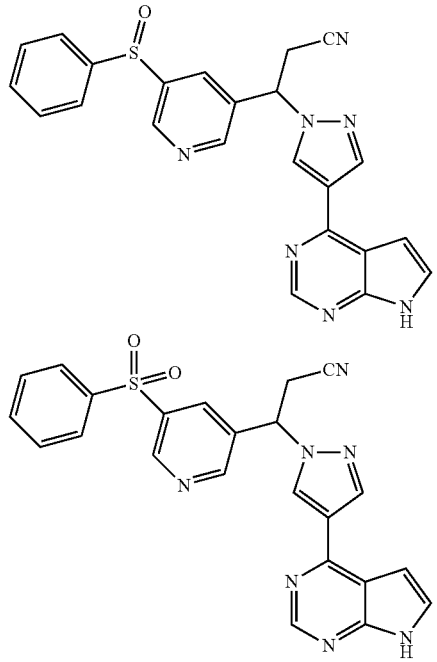

To the solution of 3-[5-(phenylthio)pyridin-3-yl]-3-[4-(7H-pyrrolo[2,3-d]pyrimidin-4-yl)-1H-pyrazol-1-ylipropanenitrile trifluoroacetate (0.050 g, 0.000093 mol) from Example 488, Step 2, in THF (1.0 mL, 0.012 mol) was added MCPBA (0.022 g, 0.00013 mol) (0.031g of 77% in water), in a water ice bath. The reaction mixture was stirred for 1h at room temperature. The crude products were purified by LCMS (pH=10). Two peaks were collected:

1—to yield 3-[5-(phenylsulfnyl)pyridin-3-yl]-3-[4-(7H-pyrrolo[2,3-d]pyrimidin-4-yl)-1H-pyrazol-1-yl]propanenitrile (8 mg, 19.57%). $^1$H NMR (400 MHz, DMSO): δ 12.1 (s), 8.89 (d), 8.80 (d), 8.70 (s), 8.62 (s), 8.40 (s), 8.19 (s), 7.70 (m), 7.58 (s), 7.42 (m), 6.90 (s), 6.20 (m), 3.82 (m), 3.65 (m). LC/MS (M+H)$^+$: m/z=440.0

2—to yield 3-[5-(phenylsulfonyl)pyridin-3-yl]-3-[4-(7H-pyrrolo[2,3-d]pyrimidin-4-yl)-1H-pyrazol-1-yl]propanenitrile (21 mg, 50%). $^1$H NMR (400 MHz, DMSO): δ 12.1 (s), 9.10 (s), 8.86 (m), 8.61(s), 8.40 (m), 7.98 (m), 7.62 (m), 7.58 (m), 6.90 (s), 6.20 (m), 3.82 (m), 3.65 (m). LC/MS (M+H)$^+$: m/z=456.0

Example 498

3-[4-(7H-Pyrrolo[2,3-d]pyrimidin-4-yl)-1H-pyrazol-1-yl]pentan-1-ol

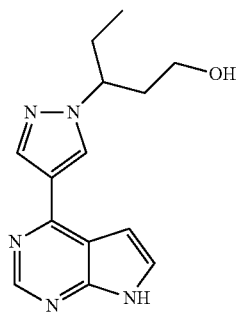 [SMILES: CCC(CCO)n1cc(-c2ncnc3[nH]ccc23)cn1]

Step 1: 3-[4-(7-[2-(Trimethylsilyl)ethoxy]methyl-7H-pyrrolo[2,3-d]pyrimidin-4-yl)-1H-pyrazol-1-yl]pentanal To a solution of 4-(1H-pyrazol-4-yl)-7-[2-(trimethylsilyl)ethoxy]methyl-7H-pyrrolo[2,3-d]-pyrimidine (100 mg, 0.0003 mol) in ACN (2 mL, 0.04 mol) and DBU (50 μL, 0.0003 mol), the (2E)-pent-2-enal (4.0E1 mg, 0.00048 mol) in 1 ml ACN was added drop wise. The reaction was stirred for 1 h, and then water was added and the resulting mixture extracted with ethyl acetate. The combined organic layers were washed with saturated sodium chloride, dried over magnesium sulfate, filtered and concentrated to give the crude as the hydrated product form. LC/MS (M+H)$^+$: m/z=400.

Step 2: 3-[4-(7-[2-(Trimethylsilyl)ethoxy]methyl-7H-pyrrolo[2,3-d]pyrimidin-4-yl)-1H-pyrazol-1-yl]pentan-1-ol A mixture of [3-[4-(7-[2-(trimethylsilyl)ethoxy]methyl-7H-pyrrolo[2,3-d]pyrimidin-4-yl)-1H-pyrazol-1-yl) pentanal (50 mg, 0.0001 mol) in methanol (2 mL, 0.05 mol) was treated with sodium tetrahydroborate (8 mg, 0.0002 mol). The mixture was stirred at room temperature for 1 h, and then water was added and the product was extracted with ethyl acetate. The combined organic layers were washed with saturated sodium chloride, dried over magnesium sulfate, filtered and concentrated to give the desired product as an oil. LC/MS (M+H)$^+$: m/z=402.

Step 3

Using a procedure analogous to Example 61 for the removal of the SEM protecting group the title compound was isolated as an amorphous white solid (6 mg, 20%). $^1$H NMR (400 MHz, DMSO): δ 8.65 (d, 1H), 8.60 (d, 1H), 7.55 (s, 1H), 6.95 (s, 1H), 4.50 (b, 1H), 4.4 (m, 1H), 3.4 (m, 1H), 3.2 (m, 1H), 2.1 (m, 1H), 1.8-2.0 (m, 3H), 0.7(t, 3H); LC/MS (M+H)$^+$: m/z=272.

Example 499

Methyl 3-[4-(7H-pyrrolo[2,3-d]pyrimidin-4-yl)-1H-pyrazol-1-yl]pentyl carbonate

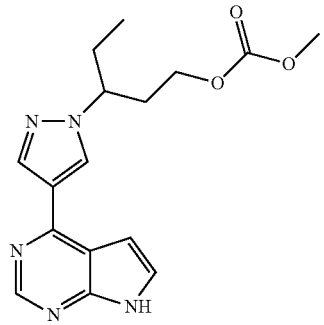 [SMILES: CCC(CCOC(=O)OC)n1cc(-c2ncnc3[nH]ccc23)cn1]

Step 1: Methyl 3-[4-(7-[2-(trimethylsilyl)ethoxy]methyl-7H-pyrrolo[2,3-d]pyrimidin-4-yl)-1H-pyrazol-1-yl]pentyl carbonate To a solution of [3-[4-(7-[2-(trimethylsilyl)ethoxy]methyl-7H-pyrrolo[2,3-d]pyrimidin-4-yl)-1H-pyrazol-1-yl] pentan-1-ol (50 mg, 0.0001 mol) from Example 498 Step 2 in pyridine (1 mL, 0.01 mol), methyl chloroformate (30 μL, 0.0003 mol) was added. The reaction was stirred for 3 h, water was added and the product was extracted with ethyl acetate. The combined organic layers were washed 1N HCl, brine, dried over magnesium sulfate, filtered and concentrated to give methyl 3-[4-(7-[2-(trimethylsilyl)ethoxy]methyl-7H-pyrrolo[2,3-d]pyrimidin-4-yl)-1H-pyrazol-1-yl] pentyl carbonate as a semisolid residue (30 mg, 50%). LC/MS (M+H)$^+$: m/z=460.

Step 2

Using a procedure analogous to Example 61 for the removal of the SEM protecting the title compound was isolated as an amorphous white solid (8 mg, 20%). $^1$H NMR (400 MHz, DMSO): δ 12.0 (b, 1H), 8.65 (d, 1H), 8.35 (s, 1H), 7.65 (b, 1H), 7.600 (s, 1H), 7.0 (s, 1H), 4.4 (m, 1H), 4.0 (m, 1H), 3.8 (m, 1H), 3.6 (s, 3H), 2.1 (m, 1H), 2.2 (m, 1H), 1.95 (m, 2H), 0.75 (t, 3H); LC/MS (M+H)$^+$: m/z=330.

Example 500(a)

(1E)-3-[4-(7H-Pyrrolo[2,3-d]pyrimidin-4-yl)-1H-pyrazol-1-yl]pentanal oxime

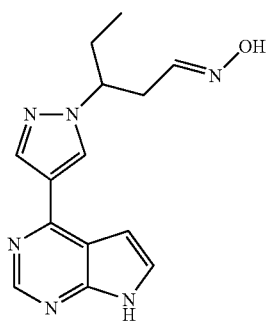 [SMILES: CCC(C/C=N/O)n1cc(-c2ncnc3[nH]ccc23)cn1]

Step 1: (1E)-3-[4-(7-[2-(Trimethylsilyl)ethoxy]methyl-7H-pyrrolo[2,3-d]pyrimidin-4-yl)-1H-pyrazol-1-yl]pentanal oxime To a solution of 3-[4-(7-[2-(trimethylsilyl)ethoxy]methyl-7H-pyrrolo[2,3-d]pyrimidin-4-yl)-1H-pyrazol-1-yl]pentanal (60 mg, 0.0002 mol) from Example 498, Step 2 in methanol (2 mL, 0.05 mol) was added hydroxylamine hydrochloride (16 mg, 0.00022 mol) and potassium bicarbonate (22 mg, 0.00022 mol). The reaction was stirred at room temperature for 2 h, water was added and the product was extracted with ethyl acetate. The combined extracts were washed with saturated sodium chloride, dried over magnesium sulfate, filtered and concentrated to give (1E)-3-[4-(7-[2-(trimethyl-silyl)ethoxy]methyl-7H-pyrrolo[2,3-d]pyrimidin-4-yl)-1H-pyrazol-1-yl]pentanal oxime as a semisolid residue (50 mg, 80%). LC/MS (M+H)$^+$: m/z=415.

Step 2

Using a procedure analogous to Example 61 for the removal of the SEM protecting the title compound was isolated as an amorphous white solid. $^1$H NMR (400 MHz, DMSO): δ☐☐ 12.0 (b, 1H), 8.6 (m, 2H), 8.2 (m, 1H), 7.5 (d, 1H), 7.1 and 6.5 (t, 1H), 4.6 (m, 1H), 4.4 (m, 1H), 2.6-2.8 (m, 2H), 1.8 (m, 2H), 0.65 (t, 3H); LC/MS (M+H)$^+$: m/z=285.

Example 501(a)

(1E)-3-[4-(7H-Pyrrolo[2,3-d]pyrimidin-4-yl)-1H-pyrazol-1-yl]pentanal O-methyloxime, and

Example 502(a)

(1Z)-3-[4-(7H-Pyrrolo[2,3-d]pyrimidin-4-yl)-1H-pyrazol-1-yl]pentanal O-methyloxime

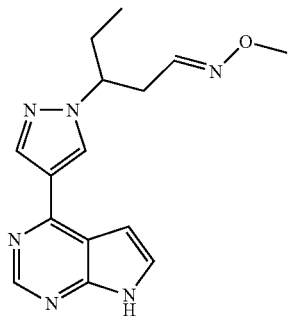 [SMILES: CCC(C/C=N/OC)n1cc(-c2ncnc3[nH]ccc23)cn1]

Step 1: (1E)-3-[4-(7-[2-(Trimethylsilyl)ethoxy]methyl-7H-pyrrolo[2,3-d]pyrimidin-4-yl)-1H-pyrazol-1-yl]pentanal O-methyloxime and (1Z)-3-[4-(7-[2-(Trimethylsilyl)ethoxy]methyl-7H-pyrrolo[2,3-d]pyrimidin-4-yl)-1H-pyrazol-1-yl]pentanal O-methyloxime To a solution of 3-[4-(7-[2-(trimethylsilyl)ethoxy]methyl-7H-pyrrolo[2,3-d]pyrimidin-4-yl)-1H-pyrazol-1-yl]pentanal (70 mg, 0.0002 mol) in methanol (2 mL, 0.05 mol) was added methoxylamine hydrochloride (19 mg, 0.00022 mol) and potassium bicarbonate (22 mg, 0.00022 mol). The reaction was stirred at room temperature for 2 h, water was added and the product was extracted with ethyl acetate. The combined extracts were washed with saturated sodium chloride, dried over magnesium sulfate, was filtered and was concentrated to give 3-[4-(7-[2-(trimethylsilyl)-ethoxy]methyl-7H-pyrrolo[2,3-d]pyrimidin-4-yl)-1H-pyrazol-1-yl]pentanal O-methyloxime as a mixture of isomers (70 mg, 90%) crude product. LC/MS (M+H)$^+$: m/z=429.

Step 2

Using a procedure analogous to Example 61 for the removal of the SEM protecting the title compound was isolated as an amorphous white solid (4 mg, 25%). Isomer 1, $^1$H NMR (400 MHz, DMSO): δ ☐☐8.7 (s, 2H), 8.3 (s, 1H), 7.6 (s, 1H), 7.3 (t, 1H), 7.0 (s, 1H), 4.6(m, 1H), 3.3 (s, 3H), 2.8 (m, 2H), 1.9 (m, 2H), 0.8 (t, 3H); LC/S (M+H)$^+$: m/z=299. Isomer 2 (3 mg, 22%), $^1$H NMR (400 MHz, DMSO): δ☐☐ 8.7 (s, 2H), 8.3 (s, 1H), 7.6 (s, 1H), 7.0 (s, 1H), 6.7 (t, 1H), 4.5(m, 1H), 3.3 (s, 3H), 2.8-3.0 (m, 2H), 1.9 (m, 2H), 0.8 (t, 3H); LC/MS (M+H)$^+$: m/z=299.

Example 503

4-[1-(4,4-Dibromo-1-ethylbut-3-en-1-yl)-1H-pyrazol-4-yl]-7H-pyrrolo[2,3-d]-pyrimidine trifluoroacetate

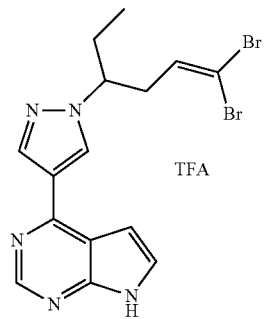 [SMILES: CCC(CC=C(Br)Br)n1cc(-c2ncnc3[nH]ccc23)cn1]

Step 1: 4-[1-(4,4-Dibromo-1-ethylbut-3-en-1-yl)-1H-pyrazol-4-yl]-7-[2-(trimethylsilyl)ethoxy]methyl-7H-pyrrolo[2,3-d]pyrimidine To a solution of 3-[4-(7-[2-(trimethylsilyl)ethoxy]methyl-7H-pyrrolo[2,3-d]pyrimidin-4-yl)-1H-pyrazol-1-yl]pentanal (300 mg, 0.0008 mol) in DCM (4 mL, 0.06 mol) cooled at 0° C., triphenylphosphine (800 mg, 0.003 mol) and carbon tetrabromide (500 mg, 0.002 mol) were added. The reaction was stirred at 0° C. for 10 min, water was added and extracted with ethyl acetate. The combined organic extracts were washed with saturated sodium chloride, dried over magnesium sulfate, filtered and concentrated. The crude product was purified by prep LC-MS (ACN, water, NH$_4$OH) to give 4-[1-(4,4-dibromo-1-ethylbut-3-en-1-yl)-1H-pyrazol-4-yl]-7-[2-(trimethylsilyl)-ethoxy]methyl-7H-pyrrolo[2,3-d]pyrimidine as an amorphous solid (50 mg, 10%). ¹H NMR (400 MHz, CDCl₃): δ □□8.9 (s, 2H), 8.4 (s, 1H), 8.3 (s, 1H), 7.4 (m, 1H), 7.3 (s, 1H), 6.9 (m, 1H), 6.4 (m, 1H), 5.7 (s, 2H), 4.2 (m, 1H), 3.6 (m, 2H), 2.8 (m, 2H), 2.1 (m, 1H), 2.0 (m, 1H), 1.0 (m, 5H), LC/MS (M+H)⁺: m/z=556

Step 2

Using a procedure analogous to Example 61 for the removal of the SEM protecting the title compound was isolated as an amorphous white solid (8 mg, 40%). ¹H NMR (400 MHz, DMSO): δ □□8.8 (s, 2H), 8.4 (s, 1H), 7.7 (b, 1H), 7.2 (b, 1H), 6.5 (t, 1H), 4.4 (m, 1H), 2.6 (m, 2H), 1.8 (m, 2H), 0.8 (t, 3H); LC/MS (M+H)⁺: m/z=: 426.

Example 506

4-[1-(1-Ethylbut-3-yn-1-yl)-1H-pyrazol-4-yl]-7H-pyrrolo[2,3-d]pyrimidine trifluoroacetate

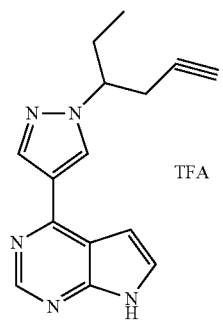 [SMILES: C#CCC(CC)n1cc(-c2ncnc3[nH]ccc23)cn1]

Step 1: 4-[1-(1-Ethylbut-3-yn-1-yl)-1H-pyrazol-4-yl]-7-[2-(trimethylsilyl)ethoxy]methyl-7H-pyrrolo[2,3-d]pyrimidine A solution of 4-[1-(4,4-dibromo-1-ethylbut-3-en-1-yl)-1H-pyrazol-4-yl]-7-[2-(trimethylsilyl)-ethoxy]methyl-7H-pyrrolo[2,3-d]pyrimidine (20 mg, 0.00004 mol) (from Example 503 Step 1) in THF (1 mL, 0.01 mol) at −78° C. was treated with 2.5 M n-butyllithium in hexane (0.032 mL). The mixture was stirred at −78° C. for 1 h and then at room temperature for 1 h. The reaction was quenched with water (1 mL, 0.06 mol) and 1N HCl. The reaction was partitioned between water and ethyl acetate. The organic extract was washed with saturated sodium chloride, dried over magnesium sulfate, filtered and concentrated to give 4-[1-(1-ethylbut-3-yn-1-yl)-1H-pyrazol-4-yl]-7-[2-(tri-methylsilyl)ethoxy]methyl-7H-pyrrolo[2,3-d]pyrimidine as a semisolid (12 mg, 80%). LC/MS (M+H)⁺: m/z=396.

Step 2

Using a procedure analogous to Example 61 for the removal of the SEM protecting the title compound was isolated as an amorphous white solid (4 mg, 30%). ¹H NMR (400 MHz, DMSO): δ□□ 12.2 (b, 1H), 8.8 (s, 2H), 8.4 (s, 1H), 7.6 (s, 1H), 7.1 (s, 1H), 4.4 (m, 1H), 2.8 (m, 3H), 1.9 (m, 2H), 0.8 (t, 3H); LC/MS(M+H)⁺: m/z=266.

Example 516

(R)-3-[3-(Ethylsulfonyl)phenyl]-3-[4-(7H-pyrrolo[2,3-d]pyrimidin-4-yl)-1H-pyrazol-1-yl]propanenitrile, and (S)-3-[3-(Ethylsulfonyl)phenyl]-3-[4-(7H-pyrrolo[2,3-d]pyrimidin-4-yl)-1H-pyrazol-1-yl]-propanenitrile

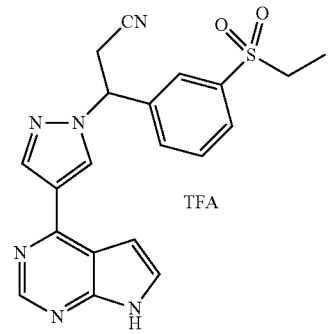 [SMILES: CCS(=O)(=O)c1cccc(C(CC#N)n2cc(-c3ncnc4[nH]ccc34)cn2)c1]

Step 1: 1-Bromo-3-(ethylthio)benzene

Iodoethane (0.46 mL, 0.0058 mol) was added to a suspension of 3-bromothiophenol (0.50 mL, 0.0048 mol), ACN (7.11 mL, 0.136 mol) and potassium carbonate (2.0 g, 0.014 mol). The reaction was stirred for 2 h at rt, was diluted with ethyl acetate and filtered to remove the solids. The reaction was concentrated in vacuo to give 1-bromo-3-(ethylthio)benzene as a colorless oil 1.0 gm, 100%

Step 2: 1-Bromo-3-(ethylsulfonyl)benzene

The MCPBA (2.37 g, 10.6 mmol) was added to a solution of 1-bromo-3-(ethylthio)benzene (1.00 g, 4.80 mmol) in DCM (10 ml, 156 mmol) cooled to 0° C. The reaction was stirred for 1 h and then was diluted with water and extracted with ethyl acetate three times. The combined organic layers were dried with magnesium sulfate, filtered, and concentrated in vacuo. The resulting crude residue was purified by flash column chromatography with a hexane: ethyl acetate gradient to give 1-bromo-3-(ethylsulfonyl)benzene as a colorless oil 1.1 gm 92%, ¹H NMR (300 MHz, CDCl₃): δ□8.09 (m, 1H), 7.85 (d, 1H), 7.78 (d, 1H) 7.45 (t, 1H), 3.14 (q, 2H), 1.25 (t, 3H).

Step 3: (2E & Z)-3-[3-(Ethylsulfonyl)phenyl]acrylonitrile

1-Bromo-3-(ethylsulfonyl)benzene (1.3 g, 0.0052 mol) was dissolved in the DMF (15.0 mL, 0.194 mol) and 2-propenenitrile (0.68 mL, 0.010 mol), TEA (1.4 mL, 0.010 mol) and triphenylphosphine (0.23 g, 0.00089 mol) were added. The resulting solution was degassed with nitrogen, and palladium acetate (0.07 g, 0.0003 mol) was added. Again the reaction was degassed with nitrogen and then heated to 110° C. in a sealed tube for 8 hrs. The reaction was complete by HPLC, and was then allowed to cool to rt and then partitioned between ethyl acetate and water. The organic layer was washed with brine, dried over magnesium sulfate and concentrated. The product was purified by FCC on silica gel eluting with a hexane; ethyl acetate gradient to give (2E&Z)-3-[3-(ethylsulfonyl)phenyl]acrylonitrile as an amber oil (1.1 gm, 92%) LC/MS (M+H)⁺: m/z=222.

Step 4: 3-[3-(Ethylsulfonyl)phenyl]-3-[4-(7-[2-(trimethylsilyl)ethoxy]methyl-7H-pyrrolo[2,3-d]pyrimidin-4-yl)-1H-pyrazol-1-yl]propanenitrile The (2E&Z)-3-[3-(ethylsulfonyl)phenyl]acrylonitrile (1.0 g, 0.0045 mol) was combined with 4-(1H-pyrazol-4-yl)-7-[2-(trimethylsilyl)ethoxy]methyl-7H-pyrrolo [2,3-d] pyrimidine (1.3 g, 0.0041 mol) and DBU (0.61 mL, 0.0041 mol) in ACN (10.0 mL, 0.191 mol) under nitrogen at rt. The reaction was stirred at rt for 24 h. This was partitioned between ethyl acetate and water, and 0.1N HCl was added to adjust the pH to 7. The combined organic extracts were washed with brine, dried over magnesium sulfate and concentrated to give a crude oil. The product was purified by FCC on silica gel eluting with a hexane: ethyl acetate gradient to give 3-[3-(ethylsulfonyl)phenyl]-3-[4-(7-[2-(trimethylsilyl)ethoxy]methyl-7H-pyrrolo[2,3-d]pyrimidin-4-yl)-1H-pyrazol-1-yl]propanenitrile as an oil (1.5 gm, 68%). LC/MS (M+H)$^+$: m/z=537. The oil was a racimate, which was separated by chiral column chromatography (Chiracel OD-H, eluting with ethanol: methanol: hexane 30:30:40, Rt 13.2 and 17.1 minutes) to give the two enantiomers, each as a glass (0.51 gm) LC/MS (M+H)$^+$: m/z=537,
$^1$H NMR (300 MHz, CDCl$_3$): δ 8.89(s, 1H), 8.45(s, 1H), 8.35(s,1H), 8.09(s, 1h), 8.05(d, 1H), 7.75(d, 1H), 7.71(t, 1H), 7.45(d, 1H), 6.83(d, 1H), 5.85(t, 1H), 5.75(s, 2H), 3.78-3.42(m, 4H), 3.18(m, 2H), 1.35(t, 3H), 0.97(t, 2H), 0.05(s, 9H).

Step 5

Using a procedure analogous to Example 61 for the removal of the SEM protecting group the title compounds were prepared to give isomer #1 as an amorphous white solid (300 mg, 80%). $^1$H NMR (400 MHz, DMSO): δ☐☐ 9.1 (s, 1H), 8.8 (s, 1H), 8.5 (s, 1H), 8.0 (s, 1H), 7.6-7.9 (m, 4H), 7.1 (s, 1H), 6.3 (m, 1H), 3.9 (m, 1H), 3.7 (m, 1H) 3.2 (q, 2H), 1.0 (t, 3H); MS(ES) (M+H)$^+$: m/z=407.

Using a procedure analogous to Example 61 for the removal of the SEM protecting group the title compounds were prepared to give isomer #2 as an amorphous white solid (300 mg, 80%).
$^1$H NMP (400 MHz, DMSO): δ ☐☐9.1 (s, 1H), 8.8 (s, 1H), 8.5 (s, 1H), 8.0 (s, 1H), 7.6-7.9 (m, 4H), 7.1 (s, 1H), 6.3 (m, 1H), 3.9 (m, 1H), 3.7 (m, 1H) 3.2 (q, 2H), 1.0 (t, 3H); MS(ES) (M+H)$^+$: m/z=407.

Example 526

4-[1-(1-Ethylbut-3-en-1-yl)-1H-pyrazol-4-yl]-7H-pyrrolo[2,3-d]pyrimidine

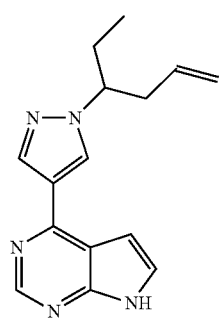 [SMILES: C=CCC(CC)n1cc(-c2ncnc3[nH]ccc23)cn1]

Step 1: 4-[1-(1-Ethylbut-3-en-1-yl)-1H-pyrazol-4-yl]-7-[2-(trimethylsilyl)ethoxy]methyl-7H-pyrrolo-[2,3-d]pyrimidine To an ice cooled solution of methyl triphenylphosphonium bromide (100 mg, 0.0004 mol) in THF (2 mL, 0.02 mol) was added 0.5 M potassium bis(trimethylsilyl)amide in toluene (0.8 mL). The mixture was stirred for 1 h at 0° C. ice bath, and was then cooled to −78° C. and treated with 3-[4-(7-[2-(trimethylsilyl)ethoxy]methyl-7H-pyrrolo[2,3-d]pyrimidin-4-yl)-1H-pyrazol-1-yl]pentanal (80 mg, 0.0002 mol) (from Example 498). The reaction was stirred at −78° C. and gradually was warmed to room temperature overnight. The reaction was partitioned between water and ethyl acetate. The organic layer was washed with saturated sodium chloride, dried over magnesium sulfate, filtered and concentrated to give 4-[1-(1-ethylbut-3-en-1-yl)-1H-pyrazol-4-yl]-7-[2-(trimethylsilyl)ethoxy]methyl-7H-pyrrolo[2,3-d]pyrimidine 150 mg as a crude product. LC/MS=398 (M+1).

Step 2: 4-[1-(1-Ethylbut-3-en-1-yl)-1H-pyrazol-4-yl]-7H-pyrrolo[2,3-d]pyrimidine Using a procedure analogous to Example 61 for the removal of the SEM protecting group the title compound was isolated as an amorphous white solid (25 mg, 1%). $^1$H NMR (400 MHz, DMSO): δ ☐8.6 (s, 2H), 8.2 (s, 1H), 7.4 (s, 1H), 6.9 (s, 1H), 5.8 (m, 1H), 5.0 (dd, 2H), 4.2 (m, 1H), 2.4-2.6 (m, 2H), 1.7-1.9 (m, 2H), 0.6 (t, 3H); LC/MS: 268 (M+1).

Example 500

(3R)- and (3S)-4,4,4-Trifluoro-3-[3-(7H-pyrrolo[2,3-d]pyrimidin-4-yl)-1H-pyrrol-1-yl]butanenitrile

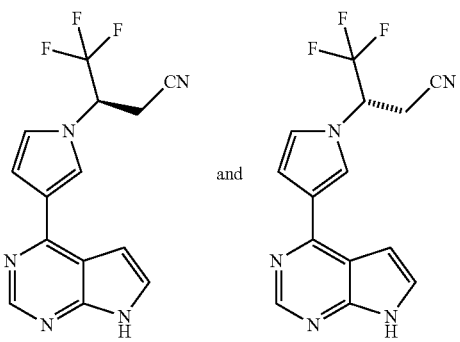 [SMILES: N#CC[C@@H](n1ccc(-c2ncnc3[nH]ccc23)c1)C(F)(F)F ; N#CC[C@H](n1ccc(-c2ncnc3[nH]ccc23)c1)C(F)(F)F]

Step 1. 4-Chloro-7-(diethoxymethyl)-7H-pyrrolo[2,3-d]pyrimidine

A mixture of 4-chloropyrrolo[2,3-d]pyrimidine (2.00 g, 0.0130 mol) and ethyl orthoformate (25 mL, 0.15 mol) was heated to reflux for 2 hours. The solvent was evaporated, and the residue was purified by flash column chromatography (eluting with ethyl acetate/hexanes) to yield the desired product (1.13 g, 34%).
$^1$H NMR (400 MHz, CDCl$_3$): δ 8.63 (s, 1H), 7.58 (d, 1H), 6.71 (s, 1H), 6.65 (d, 1H), 3.77-3.67 (m, 2H), 3.58-3.49 (m, 2H), 1.23 (t, 3H), 1.23 (t, 3H).

Step 2. 7-(Diethoxymethyl)-4-(1H-pyrrol-3-yl)-7H-pyrrolo[2,3-d]pyrimidine

To a degassed solution of 4-chloro-7-(diethoxymethyl)-7H-pyrrolo[2,3-d]pyrimidine (1.13 g, 0.00442 mol) and 1-(triisopropylsilyl)-3-boronic acid (1.00 g, 0.00374 mol) and sodium carbonate (0.396 g, 0.00374 mol) in 1,2-dimethoxyethane (15 mL) and water (3 mL) was added tetrakis(triphenylphosphine)palladium(0) (0.22 g, 0.00019 mol). This mixture was stirred at ambient temperature for 2 hours, and then was heated to reflux for 4 hours. The mixture was then cooled, concentrated, and purified by flash column chromatography (eluting with ethyl acetate/hexanes) to afford a residue as an oil. ACN was added to the residue, and the product which precipitated was filtered off and washed with a small quantity of ACN (165 mg, 13%).

$^1$H NMR (400 MHz, D$_6$dmso) δ ☐11.44 (br s, 1H), 8.66 (s, 1H), 7.80-7.78 (m, 1H), 7.58 (d, 1H), 7.03 (d, 1H), 6.94 (dd, 1H), 6.90 (dd, 1H), 6.75 (s, 1H), 3.74-3.65 (m, 2H), 3.59-3.50 (m, 2H), 1.15 (t, 6H); MS(ES): M+H=287.

Step 3

To a solution of 7-(diethoxymethyl)-4-(1H-pyrrol-3-yl)-7H-pyrrolo[2,3-d]pyrimidine (0.125 g, 0.436 mmol) and 4,4,4-trifluorobut-2-enenitrile (0.0476 mL, 0.480 mmol) in ACN (1 mL) was added DBU (0.0653 mL, 0.436 mmol). TFA (0.5 mL) was added and the mixture was stirred for 1 hour. The TFA and solvent was removed in vacuo. The residue was purified by preparative-HPLC/MS (C-18 eluting with a gradient of H$_2$O/ACN containing 0.15% NH$_4$OH) to afford the product (102 mg, 76%). Where desired, the enantiomers were separated in substantially pure form by chiral HPLC (AD-H, 20% EtOH/Hexane).

$^1$H NMR (300 MHz, D$_6$dmso) δ 12.05 (br s, 1H), 8.65 (s, 1H), 8.04 (s, 1H), 7.56 (dd, 1H), 7.21 (t, 1H), 7.02 (dd, 1H), 6.93 (dd, 1H), 5.89-5.74 (m, 1H), 3.95 (dd, 1H), 3.66 (dd, 1H); MS(ES): M+H=306.

The analog in Table 12 was prepared in racemic form according to the same procedure, using a different conjugate acceptor and with the exception that in the conjugate addition in Step 3, the reaction was carried out at 40° C. for 3 days.

TABLE 12

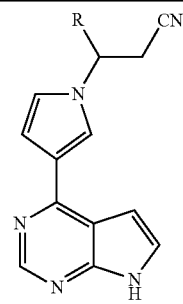

| Ex. No. | Name | R | MS (ES) (M + 1) | Method of preparation and chiral separation |
|---|---|---|---|---|
| 501 | 3-[3-(7H-pyrrolo[2,3-d]pyrimidin-4-yl)-1H-pyrrol-1-yl]butanenitrile | CH$_3$ | 252 | Ex. 500, enantiomers not separated |

The following compounds in Table 13 were prepared as indicated in the column labeled "Method of Prep." and the details of certain exemplary synthetic procedures are provided following Table 13.

TABLE 13

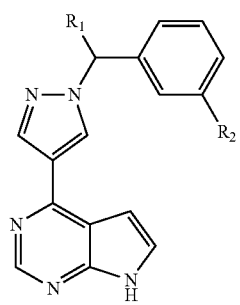

| Ex. # | R$^1$ | R$^2$ | M + 1 | Name | Method of prep. |
|---|---|---|---|---|---|
| 601 | CH$_2$CN | ![N-H-C(=O)-phenyl-CF$_3$] | 502 | N-(3-{2-cyano-1-[4-(7H-pyrrolo[2,3-d]pyrimidin-4-yl)-1H-pyrazol-1-yl]ethyl}phenyl)-3-(trifluoromethyl)benzamide | Ex 468 |
| 602 | H | ![N-H-C(=O)-phenyl-CF$_3$] | 463 | N-(3-{[4-(7H-pyrrolo[2,3-d]pyrimidin-4-yl)-1H-pyrazol-1-yl]methyl}phenyl)-3-(trifluoromethyl)benzamide | Ex 468 |

TABLE 13-continued

| Ex. # | R¹ | R² | M + 1 | Name | Method of prep. |
|---|---|---|---|---|---|
| 603 ee#1 | CH₂CN | SO₂CH₃ | 393 | 3-[3-(methylsulfonyl)phenyl]-3-[4-(7H-pyrrolo[2,3-d]pyrimidin-4-yl)-1H-pyrazol-1-yl]-propanenitrile | Ex 516 |
| 603 ee#2 | CH₂CN | SO₂CH₃ | 393 | 3-[3-(methylsulfonyl)phenyl]-3-[4-(7H-pyrrolo[2,3-d]pyrimidin-4-yl)-1H-pyrazol-1-yl]-propanenitrile | Ex 516 |
| 604 | H | -NH-SO₂-phenyl | 431 | N-(3-{[4-(7H-pyrrolo[2,3-d]-pyrimidin-4-yl)-1H-pyrazol-1-yl]methyl}phenyl)benzene-sulfonamide | Ex 469 |
| 605 | H | -C(O)-N(phenyl-CF₃)- | 463 | 3-{[4-(7H-pyrrolo[2,3-d]-pyrimidin-4-yl)-1H-pyrazol-1-yl]methyl}-N-[3-(trifluoro-methyl)phenyl]benzamide | Ex 472 |
| 606 ee#1 | CH₂CN | -SO₂-N(CH₃)₂ | 422 | 3-{2-cyano-1-[4-(7H-pyrrolo[2,3-d]pyrimidin-4-yl)-1H-pyrazol-1-yl]ethyl}-N,N-dimethylbenzenesulfonamide | Ex 649 |
| 606 ee#2 | CH₂CN | -SO₂-N(CH₃)₂ | 422 | 3-{2-cyano-1-[4-(7H-pyrrolo[2,3-d]pyrimidin-4-yl)-1H-pyrazol-1-yl]ethyl}-N,N-dimethylbenzenesulfonamide | Ex 649 |
| 607 | CH₂CN | -SO₂-NH-CH₂-phenyl | 484 | N-benzyl-3-{2-cyano-1-[4-(7H-pyrrolo[2,3-d]pyrimidin-4-yl)-1H-pyrazol-1-yl]ethyl}benzene-sulfonamide trifluoroacetate | Ex 649 |
| 608 | CH₂CN | -C(O)-NH-CH₂-phenyl | 448 | N-benzyl-3-{2-cyano-1-[4-(7H-pyrrolo[2,3-d]pyrimidin-4-yl)-1H-pyrazol-1-yl]ethyl}-benzamide | Ex 472 |
| 609 | CH₂CN | -C(O)-NH-phenyl | 434 | 3-{2-cyano-1-[4-(7H-pyrrolo[2,3-d]pyrimidin-4-yl)-1H-pyrazol-1-yl]ethyl}-N-phenylbenzamide trifluoroacetate | Ex 472 |

TABLE 13-continued

| Ex. # | R¹ | R² | M + 1 | Name | Method of prep. |
|---|---|---|---|---|---|
| 610 | CH₂CN | -C(O)NH-C₆H₄-CF₃ (3-CF₃) | 502 | 3-{2-cyano-1-[4-(7H-pyrrolo[2,3-d]pyrimidin-4-yl)-1H-pyrazol-1-yl]ethyl}-N-[3-(trifluoromethyl)phenyl]-benzamide trifluoroacetate | Ex 472 |
| 611 | H | -C(O)NH-C₆H₄-CN (3-CN) | 420 | N-(3-cyanophenyl)-3-{[4-(7H-pyrrolo[2,3-d]pyrimidin-4-yl)-1H-pyrazol-1-yl]-methyl}benzamide | Ex 472 |
| 612 | H | -C(O)NH-CH₂-C₆H₅ | 409 | N-benzyl-3-{[4-(7H-pyrrolo-[2,3-d]pyrimidin-4-yl)-1H-pyrazol-1-yl]methyl}benzamide | Ex 472 |
| 613 | H | -C(O)NH-(1-naphthyl) | 445 | N-1-naphthyl-3-{[4-(7H-pyrrolo[2,3-d]pyrimidin-4-yl)-1H-pyrazol-1-yl]methyl}-benzamide | Ex 472 |
| 614 | H | -C(O)NH-(2-naphthyl) | 445 | N-2-naphthyl-3-{[4-(7H-pyrrolo[2,3-d]pyrimidin-4-yl)-1H-pyrazol-1-yl]methyl}-benzamide | Ex 472 |
| 615 | H | -NH-C(O)-(2-naphthyl) | 445 | N-(3-{[4-(7H-pyrrolo[2,3-d]-pyrimidin-4-yl)-1H-pyrazol-1-yl]methyl}phenyl)-2-naphthamide trifluoroacetate | Ex 468 |
| 616 | H | -NH-C(O)-(1-naphthyl) | 445 | N-(3-{[4-(7H-pyrrolo[2,3-d]-pyrimidin-4-yl)-1H-pyrazol-1-yl]methyl}phenyl)-1-naphthamide trifluoroacetate | Ex 468 |

TABLE 13-continued

| Ex. # | R¹ | R² | M + 1 | Name | Method of prep. |
|---|---|---|---|---|---|
| 617 | H | NHC(O)CH₂-phenyl | 409 | 2-phenyl-N-(3-{[4-(7H-pyrrolo[2,3-d]pyrimidin-4-yl)-1H-pyrazol-1-yl]methyl}-phenyl)acetamide trifluoroacetate | Ex 468 |
| 618 | H | NHC(O)-(3-chlorophenyl) | 429 | 3-chloro-N-(3-{[4-(7H-pyrrolo-[2,3-d]pyrimidin-4-yl)-1H-pyrazol-1-yl]methyl}phenyl)-benzamide trifluoroacetate | Ex 468 |
| 619 | CH₂CN | NHC(O)-(2-naphthyl) | 484 | N-(3-{2-cyano-1-[4-(7H-pyrrolo[2,3-d]pyrimidin-4-yl)-1H-pyrazol-1-yl]ethyl}phenyl)-2-naphthamide trifluoroacetate | Ex 468 |
| 620 | CH₂CN | NHC(O)-(1-naphthyl) | 484 | N-(3-{2-cyano-1-[4-(7H-pyrrolo[2,3-d]pyrimidin-4-yl)-1H-pyrazol-1-yl]ethyl}phenyl)-1-naphthamide trifluoroacetate | Ex 468 |
| 621 | CH₂CN | NHC(O)CH₂-phenyl | 448 | N-(3-{2-cyano-1-[4-(7H-pyrrolo[2,3-d]pyrimidin-4-yl)-1H-pyrazol-1-yl]-ethyl}phenyl)-2-phenylacetamide trifluoroacetate | Ex 468 |
| 622 | CH₂CN | NHC(O)-(3-cyanophenyl) | 459 | 3-cyano-N-(3-{2-cyano-1-[4-(7H-pyrrolo[2,3-d]pyrimidin-4-yl)-1H-pyrazol-1-yl]-ethyl}phenyl)benzamide trifluoroacetate | Ex 468 |
| 623 | CH₂CN | NHC(O)-phenyl | 434 | N-(3-{2-cyano-1-[4-(7H-pyrrolo[2,3-d]pyrimidin-4-yl)-1H-pyrazol-1-yl]ethyl}-phenyl)benzamide trifluoroacetate | Ex 468 |
| 624 | CH₂CN | NHC(O)-(4-trifluoromethylphenyl) | 502 | N-(3-{2-cyano-1-[4-(7H-pyrrolo[2,3-d]pyrimidin-4-yl)-1H-pyrazol-1-yl]ethyl}phenyl)-4-(trifluoromethyl)benzamide trifluoroacetate | Ex 468 |

TABLE 13-continued

| Ex. # | R¹ | R² | M + 1 | Name | Method of prep. |
|---|---|---|---|---|---|
| 625 | CH₂CN | -NH-C(O)-NH-phenyl | 449 | N-(3-{2-cyano-1-[4-(7H-pyrrolo[2,3-d]pyrimidin-4-yl)-1H-pyrazol-1-yl]ethyl}phenyl)-N'-phenylurea trifluoroacetate | Ex 480 |
| 626 | CH₂CN | -C(O)-NH-(4-CF₃-phenyl) | 502 | 3-{2-cyano-1-[4-(7H-pyrrolo-[2,3-d]pyrimidin-4-yl)-1H-pyrazol-1-yl]ethyl}-N-[4-(trifluoromethyl)phenyl]-benzamide trifluoroacetate | Ex 472 |
| 627 | CH₂CN | -C(O)-NH-(4-CH₃-phenyl) | 448 | 3-{2-cyano-1-[4-(7H-pyrrolo-[2,3-d]pyrimidin-4-yl)-1H-pyrazol-1-yl]ethyl}-N-(4-methylphenyl)benzamide trifluoroacetate | Ex 472 |
| 628 | CH₂CN | -C(O)-NH-(4-CN-phenyl) | 459 | N-(4-cyanophenyl)-3-{2-cyano-1-[4-(7H-pyrrolo[2,3-d]-pyrimidin-4-yl)-1H-pyrazol-1-yl]ethyl}benzamide trifluoroacetate | Ex 472 |
| 629 | CH₂CN | -C(O)-NH-(2-naphthyl) | 484 | 3-{2-cyano-1-[4-(7H-pyrrolo-[2,3-d]pyrimidin-4-yl)-1H-pyrazol-1-yl]ethyl}-N-2-naphthylbenzamide trifluoro-acetate | Ex 472 |
| 630 | CH₂CN | -C(O)-NH-(1-naphthyl) | 484 | 3-{2-cyano-1-[4-(7H-pyrrolo-[2,3-d]pyrimidin-4-yl)-1H-pyrazol-1-yl]ethyl}-N-1-naphthylbenzamide tri-fluoroacetate | Ex 472 |
| 631 | CH₂CN | -C(O)-N(CH₃)₂ | 386 | 3-{2-cyano-1-[4-(7H-pyrrolo-[2,3-d]pyrimidin-4-yl)-1H-pyrazol-1-yl]ethyl}-N,N-dimethylbenzamide tri-fluoroacetate | Ex 472 |
| 632 | CH₂CN | -C(O)-NH-(pyridin-3-yl) | 435 | 3-{2-cyano-1-[4-(7H-pyrrolo-[2,3-d]pyrimidin-4-yl)-1H-pyrazol-1-yl]ethyl}-N-pyridin-3-ylbenzamide trifluoroacetate | Ex 472 |

TABLE 13-continued

| Ex. # | R¹ | R² | M + 1 | Name | Method of prep. |
|---|---|---|---|---|---|
| 633 | CH₂CN | N-methyl-N-phenyl amide | 448 | 3-{2-cyano-1-[4-(7H-pyrrolo-[2,3-d]pyrimidin-4-yl)-1H-pyrazol-1-yl]ethyl}-N-methyl-N-phenylbenzamide trifluoroacetate | Ex 472 |
| 634 | CH₂CN | N-cyclohexyl amide | 440 | 3-{2-cyano-1-[4-(7H-pyrrolo-[2,3-d]pyrimidin-4-yl)-1H-pyrazol-1-yl]ethyl}-N-cyclohexylbenzamide trifluoroacetate | Ex 472 |
| 635 | CH₂CN | N-(4-phenoxyphenyl) amide | 526 | 3-{2-cyano-1-[4-(7H-pyrrolo-[2,3-d]pyrimidin-4-yl)-1H-pyrazol-1-yl]ethyl}-N-(4-phenoxyphenyl)benzamide trifluoroacetate | Ex 472 |
| 636 | CH₂CN | N-(3-cyanophenyl) amide | 459 | N-(3-cyanophenyl)-3-{2-cyano-1-[4-(7H-pyrrolo[2,3-d]-pyrimidin-4-yl)-1H-pyrazol-1-yl]ethyl}benzamide trifluoroacetate | Ex 472 |
| 637 | CH₂CN | N-biphenyl-4-yl amide | 510 | N-biphenyl-4-yl-3-{2-cyano-1-[4-(7H-pyrrolo[2,3-d]pyrimidin-4-yl)-1H-pyrazol-1-yl]ethyl}benzamide trifluoroacetate | Ex 472 |
| 638 | CH₂CN | N-(4-chlorophenyl) amide | 468 | N-(4-chlorophenyl)-3-{2-cyano-1-[4-(7H-pyrrolo[2,3-d]-pyrimidin-4-yl)-1H-pyrazol-1-yl]ethyl}benzamide trifluoroacetate | Ex 472 |
| 639 | CH₂CN | N-(3,4-dimethylphenyl) amide | 462 | 3-{2-cyano-1-[4-(7H-pyrrolo-[2,3-d]pyrimidin-4-yl)-1H-pyrazol-1-yl]ethyl}-N-(3,4-dimethylphenyl)benzamide trifluoroacetate | Ex 472 |
| 640 | CH₂CN | N-(3-methoxyphenyl) amide | 464 | 3-{2-cyano-1-[4-(7H-pyrrolo-[2,3-d]pyrimidin-4-yl)-1H-pyrazol-1-yl]ethyl}-N-(3-methoxyphenyl)benzamide trifluoroacetate | Ex 472 |

TABLE 13-continued

| Ex. # | R¹ | R² | M + 1 | Name | Method of prep. |
|---|---|---|---|---|---|
| 641 | CH₂CN | -C(O)NH-C₆H₄-OCH₃ (4-methoxyphenyl amide) | 464 | 3-{2-cyano-1-[4-(7H-pyrrolo-[2,3-d]pyrimidin-4-yl)-1H-pyrazol-1-yl]ethyl}-N-(4-methoxyphenyl)benzamide trifluoroacetate | Ex 472 |
| 642 | CH₂CN | -C(O)NH-isoxazol-3-yl | 425 | 3-{2-cyano-1-[4-(7H-pyrrolo-[2,3-d]pyrimidin-4-yl)-1H-pyrazol-1-yl]ethyl}-N-isoxazol-3-ylbenzamide trifluoroacetate | Ex 472 |
| 643 | CH₂CN | -SO₂N(CH₃)(C₆H₅) | 484 | 3-{2-cyano-1-[4-(7H-pyrrolo-[2,3-d]pyrimidin-4-yl)-1H-pyrazol-1-yl]ethyl}-N-methyl-N-phenylbenzenesulfonamide | Ex 649 |
| 644 | CH₂CN | -SO₂NH-propyl | 436 | 3-{2-cyano-1-[4-(7H-pyrrolo-[2,3-d]pyrimidin-4-yl)-1H-pyrazol-1-yl]ethyl}-N-propylbenzenesulfonamide | Ex 649 |
| 645 | CH₂CN | -SO₂NH-C₆H₅ | 470 | 3-{2-cyano-1-[4-(7H-pyrrolo-[2,3-d]pyrimidin-4-yl)-1H-pyrazol-1-yl]ethyl}-N-phenylbenzenesulfonamide | Ex 649 |
| 646 | CH₂CN | -SO₂NH-(2-naphthyl) | 520 | 3-{2-cyano-1-[4-(7H-pyrrolo-[2,3-d]pyrimidin-4-yl)-1H-pyrazol-1-yl]ethyl}-N-2-naphthylbenzenesulfonamide | Ex 649 |
| 647 | CH₂CN | -SO₂NH-cyclopropyl | 434 | 3-{2-cyano-1-[4-(7H-pyrrolo-[2,3-d]pyrimidin-4-yl)-1H-pyrazol-1-yl]ethyl}-N-cyclopropylbenzenesulfonamide | Ex 649 |
| 648 | CH₂CN | -SO₂-piperidin-1-yl | 462 | 3-[3-(piperidin-1-ylsulfonyl)-phenyl]-3-[4-(7H-pyrrolo[2,3-d]pyrimidin-4-yl)-1H-pyrazol-1-yl]propanenitrile | Ex 649 |

TABLE 13-continued

| Ex. # | R¹ | R² | M + 1 | Name | Method of prep. |
|---|---|---|---|---|---|
| 649 | CH₂CN | 3-(morpholin-4-ylsulfonyl)phenyl | 464 | 3-[3-(morpholin-4-ylsulfonyl)-phenyl]-3-[4-(7H-pyrrolo[2,3-d]pyrimidin-4-yl)-1H-pyrazol-1-yl]propanenitrile | Ex 649 |
| 650 | CH₂CN | -SO₂-NH-(4-methylphenyl) | 484 | 3-{2-cyano-1-[4-(7H-pyrrolo-[2,3-d]pyrimidin-4-yl)-1H-pyrazol-1-yl]ethyl}-N-(4-methylphenyl)benzene-sulfonamide trifluoroacetate | Ex 649 |
| 651 | CH₂CN | -SO₂-NH-(3,4-dimethylphenyl) | 498 | 3-{2-cyano-1-[4-(7H-pyrrolo-[2,3-d]pyrimidin-4-yl)-1H-pyrazol-1-yl]ethyl}-N-(3,4-dimethylphenyl)benzene-sulfonamide trifluoroacetate | Ex 649 |
| 652 | CH₂CN | -SO₂-NH-(3-methoxyphenyl) | 500 | 3-{2-cyano-1-[4-(7H-pyrrolo-[2,3-d]pyrimidin-4-yl)-1H-pyrazol-1-yl]ethyl}-N-(3-methoxyphenyl)benzene-sulfonamide trifluoroacetate | Ex 649 |
| 653 | CH₂CN | -SO₂-NH-(4-methoxyphenyl) | 500 | 3-{2-cyano-1-[4-(7H-pyrrolo-[2,3-d]pyrimidin-4-yl)-1H-pyrazol-1-yl]ethyl}-N-(4-methoxyphenyl)benzene-sulfonamide trifluoroacetate | Ex 649 |
| 654 | CH₂CN | -C(O)-NH-(3,5-dimethoxyphenyl) | 494 | 3-{2-cyano-1-[4-(7H-pyrrolo-[2,3-d]pyrimidin-4-yl)-1H-pyrazol-1-yl]ethyl}-N-(3,5-dimethoxyphenyl)benzamide trifluoroacetate | Ex 472 |
| 655 | CH₂CN | -C(O)-NH-[4-(dimethylamino)phenyl] | 477 | 3-{2-cyano-1-[4-(7H-pyrrolo-[2,3-d]pyrimidin-4-yl)-1H-pyrazol-1-yl]ethyl}-N-[4-(dimethylamino)phenyl]-benzamide trifluoroacetate | Ex 472 |

TABLE 13-continued

| Ex. # | R¹ | R² | M + 1 | Name | Method of prep. |
|---|---|---|---|---|---|
| 656 | CH₂CN | -S(O)₂-CH₂-phenyl | 469 | 3-[3-(benzylsulfonyl)phenyl]-3-[4-(7H-pyrrolo[2,3-d]pyrimidin-4-yl)-1H-pyrazol-1-yl]-propanenitrile | Ex 516 |
| 657 | CH₂CN | -S-CH₂-phenyl | 437 | 3-[3-(benzylthio)phenyl]-3-[4-(7H-pyrrolo[2,3-d]pyrimidin-4-yl)-1H-pyrazol-1-yl]-propanenitrile | Ex 514 |
| 658 | CH₂CN | -S(O)₂-CH₂-(4-CN-phenyl) | 494 | 4-{[(3-{2-cyano-1-[4-(7H-pyrrolo[2,3-d]pyrimidin-4-yl)-1H-pyrazol-1-yl]ethyl}phenyl)-sulfonyl]methyl}benzonitrile | Ex 516 |
| 659 | CH₂CN | -S(O)₂-NH-CH₃ | 408 | 3-{2-cyano-1-[4-(7H-pyrrolo-[2,3-d]pyrimidin-4-yl)-1H-pyrazol-1-yl]ethyl}-N-methyl-benzenesulfonamide | Ex 649 |
| 660 | CH₂CN | -S(O)₂-NH-(1-naphthyl) | 520 | 3-{2-cyano-1-[4-(7H-pyrrolo-[2,3-d]pyrimidin-4-yl)-1H-pyrazol-1-yl]ethyl}-N-1-naphthylbenzenesulfonamide | Ex 649 |
| 661 | CH₂CN | -S(O)₂-NH-(biphenyl-4-yl) | 546 | N-biphenyl-4-yl-3-{2-cyano-1-[4-(7H-pyrrolo[2,3-d]pyrimidin-4-yl)-1H-pyrazol-1-yl]ethyl}-benzenesulfonamide | Ex 649 |
| 662 | CH₂CN | -C(O)-NH-(4-OCF₃-phenyl) | 518 | 3-{2-cyano-1-[4-(7H-pyrrolo-[2,3-d]pyrimidin-4-yl)-1H-pyrazol-1-yl]ethyl}-N-[4-(trifluoromethoxy)phenyl]-benzamide trifluoroacetate | Ex 472 |

TABLE 13-continued

| Ex. # | R¹ | R² | M + 1 | Name | Method of prep. |
|---|---|---|---|---|---|
| 663 | CH₂CN | (2-methoxyphenyl)benzamide group | 464 | 3-{2-cyano-1-[4-(7H-pyrrolo-[2,3-d]pyrimidin-4-yl)-1H-pyrazol-1-yl]ethyl}-N-(2-methoxyphenyl)benzamide trifluoroacetate | Ex 472 |
| 664 | CH₂CN | benzyloxy group | 421 | 3-[3-(benzyloxy)phenyl]-3-[4-(7H-pyrrolo[2,3-d]pyrimidin-4-yl)-1H-pyrazol-1-yl]-propanenitrile | Ex 514 |
| 665 | CH₂CN | N-cyclohexylsulfonamide group | 476 | 3-{2-cyano-1-[4-(7H-pyrrolo-[2,3-d]pyrimidin-4-yl)-1H-pyrazol-1-yl]ethyl}-N-cyclohexylbenzenesulfonamide trifluoroacetate | Ex 649 |
| 666 | CH₂CN | 3,4-dihydroisoquinolin-2(1H)-ylsulfonyl group | 510 | 3-[3-(3,4-dihydroisoquinolin-2(1H)-ylsulfonyl)phenyl]-3-[4-(7H-pyrrolo[2,3-d]pyrimidin-4-yl)-1H-pyrazol-1-yl]propane-nitrile trifluoroacetate | Ex 649 |
| 667 | CH₂CN | N-(2-methoxyethyl)sulfonamide group | 452 | 3-{2-cyano-1-[4-(7H-pyrrolo-[2,3-d]pyrimidin-4-yl)-1H-pyrazol-1-yl]ethyl}-N-(2-methoxyethyl)benzene-sulfonamide trifluoroacetate | Ex 649 |
| 668 | CH₂CN | N,N-diethylsulfonamide group | 450 | 3-{2-cyano-1-[4-(7H-pyrrolo-[2,3-d]pyrimidin-4-yl)-1H-pyrazol-1-yl]ethyl}-N,N-diethylbenzenesulfonamide | Ex 649 |
| 669 | CH₂CN | 4-methylpiperazin-1-ylsulfonyl group | 491 | 3-{3-[(4-ethylpiperazin-1-yl)-sulfonyl]phenyl}-3-[4-(7H-pyrrolo[2,3-d]-pyrimidin-4-yl)-1H-pyrazol-1-yl]propanenitrile | Ex 649 |
| 670 | CH₂CN | N-(1,3-benzodioxol-5-yl)sulfonamide group | 514 | N-1,3-benzodioxol-5-yl-3-{2-cyano-1-[4-(7H-pyrrolo[2,3-d]-pyrimidin-4-yl)-1H-pyrazol-1-yl]ethyl}benzenesulfonamide | Ex 649 |

TABLE 13-continued

| Ex. # | R¹ | R² | M + 1 | Name | Method of prep. |
|---|---|---|---|---|---|
| 671 | CH₂CN | ~S(O)₂-CH₂-C₆H₄-OCH₃ (3-methoxybenzyl sulfonyl) | 499 | 3-{3-[(3-methoxybenzyl)-sulfonyl]phenyl}-3-[4-(7H-pyrrolo[2,3-d]pyrimidin-4-yl)-1H-pyrazol-1-yl]-propanenitrile | Ex 516 |
| 672 | CH₂CN | ~S(O)₂-CH₂-C₆H₄-OCH₃ (4-methoxybenzyl sulfonyl) | 499 | 3-{3-[(4-methoxybenzyl)-sulfonyl]phenyl}-3-[4-(7H-pyrrolo[2,3-d]pyrimidin-4-yl)-1H-pyrazol-1-yl]-propanenitrile | Ex 516 |
| 673 | CH₂CN | 2,6-dimethylmorpholin-4-ylsulfonyl | 492 | 3-{3-[(2,6-dimethylmorpholin-4-yl)sulfonyl]phenyl}-3-[4-(7H-pyrrolo[2,3-d]pyrimidin-4-yl)-1H-pyrazol-1-yl]-propanenitrile | Ex 649 |
| 674 | CH₂CN | 4-oxopiperidin-1-ylsulfonyl | 476 | 3-{3-[(4-oxopiperidin-1-yl)-sulfonyl]phenyl}-3-[4-(7H-pyrrolo[2,3-d]pyrimidin-4-yl)-1H-pyrazol-1-yl]propanenitrile trifluoroacetate | Ex 649 |
| 675 | CH₂CN | isopropylsulfonyl | 421 | 3-[3-(isopropylsulfonyl)phenyl]-3-[4-(7H-pyrrolo[2,3-d]-pyrimidin-4-yl)-1H-pyrazol-1-yl]propanenitrile trifluoroacetate | Ex 516 |
| 676 | CH₂CN | cyclohexylmethylsulfonyl | 475 | 3-{3-[(cyclohexylmethyl)-sulfonyl]phenyl}-3-[4-(7H-pyrrolo[2,3-d]pyrimidin-4-yl)-1H-pyrazol-1-yl]-propanenitrile trifluoroacetate | Ex 516 |
| 677 | CH₂CN | octahydroisoquinolin-2(1H)-ylsulfonyl | 516 | 3-[3-(octahydroisoquinolin-2(1H)-ylsulfonyl)phenyl]-3-[4-(7H-pyrrolo[2,3-d]pyrimidin-4-yl)-1H-pyrazol-1-yl]propanenitrile trifluoroacetate | Ex 649 |
| 678 | CH₂CN | 2-phenylethylsulfonyl | 483 | 3-{2-cyano-1-[4-(7H-pyrrolo-[2,3-d]pyrimidin-4-yl)-1H-pyrazol-1-yl]ethyl}-N-(2-phenylethyl)benzene sulfonamide trifluoroacetate | Ex 516 |

TABLE 13-continued

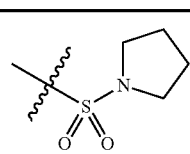

| Ex. # | R¹ | R² | M + 1 | Name | Method of prep. |
|---|---|---|---|---|---|
| 679 | CH₂CN | 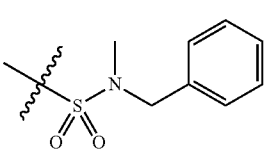 [SMILES: *S(=O)(=O)N(C)Cc1ccccc1] | 448 | 3-[3-(pyrrolidin-1-ylsulfonyl)-phenyl]-3-[4-(7H-pyrrolo[2,3-d]-pyrimidin-4-yl)-1H-pyrazol-1-yl]propanenitrile | Ex 649 |
| 680 | CH₂CN | 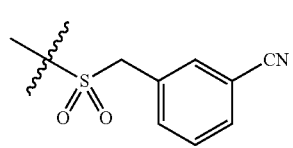 [SMILES: *S(=O)(=O)Cc1cccc(C#N)c1] | 498 | N-benzyl-3-{2-cyano-1-[4-(7H-pyrrolo[2,3-d]pyrimidin-4-yl)-1H-pyrazol-1-yl]ethyl}-N-methylbenzenesulfonamide | Ex 649 |
| 681 | CH₂CN | 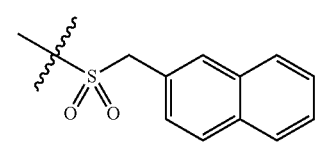 [SMILES: *S(=O)(=O)Cc1ccc2ccccc2c1] | 494 | 3-{[(3-{2-cyano-1-[4-(7H-pyrrolo[2,3-d]pyrimidin-4-yl)-1H-pyrazol-1-yl]ethyl}-phenyl)sulfonyl]methyl}-benzonitrile | Ex 516 |
| 682 | CH₂CN | 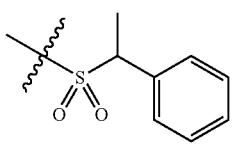 [SMILES: *S(=O)(=O)C(C)c1ccccc1] | 519 | 3-{3-[(2-naphthylmethyl)-sulfonyl]phenyl}-3-[4-(7H-pyrrolo[2,3-d]pyrimidin-4-yl)-1H-pyrazol-1-yl]propanenitrile | Ex 516 |
| 683 | CH₂CN | 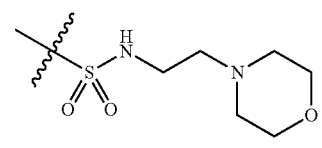 [SMILES: *S(=O)(=O)NCCN1CCOCC1] | 483 | 3-{3-[(1-phenylethyl)sulfonyl]-phenyl}-3-[4-(7H-pyrrolo[2,3-d]-pyrimidin-4-yl)-1H-pyrazol-1-yl]propanenitrile | Ex 516 |
| 684 | CH₂CN | 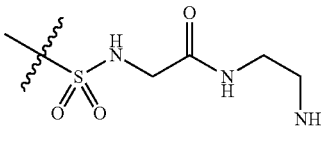 | 507 | 3-{2-cyano-1-[4-(7H-pyrrolo-[2,3-d]pyrimidin-4-yl)-1H-pyrazol-1-yl]ethyl}-N-(2-morpholin-4-ylethyl)-benzenesulfonamide | Ex 649 |
| 685 | CH₂CN | 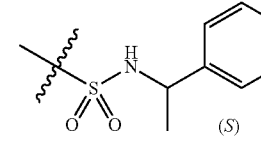 | 494 | N-(2-aminoethyl)-2-{[(3-{2-cyano-1-[4-(7H-pyrrolo[2,3-d]-pyrimidin-4-yl)-1H-pyrazol-1-yl]ethyl}phenyl)sulfonyl]-amino}acetamide | Ex 649 |
| 686 | CH₂CN |  | 498 | 3-{2-cyano-1-[4-(7H-pyrrolo-[2,3-d]pyrimidin-4-yl)-1H-pyrazol-1-yl]ethyl}-N-[(1S)-1-phenylethyl]benzenesulfonamide | Ex 649 |

TABLE 13-continued

| Ex. # | R¹ | R² | M + 1 | Name | Method of prep. |
|---|---|---|---|---|---|
| 687 ee#1 | CH₂CN | –C(O)NH-phenyl | 434 | 3-{2-cyano-1-[4-(7H-pyrrolo-[2,3-d]pyrimidin-4-yl)-1H-pyrazol-1-yl]ethyl}-N-phenyl-benzamide trifluoroacetate | Ex 472 |
| 687 ee#2 | CH₂CN | –C(O)NH-phenyl | 434 | 3-{2-cyano-1-[4-(7H-pyrrolo-[2,3-d]pyrimidin-4-yl)-1H-pyrazol-1-yl]ethyl}-N-phenyl-benzamide trifluoroacetate | Ex 472 |
| 688 | CH₂CN | –S(O)₂NHCH₂-(tetrahydrofuran-2-yl) | 478 | 3-{2-cyano-1-[4-(7H-pyrrolo-[2,3-d]pyrimidin-4-yl)-1H-pyrazol-1-yl]ethyl}-N-(tetrahydrofuran-2-yl-methyl)benzenesulfonamide | Ex 472 |
| 689 | CH₂CN | –S(O)₂CH₂-cyclopropyl | 433 | 3-{3-[(cyclopropylmethyl)sulfonyl]phenyl}-3-[4-(7H-pyrrolo[2,3-d]pyrimidin-4-yl)-1H-pyrazol-1-yl]propanenitrile trifluoroacetate | Ex 516 |
| 690 | CH₂CN | –S(O)₂-(4-methylpiperazin-1-yl) | 477 | 3-{3-[(4-methylpiperazin-1-yl)-sulfonyl]phenyl}-3-[4-(7H-pyrrolo[2,3-d]pyrimidin-4-yl)-1H-pyrazol-1-yl]propanenitrile | Ex 472 |
| 691 | CH₂CN | –S(O)₂-(3-(N,N-diethylcarboxamido)piperidin-1-yl) | 561 | 1-[(3-{2-cyano-1-[4-(7H-pyrrolo-[2,3-d]pyrimidin-4-yl)-1H-pyrazol-1-yl]ethyl}-phenyl)sulfonyl]-N,N-diethyl-piperidine-3-carboxamide | Ex 472 |
| 692 | CH₂CN | –S(O)₂-(1-oxidothiomorpholin-4-yl) | 496 | 3-{3-[(1-oxidothiomorpholin-4-yl)sulfonyl]phenyl}-3-[4-(7H-pyrrolo[2,3-d]pyrimidin-4-yl)-1H-pyrazol-1-yl]propanenitrile | Ex 472 |
| 693 | CH₂CN | –S(O)₂-(piperazin-1-yl) | 463 | 3-[3-(piperazin-1-ylsulfonyl)-phenyl]-3-[4-(7H-pyrrolo[2,3-d]-pyrimidin-4-yl)-1H-pyrazol-1-yl]propanenitrile | Ex 472 |

TABLE 13-continued

| Ex. # | R¹ | R² | M + 1 | Name | Method of prep. |
|---|---|---|---|---|---|
| 694 | CH₂CN | (thiomorpholine sulfonyl with gem-dimethyl) | 480 | 3-[4-(7H-pyrrolo[2,3-d]pyrimidin-4-yl)-1H-pyrazol-1-yl]-3-[3-(thiomorpholin-4-yl-sulfonyl)phenyl]propanenitrile | Ex 472 |
| 695 | CH₂CN | (4-hydroxypiperidin-1-yl sulfonyl) | 478 | 3-{3-[(4-hydroxypiperidin-1-yl)-sulfonyl]phenyl}-3-[4-(7H-pyrrolo[2,3-d]pyrimidin-4-yl)-1H-pyrazol-1-yl]propanenitrile trifluoroacetate | Ex 472 |
| 696 | CH₂CN | (isobutylsulfonyl) | 435 | 3-[3-(isobutylsulfonyl)phenyl]-3-[4-(7H-pyrrolo[2,3-d]pyrimidin-4-yl)-1H-pyrazol-1-yl]propane-nitrile trifluoroacetate | Ex 516 |
| 697 | CH₂CN | ((tetrahydro-2H-pyran-4-ylmethyl)sulfonyl) | 477 | 3-[4-(7H-pyrrolo[2,3-d]-pyrimidin-4-yl)-1H-pyrazol-1-yl]-3-{3-[(tetrahydro-2H-pyran-4-ylmethyl)sulfonyl]-phenyl}propanenitrile trifluoroacetate | Ex 516 |
| 698 | CH₂CN | ((2-methoxyethyl)sulfonyl) | 437 | 3-{3-[(2-methoxyethyl)sulfonyl]-phenyl}-3-[4-(7H-pyrrolo[2,3-d]pyrimidin-4-yl)-1H-pyrazol-1-yl]propanenitrile trifluoroacetate | Ex 516 |
| 699 | CH₂CN | ((3-furylmethyl)sulfonyl) | 459 | 3-{3-[(3-furylmethyl)sulfonyl]-phenyl}-3-[4-(7H-pyrrolo[2,3-d]pyrimidin-4-yl)-1H-pyrazol-1-yl]propanenitrile trifluoroacetate | Ex 516 |
| 700 | CH₂CN | (1,1-dioxidothiomorpholin-4-yl sulfonyl) | 512 | 3-{3-[(1,1-dioxidothiomorpholin-4-yl)sulfonyl]phenyl}-3-[4-(7H-pyrrolo[2,3-d]pyrimidin-4-yl)-1H-pyrazol-1-yl]propanenitrile | Ex 649 |
| 701 | CH₂CN | (4-acetylpiperazin-1-yl sulfonyl) | 505 | 3-{3-[(4-acetylpiperazin-1-yl)-sulfonyl]phenyl}-3-[4-(7H-pyrrolo[2,3-d]pyrimidin-4-yl)-1H-pyrazol-1-yl]propanenitrile | Ex 649 |

TABLE 13-continued

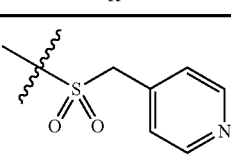

| Ex. # | R¹ | R² | M + 1 | Name | Method of prep. |
|---|---|---|---|---|---|
| 702 | CH₂CN | 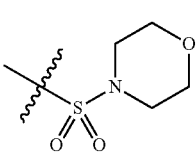 [SMILES: *S(=O)(=O)N1CCOCC1] | 470 | 3-{3-[(pyridin-4-ylmethyl)-sulfonyl]phenyl}-3-[4-(7H-pyrrolo[2,3-d]pyrimidin-4-yl)-1H-pyrazol-1-yl]propanenitrile | Ex 516 |
| 703 | CH₂C≡CH | H | 314 | 4-[1-(1-phenylbut-3-yn-1-yl)-1H-pyrazol-4-yl]-7H-pyrrolo[2,3-d]-pyrimidine trifluoroacetate | Ex 705 |
| 704 | CH₂C≡CH | 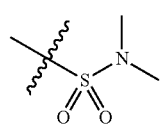 [SMILES: *S(=O)(=O)N(C)C] | 463 | 4-(1-{1-[3-(morpholin-4-yl-sulfonyl)phenyl]but-3-yn-1-yl}-1H-pyrazol-4-yl)-7H-pyrrolo[2,3-d]pyrimidine | Ex 705 |
| 705 | CH₂C≡CH | CN | 339 | 3-{1-[4-(7H-pyrrolo[2,3-d]-pyrimidin-4-yl)-1H-pyrazol-1-yl]but-3-yn-1-yl}benzonitrile trifluoroacetate | Ex 705 |
| 706 | CH₂C≡CH | CH=O | 342 | 3-{1-[4-(7H-pyrrolo[2,3-d]-pyrimidin-4-yl)-1H-pyrazol-1-yl]but-3-yn-1-yl}benzaldehyde trifluoroacetate | Ex 706 |
| 707 | CH₂CO₂CH₃ | CN | 373 | methyl 3-(3-cyanophenyl)-3-[4-(7H-pyrrolo[2,3-d]pyrimidin-4-yl)-1H-pyrazol-1-yl]propanoate trifluoroacetate | Ex 712 |
| 708 | CH₂C≡CH | 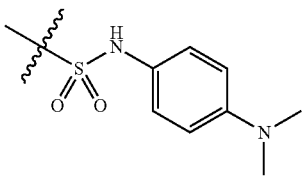 [SMILES: *S(=O)(=O)Nc1ccc(N(C)C)cc1] | 421 | N,N-dimethyl-3-{1-[4-(7H-pyrrolo[2,3-d]pyrimidin-4-yl)-1H-pyrazol-1-yl]but-3-yn-1-yl}-benzenesulfonamide trifluoroacetate | Ex 705 |
| 709 | CH₂CN | 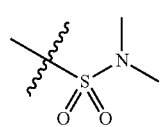 [SMILES: *S(=O)(=O)N(C)C] | 513 | 3-{2-cyano-1-[4-(7H-pyrrolo[2,3-d]pyrimidin-4-yl)-1H-pyrazol-1-yl]ethyl}-N-[4-(dimethylamino)phenyl]-benzenesulfonamide | Ex 649 |
| 710 | CH₂CH₂—OCH₃ | 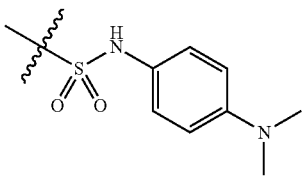 [SMILES: *S(=O)(=O)Nc1ccc(N(C)C)cc1] | 441 | 3-{3-methoxy-1-[4-(7H-pyrrolo-[2,3-d]pyrimidin-4-yl)-1H-pyrazol-1-yl]propyl}-N,N-dimethylbenzenesulfonamide trifluoroacetate | Ex 712 |
| 711 | CH₂C≡CH | 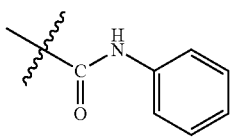 [SMILES: *C(=O)Nc1ccccc1] | 433 | N-phenyl-3-{1-[4-(7H-pyrrolo-[2,3-d]pyrimidin-4-yl)-1H-pyrazol-1-yl]but-3-yn-1-yl}-benzamide trifluoroacetate | Ex 705 |

TABLE 13-continued

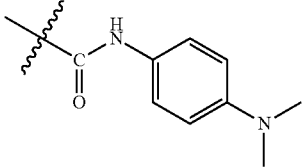 [SMILES: *C(=O)Nc1ccc(N(C)C)cc1]

| Ex. # | R¹ | R² | M + 1 | Name | Method of prep. |
|---|---|---|---|---|---|
| 712 | CH₂CH₂—OCH₃ | H | 334 | 4-[1-(3-methoxy-1-phenyl-propyl)-1H-pyrazol-4-yl]-7H-pyrrolo[2,3-d]pyrimidine trifluoroacetate | Ex 712 |
| 713 | CH₂C≡CH | 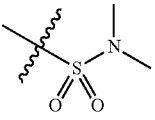 [SMILES: *S(=O)(=O)N(C)C] | 476 | N-[4-(dimethylamino)phenyl]-3-{1-[4-(7H-pyrrolo[2,3-d]pyrimidin-4-yl)-1H-pyrazol-1-yl]but-3-yn-1-yl}benzamide trifluoroacetate | Ex 705 |
| 714 | CH₂CH₂OH | 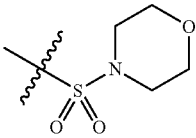 [SMILES: *S(=O)(=O)N1CCOCC1] | 427 | 3-{3-hydroxy-1-[4-(7H-pyrrolo-[2,3-d]pyrimidin-4-yl)-1H-pyrazol-1-yl]propyl}-N,N-dimethylbenzenesulfonamide trifluoroacetate | Ex 712 |
| 715 | CH₂—CH=CH₂ | CN | 341 | 3-{1-[4-(7H-pyrrolo[2,3-d]-pyrimidin-4-yl)-1H-pyrazol-1-yl]but-3-en-1-yl}benzonitrile trifluoroacetate | Ex 715 |
| 716 | CH₂—CH=CH₂ | Br | 394, 396 | 4-{1-[1-(3-bromophenyl)but-3-en-1-yl]-1H-pyrazol-4-yl}-7H-pyrrolo[2,3-d]pyrimidine trifluoroacetate | Ex 716 |
| 717 | CH₂CH=CF₂ | CN | 377 | 3-{4,4-difluoro-1-[4-(7H-pyrrolo[2,3-d]pyrimidin-4-yl)-1H-pyrazol-1-yl]but-3-en-1-yl}-benzonitrile | Ex 717 |
| 718 | CH₂CH=CF₂ | 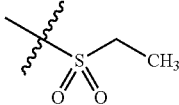 [SMILES: *S(=O)(=O)CC] | 501 | 4-(1-{4,4-difluoro-1-[3-(morpholin-4-ylsulfonyl)-phenyl]but-3-en-1-yl}-1H-pyrazol-4-yl)-7H-pyrrolo[2,3-d]-pyrimidine trifluoroacetate | Ex 717 |
| 719 | CH₂CH=CF₂ | 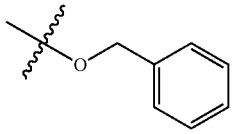 | 444 | 4-(1-{1-[3-(ethylsulfonyl)-phenyl]-4,4-difluorobut-3-en-1-yl}-1H-pyrazol-4-yl)-7H-pyrrolo[2,3-d]pyrimidine trifluoroacetate | Ex 717 |
| 720 | CH₂CH=CF₂ |  | 458 | 4-(1-{1-[3-(benzyloxy)phenyl]-4,4-difluorobut-3-en-1-yl}-1H-pyrazol-4-yl)-7H-pyrrolo[2,3-d]-pyrimidine trifluoroacetate | Ex 717 |
| 721 | CH₂OCH₃ | H | 320 | 4-[1-(2-methoxy-1-phenylethyl)-1H-pyrazol-4-yl]-7H-pyrrolo-[2,3-d]pyrimidine | Ex 712 |

TABLE 13-continued

| Ex. # | R¹ | R² | M + 1 | Name | Method of prep. |
|---|---|---|---|---|---|
| 722 | $CH_2CH=CF_2$ | -S(=O)₂-CH₃ | 430 | 4-(1-{4,4-difluoro-1-[3-(methyl-sulfonyl)phenyl]but-3-en-1-yl}-1H-pyrazol-4-yl)-7H-pyrrolo-[2,3-d]pyrimidine trifluoroacetate | Ex 717 |
| 723 | H | CN | 301 | 3-{[4-(7H-pyrrolo[2,3-d]-pyrimidin-4-yl)-1H-pyrazol-1-yl]methyl}benzonitrile | Ex 250 |
| 724 | $CH_2CH_2CH_3$ | CN | 343 | 3-{1-[4-(7H-pyrrolo[2,3-d]-pyrimidin-4-yl)-1H-pyrazol-1-yl]butyl}benzonitrile | Ex 250 |
| 725 | $CH_2CH_2CHF_2$ | -S(=O)₂-CH₂CH₃ | 446 | 4-(1-{1-[3-(ethylsulfonyl)-phenyl]-4,4-difluorobutyl}-1H-pyrazol-4-yl)-7H-pyrrolo[2,3-d]-pyrimidine trifluoroacetate | Ex 717 |
| 726 | $CH_2CH=CF_2$ | -S(=O)₂-CH₂CH₂-O-CH₃ | 474 | 4-[1-(4,4-difluoro-1-{3-[(2-methoxyethyl)sulfonyl]phenyl}-but-3-en-1-yl)-1H-pyrazol-4-yl]-7H-pyrrolo[2,3-d]pyrimidine trifluoroacetate | Ex 717 |

Example 649

3-[3-(Morpholin-4-ylsulfonyl)phenyl]-3-[4-(7H-pyrrolo[2,3-d]pyrimidin-4-yl)-1H-pyrazol-1-yl]propanenitrile

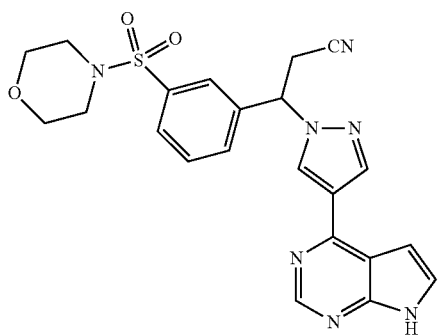 [SMILES: N#CCC(c1cccc(S(=O)(=O)N2CCOCC2)c1)n1cc(-c2ncnc3[nH]ccc23)cn1]

Step 1: 4-[(3-Bromophenyl)sulfonyl]morpholine

Morpholine (0.19 mL, 0.0022 mol) in 1.0 ml of THF was added dropwise to a solution of 3-bromobenzenesulfonyl chloride (0.3 mL, 0.002 mol) and TEA (0.30 mL, 0.0022 mol) in dry 4.0 mL of THF cooled in an ice bath. The reaction mixture was stirred overnight at room temperature and was then partitioned between 0.05N HCl and ethyl acetate. The organic layer was washed with water (2×), and brine (1×), and was then dried over anhydrous magnesium sulfate, filtered and then was concentrated in vacuo to give 4-[(3-bromophenyl)sulfonyl]morpholine as a white crystalline product (470 mg, 78%). LCMS (M+H)⁻: m/z=306, 308.

Step 2: (2E&Z)-3-[3-(Morpholin-4-ylsulfonyl)phenyl]acrylonitrile

The 4-[(3-bromophenypsulfonyl]morpholine (0.250 g, 0.000816 mol) was dissolved in dry DMF (2.5 mL, 0.032 mol) and the mixture was degassed using a stream of nitrogen. To this mixture was added TEA (0.23 mL, 0.0016 mol), 2-propenenitrile (0.11 mL, 0.0016 mol), palladium acetate (0.011 g, 0.000049 mol), and triphenylphosphine (0.0364 g, 0.000139 mol) and again the mixture was degassed with nitrogen. The reaction mixture in a sealed tube was heated at 110° C. for 16 hours. The reaction mixture, after cooling to room temperature, was partitioned between 0.05N HCl and ethyl acetate. The organic layer was washed with water (2×), and brine (1×), dried over anhydrous magnesium sulfate, filtered, and concentrated in vacuo, to give (2E & Z)-3-[3-(morpholin-4-yl-sulfonyl)phenyl]acrylonitrile as an oil (0.240 gm, 85%) which was a mixture of cis and trans isomers. LCMS (M+H)⁺: m/z=279.

Step 3: 3-[3-(Morpholin-4-ylsulfonyl)phenyl]-3-[4-(7-[2-(trimethylsilyl)ethoxy]methyl-7H-pyrrolo-[2,3-d]pyrimidin-4-yl)-1H-pyrazol-1-yl]panenitrile To a mixture of 4-(1H-pyrazol-4-yl)-7-[2-(trimethylsilyl) ethoxmethyl-7H-pyrrolo[2,3-d]-pyrimidine (0.100 g, 0.000317 mol) and (2E & Z)-3 -(morpholin-4-ylsulfonyl) phenyl]acrylonitrile (0.097 g, 0.00035 mol) in dry ACN (2.0 mL, 0.038 mol) was added DBU (0.095 mL, 0.00063 mol), and the resulting mixture was stirred at room temperature overnight. The reaction mixture was then diluted with water and extracted with ethyl acetate. The combined organic phase was washed with water (2×), and brine (1×), dried over magnesium sulfate, filtered and then concentrated in vacuo to give the crude product. The crude product was purified by silica gel flash column chromatography using ethyl acetate-hexanes (6:4) as an eluent to give 3-[3-(morpholin-4-ylsulfonyl)phenyl]-3-[4-(7-[2-(trimethylsilyl) ethoxy]methyl-7H-pyrrolo[2,3-d]pyrimidin-4-yl)-1H-pyrazol-1-yl]propanenitrile as a viscous oil (62 mg, 32.94%). LCMS (M+H)$^+$: m/z=594

Step 4

Using a procedure analogous to Example 61 for the removal of the SEM protecting the title compound was isolated as an amorphous white solid (30 mg, 63.84%. LCMS (M+H)$^+$: m/z=464. $^1$H NMR (400 MHz, DMSO-d6): δ☐ 8.88 (s), 8.62 (s), 8.1(s), 7.78(m), 7.70(m), 7.58(m), 6.95(m), 6.20(m), 3.84(m), 3.70(m),3.45(m), 2.78(m).

Example 679 cis-4-[4-(7H-Pyrrolo[2,3-d]pyrimidin-4-yl)-1H-pyrazol-1-yl]cyclohexyl-acetonitrile

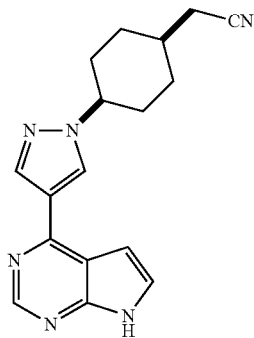

Step 1: 4-(Hydroxymethyl)cyclohexanol

Ethyl 4-oxocyclohexanecarboxylate (2.0 g, 0.012 mol) was dissolved in ether (20.0 mL) and was then cooled at 0° C. Into the mixture was added 1 M lithium tetrahydroaluminate in ether (20 mL) and the resulting mixture was stirred at 0° C. for 2 hours. The reaction was quenched with water (2 mL) and 1 N NaOH (2 mL) and ether was added (100 mL). The precipitated solids were filtered off and the residue was used in the next reaction. $^1$H NMR (CDCl$_3$): δ 4.02 and 3.75 (m, 1H), 3.45-3.61 (m, 2H), 2.02 (m, 2H), 1.84 (m, 1H), 1.52-1.80 (m, 2H), 1.44 (m, 1H), 1,32 (m, 2H), 1.03 (m, 1H).

Step 2: 4-[(Trityloxy)methyl]cyclohexanol 4-(Hdroxymethyl)cyclohexanol (2.0 g, 0.015 mol) was dissolved in pyridine (15.0 mL) and the mixture was cooled to 0° C. To the reaction was added triphenylmethyl chloride (4.7 g, 0.017 mol) and the resulting mixture was stirred at 0° C. for 2 hours and at 25° C. for 16 hours. The reaction was then concentrated using a rotory evaporator, and the concentrate was extracted with ethyl acetate. The organic extracts were washed with water, saturated NaCl, dried (MgSO$_4$) and then concentrated in vacuo. The reaction was chromatographed on silica gel using 30% EtOAc/hexanes to give the cis isomer (0.74 g) $^1$H NMR (CDCl$_3$): ☐δ 7.52 (m, 6H), 7.27 (m, 9H), 3.98 (m, 1H), 2.93 (m, 2H), 1.21-1.68 (m, 9H); and the trans isomer (2.72 g) $^1$H NMR (CDCl$_3$): ☐δ 7.44 (m, 6H), 7.20-7.31 (m, 9H), 3.54 (m, 1H), 2.88 (m, 2H), 1. 98 (m, 2H), 1.88 (m, 2H), 1.60 (m, 1H), 0.99-1.37 (m, 4H).

Step 3: trans-4-[(Trityloxy)methyl]cyclohexyl methanesulfonate trans-4-[(Trityloxy)methyl]cyclohexanol (2.72 g, 0.00730 mol) was dissolved in chloroform (30.0 mL) and the mixture was cooled at 0° C. To this mixture was added TEA (1.4 mL, 0.010 mol) and methanesulfonyl chloride (0.68 mL, 0.0088 mol) and the resulting mixture was stirred at 0° C. for 2 hours The reaction was then extracted with ethyl acetate and the organic extracts were washed with water, saturated NaCl, dried (MgSO$_4$) and the concentrated in vacuo. $^1$H NMR (CDCl$_3$): ☐δ 7.43 (m, 6H), 7.20-7.31 (m, 9H), 4.57 (m, 1H), 3.00 (m, 3H), 2.90 (m, 2H), 2.16 (m, 2H), 1.93 (m, 2H), 1.09-1.60 (m, 5H).

Step 4: 7-[2-(Trimethylsilyl)ethoxy]methyl-4-(1-cis-4-[(trityloxy)methyl]cyclohexyl-1H-pyrazol-4-yl)-7H-pyrrolo[2,3-d]pyrimidine 4-(1H-Pyrazol-4-yl)-7-[2-(trimethylsilyl)ethoxy]methyl-7H-pyrrolo[2,3-d]pyrimidine (1.5 g, 0.0048 mol) was mixed with sodium hydride (0.34 g, 0.0086 mol) and trans-4-] (trityloxy)methyl]cyclohexyl methanesulfonate (3.00 g, 0.00666 mol) and the mixture was cooled to −78° C. To this mixture was added DMF (8.3 mL) and the mixture was allowed to warm to 25° C. and was stirred for 20 minutes. The warmed mixture was stirred at 55° C. for 48 hours. The reaction was extracted with ethyl acetate and the organic extracts were washed with water, saturated NaCl, dried (MgSO$_4$) and then concentrated in vacuo. The concentrate was chromatographed on silica gel using 40% EtOAc/hexanes to give the product. LC/MS (M+H)$^+$: 670, $^1$H NMR(CDCl$_3$): ☐δ 8.89 (s, 1H), 8.27 (s, 1H), 8.24 (s, 1H), 6.84-7.51 (m, 10H), 6.87 (d, 1H), 5.73 (s, 2H), 4.39 (m, 1H), 3.60 (m, 2H), 3.12 (m, 2H), 1.76-2.11 (m, 9H), 0.96 (m, 2H), 0.00 (s, 9H).

Step 5: cis-4-[4-(7-[2-(Trimethylsilyl)ethoxy] methyl-7H-pyrrolo[2,3-d]pyrimidin-4-yl)-1H-pyrazol-1-yl]cyclohexylmethanol 7-[2-(Trimethylsilyl)ethoxy]methyl-4-(1-cis-4-[(trityloxy)methyl]cyclohexyl-1H-pyrazol-4-yl)-7H-pyrrolo[2,3- d]pyrimidine (0.3 g, 0.0004 mol) was dissolved in methanol (7.0 mL) and THF (2.0 mL, 0.025 mol) and 4.0 M HCl in 1,4-dioxane (0.5 mL) was added. The reaction was then stirred at 25° C. for 2 hours TLC analysis showed no starting material present and LCMS analysis showed the presence of the product. The reaction was added to a saturated NaHCO₃ solution and was extracted with ethyl acetate. The organic extracts were washed with water, saturated NaCl, dried (MgSO₄) and concentrated in vacuo. The concentrate was chromatographed on silica gel using EtOAc as eluent to give the product. LC/MS (M+H)⁺: 428

¹H NMR (CDCl₃): □δ 8.89 (s, 1H), 8.37 (s, 1H), 8.31 (s, 1H), 7.44 (d, 1H), 6.87 (d, 1H), 5.73 (d, 2H), 4.41 (m, 1H), 3.51-3.71 (m, 4H), 2.31 (m, 2H), 2.08 (m, 3H), 1.70-1.93 (m, 4H), 0.98 (m, 2H), 0.00 (s, 9H).

Step 6: cis-4-[4-(7-[2-(Trimethylsilyl)ethoxy]methyl-7H-pyrrolo[2,3-d]pyrimidin-4-yl)-1H-pyrazol-1-yl]cyclohexylmethyl methanesulfonate cis-4-[4-(7-[2-(Trimethylsilyl)ethoxy]methyl-7H-pyrrolo[2,3-d]pyrimidin-4-yl)-1H-pyrazol-1-yl]cyclohexylmethanol was dissolved in chloroform (3.00 mL) and was cooled to 0° C. To the reaction was added TEA (0.10 mL, 0.00072 mol) and methanesulfonyl chloride (0.05 mL, 0.0006 mol) and this mixture was stirred at 0° C. for 2 hours at which time LCMS analysis showed mainly the product present in the mixture. The reaction was extracted with ethyl acetate and the organic extracts were washed with water, saturated NaCl, dried (MgSO4) and concentrated in vacuo. LC/MS (M+H)⁺: 506

Step 7: cis-4-[4-(7-[2-(Trimethylsilyl)ethoxy]methyl-7H-pyrrolo[2,3-dlpyrimidin-4-yl)-1H-pyrazol-1-yl]cyclohexylacetonitrile cis-4-[4-(7-[2-(Trimethylsilyl)ethoxy]methyl-7H-pyrrolo[2,3-d]pyrimidin-4-yl)-1H-pyrazol-1-ylicyclohexylmethyl methanesulfonate (0.10 g, 0.00020 mol) and sodium cyanide (0.050 g, 0.0010 mol) and DMSO (1.0 mL) were mixed. The mixture was stirred at 60° C. for 24 hours, at which time LCMS analysis showed most of the starting material had been consumed. The reaction was extracted with ethyl acetate and the organic extracts were washed with water, saturated NaCl, dried (MgSO₄) and concentrated in vacuo. The concentrate was chromatographed on silica gel using EtOAc as eluent to give the product. LC/MS (M+H)⁺: 437, ¹H NMR (CDCl₃): □δ 8.90 (s, 1H), 8.36 (s, 1H), 8.31 (s, 1H), 7.45 (d, 1H), 6.87 (d, 1H), 5.73 (S, 2H), 4.43 (m, 1H), 3.60 (m, 2H), 2.45(d, 2H, J=7.6 Hz), 2.37 (m, 2H), 2.10 (m, 4H), 1.70-1.93 (m, 3H), 0.98 (m, 2H), 0.00 (s, 9H).

Step 8: cis-4-[4-(7H-Pyrrolo[2,3-d]pyrimidin-4-yl)-1H-pyrazol-1-yl]cyclohexylacetonitrile cis-4-[4-(7-[2-(Trimethylsilyl)ethoxy]methyl-7H-pyrrolo[2,3-d]pyrimidin-4-yl)-1H-pyrazol-1-yl]cyclohexylacetonitrile (0.080 g, 0.00018 mol) and TFA (0.50 mL, 0.0065 mol) were added to DCM (3.00 mL, 0.0468 mol) and the mixture was stirred at 25° C. for 16 hours. The reaction was concentrated by roto-evaporation and the concentrate was dissolved in methanol (3.0 mL, 0.074 mol) and ammonium hydroxide (0.5 mL, 0.01 mol) was added This reaction was stirred at 25° C. for 6 hours at which time LCMS analysis showed no starting material present. The reaction was chromatographed on silica gel using 5% MeOH/EtOAc to give the product.

LC/MS (M+H)⁺: 307, ¹H NMR (CD₃OD): □δ 8.64 (s, 1H), 8.55 (s, 1H), 8.31 (s, 1H), 7.50 (d, 1H), 6.96 (d, 1H), 4.42 (m, 1H), 2.61(d, 2H, J=8.0 Hz), 2.27 (m, 2H), 1.70-2.15 (m, 7H).

Example 680 cis-4-[4-(7H-Pyrrolo[2,3-d]pyrimidin-4-yl)-1H-pyrazol-1-yl]cyclohexylmethyl thiocyanate

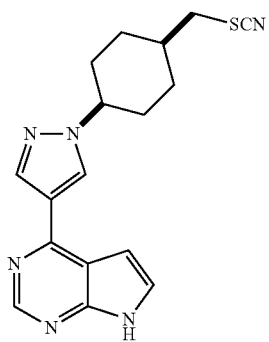

Step 1: cis-4-[4-(7-[2-(Trimethylsilyl)ethoxy]methyl-7H-pyrrolo[2,3-dlpyrimidin-4-yl)-1H-pyrazol-1-yl]cyclohexylmethyl thiocyanate cis-4-[4-(7-[2-(Trimethylsilyl)ethoxy]methyl-7H-pyrrolo[2,3-d]pyrimidin-4-yl)-1H-pyrazol-1-yl]cyclohexylmethyl methanesulfonate (0.10 g, 0.00020 mol) was dissolved in DMSO (1.00 mL) with potassium thiocyanate (0.082 g, 0.00084 mol). The reaction was heated at 68° C. for 4 days at which time LCMS analysis showed ~4:1 product/starting material ratio. The reaction was extracted with ethyl acetate and the organic extracts were washed with water, saturated NaCl, dried (MgSO₄) and concentrated in vacuo. The concentrate was chromatographed on silica gel using 1:1 EtOAc/hexanes to give the product. LC/MS (M+H)⁺: 469, ¹H NMR (CDCl₃): □δ 8.89 (s, 1H), 8.36 (s, 1H), 8.31 (s, 1H), 7.45 (d, 1H), 6.87 (d, 1H), 5.73 (S, 2H), 4.45 (m, 1H), 3.60 (m, 2H), 3.05 (m, 2H), 2.37 (m, 2H), 2.10 (m, 4H), 1.70-1.93 (m, 3H), 0.98 (m, 2H), 0.00 (s, 9H).

Step 2: cis-4-[4-(7H-Pyrrolo[2,3-d]pyrimidin-4-yl)-1H-pyrazol-1-yl]cyclohexylmethyl thiocyanate cis-4-[4-(7-[2-(Trimethylsilyl)ethoxy]methyl-7H-pyrrolo[2,3-d]pyrimidin-4-yl)-1H-pyrazol-1-yl]cyclohexylmethyl thiocyanate was dissolved in methanol (2.0 mL, 0.049 mol) and DCM (2.0 mL, 0.031 mol), and TFA (0.5 mL, 0.006 mol) was added. The resulting mixture was stirred at 25° C. for 16 hours. TLC analysis showed no starting material present and LCMS analysis showed product. The reaction was concentrated using a rotary evaporator and the concentrate was chromatographed on silica gel using 2% MeOH/EtOAc to give the product. LC/MS (M+H)⁺: 339, ¹H NMR (CD₃OD) δ 8.65 (s, 1H), 8.55 (s, 1H), 8.31 (s, 1H), 7.50 (d, 1H), 6.96 (d, 1H), 4.43 (m, 1H), 3.20 (d, 2H, J=7.6 Hz), 2.24 (m, 2H), 1.80-2.17 (m, 7H).

Example 681

N-5-[(cis-4-[4-(7H-Pyrrolo[2,3-d]pyrimidin-4-yl)-1H-pyrazol-1-yl]cyclohexyl-methyl)thio]-4H-1,2,4-triazol-3-ylpyrimidin-2-amine trifluoroacetate

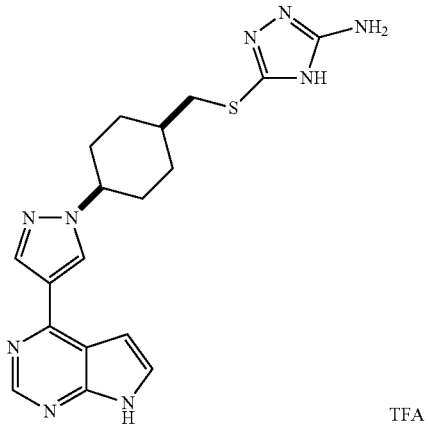 [SMILES: Nc1nnc(SC[C@H]2CC[C@@H](n3cc(-c4ncnc5[nH]ccc45)cn3)CC2)[nH]1]

Step 1: 5-[(cis-4-[4-(7-[2-(Trimethylsilyl)ethoxy]methyl-7H-pyrrolo[2,3-d]pyrimidin-4-yl)-1H-pyrazol-1-yl]cyclohexylmethyl)thio]-4H-1,2,4-triazol-3-amin cis-4-[4-(7-[2-(Trimethylsilyl)ethoxy]methyl-7H-pyrrolo[2,3-d]pyrimidin-4-yl)-1H-pyrazol-1-yl]cyclohexylmethyl methanesulfonate (124.56 mg, 0.00024 mol), and 5-amino-4H-1,2,4-triazole-3-thiol (43.00 mg, 0.0003702 mol) were dissolved in DMF (1.20 mL) and potassium carbonate (0.122 g, 0.000887 mol) was added. The reaction was stirred at 50° C. for 18 h, at which time LCMS showed nearly complete reaction, and product present. The reaction was extracted with ethyl acetate and the organic extracts were washed with water, saturated NaCl, dried (MgSO$_4$) and concentrated in vacuo. The concentrate was chromatographed on silica gel using EtOAc as eluent to give the product. LC/MS (M+H)$^+$: 526, $^1$H NMR (CDCl$_3$): □δ 8.90 (s, 1H), 8.40 (s, 1H), 8.30 (s, 1H), 7.45 (d, 1H), 6.87 (d, 1H), 5.73 (S, 2H), 4.45 (brs, 2H), 4.41 (m, 1H), 3.60 (m, 2H), 3.22 (d, 2H, J=7.2 Hz), 2.29 (m, 2H), 1.70-2.10 (m, 7H), 0.98 (m, 2H), 0.00 (s, 9H).

Step 2: 5-[(cis-4-[4-(7H-Pyrrolo[2,3-d]pyrimidin-4-yl)-1H-pyrazol-1-yl]cyclohexylmethyl)thio]-4H-1,2,4-triazol-3-amine 5-[(cis-4-[4-(7-[2-(Trimethylsilyl)ethoxy]methyl-7H-pyrrolo[2,3-d]pyrimidin-4-yl)-1H-pyrazol-1-yl]cyclohexylmethyl)thio]-4H-1,2,4-triazol-3-amine (9a) was dissolved in TFA (1 mL) and was stirred for 2 h. The solution was concentrated using a rotary evaporator to remove TFA. The residue was dissolved in methanol (1 mL) and ammonium hydroxide (1 mL) added. The solution was stirred overnight. LCMS showed complete de-protection. The solution was concentrated using a rotary evaporator. The product was isolated by prep LCMS using a 30 mm×100 mm C18 column; 11% CH$_3$CN—H$_2$O (0.1% TFA), 1.5 min, to 33% at 6 min; 60 mL/min; detector set at m/z 396; retention time, 5.5 min (2 runs). The eluate was freeze dried. Yield 21 mg (di-TFA salt). LC/MS (M+H)$^+$: 396, $^1$H NMR (d$_6$-DMSO) δ 12.9 (br s, 1H, NH); 8.9 (2 singlets, 2H); 8.5 (s, 1H); 7.9 (m, 1H); 7.3 (m, 1H); 4.4 (m, 1H, NCH); 3.1 (d, 2H); 2.2 (m, 2H); 1.9 (m, 3H); 1.7 (m, 2H); 1.6 (m, 2H). MS(ES) 396 (M+1).

Example 682

N-5-[(cis-4-[4-(7H-Pyrrolo[2,3-d]pyrimidin-4-yl)-1H-pyrazol-1-yl]cyclohexyl-methyl)thio]-4H-1,2,4-triazol-3-ylpyrimidin-2-amine trifluoroacetate

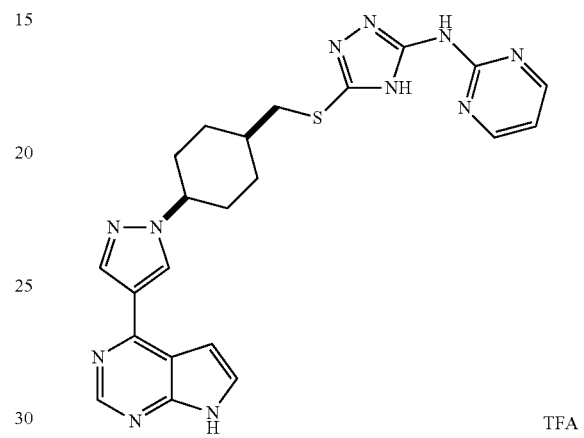

Step 1: N-5-[(cis-4-[4-(7-[2-(Trimethylsilyl)ethoxy]methyl-7H-pyrrolo[2,3-d]pyrimidin-4-yl)-1H-pyrazol-1-yl]cyclohexylmethyl)thio]-4H-1,2,4-triazol-3-ylpyrimidin-2-amine In a vial [A] 5-[(cis-4-[4-(7-[2-(trimethylsilyl)ethoxy]methyl-7H-pyrrolo[2,3-d]pyrimidin-4-yl)-1H-pyrazol-1-yl]cyclohexylmethyl)thio]-4H-1,2,4-triazol-3-amine (0.047 g, 0.000089 mol) was heated with 2-chloropyrimidine (0.011 g, 0.000096 mol) in 1,4-dioxane (1.00 mL, 0.0128 mol) at 150° C. for 40 minutes in a microwave reactor. LCMS analysis showed that no reaction had taken place. To the reaction was added 2-chloropyrimidine (0.020 g, 0.00017 mol) with cesium carbonate (0.033 g, 0.00010 mol) and copper(I) iodide (4.00 mg, 0.0000210 mol) and this mixture was heated at 115° C. for 3 hours, at which time LCMS analysis showed no starting material present and mainly product was present. The reaction was chromatographed on silica gel using 2% MeOH/EtOAc to give the product. LC/MS (M+1)$^+$: 604, $^1$H NMR (CDCl$_3$): 8.89 (s, 1H), 8.82 m, 2H), 8.43 (s, 1H), 8.30 (s, 1H), 7.44 (d, 1H), 7.23 (m, 1H), 7.03 (br s, 2H), 6.88 (d, 1H), 5.73 (s, 2H), 4.40 (m, 1H), 3.60 (m, 2H), 3.35 (d, 2H), 2.34 (m, 2H), 1.80-2.15 (m, 7H), 0.98 (m, 2H), 0.00 (s, 9H).

Step 2: N-5-[(cis-4-[4-(7H-Pyrrolo[2,3-d]pyrimidin-4-yl)-1H-pyrazol-1-yl]cyclohexylmethyl)thio]-4H-1,2,4-triazol-3-ylpyrimidin-2-amine N-5-[(cis-4-[4-(7-[2-(Trimethylsilyl)ethoxy]methyl-7H-pyrrolo[2,3-d]pyrimidin-4-yl)-1H-pyrazol-1-yl]cyclohexyl-methyl)thio]-4H-1,2,4-triazol-3-ylpyrimidin-2-amine (0.024 g, 0.000040 mol) was dissolved in DCM (4.00 mL), and TFA (0.50 mL, 0.0065 mol) was added. The reaction was stirred at 25° C. for 16 hours and was concentrated in vacuo. The residue was dissolved in methanol (3.00 mL) and concentrated ammonium hydroxide (0.50 mL) was added. This reaction was stirred at 25° C. for 2 hours at which time LCMS analysis showed mostly product. The reaction was concentrated using a rotary evaporator and the concentrate was purified by prep LC to give the product as the trifluoroacetate salt. LC/MS (M+H)+: 474, $^1$H NMR(CD$_3$OD) δ 8.87 (s, 1H), 8.85 (s, 1H), 8.81 (s, 1H), 8.79 (s, 1H), 8.45 (s, 1H), 7.85 (d, 1H), 7.34 (m, 2H), 4.43 (m, 1H), 3.20 (d, 2H, J=7.6 Hz), 2.24 (m, 2H), 1.80-2.17 (m, 7H).

Example 683

3-cis-4-[4-(7H-Pyrrolo[2,3-d]pyrimidin-4-yl)-1H-pyrazol-1-yl]cyclohexylpropane-nitrile trifluoroacetate

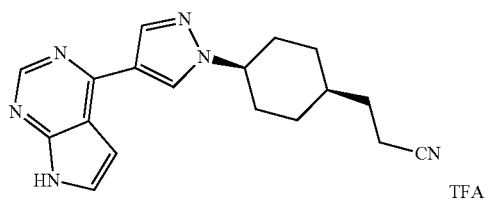 [SMILES: N#CCC[C@H]1CC[C@@H](n2cc(-c3ncnc4[nH]ccc34)cn2)CC1]

Step 1: 2-(1,4-Dioxaspiro[4.5]dec-8-yl)ethanol

Ethyl 1,4-dioxaspiro[4.5]dec-8-ylacetate (3.40 g, 0.0149 mol) prepared according to the procedure of Itagaki, Noriaki; Kimura, Mari; Sugahara, Tsutomu; Iwabuchi, Yoshiharu. (*Organic Letters* 2005; 7(19); 4181-4183.) was dissolved in ether (30.00 mL) and the mixture was cooled to 0° C. To the reaction was added 1.00 M lithium tetrahydroaluminate in ether (15.0 mL) and the resulting mixture was stirred at 0° C. for 60 minutes and at 25° C. for 2 hours. The reaction was cooled and water (0.40 mL, 0.022 mol) was added, followed by 1.00 M sodium hydroxide (0.40 mL). To the reaction was then added ether (100.00 mL) and the solid that precipitated was filtered off. The filtrate was concentrated using a rotary evaporator to give the product. $^1$H NMR (CDCl$_3$): 3.94 (s, 4H), 3.67 (t, 2H), 1.20-1.80 (m, 11H).

Step 2: 4-(2-Hydroxyethyl)cyclohexanone 2-(1,4-Dioxaspiro[4.5]dec-8-yl)ethanol (2.70 g, 0.0145 mol) was dissolved in acetone (10.00 mL) and THF (10.00 mL) and 6.00 M HCl (6.00 mL) was added. The reaction was stirred at 25° C. for 16 hours, neutralized with NaHCO$_3$ solution and was then extracted with ethyl acetate. The organic extracts were washed with water, and with saturated NaCl, then dried (MgSO$_4$) and concentrated in vacuo. The crude product was used in the next reaction without further purification.
$^1$H NMR (CDCl$_3$): 3.75 (m, 2H), 2.36 (m, 4H), 1.20-2.13 (m, 7H).

Step 3: 4-(2-Hydroxyethyl)cyclohexanol 4-(2-Hydroxyethyl)cyclohexanone (2.00 g, 0.0141 mol) was dissolved in ether (30.00 mL) and was cooled at 0° C. To the reaction was added 1.0 M lithium tetrahydroalumi-nate in ether (14.1 mL) and the resulting mixture was stirred at 0° C. for 2 hours and at 25° C. for 16 hours. To the reaction was added THF (20.00 mL) and this mixture was cooled at 0° C. and then water (0.40 mL, 0.022 mol) was added, followed by 1.00 M sodium hydroxide (0.40 mL). To the reaction was then added ether (100.00 mL) and the resulting mixture was stirred for 10 minutes, then was filtered and the filtrate was concentrated using a rotary evaporator to provide the crude product. The crude product was used in the next reaction without further purification.
$^1$H NMR (CDCl$_3$): 3.96 and 3.57 (m, 1H) minor and major CHOH (~1:5 ratio) 3.70 (m, 2H), 0.94-2.02 (m, 11H).

Step 4: 4-[2-(Trityloxy)ethyl]cyclohexanol 4-(2-Hydroxyethyl)cyclohexanol (crude from the previous reaction) (1.88 g, 0.0130 mol) was dissolved in pyridine (20.00 mL) and was cooled at 0° C. To the reaction was added triphenylmethyl chloride (4.0 g, 0.014 mol) and this mixture was stirred at 0° C. for 2 hours and at 25° C. for 16 hours. The reaction was concentrated using a rotary evaporator and the concentrate was extracted with ethyl acetate. The organic extracts were washed with water, and saturated NaCl, then dried (MgSO$_4$) and concentrated in vacuo. The concentrate was chromatographed on silica gel (30% EtOAc/hexanes) to give the trans isomer (1.98 g)
$^1$H NMR (CDCl$_3$): 7.42-7.45 (m, 6H), 7.20-7.30 (m, 9H), 3.50 (m, 1H), 3.07 (m, 2H), 1.93 (m, 2H), 1.66 (m, 2H), 1.17-1.60 (m, 5H), 0.89 (m, 2H).

Step 5: trans-4-[2-(Trityloxy)ethyl]cyclohexyl methanesulfonate trans-4-[2-(Trityloxy)ethyl]cyclohexanol (1.95 g, 0.00504 mol) was dissolved in chloroform (40.00 mL) and the mixture was cooled to 0° C. To the reaction was added TEA (0.98 mL, 0.0071 mol) and methanesulfonyl chloride (0.47 mL, 0.0060 mol) and this mixture was stirred at 0° C. for 2 hours The reaction was then extracted with ethyl acetate and the organic extracts were washed with water, and saturated NaCl, then dried (MgSO$_4$) and concentrated in vacuo.
$^1$H NMR (CDCl$_3$): 7.41-7.45 (m, 6H), 7.20-7.32 (m, 9H), 4.55 (m, 1H), 3.07 (m, 2H), 2.10 (m, 2H), 1.70 (m, 2H), 1.20-1.60 (m, 5H), 0.95 (m, 2H).

Step 6: 7-[2-(Trimethylsilyl)ethoxy]methyl-4-(1-cis-4-[2-(trityloxy)ethyl]cyclohexyl-1H-pyrazol-4-yl)-7H-pyrrolo[2,3-d]pyrimidine 4-(1H-Pyrazol-4-yl)-7-[2-(trimethylsilyl)ethoxy]methyl-7H-pyrrolo[2,3-d]pyrimidine (1.0 g, 0.0032 mol) was mixed with sodium hydride (0.23 g, 0.0058 mol) and trans-4-[2-(trityloxy)ethyl]cyclohexyl methanesulfonate (2.10 g, 0.00452 mol) and this mixture was cooled to −78° C. To the reaction was added DMF (6.00 mL) and this mixture was allowed to warm to 25° C. and was then stirred for 20 minutes. The reaction was stirred at 55° C. for 48 hours at which time LCMS analysis showed mostly product. The reaction was extracted with ethyl acetate and the organic extracts were washed with water and saturated NaCl, then dried (MgSO$_4$) and concentrated in vacuo. The concentrate was chromatographed on silica gel using 40% EtOAc/hexanes to give the product.
LC/MS (M+H)+: 684, $^1$H NMR (CDCl$_3$): 8.89 (s, 1H), 8.35 (br s, 1H), 8.30 (s, 1H), 7.50 (m, 6H), 7.44 (d, 1H), 7.27-7.32 (m, 9H), 6.87 (d, 1H), 5.73 (s, 2H), 4.33 (m, 1H), 3.60 (m, 2H), 3.17 (t, 2H), 1.50-2.25 (m, 11H). 0.98 (m, 2H), 0.00(s, 9H).

Step 7: 2-cis-4-[4-(7-[2-(Trimethylsilyl)ethoxy]methyl-7H-pyrrolo[2,3-d]pyrimidin-4-yl)-1H-pyrazol-1-yl]cyclohexylethanol (7b)

7-[2-(Trimethylsilyl)ethoxy]methyl-4-(1-cis-4-[2-(trityloxy)ethyl]cyclohexyl-1H-pyrazol-4-yl)-7H-pyrrolo[2,3-d]pyrimidine (1.45 g, 0.00212 mol) was dissolved in methanol (30.00 mL) and THF (10.00 mL) and 4.0 M HCl in 1,4-dioxane (2.00 mL) was added. The mixture was stirred at 25° C. for 2 hours, at which time, TLC analysis showed no starting material present and LCMS analysis showed the presence of the product. The reaction was added into a saturated NaHCO$_3$ solution, and was then extracted with ethyl acetate. The organic extracts were washed with water and saturated NaCl, then dried (MgSO$_4$) and concentrated in vacuo. The concentrate was chromatographed on silica gel using EtOAc as eluent to give the product. LC/MS (M+H)$^+$: 442

Step 8: 2-cis-4-[4-(7-[2-(Trimethylsilyl)ethoxy]methyl-7H-pyrrolo[2,3-d]pyrimidin-4-yl)-1H-pyrazol-1-yl]cyclohexylethyl methanesulfonate (8b)

2-cis-4-[4-(7-[2-(Trimethylsilyl)ethoxy]methyl-7H-pyrrolo[2,3-d]pyrimidin-4-yl)-1H-pyrazol-1-yl]cyclohexylethanol (0.89 g, 0.0020 mol) was dissolved in DCM (12.00 mL, 0.1872 mol) and was cooled at 0° C. To the reaction was added TEA (0.43 mL, 0.0031 mol) and methanesulfonyl chloride (0.19 mL, 0.0024 mol) and this mixture was stirred at 0° C. for 2 hours at which time LCMS analysis showed mainly product present. The reaction was extracted with ethyl acetate and the organic extracts were washed with water and saturated NaCl, then dried (MgSO$_4$) and concentrated in vacuo.
LC/MS (M+H)$^+$: 520, $^1$H NMR (CDCl$_3$): 8.90 (s, 1H), 8.38 (br s, 1H), 8.31 (s, 1H), 7.45 (d, 1H), 6.88 (d, 1H), 5.73 (s, 2H), 4.40 (m, 1H), 4.27 (t, 2H), 3.60 (m, 2H), 3.07 (s, 3H), 1.60-2.40 (m, 11H). 0.98 (m, 2H), 0.00(s, 9H)

Step 9: 3-cis-4-[4-(7H-Pyrrolo[2,3-d]pyrimidin-4-yl)-1H-pyrazol-1-yl]cyclohexylpropanenitrile trifluoroacetate (9b)

2-cis-4-[4-(7-[2-(Trimethylsilyl)ethoxy]methyl-7H-pyrrolo[2,3-d]pyrimidin-4-yl)-1H-pyrazol-1-yl) cyclohexylethyl methanesulfonate (0.075 g, 0.00014 mol) was dissolved in DMSO (1.50 mL) and sodium cyanide (0.035 g, 0.00072 mol) was added. The reaction was stirred at 40° C. for 16 hours at which time LCMS analysis showed no starting material present. The reaction was then extracted with ethyl acetate and the organic extracts were washed with water and saturated NaCl, then dried (MgSO$_4$) and concentrated in vacuo. The residue was dissolved in DCM (3.00 mL) and TFA (0.50 mL, 0.0065 mol) was added. This mixture was stirred at 25° C. for 16 hours at which time LCMS analysis showed mostly the hydroxymethyl intermediate. The mixture was concentrated using a rotary evaporator and the concentrate was dissolved in methanol (3.00 mL) and concentrated ammonium hydroxide (0.50 mL) was added. The reaction was stirred at 25° C. for 3 hours at which time LCMS analysis showed no starting material present. The reaction was then concentrated using a rotary evaporator and the concentrate was purified by prep LC to give the product as the TFA salt (47.8 mg). LC/MS (M+H)$^+$: 321, $^1$H NMR (CD$_3$OD): 8.86 (s, 1H), 8.81(s, 1H), 8.44 (s, 1H), 7.84 (d, 1H), 7.31 (d, 1H), 4.48 (m, 1H), 2.51 (m, 2H), 2.28 (m, 2H), 2.00 (m, 2H), 1.80 (m, 5H), 1.67 (m, 2H).

Example 684

5-[(2-cis-4-[4-(7H-Pyrrolo[2,3-d]pyrimidin-4-yl)-1H-pyrazol-1-yl]cyclohexyl-ethyl)thio]-4H-1,2,4-triazol-3-amine trifluoroacetate

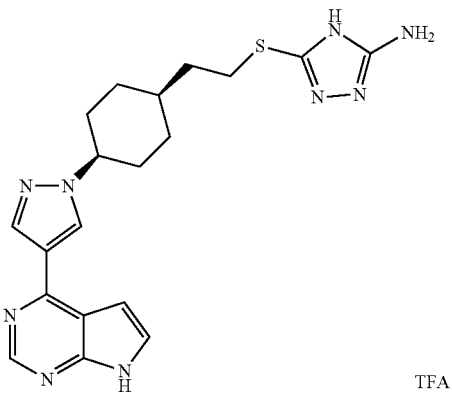 [SMILES: Nc1nnc(SCC[C@H]2CC[C@@H](n3cc(-c4ncnc5[nH]ccc45)cn3)CC2)[nH]1]

TFA 2-cis-4-[4-(7-[2-(Trimethylsilyl)ethoxy]methyl-7H-pyrrolo[2,3-d]pyrimidin-4-yl)-1H-pyrazol-1-yl) cyclohexylethyl methanesulfonate (0.060 g, 0.00012 mol) was dissolved in DMF (1.31 mL) with 5-amino-4H-1,2,4-triazole-3-thiol (0.020 g, 0.00017 mol) and potassium carbonate (0.024 g, 0.00017 mol). This mixture was heated at 40° C. for 18 hours at which time LCMS analysis showed no starting material present. The reaction was diluted with EtOAc, filtered and was then concentrated using a rotary evaporator. The residue was dissolved in DCM (3.60 mL) and TFA (0.60 mL, 0.0078 mol) was added. This mixture was stirred at 25° C. for 5 hours and was then concentrated using a rotary evaporator. The residue was dissolved in methanol (3.60 mL) and concentrated ammonium hydroxide (0.60 mL) was added and this mixture was stirred at 25° C. for 2 hours. The reaction was concentrated using a rotary evaporator and the concentrate was purified by prep. LC to give the product. LC/MS (M+H)$^+$: 410, $^1$H NMR (CD$_3$OD): 8.85 (s, 1H), 8.80(s, 1H), 8.44 (s, 1H), 7.83 (d, 1H), 7.30 (d, 1H), 4.46 (m, 1H), 3.17 (m, 2H), 2.27 (m, 2H), 2.00 (m, 2H), 1.62-1.90 (m, 7H).

Example 685

4-[4-(7H-Pyrrolo[2,3-d]pyrimidin-4-yl)-1H-pyrazol-1-yl]cyclohexylideneaceto-nitrile trifluoroacetate

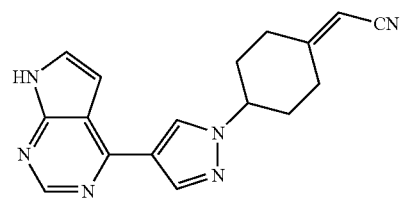

TFA

Step 1: 1,4-Dioxaspiro[4.5]decan-8-ol 1,4-Dioxa-spiro[4.5]decan-8-one (2.00 g, 0.0128 mol) was dissolved in ether (50 mL) and the mixture was cooled to 0° C. To the reaction was added 1 M lithium tetrahydroaluminate in ether (7.0 mL) and this mixture was stirred at 0° C. for 2 hours at which time TLC analysis showed no starting material present. The reaction was then quenched with water and 1 N NaOH (0.5 mL of each) and then filtered. The filtered solid was washed with ether and the combined ether filtrate was concentrated using a rotary evaporator to give the product. NMR (CDCl$_3$): 3.94 (m, 4H), 3.81 (m, 1H), 1.79-1.92 (m, 4H), 1.54-1.70 (m, 4H).

Step 2: 1,4-Dioxaspiro[4.5]dec-8-ylmethanesulfonate 1,4-Dioxaspiro[4.5]decan-8-ol (0.40 g, 0.0025 mol) was dissolved in chloroform (10.0 mL) and the resulting mixture was cooled at 0° C. To the mixture was added TEA (0.49 mL, 0.0035 mol) and methanesulfonyl chloride (0.23 mL, 0.0030 mol) and this mixture was stirred at 0° C. for 2 hours. The reaction was extracted with ethyl acetate and the organic extracts were washed with water, and saturated NaCl, then dried (MgSO$_4$) and concentrated in vacuo. The crude product was used in the next reaction without further purification.
$^1$H NMR (CDCl$_3$): 4.85 (m, 1H), 3.95 (m, 4H), 3.02 (s, 3H), 1.98-2.05 (m, 4H), 1.82-1.89 (m, 2H), 1.61-1.70 (m, 2H).

Step 3: 4-[1-(1,4-Dioxaspiro[4.5]dec-8-yl)-1H-pyrazol-4-yl]-7-[2-(trimethylsilyl)ethoxy]methyl-7H-pyrrolo[2,3-d]pyrimidine A mixture of 1,4-dioxaspiro[4.5]dec-8-yl methanesulfonate (0.50 g, 0.0015 mol) with 4-(1H-pyrazol-4-yl)-7-[2-(trimethylsilyl)ethoxy]methyl-7H-pyrrolo[2,3-d]pyrimidine (0.36 g, 0.0011 mol) and sodium hydride (0.082 g, 0.0020 mol) was cooled at −78° C. and DMF (2.0 mL) was added. The reaction was allowed to warm to 25° C. and was then stirred for 20 minutes and was then heated to 55° C. for 24 hours. The reaction was then extracted with ethyl acetate. The organic extracts were washed with water and saturated NaCl, then dried (MgSO$_4$) and concentrated in vacuo. The concentrate was chromatographed on silica gel using 1:1 EtOAc/hexanes to give the product. LC/MS (M+H)$^+$: 456, $^1$H NMR (CDCl$_3$): 8.89 (s, 1H), 8.35 (s, 1H), 8.30 (s, 1H), 7.44 (d, 1H), 6.87 (d, 1H), 5.73 (s, 2H), 4.38 (m, 1H), 4.06 (s, 4H), 3.60 (m, 2H), 2.22-2.31 (m, 4H), 2.00 (m, 2H), 1.86 (m, 2H), 0.98 (m, 2H), 0.00(s, 9H)

Step 4: 4-[4-(7-[2-(Trimethylsilyl)ethoxy]methyl-7H-pyrrolo[2,3-d]pyrimidin-4-yl)-1H-pyrazol-1-yl]cyclohexanone To 4-[1-(1,4-dioxaspiro[4.5]dec-8-yl)-1H-pyrazol-4-yl]-7-[2-(trimethylsilyl)ethoxy]methyl-7H-pyrrolo[2,3-d]pyrimidine (2.13 g, 0.00467 mol), was added acetone (85 mL) followed by 12 M HCl in water (4.0 mL). The reaction was stirred at RT. After 1 h, LCMS analysis showed 66% reaction. After 4 h, HPLC showed 80% reaction. After 20 h, HPLC showed no change (and no loss of SEM). The reaction mixture was quenched into excess sat'd NaHCO$_3$. The acetone was removed by roto-evaporation. The resulting mixture of aqueous bicarbonate and a white solid was then extracted with EtOAc. The combined organic extract was shaken with sat'd NaCl, dried over Na$_2$SO$_4$, then concentrated to dryness to leave 2.0 g of a crude product. TLC (5% iPrOH-40% EtOAc-hexane): product Rf 0.12 (ketal 0.22). The crude product was purified by automatic flash chromatography on silica gel. Used a 40 g column; flow 40 mL/min; [A=2% iPrOH-hexane] [B=6% iPrOH-50% EtOAc/hexane]; A, 2 min; Gradient to B in 25 min, then B for 10 min. The eluent was concentrated using a rotary evaporator to give 1.3 g of a white solid. HPLC Method: Zorbax SB C18, 5 µm, 15 cm, 35° C., flow 1.2 mL/min, 10% CH$_3$CN—H$_2$O (0.05% TFA), to 100% CH$_3$CN in 9.0 min; stop time 12.3 min; detector 268 nm; retention time starting material, 7.4 min; product, 6.9 min (UV max 220, 268, 300, 322 nm).
$^1$H NMR (CDCl$_3$) δ 8.8 (s, 1H); 8.3 (m, 2H); 7.4 (d, 1H); 7.3 (s, 1H); 6.8 (d, 1H); 5.7 (s, 2H); 4.7 (m, 1H, NCH); 3.6 (t, 2H); 2.3-2.5 (m, 8H); 0.9 (t, 2H); −0.1 (s, 9H). MS(ES) 412 (M+1).

Step 5: 4-[4-(7-[2-(Trimethylsilyl)ethoxy]methyl-7H-pyrrolo[2,3-d]pyrimidin-4-yl)-1H-pyrazol-1-yl]cyclohexylideneacetonitrile To a solution of 1.0 M potassium tert-butoxide in THF (1.90 mL) at 0° C. was added a solution of diethyl cyanomethylphosphonate (321 µL, 0.00198 mol) in THF (4 mL) dropwise. The reaction was held for 10 min, then it was added to a solution of 4-[4-(7-[2-(trimethylsilyl)-ethoxy]methyl-7H-pyrrolo[2,3-d]pyrimidin-4-yl)-1H-pyrazol-1-yl]cyclohexanone (743 mg, 0.00180 mol) in THF (5 mL) stirring at 0° C. under a nitrogen atmosphere. The reaction was stirred 1.5 h at rt. LCMS analysis showed clean conversion to the desired product. To the reaction mixture was then added water and EtOAc. The phases were separated and the aqueous phase was extracted with EtOAc. The combined organic extract was washed with water, then sat'd NaCl, then dried over Na$_2$SO$_4$, and concentrated to dryness to yield 0.76 g of a white crystalline solid (TLC (EtOAc) Rf 0.33). The product was purified by automatic flash chromatography on silica gel. Used 40 g column; flow 40 mL/min; [A=hexane] [B=EtOAc]; A, 2 min; Gradient to B in 20 min. Rotary evaporation yielded 0.70 g of a white crystalline solid (89% yield). $^1$H NMR (CDCl$_3$) δ 8.9 (s, 1H); 8.3 (s, 2H); 7.4 (d, 1H); 7.3 (s, 1H); 6.9 (d, 1H); 5.7 (s, 2H); 5.3 (s, 1H, olefin); 4.5 (m, 1H, NCH); 3.6 (m, 2H); 3.2 (m, 1H); 2.7 (m, 1H); 2.5 (m, 4H); 2.1 (m, 2H); 1.0 (m, 2H); −0.1 (s, 9H). MS(ES) 435 (M+1).

Step 6: 4-[4-(7H-Pyrrolo[2,3-d]pyrimidin-4-yl)-1H-pyrazol-1-yl]cyclohexylideneacetonitrile A solution of TFA (0.5 mL, 0.006 mol) and 4-[4-(7-[2-(trimethylsilyl)ethoxy]methyl-7H-pyrrolo[2,3-d]pyrimidin-4-yl)-1H-pyrazol-1-yl]cyclohexylideneacetonitrile (22.7 mg, 0.0000522 mol), was stirred for 1.5 h. The solution was then concentrated using a rotary evaporator to remove TFA. LCMS analysis showed conversion to the hydroxymethyl intermediate, M+H 335. Methanol was added; and the methanol mixture was concentrated again using a rotary evaporator. The resulting residue was dissolved in methanol (1 mL) and ammonium hydroxide (0.25 mL, 0.0064 mol) was added. The resulting solution was stirred for 16 h. LCMS analysis showed complete de-protection. The solution was then concentrated using a rotary evaporator. The product was isolated by prep HPLC using a 30 mm×100 mm C18 column; 18% CH$_3$CN—H$_2$O (0.1% TFA), 1 min, to 35% at 6 min; 60 mL/min; detector set at 254 nm; retention time, 4.4 min. The eluate was freeze dried. yield 7.6 mg of a white solid (TFA salt; racemic; 34.6%). $^1$H NMR (d$_6$-

DMSO) δ 12.9 (br s, 1H, NH); 8.9 (s, 2H); 8.5 (s, 1H); 7.8 (m, 1H); 7.3 (m, 1H); 5.6 (s, 1H, olefin); 4.6 (m, 1H, NCH); 2.8 (m, 1H); 2.6 (m, 1H); 2.5 (m, 2H); 2.3 (m, 2H) 2.0 (m, 2H). MS(ES) 305 (M+1).

Example 686 cis-4-[4-(7H-Pyrrolo[2,3-d]pyrimidin-4-yl)-1H-pyrazol-1-yl]cyclohexanecarbo-nitrite trifluoroacetate

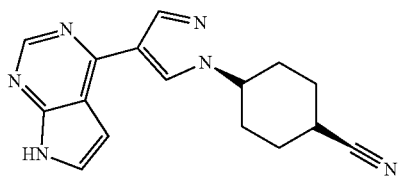

Step 1: cis-4-[4-(7-[2-(Trimethylsilyl)ethoxy]methyl-7H-pyrrolo[2,3-d]pyrimidin-4-yl)-1H-pyrazol-1-yl]cyclohexanecarbaldehyde oxime A solution of sulfur trioxide-pyridine complex (53.4 mg, 0.000336 mol) in DMSO (0.3 mL, 0.004 mol) was added to a solution of cis-4-[4-(7-[2-(trimethylsilyl)ethoxy]methyl-7H-pyrrolo[2,3-d]pyrimidin-4-yl)-1H-pyrazol-1-yl]cyclohexylmethanol (57.4 mg, 0.000134 mol) and TEA (56.1 µL, 0.000403 mol) in DCM (0.3 mL, 0.004 mol) at –10° C. The mixture was stirred vigorously at 10-20° C. for one hour. LCMS analysis showed conversion to the aldehyde. The mixture was then poured into ice-water, and extracted with DCM. The extracts were washed with 10% citric acid, water, saturated aqueous sodium bicarbonate, water, and brine, and then dried over sodium sulfate. Concentration gave 57 mg of a residue.

To the resulting residue was added hydroxylamine-HCl (50 mg), 1 mL 20% K$_2$CO$_3$, and 3 mL MeOH and this mixture was stirred at rt until LCMS showed conversion to the corresponding oxime, M+H 441. The product was isolated by prep HPLCMS using a 30 mm×10, 0 mm, C18 column; 30% CH$_3$CN—H$_2$O (0.1%TFA), 1 min, to 60% at 6 min; 60 mL/min; detector set at m/z 441; retention time, 6.0min. freeze-dried. yield 17.4 mg of a white solid.

Step 2: cis-4-[4-(7H-Pyrrolo[2,3-]pyrimidin-4-yl)-1H-pyrazol-1-yl]cyclohexanecarbonitrile

[A] cis-4-[4-(7-[2-(Trimethylsilyl)ethoxy]methyl-7H-pyrrolo[2,3-d]pyrimidin-4-yl)-1H-pyrazol-1-yl]cyclohexanecarbaldehyde oxime (11.0 mg, 0.0000250 mol) was dissolved in pyridine (0.25 mL, 0.0031 mol), and benzenesulfonyl chloride (10.0 µL, 0.0000784 mol) was added and the resulting mixture was stirred at rt. After stirring 15 h, LCMS analysis showed formation of the product, M+H 423. The product was isolated by prep HPLCMS using a 19 mm×100 mm C18 column; 45% CH$_3$CN—H$_2$O (0.1% NH$_4$OH), 1 min, to 75% at 6 min; 30 mL/min; detector set at m/z 423; retention time, 4.8 min. The eluent was concentrated using a rotary evaporator to give 8 mg of the desired product.

The product was dissolved in TFA (0.25 mL). stirred for 2 h. The solution was concentrated using a rotary evaporator to remove TFA. Methanol was added and the mixture was concentrated again. LCMS showed clean conversion to the hydroxymethyl intermediate (M+H 323). The residue was dissolved in methanol (1 mL) and ammonium hydroxide (0.25 mL) was added. The solution was stirred 0.5 h, at which time, LCMS showed complete de-protection to the desired product M+H 293. The mixture was then concentrated by roto-evaporation, and the product was isolated by prep HPLCMS using a 19 mm×100 mm C18 column; 15% CH$_3$CN—H$_2$O (0.1% TFA), 1.5 min, to 30% at 6 min; 30 mL/min; detector set at m/z 293; retention time, 5.2 min. The eluate was freeze dried to yield 5.5 mg of the product as a TFA salt. $^1$H NMR (d$_6$-DMSO) δ 12.82 (br s, 1H, NH); 8.87 (s, 1H); 8.85 (s, 1H); 8.48 (s, 1H); 7.82 (m, 1H); 7.24 (m, 1H); 4.40 (m, 1H, NCH); 3.22 (m, 1H); 2.05 (m, 6H); 1.79 (m, 2H). MS(ES) 293 (M+1).

Example 687

2-1(cis-4-[4-(7H-Pyrrolo[2,3-d]pyrimidin-4-yl)-1H-pyrazol-1-yl]cyclohexyl-methyl)sulfinyl]benzonitrile trifluoroacetate

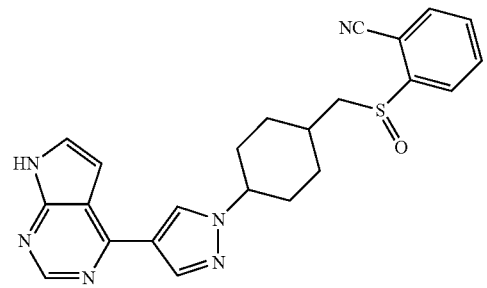 [SMILES: N#Cc1ccccc1S(=O)CC1CCC(n2cc(-c3ncnc4[nH]ccc34)cn2)CC1]

Step 1: 4-[1-(cis-4-[(2-Bromophenyl)thio]methylcyclohexyl)-1H-pyrazol-4-yl]-7-[2-(trimethylsilyl)-ethoxy]methyl-7H-pyrrolo[2,3-d]pyrimidine This compound was prepared from (cis-4-[4-(7-[2-(trimethylsilyl)ethoxy]methyl-7H-pyrrolo[2,3 -d]pyrimidin-4-yl)-1H-pyrazol-1-yl]cyclohexylmethyl methanesulfonate as in Example 686[A]. Yield 73%. The product was purified using the following HPLC method: Zorbax SB C18, 5 µm, 15 cm, 35 C, flow 1.2 mL/min, 10% CH$_3$CN—H$_2$O (0.05% TFA), to 100% CH$_3$CN in 9.0 min; stop time 12.3 min; detector 254 nm; retention time starting mesylate, 7.5 min; product, 9.9 min (UV max 215, 258, 300, & 326 nm). TLC: Rf 0.3 using 35% EtOAc/5% iPrOH/hexane. The product was purified by automated silica gel flash chromatography using 30% EtOAc/5% iPrOH/hexane. $^1$H NMR (CDCl$_3$) δ 8.84 (s, 1H); 8.31 (s, 1H); 8.26 (s, 1H); 7.55 (m, 1H); 7.39 (d, 1H); 7.27 (m, 2H); 7.03 (m, 1H); 6.82 (d, 1H); 5.67 (s, 2H); 4.34 (m, 1H, NCH); 3.55 (m, 2H); 2.98 (d, 2H); 2.28 (m, 2H); 2.02 (m, 3H); 1.83 (m, 4H); 0.92 (m, 2H); –0.06 (s, 9H). MS(ES) 598/600 1:1 (M+1).

Step 2: 2-[(cis-4-[4-(7-[2-(Trimethylsilyl)ethoxy]methyl-7H-pyrrolo[2,3-d]pyrimidin-4-yl)-1H-pyrazol-1-yl]cyclohexylmethyl)thio]benzonitrile 4-[1-(cis-4-[(2-Bromophenyl)thio]methylcyclohexyl)-1H-pyrazol-4-yl]-7-[2-(trimethylsilyl)-ethoxy]methyl-7H-pyrrolo[2,3-d]pyrimidine (62.7 mg, 0.000105 mol), zinc cyanide (123 mg, 0.00105 mol), and tetrakis(triphenylphosphine)palladium(0) (30.2 mg, 0.0000262 mol) were stirred in DMF (3 mL) and the solution was flushed with nitrogen. The solution was then heated to 100° C. for 25 min in a microwave reactor. LCMS and HPLC analyses showed >90% reaction. The product was isolated by prep HPLCMS using a 30 mm×100 mm C18 column; 52% $CH_3CN$—$H_2O$ (0.1% TFA), 1.5 min, to 75% at 6 min; 60 mL/min; detector set at 545 nm. The eluent was concentrated using a rotary evaporator to give 37 mg of the 2-cyanophenylsulfide TFA salt. HPLC Method: Zorbax SB C18, 5 μm, 15 cm, 35 C, flow 1.2 mL/min, 10% $CH_3CN$—$H_2O$ (0.05% TFA), to 100% $CH_3CN$ in 9.0 min; stop time 12.3 min; detector 265 nm; retention time starting material, 9.9 min; product, 8.9 min. MS(ES) 545 (M+1).

Step 3: 2-[(cis-4-[4-(7H-Pyrrolo[2,3-d]pyrimidin-4-yl)-1H-pyrazol-1-yl]cyclohexylmethyl)sutfinyl]-benzonitrile A solution of 2-[(cis-4-[4-(7-[2-(trimethylsilyl)ethoxy]methyl-7H-pyrrolo[2,3-d]pyrimidin-4-yl)-1H-pyrazol-1-yl]cyclohexylmethyl)thio]benzonitrile (30.6 mg, 0.0000562 mol), in TFA (1 mL) was stirred for 2 h. The solution was concentrated using a rotary evaporator to remove TFA. Methanol was added, and the mixture was concentrated again. The resulting residue was dissolved in methanol (1 mL) and ammonium hydroxide (1 mL) was added. The resulting solution was stirred overnight, at which time HPLC showed complete deprotection. The product was isolated by prep HPLCMS using a 19 mm×100 mm C18 column; 30% $CH_3CN$—$H_2O$ (0.1% TFA), 1.5 min, to 59% at 6 min; 30 mL/min; detector set at m/z 415 nm; retention time, 4.7 min. The eluate was concentrated using a rotary evaporator to give 36 mg of the sulfide TFA salt, a colorless glassy material. NMR ($d_6$-DMSO) δ 12.82 (br s, 1H, NH); 8.84 (2 singlets, 2H); 8.45 (s, 1H); 7.8 (m, 2H); 7.64 (m, 2H); 7.34 (td, 1H); 7.24 (s, 1H); 4.39 (m, 1H, NCH); 3.23 (d, 2H); 2.19 (m, 2H); 1.89 (m, 3H); 1.72 (m, 4H). MS(ES) 415 (M+1). This material was then dissolved in $CH_2Cl_2$ and cooled to 0° C. To the cooled mixture was added MCPBA (12.9 mg, 0.0000562 mol), and the resulting mixture was stirred for 1 h. LCMS showed conversion to the product, and no remaining sulfide. The reaction mixture was concentrated by rotovap, and the product was isolated by prep HPLCMS using a 19 mm×100 mm C18 column; 18% $CH_3CN$—$H_2O$ (0.1% TFA), 1.0 min, to 35% at 6 min; 30 mL/min; detector set at m/z 431 nm; retention time, 5.6 min. The product was isolated from the eluent by freeze-drying. The yield was 27.6 mg of the TFA salt. The HPLC method was: Zorbax SB C18, 5 μm, 15 cm, 35° C., flow 1.2 mL/min, 10% $CH_3CN$—$H_2O$ (0.05% TFA), to 100% $CH_3CN$ in 9.0 min; stop time 12.3 min; detector 268 nm; retention time starting material, 5.6 min; sulfoxide, 4.8 min; sulfone, 5.2 min; MCPBA, 6.0 min. $^1$H NMR ($CDCl_3$) δ 12.1 (br s, 1H, NH); 9.0 (s, 1H); 8.9 (s, 1H); 8.3 (s, 1H); 8.1 (m, 1H); 7.9 (m, 1H); 7.8 (m, 1H); 7.6 (m, 2H); 7.0 (m, 1H); 4.4 (m, 1H, NCH); 3.1 (dd, 1H); 2.9 (dd, 1H); 2.5 (m, 1H); 2.3 (m, 1H); 2.3-1.7 (m, 7H). MS(ES) 431 (M+1).

Example 688

2-[(cis-4-[4-(7H-Pyrrolo[2,3-d]pyrimidin-4-yl)-1H-pyrazol-1-yl]cyclohexyl-methyl)sulfonyl]benzonitrile trifluoroacetate

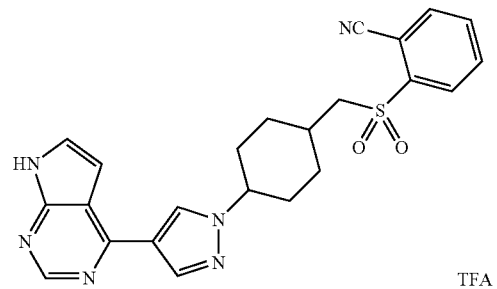 [SMILES: N#Cc1ccccc1S(=O)(=O)CC1CCC(n2cc(-c3ncnc4[nH]ccc34)cn2)CC1]

2-[(cis-4-[4-(7H-Pyrrolo[2,3-d]pyrimidin-4-yl)-1H-pyrazol-1-yl]cyclohexylmethyl)sulfinyl]-benzonitrile (17.2 mg, 0.0000400 mol) (21 mg TFA salt), was dissolved in DCM (10 mL) and cooled to 0° C. To this mixture was added MCPBA (18 mg, 0.0000800 mol). The resulting mixture was stirred for 1 h at 0° C., and then for 16 h at rt. HPLC and LCMS showed 80 area % product, and 3 area % sulfoxide. The MCPBA was removed using a sat'd $NaHCO_3$ wash, and the resulting washed mixture was concentrated by rotoevaporation. The product was isolated by prep HPLCMS using a 19 mm×100 mm C18 column; 23% $CH_3CN$—$H_2O$ (0.1% TFA), 1.0 min, to 43% at 6 min; 30 mL/min; detector set at m/z 447 nm; retention time, 5.1 min. The product was isolated from the eluent by freeze-drying. The yield was 5 mg of the TFA salt. $^1$H NMR ($d_6$-DMSO) δ 12.70 (br s, 1H, NH); 8.83 (s, 1H); 8.82 (s, 1H); 8.41 (s, 1H); 8.21 (dd, 1H); 8.16 (dd, 1H); 8.01 (td, 1H); 7.95 (td, 1H); 7.78 (s, 1H); 7.19 (s, 1H); 4.34 (m, 1H, NCH); 3.62 (d, 2H); 2.28 (m, 1H); 2.10 (m, 2H); 1.90 (m, 2H); 1.72 (m, 4H). MS(ES) 447 (M+1).

Example 689

3-[4-(7H-Pyrrolo[2,3-d]pyrimidin-4-yl)-1H-pyrazol-1-yl]cyclohexylacetonitrile trifluoroacetate

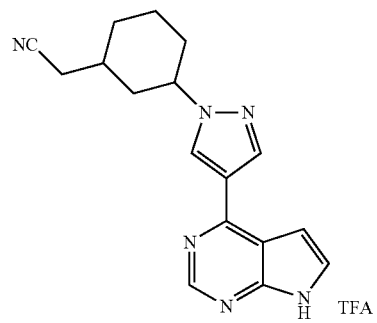 [SMILES: N#CCC1CCCC(n2cc(-c3ncnc4[nH]ccc34)cn2)C1]

Step 1: 3-[4-(7-[2-(Trimethylsilyl)ethoxy]methyl-7H-pyrrolo[2,3-d]pyrimidin-4-yl)-1H-pyrazol-1-yl]-cyclohexanone To a solution of 4-(1H-pyrazol-4-yl)-7-[2-(trimethylsilyl)ethoxy]methyl-7H-pyrrolo[2,3-d]-pyrimidine (309 mg, 0.980 mmol) in ACN (6 mL) was added 2-cyclohexen-1-one (190 µL, 01.96 mmol), followed by DBU (40 µL, 0.3 mmol). The resulting mixture was stirred for one hour at which point LCMS indicated complete addition. The mixture was reduced in vacuo and the crude product was purified by column chromatography to obtain the product (397 mg, 98%). $^1$H NMR (400 MHz, CDCl$_3$): δ 8.84 (s, 1H), 8.27 (s, 1H), 8.25 (s, 1H), 7.45 (d, 1H), 6.79 (d, 1H), 5.67 (s, 2H), 4.61 (m, 1H), 3.55 (m, 2H), 3.05-2.90 (m, 2H), 2.45-2.30 (m, 4H), 2.05 (m, 1H), 1.90 (m, 1H), 0.92 (m, 2H), −0.06 (s, 9H). MS (EI) m/z=412.2 (M+H).

Step 2: (2E,Z)-3-[4-(7-[2-(Trimethylsilyl)ethoxy]methyl-7H-pyrrolo[2,3-d]pyrimidin-4-yl)-1H-pyrazol-1-yl]cyclohexylideneacetonitrile To a solution of t-BuOK in THF (1.0 M, 0.255 mL, 0.255 mmol) at 0° C. was added a solution of diethyl cyanomethylphosphonate (43 µL, 0.27 mmol) in THF (0.6 mL) dropwise. The reaction was held for 10 minutes, then a solution of 3-[4-(7-[2-(trimethylsilyl)ethoxy]methyl-7H-pyrrolo[2,3-d]-pyrimidin-4-yl)-1H-pyrazol-1-yl]cyclohexanone (100.0 mg, 0.2430 mmol) in THF (0.34 mL) was added dropwise. After complete addition, the cooling bath was removed and the reaction was held at ambient temperature for 16 hours, at which point LCMS indicated complete addition to yield the desired product as a mixture of E and Z isomers (87.9 mg, 83%). $^1$H NMR (400 MHz, CDCl$_3$): δ 8.84 (s, 0.5H), 8.83 (s, 0.5 H), 8.27 (d, 1H), 8.25 (s, 1H), 7.40 (s, 0.5H), 7.39 (s, 0.5H), 6.81 (d, 0.5H), 6.79 (d, 0.5H), 5.67 (s, 2H), 5.28 (s, 0.5H), 5.24 (s, 0.5H), 4.4 (m, 1H), 3.55 (m, 2H), 3.1-2.8 (m, 2H), 2.5-2.1 (m, 6H), 0.92 (m, 2H), -0.06 (s, 9H). MS (EI) m/z=435.2 (M+H).

Step 3: 3-[4-(7-[2-(Trimethylsilyl)ethoxy]methyl-7H-pyrrolo[2,3-d]pyrimidin-4-yl)-1H-pyrazol-1-yl]-cyclohexylacetonitrile To (2E,Z)-3-[4-(7-[2-(trimethylsilyl)ethoxy]methyl-7H-pyrrolo[2,3-d]pyrimidin-4-yl)-1H-pyrazol-1-yl]cyclohexylideneacetonitrile (42.0 mg, 0.0966 mmol) was added THF (0.5 mL). The resulting solution was cooled to −78° C., and then 1.0 M L-Selectride® in THF (120 µL, 0.12 mmol) was added dropwise. The reaction was held at −78° C. for 1 h at which point LCMS indicated complete reduction. The reaction was quenched at −78° C. by addition of saturated aqueous NH$_4$Cl and EtOAc, and was then allowed to warm to ambient temperature. The phases were separated and the aqueous phase was extracted with additional EtOAc. The combined organic phase was washed with water, then saturated NaCl, and then was dried over MgSO$_4$. The crude product was purified by column chromatography to obtain the product (26.5 mg, 63%). $^1$H NMR (400 MHz, CDCl$_3$): δ 8.84 (s, 1H), 8.32 (s, 1H), 8.25 (s, 1H), 7.39 (d, 1H), 6.81 (d, 1H), 5.67 (s, 2H), 4.53 (m, 1H), 3.52 (m, 2H), 2.6-1.4 (m, 11H), 0.92 (m, 2H), −0.06 (s, 9H). MS (EI) m/z=437.2 (M+H).

Step 4: 3-[4-(7H-Pyrrolo[2,3-d]pyrimidin-4-yl)-1H-pyrazol-1-yl]cyclohexylacetonitrile trifluoroacetate To 3-[4-(7-[2-(trimethylsilyl)ethoxy]methyl-7H-pyrrolo[2,3-d]pyrimidin-4-yl)-1H-pyrazol-1-yl]cyclohexylacetonitrile (30.1 mg, 0.0689 mmol) was added DCM (1.0 mL) and TFA (1.0 mL). The resulting mixture was stirred for 1 hour at ambient temperature, at which point LCMS indicated complete cleavage to the N-hydroxymethyl intermediate. The solvent was removed and to the residue was added methanol (1.0 mL) followed by ethylenediamine (37 µL, 0.55 mmol), after which the reaction was stirred for 5 hours, at which point LCMS indicated complete reaction. The solvent was removed and the residue was purified by preparative LCMS to provide the product as a TFA salt (24 mg, 83%). $^1$H NMR (400 MHz, CD$_3$OD): δ 8.91 (s, 1H), 8.82 (s, 1H), 8.45 (s, 1H), 7.84 (s, 1H), 7.31 (s, 1H), 4.69 (s, 1H), 2.58 (d, 2H), 2.5-1.5 (m, 9H). MS (EI) m/z=307.10 (M+H).

Example 690

5-({cis-4-[4-(7H-Pyrrolo[2,3-d]pyrimidin-4-yl)-1H-pyrazol-1-yl]cyclohexyl}thio)-1H-1,2,4-triazol-3-amine bis(trifluoroacetate)

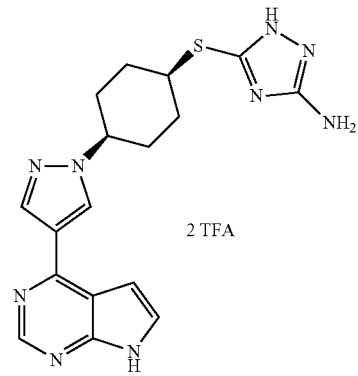 [SMILES: Nc1n[nH]c(S[C@H]2CC[C@@H](n3cc(-c4ncnc5[nH]ccc45)cn3)CC2)n1]

Step 1: trans-4-[4-(7-[2-(Trimethylsilyl)ethoxy]methyl-7H-pyrrolo[2,3-d]pyrimidin-4-yl)-1H-pyrazol-1-yl]cyclohexanol A solution of 4-[4-(7-[2-(trimethylsilyl)ethoxy]methyl-7H-pyrrolo[2,3-d]pyrimidin-4-yl)-1H-pyrazol-1-yl]cyclohexanone (662 mg, 1.61 mmol) in THF (5 mL) was cooled to 0° C. and lithium tetrahydroaluminate (2M in THF, 0.804 mL, 1.61 mmol) was added slowly. The mixture was allowed to warm slowly to ambient temperature until LCMS indicated complete reduction. The reaction was cooled to 0° C. and quenched with dropwise addition of water (0.5 mL). DCM was added, and the mixture was stirred for 1 hour at ambient temperature, after which the precipitated solids were removed by filtration. The filtrate was reduced in vacuo to leave a white solid (0.63 g, 99%). HPLC of the solid showed an approximately 4:1 ratio of trans to cis product. Tlc (6:3:1 EtOAc:hexanes:isopropanol) gave an Rf of 0.25 for the cis product, and 0.18 for the trans product. The product was purified by flash chromatography on silica gel to recover 230 mg of the pure trans alcohol and 25 mg pure of the cis alcohol, and 350 mg of mixed isomers.

$^1$H NMR (400 MHz, CDCl$_3$): δ 8.83 (s, 1H), 8.27 (s, 1H), 8.24 (s, 1H), 7.39 (d, 1H), 6.81 (d, 1H), 5.67 (s, 2H), 4.24 (m, 1H), 3.79 (m, 1H), 3.54 (m, 2H), 2.28 (m, 2H), 2.17 (m, 2H), 1.94 (m, 2H), 1.53 (m, 2H), 0.92 (m, 2H), −0.06 (s, 9H). MS (EI) m/z=414 (M+H).

Step 2: trans-4-[4-(7-[2-(Trimethylsilyl)ethoxy] methyl-7H-pyrrolo[2,3-d]pyrimidin-4-yl)-1H-pyrazol-1-yl]cyclohexyl methanesulfonate To trans -4-[4-(7-[2-(trimethylsilyl)ethoxy]methyl-7H-pyrrolo[2,3-d]pyrimidin-4-yl)-1H-pyrazol-1-yl]cyclohexanol (154 mg, 0.372 mmol) was added DCM (1.0 mL) and TEA (73 μL, 0.52 mmol). The resulting solution was then cooled to 0° C. and methanesulfonyl chloride (34 μL, 0.45 mmol) was added. The reaction was held for 2 hours, at which point tlc and LCMS indicated complete reaction. The reaction was partitioned between water and DCM, the phases were separated and the aqueous phase was extracted with additional solvent. The combined organic phase was washed with water, then saturated NaCl, then was dried over MgSO$_4$ and reduced in vacuo to give the crude product which was used without further purification (173 mg, 95%). $^1$H NMR (400 MHz, CDCl$_3$): δ 8.83 (s, 1H), 8.24 (s, 2H), 8.24 (s, 1H), 7.39 (d, 1H), 6.80 (d, 1H), 5.67 (s, 2H), 4.77 (m, 1H), 4.27 (m, 1H), 3.54 (m, 2H), 3.06 (s, 3H), 2.36 (m, 4H), 2.03 (m, 2H), 1.82 (m, 2H), 1.53 (m, 2H), 0.92 (m, 2H), −0.06 (s, 9H). MS (EI) m/z=492.1 (M+H).

Step 3: 5-({cis-4-[4-(7H-Pyrrolo[2,3-d]pyrimidin-4-yl)-1H-pyrazol-1-yl]cyclohexyl}thio)-1H-1,2,4-triazol-3-amine bis(trifluoroacetate)

To a solution of trans-4-[4-(7-[2-(trimethylsilyl)ethoxy] methyl-7H-pyrrolo[2,3-d]pyrimidin-4-yl)-1H-pyrazol-1-yl] cyclohexyl methanesulfonate (42 mg, 0.085 mmol) in DMF (800 μL) was added 3-amino-1H-1,2,4-triazole-5-thiol (30 mg, 0.26 mmol) and K$_2$CO$_3$ (36 mg, 0.26 mmol). The reaction was sealed and held at 100° C. for 2 hours at which point LCMS indicated conversion to desired product. The reaction was diluted with water and extracted successively with ether, ethyl acetate, and 3:1 chloroform:isopropyl alcohol. The combined organic phase was washed with water, then saturated NaCl, dried over MgSO$_4$ and reduced in vacuo, and the crude product was purified by column chromatography to give 5-({cis-4-[4-(7-{[2-(trimethylsilyl) ethoxy]methyl}-7H-pyrrolo[2,3-d]pyrimidin-4-yl)-1H-pyrazol-1-yl]cyclohexyl}thio)-1H-1,2,4-triazol-3-amine (27.3 mg, 63%). To the product was added DCM (0.5 mL) and TFA (0.5 mL), and the reaction was stirred for 1 hour at ambient temperature at which point LCMS indicated complete cleavage to the N-hydroxymethyl intermediate. The solvent was removed and to the residue was added methanol (1.0 mL) followed by NH$_4$OH (0.3 mL), the reaction was stirred for 16 hours at which point LCMS indicated complete deprotection. The solvent was removed and the residue was purified by preparative LCMS to provide the product as a bis-TFA salt (15.1 mg, 29%). $^1$H NMR (400 MHz, CD$_3$OD): δ 8.77 (s, 1H), 8.72 (s, 1H), 8.37 (s, 1H), 7.74 (d, 1H), 7.21 (d, 1H), 4.40 (m, 1H), 3.97 (m, 1H), 2.25 (m, 2H), 2.04 (m, 6H). MS (EI) m/z=382.2 (M+H).

Example 691

N-{5-[({cis-4-[4-(7H-Pyrrolo[2,3-d]pyrimidin-4-yl)-1H-pyrazol-1-yl]cyclohexyl}-methyl)thio]-4H-1,2,4-triazol-3-yl}methanesulfonamide trifluoroacetate

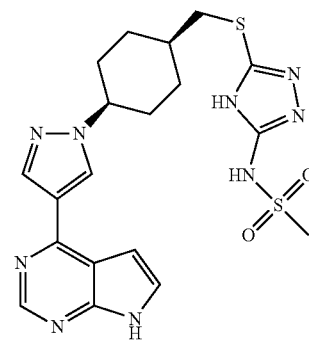

TFA

Step 1. N-5-[(cis-4-[4-(7-[2-(Trimethylsilyl)ethoxy] methyl-7H-pyrrolo[2,3-d]pyrimidin-4-yl)-1H-pyrazol-1-yl]cyclohexylmethyl)thio]-4H-1,2,4-triazol-3-ylmethanesulfonamide 5-[(cis-4-[4-(7-[2-(Trimethylsilyl)ethoxy]methyl-7H-pyrrolo[2,3-d]pyrimidin-4-yl)-1H-pyrazol-1-yl]cyclohexylmethyl)thio9 -4H-1,2,4-triazol-3-amine (30.00 mg, 5.706E-5 mol) was dissolved in DCM (2.00 mL, 0.0312 mol) with TEA (0.024 mL, 0.00017 mol) and was cooled at 0° C. To the reaction was added methanesulfonyl chloride (0.0066 mL, 0.000086 mol) and the resulting mixture was stirred at 0° C. for 60 minutes, at which time LCMS analysis showed mostly product. The reaction was chromatographed on silica gel using EtOAc as eluent to give the product. LC/MS (M+1)$^-$: 604

Step 2. N-5-[(cis-4-[4-(7H-Pyrrolo[2,3-d]pyrimidin-4-yl)-1H-pyrazol-1-yl]cyclohexylmethyl)thio]-4H-1,2,4-triazol-3-ylmethanesulfonamide Into a 1-neck round-bottom flask [A] N-5-[(cis-4-[4-(7-[2-(trimethylsilyl)ethoxy]methyl-7H-pyrrolo[2,3 -d]pyrimidin-4-yl)-1H-pyrazol-1-yl]cyclohexylmethyl)thio]-4H-1,2, 4-triazol-3-ylmethane-ulfonamide (0.025 g, 0.000041 mol) was dissolved in DCM (3.00 mL, 0.0468 mol) and TFA (mL, 0.006 mol) was added. The reaction was stirred at 25° C. for 16 hours at which time LCMS analysis showed no starting material present. The reaction was concentrated using a rotary evaporator and was dissolved in methanol (2.00 mL, 0.0494 mol) and 16 M ammonia in water (0.2 mL) was

Example 692

[cis-4-[4-(7H-Pyrrolo[2,3-d]pyrimidin-4-yl)-1H-pyrazol-1-yl]-1-(1H-1,2,4-triazol-1-yl)cyclohexyl]acetonitrile

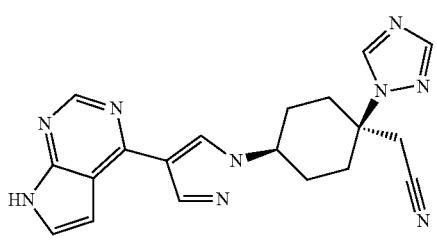 [SMILES: N#CC[C@]1(n2cncn2)CC[C@@H](N/C=C(\C=N)c2ncnc3[nH]ccc23)CC1]

1H-1,2,4-Triazole (91.0 mg, 0.00132 mol), DBU (174 µL, 0.00070 mol), [A] 4-[4-(7-[2-(trimethylsilyl)ethoxy]methyl-7H-pyrrolo[2,3-d]pyrimidin-4-yl)-1H-pyrazol-1-yl]cyclohexylidene-acetonitrile (86.4 mg, 0.000199 mol), and ACN (2.0 mL) were stirred at rt. After 4 d, LCMS showed about 58 area % product (two peaks, M+H 504, ratio 1:1). The DBU in the reaction was neutralized with TFA. The product was isolated by prep HPLC using a 30 mm×100 mm C18 column; 32% CH$_3$CN—H$_2$O (0.1% TFA), 1 min, to 47% at 6 min; 60 mL/min; detector set at 254 nm; retention time, 5.1(A) & 5.4 (B) min. The eluent was concentrated using a rotary evaporator to give 22 mg of (A) & 36 mg of (B).

Deprotection: The products were dissolved separately in TFA (0.5 mL) and stirred for 1 h. LCMS showed conversion to the hydroxymethyl derivative (M+H 404). The solutions were concentrated using a rotary evaporator to remove TFA. Methanol was added, and the resulting mixtures were concentrated again. The resulting residue was dissolved in methanol (1 mL), and ammonium hydroxide (0.25 mL) added. The solution was stirred 0.5 h. LCMS showed complete de-protection (M+H 374) and the mixture was then concentrated by roto-evaporation. Each isomer was isolated by prep HPLCMS using a 19 mm×100 mm C18 column; 15% CH$_3$CN—H$_2$O (0.1% TFA), 1.5 min, to 32% at 6 min; 30 mL/min; detector set at m/z 374; retention time, 4.5 min (A) & 4.7 min (B). The eluates were freeze dried. Yield 13 mg isomer A and 24 mg isomer B (TFA salts, white solids). NMR analysis (including NOE & COSY) was consistent with expectation for the structures, with A=cis, and B=trans. NMR (d$_6$-DMSO) δ cis: 12.94 (br s, 1H, NH); 8.95 (s, 1H); 8.87 (s, 1H); 8.81 (s, 1H); 8.42 (s, 1H); 8.14 (s, 1H); 7.85 (m, 1H); 7.22 (m, 1H); 4.48 (m, 1H, NCH); 3.12 (s, 2H); 2.84 (m, 2H); 2.07 (m, 4H); 1.69 (m, 2H). MS(ES) 374 (M+1). trans: 12.85 (br s, 1H, NH); 8.94 (s, 1H); 8.89 (s, 1H); 8.84 (s, 1H); 8.47 (s, 1H); 8.11 (s, 1H); 7.84 (m, 1H); 7.26 (m, 1H); 4.50 (m, 1H, NCH); 3.48 (s, 2H); 2.42-2.10 (m, 8H). MS(ES) 374 (M+1).

Example 705

3-1-[4-(7H-Pyrrolo[2,3-d]pyrimidin-4-yl)-1H-pyrazol-1-yl]but-3-yn-1-yl-benzo-nitrile trifluoroacetate

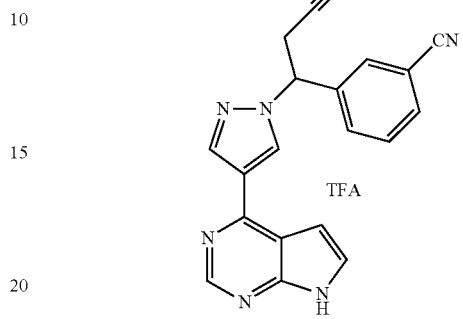

Step 1: 3-{1-[4-(7-{[2-(Trimethylsily)ethoxy]methyl}-7H-pyrrolo[2,3-d]pyrimidin-4-yl)-1H-pyrazol-1-yl]but-3-yn-1-yl}benzonitrile

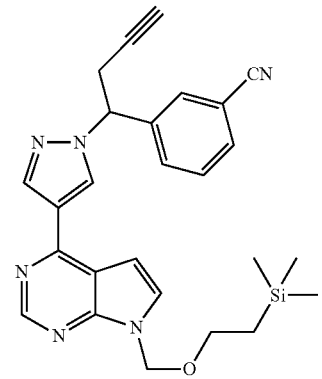 [SMILES: C#CCC(c1cccc(C#N)c1)n1cc(-c2ncnc3c2ccn3COCC[Si](C)(C)C)cn1]

1 M Diisobutylaluminum hydride in hexane (0.31 mL) was added dropwise to a solution of methyl 3-(3-cyanophenyl)-3-[4-(7-[2-(trimethylsilyl)ethoxy]methyl-7H-pyrrolo[2,3-d]pyrimidin-4-yl)-1H-pyrazol-1-yl]propanoate (100 mg, 0.0002 mol) (prepared by using a procedure analogous to Example 712, Step 1) in DCM (3 mL, 0.05 mol) and the mixture was cooled to −78° C. The reaction mixture was stirred at −78° C. for 4 h and was afterward quenched with cold methanol (3 mL, 0.07 mol). The reaction was allowed to warm to 0° C. and potassium carbonate (60 mg, 0.0004 mol) and Bestmann-Ohira reagent (1.5 eq, 57 mg) (E. Quesada et al, *Tetrahedron*, 62 (2006) 6673-6680) were added. The reaction was stirred at room temperature overnight, and then partitioned between ethyl acetate and water. The organic layer was washed with saturated NaCl, dried over MgSO$_4$, filtered and concentrated to give the crude product. The crude product was purified using silica gel (EtOAC/Hexane 1:3 to 1:1) to give the desired product, 3-{1-[4-(7-{[2-(trimethylsilyl)ethoxy]-methyl}-7H-pyrrolo[2,3-d]pyrimidin-4-yl)-1H-pyrazol-1-yl]but-3-yn-1-yl}benzonitrile (40 mg of mixture). m/z=469 (M+1).

Step 2: 3-1-[4-(7H-Pyrrolo[2,3-d]pyrimidin-4-yl)-1H-pyrazol-1-yl]but-3-yn-1-ylbenzonitrile trifluoroacetate Using a procedure analogous to Example 712, Step 4, the title compound was prepared (4.5 mg, 46%) as an amorphous white solid. ¹H NMR (500 MHz, DMSO): δ 12.5 (b, 1H), 9 (s, 1H), 8.8 (s, 1H), 8.4 (s, 1H), 8 (s, 1H), 7.8 (m 2H), 7.7 (s, 1H), 7.6 (m, 1H), 7 (m, 1H), 5.9 (m, 1H), 3.4 (dd, 1H), 3.2 (dd, 1H), 2.9 (s, 1H). m/z=339 (M+1).

Example 706

3-{1-[4-(7H-Pyrrolo[2,3-d]pyrimidin-4-yl)-1H-pyrazol-1-yl]but-3-yn-1-yl}benz-aldehyde trifluoroacetate

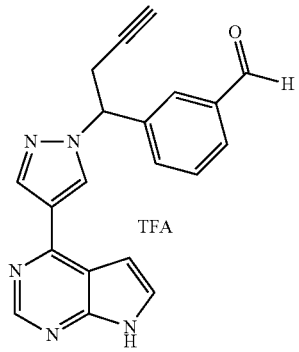 [SMILES: C#CCC(c1cccc(C=O)c1)n1cc(-c2ncnc3[nH]ccc23)cn1]

Using the procedure of Example 705, the title compound was prepared as a secondary product (4.5 mg, 46%) as an amorphous white solid. ¹H NMR (400 MHz, CDCl₃): δ 10 (s, 1H), 9 (s, 1H), 8.8 (s, 1H), 8.4 (s, 1H), 8 (s, 1H), 7.9 (m 1H), 7.8 (m, 1H), 7.7 s, 1H), 7.6 (m, 1H), 7.1 (s, 1H), 5.9 (m, 1H), 3.4 (dd, 1H), 3.2 (dd, 1H), 2.9 (s, 1H). m/z=342.

Example 712

4-[1-(3-Methoxy-1-phenylpropyl)-1H-pyrazol-4-yl]7H-pyrrolo[2,3-d]pyrimidine trifluoroacetate

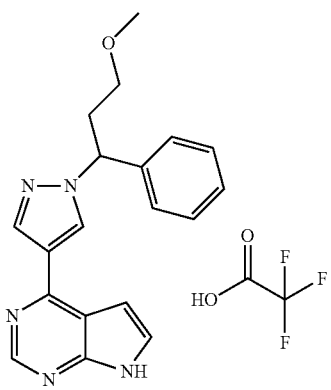

Step 1: Methyl 3-phenyl-3-[4-(7-[2-(trimethylsilyl)ethoxy]methyl-7H-pyrrolo[2,3-d]pyrimidin-4-yl)-1H-pyrazol-1-yl]propanoate

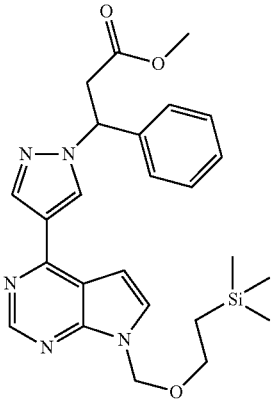 [SMILES: COC(=O)CC(c1ccccc1)n1cc(-c2ncnc3c2ccn3COCC[Si](C)(C)C)cn1]

A solution of methyl (2E)-3-phenylacrylate (500 mg, 0.003 mol) in ACN (2 mL, 0.04 mol) was slowly added to a solution of 4-(1H-pyrazol-4-yl)-7-[2-(trimethylsilyl)ethoxy]methyl-7H-pyrrolo[2,3-d]pyrimidine (0.5 g, 0.002 mol) in ACN (2 mL, 0.04 mol) and DBU (500 μL, 0.003 mol). The reaction was stirred at room temperature over the weekend. The reaction was partitioned between water and EtOAc. The organic layer was washed with saturated sodium chloride, dried over MgSO₄, filtered and concentrated to give an oil. The product was purified by FCC on silica gel using EtOAc/Hexane (1:2 to 1:1) gave methyl 3-phenyl-3-[4-(7-[2-(trimethylsilyl)ethoxy]methyl-7H-pyrrolo[2,3-d]pyrimidin-4-yl)-1H-pyrazol-1-yl]propanoate (500 mg, 70%) as a semisolid residue.

¹H NMR (400 MHz, CDCl₃): δ 8.9 (s, 1H), 8.4 (s, 2H), 7.4 (m, 5H), 6.8 (d, 1H), 6 (m, 1H), 5.7 (s, 2H), 3.7-3.8 (m, 3H), 3.6 (m, 2H), 2.2 (m, 1H), 1.4 (m, 2H), 1.1 (m, 2H), 0.02 (s, 9H), m/z=478 (M+1).

Step 2: 3-Phenyl-3-[4-(7-[2-(trimethylsilyl)ethoxy]methyl-7H-pyrrolo[2,3-d]pyrimidin-4-yl)-1H-pyrazol-1-yl]propan-1-ol

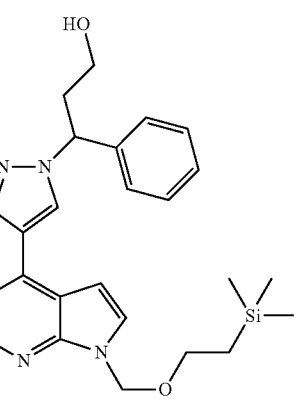

Diisobutylaluminum hydride in hexane (1 M, 0.69 mL) was added to a solution of methyl 3-phenyl-3-[4-(7-[2-(trimethylsilyl)ethoxy]methyl-7H-pyrrolo[2,3-d]pyrimidin- 4-yl)-1H-pyrazol-1-yl]-propanoate (150 mg, 0.00031 mol) in DCM (3 mL, 0.05 mol) and the mixture was cooled to −78° C. under a nitrogen atmosphere. The reaction was stirred for 1 h at −78° C. and was allowed to warm to room temperature for 4 hrs. The reaction was quenched with methanol (100 μL), and saturated ammonium chloride (100 μL), and then taken up in ethyl acetate dried over MgSO₄ and filtered. The filtrate was concentrated to give 3-phenyl-3-[4-(7-[2-(trimethylsilyl)ethoxy]methyl-7H-pyrrolo[2,3-d]pyrimidin-4-yl)-1H-pyrazol-1-yl]propan-1-ol (130 mg, 92%) as an oil. m/z=450 (M+1).

Step 3: 4-[1-(3-Methoxy-1-phenylpropyl)-1H-pyrazol-4-yl]-7-[2-(trimethylsilyl)ethoxy]methyl-7H-pyrrolo[2,3-d]pyrimidine

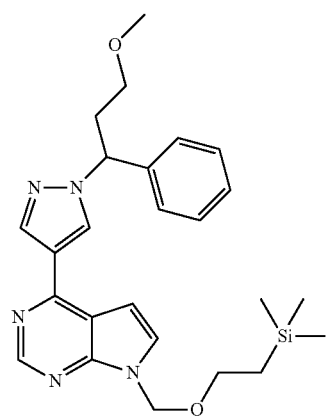 [SMILES: COCCC(c1ccccc1)n1cc(-c2ncnc3c2ccn3COCC[Si](C)(C)C)cn1]

Sodium hydride (9.6 mg, 0.00040 mol) was added to a solution of 3-phenyl-3-[4-(7-[2-(tri-methylsilyl)ethoxy]methyl-7H-pyrrolo[2,3-d]pyrimidin-4-yl)-1H-pyrazol-1propan-1-ol (120 mg, 0.00027 mol) in DMF (3 mL, 0.04 mol) and the mixture was cooled to 0° C. The reaction was stirred for 20 min and methyl iodide (22 μL, 0.00035 mol) was added. The reaction was allowed to warm to room temperature and stirred overnight. The reaction was partitioned between water and EtOAc. The organic layer was washed with saturated NaCl, dried over MgSO₄, filtered and concentrated to give 4-[1-(3-methoxy-1-phenylpropyl)-1H-pyrazol-4-yl]-7-[2-(trimethylsilyl)ethoxy]methyl-7H-pyrrolo[2,3-d]pyrimidine (100 mg, 88%) as a semisolid. m/z=464 (M+1).

Step 4: 4-[1-(3-Methoxy-1-phenylpropyl)-1H-pyrazol-4-yl]-7H-pyrrolo[2,3-d]pyrimidine trifluoroacetate Trifluoroacetic Acid (2 mL, 0.02 mol) was added to a mixture of 4-[1-(3-methoxy-1-phenylpropyl)-1H-pyrazol-4-yl]-7-[2-(trimethylsilyl)ethoxy]methyl-7H-pyrrolo[2,3-d]pyrimidine (80 mg, 0.0002 mol) in DCM (3 mL, 0.05 mol) at room temperature. The starting material was consumed after stirring for 2 hrs and the reaction solution was concentrated to remove the TFA. The crude reaction was diluted with methanol (3 mL, 0.07 mol) and was treated with ethylenediamine (0.3 mL, 0.004 mol) at room temperature. The reaction mixture was stirred for 18 hs and was concentrated and purified using HPLC on a C-18 column eluting with an ACN: water gradient containing 0.2% TFA, to give the title compound (43 mg, 60%) as a white amorphous solid. ¹H NMR (400 MHz, CDCl₃): δ 8.9 (s, 1H), 8.8 (s, 1H), 8.4 (s, 1H), 7.8 (s, 1H), 7.4 (m, 1H), 7.3 (m, 5H), 7.2 (b, 1H), 5.7 (m, 1H), 3.3 (m, 1H), 3.2 (s, 3H), 2.7 (m, 1H), 2.4 (m, 1H). m/z=334 (M+1).

Example 715

3-1-[4-(7H-Pyrrolo[2,3-d]pyrimidin-4-yl)-1H-pyrazol-1-yl]but-3-en-1-ylbenzo-nitrile trifluoroacetate

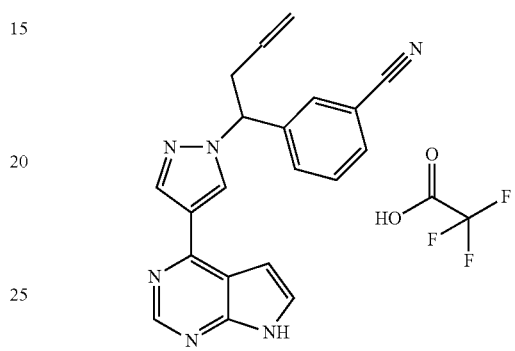

A mixture of [4-1-[1-(3-bromophenyl)but-3-en-1-yl]-1H-pyrazol-4-yl-7H-pyrrolo[2,3-d]-pyrimidine (20 mg, 0.00005 mol) in DMF (2 mL, 0.02 mol) and zinc cyanide (60 mg, 0.0005 mol) was degassed with a nitrogen stream. The mixture was then treated with tetrakis(triphenyl-phosphine)palladium(0) (40 mg, 0.00003 mol), again degassed with nitrogen, and was then heated in a microwave reactor to 170° C. for 15 min. The reaction was allowed to cool, was filtered and purified by HPLC on a C-18 column eluting with an ACN/water/TFA gradient to give the title compound (10 mg, 40%) as a white amorphous solid.

¹H NMR (400 MHz, DMSO): δ 8.9 (s, 1H), 8.8 (s, 1H), 8.4 (s, 1H), 7.9 (s, 1H), 7.8 (m, 3H), 7.6 (m, 1H), 7.1 (b, 1H), 5.6-5.8 (m, 2H), 5.1 (d, 1H), 5 (d, 1H), 3.3 (m, 1H), 3 (m, 1H). m/z=341 (M+1).

Example 716

4-1-[1-(3-Bromophenyl)but-3-en-1-yl]-1H-pyrazol-4-yl-7H-pyrrolo[2,3-d]-pyrimidine

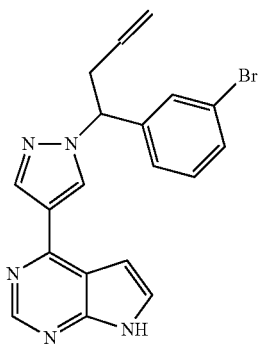 [SMILES: C=CCC(c1cccc(Br)c1)n1cc(-c2ncnc3[nH]ccc23)cn1]

Step 1: 3-(3-Bromophenyl)-3-[4-(7-[2-(trimethylsilyl)ethoxy]methyl-7H-pyrrolo[2,3-d]pyrimidin-4-yl)-1H-pyrazol-1-yl]propanal

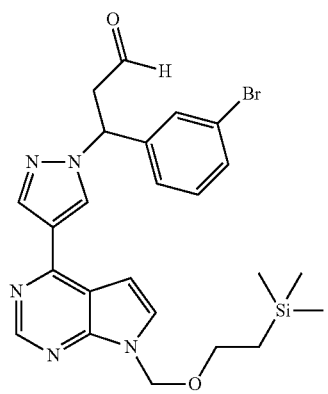 [SMILES: C[Si](C)(C)CCOCn1ccc2c(-c3cnn(C(CC=O)c4cccc(Br)c4)c3)ncnc21]

Diisobutylaluminum hydride in hexane (1 M, 4 mL) was added to a −78° C. solution of ethyl 3-(3-bromophenyl)-3-[4-(7-[2-(trimethylsilyl)ethoxy]methyl-7H-pyrrolo[2,3-d]pyrimidin-4-yl)-1H-pyrazol-1-yl]propanoate (600 mg, 0.001 mol) in DCM (6 mL, 0.09 mol). After stirring for 4 h, the reaction was quenched with cold methanol (300 μL), and then saturated ammonium chloride (500 μL) was added and the resulting solution was stirred for 1 h. The reaction was partitioned between water and EtOAc. The organic layer was washed with brine, dried over MgSO₄, filtered and concentrated. The product was purified by flash chromatography on silica gel eluting with hexane: EtOAc, (2:1 to 1:2), to give 3-(3-bromophenyl)-3-[4-(7-[2-(trimethylsilyl)ethoxy]methyl-7H-pyrrolo[2,3-d]-pyrimidin-4-yl)-1H-pyrazol-1-yl]propanal (400 mg, 70%) as an oil. ¹H NMR (400 MHz, CDCl₃): δ☐ 9.9 (s, 1H), 8.9 (s, 1H), 8.4 (s, 2H), 7.6 (d, 1H), 7.5 (d, 1H), 7.4 (d, 1H), 7.3-7.4 (m, 2H), 6.8 (d, 1H), 6.1 (m, 1H), 5.7 (s, 2H), 4 (m, 1H), 3.6 (m, 2H), 3.3 (dd, 1H), 1.0 (m, 2H), 0.01(s, 9H). m/z=526, 528 (M+1).

Step 2: 4-1-[1-(3-Bromophenyl)but-3-en-1-yl]-1H-pyrazol-4-yl-7-[2-(trimethylsilyl)ethoxy]methyl-7H-pyrrolo[2,3-d]pyrimidine

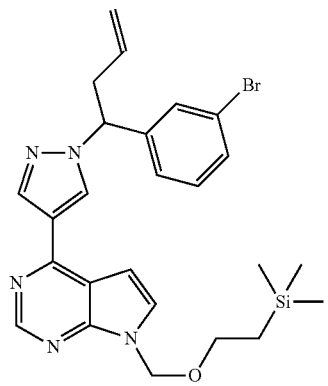 [SMILES: C=CCC(c1cccc(Br)c1)n1cc(-c2ncnc3c2ccn3COCC[Si](C)(C)C)cn1]

Potassium tert-butoxide in THF (!M, 200 μL) was added to a solution of methyltriphenyl-phosphonium iodide (80 mg, 0.0002 mol) in THF (2 mL, 0.02 mol) at 0° C. The reaction was stirred at room temperature for 1 h and then cooled to −78° C. The 3-(3-bromophenyl)-3-[4-(7-[2-(trimethyl-silyl)ethoxy]methyl-7H-pyrrolo[2,3-d]pyrimidin-4-yl)-1H-pyrazol-1-yl]propanal (90 mg, 0.0002 mol) in THF (2 mL, 0.02 mol) was added dropwise. The reaction was allowed to warm to room temperature gradually. The reaction was partitioned between water and EtOAc. The organic layer was washed with saturated NaCl, dried over MgSO₄, filtered and concentrated to give an oil. The product was purified by FCC on silica gel eluting with EtOAc:Hexane, (1:1) to give 4-1-[1-(3-bromophenyl)but-3-en-1-yl]-1H-pyrazol-4-yl-7-[2-(trimethylsilyl)ethoxy]methyl-7H-pyrrolo[2,3-d]pyrimidine (35 mg, 40%) as an oil. m/z=524, 526 (M+1).

Step 3: 4-1-[1-(3-Bromophenyl)but-3-en-1-yl1-1H-pyrazol-4-yl-7H-pyrrolo[2,3-d]pyrimidine Using a procedure analogous to Example 712, Step 4, but using 4-1-[1-(3-bromophenyl)but-3-en-1-yl]-1H-pyrazol-4-yl-7-[2-(trimethylsilyl)ethoxy]methyl-7H-pyrrolo[2,3-d]pyrimidine the title compound was prepared (10 mg, 30%) as a white amorphous solid, ¹H NMR (400 MHz, DMSO): δ☐ 8.9(s,1H), 8.8(s,1H), 8.4(s,1H), 7.8(s,1H), 7.7(s,1H), 7.5 (m,2H), 7.3(m,1H), 7.1(s,1H), 5.7(m, 2H), 5.2(d,1H), 5.0(d, 1H), 3.2(m,1H), 3.0(m,1H). m/z=394, 396 (M+1).

Example 717

3-(4,4-Difluoro)-1-[4-(7H-pyrrolo[2,3-d]pyrimidin-4-yl)-1H-pyrazol-1-yl]but-3-en-1-ylbenzonitrile

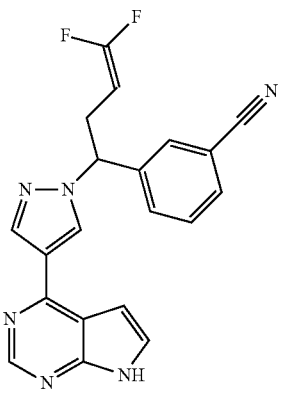 [SMILES: N#Cc1cccc(C(CC=C(F)F)n2cc(-c3ncnc4[nH]ccc34)cn2)c1]

Step 1: 4-{1-[1-(3-Bromophenyl)-4,4-difluorobut-3-en-1-yl1-1H-pyrazol-4-yl}-7-{[2-(trimethylsilyl)-ethoxy]methyl}-7H-pyrrolo[2,3-d]pyrimidine

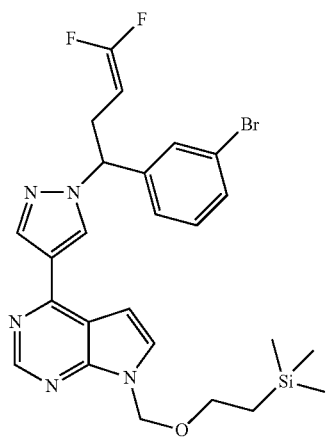 [SMILES: C[Si](C)(C)CCOCn1ccc2c(-c3cnn(C(CC=C(F)F)c4cccc(Br)c4)c3)ncnc21]

To a solution of 3-(3-bromophenyl)-3-[4-(7-[2-(trimethylsilyl)ethoxy]methyl-7H-pyrrolo[2,3-d]pyrimidin-4-yl)-1H-pyrazol-1-yl]propanal (0.05 g, 0.00009 mol) in N,N-dimethylacetamide (2 mL, 0.02 mol) was added triphenylphosphine (0.1 g, 0.0006 mol), dibromodifluoromethane (50 uL, 0.0006 mol) and 0.76 M zinc in THF (0.7 mL). The reaction was stirred at room temperature for 18 hs. The reaction was partitioned between water and EtOAc. The organic layer was washed with saturated NaCl, dried over MgSO$_4$, filtered and concentrated to give an oil. The product was purified by FCC on silica gel eluting with EtOAc, Hexane (1:2) to give 4-{1-[1-(3-bromophenyl)-4,4-difluorobut-3-en-1-yl]-1H-pyrazol-4-yl}-7-{[2-(trimethylsilyl)ethoxy]methyl}-7H-pyrrolo[2,3-d]pyrimidine (20 mg, 40%) as a clear oil. m/z=560, 562 (M+1).

Step 2: 4-1-[1-(3-Bromophenyl)-4,4-difluorobut-3-en-1-yl]-1H-pyrazol-4-yl-7H-pyrrolo[2,3-d]-pyrimidine

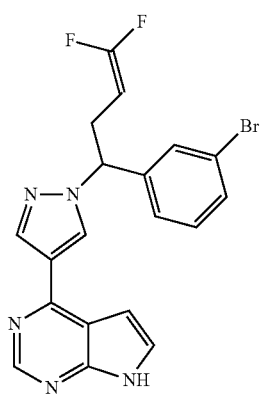 [SMILES: FC(F)=CCC(c1cccc(Br)c1)n1cc(-c2ncnc3[nH]ccc23)cn1]

Using a procedure analogous to Example 712, Step 4, but using 4-{1-[1-(3-bromophenyl)-4,4-difluorobut-3-en-1-yl]-1H-pyrazol-4-yl-7-{[2-(trimethylsilyl)ethoxy]methyl}-7H-pyrrolo[2,3-d]pyrimidine, the compound 4-1-[1-(3-bromophenyl)-4,4-difluorobut-3-en-1-yl]-1H-pyrazol-4-yl-7H-pyrrolo[2,3-d]pyrimidine was prepared (30 mg, 99%) as an oil. m/z=430, 432 (M+1).

Step 3: 3-4,4-Difluoro-1-[4-(7H-pyrrolo[2,3-d]pyrimidin-4-yl)-1H-pyrazol-1-yl]but-3-en-1-yl-benzonitrile

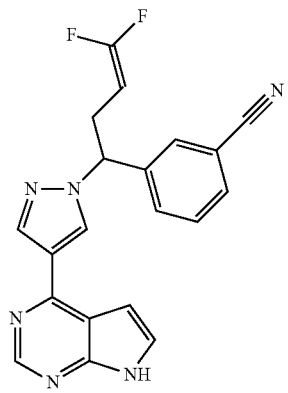 [SMILES: N#Cc1cccc(C(CC=C(F)F)n2cc(-c3ncnc4[nH]ccc34)cn2)c1]

A mixture of 4-1-[1-(3-bromophenyl)-4,4-difluorobut-3-en-1-yl]-1H-pyrazol-4-yl-7H-pyrrolo[2,3-d]pyrimidine (30 mg, 0.00007 mol) in DMF (2 mL, 0.02 mol) and zinc cyanide (80 mg, 0.0007 mol) was degassed with nitrogen. The mixture was then treated with tetrakis(triphenyl-phosphine)palladium(0) (50 mg, 0.00004 mol) and was degassed with nitrogen, and then was heated in microwave at 170° C. for 15 min. The reaction was then allowed to cool, filtered and purified by HPLC on a C-18 column eluting with an ACN/water/TFA gradient to give the title compound (10 mg, 30%) as a white amorphous solid. $^1$H NMR (400 MHz, DMSO): δ 8.9 (s, 1H), 8.7 (s, 1H), 8.4 (s, 1H), 7.9 (s, 1H), 7.7-7.8 (m, 3H), 7.5 (m, 1H), 7.1 (m, 1H), 5.7 (m, 1H), 4.3-4.4 (m, 1H), 3.1 (m, 1H), 2.9 (m, 1H). m/z=377 (M+1).

The following compounds in Table 14 were prepared as indicated in the column labeled "Prep. Ex. No." and the details of certain exemplary synthetic procedures are provided following Table 14.

TABLE 14

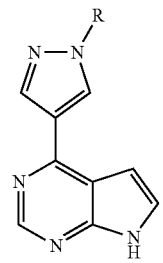

| Ex. No. | Structure of R | MS (M + H) | Name | Prep. Ex. No. |
|---|---|---|---|---|
| 727 | 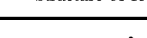 | 308 | 4-[1-(1-cyclopentylbut-3-en-1-yl)-1H-pyrazol-4-yl]-7H-pyrrolo[2,3-d]pyrimidine-trifluoroacetate salt | 727 |

TABLE 14-continued

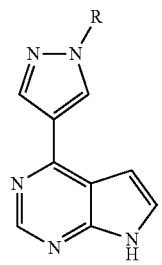

| Ex. No. | Structure of R | MS (M + H) | Name | Prep. Ex. No. |
|---|---|---|---|---|
| 728 | | 254 | 4-[1-(1-methylbut-3-en-1-yl)-1H-pyrazol-4-yl]-7H-pyrrolo[2,3-d]-pyrimidine☐trifluoroacetate salt | 727 |
| 729 | | 452 | 4-[1-(1-cyclopentyl-2-cyclopropylethyl)-1H-pyrazol-4-yl]-7H-pyrrolo[2,3-d]-pyrimidine☐trifluoroacetate salt | 727 |
| 730 | | 306 | 4-[1-(1-cyclopentylbut-3-yn-1-yl)-1H-pyrazol-4-yl]-7H-pyrrolo[2,3-d]pyrimidine ☐trifluoroacetate salt | 727 |
| 731 | | 310 | 4-[1-(1-cyclopentylbutyl)-1H-pyrazol-4-yl]-7H-pyrrolo[2,3-d]-pyrimidine☐trifluoroacetate salt | 729 |
| 732 | | 344 | 4-[1-(1-cyclopentyl-4,4-difluorobut-3-en-1-yl)-1H-pyrazol-4-yl]-7H-pyrrolo[2,3-d]-pyrimidine☐trifluoroacetate salt | 727 |
| 733 | | 346 | 4-1-[4,4-difluoro-1-(tetrahydro-furan-3-yl)but-3-en-1-yl]-1H-pyrazol-4-yl-7H-pyrrolo[2,3-d]-pyrimidine trifluoroacetate salt | 727 Step 3 & 4, then 731, step 1* |
| 734 | | 254 | 4-[1-(1-methylbut-3-en-1-yl)-1H-pyrazol-4-yl]-7H-pyrrolo[2,3-d]-pyrimidine trifluoroacetate salt | 727 Step 3 & 4, then 731 |
| 735 | | 316 | 4-[1-(1-cyclopropyl-4,4-difluoro-but-3-en-1-yl)-1H-pyrazol-4-yl]-7H-pyrrolo[2,3-d]pyrimidine trifluoroacetate salt | 727 Step 3 & 4, then 731 |

TABLE 14-continued

| Ex. No. | Structure of R | MS (M + H) | Name | Prep. Ex. No. |
|---|---|---|---|---|
| 736 | cyclopentyl-CH(-)-CH2-CHF2 | 346 | 4-[1-(1-cyclopentyl-4,4-difluorobutyl)-1H-pyrazol-4-yl]-7H-pyrrolo[2,3-d]pyrimidine trifluoroacetate salt | 731 |
| 737 | (1-methylcyclopentyl)-CH(-)-CH2-CN | 321 | 3-(1-methylcyclopentyl)-3-[4-(7H-pyrrolo[2,3-d]pyrimidin-4-yl)-1H-pyrazol-1-yl]propanenitrile trifluoroacetate salt | 737 |
| 738 | t-Bu-CH(-)-CH2-CN | 295 | (3R)- and (3S)-4,4-dimethyl-3-[4-(7-[2-(trimethylsilyl)ethoxy]-methyl-7H-pyrrolo[2,3-d]-pyrimidin-4-yl)-1H-pyrazol-1-yl]pentanenitrile trifluoroacetate salt | 737 |
| 739 | (1-cyanocyclopropyl)-CH(-)-CH2-CN | 304 | 1-2-cyano-1-[4-(7H-pyrrolo[2,3-d]pyrimidin-4-yl)-1H-pyrazol-1-yl]ethylcyclopropanecarbonitrile trifluoroacetate salt | 739 |
| 740 | 1-(benzamidomethyl)cyclopentyl-CH(-)-CH2-CN | 440 | N-[(1-2-cyano-1-[4-(7H-pyrrolo[2,3-d]pyrimidin-4-yl)-1H-pyrazol-1-yl]ethylcyclopentyl)methyl]benzamide | 740 |
| 741 | 1-(benzyloxymethyl)cyclopentyl-CH(-)-CH2-CN | 427 | 3-1-[(Benzyloxy)methyl]cyclopentyl-3-[4-(7H-pyrrolo[2,3-d]-pyrimidin-4-yl)-1H-pyrazol-1-yl]propanenitrile trifluoroacetate salt | 741 |
| 742 | 1-(methylsulfonyl)pyrrolidin-3-yl-CH(-)-CH2-CN | 386 | 3-[1-(methylsulfonyl)pyrrolidin-3-yl]-3-[4-(7H-pyrrolo[2,3-d]-pyrimidin-4-yl)-1H-pyrazol-1-yl]propanenitrile trifluoroacetate salt | 742 |

TABLE 14-continued

[Structure: 4-(1H-pyrazol-4-yl)-7H-pyrrolo[2,3-d]pyrimidine core with R group on pyrazole N]

| Ex. No. | Structure of R | MS (M + H) | Name | Prep. Ex. No. |
|---|---|---|---|---|
| 743 | piperidine with CH₂CN substituent and N-C(=N-CN)NH₂ carboximidamide | 375 | N'-cyano-4-(cyanomethyl)-4-[4-(7H-pyrrolo[2,3-d]pyrimidin-4-yl)-1H-pyrazol-1-yl]piperidine-1-carboximidamide | 743 |
| 744 | CH(CF₃)CH₂-(1H-imidazol-2-yl) | 348 | 4-1-[2,2,2-trifluoro-1-(1H-imidazol-2-ylmethyl)ethyl]-1H-pyrazol-4-yl-7H-pyrrolo[2,3-d]-pyrimidine | 744 |
| 745 | CH(CF₃)CH₂-(4-methyl-1,3-thiazol-2-yl) | 379 | 4-(1-(1R)-2,2,2-trifluoro-1-[(4-methyl-1,3-thiazol-2-yl)-methyl]ethyl-1H-pyrazol-4-yl)-7H-pyrrolo[2,3-d]pyrimidine | 745 |
| 746 | CH(CF₃)CH₂C≡CH | 306 | 4-1-[1-(trifluoromethyl)but-3-yn-1-yl]-1H-pyrazol-4-yl-7H-pyrrolo[2,3-d]pyrimidine | 730 |
| 747 | CH(CF₃)CH₂CH=CH₂ | 308 | 4-1-[1-(trifluoromethyl)but-3-en-1-yl]-1H-pyrazol-4-yl-7H-pyrrolo[2,3-d]pyrimidine | 727 |
| 748 | CH(CF₃)CH₂CH₂CH₃ | 310 | 4-1-[1-(trifluoromethyl)butyl]-1H-pyrazol-4-yl-7H-pyrrolo-[2,3-d]pyrimidine | 731 |
| 749 | CH(CF₃)CH₂CH=CF₂ | 344 | 4-1-[4,4-difluoro-1-(trifluoromethyl)but-3-en-1-yl]-1H-pyrazol-4-yl-7H-pyrrolo[2,3-d]-pyrimidine | 732 |
| 750 | CH(CF₃)CH₂CHF-CHF₂ | 346 | 4-1-[4,4-difluoro-1-(trifluoromethyl)butyl]-1H-pyrazol-4-yl-7H-pyrrolo[2,3-d]pyrimidine | 731 |

*Step 1 of example 731 was modified as follows: The Ph₃P and CF₂Br₂ were combined in DMAC at 0° C. and then allowed to warm to room temperature until the ylid formation was complete as determined by LCMS. The solution of the ylid was then re-cooled to 0° C. and the aldehyde and zinc were added to the ylid solution and the reaction was slowly warmed to room temperature.

Example 727

4-[1-(1-Cyclopentylbut-3-en-1-yl)-1H-pyrazol-4-yl]-7H-pyrrolo[2,3-d]pyrimidine trifluoroacetate salt

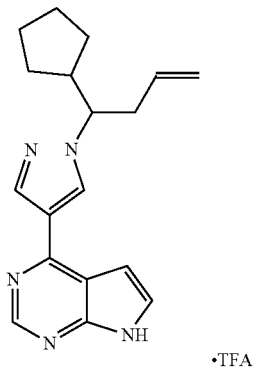 [SMILES: C=CCC(N/C=C(\C=N)c1ncnc2[nH]ccc12)C1CCCC1]

Step 1: (2E)-3-Cyclopentylacrylic acid

To a solution of malonic acid (1.06 g, 10.2 mol) in pyridine (1.25 mL) was added piperidine (0.15 mL) and cyclopentanecarbaldehyde (1.00 g, 10.2 mmol). The mixture was heated to 40° C. for 2 hours, followed by stirring at room temperature for 16 hours. The mixture was then cooled in an ice bath and 2N HCl was added to acidify. The product was extracted with ether. The ether extract was washed with aq. HCl and brine, dried over sodium sulfate, filtered, and the solvent was removed in vacuo to afford the product (1.30 g, 77%), which was used without further purification.

$^1$H NMR (300 MHz, CDCl$_3$): δ 7.06 (dd, 1H), 5.80 (dd, 1H), 2.70-2.54 (m, 1H), 1.93-1.32 (m, 8H); MS(ES): 141 (M+H).

Step 2. Methyl (2E)-3-cyclopentylacrylate

To a solution of (2E)-3-cyclopentylacrylic acid (1.3 g, 9.3 mmol) in DCM (65 mL) at 0° C. was added oxalyl chloride (3.1 mL, 37 mmol), dropwise. The resulting solution was stirred at 0° C. for 40 minutes, then at room temperature for 2 hours. The volatiles were evaporated to afford (2E)-3-cyclopentylacryloyl chloride as a colorless liquid. A portion of this (2E)-3-cyclopentylacryloyl chloride (0.75 g, 4.7 mol) was dissolved in methanol (10 mL) and the resulting solution was stirred for 2 hours. The solvent was evaporated to afford the product (700 mg, 96%).

$^1$H NMR (300 MHz, CDCl$_3$): δ 6.94 (dd, 1H), 5.79 (dd, 1H), 3.71 (s, 3H), 2.66-2.50 (m, 1H), 1.92-1.27 (m, 8H).

Step 3. Methyl 3-cyclopentyl-3-—4-(7-[2-(trimethylsilyl)ethoxy]methyl-7H-pyrrolo[2,3-d]pyrimidin-4-yl)-1H-pyrazol-1-yl]propanoate To a solution of 4-(1H-pyrazol-4-yl)-7-[2-(trimethylsilyl)ethoxy]methyl-7H-pyrrolo[2,3-d]pyrimidine (2.9 g, 9.2 mmol) and methyl (2E)-3-cyclopentylacrylate (1.70 g, 11.0 mmol) in ACN (100 mL), was added DBU (2.7 mL, 18 mmol). The resulting mixture was stirred for 96 hours. The ACN was removed in vacuo, and the resulting residue was dissolved in ethyl acetate. This solution was washed with 1.0 N HCl, followed by brine, and then dried over sodium sulfate, and the solvent removed in vacuo. Flash column chromatography (eluting with a gradient from 0-70% ethyl acetate in hexanes) afforded the product (2.73 g, 63%).

$^1$H NMR (300 MHz, CDCl$_3$): δ 8.84 (s, 1H), 8.28 (s, 2H), 7.39 (d, 1H), 6.81 (d, 1H), 5.67 (s, 2H), 4.46 (dt, 1H), 3.60 (s, 3H), 3.54 (t, 2H), 3.18 (dd, 1H), 2.89 (dd, 1H), 2.59-2.42 (m, 1H), 1.95-1.80 (m, 1H), 1.75-1.10 (m, 7H), 0.92 (t, 2H), -0.06 (s, 9H); MS(ES): 470 (M+H).

Step 4. 3-Cyclopentyl-3-[4-(7-[2-(trimethylsilyl)ethoxy]methyl-7H-pyrrolo[2,3-d]pyrimidin-4-yl)-1H-pyrazol-1-yl]propanal To a solution of methyl 3-cyclopentyl-3-[4-(7-[2-(trimethylsilyl)ethoxy]methyl-7H-pyrrolo-[2,3-d]pyrimidin-4-yl)-1H-pyrazol-1-yl]propanoate (0.501 g, 1.07 mmol) in THF (5.0 mL) at −78° C. was added 1.00 M diisobutylaluminum hydride in DCM (2.35 mL) dropwise. The reaction was stirred with gradual warming to −10° C. over the course of 2 hours. At this temperature, a further portion of 1.0 M diisobutylaluminum hydride in DCM (1.50 mL) was added. When the reaction was determined to be complete by LCMS, a saturated solution of K/Na tartrate was added, followed by ether. The resulting mixture was stirred for two hours at room temperature. The organic layer was separated and washed with water, and brine, then dried over sodium sulfate and the solvent was removed in vacuo to give a viscous oil, which was used without further purification. MS(ES): 442 (M+H).

To a solution of oxalyl chloride (0.108 mL, 1.28 mmol) in DCM (10.0 mL) at −78° C. was added DMSO (151 µL, 2.13 mmol). After stirring for 5 minutes, 3-cyclopentyl-3-[4-(7-[2-(trimethylsilyl)ethoxy]methyl-7H-pyrrolo[2,3-d]pyrimidin-4-yl)-1H-pyrazol-1-yl) propan-1-ol (471 mg, 1.07 mmol) in DCM (3.00 mL) was added. The mixture was stirred for 30 minutes at −78° C. TEA (594 µL, 4.26 mmol) was then added. The resulting mixture was then allowed to warm to room temperature over the course of 30 minutes. Water was added, and the layers were separated. The organic layer was washed successively with 0.1 N HCl, water, saturated sodium bicarbonate solution, and brine, and was then dried over sodium sulfate and the solvent was removed in vacuo. Flash column chromatography (eluting with a gradient of 0-60% ethyl acetate in hexanes) afforded the product (384 mg, 82%).

$^1$H NMR (300 MHz, CDCl$_3$): δ 9.73 (s, 1H), 8.87 (s, 1H), 8.71 (br s, 1H), 8.30 (s, 1H), 7.47 (br s, 1H), 6.88 (br s, 1H), 5.69 (s, 2H), 4.66-4.49 (m, 1H), 3.54 (t, 2H), 3.40 (ddd, 1H), 2.95 (ddd, 1H), 2.55-2.44 (m, 1H), 2.01-1.21 (m, 8H), 0.98 (t, 2H), 0.00 (s, 9H); MS(ES): 440 (M+H).

Step 5. 4-[1-(1-Cyclopentylbut-3-en-1-yl)-1H-pyrazol-4-yl]-7-[2-(trimethylsilyl)ethoxy]methyl-7H-pyrrolo[2,3-d]pyrimidine To a solution of 1.0 M potassium tert-butoxide in THF (0.207 mL) in THF (2.0 mL) at 0° C. was added triphenylmethylphosphonium bromide (77.8 mg, 0.218 mmol). The resulting mixture was warmed to room temperature and allowed to stir for 30 minutes. A solution of 3-cyclopentyl-3-[4-(7-[2-(trimethylsilyl)ethoxy]methyl-7H-pyrrolo[2,3-d]pyrimidin-4-yl) -1H-pyrazol-1-yl]propanal (0.100 g, 0.228 mmol) in THF (2.0 mL) was added. After 30 minutes, the mixture was quenched by the addition of saturated ammonium chloride solution and the product was then extracted with ether. The ether extract was dried over sodium sulfate and the solvent was removed in vacuo. Flash column chromatography (eluting with a gradient of 0-40% ethyl acetate in hexanes) afforded the product (40 mg, 44%).

$^1$N NMR (400 MHz, CDCl$_3$): δ 8.84 (s, 1H), 8.26 (s, 1H), 8.19 (br s, 1H), 7.40 (s, 1H), 6.83 (br s, 1H), 5.67 (s, 2H), 5.60 (ddt, 1H), 5.01 (dq, 1H), 4.97-4.93 (m, 1H), 3.99 (dt, 1H), 3.54 (t, 2H), 2.79-2.60 (m, 2H), 2.60-2.40 (m, 1H), 1.99-1.89 (m, 1H), 1.75-1.41 (m, 5H), 1.37-1.12 (m, 2H), 0.92 (t, 2H), −0.06 (s, 9H); MS(ES): 438 (M+H).

Step 6. 4-[1-(1-Cyclopentylbut-3-en-1-yl)-1H-pyrazol-4-yl]-7H-pyrrolo[2,3-d]pyrimidine trifluoroacetate salt 4-[1-(1-Cyclopentylbut-3-en-1-yl)-1H-pyrazol-4-yl)-7-[2-(trimethylsilyl)ethoxy]methyl-7H-pyrrolo[2,3-d]pyrimidine (13 mg, 0.030 mmol) was dissolved in DCM (3 mL) and TFA (0.5 mL) was added. The resulting solution was stirred at room temperature for 3 hours. The solvent was removed in vacuo. The residue was dissolved in THF (2 mL), and 6 N NaOH (1 mL) was added. The mixture was stirred at room temperature for 1 hour, and then was partitioned between water and ethyl acetate. The organic layer was dried over sodium sulfate and the solvent was removed in vacuo. Purification via preparative-HPLC/MS (C18 eluting with a gradient of H$_2$O and ACN containing 0.1% TFA) afforded the product (10 mg, 80%).

$^1$H NMR (400 MHz, d$_6$-DMSO): δ 12.73 (s, 1H), 8.88 (s, 2H), 8.43 (s, 1H), 7.79 (t, 1H), 7.19 (dd, 1H), 5.60 (ddt, 1H), 5.00-4.93 (m, 1H), 4.91-4.87 (m, 1H), 4.23 (dt, 1H), 2.76-2.59 (m, 2H), 2.47-2.34 (m, 1H), 1.92-1.82 (m, 1H), 1.68-1.22 (m, 6H), 1.21-1.09 (m, 1H); MS(ES): 308 (M+H).

Example 729

4-[1-(1-Cyclopentyl-2-cyclopropylethyl)-1H-pyrazol-4-yl]-7H-pyrrolo[2,3-d]-pyrimidine ☐trifluoroacetate salt

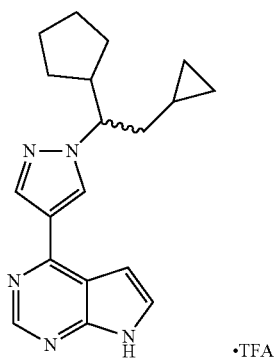 [SMILES: c1nc(-c2cnn(C(CC3CC3)C3CCCC3)c2)c2cc[nH]c2n1]

Step 1. 4-1-(1-Cyclopentyl-2-cyclopropylethyl)-1H-pyrazol-4-yl]-7-[2-(trimethylsilyl)ethoxy]methyl-7H-pyrrolo[2,3-d]pyrimidine trifluoroacetate salt A solution of 4-[1-(1-cyclopentylbut-3-en-1-yl)-1H-pyrazol-4-yl]-7-[2-(trimethylsilyl)-ethoxy]methyl-7H-pyrrolo[2,3-d]pyrimidine (prepared in Example 727, Step 5) (54.0 mg, 0.123 mmol) in DCM (1 mL) was added to a freshly prepared ethereal solution of excess CH$_2$N$_2$ held at 0° C. Palladium acetate (10.0 mg, 0.044 mol) was added. After standing for 2 hours, the excess CH$_2$N$_2$ was quenched by the addition of acetic acid. The solution was then diluted with further DCM, washed successively with saturated sodium bicarbonate solution, water, and brine, and dried over sodium sulfate, and the solvent was removed in vacuo. Purification via preparative-HPLC/MS (C18 eluting with a gradient of H$_2$O and ACN containing 0.1% TFA) afforded the product (13 mg, 18%).

$^1$H NMR (300 MHz, CDCl$_3$): δ☐ 9.05 (s, 1H), 8.81 (d, 1H), 8.35 (s, 1H), 7.59 (t, 1H), 7.03 (t, 1H), 5.76 (s, 2H), 4.10 (t, 1H), 3.59 (t, 2H), 2.57-2.36 (m, 1H), 2.15-2.00 (m, 1H), 2.00-1.83 (m, 1H), 1.79-1.40 (m, 6H), 1.37-1.09 (m, 2H), 0.97 (t, 2H), 0.55-0.26 (m, 3H), 0.07-⁻0.15 (m, 11H); MS(ES): 452 (M+H).

Step 2. 4-1-(1-Cyclopentyl-2-cyclopropylethyl)-1H-pyrazol-4-yl]-7H-pyrrolo[2,3-d]pyrimidine☐trifluoroacetate salt 4-[1-(1-Cyclopentyl-2-cyclopropylethyl)-1H-pyrazol-4-yl]-7-[2-(trimethylsilyl)ethoxy]-methyl-7H-pyrrolo[2,3-d]pyrimidine trifluoroacetate salt (13 mg, 0.023 mol) was stirred at room temperature in a solution of DCM (2 mL) containing TFA (1.5 mL) for two hours. The solvent was removed in vacuo. The resulting residue was redissolved in THF (3 mL), and 6N NaOH (2 mL) was added. After stirring for one hour, the mixture was partitioned between water and ethyl acetate. The organic layer was dried over sodium sulfate and the solvent was removed in vacuo. Purification via preparative-HPLC/MS (C18 eluting with a gradient of H$_2$O and ACN containing 0.1% TFA) afforded the product (9 mg, 90%).

$^1$H NMR (400 MHz, d$_6$DMSO): δ☐ 12.75 (s, 1H), 8.90 (s, 1H), 8.84 (s, 1H), 8.47 (s, 1H), 7.81 (s, 1H), 7.22 (s, 1H), 4.19 (dt, 1H), 2.43-2.29 (m, 1H), 2.03-1.92 (m, 1H), 1.88-1.76 (m, 1H), 1.68-1.37 (m, 5H), 1.35-1.08 (m, 3H), 0.43-0.26 (m, 2H), 0.24-0.13 (m, 1H), 0.07-⁻0.03 (m, 1H), ⁻0.14-⁻0.24 (m, 1H); MS(ES): 322(M+H).

Example 730

4-[1-(1-Cyclopentylbut-3-yn-1-yl)-1H-pyrazol-4-yl]-7H-pyrrolo[2,3-d]pyrimidine trifluoroacetate salt

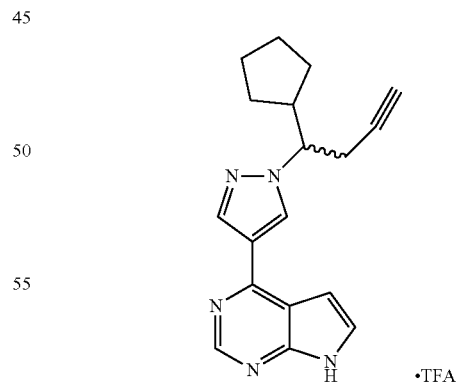

Step 1. 4-1-(1-Cyclopentylbut-3-yn-1-yl)-1H-pyrazol-4-yl]-7-[2-(trimethylsilyl)ethoxy]methyl-7H-pyrrolo[2,3-d]pyrimidine To a mixture of potassium carbonate (38.4 mg, 0.278 mmol) in methanol (2.0 mL) at 0° C. was added a solution of 3-cyclopentyl-3-[4-(7-[2-(trimethylsilyl)ethoxy]methyl-7H-pyrrolo[2,3-d]-pyrimidin-4-yl)-1H-pyrazol-1-yl]propanal (prepared as in Example 727, step 4) (61.0 mg, 0.139 mmol) in methanol (1.0 mL), followed by a solution of dimethyl (1-diazo-2-oxopropyl)phosphonate (40.0 mg, 0.208 mmol) in methanol (1.0 mL). The mixture was slowly warmed to ambient temperature and stirred for 16 hours. The mixture was then diluted with water and extracted with ethyl acetate. The combined extracts were washed with water, saturated ammonium chloride, and then dried over sodium sulfate and the solvent was removed in vacuo to afford the product, which was used without further purification (52 mg, 86%).

$^1$H NMR (300 MHz, CDCl$_3$): δ □8.85 (s, 1H), 8.47 (s, 1H), 8.29 (s, 1H), 7.41 (d, 1H), 6.84 (d, 1H), 5.67 (s, 2H), 4.14 (ddd, 1H), 3.53 (t, 2H), 2.90 (ddd, 1H), 2.79 (ddd, 1H), 2.66-2.49 (m, 1H), 1.98 (t, 1H), 2.00-1.88 (m, 1H), 1.78-1.44 (m, 5H), 1.39-1.11 (m, 2H), 0.92 (t, 2H), −0.06 (s, 9H); MS(ES): 436(M+H).

Step 2. 4-1-(1-Cyclopentylbut-3-yn-1-yl)-1H-pyrazol-4-yl]-7H-pyrrolo[2,3-d]pyrimidine□trifluoroacetate salt A solution of 4-[1-(1-cyclopentylbut-3-yn-1-yl)-1H-pyrazol-4-yl]-7-[2-(trimethylsilyl)-ethoxy]methyl-7H-pyrrolo[2,3-d]pyrimidine (52 mg, 0.12 mmol) in DCM (3 mL) and TFA (1 mL) was stirred for 2 hours. The solvents were removed in vacuo. The resulting residue was dissolved in THF (3 mL) and 6N NaOH (2 mL) was added. After stirring for 1 hour, the mixture was partitioned between water and ethyl acetate. The organic layer was dried over sodium sulfate and the solvent was removed in vacuo. Purification via preparative-HPLC/MS (C18 eluting with a gradient of H$_2$O and ACN containing 0.1% TFA) afforded product (30 mg, 60%).

$^1$H NMR (300 MHz, d$_6$-DMSO): δ □12.72 (s, 1H), 8.91 (s, 1H), 8.84 (s, 1H), 8.47 (s, 1H), 7.80 (s, 1H), 7.19 (s, 1H), 4.34 (dt, 1H), 2.97-2.69 (m, 3H), 2.50-2.32 (m, 1H), 1.93-1.77 (m, 1H), 1.70-1.09 (m, 7H); MS(ES): 306(M+H).

Example 731

4-[1-(1-Cyclopentylbutyl)-1H-pyrazol-4-yl]-7H-pyrrolo[2,3-d]pyrimidine□ trifluoroacetate salt

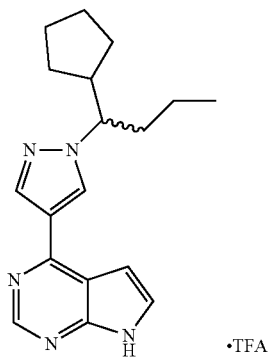 [SMILES: CCCC(C1CCCC1)n1cc(-c2ncnc3[nH]ccc23)cn1]

4-[1-(1-Cyclopentylbut-3-yn-1-yl)-1H-pyrazol-4-yl]-7H-pyrrolo[2,3-d]pyrimidine trifluoro-acetate salt (prepared in Example 729) (20 mg, 0.048 mmol) was dissolved in methanol (2 mL) and a catalytic amount of 5% Pd—C was added. The mixture was stirred under 1 atmosphere of hydrogen via an affixed balloon. After 2 hours, the mixture was filtered and purified via preparative-HPLC/MS (C18 eluting with a gradient of H$_2$O and ACN containing 0.1% TFA) to afford the product (14 mg, 69%).

$^1$H NMR (400 MHz, d$_6$-DMSO): δ□ 12.73 (s, 1H), 8.86 (s, 1H), 8.83 (s, 1H), 8.45 (s, 1H), 7.79 (t, 1H), 7.20 (d, 1H), 4.11 (dt, 1H), 2.43-2.26 (m, 1H), 2.02-1.70 (m, 3H), 1.68-1.35 (m, 4H), 1.33-0.89 (m, 5H), 0.83 (t, 3H); MS(ES): 310(M+H).

Example 732

4-[1-(1-Cyclopentyl-4,4-difluorobut-3-en-1-yl)-1H-pyrazol-4-yl]-7H-pyrrolo[2,3-d]pyrimidine□ trifluoroacetate salt

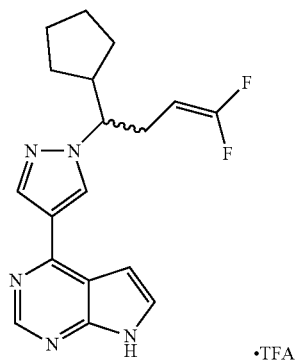 [SMILES: FC(F)=CCC(C1CCCC1)n1cc(-c2ncnc3[nH]ccc23)cn1]

Step 1. 4-[1-(1-Cyclopentyl-4,4-difluorobut-3-en-1-yl)-1H-pyrazol-4-yl]-7-[2-(trimethylsilyl)ethoxy]-methyl-7H-pyrrolo[2,3-d]pyrimidine To a solution of 3-cyclopentyl-3-[4-(7-[2-(trimethylsilyl)ethoxy]methyl-7H-pyrrolo[2,3-d]-pyrimidin-4-yl)-1H-pyrazol-1-yl]propanal (prepared as in Example 727, Step 4) (181 mg, 0.41 mmol) in N,N-dimethylacetamide (3.6 mL) was added triphenylphosphine (294 mg, 1.12 mmol) followed by dibromodifluoromethane (235 mg, 1.12 mmol). Rieke® Zinc (1.8 mL of a suspension of 2.5 g in 50 ml THF) was then added in one portion. The resulting mixture was stirred at room temperature for 4.5 hours. The mixture was filtered through diatomaceous earth. The filtrate was partitioned between ether and water. The ether layer was washed with water, and brine, then dried over sodium sulfate, and the solvent was removed in vacuo. Flash column chromatography (eluting with a gradient from 0-30% ethyl acetate in hexanes) afforded product (104 mg, 53%).

$^1$H NMR (400 MHz, CDCl$_3$): δ □ 8.91 (s, 1H), 8.51 (br s, 1H), 8.34 (s, 1H), 7.51 (d, 1H), 6.93 (d, 1H), 5.74 (s, 2H), 4.05 (ddd, 1H), 4.04-3.96 (m, 1H), 3.60 (t, 2H), 2.78-2.62 (m, 2H), 2.58-2.45 (m, 1H), 2.07-0.87 (m, 10H), 0.00 (s, 9H); MS(ES): 474(M+H).

Step 2. 4-1-(1-Cyclopentyl-4,4-difluorobut-3-en-1-yl)-1H-pyrazol-4-yl]-7H-pyrrolo[2,3-d]pyrimidine□ trifluoroacetate salt A solution of 4-[1-(1-cyclopentyl-4,4-difluorobut-3-en-1-yl)-1H-pyrazol-4 -yl)-7-[2-(tri-methylsilyl)ethoxy]methyl-7H-pyrrolo[2,3-d]pyrimidine (41 mg, 0.086 mmol) in DCM (3 mL) and TFA (1.5 mL) was stirred for two hours at room temperature. The solution was then concentrated in vacuo. The resulting residue was redissolved in THF (3 mL), and 6N NaOH (2 mL) was added. After stirring for 1 hour, the mixture was partitioned between water and ethyl acetate. The organic layer was dried over sodium sulfate and the solvent was removed in vacuo. Purification via preparative-HPLC/MS (C18 eluting with a gradient of H₂O and ACN containing 0.1% TFA) afforded the desired product (39 mg, 98%).

¹H NMR (400 MHz, d₆-DMSO): δ☐ 12.72 (s, 1H), 8.84 (s, 1H), 8.83 (s, 1H), 8.45 (s, 1H), 7.80 (t, 1H), 7.18 (d, 1H), 4.32 (ddt 1H), 4.20 (dt, 1H), 2.72-2.37 (m, 3H), 1.95-1.81 (m, 1H), 1.69-1.06 (m, 7H); MS(ES): 344(M+H).

Where conjugate acceptors, such as were used in Example 737, Step 3 were not commercially available, such compounds were generated according to the procedure provided below for ethyl (2E)-3-(tetrahydrofuran-3-yl)acrylate (toward the preparation of Example 733).

Preparation of ethyl (2E)-3-(tetrahydrofuran-3-yl)acrylate:

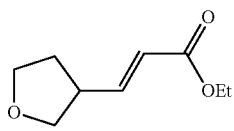 [SMILES: CCOC(=O)/C=C/C1CCOC1]

Step A: Tetrahydrofuran-3-carbaldehyde

To a solution of Dess-Martin periodinane (3.37 g, 7.95 mmol) in DCM (20 mL) was added tetrahydrofuran-3-ylmethanol (0.701 mL, 7.23 mmol). The reaction was stirred at ambient temperature for 2 hours, and the solvent was then removed in vacuo. Flash column chromatography (using DCM as eluent) afforded the product as a clear oil, which was used without further purification.

¹H NMR (400 MHz, CDCl₃): δ☐ 9.65 (d, 1H), 4.12-4.07 (m, 1H), 3.92-3.85 (m, 2H), 3.80-3.73 (m, 1H), 3.10-3.02 (m, 1H), 2.26-2.10 (m, 2H).

Step B: Ethyl(2E)-3-(tetrahydrofuran-3-yl)acrylate

To a 0° C. mixture of sodium hydride (60% in mineral oil) (382 mg, 9.40 mmol) in DMF (15.0 mL) (THF may also be used) was added triethyl phosphonoacetate (1.72 mL, 8.68 mmol) dropwise. The resulting mixture was warmed to room temperature and stirred for 30 minutes, then was re-cooled to 0° C., at which time a solution of tetrahydrofuran-3-carbaldehyde (724 mg, 7.23 mmol) in DMF (4.0 mL) was added dropwise. The resulting mixture was stirred at this temperature for 1.5 hours, at which time the mixture was diluted with water and the product was extracted with ether. The combined extracts were washed with water and brine, dried over sodium sulfate and the solvent removed in vacuo. Flash column chromatography (eluting with a gradient from 0-40% ethyl acetate in hexanes) afforded the product (640 mg, 52%).

¹H NMR (400 MHz, CDCl₃): δ ☐6.87 (dd, 1H), 5.86 (dd, 1H), 3.96-3.88 (m, 2H), 3.81 (dd, 1H), 3.53 (dd, 1H), 3.04-2.93 (m, 1H), 2.20-2.10 (m, 2H), 2.03 (s, 3H), 1.79 (dq, 1H).

Example 736

4-[1-(1-Cyclopentyl-4,4-difluorobutyl)-1H-pyrazol-4-yl]-7H-pyrrolo[2,3-d]-pyrimidine trifluoroacetate salt

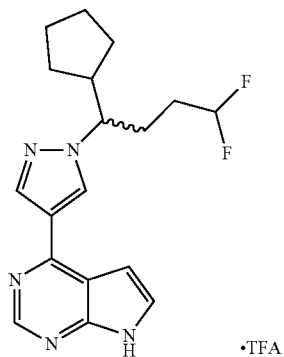 [SMILES: FC(F)CCC(C1CCCC1)n1cc(-c2ncnc3[nH]ccc23)cn1]

4-[1-(1-Cyclopentyl-4,4-difluorobut-3-en-1-yl)-1H-pyrazol-4-yl]-7H-pyrrolo[2,3-d]-pyrimidine trifluoroacetate salt (prepared as in Example 731) (20.0 mg, 0.041 mmol) was dissolved in methanol (3 mL), and a catalytic amount of 5% Pd on C was added. The mixture was stirred at room temperature for 2 hours, under an atmosphere of hydrogen provided by an affixed balloon. The mixture was filtered and purified via preparative-HPLC/MS (C18 eluting with a gradient of H₂O and ACN containing 0.1% TFA) to afford product (4 mg, 21%).

¹H NMR (400 MHz, d₆-DMSO): δ 12.74 (s, 1H), 8.88 (s, 1H), 8.85 (s, 1H), 8.48 (s, 1H), 7.80 (t, 1H), 7.20 (dd, 1H), 6.05 (tt, 1H), 4.17 (dt, 1H), 2.47-2.34 (m, 1H), 2.14-1.08 (m, 12H); MS(ES): 346(M+H).

Example 737

3-(1-Methylcyclopentyl)-3-[4-(7H-pyrrolo[2,3-d]pyrimidin-4-yl)-1H-pyrazol-1-yl]propanenitrile trifluoroacetate salt

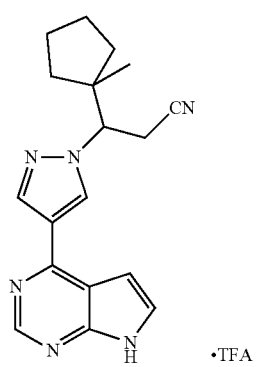 [SMILES: CC1(C(CC#N)n2cc(-c3ncnc4[nH]ccc34)cn2)CCCC1]

Step 1. 1-Methylcyclopentanecarbaldehyde

To a solution of cyclopentanecarbaldehyde (1.00 mL, 9.36 mmol) in DCM (47 mL) at 0° C. was added solid potassium tert-butoxide (1.44 g, 12.2 mmol) in one portion

353 followed by methyl iodide (1.7 mL, 28 mmol) in one portion. After 30 minutes at 0° C., the reaction mixture was allowed to warm to room temperature and stirred at that temperature for 16 hours. The mixture was poured into brine, and the layers were separated. The organic layer was dried over sodium sulfate, decanted and concentrated, and used without further purification in Step 2.

Step 2: (2Z)- and (2E)-3-(1-Methylcyclopentyl)acrylonitrile

To a solution of 1.0 M potassium tert-butoxide in THF (9.36 mL) at 0° C. was added a solution of diethyl cyanomethylphosphonate (1.59 mL, 9.81 mmol) in THF (10 mL) dropwise. The cooling bath was removed and the reaction was warmed to room temperature followed by re-cooling to 0° C., at which time a solution of 1-methylcyclopentanecarbaldehyde (1.0 g, generated in Step 1) in THF (2 mL) was added dropwise. The bath was removed and the reaction was stirred at ambient temperature for 3 hours. To the mixture was added water and ethyl ether. The aqueous layer was further extracted with ethyl ether. The combined extracts were washed with brine, dried over sodium sulfate, filtered and adsorbed onto silica gel in vacuo. Flash column chromatography (eluting with a gradient from 0-10% ethyl acetate in hexanes) afforded product as a mixture with hexanes, which product was used without further purification in Step 3.

Step 3: 3-(1-Methylcyclopentyl)-3-[4-(7H-pyrrolo [2,3-d]pyrimidin-4-yl)-1H-pyrazol-1-yl]propanenitrile trifluoroacetate salt To a mixture of 4-(1H-pyrazol-4-yl)-7-[2-(trimethylsilyl) ethoxy]methyl-7H-pyrrolo[2,3-d]pyrimidine (0.134 g, 0.426 mmol) in ACN (3 mL) was added a mixture of (2Z)- and (2E)-3-(1-methylcyclopentyl)acrylonitrile (0.12 g, 0.9 mmol) followed by DBU (0.13 mL, 0.90 mmol). The reaction was heated to 60° C. for 6 h. The ACN was removed in vacuo. Ethyl acetate was added, followed by 0.1 N HCl. The aqueous layer was extracted with three portions of ethyl acetate. The combined organic extracts were washed with brine, dried over sodium sulfate, filtered and the solvent was evaporated. The crude material was deprotected by stirring with TFA (2 mL) in DCM (8 mL) for 2 hours. The solvent and TFA were removed in vacuo. THF (8 mL) was used to dissolve the residue, and 6.0 M sodium hydroxide in water (8 mL) was added. The reaction was stirred in this basic mixture for 2 hours. Ethyl acetate was used to extract the product. The combined extracts were dried ($Na_2SO_4$) and the solvent was removed in vacuo. Purification via preparative-HPLC/MS (C18 eluting with a gradient of $H_2O$ and ACN containing 0.1% TFA) afforded product (44 mg, 24%).

$^1$H NMR (400 MHz, $d_6$DMSO): δ 12.71 (s, 1H), 9.00 (s, 1H), 8.85 (s, 1H), 8.51 (s, 1H), 7.81 (s, 1H), 7.18 (s, 1H), 4.72 (dd, 1H), 3.47 (dd, 1H), 3.21 (dd, 1H), 1.74-1.51 (m, 6H), 1.44-1.32 (m, 1H), 1.09-1.00 (m, 1H), 0.97 (s, 3H); MS(ES): 321(M+H).

354

Example 739

1-2-Cyano-1-[4-(7H-pyrrolo[2,3-d]pyrimidin-4-yl)-1H-pyrazol-1-yl]ethylcyclo-propanecarbonitrile trifluoroacetate salt

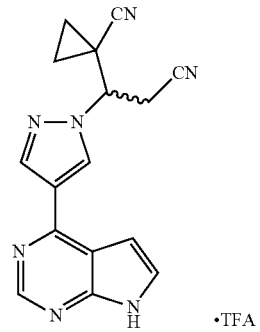 [SMILES: N#CCC(n1cc(-c2ncnc3[nH]ccc23)cn1)C1(C#N)CC1]

Step 1: 1-(Hydroxymethyl)cyclopropanecarbonitrile

Ethyl 1-cyanocyclopropanecarboxylate (801 mg, 5.76 mmol) in THF (12.0 mL) was treated with lithium tetrahydroborate (251 mg, 11.5 mmol). The solution was heated to reflux for 1.5 hours. Upon cooling to room temperature, the reaction was quenched with water, and extracted with ethyl acetate. The combined extracts were dried over $MgSO_4$, filtered and concentrated to afford a clear oil, which was used without further purification in the following step (482 mg, 86%).

$^1$H NMR (400 MHz, $CDCl_3$): δ 3.61 (s, 2H), 1.27 (dd, 2H), 0.98 (dd, 2H).

Step 2: 1-Formylcyclopropanecarbonitrile

Dess-Martin periodinane (1.11 g, 2.62 mmol) was dissolved in DCM (12 mL) and 1-(hydroxymethyl)cyclopropanecarbonitrile (231 mg, 2.38 mmol) was added. The reaction was stirred at ambient temperature for one hour. The mixture was then purified by flash column chromatography (eluting with a gradient from 0-80% ethyl acetate in hexanes) to afford the product (106 mg, 46%).

$^1$H NMR (400 MHz, $CDCl_3$): δ 9.35 (s, 1H), 1.79-1.74 (m, 4H).

Step 3: 1-[(E)-2-Cyanovinyl]cyclopropanecarbonitrile

To a solution of 1.0 M potassium tert-butoxide in THF (1.12 mL) at 0° C. was added slowly dropwise a solution of diethyl cyanomethylphosphonate (210 mg, 1.2 mmol) in THF (2 mL). The cold bath was removed and the reaction was warmed to ambient temperature. The solution was then re-cooled to 0° C. and a solution of 1-formylcyclopropanecarbonitrile (101 mg, 1.06 mmol) in THF (1.0 mL) was added dropwise. The cold bath was removed and the reaction was stirred for 3 hours at ambient temperature. The mixture was then diluted with ether and water, the ether solution was separated, washed with brine, dried over sodium sulfate, filtered and the solvent was removed in vacuo. Flash column chromatography (eluting with a gradient from 0-60% ethyl ether in hexanes) afforded the product (24 mg, 19%).

¹H NMR (400 MHz, CDCl₃): δ 5.94 (d, 1H), 5.82 (d, 1H), 1.80 (dd, 2H), 1.39 (dd, 2H).

Step 4: 1-2-Cyano-1-[4-(7-[2-(trimethylsilyl)ethoxy]methyl-7H-pyrrolo[2,3-d]pyrimidin-4-yl)-1H-pyrazol-1-yl]ethylcyclopropanecarbonitrile To a solution of 4-(1H-pyrazol-4-yl)-7-[2-(trimethylsilyl)ethoxy]methyl-7H-pyrrolo[2,3-d]-pyrimidine (61.4 mg, 0.195 mmol) and 1-[(E)-2-cyanovinyl]cyclopropanecarbonitrile (23 mg, 0.19 mmol) in ACN (2 mL) was added DBU (58 uL, 0.39 mmol) and the resulting mixture was stirred for 16 hours. The ACN was evaporated, and the residue was dissolved in ethyl acetate. This solution was washed with 1.0 N HCl, water, and brine, and dried over sodium sulfate, and the solvent removed in vacuo. Flash column chromatography (eluting with a gradient from 0-80% ethyl acetate in hexanes) afforded the product (49 mg, 58%).
¹H NMR (400 MHz, CDCl₃): δ 8.85 (s, 1H), 8.43 (s, 1H), 8.34 (s, 1H), 7.43 (d, 1H), 6.80 (d, 1H), 5.68 (s, 2H), 3.54 (dd, 1H), 3.51 (dd, 1H), 3.36 (dd, 1H), 1.62 (ddd, 1H), 1.45 (ddd, 1H), 1.34 (ddd, 1H), 1.25 (ddd, 1H), 0.92 (t, 2H), -0.06 (s, 9H); MS(ES): 434(M+H).

Step 5: 1-2-Cyano-1-[4-(7H-pyrrolo[2,3-d]pyrimidin-4-yl)-1H-pyrazol-1-yl]ethylcyclopropane-carbonitrile trifluoroacetate salt 1-2-cyano-1-(7-[2-(trimethylsilyl)ethoxy]methyl-7H-pyrrolo[2,3-d]pyrimidin-4-yl)-1H-pyrazol-1-yl]ethylcyclopropanecarbonitrile (48 mg, 0.11 mmol) was stirred in a mixture of DCM (3 mL) and TFA (2 mL) for 3 hours. The solvents were removed in vacuo and the residue was re-dissolved in THF (3 mL). 6N NaOH (2 mL) was added and the resulting mixture was stirred at ambient temperature for 3 hours. The crude reaction mixture was partitioned between ethyl acetate and water. The layers were separated and the organic layer was dried over sodium sulfate and the solvent was removed in vacuo. Purification via preparative-HPLC/MS (C18 eluting with a gradient of H₂O and ACN containing 0.1% TFA) afforded product (20 mg, 43%).
¹H NMR (400 MHz, d₆-DMSO): δ 12.74 (s, 1H), 8.99 (s, 1H), 8.88 (s, 1H), 8.60 (s, 1H), 7.83 (t, 1H), 7.17 (dd, 1H), 4.55 (dd, 1H), 3.66 (dd, 1H), 3.54 (dd, 1H), 1.55-1.30 (m, 4H); MS(ES): 304(M+H).

Example 740

N-[(1-2-Cyano-1-[4-(7H-pyrrolo[2,3-d]pyrimidin-4-yl)-1H-pyrazol-1-yl]ethyl-cyclopentyl)methyl]benzamide

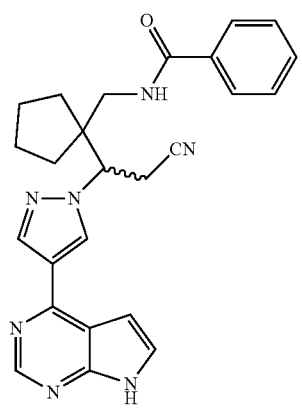 [SMILES: N#CCC(n1cc(-c2ncnc3[nH]ccc23)cn1)C1(CNC(=O)c2ccccc2)CCCC1]

Step 1: Methyl 1-cyanocyclopentanecarboxylate

To a solution of acetic acid, cyano-, methyl ester (2.66 mL, 30.3 mmol) and 1,4-dibromobutane, (3.62 mL, 30.3 mmol) in acetone (50 mL) was added potassium carbonate (8.37 g, 60.6 mmol). The reaction was stirred at ambient temperature for 16 hours. The reaction was filtered through diatomaceous earth and concentrated. The resulting residue was partitioned between ether and saturated NH₄Cl solution, and the aqueous layer was extracted with two further portions of ether. The combined ethereal extracts were washed with brine, and dried over sodium sulfate, then filtered and the solvent was removed in vacuo. Flash column chromatography (eluting with a gradient from 0-30% ethyl acetate in hexanes) afforded the product (2.92 g, 63%).
¹H NMR (300 MHz, CDCl₃): δ 3.82 (s, 3H), 2.30-2.21 (m, 4H), 1.93-1.82 (m, 4H).

Step 2: Methyl 1-[(tert-butoxycarbonyl)amino]methylcyclopentanecarboxylate

To a solution of methyl 1-cyanocyclopentanecarboxylate (1.26 g, 8.22 mmol) in methanol (100 mL) was added cobalt dichloride (2.1 g, 16.0 mmol). The purple mixture was cooled in an ice-water bath. Sodium tetrahydroborate (3.11 g, 82.2 mmol) was added portionwise with caution (exothermic) to provide a black mixture. Upon complete addition, cooling was discontinued and the reaction was stirred for 40 minutes under nitrogen and the reaction was quenched by the careful addition of 1N HCl (700 ml). The methanol was removed in vacuo, and the solution was then made alkaline (pH ~9) by the addition of concentrated NH₄OH (aq). The mixture was extracted with DCM (6 times), and the combined DCM extracts were dried over sodium sulfate and concentrated to afford the crude product as a light yellow oil. To this crude amine in DCM (50 ml) was added di-tert-butyldicarbonate (1.31 g, 6.01 mmol) and the reaction was stirred at 25° C. for 30 minutes. The reaction was diluted with water and extracted with ethyl acetate three times. The combined extracts were dried over sodium sulfate, filtered, and the solvent removed in vacuo. The crude residue was purified by flash column chromatography to yield the desired product (1.5 g, 71%).
¹H NMR (300 MHz, CDCl₃): δ 5.03 (s, 1H), 3.69 (s, 3H), 3.26 (d, 2H), 2.02-1.33 (m, 17H).

Step 3: tert-Butyl[1-(hydroxymethyl)cyclopentyl]nethylcarbamate

To a solution of methyl 1-[(tert-butoxycarbonyl)amino]methylcyclopentanecarboxylate (1.50 g, 5.83 mmol) in THF (25.0 mL) at −78° C. was added dropwise 1.0 M diisobutylaluminum hydride in DCM (17.5 mL). The reaction was stirred for 2 hours with slow warming to −10° C. A saturated solution of K/Na tartrate was added, followed by ether. This mixture was stirred for 30 minutes at ambient temperature and the organic layer was separated and washed with water, and brine. The organic layer was then dried over sodium sulfate, and the solvent was removed in vacuo to afford the product (1.03 g, 77%). ¹H NMR (300 MHz, CDCl₃): δ 4.90 (br s, 1H), 3.27 (s, 2H), 3.06 (d, 2H), 1.5-1.17 (m, 8H), 1.44 (s, 9H).

Step 4: tert-Butyl[(1-formylcyclopentyl)methyl]carbamate

To a solution of oxalyl chloride (456 μL, 5.38 mmol) in DCM (30.0 mL) at −78° C. was added DMSO (637 μL, 8.97 mmol) and the resulting mixture was stirred for 5 minutes. tert-Butyl[1-(hydroxymethyl)cyclopentyl]methylcarbamate (1.03 g, 4.48 mmol) in DCM (10.0 mL) was added and the resulting mixture was stirred for 30 minutes at −78° C. TEA (2.50 mL, 17.9 mmol) was added and the resulting mixture was allowed to warm to ambient temperature over 30 minutes. Water was added. The organic phase was washed sequentially with 0.1 N HCl, water, saturated sodium bicarbonate solution, and brine, and then dried over sodium sulfate and the solvent was removed in vacuo to afford the product (957 mg, 94%). $^1$H NMR (300 MHz, CDCl$_3$): δ 9.39 (s, 1H), 4.94 (br s, 1H), 3.25 (d, 2H), 1.89-1.46 (m, 8H), 1.41 (s, 9H).

Step 5: tert-Butyl(1-[(E)-2-cyanovinyl]cyclopentylmethyl)carbamate and tert-butyl (1-[(Z)-2-cyanovinyl]cyclopentylmethyl)carbamate To a solution of 1.0 M potassium tert-butoxide in THF (4.4 mL) at 0° C. was added a solution of diethyl cyanomethylphosphonate (820 mg, 4.6 mmol) in THF (6.0 mL) dropwise. The cold bath was removed and the reaction was warmed to ambient temperature. The mixture was then re-cooled to 0° C. and a solution of tert-butyl [(1-formylcyclopentyl)methyl]carbamate (952 mg, 4.19 mmol) in THF (4.0 mL) was added dropwise. The reaction was allowed to warm to ambient temperature and the warmed mixture was stir for 16 hours. The reaction mixture was then diluted with ether and water. The organic layer was separated and washed sequentially with water and brine, then dried over sodium sulfate, then filtered, and the solvent was removed in vacuo to afford the product (1.05 g, 99%) as a mixture of (E) and (Z) isomers.
$^1$H NMR (300 MHz, CDCl$_3$): δ 6.71 (d, 1H, E), 6.46 (d, 1H, Z), 5.36 (d, 1H, Z), 5.36 (d, 1H, E), 4.70 (br s, 1H, Z), 4.51 (br s, 1H, E), 3.25 (d, 2H, Z), 3.18 (d, 2H, E), 1.88-1.48 (m, 8H (E) and 8H (Z)), 1.43 (s, 9H (E) and 9H (Z)); MS(ES): 151(M+H-Boc).

Step 6: tert-Butyl[(1-2-cyano-1-[4-(7-[2-(trimethylsilyl)ethoxy]methyl-7H-pyrrolo[2,3-d]pyrimidin-4-yl)-1H-pyrazol-1-yl]ethylcyclopentyl)methyl]carbamate To a solution of 4-(1H-pyrazol-4-yl)-7-[2-(trimethylsilyl)ethoxy]methyl-7H-pyrrolo[2,3-d]-pyrimidine (355 mg, 1.12 mmol) and tert-butyl (1-[(E)-2-cyanovinyl]cyclopentylmethyl)carbamate and tert-butyl (1-[(Z)-2-cyanovinyl]cyclopentylmethyl)carbamate as a mixture of isomers (329 mg, 1.31 mmol) in ACN (10 mL) was added DBU (0.168 mL, 1.12 mmol). The resulting mixture was stirred at ambient temperature for 3 hours followed by heating to 60° C. for 2.5 hours. The ACN was removed in vacuo and the resulting residue was purified by flash column chromatography (eluting with 0-55% ethyl acetate in hexanes) to afford the product (350 mg, 55%).
$^1$H NMR (300 MHz, CDCl$_3$): δ 8.85 (s, 1H), 8.37 (br s, 1H), 8.34 (s, 1H), 7.41 (d, 1H), 6.82 (d, 1H), 5.68 (s, 2H), 5.37 (br s, 1H), 4.52 (dd, 1H), 3.54 (t, 2H), 3.40 (dd, 1H), 3.23 (dd, 1H), 3.08 (d, 1H), 2.90 (dd, 1H), 1.84-1.47 (m, 8H), 1.45 (s, 9H), 0.92 (t, 2H), −0.06 (s, 9H); MS(ES): 566(M+H).

Step 7: N-[(1-2-Cyano-1-[4-(7H-pyrrolo[2,3-d]pyrimidin-4-yl)-1H-pyrazol-1-yl]ethylcyclopentyl)methyl]benzamide A solution of tert-butyl [(1-2-cyano-1-[4-(7-[2-(trimethylsilyl)ethoxy]methyl-7H-pyrrolo[2,3-d]pyrimidin-4-yl)-1H-pyrazol-1-yl]ethylcyclopentyl)methyl]carbamate (175 mg, 0.309 mmol) in DCM (5 mL) and TFA (5 mL) was stirred for 3 hours and the solvents were then removed in vacuo. The resulting residue was stirred in a mixture of THF (3 mL) and 6N NaOH (3 mL) for 3 hours. The THF was removed in vacuo, and water (10 mL) was added. The mixture was extracted with several portions of DCM containing 15% isopropanol. The combined extracts were dried over sodium sulfate and the solvents were removed in vacuo to afford the product, which was used without further purification. MS(ES): 336 (M+H).

To a solution of 3-[1-(aminomethyl)cyclopentyl]-3-[4-(7H-pyrrolo[2,3-d]pyrimidin-4-yl)-1H-pyrazol-1-yl]propanenitrile (31 mg, 0.060 mmol) and benzoyl chloride (7.0 μL, 0.060 mol) in DCM (1.0 mL), was added TEA (17 μL, 0.12 mmol). After 15 minutes, the solvent was removed in vacuo and the mixture was purified via preparative-HPLC/MS (C18 eluting first with a gradient of H$_2$O and ACN containing 0.1% TFA, followed by chromatographic purification, eluting with a gradient of H$_2$O and ACN containing 0.15% NH$_4$OH) to afford the product (7 mg, 27%).
$^1$H NMR (400 MHz, d$_6$-DMSO): δ 12.12 (s, 1H), 8.95 (s, 1H), 8.68 (s, 1H), 8.55 (s, 1H), 8.41 (s, 1H), 7.92-7.87 (m, 2H), 7.60 (d, 1H), 7.59-7.48 (m, 3H), 7.02 (d, 1H), 4.83 (dd, 1H), 3.52-3.45 (m, 2H), 3.42 (dd, 1H), 3.27 (dd, 1H), 2.06-1.95 (m, 1H), 1.68-1.12 (m, 7H); MS(ES): 440(M+H).

Example 741

3-1-[(Benzyloxy)methyl]cyclopentyl-3-[4-(7H-pyrrolo[2,3-d]pyrimidin-4-yl)-1H-pyrazol-1-yl]propanenitrile trifluoroacetate salt

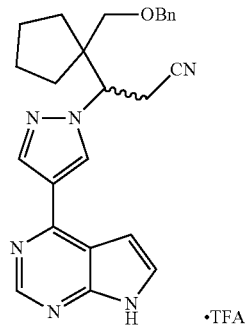 [SMILES: N#CCC(n1cc(-c2ncnc3[nH]ccc23)cn1)C1(COCc2ccccc2)CCCC1]

Step 1: 1-(Hydroxymethyl)cyclopentanecarbonitrile

A mixture of methyl 1-cyanocyclopentanecarboxylate (prepared in Example 740, Step 1) (500 mg, 3.0 mmol) in THF (7 mL) was treated with lithium tetrahydroborate (100 mg, 6.0 mmol). The resulting solution was heated to reflux for 3 hours, then stirred at ambient temperature for 16 hours. The mixture was quenched by the addition of water, and was extracted with ethyl acetate. The combined organic extracts were dried over Na$_2$SO$_4$, then filtered and the solvent was removed in vacuo to afford the product (387 mg, 95%). $^1$H NMR (300 MHz, CDCl$_3$): δ 3.62 (s, 2H), 2.39-1.60 (m, 8H).

Step 2: 1-[(Benzyloxy)methyl]cyclopentanecarbonitrile

To a solution of 1-(hydroxymethyl)cyclopentanecarbonitrile (0.30 g, 2.0 mmol) in DMF (4 mL) was added sodium hydride (60% dispersion in mineral oil, 0.101 g, 2.52 mol). The resulting mixture was stirred for 20 minutes, followed by the addition of benzyl bromide (0.28 mL, 2.4 mmol). The reaction was stirred at ambient temperature for 64 hours. Additional sodium hydride (60% dispersion in mineral oil, 0.060 g, 1.5 mmol) and benzyl bromide (0.18 mL, 1.5 mmol) were added and the reaction was stirred for an additional 30 minutes. Water was then added to the mixture, followed by brine, and the aqueous layer was extracted with ethyl acetate. The extracts were combined and dried over sodium sulfate, and the solvent was then removed in vacuo. To the resulting residue was added water. The product was isolated by extraction with diethyl ether. The ethereal extracts were dried over sodium sulfate, and the solvent was evaporated. Flash column chromatography (eluting with a gradient from 0-30% ethyl acetate in hexanes) afforded product (330 mg, 64%).

$^1$H NMR (300 MHz, CDCl$_3$): δ 7.40-7.27 (m, 5H), 4.62 (s, 2H), 3.44 (s, 2H), 2.18-2.03 (m, 2H), 1.90-1.62 (m, 6H).

Step 3: 1-[(Benzyloxy)methyl]cyclopentanecarbaldehyde

To a mixture containing 1-[(benzyloxy)methyl]cyclopentanecarbonitrile (0.16 g, 0.75 mmol) in toluene (5 mL) at 0° C. was added 1.0 M diisobutylaluminum hydride in hexanes (0.8 mL). The reaction was stirred at 0° C. for 1.5 hours, during which time the starting nitrile was consumed. The reaction was cooled to −78° C. and quenched by the addition of methanol. The mixture was warmed to ambient temperature and 3 N HCl was added. Following stirring for 45 minutes, solid NaCl was added, and the mixture was extracted with three portions of ethyl acetate. The combined extracts were dried (Na$_2$SO$_4$), and filtered, and the solvent was removed in vacuo. Flash column chromatography of the resulting residue (eluting with a gradient from 0-30% ethyl acetate in hexanes) afforded the product (20 mg, 12%).

$^1$H NMR (300 MHz, CDCl$_3$): δ 9.60 (s, 1H), 7.38-7.26 (m, 5H), 4.52 (s, 2H), 3.54 (s, 2H), 2.00-1.89 (m, 2H), 1.66-1.46 (m, 6H).

Step 4: (2E)- and (2Z)-3-1-[(Benzyloxy)methyl]cyclopentylacrylonitrile

To a stirred solution of diethyl cyanomethylphosphonate (18 µL, 0.11 mmol) in THF (1 mL) was added 1.0 M potassium tert-butoxide in THF (0.10 mL). The resulting mixture was stirred 30 minutes, after which a solution of 1-[(benzyloxy)methyl]cyclopentanecarbaldehyde (0.020 g, 0.092 mmol) in THF (1 mL) was added. The resulting mixture was stirred for 16 hours. Water was then added to the reaction and the resulting mixture was extracted with three portions of ethyl ether. The combined extracts were washed with brine, then dried over sodium sulfate, decanted from the sodium sulfate, and the solvent was removed in vacuo to afford the product, which was used without further purification in the subsequent conjugate addition step.

$^1$H NMR (400 MHz, CDCl$_3$): δ 7.37-7.27 (m, 5H), 6.80 (d, 1H (E)), 6.59 (d, 1H (Z)), 5.34 (d, 1H (E)), 5.33 (d, 1H (Z)), 4.53 (s, 2H (Z)), 4.50 (s, 2H (E)), 3.45 (s, 2H (Z)), 3.31 (s, 2H (E)), 1.80-1.55 (m, 8H); MS(ES)=242(M+H).

Step 5: 3-1-[(Benzyloxy)methyl]cyclopentyl-3-[4-(7H-pyrrolo[2,3-d]pyrimidin-4-yl)-1H-pyrazol-1-yl]propanenitrile trifluoroacetate salt To a mixture of (2E)- and (2Z)-3-1-[(benzyloxy)methyl]cyclopentylacrylonitrile (generated in Step 4) and 4-(1H-pyrazol-4-yl)-7-[2-(trimethylsilyl)ethoxy]methyl-7H-pyrrolo[2,3-d]pyrimidine (0.037 g, 0.12 mmol) in ACN (1.5 mL) was added DBU (18 µL, 0.12 mmol). The resulting mixture was stirred at ambient temperature for 3 hours, and then was heated to 60° C. for 28 hours. The reaction mixture was diluted with diethyl ether and 0.1 N HCl. The layers were separated and the aqueous layer was extracted with ethyl acetate. The ethyl acetate extract was washed with brine, dried over sodium sulfate, decanted, and the solvent was removed in vacuo. The resulting residue was dissolved in DCM (3 mL) and TFA (0.75 mL), and this solution was stirred for 3 hours. The solvents were removed in vacuo, and the resulting residue was dissolved in THF (5 mL) and 6.0 M sodium hydroxide in water (3 mL) and stirred for 2 hours. The reaction mixture was extracted with three portions of ethyl acetate. The combined extracts were washed with brine, dried over sodium sulfate, decanted, and the solvent was removed in vacuo. The crude mixture was purified by preparative-HPLC/MS (C18 eluting with a gradient of H$_2$O and ACN containing 0.1% TFA) and lyophilized to afford the desired product (10 mg, 20% over the two steps).

$^1$H NMR (400 MHz, d$_6$-DMSO): δ 12.71 (br s, 1H), 8.99 (s, 1H), 8.86 (s, 1H), 8.52 (s, 1H), 7.80 (s, 1H), 7.38-7.23 (m, 5H), 7.19-7.16 (m, 1H), 4.92 (dd, 1H), 4.50 (d, 1H), 4.44 (d, 1H), 3.49 (dd, 1H), 3.35 (d, 1H), 3.23 (dd, 1H), 3.05 (d, 1H), 1.92-1.82 (m, 1H), 1.66-1.27 (m, 7H); MS(ES): 427(M+H).

Example 742

3-[1-(Methylsulfonyl)pyrrolidin-3-yl]-3-[4-(7H-pyrrolo[2,3-d]pyrimidin-4-yl)-1H-pyrazol-1-yl]propanenitrile trifluoroacetate salt

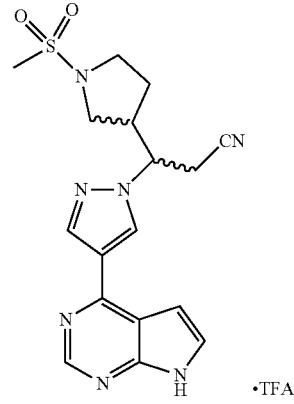 [SMILES: CS(=O)(=O)N1CCC(C(CC#N)n2cc(-c3ncnc4[nH]ccc34)cn2)C1]

Step 1: Benzyl 3-(hydroxymethyl)pyrrolidine-1-carboxylate

To a solution of 1-[(benzyloxy)carbonyl]pyrrolidine-3-carboxylic acid (1.0 g, 4.0 mmol) in THF (37 mL) at 0° C. was added dropwise a solution of 1.0 M borane in THF (16.4 mL). The reaction was allowed to warm to room temperature and stir for 16 hours. The mixture was cooled to 0° C. and 10% HCl (50 mL) was added. After the addition, the mixture was extracted with DCM, and the extract was washed sequentially with saturated NaHCO$_3$ solution and brine, then dried over sodium sulfate, filtered and the solvent was removed in vacuo. The product was used without further purification in the subsequent oxidation step.

¹H NMR (300 MHz, CDCl₃): δ 7.39-7.26 (m, 5H), 5.11 (s, 2H), 3.61-3.31 (m, 5H), 3.18 (dt, 1H), 2.75 (br s, 0.45H), 2.59 (br s, 0.45H), 2.49-2.31 (m, 1H), 2.19 (br s, 0.1H), 2.05-1.89 (m, 1H), 1.77-1.58 (m, 1H); MS(ES): 236(M+H).

Step 2: Benzyl 3-formylpyrrolidine-1-carboxylate

DMSO (597 μL, 8.42 mmol) was added to a solution of oxalyl chloride (427 μL, 5.05 mmol) in DCM (25 mL) at −78° C. After 5 minutes, benzyl 3-(hydroxymethyl)pyrrolidine-1-carboxylate (generated in Step 1) was added. The reaction was continued for 30 minutes at −78° C. TEA (2.3 mL, 17 mmol) was then added. The resulting mixture was then allowed to warm to room temperature over the course of 30 minutes. Water was then added. The layers were separated and the organic phase was washed sequentially with 0.1 N HCl, water, saturated NaHCO3, and brine. The organic phase was then dried over sodium sulfate and the solvent was removed in vacuo to afford the product (0.82 g, 88% over two steps).

¹H NMR (300 MHz, CDCl₃): δ 9.68 (d, 1H), 7.38-7.28 (m, 5H), 5.13 (s, 2H), 3.79 (dd, 1H), 3.65-3.35 (m, 3H), 3.11-2.99 (m, 1H), 2.32-2.04 (m, 2H).

Step 3: Benzyl 3-[(E)-2-cyanovinyl]pyrrolidine-1-carboxylate and benzyl 3-[(Z)-2-cyanovinyl]-pyrrolidine-1-carboxylate To a solution of 1.0 M potassium tert-butoxide in THF (4.40 mL) at 0° C. was added a solution of diethyl cyanomethylphosphonate (820 mg, 4.6 mmol) in THF (6.0 mL) dropwise. The cold bath was removed and the reaction was warmed to room temperature and stirred for 15 minutes. The mixture was cooled to 0° C. and a solution of benzyl 3-formylpyrrolidine-1-carboxylate (0.82 g, 2.3 mmol) in THF (4.00 mL) was added dropwise. Cooling was discontinued and the reaction stirred for 16 hours at ambient temperature. The mixture was diluted with ether and water, the layers were separated and the organic layer was washed with water, followed by brine, and then dried over sodium sulfate, filtered and the solvent was removed in vacuo. The resulting residue was purified by flash column chromatography (eluting with a gradient from 0-35% ethyl acetate in hexanes) to afford the product as a mixture of E and Z isomers (246 mg, 42%).

¹H NMR (300 MHz, CDCl₃): δ 7.41-7.27 (m, 5H), 6.70-6.58 (m, 0.3H (E)), 6.38 (dt, 0.7H (Z)), 5.50-5.30 (m, 1H), 5.14 (s, 2H), 3.79-3.11 (m, 5H), 2.27-2.06 (m, 1H), 1.90-1.70 (m, 1H); MS(ES): 279(M+Na).

Step 4: Benzyl 3-2-cyano-1-[4-(7-[2-(trimethylsilyl)ethoxy]methyl-7H-pyrrolo[2,3-d]pyrimidin-4-yl)-1H-pyrazol-1-yl]ethylpyrrolidine-1-carboxylate To a mixture of benzyl 3-[(E)-2-cyanovinyl]pyrrolidine-1-carboxylate and benzyl 3-[(Z)-2-cyanovinyl]pyrrolidine-1-carboxylate (241 mg, 0.940 mmol) and DBU (234 μL, 1.57 mmol) in ACN (13 mL) was added 4-(1H-pyrazol-4-yl)-7-[2-(trimethylsilyl)ethoxy]methyl-7H-pyrrolo[2,3-d]pyrimidine (250 mg, 0.78 mmol). The mixture was stirred at ambient temperature for 3 hours. The solvent was removed in vacuo. The resulting residue was dissolved in ethyl acetate, and the organic layer was washed sequentially with 1N HCl, water, saturated NaHCO₃, and brine. The washed solution was dried over sodium sulfate and the solvent was removed in vacuo. Purification via flash column chromatography (eluting with a gradient of 0-100% [5% MeOH/DCM] in hexanes) afforded the produce as a mixture of diastereomers (400 mg, 89%).

¹H NMR (400 MHz, CDCl₃ a mixture of diastereomers): δ 8.85 (s, 1H), 8.35-8.28 (m, 2H), 7.42-7.25 (m, 6H), 6.80-6.76 (m, 1H), 5.69-5.66 (m, 2H), 5.15-5.04 (m, 2H), 4.46-4.32 (m, 1H), 3.84-3.84 (m, 6H), 3.54 (t, 2H), 2.26-2.13 (m, 1H), 1.84-1.54 (m, 2H), 0.95-0.89 (m, 2H), −0.06 (s, 9H); MS(ES): 572(M+H).

Step 5. 3-Pyrrolidin-3-yl-3-[4-(7-[2-(trimethylsilyl)ethoxy]methyl-7H-pyrrolo[2,3-d]pyrimidin-4-yl)-1H-pyrazol-1-yl]propanenitrile Benzyl 3-2-cyano-1-[4-(7-[2-(trimethylsilyl)ethoxy]methyl-7H-pyrrolo[2,3-d]pyrimidin-4-yl)-1H-pyrazol-1-yl]ethylpyrrolidine-1-carboxylate (161 mg, 0.282 mmol) was dissolved in methanol (5 mL), and a catalytic amount of 5% Pd—C was added. The suspension was stirred at ambient temperature for 1 hour under an atmosphere of hydrogen provided by a balloon. A catalytic amount of 10% Pd—C was then added, and the reaction stirred for 2 hours under an atmosphere of hydrogen provided by a balloon. The mixture was then filtered, and purified via preparative-HPLC/MS (C18 eluting with a gradient of H₂O and ACN containing 0.15% NH₄OH) to afford the product as a mixture of diastereomers (57 mg, 46%).

¹H NMR (400 MHz, CDCl₃, a mixture of diastereomers): δ 8.84 (s, 1H), 8.34-8.32 (m, 2H), 7.40 (d, 1H), 6.81-6.78 (m, 1H), 5.67 (s, 2H), 4.38 (dt, 1H), 3.54 (t, 2H), 3.30-1.38 (m, 9H), 0.92 (t, 2H), −0.06 (s, 9H); MS(ES): 438(M+H).

Step 6: 3-[1-(Methylsulfonyl)pyrrolidin-3-yl]-3-[4-(7H-pyrrolo[2,3-d]pyrimidin-4-yl)-1H-pyrazol-1-yl]propanenitrile trifluoroacetate salt To a solution of 3-pyrrolidin-3-yl-3-[4-(7-{[2-(trimethylsilyl)ethoxy]methyl}-7H-pyrrolo[2,3-d]pyrimidinyl)1H-pyrazol-1-yl]propanenitrile (25 mg, 0.057 mmol) and TEA (10 μL, 0.074 mmol) in DCM (1.0 mL) at 0° C. was added methanesulfonyl chloride (6 μL, 0.074 mmol). The reaction was allowed to reach ambient temperature and stir for 16 hours. Half of the solvent was removed in vacuo and TFA (1 mL) was added to the vial. After stirring for 1 hour at room temperature, the solvents were removed in vacuo and the resulting residue reconstituted in THF (0.5 mL). To this was added 6 N NaOH (1 mL) and this solution was stirred for 2 hours. The reaction mixture was extracted with five portions of ethyl acetate. The combined extracts were dried (Na₂SO₄), decanted and concentrated. Preparative-HPLC/MS (C18 eluting with a gradient of H₂O and ACN containing 0.1% TFA) was used to afford the product (16 mg, 57%).

¹H NMR (400 MHz, d₆-DMSO, a mixture of diastereomers): δ 12.69 (s, 1H), 8.98 (s, 0.5H), 8.95 (s, 0.5H), 8.84 (s, 1H), 8.53-8.51 (m, 1H), 7.80-7.77 (m, 1H), 7.16-7.13 (m, 1H), 4.86-4.75 (m, 1H), 3.55-3.48 (m, 1H), 3.42-3.08 (m, 4H), 2.99-2.91 (m, 1H), 2.90 (s, 1.5H), 2.85 (s, 1.5H), 2.16-2.07 (m, 1H), 1.82-1.70 (m, 1H), 1.64-1.48 (m, 1H); MS(ES): 386(M+H).

Example 743

N'-Cyano-4-(cyanomethyl)-4-[4-(7H-pyrrolo[2,3-d]pyrimidin-4-yl)-1H-pyrazol-1-yl]piperidine-1-carboximidamide

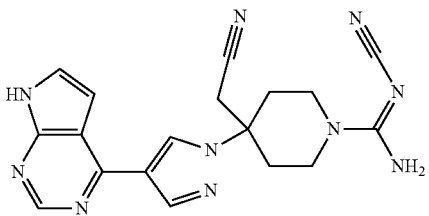 [SMILES: N#CCC1(N/C=C(\C=N)c2ncnc3[nH]ccc23)CCN(/C(N)=N\C#N)CC1]

Step 1: tert-Butyl 4-(cyanomethylene)piperidine-1-carboxylate

To a solution of 1.0 M potassium tert-butoxide in THF (10.1 mL) at 0° C. was added a solution of diethyl cyanomethylphosphonate (1.66 mL, 0.0102 mol) in THF (20 mL) dropwise. The reaction was held for 10 min, then added to a solution of tert-butyl 4-oxo-1-piperidinecarboxylate (2.00 g, 0.0100 mol) in THF (30 mL) stirring at 0° C. under an atmosphere of nitrogen. After complete addition, the cold bath was removed and the reaction was allowed to stir 1.0 h at 20° C. LCMS analysis showed the desired product and no remaining starting material. HPLC showed the product $UV_{max}$ at 200 & 230 nm. Water and EtOAc were added to the reaction mixture. The phases were separated, and the aqueous phase was extracted with EtOAc. The combined organic phase was washed with water, then saturated NaCl, then dried over $Na_2SO_4$, and concentrated to dryness to provide 2.5 g of the product as a yellow oil. TLC (25% EtOAc/hexane) $R_f$ 0.22. The product was purified by automatic flash chromatography on silica gel. Used a 40 g column; flow 40 mL/min; [A=hexane] [B=EtOAc]. A, 4 min; Gradient to 20% B in 30 min. Collected 44 mL fractions. The product eluted in 21-27 min. The fractions were contrated to yield 0.67 g of a white solid. $^1$H NMR (CDCl$_3$) δ 5.19 (s, 1H); 3.51 (m, 4H); 2.56 (t, 2H); 2.33 (t, 2H); 1.50 (s, 9H). MS(ES) 245 (M+Na, weak; base peak M+H-56 =167).

Step 2: tert-Butyl 4-(cyanomethyl)-4-[4-(7-[2-(trimethylsilyl)ethoxy]methyl-7H-pyrrolo[2,3-d]-pyrimidin-4-yl)-1H-pyrazol-1-yl]piperidine-1-carboxylate 4-(1H-Pyrazol-4-yl)-7-[2-(trimethylsilyl)ethoxy]methyl-7H-pyrrolo[2,3-d]pyrimidine (0.840 g, 2.66 mmol) was slurried in a mixture of ACN (20 mL) and DBU (398 μL, 2.66 mmol), and tert-butyl 4-(cyanomethylene)piperidine-1-carboxylate (0.651 g, 2.93 mmol) was added. The pyrazole did not dissolve at 20° C., but a solution was formed when the mixture was heated to 40° C. for 1 h. LCMS and HPLC analyses showed about 20% conversion to product. The mixture was stirred at 40-45° C. overnight. HPLC showed 60 area % product. The ACN was removed by rotory evaporator at 20° C. To the resulting residue was added saturated NaHCO$_3$ and EtOAc. The organic layer was shaken with more aqueous saturated NaHCO$_3$, then dried (Na$_2$SO$_4$) and rotovaped to give 1.6 g of a brown oil residue. TLC (60% EtOAc/hexane): product $R_f$=0.25. The product was purified by automatic flash chromatography on silica gel, using a 40 g column, at a flow of 40 mL/min; [A=hexane] [B=EtOAc]. A, 3min; Gradient to 100% B in 50 min. Collected 44 mL fractions. The product eluted in 24-29 min; the pyrazole in 39-46 min; and the olefin in 13-15 min. Solvent was removed in vacuo for the appropriate fractions to give 0.27 g olefin; 0.30 g pyrazole; and a yield of 0.67 g of the product, all of which were isolated as white solids. $^1$H NMR (CDCl$_3$) δ 8.84 (s, 1H); 8.42 (s, 1H); 8.33 (s, 1H); 7.40 (d, 1H); 6.79 (d, 1H); 5.67 (s, 2H); 3.94 (m, 2H); 3.54 (m, 2H); 3.07 (m, 2H); 2.90 (s, 2H); 2.72 (m, 2H); 2.08 (m, 2H); 1.45 (s, 9H); 0.91 (m, 2H); −0.06 (s, 9H). MS(ES) 538 (M+H).

Step 3: 4-[4-(7H-Pyrrolo[2,3-d]pyrimidin-4-yl)-1H-pyrazol-1-y]piperidin-4-ylacetonitrile tert-Butyl 4-(cyanomethyl)-4-[4-(7-[2-(trimethylsilyl)ethoxy]methyl-7H-pyrrolo[2,3-d]-pyrimidin-4-yl)-1H-pyrazol-1-yl]piperidine-1-carboxylate (0.670 g, 1.24 mmol) was dissolved in TFA (5.0 mL, 65 mmol) and was stirred for 1.3 h. LCMS showed conversion to the hydroxymethyl intermediate, M+H 338. The solution was concentrated to remove the TFA. Methanol was added to the resulting residue, and the resulting mixture was concentrated. The resulting residue was dissolved in methanol (10 mL) and 15.0 M ammonium hydroxide in water (1.66 mL) was added. The resulting solution was stirred for 2 h. LCMS and HPLC analyses showed complete deprotection. The mixture was concentrated. Toluene was added to the resulting residue and the resulting mixture was concentrated to provide a white semisolid. Most of this intermediate product was used for the next step. The rest was purified by prep HPLC using a 30 mm×100 mm C18 column; 8% ACN-H$_2$O (0.1% NH$_4$OH), 1.0min, to 27% at 6min; 60 mL/min; detector set at m/z 308; retention time, 5.4 min. Tubes containing pure product were combined and freeze dried to give 13.6 mg of the product.

$^1$H NMR (d$_6$-DMSO) δ 12.07 (s, 1H); 8.68 (s, 1H); 8.62 (s, 1H); 8.36 (s, 1H); 7.54 (d, 1H); 7.00 (d, 1H); 3.16 (s, 2H); 2.87 (m, 2H); 2.55 (m, 4H); 1.94 (m, 2H). MS(ES) 308 (M+H).

Step 4: Methyl N-cyano-4-(cyanomethyl)-4-[4-(7H-pyrrolo[2,3-d]pyrimidin-4-yl)-1H-pyrazol-1-yl]-piperidine-1-carbimidothioate 4-[4-(7H-Pyrrolo[2,3-d]pyrimidin-4-yl)-1H-pyrazol-1-yl]piperidin-4-ylacetonitrile (361 mg, 1.17 mmol) and N-cyano-S,S'-dimethyldithioimido carbonate (344 mg, 2.35 mmol) were dissolved in isopropyl alcohol (2.5 mL) and DMSO (2.5 mL) at 20° C. After 16 h reaction time, LCMS analysis showed the presence of some product, M+H 406; of the reagent, M+H 147; and of the piperidine, M+H 308. HPLC analysis showed about 2% reaction. The HPLC method was: Zorbax SB C18, 5 μm, 15 cm, 35° C., flow 1.2 mL/min, 5% ACN-H$_2$O (0.05% TFA), 1.5 min, to 100% ACN in 15.0 min; detector set at 324, 225, and 265 nm. The retention time of the starting material was 4.9 min (UV max 224, 262, 292, & 325 nm); of the product, 6.5 min (UV max 226, 262, 290, & 324 nm); and of the reagent, 7.7 min (UV max 265 nm). To the product was added TEA (327 μL, 2.35 mmol), and the resulting mixture was stirred at RT. After stirring for 3 h, HPLC and LCMS analyses showed 60% reaction. The product and the unreacted piperidine were isolated by prep HPLC using a 30 mm×100 mm C18 column; 5% ACN-H₂O (0.1% TFA), 1.0 min, to 35% at 6 min; 60 mL/min; detector set at 326 nm. The retention time for the product was 5.9 min; and for the starting piperidine was 3.5-4.3 min. The product was freeze dried to yield 301 mg of a white solid TFA salt. ¹H NMR (d₆-DMSO) δ 12.85 (s, 1H); 9.01 (s, 1H); 8.90 (s, 1H); 8.59 (s, 1H); 7.85 (m, 1H); 7.30 (m, 1H); 4.23 (m, 2H); 3.35 (m, 2H); 3.30 (s, 2H); 2.78 (m, 2H); 2.68 (s, 3H); 2.16 (m, 2H). MS(ES) 406 (M+H).

Step 5: N'-Cyano-4-(cyanomethyl)-4-[4-(7H-pyrrolo[2,3-d]pyrimidin-4-yl)-1H-pyrazol-1-yl]piperidine-1-carboximidamide Methyl N-cyano-4-(cyanomethyl)-4-[4-(7H-pyrrolo[2,3-d]pyrimidin-4-yl]-1H-pyrazol-piperidine-1-carbimidothioate (41.3 mg, 0.102 mmol) (53 mg TFA salt) was dissolved in 2.0 M ammonia in isopropyl alcohol (4.00 mL). The resulting mixture was heated to 100° C. for 1 h in a microwave reactor. Analysis by HPLC and LCMS showed 60% reaction to give the expected M+H 375 (50 area %). To this mixture was added 2 mL of 7 N NH₃/MeOH. The resulting mixture was heated at 120° C. for one hour. HPLC and LCMS analyses showed no remaining starting material. The reaction mixture was concentrated on a rotory evaporator. The product was isolated by prep HPLC using a 30 mm×100 mm C18 column, eluting with a solvent gradient; 10% ACN-H₂O (0.1% TFA), 1.5 min, to 30% at 6 min; 60 mL/min; detector set at m/z 375; retention time, 4.7 min. The eluate was freeze-dried to yield 11.7 mg of the product TFA salt as a white solid. ¹H NMR (d₆-DMSO) δ 12.69 (s, 1H, NH); 8.92 (s, 1H); 8.81 (s, 1H); 8.51 (s, 1H); 7.75 (m, 1H); 7.22 (m, 1H); 7.18 (s, 2H, NH2); 3.84 (m, 2H); 3.23 (s, 2H); 2.99 (m, 2H); 2.60 (m, 2H); 1.97 (m, 2H). MS(ES) 375 (M+H).

Example 744

4-1-[2,2,2-Trifluoro-1-(1H-imidazol-2-ylmethyl)ethyl]-1H-pyrazol-4-yl-7H-pyrrolo[2,3-d]pyrimidine

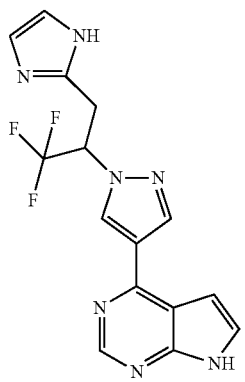 [SMILES: FC(F)(F)C(Cc1ncc[nH]1)n1cc(-c2ncnc3[nH]ccc23)cn1]

Step 1: (3R)-4,4,4-Trifluoro-3-[4-(7-[2-(trimethylsilyl)ethoxy]methyl-7H-pyrrolo[2,3-d]pyrimidin-4-yl)-1H-pyrazol-1-yl]butanal

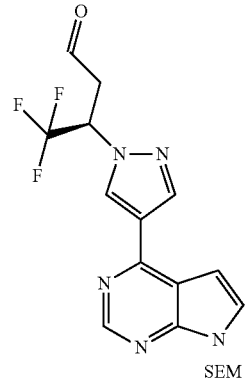 [SMILES: O=CC[C@@H](n1cc(-c2ncnc3[nH]ccc23)cn1)C(F)(F)F]

To a −70° C. solution of (3R)-4,4,4-trifluoro-3-[4-(7-[2-(trimethylsilyl)ethoxy]methyl-7H-pyrrolo[2,3-d]pyrimidin-4-yl)-1H-pyrazol-1-yl]butanenitrile (1.06 g, 0.00243 mol) (see, Example 93, Step 1) in DCM (10 mL, 0.2 mol) was added 1.0 M diisobutylaluminum hydride in DCM (4.8 mL). The resulting mixture was stirred for 3 h and allowed to warm during this time interval from −70 to −25° C., after which the reaction was cooled back at −70° C. Methanol (1.5 mL, 0.037 mol) was added, followed by 2.0 M HCl in water (15 mL). Insoluble material was then filtered from the reaction mixture. The organic filtrate was washed sequentially with: 2.0 M HCl in water, water and saturated aqueous NaCl. The washed organic phase was dried over sodium sulfate and was concentrated using a rotory evaporator to give 0.58 g of the crude product as a pale yellow foam/solid. The crude product was chromatographed with 0-80% ethyl acetate/hexanes to give the purified product (0.9 g) as a pale orange oil (47% yield).

¹H NMR (400 MHz, CDCl₃): δ 9.85 (1H, s); 8.95 (1H, s); 8.5 (1H, s); 8.4 (1H, s); 7.5 (1H, d); 6.85 (1H, d); 5.75 (2H, s); 5.5 (1H, m); 4.0 (1H, dd); 3.6 (2H, t); 3.3 (1H, dd); 1.99 (2H, t); 0.0 (9H, s). MS (M+H): 440.

Step 2: 4-1-[2,2,2-Trifluoro-1-(1H-imidazol-2-ylmethyl)ethyl]-1H-pyrazol-4-yl-7-[2-(trimethylsilyl)ethoxy]methyl-7H-pyrrolo[2,3-d]pyrimidine

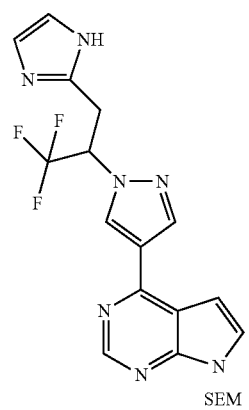 [SMILES: FC(F)(F)C(Cc1ncc[nH]1)n1cc(-c2ncnc3[nH]ccc23)cn1]

A solution of 4,4,4-trifluoro-3-[4-(7-[2-(trimethylsilyl)ethoxy]methyl-7H-pyrrolo[2,3-d]-pyrimidin-4-yl)-1H-pyrazol-1-yl]butanal (0.138 g, 0.000314 mol), 7.0 M ammonia in methanol (1 mL), ethanedial (0.5 mL, 0.004 mol) and acetic acid (20 uL, 0.0004 mol) in methanol (2 mL, 0.05 mol) was microwaved on 100 watts, at 80° C. for 60 minutes. Following the microwave reaction, ethyl acetate/water was added. The organic phase was separated and washed with saturated NaHCO₃ and saturated NaCl. The washed organic phase was dried and concentrated (rotory evaporator) to give 196 mg of the crude product as an orange glass. The crude product was purified by chromatography with 0-100% ethyl acetate/hexanes to give 57 mg of purified product as an off-white solid (38% yield).

¹H NMR (400 MHz, CDCl₃): δ 8.91 (1H, s); 8.4 (1H, s); 8.2 (1H, s); 7.5 (1H, d); 7.0 (2H, s); 6.83 (1H, d); 5.75 (2H, s); 5.62 (1H, m); 4.15 (1H, dd); 3.8 (1H, dd); 3.6 (2H, t); 1.99 (2H, t); 0.0 (9H, s). MS (M+H): 478.

Step 3: 4-1-[2,2,2-Trifluoro-1-(1H-imidazol-2-ylmethyl)ethyl]-1H-pyrazol-4-yl-7H-pyrrolo[2,3-d]-pyrimidine A solution of 4-1-[2,2,2-trifluoro-1-(1H-imidazol-2-ylmethypethyl]-1H-pyrazol-4-yl-7-[2-(trimethylsilyl)ethoxy]methyl-7H-pyrrolo[2,3-d]pyrimidine (0.055 g, 0.12 mmol) in 1,2-dichloro-ethane (1 mL, 10 mmol) and TFA (0.5 mL, 6 mmol) was stirred overnight. The reaction was concentrated to provide an orange oil. The oil was stirred in methanol (1 mL, 20 mmol) and 8.0 M ammonium hydroxide in water (1 mL) for 4h. This mixture was then concentrated to provide a crude product as an orange glass/solid. The crude product was purified by Prep HPLC (pH10) to give 28 mg of purified product as a colorless glass, which was triturated with 2-methoxy-2-methylpropane (1 mL, 8 mmol), and then filtered and washed to provide 15 mg of the product as a white solid (38% yield) which then was dried rt-50° C. for 3 h.

¹H NMR (400 MHz, DMSO): δ 12.13 (1H, s); 11.89 (1H, s); 8.65 (1H, s); 8.37 (1H, s); 7.6 (1H, d); 6.95 (1H, d); 6.92 (1H, d); 5.91 (1H, m); 3.78 (1H, dd); 3.47 (H, dd). MS (M+H): 348.

Example 745

4-(1-(1R)-2,2,2-Trifluoro-1-[(4-methyl-1,3-thiazol-2-yl)methyl]ethyl-1H-pyrazol-4-yl)-7H-pyrrolo[2,3-d]pyrimidine

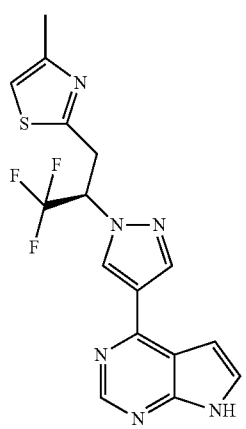 [SMILES: Cc1csc(C[C@@H](n2cc(-c3ncnc4[nH]ccc34)cn2)C(F)(F)F)n1]

Step 1: (3R)-4,4,4-Trifluoro-3-[4-(7H-pyrrolo[2,3-d]pyrimidin-4-yl)-1H-pyrazol-1-yl]butane-thioamide

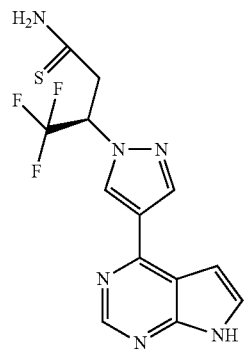 [SMILES: NC(=S)C[C@@H](n1cc(-c2ncnc3[nH]ccc23)cn1)C(F)(F)F]

A suspension of phosphorus pentasulfide (0.46 g, 1.0 mmol) in ethanol (0.5 mL, 8 mmol) was stirred for 1 h. (3R)-4,4,4-Trifluoro-3-[4-(7H-pyrrolo[2,3-d]pyrimidin-4-yl)-1H-pyrazol-1-yl) butane-nitrile (0.15 g, 0.50 mmol) (see, Example 93) was added and the resulting mixture was heated at 80° C. in a sealed vial for 0.5h, during which reaction the mixture became a yellow solution. The reaction was heated overnight. The reaction was then cooled to rt. Water (1 g, 60 mmol) and ethyl acetate were added to the mixture. The organic phase was separated and washed with saturated NaHCO₃ and saturated aqueous NaCl. The washed organic phase was then dried and concentrated to give 387 mg of a crude product as a white glass/oil. The crude product was chromatographed with 0-10% MeOH/DCM, 0-1% NH₄OH to give 0.13 g of the purified product as a white solid (76% yield).

¹H NMR (400 MHz, CDCl₃): δ 8.7 (1H, s); 8.5 (1H, s); 8.3 (1H, s); 7.4 (1H, d); 7.0 6.75 (1H, d); 5.82 (1H, m); 3.75 (1H, dd); 3.2 (1H, dd). MS (M+H): 341.

A suspension of (3R)-4,4,4-trifluoro-3-[4-(7H-pyrrolo[2,3-d]pyrimidin-4-yl)-1H-pyrazol-1-yl]butanethioamide (0.038 g, 0.00011 mol), chloroacetone (15 uL, 0.00019 mol) in ethanol (1 mL, 0.02 mol) and 1,2-dichloroethane (1 mL, 0.01 mol) was heated to reflux overnight. Following this, the reaction mixture was filtered to remove insoluble material. The filtrate was dissolved in MeOH (1 mL) and DMF (1 mL) and purified by prep HPLC at pH 10 to provide 6 mg of the purified product as a colorless glass/oil, which was then triturated with MTBE/hexanes and was dried at 40° C. overnight to give 5.2 mg of the purified product as an off-white solid (13% yield).

¹H NMR (400 MHz, CDCl₃): δ 10.11 (1H, s); 8.88 (1H, s); 8.42 (1H, s); 8.38 (1H, s); 7.45 (1H, d); 6.79 (1H, s); 6.65 (1H, d); 5.41 (1H, m); 4.15 (1H, dd); 3.75 (H, dd); 2.18 (3H, s). MS (M+H): 379.

Example A

In vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), Jak2 (a.a. 828-1132) and Jak3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions was 90 µM for Jak1, 30 µM for Jak2 and 3 µM for Jak3. Reactions were carried out at room temperature for 1 hr and then stopped with 20 µL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). Compounds having an $IC_{50}$ of 10 µM or less for any of the above-mentioned JAK targets were considered active.

Example B

Cellular Assays

One or more compounds herein were tested for inhibitory activity of JAK targets according to at least one of the following cellular assays.

Cancer cell lines dependent on cytokines and hence JAK/STAT signal transduction, for growth, were plated at 6000 cells per well (96 well plate format) in RPMI 1640, 10% FBS, and 1 nG/mL of appropriate cytokine. Compounds were added to the cells in DMSO/media (final concentration 0.2% DMSO) and incubated for 72 hours at 37° C., 5% $CO_2$. The effect of compound on cell viability was assessed using the CellTiter-Glo Luminescent Cell Viability Assay (Promega) followed by TopCount (Perkin Elmer, Boston, Mass.) quantitation. Potential off-target effects of compounds were measured in parallel using a non-JAK driven cell line with the same assay readout. Compounds having an $IC_{50}$ of 10 µM or less with selectivity for JAK driven proliferation were considered active. All experiments were performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. Nature 434:1144-1148; Staerk, J., et al. JBC 280: 41893 -41899). Endpoints include the effects of compounds on cell survival, proliferation, and phosphorylated JAK, STAT, Akt, or Erk proteins.

Certain compounds herein have been or can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 µg/ml streptomycin) at a density of $2 \times 10^6$ cells/ml at 37° C. for up to 2 days. For IL-2 stimulated cell proliferation analysis, T-cells are first treated with Phytohemagglutinin (PHA) at a final concentration of 10 µg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In vivo Anti-tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. Hematol J. 2:42-53, 2001). Tumor bearing animals can then be randomized into drug or vehicle treatment groups and different doses of compounds can be administered by any number of the usual routes including oral, i.p., or continuous infusion using implantable pumps Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (Immunol Today. 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds was given throughout the sensitization and challenge phases (day −1 to day 7) or prior to and throughout the challenge phase (usually afternoon of day 4 to day 7). Treatment of the test compounds (in different concentration) was administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In vivo Anti-inflammatory Activity

Compounds herein can be or have been evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003.).

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A method of treating lymphoma in a patient, comprising administering a therapeutically effective amount of a compound, which is 3-cyclopentyl-3-[4-(7H-pyrrolo[2,3-d]pyrimidin-4-yl)-1H-pyrazol-1-yl]propanenitrile, or a pharmaceutically acceptable salt thereof, wherein the treating refers to ameliorating or inhibiting lymphoma in the patient.

2. The method of claim 1, wherein the compound is (3R)-3-cyclopentyl-3-[4-(7H-pyrrolo[2,3-d]pyrimidin-4-yl)-1H-pyrazol-1-yl]propanenitrile, or a pharmaceutically acceptable salt thereof.

3. The method of claim 2, wherein the lymphoma is cutaneous T-cell lymphoma (CTCL).

4. The method of claim 3, wherein the cutaneous T-cell lymphoma is Sezary syndrome.

5. The method of claim 3, wherein the cutaneous T-cell lymphoma is mycosis fungoides.

6. The method of claim 2, wherein the lymphoma is adult T cell leukemia/lymphoma (ATLL).

7. The method of claim 2, wherein the lymphoma is cutaneous B-cell lymphoma.

\* \* \* \* \*

UNITED STATES PATENT AND TRADEMARK OFFICE
CERTIFICATE OF CORRECTION

PATENT NO. : 10,398,699 B2  
APPLICATION NO. : 15/960069  
DATED : September 3, 2019  
INVENTOR(S) : James D. Rodgers and Stacey Shepard Page 1 of 1

It is certified that error appears in the above-identified patent and that said Letters Patent is hereby corrected as shown below:

In the Claims

Column 372, Line 47, Claim 6, delete "T cell" and insert -- T-cell --.

Signed and Sealed this
Nineteenth Day of November, 2019

Andrei Iancu
*Director of the United States Patent and Trademark Office*